under 35 U.S.C. 154(b) by 216 days.

United States Patent
Babaoglu et al.

(10) Patent No.: US 9,102,614 B2
(45) Date of Patent: Aug. 11, 2015

(54) NAPHTH-2-YLACETIC ACID DERIVATIVES TO TREAT AIDS

(75) Inventors: Kerim Babaoglu, Lansdale, PA (US); Elizabeth Bacon, Burlingame, CA (US); Kyla Bjornson, San Mateo, CA (US); Hongyan Guo, San Mateo, CA (US); Randall L. Halcomb, Foster City, CA (US); Paul Hrvatin, South San Francisco, CA (US); John O. Link, San Francisco, CA (US); Hongtao Liu, Cupertino, CA (US); Ryan Mcfadden, Foster City, CA (US); Michael L. Mitchell, Hayward, CA (US); Paul Roethle, San Francisco, CA (US); James Taylor, San Mateo, CA (US); James D. Trenkle, Oakland, CA (US); Randall W. Vivian, San Mateo, CA (US); Lianhong Xu, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 216 days.

(21) Appl. No.: 13/806,067

(22) PCT Filed: Jul. 1, 2011

(86) PCT No.: PCT/US2011/042880
§ 371 (c)(1),
(2), (4) Date: Apr. 26, 2013

(87) PCT Pub. No.: WO2012/003497
PCT Pub. Date: Jan. 5, 2012

(65) Prior Publication Data
US 2013/0203727 A1    Aug. 8, 2013

Related U.S. Application Data

(60) Provisional application No. 61/361,314, filed on Jul. 2, 2010.

(51) Int. Cl.
*C07D 295/073*    (2006.01)
*C07D 295/155*    (2006.01)
(Continued)

(52) U.S. Cl.
CPC ............... *C07C 59/64* (2013.01); *C07C 229/34* (2013.01); *C07C 233/47* (2013.01); *C07C 255/57* (2013.01); *C07C 271/22* (2013.01); *C07C 311/16* (2013.01); *C07D 205/04* (2013.01); *C07D 211/48* (2013.01); *C07D 213/64* (2013.01); *C07D 213/65* (2013.01); *C07D 213/73* (2013.01); *C07D 215/04* (2013.01); *C07D 215/14* (2013.01); *C07D 231/12* (2013.01); *C07D 233/58* (2013.01); *C07D 239/26* (2013.01); *C07D 239/34* (2013.01); *C07D 239/36* (2013.01); *C07D 239/42* (2013.01); *C07D 241/12* (2013.01); *C07D 295/073* (2013.01); *C07D 295/155* (2013.01); *C07D 309/10* (2013.01); *C07D 311/20* (2013.01); *C07D 311/58* (2013.01); *C07D 487/04* (2013.01); *C07D 491/06* (2013.01); *C07D 493/04* (2013.01)

(58) Field of Classification Search
CPC .. C07D 205/04; C07D 213/64; C07D 213/73; C07D 213/65; C07D 231/12; C07D 239/34; C07D 239/36; C07D 295/073; C07D 295/155; C07D 311/20; C07D 311/58; C07D 493/04; C07D 215/14
See application file for complete search history.

(56) References Cited

U.S. PATENT DOCUMENTS 3,895,028  A    7/1975  Wada et al.
3,900,486  A    8/1975  Suzuki et al.
(Continued)

FOREIGN PATENT DOCUMENTS

CA    1144556 A1    4/1983
CN    1123275 A     5/1996
(Continued)

OTHER PUBLICATIONS

Benzaria, S. et al. (Dec. 6, 1996). "Synthesis, in Vitro Antiviral Evaluation, and Stability Studies of Bis(S-Acyl-2-Thioethyl) Ester Derivatives of 9-[2-(Phosphonomethoxy)Ethyl]adenine (PMEA) as Potential PMEA Prodrugs with Improved Oral Bioavailability," *J. Med. Chem.* 39(25):4958-4965.

Bundgaard, H. (1991). "Design and Application of Prodrugs," Chapter 5 in *A Textbook of Drug Design and Development*, Krogsgaard-Larsen, P. et al. eds., Harwood Academic Publishers, Chur, Switzerland, pp. 113-191.

(Continued)

*Primary Examiner* — Rebecca Anderson

(57) ABSTRACT

The invention provides compounds of formula (I): or a salt thereof as described herein. The invention also provides pharmaceutical compositions comprising a compound of formula I, processes for preparing compounds of formula (I), intermediates useful for preparing compounds of formula I and therapeutic methods for treating the proliferation of the HIV virus, treating AIDS or delaying the onset of AIDS or ARC symptoms in a mammal using compounds of formula (I).

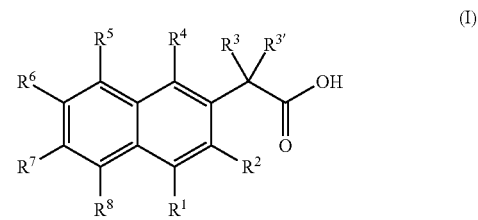

23 Claims, No Drawings

(51) Int. Cl.

| | |
|---|---|
| *C07D 493/04* | (2006.01) |
| *C07D 311/20* | (2006.01) |
| *C07D 311/58* | (2006.01) |
| *C07D 239/34* | (2006.01) |
| *C07D 239/36* | (2006.01) |
| *C07D 231/12* | (2006.01) |
| *C07D 213/64* | (2006.01) |
| *C07D 213/73* | (2006.01) |
| *C07D 213/65* | (2006.01) |
| *C07D 205/04* | (2006.01) |
| *C07D 215/14* | (2006.01) |
| *C07C 59/64* | (2006.01) |
| *C07D 211/48* | (2006.01) |
| *C07D 215/04* | (2006.01) |
| *C07D 233/58* | (2006.01) |
| *C07D 241/12* | (2006.01) |
| *C07D 309/10* | (2006.01) |
| *C07D 491/06* | (2006.01) |
| *C07C 229/34* | (2006.01) |
| *C07C 233/47* | (2006.01) |
| *C07C 255/57* | (2006.01) |
| *C07C 271/22* | (2006.01) |
| *C07C 311/16* | (2006.01) |
| *C07D 239/26* | (2006.01) |
| *C07D 239/42* | (2006.01) |
| *C07D 487/04* | (2006.01) |

(56) References Cited

U.S. PATENT DOCUMENTS

| | | | |
|---|---|---|---|
| 4,816,570 A | 3/1989 | Farquhar | |
| 4,968,788 A | 11/1990 | Farquhar | |
| 5,434,188 A | 7/1995 | Boschelli et al. | |
| 5,663,159 A | 9/1997 | Starrett, Jr. et al. | |
| 5,733,906 A | 3/1998 | Jungheim et al. | |
| 5,738,985 A | 4/1998 | Miles et al. | |
| 5,792,756 A | 8/1998 | Starrett, Jr. et al. | |
| 5,798,365 A | 8/1998 | Kirsch et al. | |
| 7,514,233 B2 | 4/2009 | Debyser et al. | |
| 8,008,470 B2 | 8/2011 | Debyser et al. | |
| 2005/0165052 A1 | 7/2005 | Fakhfakh et al. | |
| 2005/0239819 A1 | 10/2005 | Satoh et al. | |
| 2005/0261336 A1 | 11/2005 | Mousnier et al. | |
| 2006/0035926 A1 | 2/2006 | Lee et al. | |
| 2006/0094755 A1 | 5/2006 | Rajagopalan et al. | |
| 2006/0275748 A1 | 12/2006 | Debyser et al. | |
| 2009/0197862 A1 | 8/2009 | Steinig et al. | |
| 2009/0203742 A1 | 8/2009 | Surleraux et al. | |
| 2010/0311735 A1 | 12/2010 | Tsantrizos et al. | |
| 2011/0223131 A1 | 9/2011 | Haolun et al. | |
| 2013/0210801 A1 | 8/2013 | Babaoglu et al. | |
| 2013/0231331 A1 | 9/2013 | Pendri et al. | |
| 2013/0281433 A1 | 10/2013 | Babaoglu et al. | |
| 2013/0281434 A1 | 10/2013 | Babaoglu et al. | |
| 2014/0045818 A1 | 2/2014 | Mitchell et al. | |

FOREIGN PATENT DOCUMENTS

| | | |
|---|---|---|
| CN | 1044117 C | 7/1999 |
| CN | 1466576 A | 1/2004 |
| DE | 24 03 682 A1 | 7/1974 |
| EP | 0 017 543 A1 | 10/1980 |
| EP | 1 441 228 A1 | 7/2004 |
| EP | 1 541 558 A1 | 6/2005 |
| EP | 1 565 471 B1 | 10/2006 |
| EP | 1 873 238 A1 | 1/2008 |
| EP | 1 873 238 B1 | 1/2008 |
| GB | 2 154 583 A | 9/1985 |
| JP | 3-287558 A | 12/1991 |
| JP | 03-287558 A | 12/1991 |
| WO | WO-91/19721 A1 | 12/1991 |
| WO | WO-94/23041 A2 | 10/1994 |
| WO | WO-94/23041 A3 | 10/1994 |
| WO | WO-99/52850 A1 | 10/1999 |
| WO | WO-00/63152 A1 | 10/2000 |
| WO | WO-02/18341 A2 | 3/2002 |
| WO | WO-02/18341 A3 | 3/2002 |
| WO | WO-2004/014371 A1 | 2/2004 |
| WO | WO-2004/046115 A1 | 6/2004 |
| WO | WO-2004/087153 A2 | 10/2004 |
| WO | WO-2004/087153 A3 | 10/2004 |
| WO | WO-2005/120508 A1 | 12/2005 |
| WO | WO-2006/001958 A2 | 1/2006 |
| WO | WO-2006/001958 A3 | 1/2006 |
| WO | WO-2006/002185 A1 | 1/2006 |
| WO | WO-2006/116412 A2 | 11/2006 |
| WO | WO-2006/116412 A3 | 11/2006 |
| WO | WO-2006/124780 A2 | 11/2006 |
| WO | WO-2006/124780 A3 | 11/2006 |
| WO | WO-2007/016392 A2 | 2/2007 |
| WO | WO-2007/016392 A3 | 2/2007 |
| WO | WO 2007/131350 A1 | 11/2007 |
| WO | WO-2007/138472 A2 | 12/2007 |
| WO | WO-2007/138472 A3 | 12/2007 |
| WO | WO-2007/147884 A1 | 12/2007 |
| WO | WO-2008/053478 A2 | 5/2008 |
| WO | WO-2008/053478 A3 | 5/2008 |
| WO | WO-2008/071587 A2 | 6/2008 |
| WO | WO-2008/071587 A3 | 6/2008 |
| WO | WO 2009/062285 A1 | 5/2009 |
| WO | WO 2009/062288 A1 | 5/2009 |
| WO | WO 2009/062289 A1 | 5/2009 |
| WO | WO-2009/062308 A1 | 5/2009 |
| WO | WO-2009/095500 A1 | 8/2009 |
| WO | WO-2010/059658 A1 | 5/2010 |
| WO | WO-2010/130034 A1 | 11/2010 |
| WO | WO-2010/130842 A1 | 11/2010 |
| WO | WO-2011/002635 A1 | 1/2011 |
| WO | WO-2011/015641 A1 | 2/2011 |
| WO | WO-2011/047129 A1 | 4/2011 |
| WO | WO-2011/076765 A1 | 6/2011 |
| WO | WO-2011/106445 A1 | 9/2011 |
| WO | WO-2011/149950 A2 | 12/2011 |
| WO | WO-2011/149950 A3 | 12/2011 |
| WO | WO-2012/003497 A1 | 1/2012 |
| WO | WO 2012/003498 A1 | 1/2012 |
| WO | WO-2012/033735 A1 | 3/2012 |
| WO | WO-2012/065963 A2 | 5/2012 |
| WO | WO-2012/065963 A3 | 5/2012 |
| WO | WO-2012/066442 A1 | 5/2012 |
| WO | WO-2012/088365 A1 | 6/2012 |
| WO | WO-2012/102985 A1 | 8/2012 |
| WO | WO 2012/137181 A1 | 10/2012 |
| WO | WO-2012/138669 A1 | 10/2012 |
| WO | WO-2012/138670 A1 | 10/2012 |
| WO | WO 2012/140243 A1 | 10/2012 |
| WO | WO 2012/145728 A1 | 10/2012 |
| WO | WO-2013/002357 A1 | 1/2013 |
| WO | WO-2013/025584 A1 | 2/2013 |
| WO | WO-2013/043553 A1 | 3/2013 |
| WO | WO-2013/058448 A1 | 4/2013 |
| WO | WO-2013/062028 A1 | 5/2013 |
| WO | WO-2013/103724 A1 | 7/2013 |
| WO | WO-2013/103738 A1 | 7/2013 |
| WO | WO-2013/106643 A2 | 7/2013 |
| WO | WO-2013/106643 A3 | 7/2013 |
| WO | WO-2013/123148 A1 | 8/2013 |
| WO | WO-2013/134113 A1 | 9/2013 |
| WO | WO-2013/134142 A1 | 9/2013 |
| WO | WO-2013/157622 A1 | 10/2013 |
| WO | WO-2013/159064 A1 | 10/2013 |
| WO | WO-2014/009794 A1 | 1/2014 |
| WO | WO-2014/028384 A1 | 2/2014 |
| WO | WO-2014/055603 A1 | 4/2014 |
| WO | WO-2014/055618 A1 | 4/2014 |

OTHER PUBLICATIONS

De Lombaert, S. et al. (Feb. 18, 1994). "*N*-Phosphonomethyl Dipeptides and Their Phosphonate Prodrugs, A New Generation of

(56) References Cited

OTHER PUBLICATIONS

Neutral Endopeptidase (NEP, EC 3.4.24.11) Inhibitors," *J. Med. Chem.* 37(4):498-511.
Farquhar, D. et al. (Mar. 1983). "Biologically Reversible Phosphate-Protective Groups," *J. Pharm. Sci.* 72(3):324-325.
Khamnei, S. et al. (Sep. 27, 1996). "Neighboring Group Catalysis in the Design of Nucleotide Prodrugs," *J. Med. Chem.* 39(20):4109-4115.
Kocienski, P.J. (May 1994). "Protecting Groups: An Overview," Chapter 1 in *Protecting Groups*, Thieme Publishing Group: New York, NY, pp. 21-94.
Kocienski, P.J. (May 1994). "Hydroxyl Protecting Groups," Chapter 2 in *Protecting Groups*, Thieme Publishing Group: New York, NY, pp. 21-94.
Kocienski, P.J. (May 1994). "Diol Protecting Groups," Chapter 3 in *Protecting Groups*, Thieme Publishing Group: New York, NY, pp. 95-117.
Kocienski, P.J. (May 1994). "Carboxyl Protecting Groups," Chapter 4 in *Protecting Groups*, Thieme Publishing Group: New York, NY, pp. 118-154.
Kocienski, P.J. (May 1994). "Carbonyl Protecting Groups," Chapter 5 in *Protecting Groups*, Thieme Publishing Group: New York, NY, pp. 155-184.
McGinnity, D.F. et al. (Nov. 2004, e-pub. Jul. 30, 2004). "Evaluation of Fresh and Cryopreserved Hepatocytes as in Vitro Drug Metabolism Tools for the Prediction of Metabolic Clearance," *Drug Metab. Dispos.* 32(11):1247-1253.
Mitchell, A.G. et al. (1992). "Bioreversible Protection for the Phospho Group: Bioactivation of the Di(4-Acyloxybenzyl) and Mono(4-acyloxybenzyl) Phosphoesters of Methylphosphonate and Phosphonoacetate," *J. Chem. Soc. Perkin Trans. II* 2345-2353.
Obach, R.S. et al. (Oct. 1997). "The Prediction of Human Pharmacokinetic Parameters from Preclinical and In Vitro Metabolism Data," *J. Pharmacol. Exp. Ther.* 283(1):46-58.
Puech, F. et al. (Oct. 1993). "Intracellular Delivery of Nucleoside Monophosphates Through a Reductase-Mediated Activation Process," *Antiviral Res.* 22(2-3):155-174.
Spivey, A.C. et al. (1999, e-pub. Dec. 4, 1999). "Configurationally Stable Biaryl Analogues of 4-(Dimethylamino) Pyridine: A Novel Class of Chiral Nucleophilic Catalysts," *J. Org. Chem.* 64(26):9430-9443.
Restriction Requirement mailed on Nov. 8, 2013 for U.S. Appl. No. 13/866,997, filed Apr. 19, 2013, eight pages.
Australian Office Action mailed on Feb. 26, 2014, for Australian Patent Application No. 2011274323, filed on Jul. 1, 2011, three pages.
Bolivian Opposition submitted to the Bolivian Patent Office for Bolivian Patent Application No. SP-0194-2011, filed on Jul. 1, 2011, two pages.
Bolivian Opposition submitted to the Bolivian Patent Office for Bolivian Patent Application No. SP-0195-2011, filed on Jul. 1, 2011, two pages.
Columbian Office Action mailed on Mar. 11, 2014, for Columbian Patent Application No. 12236161 filed on Jul. 1, 2011, 10 pages.
Costa Rican Office Action mailed on Aug. 23, 2013 for Costa Rican Patent Application No. 20130045, filed on Jul. 1, 2011, three pages.
Costa Rican Opposition submitted to the Costa Rican Patent Office for Costa Rican Patent Application No. 20130043, filed on Jul. 1, 2011, three pages.
European Communication mailed on Feb. 8, 2013 for European Patent Application No. 11738878.5 filed on Jul. 1, 2011, two pages.
Pakistani Office Action mailed on Nov. 10, 2012 for Pakistani Patent Application No. 4932011, filed on Jul. 1, 2011, two pages.
Pakistani Office Action mailed on Nov. 10, 2012 for Pakistani Patent Application No. 4942011, filed on Jul. 1, 2011, two pages.
Taiwanese Office Action mailed on Nov. 5, 2013 for Taiwanese Patent Application No. 100123357, filed on Jul. 1, 2011, nine pages.
Al-Mawsawi, L.Q. et al. (Feb. 7, 2011; e-pub. Jan. 12, 2011). "Allosteric inhibitor development targeting HIV-1 integrase," *ChemMedChem.* 6(2):228-241.
Balakrishnan, M. et al. (Sep. 9, 2013). "Non-catalytic site HIV-1 integrase inhibitors disrupt core maturation and induce a reverse transcription block in target cells," *PloS One* 8(9):e74163, 12 Total Pages.
Bartholomeeusen, K. et al. (Apr. 24, 2009; e-pub. Feb. 25, 2009). "Lens epithelium-derived growth factor/p75 interacts with the transposase-derived DDE domain of PogZ," *J. Biol. Chem.* 284(17):11467-11477.
Busschots, K. et al. (Feb. 2, 2007; e-pub. Nov. 3, 2006). "Identification of the LEDGF/p75 binding site in HIV-1 integrase," *J. Mol. Biol.* 365(5):1480-1492.
Busschots, K. et al. (Jan. 2009; e-pub. Oct. 16, 2008). "In search of small molecules blocking interactions between HIV proteins and intracellular cofactors," *Mol. Biosyst.* 5(1):21-31.
Chakraborty, A. et al. (Mar. 1, 2013; e-pub. Dec. 25, 2012). "Biochemical interactions between HIV-1 integrase and reverse transcriptase," *FEBS Letters* 587(5):425-429.
Cherepanov, P. et al. (Jun. 2005; e-pub. May 15, 2005). "Solution structure of the HIV-1 integrase-binding domain in LEDGF/p75," *Nat. Struct. Mol. Biol.* 12(6):526-532.
Cherepanov, P. et al. (Nov. 29, 2005; e-pub. Oct. 31, 2005). "Structural basis for the recognition between HIV-1 integrase and transcriptional coactivator p75," *PNAS* 102(48):17308-17313.
Christ, F. et al. (Aug. 2012; e-pub. Jun. 4, 2012). "Small-molecule inhibitors of the LEDGF/p75 binding site of integrase block HIV replication and modulate integrase multimerization," *Antimicrob. Agents Chemother.* 56(8):4365-4374.
Christ, F. et al. (Jun. 2010; e-pub. May 16, 2010). "Rational design of small-molecule inhibitors of the LEDGF/p75-integrase interaction and HIV replication," *Nat. Chem. Biol.*, 25 Total Pages.
De Luca, L. et al. (Jul. 2011). "Inhibition of the interaction between HIV-1 integrase and its cofactor LEDGF/p75: a promising approach in anti-retroviral therapy," *Mini Rev. Med. Chem.* 11(8):714-727.
Desimmie, B.A. et al. (May 30, 2013). "LEDGINs inhibit late stage HIV-1 replication by modulating integrase multimerization in the virions," *Retrovirology* 10:57, 16 Total Pages.
Engelman, A. et al. (Mar. 28, 2008). "The lentiviral integrase binding protein LEDGF/p75 and HIV-1 replication," *PloS Pathog.* 4(3):e1000046, 9 Total Pages.
Graham, R.L.J. et al. (2011). "Proteomic Analysis of LEDGF/p75 Interactions with Nuclear Proteins," ASMS Poster, 1 page.
Hauser, F.M. et al. (1978). "Singlet Oxygen and Epoxidation from the Dehydration of Hydrogen Peroxide," *J. Org. Chem.* 43(1):180.
Hayouka, Z. et al. (2010). "Cyclic Peptide Inhibitors of HIV-1 Integrase Derived from the LEDGF/p75 Protein," *Bioorganic & Medicinal Chemistry* 18:8388-8395.
Hombrouck, A. et al. (Mar. 2007). "Virus Evolution Reveals an Exclusive Role for LEDGF/p75 in Chromosomal Tethering of HIV," *PloS* 3(3):e47, 13 Total Pages.
Huang, X. et al. (2007). "A Novel Multicomponent Reaction of Arynes, β-Keto Sulfones, and Michael-Type Acceptors: A Direct Synthesis of Polysubstituted Naphthols and Naphthalenes," *J. Org. Chem.* 72:3965-3968.
Johns, B.A. et al. (2013). "Hiv Integrase Inhibitors," Chapter 6 in *Successful Strategies for the Discovery of Antiviral Drugs*, Desai, M.C. et al. eds., RSC Publishing, pp. 149-188.
Jurado, K.A. et al. (May 21, 2013). "Allosteric Integrase Inhibitor Potency is Determined through the Inhibition of HIV-1 Particle Maturation," *PNAS* 110(21):8690-8695.
Kessl, J.J. et al. (2011). "FRET Analysis Reveals Distinct Conformations of IN Tetramers in the Presence of Viral DNA or LEDGF/p75," *Nuc. Acids Res.*, pp. 1-14.
Llano, M. et al. (Sep. 2004). "LEDGF/p75 determines cellular trafficking of diverse lentiviral but not murine oncoretroviral integrase proteins and is a component of functional lentiviral preintegration complexes," *J. Virol.* 78(17):9524-9537.
Llano, M. et al. (Oct. 20, 2006; e-pub. Sep. 7, 2006). "An essential role for LEDGF/p75 in HIV integration," *Science* 314(5798):461-464.

(56) References Cited

OTHER PUBLICATIONS

Poeschla, E.M. et al. (2008). "Integrase, LEDGF/p75 and HIV Replication," *Cell. Mol. Life Sci.* 65:1403-1424.
Rain, J.C. et al. (2009). "Yeast-Two Hybrid Detection of Integrase-Host Factor Interactions," *Methods*, 7 Total Pages.
Rhodes, D.I. et al. (Oct. 17, 2011; e-pub. Aug. 17, 2011). "Crystal structures of novel allosteric peptide inhibitors of HIV integrase identify new interactions at the LEDGF binding site," *Chembiochem.* 12(15):2311-2315.
Shun, M.C. et al. (Jul. 15, 2007). "LEDGF/p75 functions downstream from preintegration complex formation to effect gene-specific HIV-1 integration," *Genes Dev.* 21(14):1767-1778.
Suzuki, Y. et al. (Mar. 2007). "The road to chromatin—nuclear entry of retroviruses," *Nat. Rev. Microbiol.* 5(3):187-196.
Tsiang, M. et al. (Jun. 15, 2012; e-pub. Apr. 25, 2012). "New class of HIV-1 integrase (IN) inhibitors with a dual mode of action," *J. Biol. Chem.* 287(25):21189-21203.
Vandekerckhove, L. et al. (Feb. 2006). "Transient and stable knock-down of the integrase cofactor LEDGF/p75 reveals its role in the replication cycle of human immunodeficiency virus," *J. Virol.* 80(4):1886-1896.
Walker, M.A. (2009). "New approaches for inhibiting HIV integrase: a journey beyond the active site," *Curr. Opin. Investig. Drugs* 10(2):129-136.
Notice of Allowance mailed on Aug. 15, 2014 for U.S. Appl. No. 14/112,473, filed Oct. 17, 2013, seven pages.
Philippine Office Action mailed on Aug. 1, 2014, for Philippine Patent Application No. 12013500011, filed on Jul. 1, 2011, two pages.
Written Opinion of the International Searching Authority mailed on Jul. 17, 2014, for PCT Patent Application No. PCT/US2013/020151 filed on Jan. 3, 2013, six pages.
Written Opinion of the International Searching Authority mailed on Jul. 17, 2014, for PCT Patent Application No. PCT/US2013/020172, filed on Jan. 3, 2013, seven pages.
Vietnamese Office Action mailed on Jul. 28, 2014, for Vietnamese Patent Application No. 1-201300326, filed on Jul. 1, 2011, two pages.
Chen, S. et al. (2009). "Design, Synthesis and Biological Evaluation of Novel Quinolone Derivatives as HIV-1 Tat-TAR Interaction Inhibitors," *Bioorganic & Medicinal Chem.* 17:1948-1956.
Pendri, A. et al. (Aug. 2011, e-pub. May 20, 2011). "New First and Second Generation Inhibitors of Human Immunodeficiency Virus-1 Integrase," *Expert Opin. Ther. Pat.* 21(8):1173-1189.
Willgerodt, C. et al. (1900). "Regarding Quino-α:p-α-Phenyl and Quino-α:p-α Methyl Quinoline-γ-Hydroxy Acid," *Reports of the German Chemical Society* 33(3):2927-2935 (with full English Translation).
Zhan, P. et al. (2009). "Synthesis and Anti-HIV Activity Evaluation of 2-(4-(Naphthalen-2-yl)-1,2,3-thiadiazol-5-ylthio)-N-Acetamides as Novel Non-Nucleosides HIV-1 Reverse Transcriptase Inhibitors," *European Journal of Medicinal Chem.* 44:4648-4653.
Zouhiri, F. et al. (2001). "HIV-1 Replication Inhibitors of the Styrylquinoline Class: Incorporation of a Masked Diketo Acid Pharmacophore," *Tetrahedron Letters* 42:8189-8192.
International Search Report mailed on Feb. 21, 2013, for PCT Patent Application No. PCT/US2013/020172 filed on Jan. 3, 2013, four pages.
International Search Report mailed on Sep. 14, 2011, for PCT Patent Application No. PCT/US2011/042881 filed on Jul. 1, 2011, seven pages.
International Search Report mailed on Mar. 26, 2013, for PCT Patent Application No. PCT/US2013/020151 filed on Jan. 3, 2013, five pages.
International Search Report mailed on Jul. 2, 2012, for PCT Patent Application No. PCT/US2012/034593 filed on Apr. 20, 2012, five pages.
International Search Report mailed on Aug. 5, 2013, for PCT Patent Application No. PCT/US2013/037483 filed on Apr. 19, 2013, three pages.

Written Opinion of the International Searching Authority mailed on Sep. 14, 2011, for PCT Patent Application No. PCT/US2011/042881 filed on Jul. 1, 2011, 12 pages.
Written Opinion of the International Searching Authority mailed on Jul. 2, 2012, for PCT Patent Application No. PCT/US2012/034593 filed on Apr. 20, 2012, six pages.
International Preliminary Report on Patentability mailed on Jan. 17, 2013, for PCT Patent Application No. PCT/US2011/042880 filed on Jul. 1, 2011, 7 pages.
European Communication mailed on Oct. 15, 2013 for European Patent Application No. 11738878.5 filed on Jul. 1, 2011, four pages.
U.S. Appl. No. 14/112,473, filed Oct. 17, 2013, by Mitchell et al.
Australian Office Action mailed on Mar. 7, 2014, for Australian Patent Application No. 2011274322 filed on Jul. 1, 2011, three pages.
Chinese Office Action mailed on Mar. 3, 2014, for Chinese Patent Application No. 201180038442.X filed on Jul. 1, 2011, eight pages.
Eurasian Office Action mailed on Mar. 19, 2014, for Eurasian Patent Application No. 201291300 filed on Jul. 1, 2011, four pages.
European Communication mailed on Mar. 12, 2014 for European Patent Application No. 11738878.5 filed on Jul. 1, 2011, eight pages.
Written Opinion of the International Searching Authority mailed on Aug. 5, 2013, for PCT Patent Application No. PCT/US2013/037483 filed on Apr. 19, 2013, seven pages.
Philippines Office Action mailed on Mar. 14, 2014 for Philippine Patent Application No. 1/2013/500011, filed on Jul. 1, 2011, two pages.
Palella et al., "Declining Morbidity and Mortality Amoung Patients with Advanced Human Immunodeficiency Virus Infection", *N. Engl. J. Med.*, vol. 338, No. 13, 853-860 (1998).
Patent Cooperation Treaty, International Searching Authority, Search Report and Written Opinion for PCT/US2011/042880, 11 pages, Sep. 1, 2011.
Pauwels et al., "Sensitive and rapid assay on MT-4 cells for detection of antiviral compounds against the AIDS virus", *Journal of Virological Methods*, 16, 171-185 (1987).
Porto et al., "Chiral Thiols: The Assignment of Their Absolute Configuration by $^1$H NMR", *Organic Letters*, vol. 9, No. 24, 5015-5018 (2007).
Richman, "HIV chemotherapy", *Nature* 410, 995-1001 (2001).
Sagar et al., "Preparation and anti-HIV activities of retrojusticidin B analogs and azalignans", *Bioorganic & Medicinal Chemistry*, 12, 4045-4054 (2004).
Wang et al., "Pharmacokinetic and Metabolic Studies of Retrojusticidin B, a Potential Anti-Viral Lignan, in Rats", *Planta Med.*, 70, 1161-1165 (2004).
De Luca, L. et al. (Feb. 2011; e-pub. Dec. 21, 2010). "HIV-1 integrase strand-transfer inhibitors: design, synthesis and molecular modeling investigation," *Eur. J. Med. Chem.* 46(2):756-764.
Mekouar, K. et al. (Jul. 16, 1998; e-pub. Jun. 25, 1998). "Styrylquinoline Derivatives: A New Class of Potent HIV-1 Integrase Inhibitors That Block HIV-1 Replication in CEM Cells," *J. Med. Chem.* 41(15):2846-2857.
Wenhua, Z. et al. (2003). "Advances on Effects of Natural Products Against AIDS Virus," *Chinese Traditional Patent Medicine* 25(9):750-752 (with English Translation).
Restriction Requirement mailed on Apr. 24, 2014 for U.S. Appl. No. 14/112,473, filed Oct. 17, 2013, eight pages.
Non-Final Office Action mailed on May 23, 2014 for U.S. Appl. No. 13/866,997, filed Apr. 19, 2013, eight pages.
Chinese Office Action mailed on Mar. 25, 2014 for Chinese Patent Application No. 201180038443.4, filed on Jul. 1, 2011, eight pages.
Costa Rican Opposition filed Apr. 28, 2014 against Costa Rican Patent Application No. 201320102, filed Jul. 1, 2011, sixteen pages.
Eurasian Office Action mailed in Apr. 9, 2014, for Eurasian Patent Application No. 201291301, filed on Jul. 1, 2011, three pages.
Israeli Office Action mailed on Mar. 3, 2014 for Israeli Patent Application No. 223558, filed on Jul. 1, 2011, two pages.

(56) References Cited

OTHER PUBLICATIONS

New Zealand Office Action mailed on Aug. 22, 2013 for New Zealand Patent Application No. 604598, filed on Jul. 1, 2011, two pages.

Ecuadoran Opposition filed Apr. 23, 2014 against Ecuadoran Patent Application No. SP1312418, filed Jul. 1, 2011, ten pages.

Ecuadoran Opposition from June of 2014, against Ecuadoran Patent Application No. SP1312417, filed Jul. 1, 2011, nine pages.

European Communication mailed on Feb. 15, 2013, for European Patent Application No. 11738339.8, filed on Jul. 1, 2011, two pages.

Mexican Office Action mailed on Mar. 13, 2014 for Mexican Patent Application No. MX/a/2012/015293, filed on Jul. 1, 2011, seven pages.

Columbian Office Action mailed on Jun. 12, 2014 for Columbian Patent Application No. 12236158, filed on Jul. 1, 2011, twelve pages.

NAPHTH-2-YLACETIC ACID DERIVATIVES TO TREAT AIDS

CROSS-REFERENCE TO RELATED APPLICATIONS

This application is a U.S. 371 application of PCT/US2011/042880, filed Jul. 1, 2011, and claims the benefit of and priority to U.S. Provisional Application Ser. No. 61/361,314, filed Jul. 2, 2010, each of which is hereby incorporated by reference in the present disclosure in its entirety.

BACKGROUND OF THE INVENTION

Human immunodeficiency virus (HIV) infection and related diseases are a major public health problem worldwide. Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al *N. Engl. J. Med*. (1998) 338:853-860; Richman, D. D. *Nature* (2001) 410:995-1001). Accordingly, there is a need for new agents that inhibit the replication of HIV. There is also a need for agents that are directed against alternate sites in the viral life cycle including agents that target the interaction of Lens Epithelial Derived Growth Factor (LEDGF/p75) and HIV-1 integrase.

SUMMARY OF THE INVENTION

In one embodiment, the invention provides a compound of the invention which is a compound of formula I:

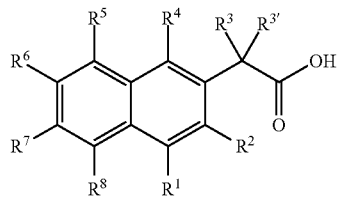

wherein:
$R^1$ is $R^{1a}$ or $R^{1b}$;
$R^2$ is $R^{2a}$ or $R^{2b}$;
$R^3$ is $R^{3a}$ or $R^{3b}$;
$R^{3'}$ is $R^{3a'}$ or $R^{3b'}$;
$R^4$ is $R^{4a}$ or $R^{4b}$;
$R^5$ is $R^{5a}$ or $R^{5b}$;
$R^6$ is $R^{6a}$ or $R^{6b}$;
$R^7$ is $R^{7a}$ or $R^{7b}$;
$R^8$ is $R^{8a}$ or $R^{8b}$;
$R^{1a}$ is selected from:
  a) H, halo, $(C_1-C_6)$alkyl and $(C_1-C_6)$haloalkyl;
  b) $(C_2-C_6)$alkenyl, $(C_2-C_6)$alkynyl, $(C_3-C_7)$cycloalkyl, nitro, cyano, aryl, heterocycle and heteroaryl;
  c) —C(=O)—$R^{11}$, —C(=O)—O—$R^{11}$, —O—$R^{11}$, —S—$R^{11}$, —S(O)—$R^{11}$, —SO$_2$—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-SO$_2$—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl; and d) —N($R^9$)$R^{10}$, —C(=O)—N($R^9$)$R^{10}$, —O—C(=O)—N($R^9$)$R^{10}$, —SO$_2$—N($R^9$)$R^{10}$, —$(C_1-C_6)$alkyl-N($R^9$)$R^{10}$, —$(C_1-C_6)$alkyl-C(=O)—N($R^9$)$R^{10}$, —$(C_1-C_6)$alkyl-O—C(=O)—N($R^9$)$R^{10}$ and —$(C_1-C_6)$alkyl-SO$_2$—N($R^9$)$R^{10}$, wherein each $R^9$ is independently selected from H, $(C_1-C_6)$alkyl and $(C_3-C_7)$cycloalkyl and wherein each $R^{10}$ is independently selected from $R^{11}$, —$(C_1-C_6)$alkyl-$R^{11}$, —SO$_2$—$R^{11}$, —C(=O)—$R^{11}$, —C(=O)O$R^{11}$ and —C(=O)N($R^9$)$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl; and
  wherein any aryl, heterocycle and heteroaryl of $R^{1a}$ is optionally substituted with one or more (e.g. 1, 2 or 3) $Z^{10}$ groups;
$R^{1b}$ is selected from:
  a) —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkyl-S(O)—$(C_1-C_6)$alkyl-$(C_3-C_7)$carbocycle, —$(C_1-C_6)$alkyl-SO$_2$—$(C_1-C_6)$alkyl-$(C_3-C_7)$carbocycle, —$(C_1-C_6)$alkyl-SO$_2$—$(C_1-C_6)$alkyl-$Z^{13}$, —C(O)—$(C_1-C_6)$alkyl-$Z^{13}$, —O—$(C_1-C_6)$alkyl-$Z^{13}$, —S—$(C_1-C_6)$alkyl-$Z^{13}$, —S(O)—$(C_1-C_6)$alkyl-$Z^{13}$, —SO$_2$—$(C_1-C_6)$alkyl-$Z^{13}$, —$(C_1-C_6)$alkyl-$Z^{14}$, —$(C_1-C_6)$alkyl-C(O)—$(C_1-C_6)$alkyl-$Z^{13}$, —$(C_1-C_6)$alkyl-C(O)—O$(C_1-C_6)$alkyl-$Z^{13}$, —$(C_1-C_6)$alkyl-O—$(C_1-C_6)$alkyl-$Z^{13}$, —$(C_1-C_6)$alkyl-S—$(C_1-C_6)$alkyl-$Z^{13}$, —$(C_2-C_6)$alkenyl-$(C_1-C_6)$haloalkyl, —$(C_2-C_6)$alkynyl-$(C_1-C_6)$haloalkyl, —$(C_3-C_7)$halocarbocycle, —NR$_a$SO$_2$NR$_c$R$_d$, —NR$_a$SO$_2$O$(C_3-C_7)$carbocycle, —NR$_a$SO$_2$Oaryl, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl —$(C_2-C_6)$alkynyl-heterocycle, —$(C_3-C_7)$carbocycle-$Z^1$ and -halo$(C_1-C_6)$alkyl-$Z^3$, wherein any $(C_1-C_6)$alkyl, $(C_1-C_6)$haloalkyl, $(C_3-C_7)$carbocycle, $(C_3-C_7)$halocarbocycle, $(C_2-C_6)$alkenyl, $(C_2-C_6)$alkynyl, aryl, heterocycle and heteroaryl, either alone or as part of a group, is optionally substituted with one or more (e.g. 1, 2, 3, 4 or 5) $Z^1$ groups;
  b) spiro-bicyclic carbocycle, fused-bicyclic carbocycle and bridged-bicyclic carbocycle, wherein any spiro-bicyclic carbocycle, fused-bicyclic carbocycle and bridged-bicyclic carbocycle is optionally substituted with one or more (e.g. 1, 2, 3, 4 or 5) $Z^1$ groups, wherein two $Z^1$ groups together with the atom or atoms to which they are attached optionally form a $(C_3-C_7)$carbocycle or heterocycle wherein the $(C_3-C_7)$carbocycle or heterocycle is optionally substituted with one or more (e.g. 1, 2, 3, 4 or 5) $Z^1$ groups;
  c) $(C_1-C_6)$alkyl, wherein $(C_1-C_6)$alkyl is substituted with one or more (e.g. 1, 2, 3, 4 or 5) $Z^2$ groups and optionally substituted with one or more (e.g. 1, 2, 3, 4 or 5) $Z^1$ groups;
  d) —X$(C_1-C_6)$alkyl, —X$(C_1-C_6)$haloalkyl, —X$(C_2-C_6)$alkenyl, —X$(C_2-C_6)$alkynyl and —X$(C_3-C_7)$carbocycle, wherein any —X$(C_1-C_6)$alkyl and —X$(C_1-C_6)$haloalkyl, is substituted with one or more (e.g. 1, 2, 3, 4 or 5) $Z^3$ groups and optionally substituted with one or more (e.g. 1, 2, 3, 4 or 5) $Z^1$ groups, and wherein any —X$(C_2-C_6)$alkenyl, —X$(C_2-C_6)$alkynyl and —X$(C_3-C_7)$carbocycle, is substituted with one or more (e.g. 1, 2, 3, 4 or 5) $Z^4$ groups and optionally substituted with one or more (e.g. 1, 2, 3, 4 or 5) $Z^1$ groups;
  e) aryl, heteroaryl, heterocycle, —Xaryl, —Xheteroaryl and —Xheterocycle, wherein any aryl, heteroaryl and heterocycle, either alone or as part of a group, is substituted with one or more (e.g. 1, 2, 3, 4 or 5) $Z^5$ groups and optionally substituted with one or more (e.g. 1, 2, 3, 4 or 5) $Z^1$ groups;
  f) $(C_1-C_6)$haloalkyl, $(C_3-C_7)$carbocycle, $(C_2-C_6)$alkenyl, and $(C_2-C_6)$alkynyl, wherein $(C_1-C_6)$haloalkyl, $(C_3-C_7)$carbocycle, ($C_2$-$C_6$)alkenyl and ($C_2$-$C_6$)alkynyl are each substituted with one or more (e.g. 1, 2, 3, 4 or 5) $Z^6$ groups and optionally substituted with one or more (e.g. 1, 2, 3, 4 or 5) $Z^1$ groups; and g) —$NR_eR_f$, —$C(O)NR_eR_f$, —$OC(O)NR_eR_f$, —$SO_2NR_eR_f$, —($C_1$-$C_6$)alkyl-$NR_eR_f$, —($C_1$-$C_6$)alkylC(O)—$NR_eR_f$, —($C_1$-$C_6$)alkyl-O—C(O)—$NR_eR_f$ and —($C_1$-$C_6$)alkyl-$SO_2NR_eR_f$, wherein any ($C_1$-$C_6$)alkyl, as part of a group is optionally substituted with one or more (e.g. 1, 2, 3, 4 or 5) $Z^1$ groups;

$R^{2a}$ is selected from:
a) H, ($C_1$-$C_6$)alkyl and —O($C_1$-$C_6$)alkyl;
b) ($C_2$-$C_6$)alkenyl, ($C_2$-$C_6$)alkynyl, ($C_1$-$C_6$)haloalkyl, ($C_3$-$C_7$)cycloalkyl, aryl, heterocycle, heteroaryl, halo, nitro and cyano;
c) —C(=O)—$R^{11}$, —C(=O)—O—$R^{11}$, —S—$R^{11}$, —S(O)—$R^{11}$, —$SO_2$—$R^{11}$, —($C_1$-$C_6$)alkyl-$R^{11}$, —($C_1$-$C_6$)alkyl-C(=O)—$R^{11}$, —($C_1$-$C_6$)alkyl-C(=O)—O—$R^{11}$, —($C_1$-$C_6$)alkyl-O—$R^{11}$, —($C_1$-$C_6$)alkyl-S—$R^{11}$, —($C_1$-$C_6$)alkyl-S(O)—$R^{11}$ and —($C_1$-$C_6$)alkyl-$SO_2$—$R^{11}$, wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl, wherein aryl, heterocycle and heteroaryl are each optionally substituted with one or more (e.g. 1, 2 or 3) $Z^{11}$ groups;
d) —OH, —O($C_2$-$C_6$)alkenyl, —O($C_2$-$C_6$)alkynyl, —O($C_1$-$C_6$)haloalkyl, —O($C_3$-$C_7$)cycloalkyl, —Oaryl, —Oheterocycle and —Oheteroaryl; and
e) —N($R^9$)$R^{10}$, —C(=O)—N($R^9$)$R^{10}$, —O—C(=O)—N($R^9$)$R^{10}$, —$SO_2$—N($R^9$)$R^{10}$, —($C_1$-$C_6$)alkyl-N($R^9$)$R^{10}$, —($C_1$-$C_6$)alkyl-C(=O)—N($R^9$)$R^{10}$, —($C_1$-$C_6$)alkyl-O—C(=O)—N($R^9$)$R^{10}$, and —($C_1$-$C_6$)alkyl-$SO_2$—N($R^9$)$R^{10}$, wherein each $R^9$ is independently selected from H, ($C_1$-$C_6$)alkyl and ($C_3$-$C_7$)cycloalkyl, and each $R^{10}$ is independently selected from $R^{11}$, —($C_1$-$C_6$)alkyl-$R^{11}$, —$SO_2$—$R^{11}$, —C(=O)—$R^{11}$, —C(=O)$OR^{11}$ and —C(=O)N($R^9$)$R^{10}$, wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl;

$R^{2b}$ is selected from:
a) —($C_1$-$C_6$)alkyl-O—($C_1$-$C_6$)alkyl-($C_3$-$C_7$)carbocycle, —($C_1$-$C_6$)alkyl-S—($C_1$-$C_6$)alkyl-($C_3$-$C_7$)carbocycle, —($C_1$-$C_6$)alkyl-S(O)—($C_1$-$C_6$)alkyl-($C_3$-$C_7$)carbocycle, —($C_1$-$C_6$)alkyl-$SO_2$—($C_1$-$C_6$)alkyl-($C_3$-$C_7$)carbocycle, —($C_2$-$C_6$)alkenyl-($C_1$-$C_6$)haloalkyl, —($C_2$-$C_6$)alkynyl-($C_1$-$C_6$)haloalkyl, —($C_1$-$C_6$)alkyl-$SO_2$—($C_1$-$C_6$)alkyl-$Z^{13}$, —C(O)—($C_1$-$C_6$)alkyl-$Z^{13}$, —O—($C_1$-$C_6$)alkyl-$Z^{13}$, —S—($C_1$-$C_6$)alkyl-$Z^{13}$, —S(O)—($C_1$-$C_6$)alkyl-$Z^{13}$, —$SO_2$—($C_1$-$C_6$)alkyl-$Z^{13}$, —($C_1$-$C_6$)alkyl-$Z^{14}$, —($C_1$-$C_6$)alkyl-C(O)—($C_1$-$C_6$)alkyl-$Z^{13}$, —($C_1$-$C_6$)alkyl-C(O)—O($C_1$-$C_6$)alkyl-$Z^{13}$, —($C_1$-$C_6$)alkyl-O—($C_1$-$C_6$)alkyl-$Z^{13}$, —($C_1$-$C_6$)alkyl-S—($C_1$-$C_6$)alkyl-$Z^{13}$, —($C_3$-$C_7$)halocarbocycle, —$NR_aSO_2NR_cR_d$, —$NR_aSO_2O(C_3$-$C_7$)carbocycle, —$NR_aSO_2$Oaryl, —($C_2$-$C_6$)alkenyl-($C_3$-$C_7$)carbocycle, —($C_2$-$C_6$)alkenyl-aryl, —($C_2$-$C_6$)alkenyl-heteroaryl, —($C_2$-$C_6$)alkenyl-heterocycle, —($C_2$-$C_6$)alkynyl-($C_3$-$C_7$)carbocycle, —($C_2$-$C_6$)alkynyl-aryl, —($C_2$-$C_6$)alkynyl-heteroaryl, —($C_2$-$C_6$)alkynyl-heterocycle, —($C_3$-$C_7$)carbocycle-$Z^1$ and -halo($C_1$-$C_6$)alkyl-$Z^3$, wherein any ($C_1$-$C_6$)alkyl, —($C_1$-$C_6$)haloalkyl, ($C_3$-$C_7$)carbocycle, ($C_3$-$C_7$)halocarbocycle, ($C_2$-$C_6$)alkenyl, ($C_2$-$C_6$)alkynyl, aryl, heterocycle and heteroaryl, either alone or as part of a group, is optionally substituted with one or more (e.g. 1, 2, 3, 4 or 5) $Z^1$ groups;
b) spiro-bicyclic carbocycle, fused-bicyclic carbocycle and bridged-bicyclic carbocycle, wherein any spiro-bicyclic carbocycle, fused-bicyclic carbocycle and bridged-bicyclic carbocycle is optionally substituted with one or more (e.g. 1, 2, 3, 4 or 5) $Z^1$ groups, wherein two $Z^1$ groups together with the atom or atoms to which they are attached optionally form a ($C_3$-$C_7$)carbocycle or heterocycle, wherein the ($C_3$-$C_7$)carbocycle or heterocycle is optionally substituted with one or more (e.g. 1, 2, 3, 4 or 5) $Z^1$ groups;
c) ($C_1$-$C_6$)alkyl, wherein ($C_1$-$C_6$)alkyl is substituted with one or more (e.g. 1, 2, 3, 4 or 5) $Z^2$ groups and optionally substituted with one or more (e.g. 1, 2, 3, 4 or 5) $Z^1$ groups;
d) —X($C_1$-$C_6$)alkyl, X($C_1$-$C_6$)haloalkyl, X($C_2$-$C_6$)alkenyl, —X($C_2$-$C_6$)alkynyl and —X($C_3$-$C_7$)carbocycle, wherein any —X($C_1$-$C_6$)alkyl and —X($C_1$-$C_6$)haloalkyl, is substituted with one or more (e.g. 1, 2, 3, 4 or 5) $Z^3$ groups and optionally substituted with one or more (e.g. 1, 2, 3, 4 or 5) $Z^1$ groups, and wherein any —X($C_2$-$C_6$)alkenyl, —X($C_2$-$C_6$)alkynyl and —X($C_3$-$C_7$)carbocycle is substituted with one or more (e.g. 1, 2, 3, 4 or 5) $Z^4$ groups and optionally substituted with one or more (e.g. 1, 2, 3, 4 or 5) $Z^1$ groups;
e) aryl, heteroaryl, heterocycle, —Xaryl, —Xheteroaryl and —Xheterocycle, wherein any aryl, heteroaryl and heterocycle, either alone or as part of a group, is substituted with one or more (e.g. 1, 2, 3, 4 or 5) $Z^5$ groups and optionally substituted with one or more (e.g. 1, 2, 3, 4 or 5) $Z^1$ groups;
f) ($C_1$-$C_6$)haloalkyl, ($C_3$-$C_7$)carbocycle, ($C_2$-$C_6$)alkenyl, and ($C_2$-$C_6$)alkynyl, wherein ($C_1$-$C_6$)haloalkyl, ($C_3$-$C_7$)carbocycle, ($C_2$-$C_6$)alkenyl and ($C_2$-$C_6$)alkynyl are each substituted with one or more (e.g. 1, 2, 3, 4 or 5) $Z^6$ groups and optionally substituted with one or more (e.g. 1, 2, 3, 4 or 5) $Z^1$ groups; and
g) —$NR_eR_f$, —$C(O)NR_eR_f$, —$OC(O)NR_eR_f$, —$SO_2NR_eR_f$, —($C_1$-$C_6$)alkyl-$NR_eR_f$, —($C_1$-$C_6$)alkylC(O)—$NR_eR_f$, —($C_1$-$C_6$)alkyl-O—C(O)—$NR_eR_f$ and —($C_1$-$C_6$)alkyl-$SO_2NR_eR_f$ wherein any ($C_1$-$C_6$)alkyl, as part of a group is optionally substituted with one or more (e.g. 1, 2, 3, 4 or 5) $Z^1$ groups;

$R^{3a}$ is ($C_1$-$C_6$)alkyl, ($C_1$-$C_6$)haloalkyl, ($C_2$-$C_6$)alkenyl, ($C_2$-$C_6$)alkynyl, —($C_1$-$C_6$)alkyl-($C_3$-$C_7$)cycloalkyl, —($C_1$-$C_6$)alkyl-aryl, —($C_1$-$C_6$)alkyl-heterocycle, —($C_1$-$C_6$)alkyl-heteroaryl, —O($C_1$-$C_6$)alkyl, —O($C_1$-$C_6$)haloalkyl, —O($C_2$-$C_6$)alkenyl, —O($C_2$-$C_6$)alkynyl, —O($C_3$-$C_7$)cycloalkyl, —Oaryl, —O($C_1$-$C_6$)alkyl-($C_3$-$C_7$)cycloalkyl, —O($C_1$-$C_6$)alkyl-aryl, —O($C_1$-$C_6$)alkyl-heterocycle or —O($C_1$-$C_6$)alkyl-heteroaryl, wherein any ($C_1$-$C_6$)alkyl, ($C_1$-$C_6$)haloalkyl, ($C_2$-$C_6$)alkenyl or ($C_2$-$C_6$)alkynyl of $R^{3a}$ either alone or as part of a group, is optionally substituted with one or more (e.g. 1, 2 or 3) groups selected from —O($C_1$-$C_6$)alkyl, halo, oxo and —CN, and wherein any ($C_3$-$C_7$)cycloalkyl, aryl, heterocycle or heteroaryl of $R^{3a}$ either alone or as part of a group, is optionally substituted with one or more (e.g. 1, 2 or 3) groups selected from ($C_1$-$C_6$)alkyl, —O($C_1$-$C_6$)alkyl, halo, oxo and —CN; and $R^{3a'}$ is H;

$R^{3b}$ is —($C_7$-$C_{14}$)alkyl, —($C_3$-$C_7$)carbocycle, aryl, heteroaryl, heterocycle, —($C_1$-$C_6$)alkylOH, —($C_1$-$C_6$)alkyl-O—($C_1$-$C_6$)alkyl-$Z^{12}$, —($C_1$-$C_6$)alkyl-O—($C_2$-$C_6$)alkenyl-$Z^{12}$, —($C_1$-$C_6$)alkyl-O—($C_2$-$C_6$)alkynyl-$Z^{12}$, —($C_1$-$C_6$)alkyl-S—($C_1$-$C_6$)alkyl-$Z^{12}$, —($C_1$-$C_6$)alkyl-S—($C_2$-$C_6$)alkenyl-$Z^{12}$, —($C_1$-$C_6$)alkyl-S—($C_2$-$C_6$)alkynyl-$Z^{12}$, —($C_1$-$C_6$)alkyl-S(O)—($C_1$-$C_6$)alkyl-$Z^{12}$, —($C_1$-$C_6$)alkyl-S(O)—($C_2$-$C_6$)alkenyl-$Z^{12}$, —($C_1$-$C_6$)alkyl-S(O)—($C_2$-$C_6$)alkynyl-$Z^{12}$, —($C_1$-$C_6$)alkyl-$SO_2$—($C_1$-$C_6$)alkyl-$Z^{12}$, —($C_1$-$C_6$)alkyl-$SO_2$—($C_2$-$C_6$)alkenyl-$Z^{12}$, —($C_1$-$C_6$)alkyl-$SO_2$—($C_2$-$C_6$)alkynyl-$Z^{12}$, —($C_1$-$C_6$)alkyl-$NR_aR_b$, —($C_1$-$C_6$)alkylOC(O)—$NR_cR_d$, —($C_1$-$C_6$)alkyl-$NR_a$—C(O)—$OR_b$, —($C_1$-$C_6$)alkyl-$NR_a$—C(O)—$NR_aR_b$, —($C_1$-$C_6$)alkyl-$SO_2(C_1$-$C_6$) alkyl, —($C_1$-$C_6$)alkyl-$SO_2NR_cR_d$, —($C_1$-$C_6$)alkyl-$NR_aSO_2NR_cR_d$, —($C_1$-$C_6$)alkyl-$NR_aSO_2O(C_3$-$C_7$)carbocycle, —($C_1$-$C_6$)alkyl-$NR_aSO_2$Oaryl, —($C_1$-$C_6$)alkyl- NR$_a$—SO$_2$—(C$_1$-C$_6$)alkyl, —(C$_1$-C$_6$)alkyl-NR$_a$—SO$_2$-halo(C$_1$-C$_6$)alkyl, —(C$_1$-C$_6$)alkyl-NR$_a$—SO$_2$—(C$_2$-C$_6$)alkenyl, —(C$_1$-C$_6$)alkyl-NR$_a$—SO$_2$—(C$_2$-C$_6$)alkynyl, —(C$_1$-C$_6$)alkyl-NR$_a$—SO$_2$—(C$_3$-C$_7$)carbocycle, —(C$_1$-C$_6$)alkyl-NR$_a$—SO$_2$-halo(C$_3$-C$_7$)carbocycle, —(C$_1$-C$_6$)alkyl-NR$_a$—SO$_2$-aryl, —(C$_1$-C$_6$)alkyl-NR$_a$—SO$_2$-heteroaryl, —(C$_1$-C$_6$)alkyl-NR$_a$—SO$_2$-heterocycle, —O(C$_7$-C$_{14}$)alkyl, —O(C$_1$-C$_6$)alkyl-NR$_a$R$_b$, —O(C$_1$-C$_6$)alkylOC(O)—NR$_c$R$_d$, —O(C$_1$-C$_6$)alkyl-NR$_a$—C(O)—OR$_b$, —O(C$_1$-C$_6$)alkyl-NR$_a$—C(O)—NR$_a$R$_b$, —O(C$_1$-C$_6$)alkyl-NR$_a$—SO$_2$—(C$_1$-C$_6$)alkyl, —O(C$_1$-C$_6$)alkyl-NR$_a$—SO$_2$-halo(C$_1$-C$_6$)alkyl, —O(C$_1$-C$_6$)alkyl-NR$_a$—SO$_2$—(C$_2$-C$_6$)alkenyl, —O(C$_1$-C$_6$)alkyl-NR$_a$—SO$_2$—(C$_2$-C$_6$)alkynyl, —O(C$_1$-C$_6$)alkyl-NR$_a$—SO$_2$—(C$_3$-C$_7$)carbocycle, —O(C$_1$-C$_6$)alkyl-NR$_a$—SO$_2$-halo(C$_3$-C$_7$)carbocycle, —O(C$_1$-C$_6$)alkyl-NR$_a$—SO$_2$-aryl, —O(C$_1$-C$_6$)alkyl-NR$_a$—SO$_2$-heteroaryl, —O(C$_1$-C$_6$)alkyl-NR$_a$—SO$_2$-heterocycle, —O(C$_1$-C$_6$)alkyl-NR$_a$—SO$_2$—NR$_a$R$_b$, —O(C$_1$-C$_6$)alkyl-NR$_a$—SO$_2$—(C$_3$-C$_7$)carbocycle, —O(C$_1$-C$_6$)alkyl-NR$_a$—SO$_2$-halo(C$_3$-C$_7$)carbocycle, —O(C$_1$-C$_6$)alkyl-NR$_a$—SO$_2$-aryl, —O(C$_1$-C$_6$)alkyl-NR$_a$SO$_2$NR$_c$R$_d$, —O(C$_1$-C$_6$)alkyl-NR$_a$SO$_2$O(C$_3$-C$_7$)carbocycle, —O(C$_1$-C$_6$)alkyl-NR$_a$SO$_2$Oaryl, —Oheteroaryl, —Oheterocycle, —Sheteroaryl, —Sheterocycle, —S(O)heteroaryl, —S(O)heterocycle, —SO$_2$heteroaryl or —SO$_2$heterocycle, wherein any (C$_1$-C$_6$)alkyl, —(C$_7$-C$_{14}$)alkyl, aryl, (C$_3$-C$_7$)carbocycle, heteroaryl or heterocycle of R$^{3b}$, either alone or as part of a group, is optionally substituted with one or more (e.g. 1, 2, 3, 4 or 5) Z$^1$ groups, and R$^{3b'}$ is H, (C$_1$-C$_6$)alkyl or —O(C$_1$-C$_6$)alkyl; or R$^{3b}$ and R$^{3b'}$ together with the carbon to which they are attached form a heterocycle or (C$_3$-C$_7$)carbocycle which heterocycle or (C$_3$-C$_7$)carbocycle of R$^{3b}$ and R$^{3b'}$ together with the carbon to which they are attached is optionally substituted with one or more (e.g. 1, 2, 3, 4 or 5) Z$^1$ groups;

R$^{4a}$ is selected from aryl, heterocycle and heteroaryl, wherein any aryl, heterocycle and heteroaryl of R$^{4a}$ is optionally substituted with one or more (e.g. 1, 2, 3, 4 or 5) groups each independently selected from halo, (C$_1$-C$_6$)alkyl, (C$_2$-C$_6$)alkenyl, (C$_1$-C$_6$)haloalkyl, (C$_3$-C$_7$)cycloalkyl, —OH, —O(C$_1$-C$_6$)alkyl, —SH, —S(C$_1$-C$_6$)alkyl, —NH$_2$, —NH(C$_1$-C$_6$)alkyl and —N((C$_1$-C$_6$)alkyl)$_2$, wherein (C$_1$-C$_6$)alkyl is optionally substituted with hydroxy, —O(C$_1$-C$_6$)alkyl, cyano or oxo;

R$^{4b}$ is selected from;

a) (C$_1$-C$_6$)alkyl, (C$_2$-C$_6$)alkenyl and (C$_2$-C$_6$)alkynyl, wherein (C$_1$-C$_6$)alkyl, (C$_2$-C$_6$)alkenyl and (C$_2$-C$_6$)alkynyl are each optionally substituted with one or more (e.g. 1, 2, 3, 4 or 5) Z$^1$ groups;

b) (C$_3$-C$_{14}$)carbocycle, wherein (C$_3$-C$_{14}$)carbocycle is optionally substituted with one or more (e.g. 1, 2, 3, 4 or 5) Z$^1$ groups, wherein two Z$^1$ groups together with the atom or atoms to which they are attached optionally form a (C$_3$-C$_7$)carbocycle or heterocycle;

c) spiro-heterocycle and bridged-heterocycle, wherein spiro-heterocycle and bridged-heterocycle are optionally substituted with one or more (e.g. 1, 2, 3, 4 or 5) Z$^1$ groups, or wherein two Z$^1$ groups together with the atom or atoms to which they are attached optionally form a (C$_3$-C$_7$)carbocycle or heterocycle; and d) aryl, heteroaryl, spiro-heterocycle, fused-heterocycle and bridged-heterocycle, wherein aryl, heteroaryl, spiro-heterocycle, fused-heterocycle and bridged-heterocycle heterocycle are each independently substituted with one or more (e.g. 1, 2, 3, 4 or 5) Z$^7$ groups and optionally substituted with one or more (e.g. 1, 2, 3, 4 or 5) Z$^1$ groups; or R$^4$ and R$^3$ together with the atoms to which they are attached form a macroheterocycle or a macrocarbocycle wherein any macroheterocycle or macrocarbocycle of R$^4$ and R$^3$ together with the atoms to which they are attached may be optionally substituted with one or more (e.g. 1, 2, 3, 4 or 5) Z$^1$ groups; and R$^{3'}$ is H, (C$_1$-C$_6$)alkyl or —O(C$_1$-C$_6$)alkyl;

R$^{5a}$ is selected from:

a) halo, nitro and cyano;

b) R$^{11}$, —C(═O)—R$^{11}$, —C(═O)—O—R$^{11}$, —O—R$^{11}$, —S—R$^{11}$, —S(O)—R$^{11}$, —SO$_2$—R$^{11}$, —(C$_1$-C$_6$)alkyl-R$^{11}$, —(C$_1$-C$_6$)alkyl-C(═O)—R$^{11}$, —(C$_1$-C$_6$)alkyl-C(═O)—O—R$^{11}$, —(C$_1$-C$_6$)alkyl-O—R$^{11}$, —(C$_1$-C$_6$)alkyl-S—R$^{11}$, —(C$_1$-C$_6$)alkyl-S(O)—R$^{11}$ and —(C$_1$-C$_6$)alkyl-SO$_2$—R$^{11}$, wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl, wherein aryl, heterocycle and heteroaryl are each optionally substituted with one or more (e.g. 1, 2 or 3) Z$^{11}$ groups; and c) —N(R$^9$)R$^{10}$, —C(═O)—N(R$^9$)R$^{10}$, —O—C(═O)—N(R$^9$)R$^{10}$, —SO$_2$—N(R$^9$)R$^{10}$, —(C$_1$-C$_6$)alkyl-N(R$^9$)R$^{10}$, —(C$_1$-C$_6$)alkyl-C(═O)—N(R$^9$)R$^{10}$, —(C$_1$-C$_6$)alkyl-O—C(═O)—N(R$^9$)R$^{10}$, and —(C$_1$-C$_6$)alkyl-SO$_2$—N(R$^9$)R$^{10}$, wherein each R$^9$ is independently selected from H, (C$_1$-C$_6$)alkyl and (C$_3$-C$_7$)cycloalkyl, and each R$^{10}$ is independently selected from R$^{11}$, —(C$_1$-C$_6$)alkyl-R$^{11}$, —SO$_2$—R$^{11}$, —C(═O)—R$^{11}$, —C(═O)OR$^{11}$ and —C(═O)N(R$^9$)R$^{10}$, wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl;

R$^{5b}$ is selected from:

a) —(C$_1$-C$_6$)alkyl-O—(C$_1$-C$_6$)alkyl-(C$_3$-C$_7$)carbocycle, —(C$_1$-C$_6$)alkyl-S—(C$_1$-C$_6$)alkyl-(C$_3$-C$_7$)carbocycle, —(C$_1$-C$_6$)alkylS(O)—(C$_1$-C$_6$)alkyl-(C$_3$-C$_7$)carbocycle, —(C$_1$-C$_6$)alkylSO$_2$(C$_1$-C$_6$)alkyl-(C$_3$-C$_7$)carbocycle, —(C$_2$-C$_6$)alkenyl-(C$_1$-C$_6$)haloalkyl, —(C$_2$-C$_6$)alkynyl-(C$_1$-C$_6$)haloalkyl, —(C$_3$-C$_7$)halocarbocycle, —NR$_a$SO$_2$NR$_c$R$_d$, —NR$_a$SO$_2$O(C$_3$-C$_7$)carbocycle, —NR$_a$SO$_2$Oaryl, —(C$_2$-C$_6$)alkenyl-(C$_3$-C$_7$)carbocycle, —(C$_2$-C$_6$)alkenyl-aryl, —(C$_2$-C$_6$)alkenyl-heteroaryl, —(C$_2$-C$_6$)alkenyl-heterocycle, —(C$_2$-C$_6$)alkynyl-(C$_3$-C$_7$)carbocycle, —(C$_2$-C$_6$)alkynyl-aryl, —(C$_2$-C$_6$)alkynyl-heteroaryl, —(C$_2$-C$_6$)alkynyl-heterocycle, —(C$_3$-C$_7$)carbocycle-Z$^1$ and -halo(C$_1$-C$_6$)alkyl-Z$^3$, wherein any (C$_1$-C$_6$)alkyl, (C$_1$-C$_6$)haloalkyl, (C$_3$-C$_7$)carbocycle, (C$_3$-C$_7$)halocarbocycle, (C$_2$-C$_6$)alkenyl, (C$_2$-C$_6$)alkynyl, aryl, heterocycle and heteroaryl, either alone or as part of a group, is optionally substituted with one or more (e.g. 1, 2, 3, 4 or 5) Z$^1$ groups;

b) spiro-bicyclic carbocycle, fused-bicyclic carbocycle and bridged-bicyclic carbocycle, wherein any spiro-bicyclic carbocycle, fused-bicyclic carbocycle or bridged-bicyclic carbocycle is optionally substituted with one or more (e.g. 1, 2, 3, 4 or 5) Z$^1$ groups, wherein two Z$^1$ groups together with the atom or atoms to which they are attached optionally form a (C$_3$-C$_7$)carbocycle or heterocycle wherein the (C$_3$-C$_7$)carbocycle or heterocycle is optionally substituted with one or more (e.g. 1, 2, 3, 4 or 5) Z$^1$ groups;

c) (C$_1$-C$_6$)alkyl, wherein (C$_1$-C$_6$)alkyl is substituted with one or more (e.g. 1, 2, 3, 4 or 5) Z$^2$ groups and optionally substituted with one or more (e.g. 1, 2, 3, 4 or 5) Z$^1$ groups;

d) —X(C$_1$-C$_6$)alkyl, —X(C$_1$-C$_6$)haloalkyl, —X(C$_2$-C$_6$)alkenyl, —X(C$_2$-C$_6$)alkynyl and —X(C$_3$-C$_7$)carbocycle, wherein any —X(C$_1$-C$_6$)alkyl and —X(C$_1$-C$_6$)haloalkyl, is substituted with one or more Z$^3$ groups and optionally substituted with one or more Z$^1$ groups, and wherein any —X(C$_2$-C$_6$)alkenyl, —X(C$_2$-C$_6$)alkynyl and —X(C$_3$-C$_7$)carbocycle is substituted with one or more (e.g. 1, 2, 3, 4 or 5) Z$^4$ groups and optionally substituted with one or more (e.g. 1, 2, 3, 4 or 5) Z$^1$ groups;

e) aryl, heteroaryl, heterocycle, —Xaryl, —Xheteroaryl and —Xheterocycle, wherein any aryl, heteroaryl and heterocycle, either alone or as part of a group, is substituted with one or more (e.g. 1, 2, 3, 4 or 5) $Z^5$ groups and optionally substituted with one or more (e.g. 1, 2, 3, 4 or 5) $Z^1$ groups;

f) $(C_1-C_6)$haloalkyl, $(C_3-C_7)$carbocycle, $(C_2-C_6)$alkenyl, and $(C_2-C_6)$alkynyl, where $(C_1-C_6)$haloalkyl, $(C_3-C_7)$carbocycle, $(C_2-C_6)$alkenyl and $(C_2-C_6)$alkynyl are each independently substituted with one or more (e.g. 1, 2, 3, 4 or 5) $Z^6$ groups and optionally substituted with one or more (e.g. 1, 2, 3, 4 or 5) $Z^1$ groups; and g) —$NR_eR_f$, —$C(O)NR_eR_f$, —$OC(O)NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—C(O)—$NR_eR_f$ and —$(C_1-C_6)$alkyl-$SO_2NR_eR_f$, wherein any $(C_1-C_6)$alkyl, as part of a group, is optionally substituted with one or more (e.g. 1, 2, 3, 4 or 5) $Z^1$ groups;

$R^{6a}$ is selected from:
a) H, halo, $(C_1-C_6)$alkyl and $(C_1-C_6)$haloalkyl
b) $(C_2-C_6)$alkenyl, $(C_2-C_6)$alkynyl, $(C_3-C_7)$cycloalkyl, nitro, cyano, aryl, heterocycle and heteroaryl;
c) —$C(=O)$—$R^{11}$, —$C(=O)$—O—$R^{11}$, —O—$R^{11}$, —S—$R^{11}$, —$S(O)$—$R^{11}$, —$SO_2$—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-$SO_2$—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl; and
d) —$N(R^9)R^{10}$, —$C(=O)$—$N(R^9)R^{10}$, —O—$C(=O)$—$N(R^9)R^{10}$, —$SO_2$—$N(R^9)R^{10}$, —$(C_1-C_6)$alkyl-$N(R^9)R^{10}$, —$(C_1-C_6)$alkyl-C(=O)—$N(R^9)R^{10}$, —$(C_1-C_6)$alkyl-O—C(=O)—$N(R^9)R^{10}$ and —$(C_1-C_6)$alkyl-$SO_2$—$N(R^9)R^{10}$, wherein each $R^9$ is independently selected from H, $(C_1-C_6)$alkyl and $(C_3-C_7)$cycloalkyl, and each $R^{10}$ is independently selected from $R^{11}$, —$(C_1-C_6)$alkyl-$R^{11}$, —$SO_2$—$R^{11}$, —$C(=O)$—$R^{11}$, —$C(=O)OR^{11}$ and —$C(=O)N(R^9)R^{10}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl;

and wherein any aryl, heterocycle and heteroaryl of $R^{6a}$ is optionally substituted with one or more (e.g. 1, 2 or 3) $Z^{10}$ groups;

$R^{6b}$ is selected from:
a) —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkyl-S(O)—$(C_1-C_6)$alkyl-$(C_3-C_7)$carbocycle, —$(C_1-C_6)$alkyl-$SO_2$—$(C_1-C_6)$alkyl-$(C_3-C_7)$carbocycle, —$(C_2-C_6)$alkenyl-$(C_1-C_6)$haloalkyl, —$(C_2-C_6)$alkynyl-$(C_1-C_6)$haloalkyl, -halo$(C_3-C_7)$carbocycle, —$NR_aSO_2NR_eR_d$, —$NR_aSO_2O(C_3-C_7)$carbocycle, —$NR_aSO_2Oaryl$, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_2-C_8)$alkynyl-$OR_a$, —$(C_2-C_6)$alkyl-$(C_3-C_7)$carbocycle-$OR_a$, —$(C_3-C_7)$carbocycle-$Z^1$ and -halo$(C_1-C_6)$alkyl-$Z^3$, wherein any $(C_1-C_6)$alkyl, $(C_1-C_6)$haloalkyl, $(C_3-C_7)$carbocycle, $(C_2-C_6)$alkenyl, $(C_2-C_6)$alkynyl, aryl, heterocycle and heteroaryl, either alone or as part of a group, is optionally substituted with one or more (e.g. 1, 2, 3, 4 or 5) $Z^1$ groups;
b) spiro-bicyclic carbocycle, fused-bicyclic carbocycle and bridged-bicyclic carbocycle, wherein any spiro-bicyclic carbocycle, fused-bicyclic carbocycle and bridged-bicyclic carbocycle is optionally substituted with one or more (e.g. 1, 2, 3, 4 or 5) $Z^1$ groups, wherein two $Z^1$ groups together with the atom or atoms to which they are attached optionally form a $(C_3-C_7)$cycloalkyl or heterocycle, wherein the $(C_3-C_7)$cycloalkyl or heterocycle is optionally substituted with one or more (e.g. 1, 2, 3, 4 or 5) $Z^1$ groups;

c) $(C_1-C_6)$alkyl, wherein $(C_1-C_6)$alkyl is substituted with one or more (e.g. 1, 2, 3, 4 or 5) $Z^2$ groups and optionally substituted with one or more (e.g. 1, 2, 3, 4 or 5) $Z^1$ groups;

d) —$X(C_1-C_6)$alkyl, —$X(C_1-C_6)$haloalkyl, —$X(C_2-C_6)$alkenyl, —$X(C_2-C_6)$alkynyl and —$X(C_3-C_7)$carbocycle, wherein any —$X(C_1-C_6)$alkyl and —$X(C_1-C_6)$haloalkyl, is substituted with one or more (e.g. 1, 2, 3, 4 or 5) $Z^3$ groups and optionally substituted with one or more (e.g. 1, 2, 3, 4 or 5) $Z^1$ groups, and wherein any —$X(C_2-C_6)$alkenyl, —$X(C_2-C_6)$alkynyl and —$X(C_3-C_7)$carbocycle, are each independently substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle, wherein any aryl, heteroaryl and heterocycle, either alone or as part of a group, is substituted with one or more (e.g. 1, 2, 3, 4 or 5) $Z^5$ groups and optionally substituted with one or more (e.g. 1, 2, 3, 4 or 5) $Z^1$ groups;

f) $(C_1-C_6)$haloalkyl, $(C_3-C_7)$carbocycle, $(C_2-C_6)$alkenyl, and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each independently substituted with one or more (e.g. 1, 2, 3, 4 or 5) $Z^6$ groups and optionally substituted with one or more (e.g. 1, 2, 3, 4 or 5) $Z^1$ groups; and g) —$NR_eR_f$, —$C(O)NR_eR_f$, —$OC(O)NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—C(O)—$NR_eR_f$ and —$(C_1-C_6)$alkyl-$SO_2NR_eR_f$, wherein any $(C_1-C_6)$alkyl, as part of a group, is optionally substituted with one or more (e.g. 1, 2, 3, 4 or 5) $Z^1$ groups;

$R^{7a}$ is selected from:
a) H, halo, $(C_1-C_6)$alkyl and $(C_1-C_6)$haloalkyl;
b) $(C_2-C_6)$alkenyl, $(C_2-C_6)$alkynyl, $(C_3-C_7)$cycloalkyl, nitro, cyano, aryl, heterocycle and heteroaryl;
c) —$C(=O)$—$R^{11}$, —$C(=O)$—O—$R^{11}$, —O—$R^{11}$, —S—$R^{11}$, —$S(O)$—$R^{11}$, —$SO_2$—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-$SO_2$—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl; and
d) —$N(R^9)R^{10}$, —$C(=O)$—$N(R^9)R^{10}$, —O—$C(=O)$—$N(R^9)R^{10}$, —$SO_2$—$N(R^9)R^{10}$, —$(C_1-C_6)$alkyl-$N(R^9)R^{10}$, —$(C_1-C_6)$alkyl-C(=O)—$N(R^9)R^{10}$, —$(C_1-C_6)$alkyl-O—C(=O)—$N(R^9)R^{10}$ and —$(C_1-C_6)$alkyl-$SO_2$—$N(R^9)R^{10}$, wherein each $R^9$ is independently selected from H, $(C_1-C_6)$alkyl and $(C_3-C_7)$cycloalkyl, and each $R^{10}$ is independently selected from $R^{11}$, —$(C_1-C_6)$alkyl-$R^{11}$, —$SO_2$—$R^{11}$, —$C(=O)$—$R^{11}$, —$C(=O)OR^{11}$ and —$C(=O)N(R^9)R^{10}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl; and wherein any aryl, heterocycle and heteroaryl of $R^{7a}$ is optionally substituted with one or more (e.g. 1, 2 or 3) $Z^{10}$ groups;

$R^{7b}$ is selected from:
a) —$(C_1-C_6)$alkyl-$SO_2$—$(C_1-C_6)$alkyl-$Z^{13}$, —$C(O)$—$(C_1-C_6)$alkyl-$Z^{13}$, —O—$(C_1-C_6)$alkyl-$Z^{13}$, —S—$(C_1-C_6)$alkyl-$Z^{13}$, —$S(O)$—$(C_1-C_6)$alkyl-$Z^{13}$, —$SO_2$—$(C_1-C_6)$alkyl-$Z^{13}$, —$(C_1-C_6)$alkyl-$Z^{14}$, —$(C_1-C_6)$alkyl-C(O)—$(C_1-C_6)$alkyl-$Z^{13}$, —$(C_1-C_6)$alkyl-C(O)—O$(C_1-C_6)$alkyl-$Z^{13}$, —$(C_1-C_6)$alkyl-O—$(C_1-C_6)$alkyl-$Z^{13}$, —$(C_1-C_6)$alkyl-S—

$(C_1-C_6)$alkyl-$Z^{13}$, —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkyl-S(O)—$(C_1-C_6)$alkyl-$(C_3-C_7)$ carbocycle, —$(C_1-C_6)$alkyl-$SO_2$—$(C_1-C_6)$alkyl-$(C_3-C_7)$ carbocycle, —$(C_2-C_6)$alkenyl-$(C_1-C_6)$haloalkyl, —$(C_2-C_6)$ alkynyl-$(C_1-C_6)$haloalkyl, —$(C_3-C_7)$halocarbocycle, —$NR_aSO_2NR_cR_d$, —$NR_aSO_2O(C_3-C_7)$carbocycle, —$NR_aSO_2$Oaryl, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_3-C_7)$ carbocycle-$Z^1$ and -halo$(C_1-C_6)$alkyl-$Z^3$, wherein any $(C_1-C_6)$alkyl, $(C_1-C_6)$haloalkyl, $(C_3-C_7)$carbocycle, $(C_3-C_7)$ halocarbocycle, $(C_2-C_6)$alkenyl, $(C_2-C_6)$alkynyl, aryl, heterocycle and heteroaryl, either alone or as part of a group, is optionally substituted with one or more (e.g. 1, 2, 3, 4 or 5) $Z^1$ groups;

b) spiro-bicyclic carbocycle, fused-bicyclic carbocycle and bridged-bicyclic carbocycle, wherein any spiro-bicyclic carbocycle, fused-bicyclic carbocycle and bridged-bicyclic carbocycle is optionally substituted with one or more (e.g. 1, 2, 3, 4 or 5) $Z^1$ groups, wherein two $Z^1$ groups together with the atom or atoms to which they are attached optionally form a $(C_3-C_7)$carbocycle or heterocycle wherein the $(C_3-C_7)$carbocycle or heterocycle is optionally substituted with one or more (e.g. 1, 2, 3, 4 or 5) $Z^1$ groups;

c) $(C_1-C_6)$alkyl, wherein $(C_1-C_6)$alkyl is substituted with one or more (e.g. 1, 2, 3, 4 or 5) $Z^2$ groups and optionally substituted with one or more (e.g. 1, 2, 3, 4 or 5) $Z^1$ groups;

d) —$X(C_1-C_6)$alkyl, $X(C_1-C_6)$haloalkyl, $X(C_2-C_6)$alkenyl, —$X(C_2-C_6)$alkynyl and —$X(C_3-C_7)$carbocycle, wherein any —$X(C_1-C_6)$alkyl and —$X(C_1-C_6)$haloalkyl, is substituted with one or more (e.g. 1, 2, 3, 4 or 5) $Z^3$ groups and optionally substituted with one or more (e.g. 1, 2, 3, 4 or 5) $Z^1$ groups, and wherein any —$X(C_2-C_6)$alkenyl, —$X(C_2-C_6)$ alkynyl and —$X(C_3-C_7)$carbocycle is substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle, wherein any aryl, heteroaryl and heterocycle, either alone or as part of a group, is substituted with one or more (e.g. 1, 2, 3, 4 or 5) $Z^5$ groups and optionally substituted with one or more (e.g. 1, 2, 3, 4 or 5) $Z^1$ groups;

f) $(C_1-C_6)$haloalkyl, $(C_3-C_7)$carbocycle, $(C_2-C_6)$alkenyl and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each substituted with one or more $Z^6$ groups and optionally substituted with one or more (e.g. 1, 2, 3, 4 or 5) $Z^1$ groups; and g) —$NR_eR_f$, —$C(O)NR_eR_f$, —$OC(O)NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—$C(O)$—$NR_eR_f$ and —$(C_1-C_6)$alkyl-$SO_2NR_eR_f$, wherein any $(C_1-C_6)$alkyl, as part of a group, is optionally substituted with one or more (e.g. 1, 2, 3, 4 or 5) $Z^1$ groups;

$R^{8a}$ is selected from:
a) halo, nitro and cyano;
b) $R^{11}$, —$C(=O)$—$R^{11}$, —$C(=O)$—O—$R^{11}$, —O—$R^{11}$, —S—$R^{11}$, —S(O)—$R^{11}$, —$SO_2$—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-$SO_2$—$R^{11}$, wherein each $R^{11}$ is independently selected from H, $(C_1-C_6)$ alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein aryl, heterocycle and heteroaryl are each optionally substituted with one or more (e.g. 1, 2 or 3) $Z^{11}$ groups;

c) —$N(R^9)R^{10}$, —$C(=O)$—$N(R^9)R^{10}$, —O—$C(=O)$—$N(R^9)R^{10}$, —$SO_2$—$N(R^9)R^{10}$, —$(C_1-C_6)$alkyl-$N(R^9)R^{10}$, —$(C_1-C_6)$alkyl-C(=O)—$N(R^9)R^{10}$, —$(C_1-C_6)$alkyl-O—C(=O)—$N(R^9)R^{10}$ and —$(C_1-C_6)$alkyl-$SO_2$—$N(R^9)R^{10}$, wherein each $R^9$ is independently selected from H, $(C_1-C_6)$ alkyl and $(C_3-C_7)$cycloalkyl, and each $R^{10}$ is independently selected from $R^{11}$, —$(C_1-C_6)$alkyl-$R^{11}$, —$SO_2$—$R^{11}$, —$C(=O)$—$R^{11}$, —$C(=O)OR^{11}$ and —$C(=O)N(R^9)R^{11}$, wherein each $R^{11}$ is independently selected from H, $(C_1-C_6)$ alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl;

$R^{8b}$ is selected from:
a) —$(C_1-C_6)$alkyl-$SO_2$—$(C_1-C_6)$alkyl-$Z^{13}$, —$C(O)$—$(C_1-C_6)$alkyl-$Z^{13}$, —O—$(C_1-C_6)$alkyl-$Z^{13}$, —S—$(C_1-C_6)$ alkyl-$Z^{13}$, —S(O)—$(C_1-C_6)$alkyl-$Z^{13}$, —$SO_2$—$(C_1-C_6)$ alkyl-$Z^{13}$, —$(C_1-C_6)$alkyl-$Z^{14}$, —$(C_1-C_6)$alkyl-C(O)—$(C_1-C_6)$alkyl-$Z^{13}$, —$(C_1-C_6)$alkyl-C(O)—O$(C_1-C_6)$alkyl-$Z^{13}$, —$(C_1-C_6)$alkyl-O—$(C_1-C_6)$alkyl-$Z^{13}$, —$(C_1-C_6)$alkyl-S—$(C_1-C_6)$alkyl-$Z^{13}$, —$(C_1-C_6)$alkyl-O—$(C_1-C_6)$alkyl-$(C_3-C_7)$ carbocycle, —$(C_1-C_6)$alkyl-S—$(C_1-C_6)$alkyl-$(C_3-C_7)$carbocycle, —$(C_1-C_6)$alkyl-S(O)—$(C_1-C_6)$alkyl-$(C_3-C_7)$ carbocycle, —$(C_1-C_6)$alkyl-$SO_2$—$(C_1-C_6)$alkyl-$(C_3-C_7)$ carbocycle, —$(C_2-C_6)$alkenyl-$(C_1-C_6)$haloalkyl, —$(C_2-C_6)$ alkynyl-$(C_1-C_6)$haloalkyl, -halo$(C_3-C_7)$carbocycle, —$NR_aSO_2NR_cR_d$, —$NR_aSO_2O(C_3-C_7)$carbocycle, —$NR_aSO_2$Oaryl, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_3-C_7)$ carbocycle-$Z^1$ and -halo$(C_1-C_6)$alkyl-$Z^3$, wherein any $(C_1-C_6)$alkyl, $(C_1-C_6)$haloalkyl, $(C_3-C_7)$carbocycle, $(C_2-C_6)$ alkenyl, $(C_2-C_6)$alkynyl, aryl, heterocycle and heteroaryl, either alone or as part of a group, is optionally substituted with one or more (e.g. 1, 2, 3, 4 or 5) $Z^1$ groups:

b) spiro-bicyclic carbocycle, fused-bicyclic carbocycle and bridged-bicyclic carbocycle, wherein any spiro-bicyclic carbocycle, fused-bicyclic carbocycle and bridged-bicyclic carbocycle is optionally substituted with one or more (e.g. 1, 2, 3, 4 or 5) $Z^1$ groups, wherein two $Z^1$ groups together with the atom or atoms to which they are attached optionally form a $(C_3-C_7)$carbocycle or heterocycle wherein the $(C_3-C_7)$carbocycle or heterocycle is optionally substituted with one or more (e.g. 1, 2, 3, 4 or 5) $Z^1$ groups;

c) $(C_1-C_6)$alkyl, wherein $(C_1-C_6)$alkyl is substituted with one or more (e.g. 1, 2, 3, 4 or 5) $Z^2$ groups and optionally substituted with one or more (e.g. 1, 2, 3, 4 or 5) $Z^1$ groups;

d) —$X(C_1-C_6)$alkyl, —$X(C_1-C_6)$haloalkyl, —$X(C_2-C_6)$ alkenyl, —$X(C_2-C_6)$alkynyl and —$X(C_3-C_7)$carbocycle, wherein any —$X(C_1-C_6)$alkyl and —$X(C_1-C_6)$haloalkyl, is substituted with one or more (e.g. 1, 2, 3, 4 or 5) $Z^3$ groups and optionally substituted with one or more (e.g. 1, 2, 3, 4 or 5) $Z^1$ groups, and wherein any —$X(C_2-C_6)$alkenyl, —$X(C_2-C_6)$ alkynyl and —$X(C_3-C_7)$carbocycle is substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle, wherein any aryl, heteroaryl and heterocycle, either alone or as part of a group, is substituted with one or more (e.g. 1, 2, 3, 4 or 5) $Z^5$ groups and optionally substituted with one or more (e.g. 1, 2, 3, 4 or 5) $Z^1$ groups;

f) $(C_1-C_6)$haloalkyl, $(C_3-C_7)$carbocycle, $(C_2-C_6)$alkenyl and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each independently substituted with one or more (e.g. 1, 2, 3, 4 or 5) $Z^6$ groups and optionally substituted with one or more (e.g. 1, 2, 3, 4 or 5) $Z^1$ groups; and g) —NR$_e$R$_f$, —C(O)NR$_e$R$_f$, —OC(O)NR$_e$R$_f$, —SO$_2$NR$_e$R$_f$, —(C$_1$-C$_6$)alkyl-NR$_e$R$_f$, —(C$_1$-C$_6$)alkylC(O)—NR$_e$R$_f$, —(C$_1$-C$_6$)alkyl-O—C(O)—NR$_e$R$_f$ and —(C$_1$-C$_6$)alkyl-SO$_2$NR$_e$R$_f$, wherein any (C$_1$-C$_6$)alkyl, as part of a group, is optionally substituted with one or more (e.g. 1, 2, 3, 4 or 5) Z$^1$ groups;

or any of R$^{5a}$ and R$^{6a}$, R$^{6a}$ and R$^{7a}$, R$^{7a}$ and R$^{8a}$, R$^1$ and R$^8$ or R$^1$ and R$^2$ together with the atoms to which they are attached form a 5 or 6-membered carbocycle or a 4, 5, 6 or 7-membered heterocycle, wherein the 5 or 6-membered carbocycle or a 4, 5 or 7-membered heterocycle is optionally substituted with one or more (e.g. 1, 2 or 3) substituents each independently selected from halo, (C$_1$-C$_6$)alkyl, (C$_2$-C$_6$)alkenyl, (C$_1$-C$_6$)haloalkyl, (C$_3$-C$_7$)cycloalkyl, —OH, —O(C$_1$-C$_6$)alkyl, —SH, —S(C$_1$-C$_6$)alkyl, —NH$_2$, —NH(C$_1$-C$_6$)alkyl and —N((C$_1$-C$_6$)alkyl)$_2$;

or any of R$^5$ and R$^6$, R$^6$ and R$^7$ or R$^7$ and R$^8$, together with the atoms to which they are attached form a 5 or 6-membered carbocycle or a 4, 5, 6 or 7-membered heterocycle, wherein the 5 or 6-membered carbocycle or a 4, 5, 6 or 7-membered heterocycle are each independently substituted with one or more (e.g. 1, 2 or 3) Z$^7$ or Z$^8$ groups, wherein when two Z$^7$ groups are on same atom the two Z$^7$ groups together with the atom to which they are attached optionally form a (C$_3$-C$_7$)carbocycle or 4, 5 or 6-membered heterocycle;

or R$^1$ and R$^8$ or R$^1$ and R$^2$ together with the atoms to which they are attached form a 5 or 6-membered carbocycle or a 4, 5, 6 or 7-membered heterocycle, wherein the 5 or 6-membered carbocycle or a 4, 5, 6 or 7-membered heterocycle are each independently substituted with one or more (e.g. 1, 2 or 3) Z$^7$ or Z$^8$ groups; wherein when two Z$^7$ groups are on same atom the two Z$^7$ groups together with the atom to which they are attached optionally form a (C$_3$-C$_7$)carbocycle or 4, 5 or 6-membered heterocycle;

X is independently selected from O, —C(O)—, —C(O)O—, —S—, —S(O)—, —SO$_2$·, —(C$_1$-C$_6$)alkylO—, —(C$_1$-C$_6$)alkylC(O)—, —(C$_1$-C$_6$)alkylC(O)O—, —(C$_1$-C$_6$)alkylS—, —(C$_1$-C$_6$)alkylS(O)— and —(C$_1$-C$_6$)alkylSO$_2$—;

each Z$^1$ is independently selected from halo, —NO$_2$, —OH, =NOR$_a$, —SH, —CN, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)carbocycle, (C$_3$-C$_7$)halocarbocycle, aryl, heteroaryl, heterocycle, —O(C$_1$-C$_6$)alkyl, —O(C$_2$-C$_6$)alkenyl, —O(C$_2$-C$_6$)alkynyl, —O(C$_1$-C$_6$)haloalkyl, —O(C$_3$-C$_7$)carbocycle, —O(C$_3$-C$_7$)halocarbocycle, —Oaryl, —Oheteroaryl, —Oheterocycle, —S(C$_1$-C$_6$)alkyl, —S(C$_2$-C$_6$)alkenyl, —S(C$_2$-C$_6$)alkynyl, —S(C$_1$-C$_6$)haloalkyl, —S(C$_3$-C$_7$)carbocycle, —S(C$_3$-C$_7$)halocarbocycle, —Saryl, —Sheteroaryl, —Sheterocycle, —S(O)(C$_1$-C$_6$)alkyl, —S(O)(C$_2$-C$_6$)alkenyl, —S(O)(C$_2$-C$_6$)alkynyl, —S(O)(C$_1$-C$_6$)haloalkyl, —S(O)(C$_3$-C$_7$)carbocycle, —S(O)(C$_3$-C$_7$)halocarbocycle, —SO$_2$(C$_1$-C$_6$)alkyl, —S(O)aryl, —S(O)carbocycle, —S(O)heterocycle, —S(O)heterocycle, —SO$_2$(C$_2$-C$_6$)alkenyl, —SO$_2$(C$_2$-C$_6$)alkynyl, —SO$_2$(C$_1$-C$_6$)haloalkyl, —SO$_2$(C$_3$-C$_7$)carbocycle, —SO$_2$(C$_3$-C$_7$)halocarbocycle, —SO$_2$aryl, —SO$_2$heteroaryl, —SO$_2$heterocycle, —SO$_2$NR$_c$R$_d$, —NR$_c$R$_d$, —NR$_a$C(O)R$_a$, —NR$_a$C(O)OR$_a$, —NR$_a$C(O)NR$_c$R$_d$, —NR$_a$SO$_2$R$_b$, —NR$_a$SO$_2$NR$_c$R$_d$, —NR$_a$SO$_2$O(C$_3$-C$_7$)carbocycle, —NR$_a$SO$_2$Oaryl, —OS(O)$_2$R$_a$, —C(O)R$_a$, —C(O)OR$_b$, —C(O)NR$_c$R$_d$, and —OC(O)NR$_c$R$_d$, wherein any (C$_1$-C$_6$)alkyl, (C$_1$-C$_6$)haloalkyl, (C$_2$-C$_6$)alkenyl, (C$_2$-C$_6$)alkynyl, (C$_3$-C$_7$)carbocycle, (C$_3$-C$_7$)halocarbocycle, aryl, heteroaryl or heterocycle of Z$^1$, either alone or as part of a group, is optionally substituted with one or more (e.g. 1, 2, 3, 4 or 5) halogen, —OH, —OR$_b$, —CN, —NR$_a$C(O)$_2$R$_b$, -heteroaryl, -heterocycle, —Oheteroaryl, —Oheterocycle, —NHheteroaryl, —NHheterocycle, or —S(O)$_2$NRCR$_d$;

each Z$^2$ is independently selected from —NO$_2$, —CN, spiro-heterocycle, bridge-heterocycle, spiro-bicyclic carbocycle, bridged-bicyclic carbocycle, NR$_a$SO$_2$(C$_3$-C$_7$)carbocycle, —NR$_a$SO$_2$aryl, —NR$_a$SO$_2$heteroaryl, —NR$_a$SO$_2$NR$_c$R$_d$, —NR$_a$SO$_2$O(C$_3$-C$_7$)carbocycle and —NR$_a$SO$_2$Oaryl;

each Z$^3$ is independently selected from —NO$_2$, —CN, —OH, oxo, =NOR$_a$, thioxo, aryl, heterocycle, heteroaryl, (C$_3$-C$_7$)halocarbocycle, —O(C$_1$-C$_6$)alkyl, —O(C$_3$-C$_7$)carbocycle, —Ohalo(C$_3$-C$_7$)carbocycle, —Oaryl, —Oheterocycle, —Oheteroaryl, —S(C$_1$-C$_6$)alkyl, —S(C$_3$-C$_7$)carbocycle, —S(C$_3$-C$_7$)halocarbocycle, —Saryl, —Sheterocycle, —Sheteroaryl, —S(O)(C$_1$-C$_6$)alkyl, —S(O)(C$_3$-C$_7$)carbocycle, —S(O)(C$_3$-C$_7$)halocarbocycle, —S(O)aryl, —S(O)heterocycle, —S(O)heteroaryl, —SO$_2$(C$_1$-C$_6$)alkyl, —SO$_2$(C$_3$-C$_7$)carbocycle, —SO$_2$(C$_3$-C$_7$)halocarbocycle, SO$_2$aryl, —SO$_2$heterocycle, —SO$_2$heteroaryl, —NR$_a$R$_b$, —NR$_a$C(O)R$_b$, —C(O)NR$_c$R$_d$, —SO$_2$NR$_c$R$_d$, —NR$_a$SO$_2$NR$_c$R$_d$, —NR$_a$SO$_2$O(C$_3$-C$_7$)carbocycle and —NR$_a$SO$_2$Oaryl;

each Z$^4$ is independently selected from halogen, (C$_1$-C$_6$)alkyl, (C$_3$-C$_7$)carbocycle, halo(C$_1$-C$_6$)alkyl, —NO$_2$, —CN, —OH, oxo, =NOR$_a$, thioxo, aryl, heterocycle, heteroaryl, (C$_3$-C$_7$)halocarbocycle, —O(C$_1$-C$_6$)alkyl, —O(C$_3$-C$_7$)carbocycle, —O(C$_3$-C$_7$)halocarbocycle, —Oaryl, —Oheterocycle, —Oheteroaryl, —S(C$_1$-C$_6$)alkyl, —S(C$_3$-C$_7$)carbocycle, —S(C$_3$-C$_7$)halocarbocycle, —Saryl, —Sheterocycle, —Sheteroaryl, —S(O)(C$_1$-C$_6$)alkyl, —S(O)(C$_3$-C$_7$)carbocycle, —S(O)(C$_3$-C$_7$)halocarbocycle, —S(O)aryl, —S(O)heterocycle, —S(O)heteroaryl, —SO$_2$(C$_1$-C$_6$)alkyl, —SO$_2$(C$_3$-C$_7$)carbocycle, —SO$_2$(C$_3$-C$_7$)halocarbocycle, SO$_2$aryl, —SO$_2$heterocycle, —SO$_2$heteroaryl, —NR$_a$R$_b$, —NR$_a$C(O)R$_a$, —C(O)NR$_c$R$_d$, —SO$_2$NR$_c$R$_d$, —NR$_a$SO$_2$NR$_c$R$_d$, —NR$_a$SO$_2$O(C$_3$-C$_7$)carbocycle and —NR$_a$SO$_2$Oaryl;

each Z$^5$ is independently selected from —NO$_2$, —CN, —NR$_a$SO$_2$NR$_c$R$_d$, -NR$_a$SO$_2$O(C$_3$-C$_7$)carbocycle, —NR$_a$SO$_2$Oaryl, —NR$_a$SO$_2$(C$_1$-C$_6$)alkyl, —NR$_a$SO$_2$(C$_2$-C$_6$)alkenyl, —NR$_a$SO$_2$(C$_2$-C$_6$)alkynyl, —NR$_a$SO$_2$(C$_3$-C$_7$)carbocycle, —NR$_a$SO$_2$(C$_3$-C$_7$)halocarbocycle, —NR$_a$SO$_2$aryl, —NR$_a$SO$_2$heteroaryl, —NR$_a$SO$_2$heterocycle, —NR$_a$SO$_2$heterocycle, —NR$_a$C(O)alkyl, —NR$_a$C(O)alkenyl, —NR$_a$C(O)alkynyl, —NR$_a$C(O)(C$_3$-C$_7$)carbocycle, —NR$_a$C(O)(C$_3$-C$_7$)halocarbocycle, —NR$_a$C(O)aryl, —NR$_a$C(O)heteroaryl, —NR$_a$C(O)heterocycle, NR$_a$C(O)NR$_c$R$_d$ and NR$_a$C(O)OR$_b$;

each Z$^6$ is independently selected from —NO$_2$, —CN, —NR$_a$R$_a$, —NR$_a$C(O)R$_b$, —NR$_a$C(O)OR$_b$, —C(O)NR$_c$R$_d$, (C$_3$-C$_7$)halocarbocycle, aryl, heteroaryl, heterocycle, —Oaryl, —Oheteroaryl, —Oheterocycle, —O(C$_3$-C$_7$)halocarbocycle, —O(C$_1$-C$_6$)alkyl, —O(C$_3$-C$_7$)carbocycle, —Ohalo(C$_1$-C$_6$)alkyl, —Saryl, —Sheteroaryl, —Sheterocycle, —S(C$_3$-C$_7$)halocarbocycle, —S(C$_1$-C$_6$)alkyl, —S(C$_3$-C$_7$)carbocycle, —S(C$_1$-C$_6$)haloalkyl, —S(O)aryl, —S(O)heteroaryl, —S(O)heterocycle, —S(O)(C$_3$-C$_7$)halocarbocycle, —S(O)(C$_1$-C$_6$)alkyl, —S(O)(C$_3$-C$_7$)carbocycle, —S(O)halo(C$_1$-C$_6$)alkyl, —SO$_2$aryl, —SO$_2$heteroaryl, —SO$_2$heterocycle, —SO$_2$(C$_1$-C$_6$)alkyl, —SO$_2$halo(C$_1$-C$_6$)alkyl, —SO$_2$(C$_3$-C$_7$)carbocycle, —SO$_2$(C$_3$-C$_7$)halocarbocycle, —SO$_2$NR$_c$R$_d$, —NR$_a$SO$_2$(C$_3$-C$_7$)halocarbocycle, —NR$_a$SO$_2$aryl, —NR$_a$SO$_2$heteroaryl, —NR$_a$SO$_2$heterocycle, —NR$_a$SO$_2$NR$_c$R$_d$, —NR$_a$SO$_2$O(C$_3$-C$_7$)carbocycle and —NR$_a$SO$_2$Oaryl;

each Z$^7$ is independently selected from —NO$_2$, =NOR$_a$, —CN, —(C$_1$-C$_6$)alkyl-Z$^{12}$, —(C$_2$-C$_6$)alkenyl-Z$^{12}$, —(C$_2$-C$_6$)alkenylOH, —(C$_2$-C$_6$)alkynyl-Z$^{12}$, —(C$_2$-C$_6$)alkynylOH, —(C$_1$-C$_6$)haloalkyl-Z$^{12}$, —(C$_1$-C$_6$)haloalkylOH, —($C_3$-$C_7$)carbocycle-$Z^{12}$, —($C_3$-$C_7$)carbocycleOH, ($C_3$-$C_7$)halocarbocycle, —($C_1$-$C_6$)alkyl$NR_cR_d$, —($C_1$-$C_6$)alkyl$NR_aC(O)R_a$, —($C_1$-$C_6$)alkyl$NR_aSO_2R_a$, aryl, heteroaryl, heterocycle, —O($C_1$-$C_6$)alkyl-$Z^{12}$, —O($C_2$-$C_6$)alkenyl, —O($C_2$-$C_6$)alkynyl, —O($C_1$-$C_6$)haloalkyl, —O($C_3$-$C_7$)carbocycle, —O($C_3$-$C_7$)halocarbocycle, —Oaryl, —O($C_1$-$C_6$)alkyl$NR_cR_d$, —O($C_1$-$C_6$)alkyl$NR_aC(O)R_a$, —O($C_1$-$C_6$)alkyl$NR_aSO_2R_a$, —Oheteroaryl, —Oheterocycle, —S($C_1$-$C_6$)alkyl-$Z^{12}$, —S($C_2$-$C_6$)alkenyl, —S($C_2$-$C_6$)alkynyl, —S($C_1$-$C_6$)haloalkyl, —S($C_3$-$C_7$)carbocycle, —S($C_3$-$C_7$)halocarbocycle, —S($C_1$-$C_6$)alkyl$NR_cR_d$, —S($C_1$-$C_6$)alkyl$NR_aC(O)R_a$, —S($C_1$-$C_6$)alkyl$NR_aSO_2R_a$, —Saryl, —Sheteroaryl, —Sheterocycle, —S(O)($C_1$-$C_6$)alkyl, —S(O)($C_2$-$C_6$)alkenyl, —S(O)($C_2$-$C_6$)alkynyl, —S(O)($C_1$-$C_6$)haloalkyl, —S(O)($C_3$-$C_7$)carbocycle, —S(O)($C_3$-$C_7$)halocarbocycle, —$SO_2$($C_1$-$C_6$)alkyl, —S(O)($C_1$-$C_6$)alkyl$NR_cR_d$, —S(O)($C_1$-$C_6$)alkyl$NR_aC(O)R_a$, —S(O)($C_1$-$C_6$)alkyl$NR_aSO_2R_a$, —S(O)aryl, —S(O)heteroaryl, —S(O)heterocycle, —$SO_2$($C_1$-$C_6$)alkyl, —$SO_2$($C_2$-$C_6$)alkenyl, —$SO_2$($C_2$-$C_6$)alkynyl, —$SO_2$($C_1$-$C_6$)haloalkyl, —$SO_2$($C_3$-$C_7$)carbocycle, —$SO_2$($C_3$-$C_7$)halocarbocycle, —$SO_2$aryl, —$SO_2$heteroaryl, —$SO_2$heterocycle, —$SO_2$($C_1$-$C_6$)alkyl$NR_cR_d$, —$SO_2$($C_1$-$C_6$)alkyl$NR_aC(O)R_a$, —$SO_2$($C_1$-$C_6$)alkyl$NR_aSO_2R_a$, —$SO_2NR_cR_d$, —$NR_aC(O)R_b$, —$NR_aC(O)OR_b$, —$NR_aC(O)NR_cR_d$—$NR_aSO_2R_b$, —$NR_aSO_2NR_cR_d$, —$NR_aSO_2O$($C_3$-$C_7$)carbocycle, —$NR_aSO_2$Oaryl, —$OS(O)_2R_a$, —C(O)$NR_cR_d$, and —OC(O)$NR_cR_d$, wherein any ($C_1$-$C_6$)alkyl, ($C_1$-$C_6$)haloalkyl, ($C_2$-$C_6$)alkenyl, ($C_2$-$C_6$)alkynyl, ($C_3$-$C_7$)carbocycle, ($C_3$-$C_7$)halocarbocycle, aryl, heteroaryl and heterocycle of $Z^7$, either alone or as part of a group, is optionally substituted with one or more (e.g. 1, 2, 3, 4 or 5) halogen, —OH, —$OR_b$, —CN, —$NR_aC(O)_2R_b$, heteroaryl, heterocycle, —Oheteroaryl, —Oheterocycle, —NHheteroaryl, —NHheterocycle or —$S(O)_2NR_cR_d$;

each $Z^8$ is independently selected from —$NO_2$ and —CN;
each $Z^9$ is independently selected from —($C_1$-$C_6$)alkyl and —O($C_1$-$C_6$)alkyl;
each $Z^{10}$ is independently selected from:
i) halo, oxo, thioxo, ($C_2$-$C_6$)alkenyl, ($C_1$-$C_6$)haloalkyl, ($C_3$-$C_7$)cycloalkyl, ($C_3$-$C_7$)cycloalkyl-($C_1$-$C_6$)alkyl-, —OH, —O($C_1$-$C_6$)alkyl, —O($C_1$-$C_6$)haloalkyl, —SH, —S($C_1$-$C_6$)alkyl, —SO($C_1$-$C_6$)alkyl, —$SO_2$($C_1$-$C_6$)alkyl, —$NH_2$, —NH($C_1$-$C_6$)alkyl and —N(($C_1$-$C_6$)alkyl)$_2$;
ii) ($C_1$-$C_6$)alkyl optionally substituted with —OH, —O—($C_1$-$C_6$)haloalkyl or —O—($C_1$-$C_6$)alkyl; and
iii) aryl, heterocycle and heteroaryl, which aryl, heterocycle and heteroaryl is optionally substituted with halo, ($C_1$-$C_6$)alkyl or COOH;
each $Z^{11}$ is independently selected from $Z^{10}$, —C(=O)—$NH_2$, —C(=O)—NH($C_1$-$C_4$)alkyl, —C(=O)—N(($C_1$-$C_4$)alkyl)$_2$, —C(=O)-aryl, —C(=O)-heterocycle and —C(=O)-heteroaryl;
each $Z^{12}$ is independently selected from —$NO_2$, =$NOR_a$, thioxo, aryl, heterocycle, heteroaryl, ($C_3$-$C_7$)halocarbocycle, ($C_3$-$C_7$)carbocycle, —O($C_3$-$C_7$)carbocycle, —Ohalo($C_3$-$C_7$)carbocycle, —Oaryl, —Oheterocycle, —Oheteroaryl, —S($C_1$-$C_6$)alkyl, —S($C_3$-$C_7$)carbocycle, —Shalo($C_3$-$C_7$)carbocycle, —Saryl, —Sheterocycle, —Sheteroaryl, —S(O)($C_1$-$C_6$)alkyl, —S(O)($C_3$-$C_7$)carbocycle, —S(O)halo($C_3$-$C_7$)carbocycle, —S(O)aryl, —S(O)heterocycle, —S(O)heteroaryl, —$SO_2$($C_1$-$C_6$)alkyl, —$SO_2$($C_3$-$C_7$)carbocycle, —$SO_2$($C_3$-$C_7$)halocarbocycle, $SO_2$aryl, —$SO_2$heterocycle, —$SO_2$heteroaryl, —$NR_aR_b$, —$NR_aC(O)R_b$, —C(O)$NR_cR_d$, —$SO_2NR_cR_d$, —$NR_aSO_2NR_cR_d$, —$NR_aSO_2O$($C_3$-$C_7$)carbocycle and —$NR_aSO_2$Oaryl;

each $Z^{13}$ is independently selected from —$NO_2$, —OH, =$NOR_a$, —SH, —CN, —($C_3$-$C_7$)halocarbocycle, —O($C_1$-$C_6$)alkyl, —O($C_2$-$C_6$)alkenyl, —O($C_2$-$C_6$)alkynyl, —O($C_1$-$C_6$)haloalkyl, —O($C_3$-$C_7$)carbocycle, —O($C_3$-$C_7$)halocarbocycle, —Oaryl, —Oheteroaryl, —Oheterocycle, —S($C_1$-$C_6$)alkyl, —S($C_2$-$C_6$)alkenyl, —S($C_2$-$C_6$)alkynyl, —S($C_1$-$C_6$)haloalkyl, —S($C_3$-$C_7$)carbocycle, —S($C_3$-$C_7$)halocarbocycle, —Saryl, —Sheteroaryl, —Sheterocycle, —S(O)($C_1$-$C_6$)alkyl, —S(O)($C_2$-$C_6$)alkenyl, —S(O)($C_2$-$C_6$)alkynyl, —S(O)($C_1$-$C_6$)haloalkyl, —S(O)($C_3$-$C_7$)carbocycle, —S(O)($C_3$-$C_7$)halocarbocycle, —S(O)aryl, —S(O)heteroaryl, —S(O)heterocycle, —$SO_2$($C_1$-$C_6$)alkyl, —$SO_2$($C_2$-$C_6$)alkenyl, —$SO_2$($C_2$-$C_6$)alkynyl, —$SO_2$($C_1$-$C_6$)haloalkyl, —$SO_2$($C_3$-$C_7$)carbocycle, —$SO_2$($C_3$-$C_7$)halocarbocycle, —$SO_2$aryl, —$SO_2$heteroaryl, —$SO_2$heterocycle, —$SO_2NR_cR_d$, —$NR_cR_d$, —$NR_aC(O)R_a$, —$NR_aC(O)OR_b$, —$NR_aC(O)NR_cR_d$—$NR_aSO_2R_b$, —$NR_aSO_2NR_cR_d$, —$NR_aSO_2O$($C_3$-$C_7$)carbocycle, —$NR_aSO_2$Oaryl, —$OS(O)_2R_a$, —C(O)$R_a$, —C(O)$OR_b$, —C(O)$NR_cR_d$, and —OC(O)$NR_cR_d$, wherein any ($C_1$-$C_6$)alkyl, ($C_2$-$C_6$)alkenyl, ($C_2$-$C_6$)alkynyl, ($C_1$-$C_6$)haloalkyl, ($C_3$-$C_7$)carbocycle, ($C_3$-$C_7$)halocarbocycle, aryl, heteroaryl or heterocycle of $Z^{13}$, either alone or as part of a group, is optionally substituted with one or more (e.g. 1, 2, 3, 4 or 5) halogen, —OH, —$OR_b$, —CN, —$NR_aC(O)_2R_b$, -heteroaryl, -heterocycle, —Oheteroaryl, —Oheterocycle, —NHheteroaryl, —NHheterocycle, or —$S(O)_2NR_cR_d$;

each $Z^{14}$ is independently selected from —$NO_2$, =$NOR_a$, —CN, ($C_3$-$C_7$)halocarbocycle, —O($C_3$-$C_7$)halocarbocycle, —S($C_3$-$C_7$)halocarbocycle, —S(O)($C_3$-$C_7$)halocarbocycle, —$SO_2$($C_3$-$C_7$)halocarbocycle, —$NR_aSO_2NR_cR_d$, —$NR_aSO_2O$($C_3$-$C_7$)halocarbocycle, —$NR_aSO_2$Oaryl and —$OS(O)_2R_a$, wherein any ($C_3$-$C_7$)halocarbocycle of $Z^{14}$, either alone or as part of a group, is optionally substituted with one or more (e.g. 1, 2, 3, 4 or 5) halogen, —OH, —$OR_b$, —CN, —$NR_aC(O)_2R_b$, -heteroaryl, -heterocycle, —Oheteroaryl, —Oheterocycle, —NHheteroaryl, —NHheterocycle, or —$S(O)_2NR_cR_d$;

each $R_a$ is independently H, ($C_1$-$C_6$)alkyl, ($C_2$-$C_6$)alkenyl, ($C_2$-$C_6$)alkynyl, ($C_3$-$C_7$)carbocycle, heterocycle, aryl, aryl($C_1$-$C_6$)alkyl-, heteroaryl or heteroaryl($C_1$-$C_6$)alkyl-, wherein any ($C_1$-$C_6$)alkyl, ($C_2$-$C_6$)alkenyl, ($C_2$-$C_6$)alkynyl, ($C_3$-$C_7$)carbocycle, heterocycle, aryl, or heteroaryl of $R_a$, either alone or as part of a group, is optionally substituted by halogen, OH and cyano;

each $R_b$ is independently ($C_1$-$C_6$)alkyl, ($C_2$-$C_6$)alkenyl, ($C_2$-$C_6$)alkynyl, ($C_3$-$C_7$)carbocycle, heterocycle, aryl, aryl($C_1$-$C_6$)alkyl-, heteroaryl or heteroaryl($C_1$-$C_6$)alkyl-, wherein any ($C_1$-$C_6$)alkyl, —($C_2$-$C_6$)alkenyl, —($C_2$-$C_6$)alkynyl, ($C_3$-$C_7$)carbocycle, heterocycle, aryl, or heteroaryl of $R_b$, either alone or as part of a group, is optionally substituted by halogen, OH and cyano;

$R_c$ and $R_d$ are each independently selected from H, ($C_1$-$C_6$)alkyl, ($C_2$-$C_6$)alkenyl, ($C_2$-$C_6$)alkynyl, ($C_3$-$C_7$)carbocycle, aryl, aryl($C_1$-$C_6$)alkyl-, heterocycle, heteroaryl and heteroaryl($C_1$-$C_6$)alkyl-, wherein any ($C_1$-$C_6$)alkyl, —($C_2$-$C_6$)alkenyl, —($C_2$-$C_6$)alkynyl, ($C_3$-$C_7$)carbocycle, heterocycle, aryl and heteroaryl of $R_c$ or $R_d$, either alone or as part of a group, is optionally substituted by halogen, OH and cyano; or $R_c$ and $R_d$ together with the nitrogen to which they are attached form a heterocycle, wherein any heterocycle of $R_c$ and $R_d$ together with the nitrogen to which they are attached is optionally substituted by halogen, OH or cyano;

each $R_e$ is independently selected from —$OR_a$, ($C_1$-$C_6$)alkyl and ($C_3$-$C_7$)carbocycle, wherein ($C_1$-$C_6$)alkyl and ($C_3$-$C_7$)carbocycle are substituted by one or more (e.g. 1, 2, 3, 4 or 5) $Z^6$ and optionally substituted with one or more (e.g. 1, 2, 3, 4 or 5) $Z^1$, $(C_2$-$C_6)$haloalkyl, $(C_2$-$C_6)$alkenyl and $(C_2$-$C_6)$alkynyl, wherein any $(C_2$-$C_6)$haloalkyl, $(C_2$-$C_6)$alkenyl and $(C_2$-$C_6)$alkynyl is optionally substituted with one or more (e.g. 1, 2, 3, 4 or 5) $Z^1$, and aryl, heterocycle and heteroaryl, wherein any aryl, heterocycle and heteroaryl are substituted by one or more $Z^5$;

each $R_f$ is independently selected from —$R_g$, —$OR_a$, —$(C_1$-$C_6)$alkyl-$Z^6$, —$SO_2R_g$, —$C(O)R_g$, $C(O)OR_g$, and —$C(O)NR_eR_g$; and each $R_g$ is independently selected from H, —$OR_a$, $(C_1$-$C_6)$ alkyl, $(C_3$-$C_7)$carbocycle, $(C_1$-$C_6)$haloalkyl, $(C_2$-$C_6)$alkenyl, $(C_2$-$C_6)$alkynyl, aryl, heterocycle and heteroaryl, wherein any $(C_1$-$C_6)$alkyl, $(C_3$-$C_7)$carbocycle, $(C_1$-$C_6)$haloalkyl, $(C_2$-$C_6)$alkenyl, $(C_2$-$C_6)$alkynyl, aryl, heterocycle or heteroaryl of $R_g$ is optionally substituted with one or more $Z^1$ groups;

or a salt thereof.

The invention also provides a pharmaceutical composition comprising a compound of formula I or a pharmaceutically acceptable salt thereof, in combination with a pharmaceutically acceptable carrier.

The invention also provides method for treating (e.g. preventing, mediating or inhibiting) the proliferation of the HIV virus, treating AIDS or delaying the onset of AIDS or ARC symptoms in a mammal (e.g. a human), comprising administering a compound of formula I, or a pharmaceutically acceptable salt thereof, to the mammal.

The invention also provides a compound of formula I, or a pharmaceutically acceptable salt thereof for use in medical therapy (e.g. for use in treating (e.g. preventing, mediating or inhibiting) the proliferation of the HIV virus or AIDS or delaying the onset of AIDS or ARC symptoms in a mammal (e.g. a human)).

The invention also provides a compound of formula I, or a pharmaceutically acceptable salt thereof for use in the manufacture of a medicament for treating (e.g. preventing, mediating or inhibiting) the proliferation of the HIV virus or AIDS or delaying the onset of AIDS or ARC symptoms in a mammal (e.g. a human).

The invention also provides a compound of formula I, or a pharmaceutically acceptable salt thereof, for use in the prophylactic or therapeutic treatment (e.g. prevention, mediation or inhibiting) of the proliferation of the HIV virus or AIDS or for use in the therapeutic treatment of delaying the onset of AIDS or ARC symptoms.

The invention also provides processes and intermediates disclosed herein that are useful for preparing compounds of formula I or salts thereof.

DETAILED DESCRIPTION OF THE INVENTION

Definitions

Unless stated otherwise, the following terms and phrases as used herein are intended to have the following meanings:

When trade names are used herein, applicants intend to independently include the tradename product and the active pharmaceutical ingredient(s) of the tradename product.

"Alkyl" is hydrocarbon containing normal, secondary or tertiary atoms. For example, an alkyl group can have 1 to 20 carbon atoms (i.e., $(C_1$-$C_{20})$alkyl), 1 to 10 carbon atoms (i.e., $(C_1$-$C_{10})$alkyl), 1 to 8 carbon atoms (i.e., $(C_1$-$C_8)$alkyl)or 1 to 6 carbon atoms (i.e., $(C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$). "Alkyl" also refers to a saturated, branched or straight chain hydrocarbon radical having two monovalent radical centers derived by the removal of two hydrogen atoms from the same or two different carbon atoms of a parent alkane. For example, an alkyl group can have 1 to 10 carbon atoms (i.e., $(C_1$-$C_{10})$alkyl), or 1 to 6 carbon atoms (i.e., $(C_1$-$C_6)$alkyl) or 1-3 carbon atoms (i.e., $(C_1$-$C_3)$alkyl). Typical alkyl radicals include, but are not limited to, methylene(—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

"Alkenyl" is a straight or branched hydrocarbon containing normal, secondary or tertiary carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkynyl" is a straight or branched hydrocarbon containing normal, secondary or tertiary carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkyne), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

The term "halo" or "halogen" as used herein refers to fluoro, chloro, bromo and iodo.

The term "haloalkyl" as used herein refers to an alkyl as defined herein, wherein one or more hydrogen atoms are each replaced by a halo substituent. For example, a $(C_1$-$C_6)$haloalkyl is a $(C_1$-$C_6)$alkyl wherein one or more of the hydrogen atoms have been replaced by a halo substituent. Such a range includes one halo substituent on the alkyl group to complete halogenation of the alkyl group.

The term "aryl" as used herein refers to a single aromatic ring or a bicyclic or multicyclic ring. For example, an aryl group can have 6 to 20 carbon atoms, 6 to 14 carbon atoms, or 6 to 12 carbon atoms. Aryl includes a phenyl radical or an ortho-fused bicyclic or multicyclic radical having about 9 to 14 atoms in which at least one ring is aromatic (e.g. an aryl fused to one or more aryl or carbocycle). Such bicyclic or multicyclic rings may be optionally substituted with one or more (e.g. 1, 2 or 3) oxo groups on any carbocycle portion of the bicyclic or multicyclic ring. It is to be understood that the point of attachment of a bicyclic or multicyclic radical, as defined above, can be at any position of the ring including an aryl or a carbocycle portion of the ring. Typical aryl groups include, but are not limited to, phenyl, indenyl, naphthyl, 1,2,3,4-tetrahydronaphthyl, anthracenyl, and the like.

"Arylalkyl" refers to an alkyl radical as defined herein in which one of the hydrogen atoms bonded to a carbon atom is replaced with an aryl radical as described herein (i.e., an aryl-alkyl-moiety). The alkyl group of the "arylalkyl" is typically 1 to 6 carbon atoms (i.e. aryl($C_1$-$C_6$)alkyl). Arylalkyl groups include, but are not limited to, benzyl, 2-phenylethan-1-yl, 1-phenylpropan-1-yl, naphthylmethyl, 2-naphthylethan-1-yl and the like.

The term "heteroaryl" as used herein refers to a single aromatic ring or a multiple condensed ring. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2 or 3 rings) wherein a heteroaryl group, as defined above, can be fused with one or more heteroaryls (e.g. naphthyridinyl), carbocycles (e.g. 5,6,7,8-tetrahydroquinolyl) or aryls (e.g. indazolyl) to form a multiple condensed ring. Such multiple condensed rings may be optionally substituted with one or more (e.g. 1, 2 or 3) oxo groups on the carbocycle portions of the condensed ring. It is to be understood that the point of attachment of a heteroaryl multiple condensed ring, as defined above, can be at any position of the ring including a heteroaryl, aryl or a carbocycle portion of the ring. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl and thianaphthenyl.

The term "heterocyclyl" or "heterocycle" as used herein refers to a single saturated or partially unsaturated ring or a multiple condensed ring system. The term includes single saturated or partially unsaturated ring (e.g. 3, 4, 5, 6 or 7-membered ring) from about 1 to 6 carbon atoms and from about 1 to 3 heteroatoms selected from the group consisting of oxygen, nitrogen and sulfur in the ring. The ring may be substituted with one or more (e.g. 1, 2 or 3) oxo groups and the sulfur and nitrogen atoms may also be present in their oxidized forms. Such rings include but are not limited to azetidinyl, tetrahydrofuranyl or piperidinyl. The term also includes multiple condensed ring systems (e.g. ring systems comprising 2 or 3 rings) wherein a heterocycle group (as defined above) can be connected to two adjacent atoms (fused heterocycle) with one or more heterocycles (e.g. decahydronapthyridinyl), heteroaryls (e.g. 1,2,3,4-tetrahydronaphthyridinyl), carbocycles (e.g. decahydroquinolyl) or aryls. It is to be understood that the point of attachment of a heterocycle multiple condensed ring, as defined above, can be at any position of the ring including a heterocycle, heteroaryl, aryl or a carbocycle portion of the ring. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl and 1,4-benzodioxanyl.

The term "bridged-heterocycle" as used herein refers to a 4, 5, 6, 7 or 8-membered heterocycle as defined herein connected at two non-adjacent atoms of the 4, 5, 6, 7 or 8-membered heterocycle with one or more (e.g. 1 or 2) 3, 4, 5 or 6-membered heterocycles or a ($C_3$-$C_7$)carbocycles as defined herein. Such bridged-heterocycles include bicyclic and tricyclic ring systems (e.g. 2-azabicyclo[2.2.1]heptane and 4-azatricyclo[4.3.1.1$^{3,8}$]undecane).

The term "spiro-heterocycle" as used herein refers to a 3, 4, 5, 6, 7 or 8-membered heterocycle as defined herein connected to one or more (e.g. 1 or 2) single atoms of the 3, 4, 5, 6, 7 or 8-membered heterocycle with one or more (e.g. 1 or 2) 3, 4, 5, 6-membered heterocycles or a ($C_3$-$C_7$)carbocycles as defined herein. Such spiro-heterocycles include bicyclic and tricyclic ring systems (e.g. 1,4-dioxaspiro[4.5]dec-7-enyl).

The term "macroheterocycle" as used herein refers to a saturated or partially unsaturated 8, 9, 10, 11 or 12-membered ring comprising about 5 to 11 carbon atoms and about 1 to 3 heteroatoms selected from the group consisting of oxygen, nitrogen and sulfur in the ring which may be optionally fused at two adjacent atoms of the macroheterocycle to one or more (e.g. 1, 2 or 3) aryls, carbocycles, heteroaryls or heterocycles. The macroheterocycle may be substituted with one or more (e.g. 1, 2 or 3) oxo groups and the sulfur and nitrogen atoms may also be present in their oxidized forms.

"Heteroarylalkyl" refers to an alkyl radical as defined herein in which one of the hydrogen atoms bonded to a carbon atom is replaced with a heteroaryl radical as described herein (i.e., a heteroaryl-alkyl-moiety). The alkyl group of the "heteroarylalkyl" is typically 1 to 6 carbon atoms (i.e. heteroaryl ($C_1$-$C_6$)alkyl). Heteroarylalkyl groups include, but are not limited to heteroaryl-$CH_2$—, heteroaryl-$CH(CH_3)$—, heteroaryl-$CH_2CH_2$—, 2-(heteroaryl)ethan-1-yl, and the like, wherein the "heteroaryl" portion includes any of the heteroaryl groups described above. One skilled in the art will also understand that the heteroaryl group can be attached to the alkyl portion of the heteroarylalkyl by means of a carbon-carbon bond or a carbon-heteroatom bond, with the proviso that the resulting group is chemically stable. Examples of heteroarylalkyls include by way of example and not limitation 5-membered sulfur, oxygen, and/or nitrogen containing heteroaryls such as thiazolylmethyl, 2-thiazolylethan-1-yl, imidazolylmethyl, oxazolylmethyl, thiadiazolylmethyl, etc., 6-membered sulfur, oxygen, and/or nitrogen containing heteroaryls such pyridinylmethyl, pyridizylmethyl, pyrimidylmethyl, pyrazinylmethyl, etc.

"Heterocyclylalkyl" refers to an alkyl radical as defined herein in which one of the hydrogen atoms bonded to a carbon atom is replaced with a heterocyclyl radical as described herein (i.e., a heterocyclyl-alkyl-moiety). The alkyl group of the "heterocyclylalkyl" is typically 1 to 6 carbon atoms (i.e. heterocyclyl($C_1$-$C_6$)alkyl). Typical heterocyclylalkyl groups include, but are not limited to heterocyclyl-$CH_2$—, heterocyclyl-$CH(CH_3)$—, heterocyclyl-$CH_2CH_2$—, 2-(heterocyclyl)ethan-1-yl, and the like, wherein the "heterocyclyl" portion includes any of the heterocyclyl groups described above. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. Examples of heterocyclylalkyls include by way of example and not limitation 5-membered sulfur, oxygen, and/or nitrogen containing heterocycles such tetrahydrofuranylmethyl and pyrroldinylmethyl, etc., and 6-membered sulfur, oxygen, and/or nitrogen containing heterocycles such as piperidinylmethyl, piperazinylmethyl, morpholinylmethyl, etc.

The term "carbocycle" or "carbocyclyl" refers to a saturated (i.e., cycloalkyl) or partially unsaturated (e.g., cycloalkenyl, cycloalkadienyl, etc.) ring having 3 to 7 carbon atoms as a monocycle or a multicyclic ring system. In one embodiment the carbocycle is a monocycle comprising 3-6 ring carbons (i.e. ($C_1$-$C_6$)carbocycle). Carbocycle includes multicyclic carbocycles have 7 to 12 carbon atoms as a bicycle, and up to about 20 carbon atoms as a polycycle provided that the largest single ring of a multicyclic carbocycle is 7 carbon atoms. The term "spiro-bicyclic carbocycle" refers to a carbocycle bicyclic ring system wherein the rings of the bicyclic ring system are connected to a single carbon atom (e.g. spiropentane, spiro[4,5]decane, spiro[4.5]decane, etc). The term "fused-bicyclic carbocycle" refers to a carbocycle bicyclic ring system wherein the rings of the bicyclic ring system are connected to two adjacent carbon atoms such as a bicyclo[4,5], [5,5], [5,6] or [6,6]system, or 9 or 10 ring atoms arranged as a bicyclo[5,6] or [6,6]system (e.g. decahydronaphthalene, norsabinane, norcarane). The term "bridged-bicyclic carbocycle" refers to a carbocycle bicyclic ring system wherein the rings of the bicyclic ring system are connected to two non-adjacent carbon atoms (e.g. norbornane, bicyclo[2.2.2] octane, etc). The "carbocycle" or "carbocyclyl" may be optionally substituted with one or more (e.g. 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

The term "halocarbocycle" as used herein refers to a carbocycle as defined herein, wherein one or more hydrogen atoms are each replaced by a halo substituent. For example, ($C_3$-$C_7$)halocarbocycle is a ($C_3$-$C_7$)carbocycle wherein one or more of the hydrogen atoms have been replaced by a halo substituent. Such a range includes one halo substituent on the carbocycle group to complete halogenation of the carbocycle group.

The term "macrocarbocycle" as used herein refers to a saturated or partially unsaturated 8, 9, 10, 11 or 12-membered ring comprising 8 to 12 carbon atoms which may be optionally fused at two adjacent atoms of the macrocarbocycle to one or more (e.g. 1, 2 or 3) aryls, carbocycles, heteroaryls or heterocycles. The macrocarbocycle may be substituted with one or more (e.g. 1, 2 or 3) oxo groups.

"Carbocyclylalkyl" refers to an alkyl radical as defined herein in which one of the hydrogen atoms bonded to a carbon atom is replaced with a carbocyclyl radical as described herein (i.e., a carbocyclyl-alkyl-moiety). The alkyl group of the "carbocyclylalkyl" is typically 1 to 6 carbon atoms (i.e. carbocyclyl($C_1$-$C_6$)alkyl). Typical carbocyclyl alkyl groups include, but are not limited to carbocyclyl-$CH_2$—, carbocyclyl-$CH(CH_3)$—, carbocyclyl-$CH_2CH_2$—, 2-(carbocyclyl)ethan-1-yl, and the like, wherein the "carbocyclyl" portion includes any of the carbocyclyl groups described above.

It is to be understood that when a variable is substituted, for example as described by the phrase "($C_1$-$C_6$)alkyl, either alone or as part of a group, is optionally substituted", the phrase means that the variable ($C_1$-$C_6$)alkyl can be substituted when it is alone and that it can also be substituted when the variable "($C_1$-$C_6$)alkyl" is part of a larger group such as for example an aryl($C_1$-$C_6$)alkyl or a —($C_1$-$C_6$)alkyl-$SO_2$—($C_1$-$C_6$)alkyl-($C_3$-$C_7$)carbocycle group. Similarly, when stated, other variables (e.g. ($C_1$-$C_6$)alkenyl, ($C_1$-$C_6$)alkynyl, aryl, heteroaryl, heterocycle, etc. . . . ) can also be substituted "either alone or as part of a group."

It is to be understood that certain variables of formula I that connect two chemical groups may be oriented in either direction. Thus, for the X group of formula I (e.g. O, —C(O)—, —C(O)O—, —S—, —S(O)—, —$SO_2$—, —($C_1$-$C_6$) alkylO—, —($C_1$-$C_6$)alkylC(O)—, —($C_1$-$C_6$)alkylC(O)O—, —($C_1$-$C_6$)alkylS—, —($C_1$-$C_6$)alkylS(O)— and —($C_1$-$C_6$) alkyl$SO_2$—) certain values of X that are not symmetric can be oriented in either direction. For example, the —C(O)O—, can be oriented as either —C(O)O— or —OC(O)—, relative to the groups it connects.

One skilled in the art will recognize that substituents and other moieties of the compounds of formula I should be selected in order to provide a compound which is sufficiently stable to provide a pharmaceutically useful compound which can be formulated into an acceptably stable pharmaceutical composition. Compounds of formula I which have such stability are contemplated as falling within the scope of the present invention.

The modifier "about" used in connection with a quantity is inclusive of the stated value and has the meaning dictated by the context (e.g., includes the degree of error associated with measurement of the particular quantity). The word "about" may also be represented symbolically by "~" in the context of a chemical measurement (e.g. ~50 mg or pH ~7).

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers or axes of chirality and whose molecules are not mirror images of one another. Diastereomers typically have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Certain compounds of the invention can exist as atropisomers. For example, it has been discovered that atropisomers exist for certain substituents at the $R^4$ position of formula I as marked by an asterisk in the formula below.

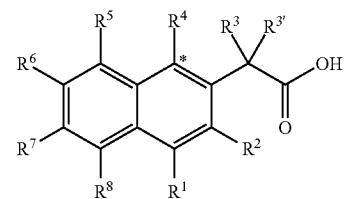

The chirality that results from the atropisomers at the asterisk position is a feature of certain compounds of the invention. Accordingly, the invention includes all atropisomers of compounds of the invention including mixtures of atropisomers and well as mixtures that are enriched in an atropisomer as well as single atropisomers, which mixtures or compounds possess the useful properties described herein.

In one embodiment, the compounds of the invention of formula I are at least 60% a single atropisomer for the $R^4$ substituent at the asterisk position. In another embodiment, the compounds of the invention of formula I are at least 70% a single atropisomer for the $R^4$ substituent at the asterisk position. In another embodiment, the compounds of the invention of formula I are at least 80% a single atropisomer for the $R^4$ substituent at the asterisk position. In another embodiment, the compounds of the invention of formula I are at least 90% a single atropisomer for the $R^4$ substituent at the asterisk position. In another embodiment, the compounds of the invention of formula I are at least 95% a single atropisomer for the $R^4$ substituent at the asterisk position. In one embodiment the stereochemistry for the $R^4$ substituent at the carbon marked with an asterisk as shown above for Formula I is the (R) stereochemistry. In another embodiment the stereochemistry for the $R^4$ substituent at the carbon marked with an asterisk as shown above for Formula I is the (S) stereochemistry.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes (D and L) or (R and S) are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. PGs do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether-nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below.

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures can be separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

Examples of pharmaceutically acceptable salts of the compounds of the invention include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a hydrogen atom or an amino group include for example salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, hydrobromic, sulfuric, phosphoric and sulfamic acids. Pharmaceutically acceptable salts of a compound of a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will typically be pharmaceutically acceptable, i.e. they will be salts derived from a physiologically acceptable acid or base. However, salts of acids or bases which are not pharmaceutically acceptable may also find use, for example, in the preparation or purification of a compound of formula I or another compound of the invention. All salts, whether or not derived from a physiologically acceptable acid or base, are within the scope of the present invention.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble metal salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the natural or unnatural amino acids are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Specific values listed below for radicals, substituents, and ranges in the embodiments of the invention are for illustration only; they do not exclude other defined values or other values within defined ranges for the radicals and substituents.

Isotopes

It is understood by one skilled in the art that this invention also includes any compound claimed that may be enriched at any or all atoms above naturally occurring isotopic ratios with one or more isotopes such as, but not limited to, deuterium ($^2H$ or D). As a non-limiting example, a —$CH_3$ group may be substituted with —$CD_3$.

Compounds of Formula I.

A specific group of compounds of formula I are compounds of formula Ia.

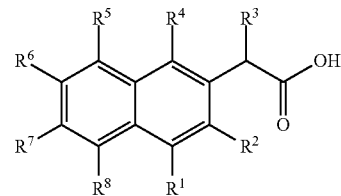

Ia

Another specific group of compounds of formula I are compounds of formula Ib.

Ib

Another specific group of compounds of formula I are compounds of formula Ic.

Ic

Another specific group of compounds of formula I are compounds of formula Id.

Id

Another specific group of compounds of formula I are compounds of formula Ie.

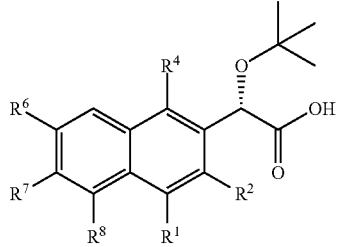

Ie

Another specific group of compounds of formula I are compounds of formula If.

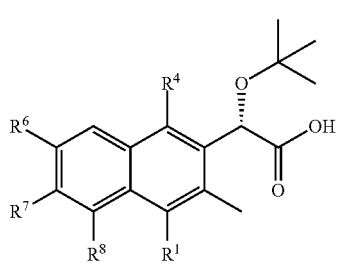

If

Another specific group of compounds of formula I are compounds of formula Ig.

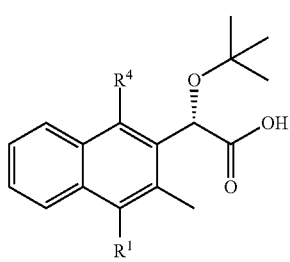

Ig

Another specific group of compounds of formula I are compounds of formula Ih.

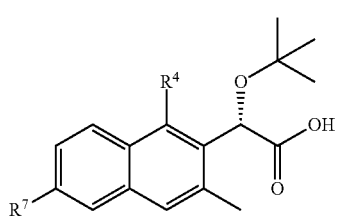

Ih

Another specific group of compounds of formula I are compounds of formula Ii.

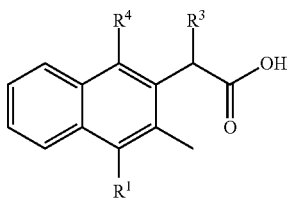

Ii

Another specific group of compounds of formula I are compounds of formula Ij.

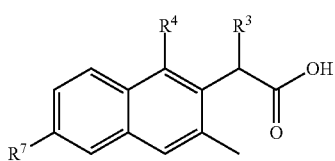

Ij

Another specific group of compounds of formula I are compounds of formula Ik.

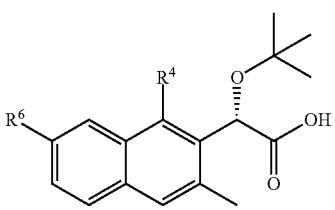

Ik

Another specific group of compounds of formula I are compounds of formula Im.

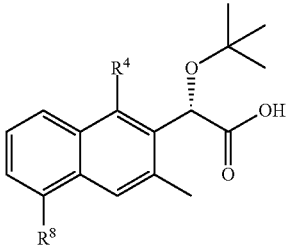

Im

Another specific group of compounds of formula I are compounds of formula In.

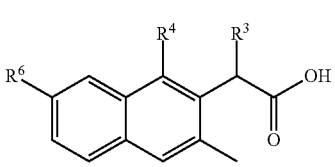

In

Another specific group of compounds of formula I are compounds of formula Io.

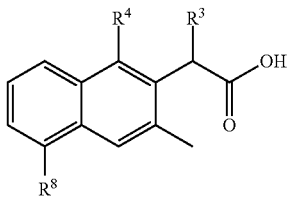

Specific values listed below are values for compounds of formula I as well as the compounds of formula Ia, Ib, Ic, Id, Ie, If, Ig, Ih, Ii, Ij, Ik, Im, In and Io.

A specific group of compounds of formula I are compounds wherein at least one of $R^1$, $R^2$, $R^3$, $R^{3'}$, $R^4$, $R^5$, $R^6$, $R^7$, or $R^8$ is selected from $R^{1b}$, $R^{2b}$, $R^{3b}$, $R^{3b'}$, $R^{4b}$, $R^{5b}$, $R^{6b}$, $R^{7b}$ and $R^{8b}$.

Another specific group of compounds of formula I are compounds wherein at least two of $R^1$, $R^2$, $R^3$, $R^{3'}$, $R^4$, $R^5$, $R^6$, $R^7$, or $R^8$ are selected from $R^{1b}$, $R^{2b}$, $R^{3b}$, $R^{3b'}$, $R^{4b}$, $R^{5b}$, $R^{6b}$, $R^{7b}$ and $R^{8b}$.

Another specific group of compounds of formula I are compounds wherein at least three of $R^1$, $R^2$, $R^3$, $R^{3'}$, $R^4$, $R^5$, $R^6$, $R^7$, or $R^8$ are independently selected from $R^{1b}$, $R^{2b}$, $R^{3b}$, $R^{3b'}$, $R^{4b}$, $R^{5b}$, $R^{6b}$, $R^{7b}$ and $R^{8b}$.

Another specific group of compounds of formula I are compounds wherein at least four of $R^1$, $R^2$, $R^3$, $R^{3'}$, $R^4$, $R^5$, $R^6$, $R^7$, or $R^8$ are selected from $R^{1b}$, $R^{2b}$, $R^{3b}$, $R^{3b'}$, $R^{4b}$, $R^{5b}$, $R^{6b}$, $R^{7b}$ and $R^{8b}$.

Another specific group of compounds of formula I wherein at least five of $R^1$, $R^2$, $R^3$, $R^{3'}$, $R^4$, $R^5$, $R^6$, $R^7$, or $R^8$ are selected from $R^{1b}$, $R^{2b}$, $R^{3b}$, $R^{3b'}$, $R^{4b}$, $R^{5b}$, $R^{6b}$, $R^{7b}$ and $R^{8b}$.

Another specific group of compounds of formula I wherein at least six of $R^1$, $R^2$, $R^3$, $R^{3'}$, $R^4$, $R^5$, $R^6$, $R^7$, or $R^8$ are independently selected from $R^{1b}$, $R^{2b}$, $R^{3b}$, $R^{3b'}$, $R^{4b}$, $R^{5b}$, $R^{6b}$, $R^{7b}$, or $R^{8b}$.

Another specific group of compounds of formula I wherein at least seven of $R^1$, $R^2$, $R^3$, $R^{3'}$, $R^4$, $R^5$, $R^6$, $R^7$, or $R^8$ are independently selected from $R^{1b}$, $R^{2b}$, $R^{3b}$, $R^{3b'}$, $R^{4b}$, $R^{5b}$, $R^{6b}$, $R^{7b}$ and $R^{8b}$.

Another specific group of compounds of formula I wherein at least eight of $R^1$, $R^2$, $R^3$, $R^{3'}$, $R^4$, $R^5$, $R^6$, $R^7$, or $R^8$ are independently selected from $R^{1b}$, $R^{2b}$, $R^{3b}$, $R^{3b'}$, $R^{4b}$, $R^{5b}$, $R^{6b}$, $R^{7b}$ and $R^{8b}$.

Another specific group of compounds of formula I wherein $R^1$, $R^2$, $R^3$, $R^{3'}$, $R^4$, $R^5$, $R^6$, $R^7$ and $R^8$ are $R^{1b}$, $R^{2b}$, $R^{3b}$, $R^{3b'}$, $R^{4b}$, $R^{5b}$, $R^{6b}$, $R^{7b}$ and $R^{8b}$.

A specific value for $R^3$ is $R^{3b}$.

A specific value for $R^{3b}$ is —OC(CH$_3$)$_2$CH$_2$OH, —OC(CH$_3$)$_2$CH$_2$OH, —O(C$_1$-C$_6$)alkyl-O—C(O)—NH$_2$, —O(C$_1$-C$_6$)alkyl-O—C(O)—N(CH$_3$)$_2$ or —O(C$_1$-C$_6$)alkyl-O—C(O)—NH(phenyl).

Another specific value for $R^{3b}$ is —(C$_1$-C$_6$)alkylOH or —O(C$_1$-C$_6$)alkyl-O—C(O)—NR$_c$R$_d$.

Another specific value for $R^3$ is $R^{3a}$

A specific value for $R^{3a}$ is (C$_1$-C$_6$)alkyl, (C$_2$-C$_6$)alkenyl or —O(C$_1$-C$_6$)alkyl, wherein any (C$_1$-C$_6$)alkyl or (C$_2$-C$_6$)alkenyl of $R^{3a}$ is optionally substituted with one or more groups selected from —O(C$_1$-C$_6$)alkyl, halo, oxo and —CN.

Another specific value for $R^{3a}$ is —OC(CH$_3$).

A specific value for $R^{3'}$ is $R^{3b'}$.

A specific value for $R^{3b'}$ is (C$_1$-C$_6$)alkyl or —O(C$_1$-C$_6$) alkyl.

A specific value for $R^{3'}$ is $R^{3a'}$.

A specific value for $R^{3a'}$ is H.

A specific group of compounds of formula I are compounds wherein $R^{3b}$ and $R^{3b'}$ together with the carbon to which they are attached form a (C$_3$-C$_7$)carbocycle or heterocycle, wherein the (C$_3$-C$_7$)carbocycle or heterocycle is optionally substituted with one or more $Z^1$ groups.

Another specific group of compounds of formula I are compounds wherein $R^{3b}$ and $R^{3b'}$ together with the carbon to which they are attached form a (C$_3$-C$_7$)carbocycle or a 4, 5 or 6-membered heterocycle, wherein the (C$_3$-C$_7$)carbocycle or the 4, 5 or 6-membered heterocycle is optionally substituted with one or more $Z^1$ groups.

Another specific group of compounds of formula I are compounds wherein $R^{3b}$ and $R^{3b'}$ together with the carbon to which they are attached form a (C$_4$-C$_6$)carbocycle or a 5 or 6-membered heterocycle, wherein the (C$_4$-C$_6$)carbocycle or the 5 or 6-membered heterocycle is optionally substituted with one or more $Z^1$ groups.

Another specific group of compounds of formula I are compounds wherein $R^{3b}$ and $R^{3b'}$ together with the carbon to which they are attached form a 5 or 6-membered heterocycle, wherein the 5 or 6-membered heterocycle is optionally substituted with one or more $Z^1$ groups.

Another specific group of compounds of formula I are compounds wherein $R^{3b}$ and $R^{3b'}$ together with the carbon to which they are attached form a tetrahydropyran or tetrahydrofuran optionally substituted with one or more $Z^1$ groups.

Another specific group of compounds of formula I are compounds wherein $R^{3b}$ and $R^{3b'}$ together with the carbon to which they are attached form:

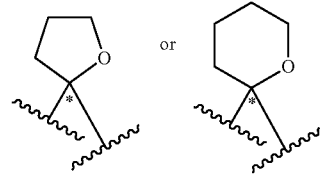 [SMILES: *C1(*)CCCO1 ; *C1(*)CCCCO1]

each of which is optionally substituted with one or more $Z^1$ groups; and wherein "*" denotes the point of attachment to the carbon of the compound of formula I.

A specific value for $R^4$ is $R^{4b}$.

A specific value for $R^{4b}$ is (C$_1$-C$_6$)alkyl, (C$_2$-C$_6$)alkenyl or (C$_2$-C$_6$)alkynyl, wherein (C$_1$-C$_6$)alkyl, (C$_2$-C$_6$)alkenyl and (C$_2$-C$_6$)alkynyl are each optionally substituted with one or more $Z^1$ groups.

Another specific value for $R^{4b}$ is:

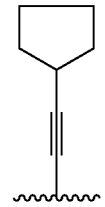

optionally substituted with one or more $Z^1$ groups.

Another specific value for $R^{4b}$ is (C$_3$-C$_7$)carbocycle, wherein (C$_3$-C$_7$)carbocycle is optionally substituted with one or more $Z^1$ groups, or wherein two $Z^1$ groups together with the atom or atoms to which they are attached optionally form a (C$_3$-C$_6$)carbocycle or 5-6-membered heterocycle.

Another specific value for $R^{4b}$ is:

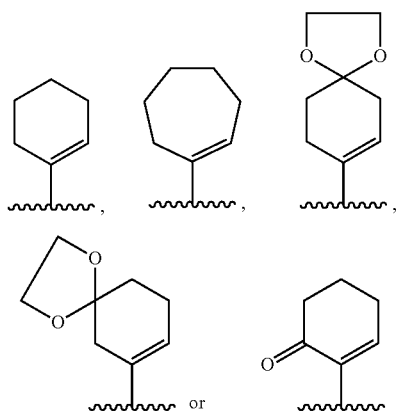

each of which is optionally substituted with one or more $Z^1$ groups.

Another specific value for $R^{4b}$ is aryl, heterocycle or heteroaryl, wherein aryl, heterocycle and heteroaryl are each independently substituted with one or more $Z^7$ groups and optionally substituted with one or more $Z^1$ groups.

Another specific value for $R^{4b}$ is:

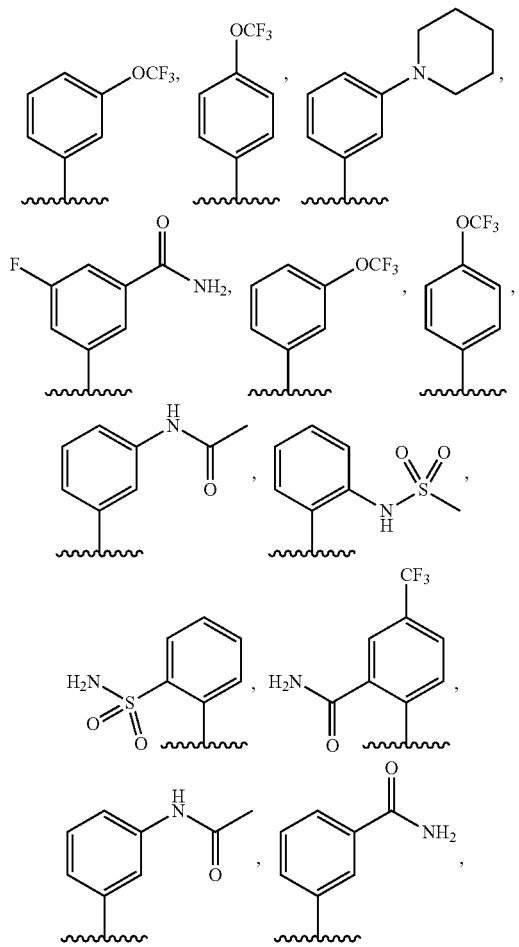

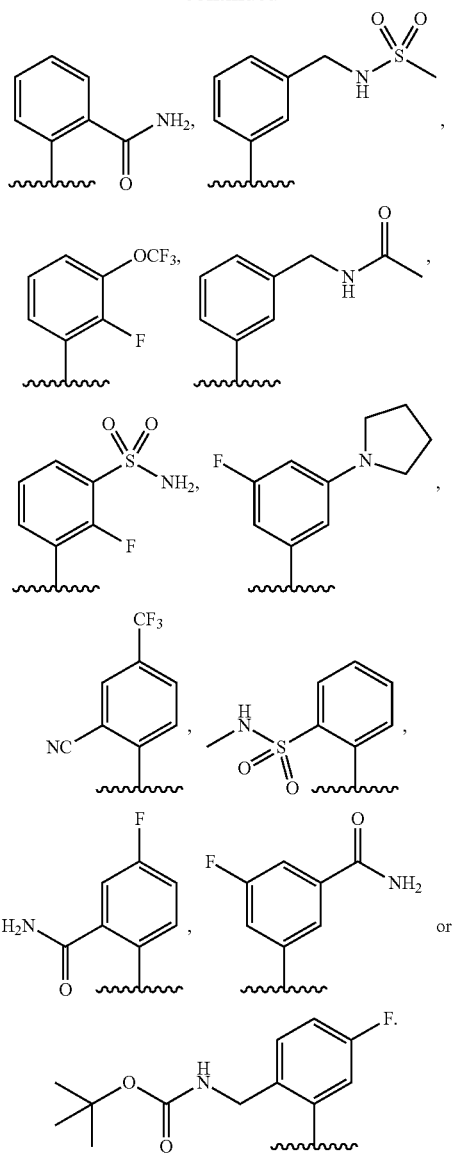

Another specific value for $R^4$ is $R^{4a}$.

A specific value for $R^{4a}$ is:

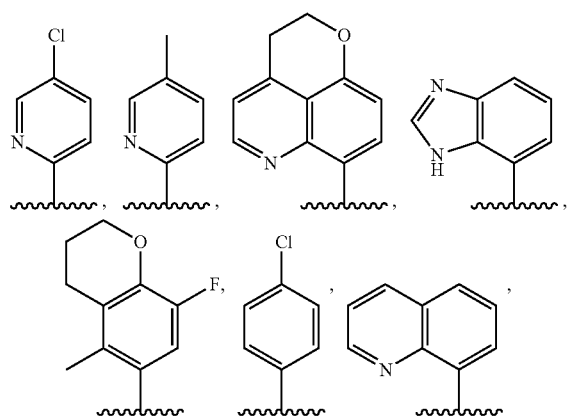

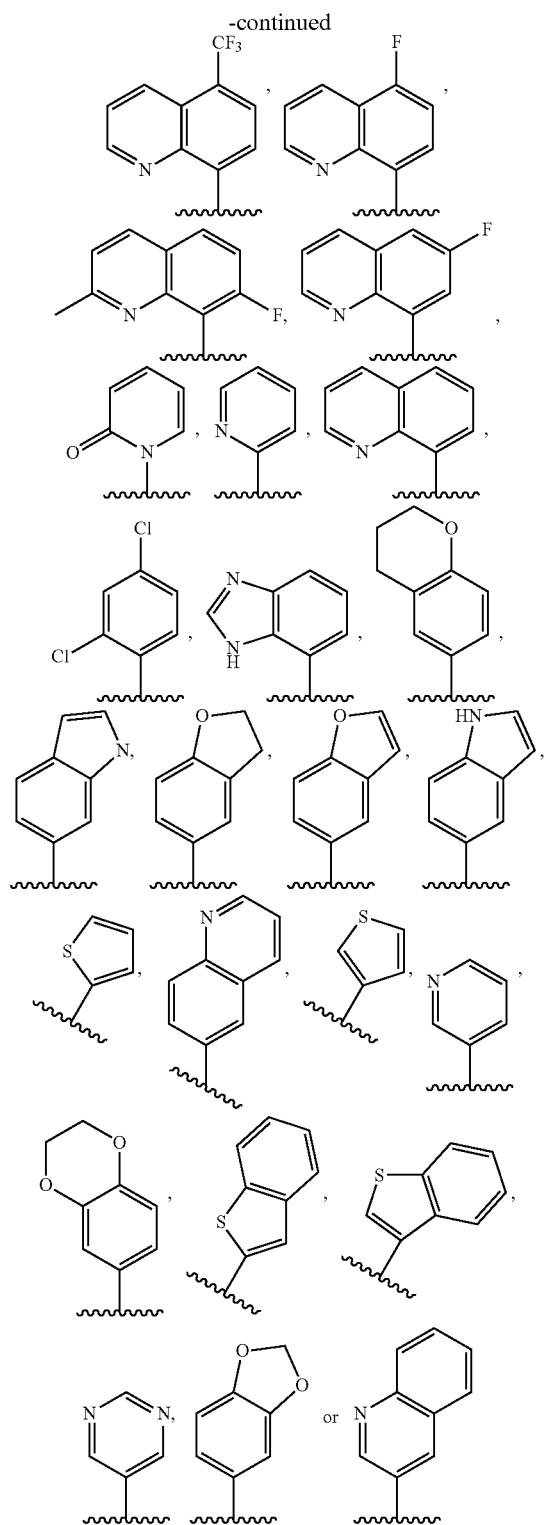

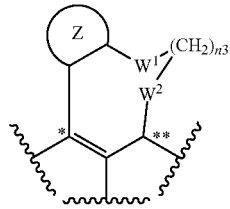

A specific group of compounds of formula I are compounds wherein $R^4$ and $R^3$ together with the atoms to which they are attached form a macroheterocycle or a macrocarbocycle, wherein any macroheterocycle or macrocarbocycle of $R^4$ and $R^3$ together with the atoms to which they are attached may be optionally substituted with one or more $Z^1$ groups; and $R^{3'}$ is H, $(C_1\text{-}C_6)$alkyl or $-O(C_1\text{-}C_6)$alkyl.

Another specific value for $R^{3'}$ is H.

Another specific group of compounds of formula I are compounds wherein $R^4$ and $R^3$ together with the atoms to which they are attached form the macroheterocycle or a macrocarbocycle further fused to a Z group:

wherein:
Z is aryl, heteroaryl or $(C_3\text{-}C_6)$carbocycle;
n3 is 2, 3 or 4; and
$W^1$ and $W^2$ are each independently O, NH or $CH_2$, and
wherein "*" denotes the $R^4$ point of attachment of the macroheterocycle or macrocarbocycle to the compound of formula I and "**" denotes the $R^3$ point of attachment of the macroheterocycle or macrocarbocycle to the compound of formula I, and wherein the macroheterocycle or a macrocarbocycle is optionally substituted with one or more $Z^1$ groups.

Another specific group of compounds of formula I are compounds wherein, $R^4$ and $R^3$ together with the atoms to which they are attached form the macroheterocycle:

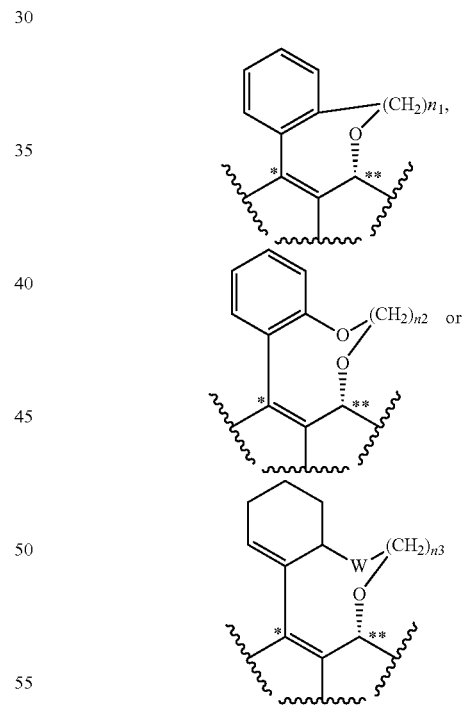

wherein:
n1 is 3 or 4; n2 is 2, 3 or 4; n3 is 2, 3 or 4; W is O, NH or $N(C_1\text{-}C_4)$alkyl; and wherein "*" denotes the $R^4$ point of attachment of the macroheterocycle to the compound of formula I and "**" denotes the $R^3$ point of attachment of the macroheterocycle to the compound of formula I, and wherein the macroheterocycle or a macrocarbocycle is optionally substituted with one or more $Z^1$ groups A specific value for $R^1$ is $R^{1b}$.
Another specific value $R^1$ is $R^{1a}$.

A specific value for $R^{1a}$ is H or —$CH_3$.
A specific value for $R^2$ is $R^{2b}$.
Another specific value $R^2$ is $R^{2a}$
A specific value for $R^{2a}$ is H or —$CH_3$.
A specific value for $R^5$ is $R^{5b}$
Another specific value for $R^5$ is $R^{5a}$
A specific value for $R^{5a}$ is H.
A specific value for $R^6$ is $R^{6b}$.
Another specific value for $R^6$ is $R^{6a}$.
A specific value for $R^{6a}$ is H.
A specific value for $R^7$ is $R^{7b}$.
Another specific value for $R^7$ is $R^{7a}$.
A specific value for $R^{7a}$ is H, —$CH_3$ or halogen.
A specific value for $R^8$ is $R^{8b}$.
Another specific value for $R^8$ is $R^{8a}$.
Another specific value for $R^{8a}$ is H.

A specific group of compounds of formula I are compounds wherein $R^{4b}$ is selected from;
  a) $(C_1-C_6)$alkyl, $(C_2-C_6)$alkenyl and $(C_2-C_6)$alkynyl, wherein $(C_1-C_6)$alkyl, $(C_2-C_6)$alkenyl and $(C_2-C_6)$alkynyl are each optionally substituted with one or more (e.g. 1, 2, 3, 4 or 5) $Z^1$ groups;
  b) $(C_3-C_{14})$carbocycle, wherein $(C_3-C_{14})$carbocycle is optionally substituted with one or more (e.g. 1, 2, 3, 4 or 5) $Z^1$ groups;
  c) Spiro-heterocycle and bridged-heterocycle, wherein spiro-heterocycle and bridged-heterocycle are each optionally substituted with one or more (e.g. 1, 2, 3, 4 or 5) $Z^1$ groups; and
  d) aryl, heterocycle and heteroaryl, wherein aryl, heterocycle and heteroaryl are each independently substituted with one or more $Z^7$ groups and optionally substituted with one or more (e.g. 1, 2, 3, 4 or 5) $Z^1$ groups; or Another specific group of compounds of formula I are compounds wherein $R^{4b}$ is selected from;
  a) $(C_1-C_6)$alkyl, $(C_2-C_6)$alkenyl and $(C_2-C_6)$alkynyl, wherein $(C_1-C_6)$alkyl, $(C_2-C_6)$alkenyl and $(C_2-C_6)$alkynyl are each optionally substituted with one or more (e.g. 1, 2, 3, 4 or 5) $Z^1$ groups;
  b) $(C_3-C_{14})$carbocycle, wherein $(C_3-C_{14})$carbocycle is optionally substituted with one or more (e.g. 1, 2, 3, 4 or 5) $Z^1$ groups, wherein two $Z^1$ groups together with the atom or atoms to which they are attached optionally form a $(C_3-C_7)$ carbocycle or heterocycle; and
  c) aryl, heterocycle and heteroaryl, wherein aryl, heterocycle and heteroaryl are each independently substituted with one or more $Z^7$ groups and optionally substituted with one or more (e.g. 1, 2, 3, 4 or 5) $Z^1$ groups; or Another specific group of compounds of formula I are compounds wherein $R^{4b}$ is selected from;
  a) $(C_1-C_6)$alkyl, $(C_2-C_6)$alkenyl and $(C_2-C_6)$alkynyl, wherein $(C_1-C_6)$alkyl, $(C_2-C_6)$alkenyl and $(C_2-C_6)$alkynyl are each optionally substituted with one or more (e.g. 1, 2, 3, 4 or 5) $Z^1$ groups;
  b) $(C_3-C_{14})$carbocycle, wherein $(C_3-C_{14})$carbocycle is optionally substituted with one or more (e.g. 1, 2, 3, 4 or 5) $Z^1$ groups; and
  c) aryl, heterocycle and heteroaryl, wherein aryl, heterocycle and heteroaryl are each independently substituted with one or more $Z^7$ groups and optionally substituted with one or more (e.g. 1, 2, 3, 4 or 5) $Z^1$ groups.

Another specific group of compounds of formula I are compounds wherein $R^3$ is $(C_1-C_6)$alkyl, $(C_2-C_6)$alkenyl or —$O(C_1-C_6)$alkyl, wherein any $(C_1-C_6)$alkyl or $(C_2-C_6)$alkenyl of $R^3$ is optionally substituted with one or more groups selected from —$O(C_1-C_6)$alkyl, halo, oxo and —CN, and wherein $R^{3'}$ is H.

Another specific group of compounds of formula I are compounds wherein $R^4$ is selected from:
  a) aryl, heterocycle and heteroaryl, wherein aryl, heterocycle and heteroaryl are each optionally substituted with one or more groups each independently selected from halo, $(C_1-C_6)$alkyl, $(C_2-C_6)$alkenyl, $(C_1-C_6)$haloalkyl, $(C_3-C_7)$cycloalkyl, —OH, —$O(C_1-C_6)$alkyl, —SH, —$S(C_1-C_6)$alkyl, —$NH_2$, —$NH(C_1-C_6)$alkyl and —$N((C_1-C_6)$alkyl$)_2$, wherein $(C_1-C_6)$alkyl is optionally substituted with hydroxy, —$O(C_1-C_6)$alkyl, cyano or oxo;
  b) $(C_3-C_{14})$carbocycle, wherein $(C_3-C_{14})$carbocycle is optionally substituted with one or more $Z^1$ groups, wherein two $Z^1$ groups together with the atom or atoms to which they are attached optionally form a $(C_3-C_7)$carbocycle or heterocycle; and
  c) aryl, heteroaryl and fused-heterocycle, wherein aryl, heteroaryl and fused-heterocycle are each independently substituted with one or more $Z^7$ groups and optionally substituted with one or more $Z^1$ groups.

Another specific group of compounds of formula I are compounds wherein $R^4$ is selected from:
  a) aryl, heterocycle and heteroaryl, wherein aryl, heterocycle and heteroaryl are each optionally substituted with one or more groups each independently selected from halo, $(C_1-C_6)$alkyl, $(C_2-C_6)$alkenyl, $(C_1-C_6)$haloalkyl, $(C_3-C_7)$cycloalkyl, —OH, —$O(C_1-C_6)$alkyl, —SH, —$S(C_1-C_6)$alkyl, —$NH_2$, —$NH(C_1-C_6)$alkyl and —$N((C_1-C_6)$alkyl$)_2$, wherein $(C_1-C_6)$alkyl is optionally substituted with hydroxy, —$O(C_1-C_6)$alkyl, cyano or oxo; and
  b) aryl, heteroaryl and fused-heterocycle, wherein aryl, heteroaryl and fused-heterocycle are each independently substituted with one or more $Z^7$ groups and optionally substituted with one or more $Z^1$ groups.

Another specific group of compounds of formula I are compounds wherein $R^4$ is selected from:
  a) heterocycle and heteroaryl, wherein heterocycle and heteroaryl are each optionally substituted with one or more groups each independently selected from halo, $(C_1-C_6)$alkyl, $(C_2-C_6)$alkenyl, $(C_1-C_6)$haloalkyl, $(C_3-C_7)$cycloalkyl, —OH, —$O(C_1-C_6)$alkyl, —SH, —$S(C_1-C_6)$alkyl, —$NH_2$, —NH$(C_1-C_6)$alkyl and —$N((C_1-C_6)$alkyl$)_2$, wherein $(C_1-C_6)$alkyl is optionally substituted with hydroxy, —$O(C_1-C_6)$alkyl, cyano or oxo; and
  b) heteroaryl and fused-heterocycle, wherein heteroaryl and fused-heterocycle are each independently substituted with one or more $Z^7$ groups and optionally substituted with one or more $Z^1$ groups.

Another specific group of compounds of formula I are compounds wherein $R^4$ is selected from:
  a) heterocycle, wherein heterocycle is optionally substituted with one or more groups each independently selected from halo, $(C_1-C_6)$alkyl, $(C_2-C_6)$alkenyl, $(C_1-C_6)$haloalkyl, $(C_3-C_7)$cycloalkyl, —OH, —$O(C_1-C_6)$alkyl, —SH, —$S(C_1-C_6)$alkyl, —$NH_2$, —$NH(C_1-C_6)$alkyl and —$N((C_1-C_6)$alkyl$)_2$, wherein $(C_1-C_6)$alkyl is optionally substituted with hydroxy, —$O(C_1-C_6)$alkyl, cyano or oxo; and
  b) fused-heterocycle, wherein fused-heterocycle is substituted with one or more $Z^7$ groups and optionally substituted with one or more $Z^1$ groups.

Another specific group of compounds of formula I are compounds wherein $R^4$ is selected from:
  a) bicyclic aryl, tricyclic aryl, bicyclic heterocycle, tricyclic heterocycle, bicyclic heteroaryl and tricyclic heteroaryl, wherein any bicyclic aryl, tricyclic aryl, bicyclic heterocycle, tricyclic heterocycle, bicyclic heteroaryl and tricyclic heteroaryl, is optionally substituted with one or more groups each independently selected from halo, $(C_1-C_6)$alkyl, $(C_2-C_6)$ alkenyl, $(C_1\text{-}C_6)$haloalkyl, $(C_3\text{-}C_7)$cycloalkyl, —OH, —O$(C_1\text{-}C_6)$alkyl, —SH, —S$(C_1\text{-}C_6)$alkyl, —NH$_2$, —NH$(C_1\text{-}C_6)$alkyl and —N$((C_1\text{-}C_6)$alkyl$)_2$, wherein $(C_1\text{-}C_6)$alkyl is optionally substituted with hydroxy, —O$(C_1\text{-}C_6)$alkyl, cyano or oxo; and b) bicyclic aryl, tricyclic aryl, bicyclic heteroaryl, tricyclic heteroaryl bicyclic fused-heterocycle, and tricyclic fused-heterocycle, wherein bicyclic aryl, tricyclic aryl, bicyclic heteroaryl, tricyclic heteroaryl bicyclic fused-heterocycle and tricyclic fused-heterocycle are each independently substituted with one or more $Z^7$ groups and optionally substituted with one or more $Z^1$ groups.

Another specific group of compounds of formula I are compounds wherein $R^4$ is selected from:

a) bicyclic heterocycle and tricyclic heterocycle, wherein bicyclic heterocycle and tricyclic heterocycle are each optionally substituted with one or more groups each independently selected from halo, $(C_1\text{-}C_6)$alkyl, $(C_2\text{-}C_6)$alkenyl, $(C_1\text{-}C_6)$haloalkyl, $(C_3\text{-}C_7)$cycloalkyl, —OH, —O$(C_1\text{-}C_6)$alkyl, —SH, —S$(C_1\text{-}C_6)$alkyl, —NH$_2$, —NH$(C_1\text{-}C_6)$alkyl and —N$((C_1\text{-}C_6)$alkyl$)_2$, wherein $(C_1\text{-}C_6)$alkyl is optionally substituted with hydroxy, —O$(C_1\text{-}C_6)$alkyl, cyano or oxo; and b) bicyclic fused-heterocycle and tricyclic fused-heterocycle wherein bicyclic fused-heterocycle and tricyclic fused-heterocycle fused-heterocycle are each substituted with one or more $Z^7$ groups and optionally substituted with one or more $Z^1$ groups.

Another specific group of compounds of formula I are compounds wherein $R^4$ is selected from:

a) bicyclic heterocycle, tricyclic heterocycle, bicyclic heteroaryl and tricyclic heteroaryl wherein bicyclic heterocycle, tricyclic heterocycle, bicyclic heteroaryl and tricyclic heteroaryl are each optionally substituted with one or more groups each independently selected from halo, $(C_1\text{-}C_6)$alkyl, $(C_2\text{-}C_6)$alkenyl, $(C_1\text{-}C_6)$haloalkyl, $(C_3\text{-}C_7)$cycloalkyl, —OH, —O$(C_1\text{-}C_6)$alkyl, —SH, —S$(C_1\text{-}C_6)$alkyl, —NH$_2$, —NH$(C_1\text{-}C_6)$alkyl and —N$((C_1\text{-}C_6)$alkyl$)_2$, wherein $(C_1\text{-}C_6)$alkyl is optionally substituted with hydroxy, —O$(C_1\text{-}C_6)$alkyl, cyano or oxo; and b) bicyclic fused-heterocycle and tricyclic fused-heterocycle, wherein bicyclic fused-heterocycle and tricyclic fused-heterocycle fused-heterocycle are each substituted with one or more $Z^7$ groups and optionally substituted with one or more $Z^1$ groups.

Another specific group of compounds of formula I are compounds wherein $R^4$ is selected from:

a) tricyclic heterocycle, wherein tricyclic heterocycle is optionally substituted with one or more groups each independently selected from halo, $(C_1\text{-}C_6)$alkyl, $(C_2\text{-}C_6)$alkenyl, $(C_1\text{-}C_6)$haloalkyl, $(C_3\text{-}C_7)$cycloalkyl, —OH, —O$(C_1\text{-}C_6)$alkyl, —SH, —S$(C_1\text{-}C_6)$alkyl, —NH$_2$, —NH$(C_1\text{-}C_6)$alkyl and —N$((C_1\text{-}C_6)$alkyl$)_2$, wherein $(C_1\text{-}C_6)$alkyl is optionally substituted with hydroxy, —O$(C_1\text{-}C_6)$alkyl, cyano or oxo; and b) tricyclic fused-heterocycle, wherein tricyclic fused-heterocycle fused-heterocycle is substituted with one or more $Z^7$ groups and optionally substituted with one or more $Z^1$ groups.

Another specific group of compounds of formula I are compounds wherein $R^4$ is selected from:

a) $(C_3\text{-}C_{14})$carbocycle, wherein $(C_3\text{-}C_{14})$carbocycle is optionally substituted with one or more $Z^1$ groups, wherein two $Z^1$ groups together with the atom or atoms to which they are attached optionally form a $(C_3\text{-}C_7)$carbocycle or heterocycle; and b) aryl, heteroaryl and fused-heterocycle, wherein aryl, heteroaryl and fused-heterocycle are each independently substituted with one or more $Z^7$ groups and optionally substituted with one or more $Z^1$ groups.

Another specific group of compounds of formula I are compounds wherein $R^4$ is selected from aryl, heteroaryl and fused-heterocycle, wherein aryl, heteroaryl and fused-heterocycle are each independently substituted with one or more $Z^7$ groups and optionally substituted with one or more $Z^1$ groups.

Another specific group of compounds of formula I are compounds wherein $R^4$ is selected from fused-heterocycle, wherein fused-heterocycle is substituted with one or more $Z^7$ groups and optionally substituted with one or more $Z^1$ groups.

Another specific group of compounds of formula I are compounds wherein $R^4$ is selected from bicyclic aryl, tricyclic aryl, bicyclic heteroaryl, tricyclic heteroaryl, bicyclic fused-heterocycle and tricyclic fused-heterocycle, wherein bicyclic aryl, tricyclic aryl, bicyclic heteroaryl, tricyclic heteroaryl, bicyclic fused-heterocycle, and tricyclic fused-heterocycle are each independently substituted with one or more $Z^7$ groups and optionally substituted with one or more $Z^1$ groups.

Another specific group of compounds of formula I are compounds wherein $R^4$ is selected from bicyclic fused-heterocycle and tricyclic fused-heterocycle, wherein bicyclic fused-heterocycle and tricyclic fused-heterocycle fused-heterocycle are each substituted with one or more $Z^7$ groups and optionally substituted with one or more $Z^1$ groups.

Another specific group of compounds of formula I are compounds wherein $R^4$ is tricyclic fused-heterocycle, wherein tricyclic fused-heterocycle fused-heterocycle is substituted with one or more $Z^7$ groups and optionally substituted with one or more $Z^1$ groups.

A specific value for $Z^{10}$ is:
i) halo, $(C_1\text{-}C_6)$haloalkyl; or
ii) $(C_1\text{-}C_6)$alkyl optionally substituted with —OH, —O—$(C_1\text{-}C_6)$haloalkyl.

Another specific value for $Z^{10}$ is halo.

Another specific group of compounds of formula I are compounds wherein $R^4$ is selected from heteroaryl and fused-heterocycle, wherein heteroaryl and fused-heterocycle are each independently substituted with one or more $Z^7$ groups and optionally substituted with one or more $Z^1$ groups.

Another specific group of compounds of formula I are compounds wherein $R^4$ is fused-heterocycle, wherein fused-heterocycle is substituted with one or more $Z^7$ groups and optionally substituted with one or more $Z^1$ groups.

Another specific group of compounds of formula I are compounds wherein $R^4$ is selected from bicyclic aryl, tricyclic aryl, bicyclic heteroaryl, tricyclic heteroaryl bicyclic fused-heterocycle, and tricyclic fused-heterocycle, wherein bicyclic aryl, tricyclic aryl, bicyclic heteroaryl, tricyclic heteroaryl bicyclic fused-heterocycle and tricyclic fused-heterocycle are each independently substituted with one or more $Z^7$ groups and optionally substituted with one or more $Z^1$ groups.

Another specific group of compounds of formula I are compounds wherein $R^4$ is selected from bicyclic fused-heterocycle and tricyclic fused-heterocycle wherein bicyclic fused-heterocycle and tricyclic fused-heterocycle fused-heterocycle are each substituted with one or more $Z^7$ groups and optionally substituted with one or more $Z^1$ groups.

Another specific group of compounds of formula I are compounds wherein $R^4$ is selected from tricyclic heterocycle, wherein tricyclic heterocycle is optionally substituted with one or more groups each independently selected from halo, $(C_1\text{-}C_6)$alkyl, $(C_2\text{-}C_6)$alkenyl, $(C_1\text{-}C_6)$haloalkyl, $(C_3\text{-}C_7)$cycloalkyl, —OH, —O$(C_1\text{-}C_6)$alkyl, —SH, —S$(C_1\text{-}C_6)$alkyl, —NH$_2$, —NH$(C_1\text{-}C_6)$alkyl and —N$((C_1\text{-}C_6)$alkyl$)_2$, wherein $(C_1\text{-}C_6)$alkyl is optionally substituted with hydroxy, —O$(C_1\text{-}C_6)$alkyl, cyano or oxo; and Another specific group of compounds of formula I are compounds wherein $R^4$ is selected from tricyclic fused-heterocycle, wherein tricyclic fused-heterocycle fused-heterocycle is substituted with one or more $Z^7$ groups and optionally substituted with one or more $Z^1$ groups.
Another specific value for $R^4$ is:
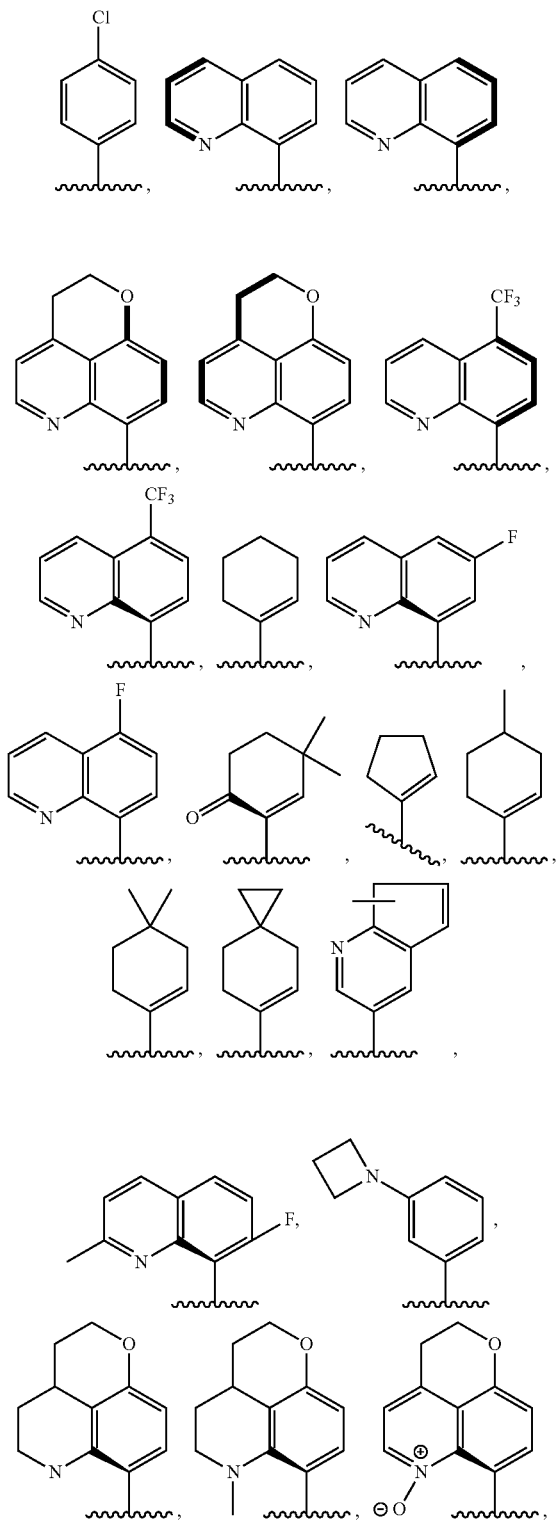
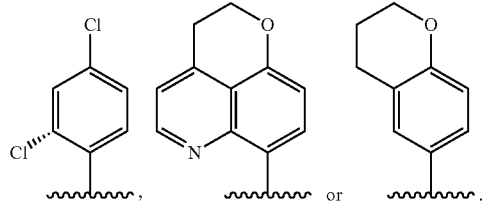
Another specific value for $R^4$ is:
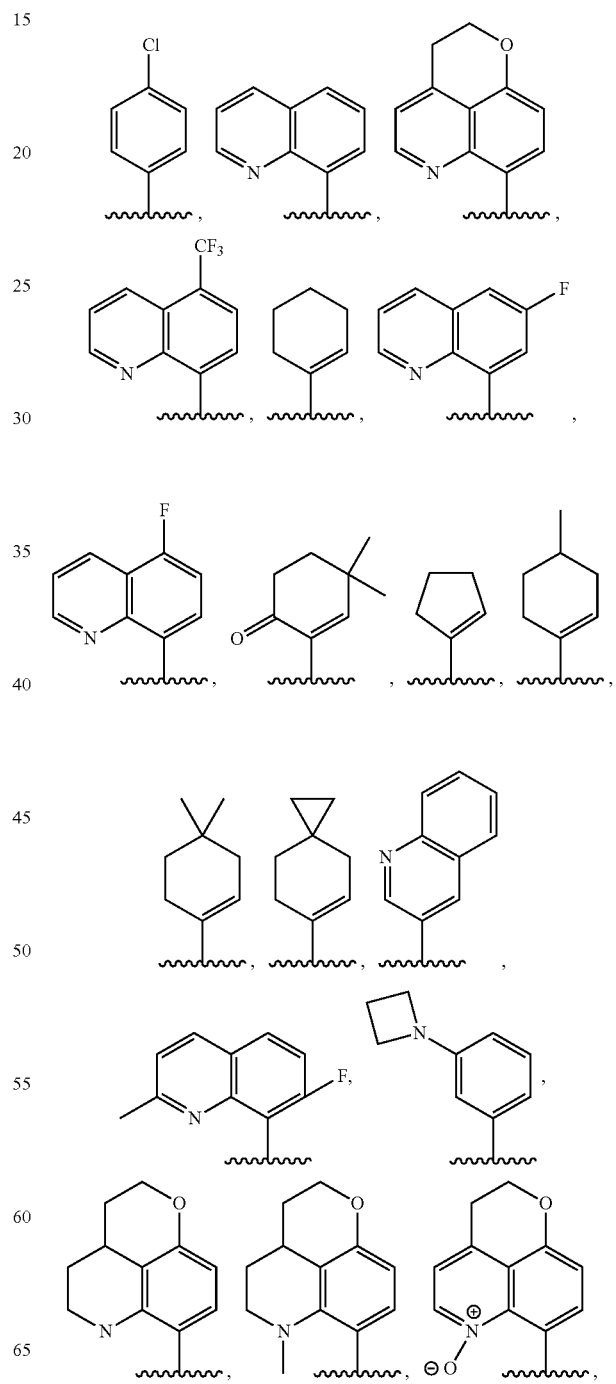

-continued
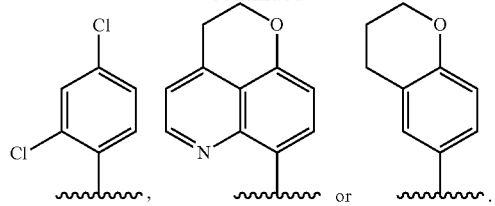
Another specific value for R⁴ is:
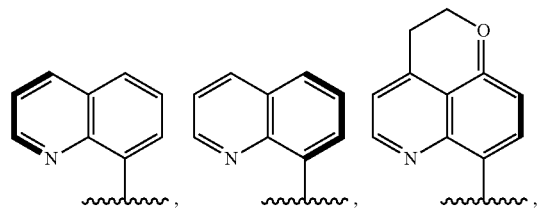
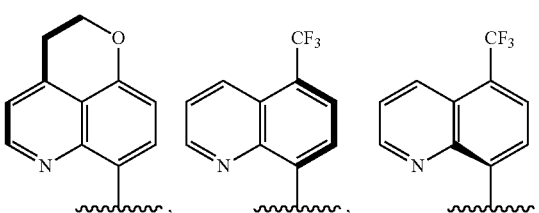
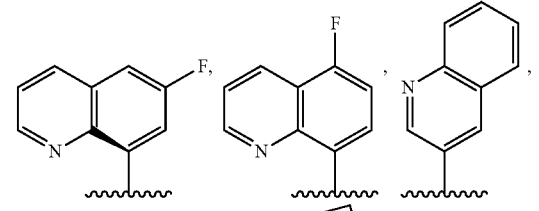
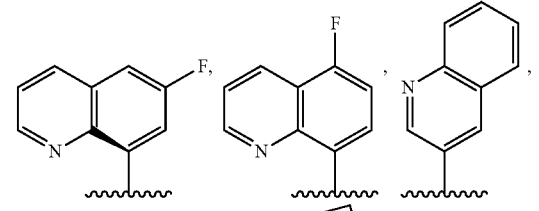
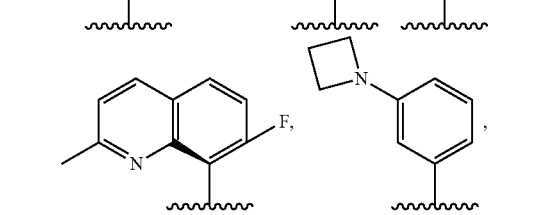
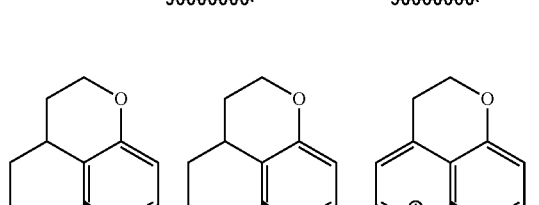
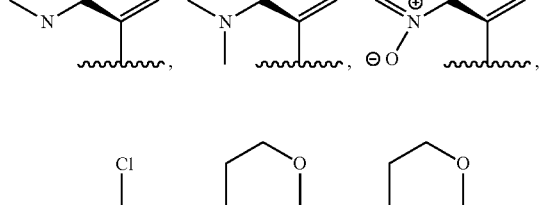
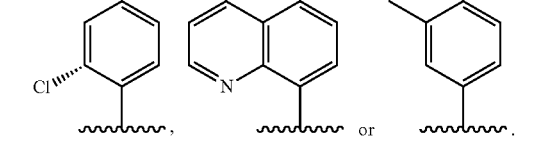
Another specific value for R⁴ is:
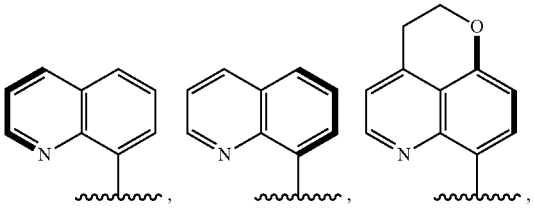
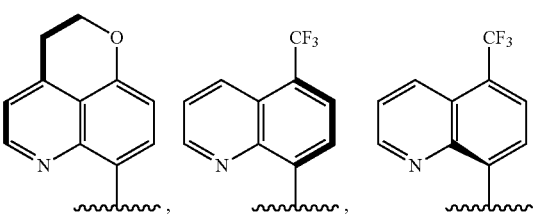
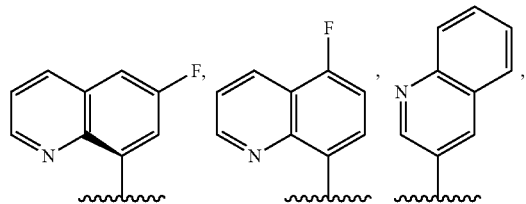
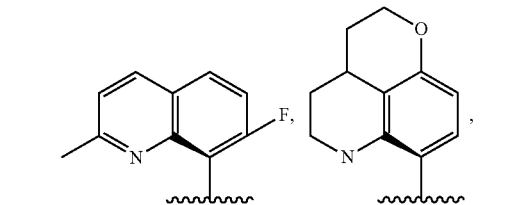
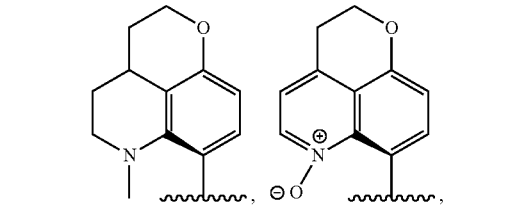
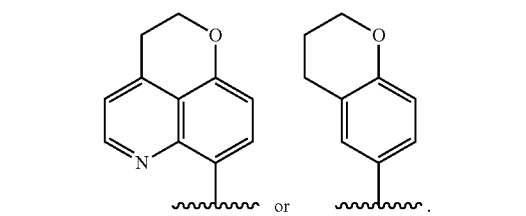
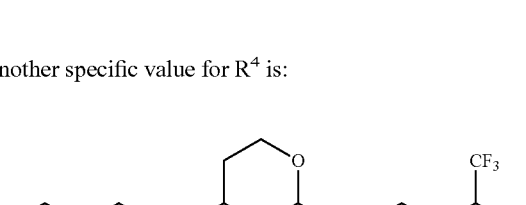
Another specific value for R⁴ is:
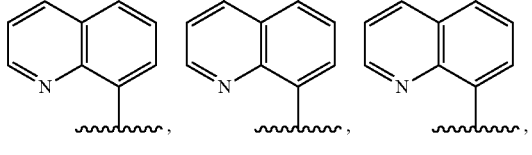

-continued

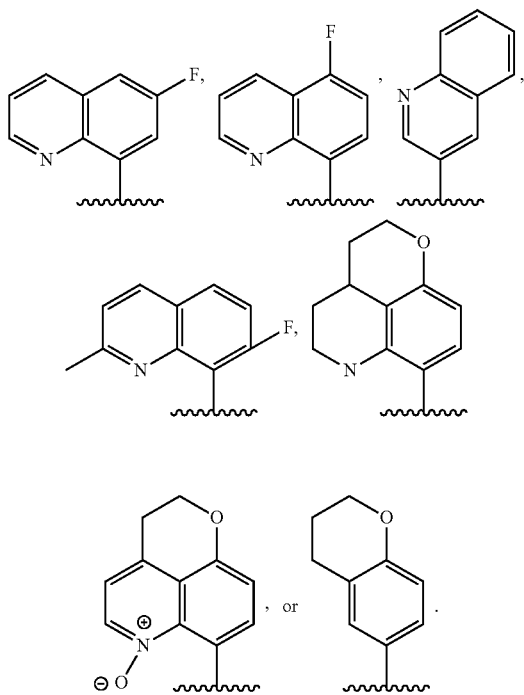

Another specific value for R⁴ is:

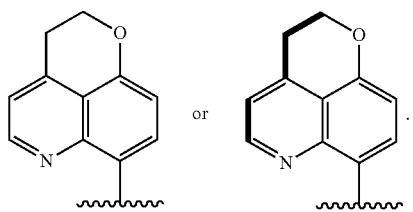

Another specific value for R⁴ is:

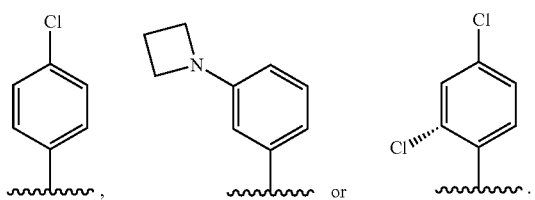

Another specific value for R⁴ is:

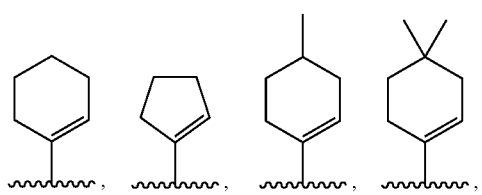

-continued

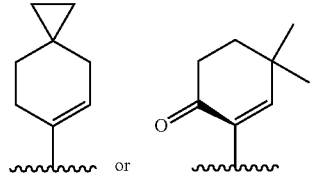

Another specific group of compounds of formula I are compounds wherein R⁴ is selected from:

a) aryl, heterocycle and heteroaryl, wherein any aryl, heterocycle and heteroaryl is optionally substituted with one or more (e.g. 1, 2, 3, 4 or 5) groups each independently selected from halo, $(C_1-C_6)$alkyl, $(C_2-C_6)$alkenyl, $(C_1-C_6)$haloalkyl, $(C_3-C_7)$cycloalkyl, —OH, —O$(C_1-C_6)$alkyl, —SH, —S$(C_1-C_6)$alkyl, —NH$_2$, —NH$(C_1-C_6)$alkyl and —N$((C_1-C_6)$alkyl$)_2$, wherein $(C_1-C_6)$alkyl is optionally substituted with hydroxy, —O$(C_1-C_6)$alkyl, cyano or oxo; and b) aryl, heteroaryl, spiro-heterocycle, fused-heterocycle, and bridged-heterocycle, wherein aryl, heteroaryl, spiro-heterocycle, fused-heterocycle and bridged-heterocycle are each independently substituted with one or more Z⁷ groups and optionally substituted with one or more (e.g. 1, 2, 3, 4 or 5) Z¹ groups.

Another specific group of compounds of formula I are compounds wherein R⁴ is selected from aryl, heteroaryl, spiro-heterocycle, fused-heterocycle, and bridged-heterocycle, wherein aryl, heteroaryl, spiro-heterocycle, fused-heterocycle and bridged-heterocycle are each independently substituted with one or more Z⁷ groups and optionally substituted with one or more (e.g. 1, 2, 3, 4 or 5) Z¹ groups.

Another specific group of compounds of formula I are compounds wherein R⁴ is selected from:

a) heterocycle, wherein any heterocycle is optionally substituted with one or more (e.g. 1, 2, 3, 4 or 5) groups each independently selected halo, $(C_1-C_6)$alkyl and $(C_1-C_6)$haloalkyl; and b) fused-heterocycle, wherein fused-heterocycle is substituted with one or more Z⁷ groups and optionally substituted with one or more (e.g. 1, 2, 3, 4 or 5) Z¹ groups.

Another specific value for R⁴ is heterocycle.

Another specific group of compounds of formula I are compounds wherein the stereochemistry of the R⁴ substituent relative to the carbon of formula I to which it is attached is the (R) stereochemistry.

Another specific group of compounds of formula I are compounds wherein the stereochemistry of the R⁴ substituent relative to the carbon of formula I to which it is attached is the (S) stereochemistry.

Another specific group of compounds of formula I are compounds wherein R¹ is selected from:

a) H, halo, $(C_1-C_6)$alkyl and $(C_1-C_6)$haloalkyl;

b) $(C_2-C_6)$alkenyl, $(C_2-C_6)$alkynyl, $(C_3-C_7)$cycloalkyl, nitro, cyano, aryl, heterocycle and heteroaryl, wherein any aryl, heterocycle or heteroaryl is optionally substituted with one or more Z¹⁰ groups;

c) —C(=O)—R¹¹, —C(=O)—O—R¹¹, —O—R¹¹, —S—R¹¹, —S(O)—R¹¹, —SO$_2$—R¹¹, —$(C_1-C_6)$alkyl-R¹¹, —$(C_1-C_6)$alkyl-C(=O)—R¹¹, —$(C_1-C_6)$alkyl-C(=O)—O—R¹¹, —$(C_1-C_6)$alkyl-O—R¹¹, —$(C_1-C_6)$alkyl-S—R¹¹, —$(C_1-C_6)$alkyl-S(O)—R¹¹ and —$(C_1-C_6)$alkyl-SO$_2$—R¹¹, wherein each R¹¹ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, and wherein any aryl, heterocycle or heteroaryl is optionally substituted with one or more $Z^{10}$ groups;

d) —N($R^9$)$R^{10}$, —C(=O)—N($R^9$)$R^{10}$, —O—C(=O)—N($R^9$)$R^{10}$, —SO$_2$—N($R^9$)$R^{10}$, —($C_1$-$C_6$)alkyl-N($R^9$)$R^{10}$, —($C_1$-$C_6$)alkyl-C(=O)—N($R^9$)$R^{10}$, —($C_1$-$C_6$)alkyl-O—C(=O)—N($R^9$)$R^{10}$ and —($C_1$-$C_6$)alkyl-SO$_2$—N($R^9$)$R^{10}$, wherein each $R^9$ is independently selected from H, ($C_1$-$C_6$)alkyl and ($C_3$-$C_7$)cycloalkyl, and each $R^{10}$ is independently selected from $R^{11}$, —($C_1$-$C_6$)alkyl-$R^{11}$, —SO$_2$—$R^{11}$, —C(=O)—$R^{11}$, —C(=O)O$R^{11}$ and —C(=O)N($R^9$)$R^{11}$, wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl, and wherein any aryl, heterocycle or heteroaryl is optionally substituted with one or more $Z^{10}$ groups;

e) ($C_1$-$C_6$)alkyl, wherein ($C_1$-$C_6$)alkyl is substituted with one or more $Z^2$ groups and optionally substituted with one or more $Z^1$ groups;

f) aryl, heteroaryl, heterocycle, —Xaryl, —Xheteroaryl and —Xheterocycle, wherein any aryl heteroaryl and heterocycle, either alone or as part of a group, is substituted with one or more (e.g. 1, 2, 3, 4 or 5) $Z^5$ groups and optionally substituted with one or more $Z^1$ groups; and g) ($C_1$-$C_6$)haloalkyl, ($C_3$-$C_7$)carbocycle, ($C_2$-$C_6$)alkenyl and ($C_2$-$C_6$)alkynyl, wherein ($C_1$-$C_6$)haloalkyl, ($C_3$-$C_7$)carbocycle, ($C_2$-$C_6$)alkenyl and ($C_2$-$C_6$)alkynyl are each substituted with one or more (e.g. 1, 2, 3, 4 or 5) $Z^6$ groups and optionally substituted with one or more $Z^1$ groups.

Another specific group of compounds of formula I are compounds wherein $R^1$ is selected from:

a) H, halo and ($C_1$-$C_6$)alkyl;

b) ($C_2$-$C_6$)alkenyl, cyano, aryl, heterocycle and heteroaryl, wherein any aryl, heterocycle or heteroaryl is optionally substituted with one or more $Z^{10}$ groups;

c) —($C_1$-$C_6$)alkyl-$R^{11}$ and —($C_1$-$C_6$)alkyl-O—$R^{11}$, wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl, wherein any aryl, heterocycle or heteroaryl is optionally substituted with one or more $Z^{10}$ groups;

d) —C(=O)—N($R^9$)$R^{10}$ and —($C_1$-$C_6$)alkyl-N($R^9$)$R^{10}$, wherein each $R^9$ is independently selected from H, ($C_1$-$C_6$)alkyl and ($C_3$-$C_7$)cycloalkyl, and each $R^{10}$ is independently selected from $R^{11}$, —($C_1$-$C_6$)alkyl-$R^{11}$, —SO$_2$—$R^{11}$, —C(=O)—$R^{11}$, —C(=O)O$R^{11}$ and —C(=O)N($R^9$)$R^{11}$, wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl, wherein any aryl, heterocycle or heteroaryl is optionally substituted with one or more $Z^{10}$ groups;

e) ($C_1$-$C_6$)alkyl, wherein ($C_1$-$C_6$)alkyl is substituted with one or more $Z^2$ groups and optionally substituted with one or more $Z^1$ groups;

f) aryl, heteroaryl and heterocycle, wherein aryl heteroaryl and heterocycle are each substituted with one or more $Z^5$ groups and optionally substituted with one or more $Z^1$ groups; and g) ($C_2$-$C_6$)alkenyl, and ($C_2$-$C_6$)alkynyl, wherein ($C_2$-$C_6$)alkenyl and ($C_2$-$C_6$)alkynyl are each substituted with one or more $Z^6$ groups and optionally substituted with one or more $Z^1$ groups.

Another specific group of compounds of formula I are compounds wherein $R^1$ is selected from:

a) H, halo and ($C_1$-$C_6$)alkyl;

b) cyano, aryl, and heteroaryl, wherein any aryl or heteroaryl is optionally substituted with one or more $Z^{10}$ groups;

c) —($C_1$-$C_6$)alkyl-$R^{11}$ and —($C_1$-$C_6$)alkyl-O—$R^{11}$, wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl, wherein any aryl, heterocycle or heteroaryl is optionally substituted with one or more $Z^{10}$ groups;

d) —C(=O)—N($R^9$)$R^{10}$ and —($C_1$-$C_6$)alkyl-N($R^9$)$R^{10}$, wherein each $R^9$ is independently selected from H, ($C_1$-$C_6$)alkyl and ($C_3$-$C_7$)cycloalkyl, and each $R^{10}$ is independently selected from $R^{11}$, —($C_1$-$C_6$)alkyl-$R^{11}$, —SO$_2$—$R^{11}$, —C(=O)—$R^{11}$, —C(=O)O$R^{11}$ and —C(=O)N($R^9$)$R^{11}$, wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl, wherein any aryl, heterocycle or heteroaryl is optionally substituted with one or more $Z^{10}$ groups;

e) ($C_1$-$C_6$)alkyl, wherein ($C_1$-$C_6$)alkyl is substituted with one or more $Z^2$ groups and optionally substituted with one or more $Z^1$ groups; and f) aryl and heteroaryl, wherein aryl and heteroaryl are each substituted with one or more $Z^5$ groups and optionally substituted with one or more $Z^1$ groups.

Another specific group of compounds of formula I are compounds wherein $R^1$ is selected from:

a) ($C_1$-$C_6$)alkyl, wherein ($C_1$-$C_6$)alkyl is substituted with one or more $Z^2$ groups and optionally substituted with one or more $Z^1$ groups;

b) aryl, heteroaryl, heterocycle, —Xaryl, —Xheteroaryl and —Xheterocycle; wherein any aryl heteroaryl and heterocycle either alone or as part of a group, is substituted with one or more (e.g. 1, 2, 3, 4 or 5) $Z^5$ groups and optionally substituted with one or more $Z^1$ groups; and c) ($C_1$-$C_6$)haloalkyl, ($C_3$-$C_7$)carbocycle, ($C_2$-$C_6$)alkenyl, and ($C_2$-$C_6$)alkynyl, wherein ($C_1$-$C_6$)haloalkyl, ($C_3$-$C_7$)carbocycle, ($C_2$-$C_6$)alkenyl and ($C_2$-$C_6$)alkynyl are each substituted with one or more (e.g. 1, 2, 3, 4 or 5) $Z^6$ groups and optionally substituted with one or more $Z^1$ groups.

Another specific group of compounds of formula I are compounds wherein $R^1$ is selected from:

a) ($C_1$-$C_6$)alkyl, wherein ($C_1$-$C_6$)alkyl is substituted with one or more $Z^2$ groups and optionally substituted with one or more $Z^1$ groups;

b) aryl, heteroaryl and heterocycle, wherein aryl heteroaryl and heterocycle are each substituted with one or more $Z^5$ groups and optionally substituted with one or more $Z^1$ groups; and c) ($C_2$-$C_6$)alkenyl, and ($C_2$-$C_6$)alkynyl, wherein ($C_2$-$C_6$)alkenyl and ($C_2$-$C_6$)alkynyl are each substituted with one or more $Z^6$ groups and optionally substituted with one or more $Z^1$ groups.

Another specific value for $R^1$ is:

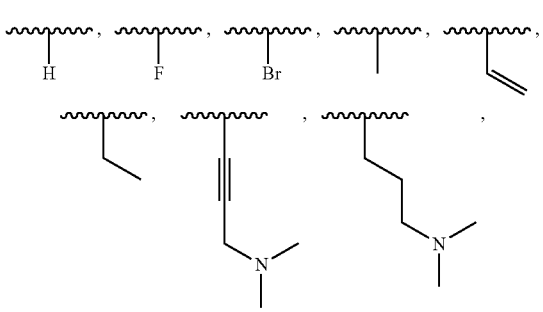

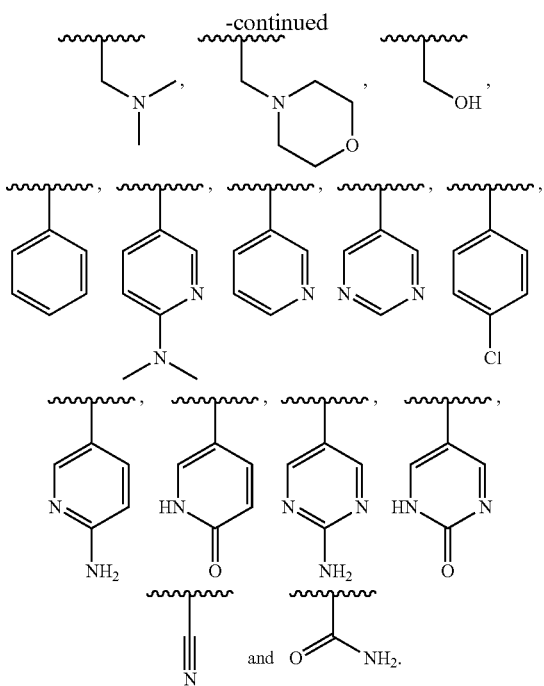

Another specific value for $R^1$ is halo.
Another specific value for $R^1$ is fluoro.
Another specific value for $R^1$ is H.
Another specific value for $R^1$H, halo or $(C_1-C_6)$alkyl.
Another specific value for $R^1$ is H or halo.

Another specific group of compounds of formula I are compounds wherein $R^2$ is selected from:

a) H, $(C_1-C_6)$alkyl and —O$(C_1-C_6)$alkyl;
b) $(C_2-C_6)$alkenyl, $(C_2-C_6)$alkynyl, $(C_1-C_6)$haloalkyl, $(C_3-C_7)$cycloalkyl, aryl, heterocycle, heteroaryl, halo, nitro and cyano;
c) C(=O)—$R^{11}$, —C(=O)—O—$R^{11}$, —S—$R^{11}$, —S(O)—$R^{11}$, —SO$_2$—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-SO$_2$—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein aryl, heterocycle or heteroaryl are each optionally substituted with one or more $Z^{11}$ groups; and d) —N($R^9$)$R^{10}$, —C(=O)—N($R^9$)$R^{10}$, —O—C(=O)—N($R^9$)$R^{10}$, —SO$_2$—N($R^9$)$R^{10}$, —$(C_1-C_6)$alkyl-N($R^9$)$R^{10}$, —$(C_1-C_6)$alkyl-C(=O)—N($R^9$)$R^{10}$, —$(C_1-C_6)$alkyl-O—C(=O)—N($R^9$)$R^{10}$, and —$(C_1-C_6)$alkyl-SO$_2$—N($R^9$)$R^{10}$, wherein each $R^9$ is independently selected from H, $(C_1-C_6)$alkyl and $(C_3-C_7)$cycloalkyl, and each $R^{10}$ is independently selected from $R^{11}$, —$(C_1-C_6)$alkyl-$R^{11}$, —SO$_2$—$R^{11}$, —C(=O)—$R^{11}$, —C(=O)O$R^{11}$ and —C(=O)N($R^9$)$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl.

e) $(C_1-C_6)$alkyl, wherein $(C_1-C_6)$alkyl is substituted with one or more $Z^2$ groups and optionally substituted with one or more $Z^1$ groups; and f) $(C_1-C_6)$haloalkyl, $(C_3-C_7)$carbocycle, $(C_2-C_6)$alkenyl and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each substituted with one or more $Z^6$ groups and optionally substituted with one or more $Z^1$ groups.

Another specific group of compounds of formula I are compounds wherein $R^2$ is selected from:

a) $(C_1-C_6)$alkyl;
b) $(C_2-C_6)$alkenyl and $(C_1-C_6)$haloalkyl;
c) —$(C_1-C_6)$alkyl-$R^{11}$ and —$(C_1-C_6)$alkyl-O—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein aryl, heterocycle or heteroaryl are each optionally substituted with one or more $Z^{11}$ groups;

d) —$(C_1-C_6)$alkyl-N($R^9$)$R^{10}$, wherein each $R^9$ is independently selected from H, $(C_1-C_6)$alkyl and $(C_3-C_7)$cycloalkyl, and each $R^{10}$ is independently selected from $R^{11}$, —$(C_1-C_6)$alkyl-$R^{11}$, —SO$_2$—$R^{11}$, —C(=O)—$R^{11}$, —C(=O)O$R^{11}$ and —C(=O)N($R^9$)$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl;

e) $(C_1-C_6)$alkyl, wherein $(C_1-C_6)$alkyl is substituted with one or more $Z^2$ groups and optionally substituted with one or more $Z^1$ groups; and f) $(C_2-C_6)$alkenyl, wherein $(C_2-C_6)$alkenyl is substituted with one or more $Z^6$ groups and optionally substituted with one or more $Z^1$ groups.

Another specific group of compounds of formula I are compounds wherein $R^2$ is selected from:

a) $(C_1-C_6)$alkyl;
b) $(C_2-C_6)$alkenyl and $(C_1-C_6)$haloalkyl;
c) —$(C_1-C_6)$alkyl-$R^{11}$ and —$(C_1-C_6)$alkyl-O—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein aryl, heterocycle or heteroaryl are each optionally substituted with one or more $Z^{11}$ groups;

d) —$(C_1-C_6)$alkyl-N($R^9$)$R^{10}$, wherein each $R^9$ is independently selected from H, $(C_1-C_6)$alkyl and $(C_3-C_7)$cycloalkyl, and each $R^{10}$ is independently selected from $R^{11}$, —$(C_1-C_6)$alkyl-$R^{11}$, —SO$_2$—$R^{11}$, —C(=O)—$R^{11}$, —C(=O)O$R^{11}$ and —C(=O)N($R^9$)$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl;

e) $(C_1-C_6)$alkyl, wherein $(C_1-C_6)$alkyl is substituted with one or more $Z^2$ groups and optionally substituted with one or more $Z^1$ groups; and f) $(C_1-C_6)$haloalkyl and $(C_2-C_6)$alkenyl, wherein $(C_1-C_6)$haloalkyl and $(C_2-C_6)$alkenyl are each substituted with one or more $Z^6$ groups and optionally substituted with one or more $Z^1$ groups.

Another specific group of compounds of formula I are compounds wherein $R^2$ is selected from:

a) $(C_1-C_6)$alkyl, wherein $(C_1-C_6)$alkyl is substituted with one or more $Z^2$ groups and optionally substituted with one or more $Z^1$ groups; and b) $(C_1-C_6)$haloalkyl, $(C_3-C_7)$carbocycle, $(C_2-C_6)$alkenyl, and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each substituted with one or more $Z^6$ groups and optionally substituted with one or more $Z^1$ groups.

Another specific group of compounds of formula I are compounds wherein $R^2$ is selected from:

a) $(C_1-C_6)$alkyl, wherein $(C_1-C_6)$alkyl is substituted with one or more $Z^2$ groups and optionally substituted with one or more $Z^1$ groups; and b) $(C_2-C_6)$alkenyl, wherein $(C_2-C_6)$alkenyl is substituted with one or more $Z^6$ groups and optionally substituted with one or more $Z^1$ groups.

Another specific group of compounds of formula I are compounds wherein $R^2$ is selected from:

a) $(C_1-C_6)$alkyl, wherein $(C_1-C_6)$alkyl is substituted with one or more $Z^2$ groups and optionally substituted with one or more $Z^1$ groups; and b) $(C_1-C_6)$haloalkyl and $(C_2-C_6)$alkenyl, wherein $(C_1-C_6)$haloalkyl and $(C_2-C_6)$alkenyl are each substituted with one or more $Z^6$ groups and optionally substituted with one or more $Z^1$ groups.

Another specific value for $R^2$ is:

[structures]

Another specific value for $R^2$ is methyl.

Another specific value for $R^2$ is H.

Another specific group of compounds of formula I are compounds wherein $R^6$ is selected from:

a) H, halo, $(C_1-C_6)$alkyl, and $(C_1-C_6)$haloalkyl;

b) $(C_2-C_6)$alkenyl, $(C_2-C_6)$alkynyl, $(C_3-C_7)$cycloalkyl, nitro, cyano, aryl, heterocycle and heteroaryl, wherein any aryl, heterocycle or heteroaryl of $R^6$ is optionally substituted with one or more $Z^{10}$ groups;

c) —C(=O)—$R^{11}$, —C(=O)—O—$R^{11}$, —O—$R^{11}$, —S—$R^{11}$, —S(O)—$R^{11}$, —SO$_2$—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-SO$_2$—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein any aryl, heterocycle or heteroaryl of $R^6$ is optionally substituted with one or more $Z^{10}$ groups;

d) —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkyl-S(O)—$(C_1-C_6)$alkyl-$(C_3-C_7)$carbocycle, —$(C_1-C_6)$alkyl-SO$_2$—$(C_1-C_6)$alkyl-$(C_3-C_7)$carbocycle, —$(C_2-C_6)$alkenyl-$(C_1-C_6)$haloalkyl, —$(C_2-C_6)$alkynyl-$(C_1-C_6)$haloalkyl, -halo$(C_3-C_7)$carbocycle, —NR$_a$SO$_2$NR$_c$R$_d$, —NR$_a$SO$_2$O$(C_3-C_7)$carbocycle, —NR$_a$SO$_2$Oaryl, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_3-C_7)$carbocycle-$Z^1$ or -halo$(C_1-C_6)$alkyl-$Z^3$, wherein any $(C_1-C_6)$alkyl, $(C_1-C_6)$haloalkyl, $(C_3-C_7)$carbocycle, $(C_2-C_6)$alkenyl, $(C_2-C_6)$alkynyl, aryl, heterocycle or heteroaryl, either alone or as part of a group, is optionally substituted with one or more $Z^1$ groups;

e) $(C_1-C_6)$alkyl, wherein $(C_1-C_6)$alkyl is substituted with one or more $Z^2$ groups and optionally substituted with one or more $Z^1$ groups;

f) aryl, heteroaryl, heterocycle, —Xaryl, —Xheteroaryl and —Xheterocycle, wherein any aryl heteroaryl and heterocycle either alone or as part of a group, is substituted with one or more $Z^5$ groups and optionally substituted with one or more $Z^1$ groups; and g) $(C_1-C_6)$haloalkyl, $(C_3-C_7)$carbocycle, $(C_2-C_6)$alkenyl and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each independently substituted with one or more $Z^6$ groups and optionally substituted with one or more $Z^1$ groups.

Another specific group of compounds of formula I are compounds wherein $R^6$ is selected from:

a) H, halo and $(C_1-C_6)$alkyl;

b) $(C_2-C_6)$alkenyl, $(C_2-C_6)$alkynyl and aryl, wherein any aryl is optionally substituted with one or more $Z^{10}$ groups;

c) —$(C_1-C_6)$alkyl-$R^{11}$ and —$(C_1-C_6)$alkyl-O—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein any aryl, heterocycle or heteroaryl of $R^6$ is optionally substituted with one or more $Z^{10}$ groups;

d) —$(C_2-C_6)$alkynyl-$(C_3-C_7)$carbocycle, —$(C_2-C_6)$alkynyl-aryl, —$(C_2-C_6)$alkynyl-heteroaryl and —$(C_2-C_6)$alkynyl-heterocycle, wherein any $(C_3-C_7)$carbocycle, $(C_2-C_6)$alkynyl, aryl, heterocycle and heteroaryl, as part of a group, is optionally substituted with one or more $Z^1$ groups;

e) $(C_1-C_6)$alkyl, wherein $(C_1-C_6)$alkyl is substituted with one or more $Z^2$ groups and optionally substituted with one or more $Z^1$ groups;

f) aryl, wherein aryl is substituted with one or more $Z^5$ groups and optionally substituted with one or more $Z^1$ groups; and g) $(C_2-C_6)$alkenyl and $(C_2-C_6)$alkynyl, wherein $(C_2-C_6)$alkenyl and $(C_2-C_6)$alkynyl are each independently substituted with one or more $Z^6$ groups and optionally substituted with one or more $Z^1$ groups.

Another specific group of compounds of formula I are compounds wherein $R^6$ is selected from:

a) H, halo, $(C_1-C_6)$alkyl, and $(C_1-C_6)$haloalkyl b) $(C_2-C_6)$alkenyl, $(C_2-C_6)$alkynyl, $(C_3-C_7)$cycloalkyl, nitro, cyano, aryl, heterocycle and heteroaryl, wherein any aryl, heterocycle and heteroaryl of $R^6$ is optionally substituted with one or more $Z^{10}$ groups;

c) —C(=O)—$R^{11}$, —C(=O)—O—$R^{11}$, —O—$R^{11}$, —S—$R^{11}$, —S(O)—$R^{11}$, —SO$_2$—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-SO$_2$—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein any aryl, heterocycle and heteroaryl of $R^6$ is optionally substituted with one or more $Z^{10}$ groups;

d) —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkyl-S(O)—$(C_1-C_6)$alkyl-$(C_3-C_7)$carbocycle, —$(C_1-C_6)$alkyl-SO$_2$—$(C_1-C_6)$alkyl-$(C_3-C_7)$carbocycle, —$(C_2-C_6)$alkenyl-$(C_1-C_6)$haloalkyl, —$(C_2-C_6)$alkynyl-$(C_1-C_6)$haloalkyl, -halo$(C_3-C_7)$carbocycle, —NR$_a$SO$_2$NR$_c$R$_d$, —NR$_a$SO$_2$O$(C_3-C_7)$carbocycle, —NR$_a$SO$_2$Oaryl, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —($C_2$-$C_6$)alkynyl-($C_3$-$C_7$)carbocycle, —($C_2$-$C_6$)alkynyl-aryl, —($C_2$-$C_6$)alkynyl-heteroaryl, —($C_2$-$C_6$)alkynyl-heterocycle, —($C_2$-$C_8$)alkynyl-$OR_a$, —($C_2$-$C_6$)alkyl-($C_3$-$C_7$)carbocycle-$OR_a$, —($C_3$-$C_7$)carbocycle-$Z^1$ and -halo($C_1$-$C_6$)alkyl-$Z^3$, wherein any ($C_1$-$C_6$)alkyl, ($C_1$-$C_6$)haloalkyl, ($C_3$-$C_7$)carbocycle, ($C_2$-$C_6$)alkenyl, ($C_2$-$C_6$)alkynyl, aryl, heterocycle and heteroaryl, either alone or as part of a group, is optionally substituted with one or more $Z^1$ groups;

e) ($C_1$-$C_6$)alkyl, wherein ($C_1$-$C_6$)alkyl is substituted with one or more $Z^2$ groups and optionally substituted with one or more $Z^1$ groups;

f) aryl, heteroaryl, heterocycle, —Xaryl, —Xheteroaryl and —Xheterocycle wherein any aryl, heteroaryl and heterocycle, either alone or as part of a group, is substituted with one or more $Z^5$ groups and optionally substituted with one or more $Z^1$ groups; and g) ($C_1$-$C_6$)haloalkyl, ($C_3$-$C_7$)carbocycle, ($C_2$-$C_6$)alkenyl and ($C_2$-$C_6$)alkynyl, wherein any ($C_1$-$C_6$)haloalkyl, ($C_3$-$C_7$)carbocycle, ($C_2$-$C_6$)alkenyl and ($C_2$-$C_6$)alkynyl is substituted with one or more $Z^6$ groups and optionally substituted with one or more $Z^1$ groups.

Another specific group of compounds of formula I are compounds wherein $R^6$ is selected from:

a) H, halo and ($C_1$-$C_6$)alkyl;

b) ($C_2$-$C_6$)alkenyl, ($C_2$-$C_6$)alkynyl and aryl, wherein any aryl is optionally substituted with one or more $Z^{10}$ groups;

c) —($C_1$-$C_6$)alkyl-$R^{11}$ and —($C_1$-$C_6$)alkyl-O—$R^{11}$, wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl, wherein any aryl, heterocycle or heteroaryl of $R^6$ is optionally substituted with one or more $Z^{10}$ groups;

d) —($C_2$-$C_6$)alkynyl-($C_3$-$C_7$)carbocycle, —($C_2$-$C_6$)alkynyl-aryl, —($C_2$-$C_6$)alkynyl-heteroaryl, —($C_2$-$C_6$)alkynyl-heterocycle, —($C_2$-$C_8$)alkynyl-$OR_a$, and —($C_2$-$C_6$)alkyl-($C_3$-$C_7$)carbocycle-$OR_a$, wherein —($C_2$-$C_6$)alkynyl-($C_3$-$C_7$)carbocycle, —($C_2$-$C_6$)alkynyl-aryl, —($C_2$-$C_6$)alkynyl-heteroaryl, —($C_2$-$C_6$)alkynyl-heterocycle, —($C_2$-$C_8$)alkynyl-$OR_a$, and —($C_2$-$C_6$)alkyl-($C_3$-$C_7$)carbocycle-$OR_a$, are optionally substituted with one or more $Z^1$ groups;

e) ($C_1$-$C_6$)alkyl, wherein ($C_1$-$C_6$)alkyl is substituted with one or more $Z^2$ groups and optionally substituted with one or more $Z^1$ groups;

f) aryl, wherein aryl is substituted with one or more $Z^5$ groups and optionally substituted with one or more $Z^1$ groups; and g) ($C_2$-$C_6$)alkenyl and ($C_2$-$C_6$)alkynyl, wherein ($C_2$-$C_6$)alkenyl and ($C_2$-$C_6$)alkynyl are each independently substituted with one or more $Z^6$ groups and optionally substituted with one or more $Z^1$ groups.

Another specific group of compounds of formula I are compounds wherein $R^6$ is selected from:

a) H, halo, ($C_1$-$C_6$)alkyl, and ($C_1$-$C_6$)haloalkyl b) ($C_2$-$C_6$)alkenyl, ($C_2$-$C_6$)alkynyl, ($C_3$-$C_7$)cycloalkyl, nitro, cyano, aryl, heterocycle and heteroaryl, wherein any aryl, heterocycle and heteroaryl of $R^6$ is optionally substituted with one or more $Z^{10}$ groups;

c) —C(=O)—$R^{11}$, —C(=O)—O—$R^{11}$, —O—$R^{11}$, —S—$R^{11}$, —S(O)—$R^{11}$, —$SO_2$—$R^{11}$, —($C_1$-$C_6$)alkyl-$R^{11}$, —($C_1$-$C_6$)alkyl-C(=O)—$R^{11}$, —($C_1$-$C_6$)alkyl-C(=O)—O—$R^{11}$, —($C_1$-$C_6$)alkyl-O—$R^{11}$, —($C_1$-$C_6$)alkyl-S—$R^{11}$, —($C_1$-$C_6$)alkyl-S(O)—$R^{11}$ and —($C_1$-$C_6$)alkyl-$SO_2$—$R^{11}$, wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl, wherein any aryl, heterocycle and heteroaryl of $R^6$ is optionally substituted with one or more $Z^{10}$ groups;

d) —($C_1$-$C_6$)alkyl-O—($C_1$-$C_6$)alkyl-($C_3$-$C_7$)carbocycle, —($C_1$-$C_6$)alkyl-S—($C_1$-$C_6$)alkyl-($C_3$-$C_7$)carbocycle, —($C_1$-$C_6$)alkyl-S(O)—($C_1$-$C_6$)alkyl-($C_3$-$C_7$)carbocycle, —($C_1$-$C_6$)alkyl-$SO_2$—($C_1$-$C_6$)alkyl-($C_3$-$C_7$)carbocycle, —($C_2$-$C_6$)alkenyl-($C_1$-$C_6$)haloalkyl, —($C_2$-$C_6$)alkynyl-($C_1$-$C_6$)haloalkyl, -halo($C_3$-$C_7$)carbocycle, —$NR_aSO_2NR_cR_d$, —$NR_aSO_2O$($C_3$-$C_7$)carbocycle, —$NR_aSO_2$Oaryl, —($C_2$-$C_6$)alkenyl-($C_3$-$C_7$)carbocycle, —($C_2$-$C_6$)alkenyl-aryl, —($C_2$-$C_6$)alkenyl-heteroaryl, —($C_2$-$C_6$)alkenyl-heterocycle, —($C_2$-$C_6$)alkynyl-($C_3$-$C_7$)carbocycle, —($C_2$-$C_6$)alkynyl-aryl, —($C_2$-$C_6$)alkynyl-heteroaryl, —($C_2$-$C_6$)alkynyl-heterocycle, —($C_2$-$C_8$)alkynyl-OH, —($C_2$-$C_6$)alkyl-($C_3$-$C_7$)carbocycle-$OR_a$, —($C_3$-$C_7$)carbocycle-Z and -halo($C_1$-$C_6$)alkyl-$Z^3$, wherein any ($C_1$-$C_6$)alkyl, ($C_1$-$C_6$)haloalkyl, ($C_3$-$C_7$)carbocycle, ($C_2$-$C_6$)alkenyl, ($C_2$-$C_6$)alkynyl, aryl, heterocycle and heteroaryl, either alone or as part of a group, is optionally substituted with one or more $Z^1$ groups;

e) ($C_1$-$C_6$)alkyl, wherein ($C_1$-$C_6$)alkyl is substituted with one or more $Z^2$ groups and optionally substituted with one or more $Z^1$ groups;

f) aryl, heteroaryl, heterocycle, —Xaryl, —Xheteroaryl and —Xheterocycle wherein any aryl, heteroaryl and heterocycle, either alone or as part of a group, is substituted with one or more $Z^5$ groups and optionally substituted with one or more $Z^1$ groups; and g) ($C_1$-$C_6$)haloalkyl, ($C_3$-$C_7$)carbocycle, ($C_2$-$C_6$)alkenyl and ($C_2$-$C_6$)alkynyl, wherein any ($C_1$-$C_6$)haloalkyl, ($C_3$-$C_7$)carbocycle, ($C_2$-$C_6$)alkenyl and ($C_2$-$C_6$)alkynyl is substituted with one or more $Z^6$ groups and optionally substituted with one or more $Z^1$ groups.

Another specific group of compounds of formula I are compounds wherein $R^6$ is selected from:

a) H, halo and ($C_1$-$C_6$)alkyl;

b) ($C_2$-$C_6$)alkenyl, ($C_2$-$C_6$)alkynyl and aryl, wherein any aryl is optionally substituted with one or more $Z^{10}$ groups;

c) —($C_1$-$C_6$)alkyl-$R^{11}$ and —($C_1$-$C_6$)alkyl-O—$R^{11}$, wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl, wherein any aryl, heterocycle or heteroaryl of $R^6$ is optionally substituted with one or more $Z^{10}$ groups;

d) —($C_2$-$C_6$)alkynyl-($C_3$-$C_7$)carbocycle, —($C_2$-$C_6$)alkynyl-aryl, —($C_2$-$C_6$)alkynyl-heteroaryl, —($C_2$-$C_6$)alkynyl-heterocycle, —($C_2$-$C_8$)alkynyl-$OR_a$, and —($C_2$-$C_6$)alkyl-($C_3$-$C_7$)carbocycle-$OR_a$, wherein —($C_2$-$C_6$)alkynyl-($C_3$-$C_7$)carbocycle, —($C_2$-$C_6$)alkynyl-aryl, —($C_2$-$C_6$)alkynyl-heteroaryl, —($C_2$-$C_6$)alkynyl-heterocycle, —($C_2$-$C_8$)alkynyl-OH, and —($C_2$-$C_6$)alkyl-($C_3$-$C_7$)carbocycle-$OR_a$, are optionally substituted with one or more $Z^1$ groups;

e) ($C_1$-$C_6$)alkyl, wherein ($C_1$-$C_6$)alkyl is substituted with one or more $Z^2$ groups and optionally substituted with one or more $Z^1$ groups;

f) aryl, wherein aryl is substituted with one or more $Z^5$ groups and optionally substituted with one or more $Z^1$ groups; and g) ($C_2$-$C_6$)alkenyl and ($C_2$-$C_6$)alkynyl, wherein ($C_2$-$C_6$)alkenyl and ($C_2$-$C_6$)alkynyl are each independently substituted with one or more $Z^6$ groups and optionally substituted with one or more $Z^1$ groups.

Another specific group of compounds of formula I are compounds wherein $R^6$ is selected from:

a) —($C_1$-$C_6$)alkyl-O—($C_1$-$C_6$)alkyl-($C_3$-$C_7$)carbocycle, —($C_1$-$C_6$)alkyl-S—($C_1$-$C_6$)alkyl-($C_3$-$C_7$)carbocycle, —($C_1$-$C_6$)alkyl-S(O)—($C_1$-$C_6$)alkyl-($C_3$-$C_7$)carbocycle, —($C_1$-$C_6$)alkyl-$SO_2$—($C_1$-$C_6$)alkyl-($C_3$-$C_7$)carbocycle, —($C_2$-$C_6$)alkenyl-($C_1$-$C_6$)haloalkyl, —($C_2$-$C_6$)alkynyl-($C_1$-$C_6$)haloalkyl, -halo($C_3$-$C_7$)carbocycle, —$NR_aSO_2NR_cR_d$, —NR$_a$SO$_2$O(C$_3$-C$_7$)carbocycle, —NR$_a$SO$_2$Oaryl, —(C$_2$-C$_6$)alkenyl-(C$_3$-C$_7$)carbocycle, —(C$_2$-C$_6$)alkenyl-aryl, —(C$_2$-C$_6$)alkenyl-heteroaryl, —(C$_2$-C$_6$)alkenyl-heterocycle, —(C$_2$-C$_6$)alkynyl-(C$_3$-C$_7$)carbocycle, —(C$_2$-C$_6$)alkynyl-aryl, —(C$_2$-C$_6$)alkynyl-heteroaryl, —(C$_2$-C$_6$)alkynyl-heterocycle, —(C$_3$-C$_7$)carbocycle-Z$^1$ and -halo(C$_1$-C$_6$)alkyl-Z$^3$, wherein any (C$_1$-C$_6$)alkyl, (C$_1$-C$_6$)haloalkyl, (C$_3$-C$_7$)carbocycle, (C$_2$-C$_6$)alkenyl, (C$_2$-C$_6$)alkynyl, aryl, heterocycle and heteroaryl, either alone or as part of a group, is optionally substituted with one or more Z$^1$ groups;

b) (C$_1$-C$_6$)alkyl, wherein (C$_1$-C$_6$)alkyl is substituted with one or more Z$^2$ groups and optionally substituted with one or more Z$^1$ groups;

c) aryl, heteroaryl, heterocycle, —Xaryl, —Xheteroaryl and —Xheterocycle wherein any aryl heteroaryl and heterocycle, either alone or as part of a group, is substituted with one or more Z$^5$ groups and optionally substituted with one or more Z$^1$ groups; and d) (C$_1$-C$_6$)haloalkyl, (C$_3$-C$_7$)carbocycle, (C$_2$-C$_6$)alkenyl and (C$_2$-C$_6$)alkynyl, wherein (C$_1$-C$_6$)haloalkyl, (C$_3$-C$_7$)carbocycle, (C$_2$-C$_6$)alkenyl and (C$_2$-C$_6$)alkynyl are each independently substituted with one or more Z$^6$ groups and optionally substituted with one or more Z$^1$ groups.

Another specific group of compounds of formula I are compounds wherein R$^6$ is selected from:

a) H, halo and (C$_1$-C$_6$)alkyl;

b) (C$_2$-C$_6$)alkenyl, (C$_2$-C$_6$)alkynyl and aryl, wherein any aryl is optionally substituted with one or more Z$^{10}$ groups;

c) —(C$_1$-C$_6$)alkyl-R$^{11}$ and —(C$_1$-C$_6$)alkyl-O—R$^{11}$, wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl, wherein any aryl, heterocycle or heteroaryl of R$^6$ is optionally substituted with one or more Z$^{10}$ groups;

d) —(C$_2$-C$_6$)alkynyl-(C$_3$-C$_7$)carbocycle, —(C$_2$-C$_6$)alkynyl-aryl, —(C$_2$-C$_6$)alkynyl-heteroaryl, —(C$_2$-C$_6$)alkynyl-heterocycle, —(C$_2$-C$_8$)alkynyl-OR$_a$ and —(C$_2$-C$_6$)alkyl-(C$_3$-C$_7$)carbocycle-OR$_a$, wherein any (C$_3$-C$_7$)carbocycle, (C$_2$-C$_6$)alkynyl, aryl, heterocycle and heteroaryl, as part of a group, is optionally substituted with one or more Z$^1$ groups;

e) (C$_1$-C$_6$)alkyl, wherein (C$_1$-C$_6$)alkyl is substituted with one or more Z$^2$ groups and optionally substituted with one or more Z$^1$ groups;

f) aryl, wherein aryl is substituted with one or more Z$^5$ groups and optionally substituted with one or more Z$^1$ groups; and g) (C$_2$-C$_6$)alkenyl and (C$_2$-C$_6$)alkynyl, wherein (C$_2$-C$_6$)alkenyl and (C$_2$-C$_6$)alkynyl are each independently substituted with one or more Z$^6$ groups and optionally substituted with one or more Z$^1$ groups.

Another specific group of compounds of formula I are compounds wherein R$^6$ is selected from:

a) —(C$_1$-C$_6$)alkyl-O—(C$_1$-C$_6$)alkyl-(C$_3$-C$_7$)carbocycle, —(C$_1$-C$_6$)alkyl-S—(C$_1$-C$_6$)alkyl-(C$_3$-C$_7$)carbocycle, —(C$_1$-C$_6$)alkyl-S(O)—(C$_1$-C$_6$)alkyl-(C$_3$-C$_7$)carbocycle, —(C$_1$-C$_6$)alkyl-SO$_2$—(C$_1$-C$_6$)alkyl-(C$_3$-C$_7$)carbocycle, —(C$_2$-C$_6$)alkenyl-(C$_1$-C$_6$)haloalkyl, —(C$_2$-C$_6$)alkynyl-(C$_1$-C$_6$)haloalkyl, -halo(C$_3$-C$_7$)carbocycle, —NR$_a$SO$_2$NR$_c$R$_d$, —NR$_a$SO$_2$O(C$_3$-C$_7$)carbocycle, —NR$_a$SO$_2$Oaryl, —(C$_2$-C$_6$)alkenyl-(C$_3$-C$_7$)carbocycle, —(C$_2$-C$_6$)alkenyl-aryl, —(C$_2$-C$_6$)alkenyl-heteroaryl, —(C$_2$-C$_6$)alkenyl-heterocycle, —(C$_2$-C$_6$)alkynyl-(C$_3$-C$_7$)carbocycle, —(C$_2$-C$_6$)alkynyl-aryl, —(C$_2$-C$_6$)alkynyl-heteroaryl, —(C$_2$-C$_6$)alkynyl-heterocycle, —(C$_2$-C$_8$)alkynyl-OH, —(C$_2$-C$_6$)alkyl-(C$_3$-C$_7$)carbocycle-OR$_a$, —(C$_3$-C$_7$)carbocycle-Z$^1$ and -halo(C$_1$-C$_6$)alkyl-Z$^3$, wherein any (C$_1$-C$_6$)alkyl, (C$_1$-C$_6$)haloalkyl, (C$_3$-C$_7$)carbocycle, (C$_2$-C$_6$)alkenyl, (C$_2$-C$_6$)alkynyl, aryl, heterocycle and heteroaryl, either alone or as part of a group, is optionally substituted with one or more Z$^1$ groups;

b) (C$_1$-C$_6$)alkyl, wherein (C$_1$-C$_6$)alkyl is substituted with one or more Z$^2$ groups and optionally substituted with one or more Z$^1$ groups;

c) aryl, heteroaryl, heterocycle, —Xaryl, —Xheteroaryl and —Xheterocycle wherein any aryl heteroaryl and heterocycle, either alone or as part of a group, is substituted with one or more $Z^5$ groups and optionally substituted with one or more $Z^1$ groups; and d) $(C_1-C_6)$haloalkyl, $(C_3-C_7)$carbocycle, $(C_2-C_6)$alkenyl and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each independently substituted with one or more $Z^6$ groups and optionally substituted with one or more $Z^1$ groups.

Another specific group of compounds of formula I are compounds wherein $R^6$ is selected from:

a) H, halo and $(C_1-C_6)$alkyl;

b) $(C_2-C_6)$alkenyl, $(C_2-C_6)$alkynyl and aryl, wherein any aryl is optionally substituted with one or more $Z^{10}$ groups;

c) —$(C_1-C_6)$alkyl-$R^{11}$ and —$(C_1-C_6)$alkyl-O—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein any aryl, heterocycle or heteroaryl of $R^6$ is optionally substituted with one or more $Z^{10}$ groups;

d) —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_2-C_8)$alkynyl-OH and —$(C_2-C_6)$alkyl-$(C_3-C_7)$carbocycle-$OR_a$, wherein any $(C_3-C_7)$carbocycle, $(C_2-C_6)$alkynyl, aryl, heterocycle and heteroaryl, as part of a group, is optionally substituted with one or more $Z^1$ groups;

e) $(C_1-C_6)$alkyl, wherein $(C_1-C_6)$alkyl is substituted with one or more $Z^2$ groups and optionally substituted with one or more $Z^1$ groups;

f) aryl, wherein aryl is substituted with one or more $Z^5$ groups and optionally substituted with one or more $Z^1$ groups; and g) $(C_2-C_6)$alkenyl and $(C_2-C_6)$alkynyl, wherein $(C_2-C_6)$alkenyl and $(C_2-C_6)$alkynyl are each independently substituted with one or more $Z^6$ groups and optionally substituted with one or more $Z^1$ groups.

Another specific value for $R^6$ is:

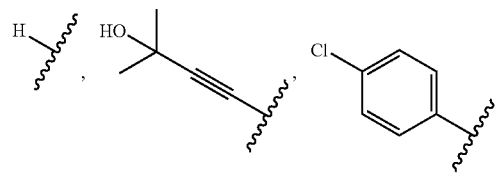

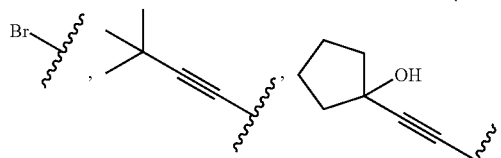

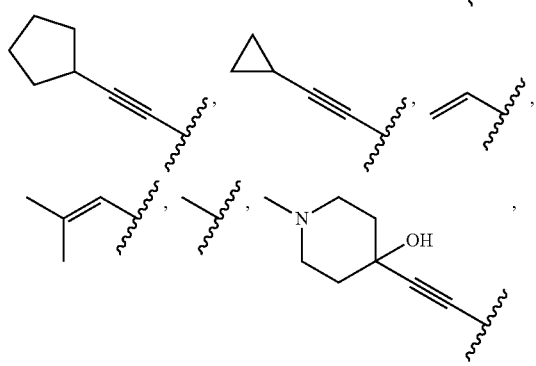

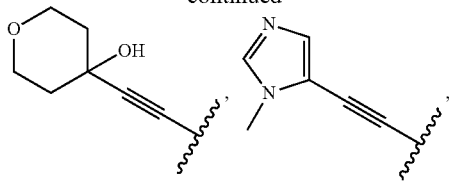

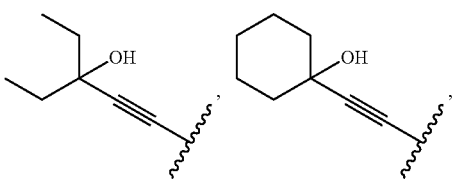

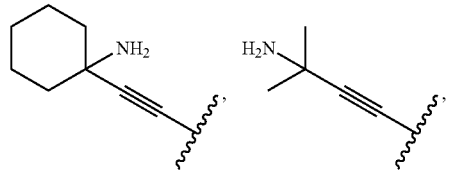

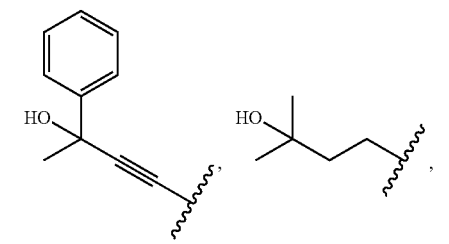

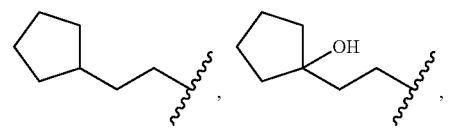

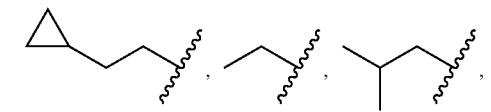

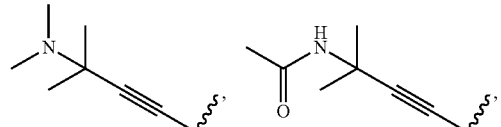

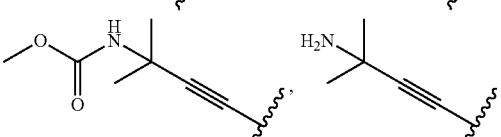

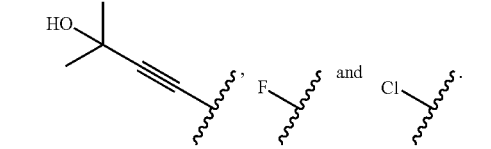

Another specific value for $R^6$ is

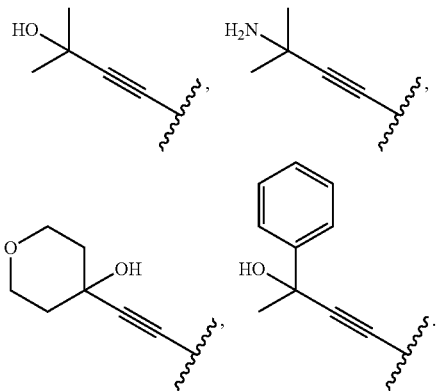

Another specific value for $R^6$ is H.

Another specific group of compounds of formula I are compounds wherein $R^7$ is selected from:
a) H, halo, $(C_1-C_6)$alkyl and $(C_1-C_6)$haloalkyl;
b) $(C_2-C_6)$alkenyl, $(C_2-C_6)$alkynyl, $(C_3-C_7)$cycloalkyl, nitro, cyano, aryl, heterocycle and heteroaryl, wherein any aryl, heterocycle or heteroaryl is optionally substituted with one or more $Z^{10}$ groups;
c) —C(=O)—$R^{11}$, —C(=O)—O—$R^{11}$, —O—$R^{11}$, —S—$R^{11}$, —S(O)—$R^{11}$, —S$_2$—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-SO$_2$—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein any aryl, heterocycle or heteroaryl is optionally substituted with one or more $Z^{10}$ groups;
d) —N($R^9$)$R^{10}$, —C(=O)—N($R^9$)$R^{10}$, —O—C(=O)—N($R^9$)$R^{10}$, —SO$_2$—N($R^9$)$R^{10}$, —$(C_1-C_6)$alkyl-N($R^9$)$R^{10}$, —$(C_1-C_6)$alkyl-C(=O)—N($R^9$)$R^{10}$, —$(C_1-C_6)$alkyl-O—C(=O)—N($R^9$)$R^{10}$ and —$(C_1-C_6)$alkyl-SO$_2$—N($R^9$)$R^{10}$, wherein each $R^9$ is independently selected from H, $(C_1-C_6)$alkyl and $(C_3-C_7)$cycloalkyl, and each $R^{10}$ is independently selected from $R^{11}$, —$(C_1-C_6)$alkyl-$R^{11}$, —SO$_2$—$R^{11}$, —C(=O)—$R^{11}$, —C(=O)O$R^{11}$ and —C(=O)N($R^9$)$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein any aryl, heterocycle or heteroaryl is optionally substituted with one or more $Z^{10}$ groups;
e) $(C_1-C_6)$alkyl, wherein $(C_1-C_6)$alkyl is substituted with one or more $Z^2$ groups and optionally substituted with one or more $Z^1$ groups;
f) aryl, heteroaryl, heterocycle, —Xaryl, —Xheteroaryl and —Xheterocycle, wherein aryl, heteroaryl and heterocycle are each substituted with one or more $Z^5$ groups and optionally substituted with one or more $Z^1$ groups;
g) $(C_1-C_6)$haloalkyl, $(C_3-C_7)$carbocycle, $(C_2-C_6)$alkenyl and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each substituted with one or more $Z^6$ groups and optionally substituted with one or more $Z^1$ groups; and
h) —NR$_e$R$_f$, —C(O)NR$_e$R$_f$, —OC(O)NR$_e$R$_f$, —SO$_2$NR$_e$R$_f$, —$(C_1-C_6)$alkyl-NR$_e$R$_f$, —$(C_1-C_6)$alkylC(O)—NR$_e$R$_f$, —$(C_1-C_6)$alkyl-O—C(O)—NR$_e$R$_f$ and —$(C_1$-$C_6)$alkyl-SO$_2$NR$_e$R$_f$, wherein each $(C_1-C_6)$alkyl is substituted with one or more $Z^6$ groups and optionally substituted with one or more $Z^1$ groups.

Another specific group of compounds of formula I are compounds wherein $R^7$ is selected from:
a) H, halo, $(C_1-C_6)$alkyl and $(C_1-C_6)$haloalkyl;
b) $(C_3-C_7)$cycloalkyl, cyano, aryl and heteroaryl, wherein any aryl, or heteroaryl is optionally substituted with one or more $Z^{10}$ groups;
c) —C(=O)—N($R^9$)$R^{10}$, wherein each $R^9$ is independently selected from H, $(C_1-C_6)$alkyl and $(C_3-C_7)$cycloalkyl, and each $R^{10}$ is independently selected from $R^{11}$, —$(C_1-C_6)$alkyl-$R^{11}$, —SO$_2$—$R^{11}$, —C(=O)—$R^{11}$, —C(=O)O$R^{11}$ and —C(=O)N($R^9$)$R^{10}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein any aryl, heterocycle or heteroaryl is optionally substituted with one or more $Z^{10}$ groups;
d) $(C_1-C_6)$alkyl, wherein $(C_1-C_6)$alkyl is substituted with one or more $Z^2$ groups and optionally substituted with one or more $Z^1$ groups;
e) aryl and heteroaryl, wherein aryl and heteroaryl are each substituted with one or more $Z^5$ groups and optionally substituted with one or more $Z^1$ groups;
f) $(C_1-C_6)$haloalkyl and $(C_3-C_7)$carbocycle, wherein $(C_1-C_6)$haloalkyl and $(C_3-C_7)$carbocycle are each substituted with one or more $Z^6$ groups and optionally substituted with one or more $Z^1$ groups; and
g) —C(O)NR$_e$R$_f$.

Another specific group of compounds of formula I are compounds wherein $R^7$ is selected from:
a) $(C_1-C_6)$alkyl, wherein $(C_1-C_6)$alkyl is substituted with one or more $Z^2$ groups and optionally substituted with one or more $Z^1$ groups;
b) aryl, heteroaryl, heterocycle, —Xaryl, —Xheteroaryl and —Xheterocycle, wherein aryl, heteroaryl and heterocycle are each substituted with one or more $Z^5$ groups and optionally substituted with one or more $Z^1$ groups;
c) $(C_1-C_6)$haloalkyl, $(C_3-C_7)$carbocycle, $(C_2-C_6)$alkenyl and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each substituted with one or more $Z^6$ groups and optionally substituted with one or more $Z^1$ groups; and
d) —NR$_e$R$_f$, —C(O)NR$_e$R$_f$, —OC(O)NR$_e$R$_f$, —SO$_2$NR$_e$R$_f$, —$(C_1-C_6)$alkyl-NR$_e$R$_f$, —$(C_1-C_6)$alkylC(O)—NR$_e$R$_f$, —$(C_1-C_6)$alkyl-O—C(O)—NR$_e$R$_f$ and —$(C_1-C_6)$alkyl-SO$_2$NR$_e$R$_f$ wherein each $(C_1-C_6)$alkyl is substituted with one or more $Z^6$ groups and optionally substituted with one or more $Z^1$ groups.

Another specific group of compounds of formula I are compounds wherein $R^7$ is selected from:
a) $(C_1-C_6)$alkyl, wherein $(C_1-C_6)$alkyl is substituted with one or more $Z^2$ groups and optionally substituted with one or more $Z^1$ groups;
b) aryl and heteroaryl, wherein aryl and heteroaryl are each substituted with one or more $Z^5$ groups and optionally substituted with one or more $Z^1$ groups;
c) $(C_1-C_6)$haloalkyl and $(C_3-C_7)$carbocycle, wherein $(C_1-C_6)$haloalkyl and $(C_3-C_7)$carbocycle are each substituted with one or more $Z^6$ groups and optionally substituted with one or more $Z^1$ groups; and
d) —C(O)NR$_e$R$_f$.

Another specific group of compounds of formula I are compounds wherein $R^7$ is selected from:
a) H, halo, $(C_1-C_6)$alkyl and $(C_1-C_6)$haloalkyl;
b) $(C_3-C_7)$cycloalkyl, cyano, aryl and heteroaryl, wherein any aryl, or heteroaryl is optionally substituted with one or more $Z^{10}$ groups;

c) —O—R$^{11}$ and —(C$_1$-C$_6$)alkyl-O—R$^{11}$, wherein any aryl, heterocycle or heteroaryl is optionally substituted with one or more Z$^{10}$ groups;

d) —C(=O)—N(R$^9$)R$^{10}$ and —(C$_1$-C$_6$)alkyl-N(R$^9$)R$^{10}$, wherein each R$^9$ is independently selected from H, (C$_1$-C$_6$)alkyl and (C$_3$-C$_7$)cycloalkyl, and each R$^{10}$ is independently selected from R$^{11}$, —(C$_1$-C$_6$)alkyl-R$^{11}$, —SO$_2$—R$^{11}$, —C(=O)—R$^{11}$, —C(=O)OR$^{11}$ and —C(=O)N(R$^9$)R$^{10}$, wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl, wherein any aryl, heterocycle or heteroaryl is optionally substituted with one or more Z$^{10}$ groups;

e) (C$_1$-C$_6$)alkyl, wherein (C$_1$-C$_6$)alkyl is substituted with one or more Z$^2$ groups and optionally substituted with one or more Z$^1$ groups;

f) aryl and heteroaryl, wherein aryl and heteroaryl are each substituted with one or more Z$^5$ groups and optionally substituted with one or more Z$^1$ groups; and g) (C$_1$-C$_6$)haloalkyl and (C$_3$-C$_7$)carbocycle, wherein (C$_1$-C$_6$)haloalkyl and (C$_3$-C$_7$)carbocycle are each substituted with one or more Z$^6$ groups and optionally substituted with one or more Z$^1$ groups; and h) —C(O)NR$_e$R$_f$.

Another specific value for R$^7$ is:

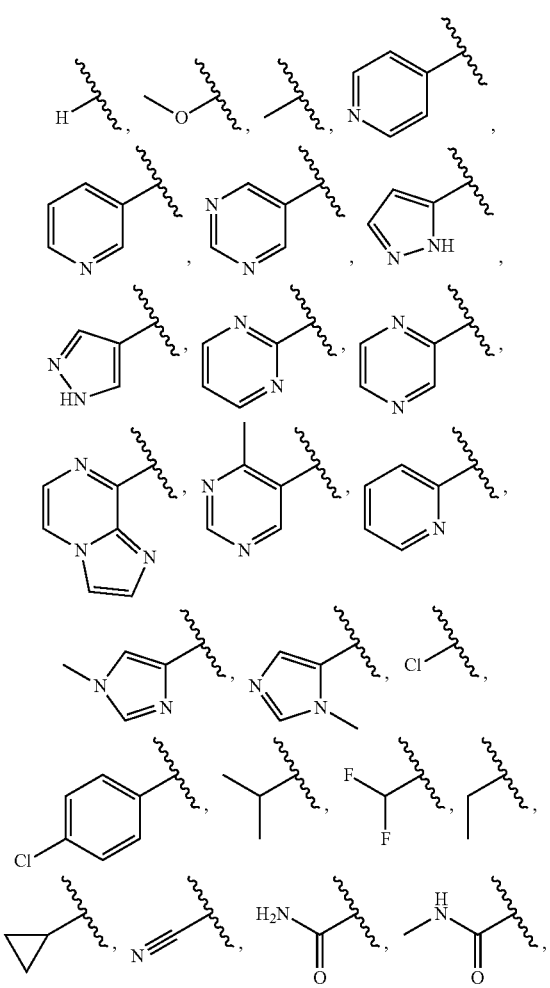

Another specific value for R$^7$ is

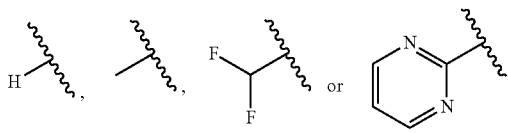

Another specific value for R$^7$ is

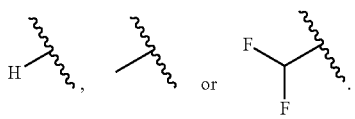

Another specific value for R$^7$ is H, halo, (C$_1$-C$_6$)alkyl, (C$_1$-C$_6$)haloalkyl and heteroaryl, wherein heteroaryl is optionally substituted with one or more Z$^{10}$ groups.

Another specific value for R$^7$ is H, (C$_1$-C$_6$)alkyl or (C$_1$-C$_6$)haloalkyl.

Another specific value for R$^7$ is H.

Another specific group of compounds of formula I are compounds wherein R$^8$ is selected from:

a) halo, nitro and cyano;

b) R$^{11}$, —C(=O)—R$^{11}$, —C(=O)—O—R$^{11}$, —O—R$^{11}$, —S—R$^{11}$, —S(O)—R$^{11}$, —SO$_2$—R$^{11}$, —(C$_1$-C$_6$)alkyl-R$^{11}$, —(C$_1$-C$_6$)alkyl-C(=O)—R$^{11}$, —(C$_1$-C$_6$)alkyl-C(=O)—O—R$^{11}$, —(C$_1$-C$_6$)alkyl-O—R$^{11}$, —(C$_1$-C$_6$)alkyl-S—R$^{11}$, —(C$_1$-C$_6$)alkyl-S(O)—R$^{11}$ and —(C$_1$-C$_6$)alkyl-SO$_2$—R$^1$ wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl, wherein aryl, heterocycle and heteroaryl are each optionally substituted with one or more Z$^1$ groups;

c) —N(R$^9$)R$^{10}$, —C(=O)—N(R$^9$)R$^{10}$, —O—C(=O)—N(R$^9$)R$^{10}$, —SO$_2$—N(R$^9$)R$^{10}$, —(C$_1$-C$_6$)alkyl-N(R$^9$)R$^{10}$, —(C$_1$-C$_6$)alkyl-C(=O)—N(R$^9$)R$^{10}$, —(C$_1$-C$_6$)alkyl-O—C(=O)—N(R$^9$)R$^{10}$ and —(C$_1$-C$_6$)alkyl-SO$_2$—N(R$^9$)R$^{10}$, wherein each R$^9$ is independently selected from H, (C$_1$-C$_6$)alkyl and (C$_3$-C$_7$)cycloalkyl, and each R$^{10}$ is independently selected from R$^{11}$, —(C$_1$-C$_6$)alkyl-R$^{11}$, —SO$_2$—R$^{11}$, —C(=O)—R$^{11}$, —C(=O)OR$^{11}$ and —C(=O)N(R$^9$)R$^{10}$, wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl;

d) (C$_1$-C$_6$)alkyl, wherein (C$_1$-C$_6$)alkyl is substituted with one or more Z$^2$ groups and optionally substituted with one or more Z$^1$ groups;

e) aryl, heteroaryl, heterocycle, —Xaryl, —Xheteroaryl and —Xheterocycle, wherein any aryl heteroaryl and heterocycle, either alone or as part of a group, is substituted with one or more Z$^5$ groups and optionally substituted with one or more Z$^1$ groups;

f) (C$_1$-C$_6$)haloalkyl, (C$_3$-C$_7$)carbocycle, (C$_2$-C$_6$)alkenyl and (C$_2$-C$_6$)alkynyl, wherein (C$_1$-C$_6$)haloalkyl, (C$_3$-C$_7$)carbocycle, (C$_2$-C$_6$)alkenyl and (C$_2$-C$_6$)alkynyl are each independently substituted with one or more $Z^6$ groups and optionally substituted with one or more $Z^1$ groups; and g) $-NR_eR_f$, $-C(O)NR_eR_f$, $-OC(O)NR_eR_f$, $-SO_2NR_eR_f$, $-(C_1-C_6)$alkyl-$NR_eR_f$, $-(C_1-C_6)$alkylC(O)—$NR_eR_f$, $-(C_1-C_6)$alkyl-O—C(O)—$NR_eR_f$ and —$(C_1-C_6)$alkyl-$SO_2NR_eR_f$, wherein any $(C_1-C_6)$alkyl, as part of a group, is substituted with one or more $Z^6$ groups and optionally substituted with one or more (e.g. 1, 2, 3, 4 or 5) $Z^1$ groups.

Another specific group of compounds of formula I are compounds wherein $R^8$ is selected from:

a) halo and cyano;
b) $R^{11}$, —O—$R^{11}$ and —$(C_1-C_6)$alkyl-$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein aryl, heterocycle and heteroaryl are each optionally substituted with one or more $Z^{11}$ groups;
c) —C(=O)—N($R^9$)$R^{10}$, wherein each $R^9$ is independently selected from H, $(C_1-C_6)$alkyl and $(C_3-C_7)$cycloalkyl, and each $R^{10}$ is independently selected from $R^{11}$, —$(C_1-C_6)$alkyl-$R^{11}$, —$SO_2$—$R^{11}$, —C(=O)—$R^{11}$, —C(=O)O$R^{11}$ and —C(=O)N($R^9$)$R^{10}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl;
d) $(C_1-C_6)$alkyl, wherein $(C_1-C_6)$alkyl is substituted with one or more $Z^2$ groups and optionally substituted with one or more $Z^1$ groups;
e) aryl and heteroaryl, wherein aryl and heteroaryl are each independently substituted with one or more $Z^5$ groups and optionally substituted with one or more $Z^1$ groups;
f) $(C_2-C_6)$alkynyl, wherein $(C_2-C_6)$alkynyl is substituted with one or more $Z^6$ groups and optionally substituted with one or more $Z^1$ groups; and
g) —C(O)$NR_eR_f$.

Another specific group of compounds of formula I are compounds wherein $R^8$ is selected from:

a) $(C_1-C_6)$alkyl, wherein $(C_1-C_6)$alkyl is substituted with one or more $Z^2$ groups and optionally substituted with one or more $Z^1$ groups;
b) aryl, heteroaryl, heterocycle, —Xaryl, —Xheteroaryl and —Xheterocycle, wherein any aryl heteroaryl and heterocycle, either alone or as part of a group, is substituted with one or more $Z^5$ groups and optionally substituted with one or more $Z^1$ groups;
c) $(C_1-C_6)$haloalkyl, $(C_3-C_7)$carbocycle, $(C_2-C_6)$alkenyl and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each independently substituted with one or more $Z^6$ groups and optionally substituted with one or more $Z^1$ groups; and
d) —$NR_eR_f$, —C(O)$NR_eR_f$, —OC(O)$NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—C(O)—$NR_eR_f$ and —$(C_1-C_6)$alkyl-$SO_2NR_eR_f$, wherein any $(C_1-C_6)$alkyl, as part of a group, is substituted with one or more $Z^6$ groups and optionally substituted with one or more (e.g. 1, 2, 3, 4 or 5) $Z^1$ groups.

Another specific group of compounds of formula I are compounds wherein $R^8$ is selected from:

a) $(C_1-C_6)$alkyl, wherein $(C_1-C_6)$alkyl is substituted with one or more $Z^2$ groups and optionally substituted with one or more $Z^1$ groups;
b) aryl and heteroaryl, wherein aryl and heteroaryl are each independently substituted with one or more $Z^5$ groups and optionally substituted with one or more $Z^1$ groups;
c) $(C_2-C_6)$alkynyl, wherein $(C_2-C_6)$alkynyl is substituted with one or more $Z^6$ groups and optionally substituted with one or more $Z^1$ groups; and
d) —C(O)$NR_eR_f$.

Another specific value for $R^8$ is.

[Structures shown]

Another specific value for $R^8$ is H.
Another specific value for $R^8$ is H, $(C_1-C_6)$alkyl or halo.
Another specific group of compounds of formula I are compounds wherein each $R_g$ is independently selected from —$OR_a$, $(C_1-C_6)$alkyl, $(C_3-C_7)$carbocycle $(C_1-C_6)$haloalkyl, $(C_2-C_6)$alkenyl, $(C_2-C_6)$alkynyl, aryl, heterocycle and heteroaryl, wherein any $(C_1-C_6)$alkyl, $(C_3-C_7)$carbocycle —$(C_1-C_6)$haloalkyl, $(C_2-C_6)$alkenyl, $(C_2-C_6)$alkynyl, aryl, heterocycle or heteroaryl of $R_g$ is optionally substituted with one or more $Z^1$ groups.

In one embodiment the compounds of formula I include compounds wherein:
$R^1$ is $R^{1a}$ or $R^{1b}$
$R^2$ is $R^{2a}$ or $R^{2b}$
$R^3$ is $R^{3a}$ or $R^{3b}$
$R^{3'}$ is $R^{3a'}$ or $R^{3b'}$
$R^4$ is $R^{4a}$ or $R^{4b}$
$R^5$ is $R^{5a}$ or $R^{5b}$
$R^6$ is $R^{6a}$ or $R^{6b}$
$R^7$ is $R^{7a}$ or $R^{7b}$
$R^8$ is $R^{8a}$ or $R^{8b}$
$R^{1a}$ is selected from:
a) H, halo, $(C_1-C_6)$alkyl and $(C_1-C_6)$haloalkyl;
b) $(C_2-C_6)$alkenyl, $(C_2-C_6)$alkynyl, $(C_3-C_7)$cycloalkyl, nitro, cyano, aryl, heterocycle and heteroaryl;
c) —C(=O)—$R^{11}$, —C(=O)—O—$R^{11}$, —O—$R^{11}$, —S—$R^{11}$, —S(O)—$R^{11}$, —$SO_2$—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-$SO_2$—$R^{11}$; wherein each $R^{11}$ is independently selected from H, $(C_1-C_6)$ alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl; and d) —N(R$^9$)R$^{10}$, —C(=O)—N(R$^9$)R$^{10}$, —O—C(=O)—N(R$^9$)R$^{10}$, —SO$_2$—N(R$^9$)R$^{10}$, —(C$_1$-C$_6$)alkyl-N(R$^9$)R$^{10}$, —(C$_1$-C$_6$)alkyl-C(=O)—N(R$^9$)R$^{10}$, —(C$_1$-C$_6$)alkyl-O—C(=O)—N(R$^9$)R$^{10}$ and —(C$_1$-C$_6$)alkyl-SO$_2$—N(R$^9$)R$^{10}$; wherein each R$^9$ is independently selected from H, $(C_1-C_6)$alkyl and $(C_3-C_7)$cycloalkyl; and
each R$^{10}$ is independently selected from R$^{11}$, —(C$_1$-C$_6$)alkyl-R$^{11}$, —SO$_2$—R$^{11}$, —C(=O)—R$^{11}$, —C(=O)OR$^{11}$ and —C(=O)N(R$^9$)R$^{11}$; wherein each R$^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl; and
wherein any aryl, heterocycle or heteroaryl of R$^{1a}$ is optionally substituted with one or more (e.g. 1, 2 or 3) Z$^{10}$ groups;

R$^{1b}$ is selected from:
a) —(C$_1$-C$_6$)alkyl-O—(C$_1$-C$_6$)alkyl-(C$_3$-C$_7$)carbocycle, —(C$_1$-C$_6$)alkyl-S—(C$_1$-C$_6$)alkyl-(C$_3$-C$_7$)carbocycle, —(C$_1$-C$_6$)alkyl-S(O)—(C$_1$-C$_6$)alkyl-(C$_3$-C$_7$)carbocycle, —(C$_1$-C$_6$)alkyl-SO$_2$—(C$_1$-C$_6$)alkyl-(C$_3$-C$_7$)carbocycle, —(C$_1$-C$_6$)alkyl-SO$_2$—(C$_1$-C$_6$)alkyl-Z$^{13}$, —C(O)—(C$_1$-C$_6$)alkyl-Z$^{13}$, —O—(C$_1$-C$_6$)alkyl-Z$^{13}$, —S—(C$_1$-C$_6$)alkyl-Z$^{13}$, —S(O)—(C$_1$-C$_6$)alkyl-Z$^{13}$, —SO$_2$—(C$_1$-C$_6$)alkyl-Z$^{13}$, —(C$_1$-C$_6$)alkyl-Z$^{14}$, —(C$_1$-C$_6$)alkyl-C(O)—(C$_1$-C$_6$)alkyl-Z$^{13}$, —(C$_1$-C$_6$)alkyl-C(O)—O(C$_1$-C$_6$)alkyl-Z$^{13}$, —(C$_1$-C$_6$)alkyl-O—(C$_1$-C$_6$)alkyl-Z$^{13}$, —(C$_1$-C$_6$)alkyl-S—(C$_1$-C$_6$)alkyl-Z$^{13}$, —(C$_2$-C$_6$)alkenyl-(C$_1$-C$_6$)haloalkyl, —(C$_2$-C$_6$)alkynyl-(C$_1$-C$_6$)haloalkyl, —(C$_3$-C$_7$)halocarbocycle, —NR$_a$SO$_2$NR$_c$R$_d$, —NR$_a$SO$_2$O(C$_3$-C$_7$)carbocycle, —NR$_a$SO$_2$Oaryl, —(C$_2$-C$_6$)alkenyl-(C$_3$-C$_7$)carbocycle, —(C$_2$-C$_6$)alkenyl-aryl, —(C$_2$-C$_6$)alkenyl-heteroaryl, —(C$_2$-C$_6$)alkenyl-heterocycle, —(C$_2$-C$_6$)alkynyl-(C$_3$-C$_7$)carbocycle, —(C$_2$-C$_6$)alkynyl-aryl, —(C$_2$-C$_6$)alkynyl-heteroaryl, —(C$_2$-C$_6$)alkynyl-heterocycle, —(C$_3$-C$_7$)carbocycle-Z$^1$ or -halo(C$_1$-C$_6$)alkyl-Z$^3$; wherein (C$_1$-C$_6$)alkyl, (C$_1$-C$_6$)haloalkyl, (C$_3$-C$_7$)carbocycle, (C$_2$-C$_6$)alkenyl, (C$_2$-C$_6$)alkynyl, aryl or heteroaryl are each optionally substituted with one or more (e.g. 1, 2, 3, 4 or 5) Z$^1$ groups;
b) spiro-bicyclic carbocycle, fused-bicyclic carbocycle and bridged-bicyclic carbocycle; wherein spiro-bicyclic carbocycle, fused-bicyclic carbocycle or bridged-bicyclic carbocycle are optionally substituted with one or more (e.g. 1, 2, 3, 4 or 5) Z$^1$ groups; wherein two Z$^1$ groups together with the atom or atoms to which they are attached optionally form a carbocycle or heterocycle wherein the carbocycle or heterocycle is optionally substituted with one or more (e.g. 1, 2, 3, 4 or 5) Z$^1$ groups;
c) (C$_1$-C$_6$)alkyl; wherein (C$_1$-C$_6$)alkyl is substituted with one or more Z$^2$ groups and optionally substituted with one or more (e.g. 1, 2, 3, 4 or 5) Z$^1$ groups;
d) —X(C$_1$-C$_6$)alkyl, —X(C$_1$-C$_6$)haloalkyl, —X(C$_2$-C$_6$)alkenyl, —X(C$_2$-C$_6$)alkynyl and —X(C$_3$-C$_7$)carbocycle; wherein (C$_1$-C$_6$)alkyl and (C$_1$-C$_6$)haloalkyl are each substituted with one or more Z$^3$ groups and optionally substituted with one or more Z$^1$ groups; and wherein (C$_2$-C$_6$)alkenyl, (C$_2$-C$_6$)alkynyl and (C$_3$-C$_7$)carbocycle are each substituted with one or more (e.g. 1, 2, 3, 4 or 5) Z$^4$ groups and optionally substituted with one or more Z$^1$ groups;
e) aryl, heteroaryl, heterocycle, —Xaryl, —Xheteroaryl and —Xheterocycle; wherein aryl heteroaryl and heterocycle are each substituted with one or more (e.g. 1, 2, 3, 4 or 5) Z$^5$ groups and optionally substituted with one or more Z$^1$ groups;
f) (C$_1$-C$_6$)haloalkyl, (C$_3$-C$_7$)carbocycle, (C$_2$-C$_6$)alkenyl, and (C$_2$-C$_6$)alkynyl; wherein (C$_1$-C$_6$)haloalkyl, (C$_3$-C$_7$)carbocycle, (C$_2$-C$_6$)alkenyl and (C$_2$-C$_6$)alkynyl are each substituted with one or more (e.g. 1, 2, 3, 4 or 5) Z$^6$ groups and optionally substituted with one or more Z$^1$ groups; and g) —NR$_e$R$_f$, —C(O)NR$_e$R$_f$, —OC(O)NR$_e$R$_f$, —SO$_2$NR$_e$R$_f$, —(C$_1$-C$_6$)alkyl-NR$_e$R$_f$, —(C$_1$-C$_6$)alkylC(O)—NR$_e$R$_f$, —(C$_1$-C$_6$)alkyl-O—C(O)—NR$_e$R$_f$ and —(C$_1$-C$_6$)alkyl-SO$_2$NR$_e$R$_f$; wherein each (C$_1$-C$_6$)alkyl is substituted with one or more (e.g. 1, 2, 3, 4 or 5) Z$^6$ groups and optionally substituted with one or more Z$^1$ groups;

R$^{2a}$ is selected from:
a) H, (C$_1$-C$_6$)alkyl and —O(C$_1$-C$_6$)alkyl;
b) (C$_2$-C$_6$)alkenyl, (C$_2$-C$_6$)alkynyl, (C$_1$-C$_6$)haloalkyl, (C$_3$-C$_7$)cycloalkyl, aryl, heterocycle, heteroaryl, halo, nitro and cyano;
c) C(=O)—R$^{11}$, —C(=O)—O—R$^{11}$, —S—R$^{11}$, —S(O)—R$^{11}$, —SO$_2$—R$^{11}$, —(C$_1$-C$_6$)alkyl-R$^{11}$, —(C$_1$-C$_6$)alkyl-C(=O)—R$^{11}$, —(C$_1$-C$_6$)alkyl-C(=O)—O—R$^{11}$, —(C$_1$-C$_6$)alkyl-O—R$^{11}$, —(C$_1$-C$_6$)alkyl-S—R$^1$, —(C$_1$-C$_6$)alkyl-S(O)—R$^{11}$ and —(C$_1$-C$_6$)alkyl-SO$_2$—R$^{11}$; wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl and heterocycle and heteroaryl; wherein aryl, heterocycle or heteroaryl are each optionally substituted with one or more (e.g. 1, 2 or 3) Z$^{11}$ groups;
d) —OH, —O(C$_2$-C$_6$)alkenyl, —O(C$_2$-C$_6$)alkynyl, —O(C$_1$-C$_6$)haloalkyl, —O(C$_3$-C$_7$)cycloalkyl, —Oaryl, —Oheterocycle and —Oheteroaryl;
e) —N(R$^9$)R$^{10}$, —C(=O)—N(R$^9$)R$^{10}$, —O—C(=O)—N(R$^9$)R$^{10}$, —SO$_2$—N(R$^9$)R$^{10}$, —(C$_1$-C$_6$)alkyl-N(R$^9$)R$^{10}$, —(C$_1$-C$_6$)alkyl-C(=O)—N(R$^9$)R$^{10}$, —(C$_1$-C$_6$)alkyl-O—C(=O)—N(R$^9$)R$^{10}$, and —(C$_1$-C$_6$)alkyl-SO$_2$—N(R$^9$)R$^{10}$; wherein each R$^9$ is independently selected from H, (C$_1$-C$_6$)alkyl and (C$_3$-C$_7$)cycloalkyl; and
each R$^{10}$ is independently selected from R$^{11}$, —(C$_1$-C$_6$)alkyl-R$^{11}$, —SO$_2$—R$^1$, —C(=O)—R$^{11}$, —C(=O)OR$^{11}$ and —C(=O)N(R$^9$)R$^{11}$; wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl;

R$^{2b}$ is selected from:
a) —(C$_1$-C$_6$)alkyl-O—(C$_1$-C$_6$)alkyl-(C$_3$-C$_7$)carbocycle, —(C$_1$-C$_6$)alkyl-S—(C$_1$-C$_6$)alkyl-(C$_3$-C$_7$)carbocycle, —(C$_1$-C$_6$)alkyl-S(O)—(C$_1$-C$_6$)alkyl-(C$_3$-C$_7$)carbocycle, —(C$_1$-C$_6$)alkyl-SO$_2$—(C$_1$-C$_6$)alkyl-(C$_3$-C$_7$)carbocycle, —(C$_2$-C$_6$)alkenyl-(C$_1$-C$_6$)haloalkyl, —(C$_2$-C$_6$)alkynyl-(C$_1$-C$_6$)haloalkyl, —(C$_1$-C$_6$)alkyl-SO$_2$—(C$_1$-C$_6$)alkyl-Z$^{13}$, —C(O)—(C$_1$-C$_6$)alkyl-Z$^{13}$, —O—(C$_1$-C$_6$)alkyl-Z$^{13}$, —S—(C$_1$-C$_6$)alkyl-Z$^{13}$, —S(O)—(C$_1$-C$_6$)alkyl-Z$^{13}$, —SO$_2$—(C$_1$-C$_6$)alkyl-Z$^{13}$, —(C$_1$-C$_6$)alkyl-Z$^{14}$, —(C$_1$-C$_6$)alkyl-C(O)—(C$_1$-C$_6$)alkyl-Z$^{13}$, —(C$_1$-C$_6$)alkyl-C(O)—O(C$_1$-C$_6$)alkyl-Z$^{13}$, —(C$_1$-C$_6$)alkyl-C$_6$)alkyl-O—(C$_1$-C$_6$)alkyl-Z$^{13}$, —(C$_1$-C$_6$)alkyl-S—(C$_1$-C$_6$)alkyl-Z$^{13}$, —(C$_3$-C$_7$)halocarbocycle, —NR$_a$SO$_2$NR$_c$R$_d$, —NR$_a$SO$_2$O(C$_3$-C$_7$)carbocycle, —NR$_a$SO$_2$Oaryl, —(C$_2$-C$_6$)alkenyl-(C$_3$-C$_7$)carbocycle, —(C$_2$-C$_6$)alkenyl-aryl, —(C$_2$-C$_6$)alkenyl-heteroaryl, —(C$_2$-C$_6$)alkenyl-heterocycle, —(C$_2$-C$_6$)alkynyl-(C$_3$-C$_7$)carbocycle, —(C$_2$-C$_6$)alkynyl-aryl, —(C$_2$-C$_6$)alkynyl-heteroaryl, —(C$_2$-C$_6$)alkynyl-heterocycle, —(C$_3$-C$_7$)carbocycle-Z$^1$ or -halo(C$_1$-C$_6$)alkyl-Z$^3$; wherein (C$_1$-C$_6$)alkyl, —(C$_1$-C$_6$)haloalkyl, (C$_3$-C$_7$)carbocycle, (C$_2$-C$_6$)alkenyl, (C$_2$-C$_6$)alkynyl, aryl or heteroaryl are each optionally substituted with one or more (e.g. 1, 2, 3, 4 or 5) Z$^1$ groups;
b) spiro-bicyclic carbocycle, fused-bicyclic carbocycle and bridged-bicyclic carbocycle; wherein spiro-bicyclic carbocycle, fused-bicyclic carbocycle or bridged-bicyclic carbocycle are optionally substituted with one or more (e.g. 1, 2, 3, 4 or 5) Z$^1$ groups; wherein two Z$^1$ groups together with the atom or atoms to which they are attached optionally form a $(C_3-C_7)$carbocycle or heterocycle wherein the $(C_3-C_6)$carbocycle or heterocycle is optionally substituted with one or more (e.g. 1, 2, 3, 4 or 5) $Z^1$ groups;

c) $(C_1-C_6)$alkyl; wherein $(C_1-C_6)$alkyl is substituted with one or more $Z^2$ groups and optionally substituted with one or more (e.g. 1, 2, 3, 4 or 5) $Z^1$ groups;

d) $-X(C_1-C_6)$alkyl, $X(C_1-C_6)$haloalkyl, $X(C_2-C_6)$alkenyl, $-X(C_2-C_6)$alkynyl and $-X(C_3-C_7)$carbocycle; wherein $(C_1-C_6)$alkyl and $(C_1-C_6)$haloalkyl are each substituted with one or more $Z^3$ groups and optionally substituted with one or more (e.g. 1, 2, 3, 4 or 5) $Z^1$ groups; and wherein $(C_2-C_6)$alkenyl, $(C_2-C_6)$alkynyl and $(C_3-C_7)$carbocycle are each substituted with one or more (e.g. 1, 2, 3, 4 or 5) $Z^4$ groups and optionally substituted with one or more $Z^1$ groups;

e) aryl, heteroaryl, heterocycle, $-$Xaryl, $-$Xheteroaryl and $-$Xheterocycle; wherein aryl heteroaryl and heterocycle are each substituted with one or more (e.g. 1, 2, 3, 4 or 5) $Z^5$ groups and optionally substituted with one or more (e.g. 1, 2, 3, 4 or 5) $Z^1$ groups;

f) $(C_1-C_6)$haloalkyl, $(C_3-C_7)$carbocycle, $(C_2-C_6)$alkenyl, and $(C_2-C_6)$alkynyl; wherein $(C_1-C_6)$haloalkyl, $(C_3-C_7)$carbocycle, $(C_2-C_6)$alkenyl and $(C_2-C_6)$alkynyl are each substituted with one or more (e.g. 1, 2, 3, 4 or 5) $Z^6$ groups and optionally substituted with one or more (e.g. 1, 2, 3, 4 or 5) $Z^1$ groups; and g) $-NR_eR_f$, $-C(O)NR_eR_f$, $-OC(O)NR_eR_f$, $-SO_2NR_eR_f$, $-(C_1-C_6)$alkyl-$NR_eR_f$, $-(C_1-C_6)$alkylC(O)$-NR_eR_f$, $-(C_1-C_6)$alkyl-O$-C(O)-NR_eR_f$ and $-(C_1-C_6)$alkyl-SO$_2NR_eR_f$; wherein each $(C_1-C_6)$alkyl is substituted with one or more (e.g. 1, 2, 3, 4 or 5) $Z^6$ groups and optionally substituted with one or more (e.g. 1, 2, 3, 4 or 5) $Z^1$ groups;

$R^{3a}$ is $(C_1-C_6)$alkyl, $(C_1-C_6)$haloalkyl, $(C_2-C_6)$alkenyl, $(C_2-C_6)$alkynyl, $-(C_1-C_6)$alkyl-$(C_3-C_7)$cycloalkyl, $-(C_1-C_6)$alkyl-aryl, $-(C_1-C_6)$alkyl-heterocycle, $-(C_1-C_6)$alkyl-heteroaryl, $-O(C_1-C_6)$alkyl, $-O(C_1-C_6)$haloalkyl, $-O(C_2-C_6)$alkenyl, $-O(C_2-C_6)$alkynyl, $-O(C_3-C_7)$cycloalkyl, $-$Oaryl, $-O(C_1-C_6)$alkyl-$(C_3-C_7)$cycloalkyl, $-O(C_1-C_6)$alkyl-aryl, $-O(C_1-C_6)$alkyl-heterocycle and $-O(C_1-C_6)$alkyl-heteroaryl; wherein any $(C_1-C_6)$alkyl, $(C_1-C_6)$haloalkyl, $(C_2-C_6)$alkenyl or $(C_2-C_6)$alkynyl of $R^{3a}$ is optionally substituted with one or more (e.g. 1, 2 or 3) groups selected from $-O(C_1-C_6)$alkyl, halo, oxo and $-$CN; and wherein any $(C_3-C_7)$cycloalkyl, aryl, heterocycle, or heteroaryl of $R^{3a}$ is optionally substituted with one or more (e.g. 1, 2 or 3) groups selected from $(C_1-C_6)$alkyl, $-O(C_1-C_6)$alkyl, halo, oxo and $-$CN; and $R^{3a'}$ is H;

$R^{3b}$ is $-(C_3-C_7)$carbocycle, aryl, heteroaryl, heterocycle, $-(C_1-C_6)$alkylOH, $-(C_1-C_6)$alkyl-O$-(C_1-C_6)$alkyl-$Z^{12}$, $-(C_1-C_6)$alkyl-O$-(C_2-C_6)$alkenyl-$Z^{12}$, $-(C_2-C_6)$alkyl-O$-(C_2-C_6)$alkynyl-$Z^{12}$, $-(C_1-C_6)$alkyl-S$-(C_1-C_6)$alkyl-$Z^2$, $-(C_1-C_6)$alkyl-S$-(C_2-C_6)$alkenyl-$Z^{12}$, $-(C_2-C_6)$alkyl-S$-(C_2-C_6)$alkynyl-$Z^{12}$, $-(C_1-C_6)$alkyl-S(O)$-(C_1-C_6)$alkyl-$Z^{12}$, $-(C_1-C_6)$alkyl-S(O)$-(C_2-C_6)$alkenyl-$Z^{12}$, $-(C_2-C_6)$alkyl-S(O)$-(C_2-C_6)$alkynyl-$Z^{12}$, $-(C_1-C_6)$alkyl-SO$_2-(C_1-C_6)$alkyl-$Z^{12}$, $-(C_1-C_6)$alkyl-SO$_2-(C_2-C_6)$alkenyl-$Z^{12}$, $-(C_2-C_6)$alkyl-SO$_2-(C_2-C_6)$alkynyl-$Z^{12}$, $-(C_2-C_6)$alkyl-$NR_aR_b$, $-(C_2-C_6)$alkylOC(O)$-NR_cR_d$, $-(C_2-C_6)$alkyl-$NR_a-C(O)-OR_b$, $-(C_2-C_6)$alkyl-$NR_a-C(O)-NR_aR_b$, $-(C_1-C_6)$alkyl-SO$_2(C_1-C_6)$alkyl, $-(C_1-C_6)$alkyl-SO$_2NR_cR_d$, $-(C_1-C_6)$alkyl-$NR_aSO_2NR_cR_d$, $-(C_1-C_6)$alkyl-$NR_aSO_2O(C_3-C_7)$carbocycle, $-(C_1-C_6)$alkyl-$NR_aSO_2Oaryl$, $-(C_1-C_6)$alkyl-$NR_a-SO_2-(C_1-C_6)$alkyl, $-(C_1-C_6)$alkyl-$NR_a-SO_2$-halo$(C_1-C_6)$alkyl, $-(C_1-C_6)$alkyl-$NR_a-SO_2-(C_2-C_6)$alkenyl, $-(C_1-C_6)$alkyl-$NR_a-SO_2-(C_2-C_6)$alkynyl, $-(C_1-C_6)$alkyl-$NR_a-SO_2-(C_3-C_7)$carbocycle, $-(C_1-C_6)$alkyl-$NR_a-SO_2$-halo$(C_3-C_7)$carbocycle, $-(C_1-C_6)$alkyl-$NR_a-SO_2$-aryl, $(C_1-C_6)$alkyl-$NR_a-SO_2$-heteroaryl, $-(C_1-C_6)$alkyl-$NR_a-SO_2$-heterocycle, $-O(C_1-C_6)$alkyl-$NR_aR_b$, $-O(C_1-C_6)$alkylOC(O)$-NR_cR_d$, $-O(C_1-C_6)$alkyl-$NR_a-C(O)-OR_b$, $-O(C_1-C_6)$alkyl-$NR_a-C(O)-NR_aR_b$, $-O(C_1-C_6)$alkyl-$NR_a-SO_2-(C_1-C_6)$alkyl, $-O(C_1-C_6)$alkyl-$NR_a-SO_2$-halo$(C_1-C_6)$alkyl, $-O(C_1-C_6)$alkyl-$NR_a-SO_2-(C_2-C_6)$alkenyl, $-O(C_1-C_6)$alkyl-$NR_a-SO_2-(C_2-C_6)$alkynyl, $-O(C_1-C_6)$alkyl-$NR_a-SO_2-(C_3-C_7)$carbocycle, $-O(C_1-C_6)$alkyl-$NR_a-SO_2$-halo$(C_3-C_7)$carbocycle, $-O(C_1-C_6)$alkyl-$NR_a-SO_2$-aryl, $-O(C_1-C_6)$alkyl-$NR_a-SO_2$-heteroaryl, $-O(C_1-C_6)$alkyl-$NR_a-SO_2$-heterocycle, $-O(C_1-C_6)$alkyl-$NR_a-SO_2-NR_aR_b$, $-O(C_1-C_6)$alkyl-$NR_a-SO_2-(C_3-C_7)$carbocycle, $-O(C_1-C_6)$alkyl-$NR_a-SO_2$-halo$(C_3-C_7)$carbocycle, $-O(C_1-C_6)$alkyl-$NR_a-SO_2$-aryl, $-O(C_1-C_6)$alkyl-$NR_aSO_2NR_cR_d$, $-O(C_1-C_6)$alkyl-$NR_aSO_2O(C_3-C_7)$carbocycle, $-O(C_1-C_6)$alkyl-$NR_aSO_2Oaryl$, $-$Oheteroaryl, $-$Oheterocycle, $-$Sheteroaryl, $-$Sheterocycle, $-$S(O)heteroaryl, $-$S(O)heterocycle, $-$SO$_2$heteroaryl or $-$SO$_2$heterocycle; wherein any $(C_1-C_6)$alkyl, aryl, $(C_3-C_7)$carbocycle, heteroaryl or heterocycle of $R^{3b}$ is optionally substituted with one or more (e.g. 1, 2, 3, 4 or 5) $Z^1$ groups; and $R^{3b'}$ is H, $(C_1-C_6)$alkyl or $-O(C_1-C_6)$alkyl; or $R^{3b}$ and $R^{3b'}$ together with the carbon to which they are attached form a heterocycle or $(C_3-C_7)$carbocycle which heterocycle or $(C_3-C_7)$carbocycle of $R^{3b}$ and $R^{3b'}$ together with the carbon to which they are attached is optionally substituted with one or more (e.g. 1, 2, 3, 4 or 5) $Z^1$ groups;

$R^{4a}$ is selected from aryl, heterocycle and heteroaryl, wherein any aryl, heterocycle and heteroaryl of $R^{4a}$ is optionally substituted with one or more (e.g. 1, 2, 3, 4 or 5) groups each independently selected from halo, $(C_1-C_6)$alkyl, $(C_2-C_6)$alkenyl, $(C_1-C_6)$haloalkyl, $(C_3-C_7)$cycloalkyl, $-$OH, $-O(C_1-C_6)$alkyl, $-$SH, $-S(C_1-C_6)$alkyl, $-$NH$_2$, $-$NH$(C_1-C_6)$alkyl and $-$N$((C_1-C_6)$alkyl$)_2$; wherein $(C_1-C_6)$alkyl is optionally substituted with hydroxy, $-O(C_1-C_6)$alkyl, cyano or oxo;

$R^{4b}$ is selected from;

a) $(C_1-C_6)$alkyl, $(C_2-C_6)$alkenyl and $(C_2-C_6)$alkynyl; wherein $(C_1-C_6)$alkyl, $(C_2-C_6)$alkenyl or $(C_2-C_6)$alkynyl are each optionally substituted with one or more (e.g. 1, 2, 3, 4 or 5) Z groups;

b) $(C_3-C_{14})$carbocycle; wherein $(C_3-C_{14})$carbocycle is optionally substituted with one or more (e.g. 1, 2, 3, 4 or 5) Z groups; wherein two $Z^1$ groups together with the atom or atoms to which they are attached optionally form a $(C_3-C_7)$carbocycle or heterocycle;

c) Spiro-heterocycle or bridged-heterocycle; wherein spiro-heterocycle or bridged-heterocycle is optionally substituted with one or more (e.g. 1, 2, 3, 4 or 5) $Z^1$ groups; or wherein two $Z^1$ groups together with the atom or atoms to which they are attached optionally form a $(C_3-C_7)$carbocycle or heterocycle;

d) aryl, heteroaryl, spiro-, fused-, or bridged-heterocycle; wherein aryl, heteroaryl, or spiro-, fused-, or bridged-heterocycle are each independently substituted with one or more $Z^7$ groups and optionally substituted with one or more (e.g. 1, 2, 3, 4 or 5) $Z^1$ groups; or $R^4$ and $R^3$ together with the atoms to which they are attached form a macroheterocycle or a macrocarbocycle wherein any macroheterocycle or macrocarbocycle of $R^4$ and $R^3$ together with the atoms to which they are attached may be optionally substituted with one or more (e.g. 1, 2, 3, 4 or 5) $Z^1$ groups; and $R^{3b'}$ is H or $(C_1-C_6)$alkyl, $-O(C_1-C_6)$alkyl.

$R^{5a}$ is selected from:

a) halo, nitro and cyano;

b) $R^{11}$, —C(=O)—$R^{11}$, —C(=O)—O—$R^{11}$, —O—$R^{11}$, —S—$R^{11}$, —S(O)—$R^{11}$, —SO$_2$—$R^{11}$, —(C$_1$-C$_6$)alkyl-$R^{11}$, —(C$_1$-C$_6$)alkyl-C(=O)—$R^{11}$, —(C$_1$-C$_6$)alkyl-C(=O)—O—$R^{11}$, —(C$_1$-C$_6$)alkyl-O—$R^{11}$, —(C$_1$-C$_6$)alkyl-S—$R^{11}$, —(C$_1$-C$_6$)alkyl-S(O)—$R^{11}$ and —(C$_1$-C$_6$)alkyl-SO$_2$—$R^{11}$; wherein each $R^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl; wherein aryl, heterocycle and heteroaryl are each optionally substituted with one or more (e.g. 1, 2 or 3) $Z^{11}$ groups;

c) —N($R^9$)$R^{10}$, —C(=O)—N($R^9$)$R^{10}$, —O—C(=O)—N($R^9$)$R^{10}$, —SO$_2$—N($R^9$)$R^{10}$, —(C$_1$-C$_6$)alkyl-N($R^9$)$R^{10}$, —(C$_1$-C$_6$)alkyl-C(=O)—N($R^9$)$R^{10}$, —(C$_1$-C$_6$)alkyl-O—C(=O)—N($R^9$)$R^{10}$, and —(C$_1$-C$_6$)alkyl-SO$_2$—N($R^9$)$R^{10}$; wherein each $R^9$ is independently selected from H, (C$_1$-C$_6$)alkyl and (C$_3$-C$_7$)cycloalkyl; and each $R^{10}$ is independently selected from $R^{11}$, —(C$_1$-C$_6$)alkyl-$R^{11}$, —SO$_2$—$R^{11}$, —C(=O)—$R^{11}$, —C(=O)O$R^{11}$ and —C(=O)N($R^9$)$R^{11}$; wherein each $R^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl;

$R^{5b}$ is selected from:

a) —(C$_1$-C$_6$)alkyl-O—(C$_1$-C$_6$)alkyl-(C$_3$-C$_7$)carbocycle, —(C$_1$-C$_6$)alkyl-S—(C$_1$-C$_6$)alkyl-(C$_3$-C$_7$)carbocycle, (C$_1$-C$_6$)alkylS(O)—(C$_1$-C$_6$)alkyl-(C$_3$-C$_7$)carbocycle, —(C$_1$-C$_6$)alkylSO$_2$(C$_3$-C$_7$)alkyl-(C$_3$-C$_7$)carbocycle, —(C$_2$-C$_6$)alkenyl-(C$_1$-C$_6$)haloalkyl, —(C$_2$-C$_6$)alkynyl-(C$_1$-C$_6$)haloalkyl, —(C$_3$-C$_7$)halocarbocycle, —NR$_a$SO$_2$NR$_c$R$_d$, —NR$_a$SO$_2$O(C$_3$-C$_7$)carbocycle, —NR$_a$SO$_2$Oaryl, —(C$_2$-C$_6$)alkenyl-(C$_3$-C$_7$)carbocycle, —(C$_2$-C$_6$)alkenyl-aryl, —(C$_2$-C$_6$)alkenyl-heteroaryl, —(C$_2$-C$_6$)alkenyl-heterocycle, —(C$_2$-C$_6$)alkynyl-(C$_3$-C$_7$)carbocycle, —(C$_2$-C$_6$)alkynyl-aryl, —(C$_2$-C$_6$)alkynyl-heteroaryl, —(C$_2$-C$_6$)alkynyl-heterocycle, —(C$_3$-C$_7$)carbocycle-$Z^1$ or -halo(C$_1$-C$_6$)alkyl-$Z^3$; wherein (C$_1$-C$_6$)alkyl, (C$_1$-C$_6$)haloalkyl, (C$_3$-C$_7$)carbocycle, (C$_2$-C$_6$)alkenyl, (C$_2$-C$_6$)alkynyl, aryl or heteroaryl are each optionally substituted with one or more (e.g. 1, 2, 3, 4 or 5) $Z^1$ groups;

b) spiro-bicyclic carbocycle, fused-bicyclic carbocycle and bridged-bicyclic carbocycle; wherein spiro-bicyclic carbocycle, fused-bicyclic carbocycle or bridged-bicyclic carbocycle are optionally substituted with one or more (e.g. 1, 2, 3, 4 or 5) $Z^1$ groups; wherein two $Z^1$ groups together with the atom or atoms to which they are attached optionally form a (C$_3$-C$_7$)carbocycle or heterocycle wherein the (C$_3$-C$_7$)carbocycle or heterocycle is optionally substituted with one or more (e.g. 1, 2, 3, 4 or 5) $Z^1$ groups;

c) (C$_1$-C$_6$)alkyl; wherein (C$_1$-C$_6$)alkyl is substituted with one or more $Z^2$ groups and optionally substituted with one or more (e.g. 1, 2, 3, 4 or 5) $Z^1$ groups;

d) —X(C$_1$-C$_6$)alkyl, —X(C$_1$-C$_6$)haloalkyl, —X(C$_2$-C$_6$)alkenyl, —X(C$_2$-C$_6$)alkynyl and —X(C$_3$-C$_7$)carbocycle; wherein (C$_1$-C$_6$)alkyl or (C$_1$-C$_6$)haloalkyl are each substituted with one or more $Z^3$ groups and optionally substituted with one or more $Z^1$ groups; and wherein (C$_2$-C$_6$)alkenyl, (C$_2$-C$_6$)alkynyl and (C$_3$-C$_7$)carbocycle are each independently substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle; wherein aryl heteroaryl are heterocycle are each independently substituted with one or more (e.g. 1, 2, 3, 4 or 5) $Z^5$ groups and optionally substituted with one or more (e.g. 1, 2, 3, 4 or 5) $Z^1$ groups;

f) (C$_1$-C$_6$)haloalkyl, (C$_3$-C$_7$)carbocycle, (C$_2$-C$_6$)alkenyl, and (C$_2$-C$_6$)alkynyl; where (C$_1$-C$_6$)haloalkyl, (C$_3$-C$_7$)carbocycle, (C$_2$-C$_6$)alkenyl and (C$_2$-C$_6$)alkynyl are each independently substituted with one or more (e.g. 1, 2, 3, 4 or 5) $Z^6$ groups and optionally substituted with one or more (e.g. 1, 2, 3, 4 or 5) $Z^1$ groups; and g) —NR$_e$R$_f$, —C(O)NR$_e$R$_f$, —OC(O)NR$_e$R$_f$, —SO$_2$NR$_e$R$_f$, —(C$_1$-C$_6$)alkyl-NR$_e$R$_f$, —(C$_1$-C$_6$)alkylC(O)—NR$_e$R$_f$, —(C$_1$-C$_6$)alkyl-O—C(O)—NR$_e$R$_f$ and —(C$_1$-C$_6$)alkyl-SO$_2$NR$_e$R$_f$; wherein each (C$_1$-C$_6$)alkyl is independently substituted with one or more (e.g. 1, 2, 3, 4 or 5) $Z^6$ groups and optionally substituted with one or more (e.g. 1, 2, 3, 4 or 5) $Z^1$ groups;

$R^{6a}$ is selected from:

a) H, halo, (C$_1$-C$_6$)alkyl, and (C$_1$-C$_6$)haloalkyl b) (C$_2$-C$_6$)alkenyl, (C$_2$-C$_6$)alkynyl, (C$_3$-C$_7$)cycloalkyl, nitro, cyano, aryl, heterocycle or heteroaryl;

c) —C(=O)—$R^{11}$, —C(=O)—O—$R^{11}$, —O—$R^{11}$, —S—$R^{11}$, —S(O)—$R^{11}$, —SO$_2$—$R^{11}$, —(C$_1$-C$_6$)alkyl-$R^{11}$, —(C$_1$-C$_6$)alkyl-C(=O)—$R^{11}$, —(C$_1$-C$_6$)alkyl-C(=O)—O—$R^{11}$, —(C$_1$-C$_6$)alkyl-O—$R^{11}$, —(C$_1$-C$_6$)alkyl-S—$R^{11}$, —(C$_1$-C$_6$)alkyl-S(O)—$R^{11}$ and —(C$_1$-C$_6$)alkyl-SO$_2$—$R^{11}$; wherein each $R^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl; and d) —N($R^9$)$R^{10}$, —C(=O)—N($R^9$)$R^{10}$, —O—C(=O)—N($R^9$)$R^{10}$, —SO$_2$—N($R^9$)$R^{10}$, —(C$_1$-C$_6$)alkyl-N($R^9$)$R^{10}$, —(C$_1$-C$_6$)alkyl-C(=O)—N($R^9$)$R^{10}$, —(C$_1$-C$_6$)alkyl-O—C(=O)—N($R^9$)$R^{10}$ and —(C$_1$-C$_6$)alkyl-SO$_2$—N($R^9$)$R^{10}$; wherein each $R^9$ is independently selected from H, (C$_1$-C$_6$)alkyl and (C$_3$-C$_7$)cycloalkyl; and each $R^{10}$ is independently selected from $R^{11}$, —(C$_1$-C$_6$)alkyl-$R^{11}$, —SO$_2$—$R^{11}$, —C(=O)—$R^{11}$, —C(=O)O$R^{11}$ and —C(=O)N($R^9$)$R^{10}$; wherein each $R^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl; and wherein any aryl, heterocycle or heteroaryl of $R^{6a}$ is optionally substituted with one or more (e.g. 1, 2 or 3) $Z^{10}$ groups;

$R^{6b}$ is selected from:

a) —(C$_1$-C$_6$)alkyl-O—(C$_1$-C$_6$)alkyl-(C$_3$-C$_7$)carbocycle, —(C$_1$-C$_6$)alkyl-S—(C$_1$-C$_6$)alkyl-(C$_3$-C$_7$)carbocycle, —(C$_1$-C$_6$)alkyl-S(O)—(C$_1$-C$_6$)alkyl-(C$_3$-C$_7$)carbocycle, —(C$_1$-C$_6$)alkyl-SO$_2$—(C$_1$-C$_6$)alkyl-(C$_3$-C$_7$)carbocycle, —(C$_2$-C$_6$)alkenyl-(C$_1$-C$_6$)haloalkyl, —(C$_2$-C$_6$)alkynyl-(C$_1$-C$_6$)haloalkyl, -halo(C$_3$-C$_7$)carbocycle, —NR$_a$SO$_2$NR$_c$R$_d$, —NR$_a$SO$_2$O(C$_3$-C$_7$)carbocycle, —NR$_a$SO$_2$Oaryl, —(C$_2$-C$_6$)alkenyl-(C$_3$-C$_7$)carbocycle, —(C$_2$-C$_6$)alkenyl-aryl, —(C$_2$-C$_6$)alkenyl-heteroaryl, —(C$_2$-C$_6$)alkenyl-heterocycle, (C$_2$-C$_6$)alkynyl-(C$_3$-C$_7$)carbocycle, —(C$_2$-C$_6$)alkynyl-aryl, —(C$_2$-C$_6$)alkynyl-heteroaryl, —(C$_2$-C$_6$)alkynyl-heterocycle, —(C$_3$-C$_7$)carbocycle-$Z^1$ or -halo(C$_1$-C$_6$)alkyl-$Z^3$; wherein (C$_1$-C$_6$)alkyl, (C$_1$-C$_6$)haloalkyl, (C$_3$-C$_7$)carbocycle, (C$_2$-C$_6$)alkenyl, (C$_2$-C$_6$)alkynyl, aryl or heteroaryl are optionally substituted with one or more (e.g. 1, 2, 3, 4 or 5) $Z^1$ groups;

b) spiro-bicyclic carbocycle, fused-bicyclic carbocycle and bridged-bicyclic carbocycle; wherein spiro-bicyclic carbocycle, fused-bicyclic carbocycle or bridged-bicyclic carbocycle are optionally substituted with one or more (e.g. 1, 2, 3, 4 or 5) $Z^1$ groups; wherein two $Z^1$ groups together with the atom or atoms to which they are attached optionally form a carbocycle or heterocycle wherein the carbocycle or heterocycle is optionally substituted with one or more $Z^1$ groups;

c) $(C_1-C_6)$alkyl; wherein $(C_1-C_6)$alkyl is substituted with one or more (e.g. 1, 2, 3, 4 or 5) $Z^2$ groups and optionally substituted with one or more (e.g. 1, 2, 3, 4 or 5) $Z^1$ groups;

d) —$X(C_1-C_6)$alkyl, —$X(C_1-C_6)$haloalkyl, —$X(C_2-C_6)$alkenyl, —$X(C_2-C_6)$alkynyl and —$X(C_3-C_7)$carbocycle; wherein $(C_1-C_6)$alkyl or $(C_1-C_6)$haloalkyl are each independently substituted with one or more (e.g. 1, 2, 3, 4 or 5) $Z^3$ groups and optionally substituted with one or more $Z^1$ groups; and wherein $(C_2-C_6)$alkenyl, $(C_2-C_6)$alkynyl and $(C_3-C_7)$carbocycle are each independently substituted with one or more $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle wherein aryl heteroaryl and heterocycle are each independently substituted with one or more $Z^5$ groups and optionally substituted with one or more (e.g. 1, 2, 3, 4 or 5) $Z^1$ groups;

f) $(C_1-C_6)$haloalkyl, $(C_3-C_7)$carbocycle, $(C_2-C_6)$alkenyl, and $(C_2-C_6)$alkynyl; wherein $(C_1-C_6)$haloalkyl, $(C_3-C_7)$carbocycle, $(C_2-C_6)$alkenyl and $(C_2-C_6)$alkynyl are each independently substituted with one or more (e.g. 1, 2, 3, 4 or 5) $Z^6$ groups and optionally substituted with one or more (e.g. 1, 2, 3, 4 or 5) $Z^1$ groups; and g) —$NR_eR_f$, —$C(O)NR_eR_f$, —$OC(O)NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—$C(O)$—$NR_eR_f$ and —$(C_1-C_6)$alkyl-$SO_2NR_eR_f$; wherein each $(C_1-C_6)$alkyl is independently substituted with one or more (e.g. 1, 2, 3, 4 or 5) $Z^6$ groups and optionally substituted with one or more (e.g. 1, 2, 3, 4 or 5) $Z^1$ groups;

$R^{7a}$ is selected from:

a) H, halo, $(C_1-C_6)$alkyl and $(C_1-C_6)$haloalkyl;

b) $(C_2-C_6)$alkenyl, $(C_2-C_6)$alkynyl, $(C_3-C_7)$cycloalkyl, nitro, cyano, aryl, heterocycle and heteroaryl;

c) —$C(=O)$—$R^{11}$, —$C(=O)$—$O$—$R^{11}$, —$O$—$R^{11}$, —$S$—$R^{11}$, —$S(O)$—$R^{11}$, —$SO_2$—$R^{11}$, —$(C_1-C_6)$alkyl-$R^{11}$, —$(C_1-C_6)$alkyl-$C(=O)$—$R^{11}$, —$(C_1-C_6)$alkyl-$C(=O)$—$O$—$R^{11}$, —$(C_1-C_6)$alkyl-$O$—$R^{11}$, —$(C_1-C_6)$alkyl-$S$—$R^{11}$, —$(C_1-C_6)$alkyl-$S(O)$—$R^{11}$ and —$(C_1-C_6)$alkyl-$SO_2$—$R^{11}$; wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl; and d) —$N(R^9)R^{10}$, —$C(=O)$—$N(R^9)R^{10}$, —$O$—$C(=O)$—$N(R^9)R^{10}$, —$SO_2$—$N(R^9)R^{10}$, —$(C_1-C_6)$alkyl-$N(R^9)R^{10}$, —$(C_1-C_6)$alkyl-$C(=O)$—$N(R^9)R^{10}$, —$(C_1-C_6)$alkyl-$O$—$C(=O)$—$N(R^9)R^{10}$ and —$(C_1-C_6)$alkyl-$SO_2$—$N(R^9)R^{10}$; wherein each $R^9$ is independently selected from H, $(C_1-C_6)$alkyl and $(C_3-C_7)$cycloalkyl; and each $R^{10}$ is independently selected from $R^{11}$, —$(C_1-C_6)$alkyl-$R^{11}$, —$SO_2$—$R^{11}$, —$C(=O)$—$R^{11}$, —$C(=O)OR^{11}$ and —$C(=O)N(R^9)R^{11}$; wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl; and wherein any aryl, heterocycle or heteroaryl of $R^{1a}$ is optionally substituted with one or more (e.g. 1, 2 or 3) $Z^{10}$ groups;

$R^{7b}$ is selected from:

a) —$(C_1-C_6)$alkyl-$SO_2$—$(C_1-C_6)$alkyl-$Z^{13}$, —$C(O)$—$(C_1-C_6)$alkyl-$Z^{13}$, —$O$—$(C_1-C_6)$alkyl-$Z^{13}$, —$S$—$(C_1-C_6)$alkyl-$Z^3$, —$S(O)$—$(C_1-C_6)$alkyl-$Z^{13}$, —$SO_2$—$(C_1-C_6)$alkyl-$Z^{13}$, —$(C_1-C_6)$alkyl-$Z^{14}$, —$(C_1-C_6)$alkyl-$C(O)$—$(C_1-C_6)$alkyl-$Z^{13}$, —$(C_1-C_6)$alkyl-$C(O)$—$O(C_1-C_6)$alkyl-$Z^{13}$, —$(C_1-C_6)$alkyl-$O$—$(C_1-C_6)$alkyl-$Z^{13}$, —$(C_1-C_6)$alkyl-$S$—$(C_1-C_6)$alkyl-$Z^{13}$, —$(C_1-C_6)$alkyl-$O$—$(C_1-C_6)$alkyl-$(C_3-C_7)$carbocycle, —$(C_1-C_6)$alkyl-$S$—$(C_1-C_6)$alkyl-$(C_3-C_7)$carbocycle, —$(C_1-C_6)$alkyl-$S(O)$—$(C_1-C_6)$alkyl-$(C_3-C_7)$carbocycle, —$(C_1-C_6)$alkyl-$S_2$—$(C_1-C_6)$alkyl-$(C_3-C_7)$carbocycle, —$(C_2-C_6)$alkenyl-$(C_1-C_6)$haloalkyl, —$(C_2-C_6)$alkynyl-$(C_1-C_6)$haloalkyl, —$(C_3-C_7)$halocarbocycle, —$NR_aSO_2NR_cR_d$, —$NR_aSO_2O(C_3-C_7)$carbocycle, —$NR_aSO_2Oaryl$, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_3-C_7)$carbocycle-$Z^1$ or -halo$(C_1-C_6)$alkyl-$Z^3$; wherein $(C_1-C_6)$alkyl, $(C_1-C_6)$haloalkyl, $(C_3-C_7)$carbocycle, $(C_2-C_6)$alkenyl, $(C_2-C_6)$alkynyl, aryl or heteroaryl are each optionally substituted with one or more (e.g. 1, 2, 3, 4 or 5) $Z^1$ groups;

b) spiro-bicyclic carbocycle, fused-bicyclic carbocycle and bridged-bicyclic carbocycle; wherein spiro-bicyclic carbocycle, fused-bicyclic carbocycle or bridged-bicyclic carbocycle are optionally substituted with one or more (e.g. 1, 2, 3, 4 or 5) $Z^1$ groups; wherein two $Z^1$ groups together with the atom or atoms to which they are attached optionally form a $(C_3-C_7)$carbocycle or heterocycle wherein the $(C_3-C_6)$carbocycle or heterocycle is optionally substituted with one or more (e.g. 1, 2, 3, 4 or 5) $Z^1$ groups;

c) $(C_1-C_6)$alkyl; wherein $(C_1-C_6)$alkyl is substituted with one or more $Z^2$ groups and optionally substituted with one or more (e.g. 1, 2, 3, 4 or 5) $Z^1$ groups;

d) —$X(C_1-C_6)$alkyl, $X(C_1-C_6)$haloalkyl, $X(C_2-C_6)$alkenyl, —$X(C_2-C_6)$alkynyl and —$X(C_3-C_7)$carbocycle; wherein $(C_1-C_6)$alkyl and $(C_1-C_6)$haloalkyl are each substituted with one or more $Z^3$ groups and optionally substituted with one or more $Z^1$ groups; and wherein $(C_2-C_6)$alkenyl, $(C_2-C_6)$alkynyl and $(C_3-C_7)$carbocycle are each substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle; wherein aryl, heteroaryl and heterocycle are each substituted with one or more $Z^5$ groups and optionally substituted with one or more (e.g. 1, 2, 3, 4 or 5) $Z^1$ groups;

f) $(C_1-C_6)$haloalkyl, $(C_3-C_7)$carbocycle, $(C_2-C_6)$alkenyl and $(C_2-C_6)$alkynyl; wherein $(C_1-C_6)$haloalkyl, $(C_3-C_7)$carbocycle, $(C_2-C_6)$alkenyl and $(C_2-C_6)$alkynyl are each substituted with one or more $Z^6$ groups and optionally substituted with one or more (e.g. 1, 2, 3, 4 or 5) $Z^1$ groups; and g) —$NR_eR_f$, —$C(O)NR_eR_f$, —$OC(O)NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—$C(O)$—$NR_eR_f$ and —$(C_1-C_6)$alkyl-$SO_2NR_eR_f$; wherein each $(C_1-C_6)$alkyl is substituted with one or more (e.g. 1, 2, 3, 4 or 5) $Z^6$ groups and optionally substituted with one or more (e.g. 1, 2, 3, 4 or 5) $Z^1$ groups;

$R^{8a}$ is selected from:

a) halo, nitro and cyano;

b) $R^{11}$, —$C(=O)$—$R^{11}$, —$C(=O)$—$O$—$R^{11}$, —$O$—$R^{11}$, —$S$—$R^{11}$, —$S(O)$—$R^{11}$, —$SO_2$—$R^{11}$, —$(C_1-C_6)$alkyl-$R^{11}$, —$(C_1-C_6)$alkyl-$C(=O)$—$R^{11}$, —$(C_1-C_6)$alkyl-$C(=O)$—$O$—$R^{11}$, —$(C_1-C_6)$alkyl-$O$—$R^{11}$, —$(C_1-C_6)$alkyl-$S$—$R^{11}$, —$(C_1-C_6)$alkyl-$S(O)$—$R^{11}$ and —$(C_1-C_6)$alkyl-$SO_2$—$R^{11}$; wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl; wherein aryl, heterocycle and heteroaryl are each optionally substituted with one or more (e.g. 1, 2 or 3) $Z^{11}$ groups;

c) —$N(R^9)R^{10}$, —$C(=O)$—$N(R^9)R^{10}$, —$O$—$C(=O)$—$N(R^9)R^{10}$, —$SO_2$—$N(R^9)R^{10}$, —$(C_1-C_6)$alkyl-$N(R^9)R^{10}$, —$(C_1-C_6)$alkyl-$C(=O)$—$N(R^9)R^{10}$, —$(C_1-C_6)$alkyl-$O$—$C(=O)$—$N(R^9)R^{10}$ and —$(C_1-C_6)$alkyl-$SO_2$—$N(R^9)R^{10}$;

wherein each $R^9$ is independently selected from H, $(C_1-C_6)$alkyl and $(C_3-C_7)$cycloalkyl; and each $R^{10}$ is independently selected from $R^{11}$, —$(C_1-C_6)$alkyl-$R^{11}$, —$SO_2$—$R^1$, —C(=O)—$R^{11}$, —C(=O)O$R^{11}$ and —C(=O)N($R^9$)$R^{10}$; wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl;

$R^{8b}$ is selected from:

a) —$(C_1-C_6)$alkyl-$SO_2$—$(C_1-C_6)$alkyl-$Z^{13}$, —C(O)—$(C_1-C_6)$alkyl-$Z^3$, —O—$(C_1-C_6)$alkyl-$Z^{13}$, —S—$(C_1-C_6)$alkyl-$Z^{13}$, —S(O)—$(C_1-C_6)$alkyl-$Z^{13}$, —$SO_2$—$(C_1-C_6)$alkyl-$Z^{13}$, —$(C_1-C_6)$alkyl-$Z^{14}$, —$(C_1-C_6)$alkyl-C(O)—$(C_1-C_6)$alkyl-$Z^{13}$, —$(C_1-C_6)$alkyl-C(O)—O$(C_1-C_6)$alkyl-$Z^{13}$, —$(C_1-C_6)$alkyl-O—$(C_1-C_6)$alkyl-$Z^{13}$, —$(C_1-C_6)$alkyl-S—$(C_1-C_6)$alkyl-$Z^{13}$, —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkyl-S(O)—$(C_1-C_6)$alkyl-$(C_3-C_7)$carbocycle, —$(C_1-C_6)$alkyl-$SO_2$—$(C_1-C_6)$alkyl-$(C_3-C_7)$carbocycle, —$(C_2-C_6)$alkenyl-$(C_1-C_6)$haloalkyl, —$(C_2-C_6)$alkynyl-$(C_1-C_6)$haloalkyl, -halo$(C_3-C_7)$carbocycle, —$NR_aSO_2NR_cR_d$, —$NR_aSO_2O(C_3-C_7)$carbocycle, —$NR_aSO_2Oaryl$, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_3-C_7)$carbocycle-$Z^1$ or -halo$(C_1-C_6)$alkyl-$Z^3$; wherein $(C_1-C_6)$alkyl, $(C_1-C_6)$haloalkyl, $(C_3-C_7)$carbocycle, $(C_2-C_6)$alkenyl, $(C_2-C_6)$alkynyl, aryl or heteroaryl are each optionally substituted with one or more (e.g. 1, 2, 3, 4 or 5) $Z^1$ groups:

b) spiro-bicyclic carbocycle, fused-bicyclic carbocycle and bridged-bicyclic carbocycle; wherein spiro-bicyclic carbocycle, fused-bicyclic carbocycle or bridged-bicyclic carbocycle are optionally substituted with one or more (e.g. 1, 2, 3, 4 or 5) $Z^1$ groups; wherein two $Z^1$ groups together with the atom or atoms to which they are attached optionally form a $(C_3-C_7)$carbocycle or heterocycle wherein the $(C_3-C_7)$carbocycle or heterocycle is optionally substituted with one or more (e.g. 1, 2, 3, 4 or 5) $Z^1$ groups;

c) $(C_1-C_6)$alkyl; wherein $(C_1-C_6)$alkyl is substituted with one or more $Z^2$ groups and optionally substituted with one or more (e.g. 1, 2, 3, 4 or 5) $Z^1$ groups;

d) —X$(C_1-C_6)$alkyl, —X$(C_1-C_6)$haloalkyl, —X$(C_2-C_6)$alkenyl, —X$(C_2-C_6)$alkynyl and —X$(C_3-C_7)$carbocycle; wherein $(C_1-C_6)$alkyl and $(C_1-C_6)$haloalkyl are each independently substituted with one or more $Z^3$ groups and optionally substituted with one or more (e.g. 1, 2, 3, 4 or 5) $Z^1$ groups; and wherein any $(C_2-C_6)$alkenyl, $(C_2-C_6)$alkynyl and $(C_3-C_7)$carbocycle are each independently substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle wherein any aryl heteroaryl and heterocycle are each independently substituted with one or more (e.g. 1, 2, 3, 4 or 5) $Z^5$ groups and optionally substituted with one or more (e.g. 1, 2, 3, 4 or 5) $Z^1$ groups;

f) $(C_1-C_6)$haloalkyl, $(C_3-C_7)$carbocycle, $(C_2-C_6)$alkenyl and $(C_2-C_6)$alkynyl; wherein $(C_1-C_6)$haloalkyl, $(C_3-C_7)$carbocycle, $(C_2-C_6)$alkenyl and $(C_2-C_6)$alkynyl are each independently substituted with one or more (e.g. 1, 2, 3, 4 or 5) $Z^6$ groups and optionally substituted with one or more (e.g. 1, 2, 3, 4 or 5) $Z^1$ groups; and g) —$NR_eR_f$, —C(O)$NR_eR_f$, —OC(O)$NR_eR_f$, —$SO_2NR_eR_f$, —$(C_1-C_6)$alkyl-$NR_eR_f$, —$(C_1-C_6)$alkylC(O)—$NR_eR_f$, $C_1-C_6$)alkyl-O—C(O)—$NR_eR_f$ and —$(C_1-C_6)$alkyl-$SO_2NR_eR_f$; wherein each $(C_1-C_6)$alkyl is independently substituted with one or more (e.g. 1, 2, 3, 4 or 5) $Z^6$ groups and optionally substituted with one or more (e.g. 1, 2, 3, 4 or 5) $Z^1$ groups;

or any of $R^{5a}$ and $R^{6a}$, $R^{6a}$ and $R^{7a}$, $R^{7a}$ and $R^{8a}$, $R^1$ and $R^8$ or $R^1$ and $R^2$ together with the atoms to which they are attached form a 5 or 6-membered carbocycle or a 4, 5, 6 or 7-membered heterocycle; wherein the 5 or 6-membered carbocycle or a 4, 5, 6 or 7-membered heterocycle is optionally substituted with one or more (e.g. 1, 2 or 3) substituents each independently selected from halo, $(C_1-C_6)$alkyl, $(C_2-C_6)$alkenyl, $(C_1-C_6)$haloalkyl, $(C_3-C_7)$cycloalkyl, —OH, —O$(C_1-C_6)$alkyl, —SH, —S$(C_1-C_6)$alkyl, —$NH_2$, —NH$(C_1-C_6)$alkyl and —N$((C_1-C_6)$alkyl$)_2$;

or any of $R^5$ and $R^6$, $R^6$ and $R^7$ or $R^7$ and $R^8$, together with the atoms to which they are attached form a 5 or 6-membered carbocycle or a 4, 5, 6 or 7-membered heterocycle; wherein the 5 or 6-membered carbocycle or a 4, 5, 6 or 7-membered heterocycle are each independently substituted with one or more (e.g. 1, 2 or 3) $Z^7$ or $Z^8$ groups; wherein when two $Z^7$ groups are on same atom the two $Z^7$ groups together with the atom to which they are attached optionally form a $(C_3-C_7)$carbocycle or 4, 5 or 6-membered heterocycle;

or $R^1$ and $R^8$ or $R^1$ and $R^2$ together with the atoms to which they are attached form a 5 or 6-membered carbocycle or a 4, 5, 6 or 7-membered heterocycle; wherein the 5 or 6-membered carbocycle or a 4, 5, 6 or 7-membered heterocycle are each independently substituted with one or more (e.g. 1, 2 or 3) $Z^7$ or $Z^8$ groups; wherein when two $Z^7$ groups are on same atom the two $Z^7$ groups together with the atom to which they are attached optionally form a $(C_3-C_7)$carbocycle or 4, 5 or 6-membered heterocycle;

X is independently selected from O, —C(O)—, —C(O)O—, —S—, —S(O)—, —$SO_2$, —$(C_1-C_6)$alkylO—, —$(C_1-C_6)$alkylC(O)—, —$(C_1-C_6)$alkylC(O)O—, —$(C_1-C_6)$alkylS—, —$(C_1-C_6)$alkylS(O)—, —$(C_1-C_6)$alkyl$SO_2$—;

each $Z^1$ is independently selected from halo, —$NO_2$, —OH, =$NOR_a$, —SH, —CN, —$(C_1-C_6)$alkyl, —$(C_2-C_6)$alkenyl, —$(C_2-C_6)$alkynyl, —$(C_1-C_6)$haloalkyl, $(C_3-C_7)$carbocycle, —$(C_3-C_7)$halocarbocycle, -aryl, -heteroaryl, -heterocycle, —O$(C_1-C_6)$alkyl, —O$(C_2-C_6)$alkenyl, —O$(C_2-C_6)$alkynyl, —O$(C_1-C_6)$haloalkyl, —O$(C_3-C_7)$carbocycle, —O$(C_3-C_7)$halocarbocycle, —Oaryl, —Oheteroaryl, —Oheterocycle, —S$(C_1-C_6)$alkyl, —S$(C_2-C_6)$alkenyl, —S$(C_2-C_6)$alkynyl, —S$(C_1-C_6)$haloalkyl, —S$(C_3-C_7)$carbocycle, —S$(C_3-C_7)$halocarbocycle, —Saryl, —Sheteroaryl, —Sheterocycle, —S(O)$(C_1-C_6)$alkyl, —S(O)$(C_2-C_6)$alkenyl, —S(O)$(C_2-C_6)$alkynyl, —S(O)$(C_1-C_6)$haloalkyl, —S(O) $(C_3-C_7)$carbocycle, —S(O)$(C_3-C_7)$halocarbocycle, —$SO_2(C_1-C_6)$alkyl, —S(O)aryl, —S(O)carbocycle, —S(O)heteroaryl, —S(O)heterocycle, —$SO_2(C_2-C_6)$alkenyl, —$SO_2(C_2-C_6)$alkynyl, —$SO_2(C_1-C_6)$haloalkyl, —$SO_2(C_3-C_7)$carbocycle, —$SO_2(C_3-C_7)$halocarbocycle, —$SO_2$aryl, —$SO_2$heteroaryl, —$SO_2$heterocycle, —$SO_2NR_cR_d$, —$NR_cR_d$, —$NR_aC(O)R_a$, —$NR_aC(O)ORa$, —$NR_aC(O)NR_cR_d$—$NR_aSO_2R_b$, —$NR_aSO_2NR_cR_d$, —$NR_aSO_2O(C_3-C_7)$carbocycle, —$NR_aSO_2Oaryl$, —OS(O)$_2R_a$, —C(O)$R_a$, —C(O)O$R_b$, —C(O)$NR_cR_d$, and —OC(O)$NR_cR_d$, wherein any $(C_1-C_6)$alkyl, $(C_2-C_6)$alkenyl, $(C_2-C_6)$alkynyl, —$(C_3-C_7)$halocarbocycle, $(C_3-C_7)$carbocycle, $(C_3-C_7)$halocarbocycle, aryl, heteroaryl or heterocycle of $Z^1$ is optionally substituted with one or more (e.g. 1, 2, 3, 4 or 5) halogen, —OH, —$OR_b$, —CN, —$NR_aC(O)_2R_b$, -heteroaryl, -heterocycle, —Oheteroaryl, —Oheterocycle, —NHheteroaryl, —NHheterocycle, or —S(O)$_2NR_cR_d$;

each $Z^2$ is independently selected from —$NO_2$, —CN, spiro-heterocycle, bridge-heterocycle, spiro-bicyclic carbocycle, bridged-bicyclic carbocycle, $NR_aSO_2(C_3-C_7)$carbocycle, —NR$_a$SO$_2$aryl, —NR$_a$SO$_2$heteroaryl, —NR$_a$SO$_2$NR$_c$R$_d$, —NR$_a$SO$_2$O(C$_3$-C$_7$)carbocycle and —NR$_a$SO$_2$Oaryl;

each Z$^3$ is independently selected from —NO$_2$, —CN, —OH, oxo, =NOR$_a$, thioxo, -aryl, -heterocycle, -heteroaryl, —(C$_3$-C$_7$)halocarbocycle, —O(C$_1$-C$_6$)alkyl, —O(C$_3$-C$_7$)carbocycle, —Ohalo(C$_3$-C$_7$)carbocycle, —Oaryl, —Oheterocycle, —Oheteroaryl, —S(C$_1$-C$_6$)alkyl, —S(C$_3$-C$_7$)carbocycle, —S(C$_3$-C$_7$)halocarbocycle, —Saryl, —Sheterocycle, —Sheteroaryl, —S(O)(C$_1$-C$_6$)alkyl, —S(O)(C$_3$-C$_7$)carbocycle, —S(O)(C$_3$-C$_7$)halocarbocycle, —S(O)aryl, —S(O)heterocycle, —S(O)heteroaryl, —SO$_2$(C$_1$-C$_6$)alkyl, —SO$_2$(C$_3$-C$_7$)carbocycle, —SO$_2$(C$_3$-C$_7$)halocarbocycle, SO$_2$aryl, —SO$_2$heterocycle, —SO$_2$heteroaryl, —NR$_a$R$_b$, —NR$_a$C(O)R$_b$, —C(O)NR$_c$R$_d$, —SO$_2$NR$_c$R$_d$, —NR$_a$SO$_2$NR$_c$R$_d$, —NR$_a$SO$_2$O(C$_3$-C$_7$)carbocycle and —NR$_a$SO$_2$Oaryl;

each Z$^4$ is independently selected from halogen, —(C$_1$-C$_6$)alkyl, (C$_3$-C$_7$)carbocycle, -halo(C$_1$-C$_6$)alkyl, —NO$_2$, —CN, —OH, oxo, =NOR$_a$, thioxo, -aryl, -heterocycle, -heteroaryl, —(C$_3$-C$_7$)halocarbocycle, —O(C$_1$-C$_6$)alkyl, —O(C$_3$-C$_7$)carbocycle, —O(C$_3$-C$_7$)halocarbocycle, —Oaryl, —Oheterocycle, —Oheteroaryl, —S(C$_1$-C$_6$)alkyl, —S(C$_3$-C$_7$)carbocycle, —S(C$_3$-C$_7$)halocarbocycle, —Saryl, —Sheterocycle, —Sheteroaryl, —S(O)(C$_1$-C$_6$)alkyl, —S(O)(C$_3$-C$_7$)carbocycle, —S(O)(C$_3$-C$_7$)halocarbocycle, —S(O)aryl, —S(O)heterocycle, —S(O)heteroaryl, —SO$_2$(C$_1$-C$_6$)alkyl, —SO$_2$(C$_3$-C$_7$)carbocycle, —SO$_2$(C$_3$-C$_7$)halocarbocycle, SO$_2$aryl, —SO$_2$heterocycle, —SO$_2$heteroaryl, —NR$_a$R$_b$, —NR$_a$C(O)R$_a$, —C(O)NR$_c$R$_d$, —SO$_2$NR$_c$R$_d$, —NR$_a$SO$_2$NR$_c$R$_d$, —NR$_a$SO$_2$O(C$_3$-C$_7$)carbocycle and —NR$_a$SO$_2$Oaryl;

each Z$^5$ is independently selected from —NO$_2$, —CN, —NR$_a$SO$_2$NR$_c$R$_d$, —NR$_a$SO$_2$O(C$_3$-C$_7$)carbocycle, —NR$_a$SO$_2$Oaryl, —NR$_a$SO$_2$(C$_1$-C$_6$)alkyl, —NR$_a$SO$_2$(C$_2$-C$_6$)alkenyl, —NR$_a$SO$_2$(C$_2$-C$_6$)alkynyl, —NR$_a$SO$_2$(C$_3$-C$_7$)carbocycle, —NR$_a$SO$_2$(C$_3$-C$_7$)halocarbocycle, —NR$_a$SO$_2$aryl, —NR$_a$SO$_2$hetearyl, —NR$_a$SO$_2$heteroaryl, —NR$_a$SO$_2$heterocycle, —NR$_a$C(O)alkyl, —NR$_a$C(O)alkenyl, —NR$_a$C(O)alkynyl, —NR$_a$C(O)(C$_3$-C$_7$)carbocycle, —NR$_a$C(O)(C$_3$-C$_7$)halocarbocycle, —NR$_a$C(O)aryl, —NR$_a$C(O)heterocycle, —NR$_a$C(O)heterocycle, NR$_a$C(O)NR$_c$R$_d$ and NR$_a$C(O)OR$_b$;

each Z$^6$ is independently selected from —NO$_2$, —CN, —NR$_a$R$_a$, NR$_a$C(O)R$_b$, —C(O)NR$_c$R$_d$, —(C$_3$-C$_7$)halocarbocycle, -aryl, -heteroaryl, -heterocycle, —Oaryl, —Oheteroaryl, —Oheterocycle, —O(C$_3$-C$_7$)halocarbocycle, —O(C$_1$-C$_6$)alkyl, —O(C$_3$-C$_7$)carbocycle, —Ohalo(C$_1$-C$_6$)alkyl, —Saryl, —Sheteroaryl, —Sheterocycle, —S(C$_3$-C$_7$)halocarbocycle, —S(C$_1$-C$_6$)alkyl, —S(C$_3$-C$_7$)carbocycle, —S(C$_1$-C$_6$)haloalkyl, —S(O)aryl, —S(O)heteroaryl, —S(O)heterocycle, —S(O)(C$_3$-C$_7$)halocarbocycle, —S(O)(C$_1$-C$_6$)alkyl, —S(O)(C$_3$-C$_7$)carbocycle, —S(O)halo(C$_1$-C$_6$)alkyl, —SO$_2$aryl, —SO$_2$heteroaryl, —SO$_2$heterocycle, —SO$_2$(C$_1$-C$_6$)alkyl, —SO$_2$halo(C$_1$-C$_6$)alkyl, —SO$_2$(C$_3$-C$_7$)carbocycle, —SO$_2$(C$_3$-C$_7$)halocarbocycle, —SO$_2$NR$_c$R$_d$, —NR$_a$SO$_2$(C$_3$-C$_7$)halocarbocycle, —NR$_a$SO$_2$aryl, —NR$_a$SO$_2$hetearyl, —NR$_a$SO$_2$heteroaryl, —NR$_a$SO$_2$NR$_c$R$_d$, —NR$_a$SO$_2$O(C$_3$-C$_7$)carbocycle and —NR$_a$SO$_2$Oaryl.

each Z$^7$ is independently selected from —NO$_2$, =NOR$_a$, —CN, —(C$_1$-C$_6$)alkyl-Z$^{12}$, —(C$_2$-C$_6$)alkenyl-Z$^{12}$, —(C$_2$-C$_6$)alkenylOH, —(C$_2$-C$_6$)alkynyl-Z$^{12}$, —(C$_2$-C$_6$)alkynylOH, —(C$_1$-C$_6$)haloalkyl-Z$^{12}$, —(C$_1$-C$_6$)haloalkylOH, —(C$_3$-C$_7$)carbocycle-Z$^{12}$, —(C$_3$-C$_7$)carbocycleOH, —(C$_3$-C$_7$)halocarbocycle, —(C$_1$-C$_6$)alkylNR$_c$R$_d$, —(C$_1$-C$_6$)alkyl-NR$_a$C(O)R$_a$, —(C$_1$-C$_6$)alkylNR$_a$SO$_2$R$_a$, -aryl, -heteroaryl, -heterocycle, —O(C$_1$-C$_6$)alkyl-Z$^{12}$, —O(C$_2$-C$_6$)alkenyl, —O(C$_2$-C$_6$)alkynyl, —O(C$_1$-C$_6$)haloalkyl, —O(C$_3$-C$_7$)carbocycle, —O(C$_3$-C$_7$)halocarbocycle, —Oaryl, —O(C$_1$-C$_6$)alkylNR$_c$R$_d$, —O(C$_1$-C$_6$)alkylNR$_a$C(O)R$_a$, —O(C$_1$-C$_6$)alkylNR$_a$SO$_2$R$_a$, —Oheterocycle, —Oheteroaryl, —S(C$_1$-C$_6$)alkyl-Z$^{12}$, —S(C$_2$-C$_6$)alkenyl, —S(C$_2$-C$_6$)alkynyl, —S(C$_1$-C$_6$)haloalkyl, —S(C$_3$-C$_7$)carbocycle, —S(C$_3$-C$_7$)halocarbocycle, —S(C$_1$-C$_6$)alkylNR$_c$R$_d$, —S(C$_1$-C$_6$)alkylNR$_a$C(O)R$_a$, —S(C$_1$-C$_6$)alkylNR$_a$SO$_2$R$_a$, —Saryl, —Sheteroaryl, —Sheterocycle, —S(O)(C$_1$-C$_6$)alkyl, —S(O)(C$_2$-C$_6$)alkenyl, —S(O)(C$_2$-C$_6$)alkynyl, —S(O)(C$_1$-C$_6$)haloalkyl, —S(O)(C$_3$-C$_7$)carbocycle, —S(O)(C$_3$-C$_7$)halocarbocycle, —SO$_2$(C$_1$-C$_6$)alkyl, —S(O)(C$_1$-C$_6$)alkylNR$_c$R$_d$, —S(O)(C$_1$-C$_6$)alkylNR$_a$C(O)R$_a$, —S(O)(C$_1$-C$_6$)alkylNR$_a$SO$_2$R$_a$, —S(O)aryl, —S(O)heteroaryl, —S(O)heterocycle, —SO$_2$(C$_1$-C$_6$)alkyl, —SO$_2$(C$_2$-C$_6$)alkenyl, —SO$_2$(C$_2$-C$_6$)alkynyl, —SO$_2$(C$_1$-C$_6$)haloalkyl, —SO$_2$(C$_3$-C$_7$)carbocycle, —SO$_2$(C$_3$-C$_7$)halocarbocycle, —SO$_2$aryl, —SO$_2$heteroaryl, —SO$_2$heterocycle, —SO$_2$(C$_1$-C$_6$)alkylNR$_c$R$_d$, —SO$_2$(C$_1$-C$_6$)alkylNR$_a$C(O)R$_a$, —SO$_2$(C$_1$-C$_6$)alkylNR$_a$SO$_2$R$_a$, —SO$_2$NR$_c$R$_d$, —NR$_a$C(O)OR$_b$, —NR$_a$C(O)NR$_c$R$_d$, —NR$_a$SO$_2$R$_b$, —NR$_a$SO$_2$NR$_c$R$_d$, —NR$_a$SO$_2$O(C$_3$-C$_7$)carbocycle, —NR$_a$SO$_2$Oaryl, —OS(O)$_2$R$_a$, —C(O)NR$_c$R$_d$ and —OC(O)NR$_c$R$_d$, wherein any (C$_1$-C$_6$)alkyl, (C$_2$-C$_6$)alkenyl, (C$_2$-C$_6$)alkynyl, (C$_3$-C$_7$)carbocycle, (C$_3$-C$_7$)halocarbocycle, aryl, heteroaryl or heterocycle of Z$^7$ is optionally substituted with one or more (e.g. 1, 2, 3, 4 or 5) halogen, —OH, —OR$_b$, —CN, —NR$_a$C(O)$_2$R$_b$, -heteroaryl, -heterocycle, —Oheteroaryl, —Oheterocycle, —NHheteroaryl, —NHheterocycle, or —S(O)$_2$NR$_c$R$_d$.

each Z$^8$ is independently selected from —NO$_2$ or —CN;

each Z$^9$ is independently selected from —(C$_1$-C$_6$)alkyl, —O(C$_1$-C$_6$)alkyl;

each Z$^{10}$ is independently selected from i) halo, oxo, thioxo, (C$_2$-C$_6$)alkenyl, (C$_1$-C$_6$)haloalkyl, (C$_3$-C$_7$)cycloalkyl, (C$_3$-C$_7$)cycloalkyl-(C$_1$-C$_6$)alkyl-, —OH, —O(C$_1$-C$_6$)alkyl, —O(C$_1$-C$_6$)haloalkyl, —SH, —S(C$_1$-C$_6$)alkyl, —SO(C$_1$-C$_6$)alkyl, —SO$_2$(C$_1$-C$_6$)alkyl, —NH$_2$, —NH(C$_1$-C$_6$)alkyl and —N((C$_1$-C$_6$)alkyl)$_2$;

ii) (C$_1$-C$_6$)alkyl optionally substituted with —OH, —O—(C$_1$-C$_6$)haloalkyl, or —O—(C$_1$-C$_6$)alkyl; and iii) aryl, heterocycle and heteroaryl, which aryl, heterocycle and heteroaryl is optionally substituted with halo, (C$_1$-C$_6$)alkyl or COOH;

each Z$^{11}$ is independently selected from Z$^{10}$, —C(=O)—NH$_2$, —C(=O)—NH(C$_1$-C$_4$)alkyl, —C(=O)—N((C$_1$-C$_4$)alkyl)$_2$, —C(=O)-aryl, —C(=O)-heterocycle and —C(=O)-heteroaryl;

each Z$^{12}$ is independently selected from —NO$_2$, =NOR$_a$, thioxo, -aryl, -heterocycle, -heteroaryl, —(C$_3$-C$_7$)halocarbocycle, —(C$_3$-C$_7$)carbocycle, —O(C$_3$-C$_7$)carbocycle, —Ohalo(C$_3$-C$_7$)carbocycle, —Oaryl, —Oheterocycle, —Oheteroaryl, —S(C$_1$-C$_6$)alkyl, —S(C$_3$-C$_7$)carbocycle, —Shalo(C$_3$-C$_7$)carbocycle, —Saryl, —Sheterocycle, —Sheteroaryl, —S(O)(C$_1$-C$_6$)alkyl, —S(O)(C$_3$-C$_7$)carbocycle, —S(O)halo(C$_3$-C$_7$)carbocycle, —S(O)aryl, —S(O)heterocycle, —S(O)heteroaryl, —SO$_2$(C$_1$-C$_6$)alkyl, —SO$_2$(C$_3$-C$_7$)carbocycle, —SO$_2$(C$_3$-C$_7$)halocarbocycle, SO$_2$aryl, —SO$_2$heterocycle, —SO$_2$heteroaryl, —NR$_a$R$_a$, —NR$_a$C(O)R$_b$, —C(O)NR$_c$R$_d$, —SO$_2$NR$_c$R$_d$, —NR$_a$SO$_2$NR$_c$R$_d$, —NR$_a$SO$_2$O(C$_3$-C$_7$)carbocycle and —NR$_a$SO$_2$Oaryl;

each Z$^{13}$ is independently selected from —NO$_2$, —OH, =NOR$_a$, —SH, —CN, —(C$_3$-C$_7$)halocarbocycle, —O(C$_1$-C$_6$)alkyl, —O(C$_2$-C$_6$)alkenyl, —O(C$_2$-C$_6$)alkynyl, —O(C$_1$-C$_6$)haloalkyl, —O(C$_3$-C$_7$)carbocycle, —O(C$_3$-C$_7$)halocarbocycle, —Oaryl, —Oheteroaryl, —Oheterocycle, —S(C$_1$-

$C_6$)alkyl, —S($C_2$-$C_6$)alkenyl, —S($C_2$-$C_6$)alkynyl, —S($C_1$-$C_6$)haloalkyl, —S($C_3$-$C_7$)carbocycle, —S($C_3$-$C_7$)halocarbocycle, —Saryl, —Sheteroaryl, —Sheterocycle, —S(O)($C_1$-$C_6$)alkyl, —S(O)($C_2$-$C_6$)alkenyl, —S(O)($C_2$-$C_6$)alkynyl, —S(O)($C_1$-$C_6$)haloalkyl, —S(O)($C_3$-$C_7$)carbocycle, —S(O)($C_3$-$C_7$)halocarbocycle, —S(O)aryl, —S(O)heteroaryl, —S(O)heterocycle, —$SO_2$($C_1$-$C_6$)alkyl, —$SO_2$($C_2$-$C_6$)alkenyl, —$SO_2$($C_2$-$C_6$)alkynyl, —$SO_2$($C_1$-$C_6$)haloalkyl, —$SO_2$($C_3$-$C_7$)carbocycle, —$SO_2$($C_3$-$C_7$)halocarbocycle, —$SO_2$aryl, —$SO_2$heteroaryl, —$SO_2$heterocycle, —$SO_2NR_cR_d$, —$NR_cR_d$, —$NR_aC(O)R_a$, —$NR_aC(O)OR_b$, —$NR_aC(O)NR_cR_d$, —$NR_aSO_2R_b$, —$NR_aSO_2NR_cR_d$, —$NR_aSO_2O(C_3$-$C_7)$carbocycle, —$NR_aSO_2Oaryl$, —$OS(O)_2R_a$, —$C(O)R_a$, —$C(O)OR_b$, —$C(O)NR_cR_d$, and —$OC(O)NR_cR_d$; wherein any ($C_1$-$C_6$)alkyl, ($C_2$-$C_6$)alkenyl, ($C_2$-$C_6$)alkynyl, —($C_3$-$C_7$)halocarbocycle, ($C_3$-$C_7$)carbocycle, ($C_3$-$C_7$)halocarbocycle, aryl, heteroaryl or heterocycle of $Z^{13}$ is optionally substituted with one or more (e.g. 1, 2, 3, 4 or 5) halogen, —OH, —$OR_b$, —CN, —$NR_aC(O)_2R_b$, -heteroaryl, -heterocycle, —Oheteroaryl, —Oheterocycle, —NHheteroaryl, —NHheterocycle, or —$S(O)_2NR_cR_d$;

each $Z^{14}$ is independently selected from —$NO_2$, =$NOR_a$, —CN, —($C_3$-$C_7$)halocarbocycle, —O($C_3$-$C_7$)halocarbocycle, —S($C_3$-$C_7$)halocarbocycle, —S(O)($C_3$-$C_7$)halocarbocycle, —$SO_2$($C_3$-$C_7$)halocarbocycle, —$NR_aSO_2NR_cR_d$, —$NR_aSO_2O(C_3$-$C_7)$carbocycle, —$NR_aSO_2Oaryl$, —OS(O)$_2$ $R_a$; wherein any —($C_3$-$C_7$)halocarbocycle of $Z^{14}$ is optionally substituted with one or more (e.g. 1, 2, 3, 4 or 5) halogen, —OH, —$OR_b$, —CN, —$NR_aC(O)_2R_b$, -heteroaryl, -heterocycle, —Oheteroaryl, —Oheterocycle, —NHheteroaryl, —NHheterocycle, or —$S(O)_2NR_cR_d$;

each $R_a$ is independently H, ($C_1$-$C_6$)alkyl, —($C_2$-$C_6$)alkenyl, —($C_2$-$C_6$)alkynyl, ($C_3$-$C_7$)carbocycle, heterocycle, aryl, aryl($C_1$-$C_6$)alkyl-, heteroaryl or heteroaryl($C_1$-$C_6$)alkyl-; wherein any ($C_1$-$C_6$)alkyl, ($C_2$-$C_6$)alkenyl, ($C_2$-$C_6$)alkynyl, ($C_3$-$C_7$)carbocycle, heterocycle, aryl, or heteroaryl of $R_a$ is optionally substituted by halogen, OH and cyano;

each $R_b$ is independently —($C_1$-$C_6$)alkyl, —($C_2$-$C_6$)alkenyl, —($C_2$-$C_6$)alkynyl, ($C_3$-$C_7$)carbocycle, heterocycle, aryl, aryl($C_1$-$C_6$)alkyl-, heteroaryl or heteroaryl($C_1$-$C_6$)alkyl-; wherein any ($C_1$-$C_6$)alkyl, —($C_2$-$C_6$)alkenyl, —($C_2$-$C_6$)alkynyl, ($C_3$-$C_7$)carbocycle, heterocycle, aryl, or heteroaryl of $R_b$ is optionally substituted by halogen, OH and cyano;

$R_c$ and $R_d$ are each independently selected from H, ($C_1$-$C_6$)alkyl, ($C_2$-$C_6$)alkenyl, ($C_2$-$C_6$)alkynyl, ($C_3$-$C_7$)carbocycle, aryl, aryl($C_1$-$C_6$)alkyl-, heterocycle, heteroaryl or heteroaryl($C_1$-$C_6$)alkyl- wherein any ($C_1$-$C_6$)alkyl, —($C_2$-$C_6$)alkenyl, —($C_2$-$C_6$)alkynyl, ($C_3$-$C_7$)carbocycle, heterocycle, aryl, or heteroaryl of $R_c$ or $R_d$ is optionally substituted by halogen, OH and cyano; or $R_c$ and $R_d$ together with the nitrogen to which they are attached form a heterocycle; wherein any heterocycle of $R_c$, and $R_d$ together with the nitrogen to which they are attached is optionally substituted by halogen, OH or cyano;

each $R_e$ is independently selected from —$OR_a$, ($C_1$-$C_6$)alkyl or ($C_3$-$C_7$)carbocycle wherein ($C_1$-$C_6$)alkyl or ($C_3$-$C_7$)carbocycle is substituted by one or more $Z_d$ and optionally substituted with one or more $Z_1$; —($C_2$-$C_6$)haloalkyl, —($C_2$-$C_6$)alkenyl, or —($C_2$-$C_6$)alkynyl wherein any haloalkyl, alkenyl or alkynyl is optionally substituted with one or more $Z_1$; aryl, heterocycle or heteroaryl wherein aryl, heterocycle or heteroaryl is substituted by one or more $Z_c$;

each $R_f$ is independently selected from —$R_g$, —$OR_a$, —($C_1$-$C_6$)alkyl-$Z^6$, —$SO_2R_g$, —$C(O)R_g$, $C(O)OR_g$, or —$C(O)NR_eR_g$; and each $R_g$ is independently selected from —$OR_a$, ($C_1$-$C_6$)alkyl, ($C_3$-$C_7$)carbocycle ($C_1$-$C_6$)haloalkyl, ($C_2$-$C_6$)alkenyl, ($C_2$-$C_6$)alkynyl, aryl, heterocycle or heteroaryl wherein any ($C_1$-$C_6$)alkyl, ($C_3$-$C_7$)carbocycle —($C_1$-$C_6$)haloalkyl, ($C_2$-$C_6$)alkenyl, ($C_2$-$C_6$)alkynyl, aryl, heterocycle or heteroaryl of $R_g$ is optionally substituted with one or more $Z_1$ groups;

or a salt thereof.

In one embodiment, the compounds of formula I include:

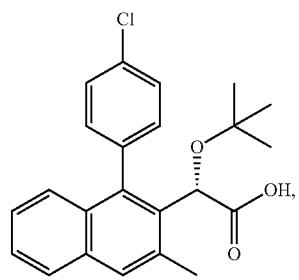

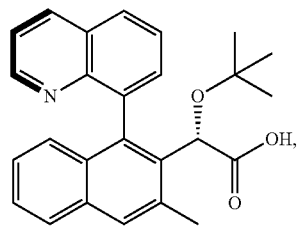

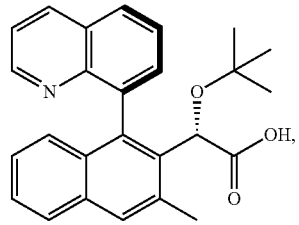

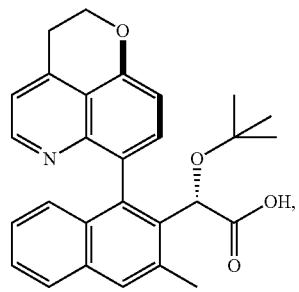

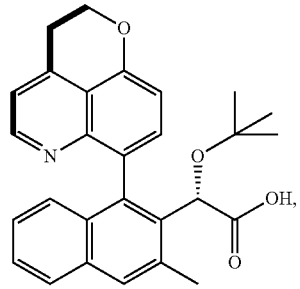

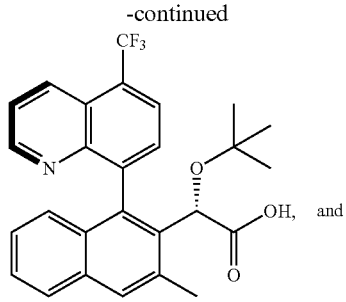
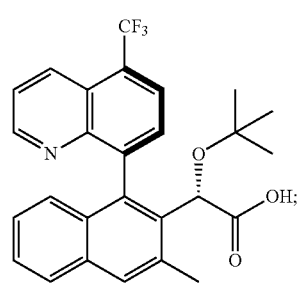
and salts thereof.
In another embodiment, the compounds of formula I include:
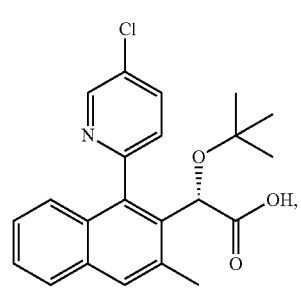
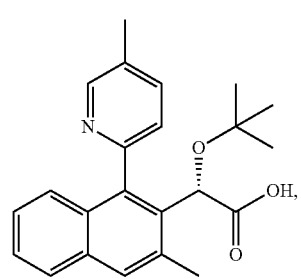
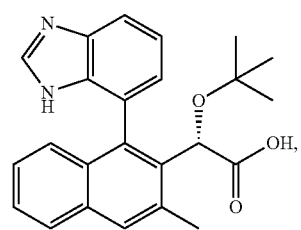
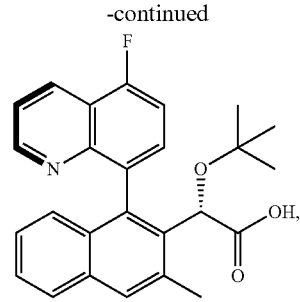
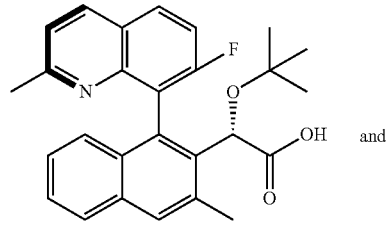
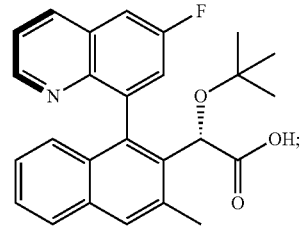
and salts thereof.
In another embodiment, the compounds of formula I include:
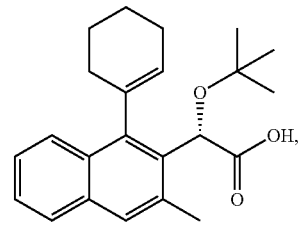
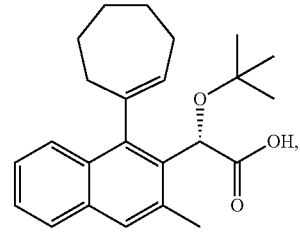
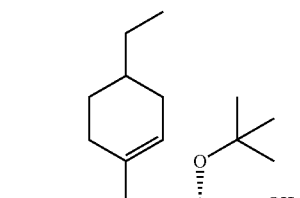

77
-continued
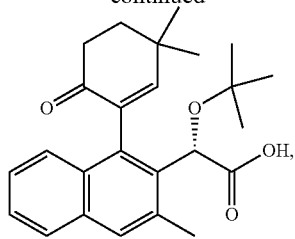
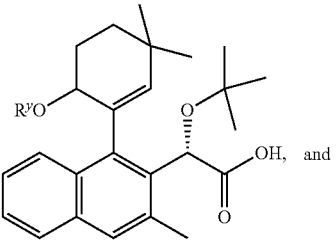
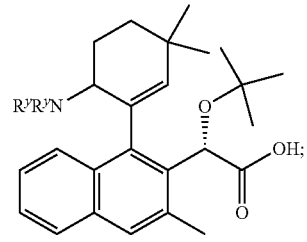
wherein each $R^y$ is independently H or $(C_1-C_6)$alkyl and salts thereof.
In another embodiment, the compounds of formula I include:
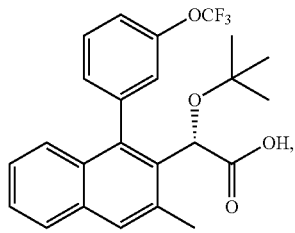
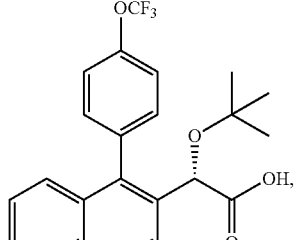
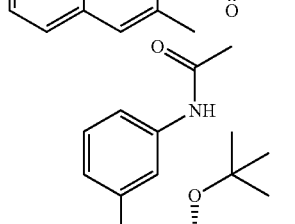
78
-continued
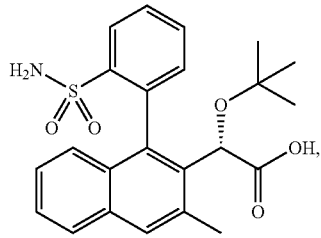
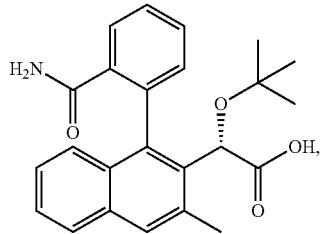
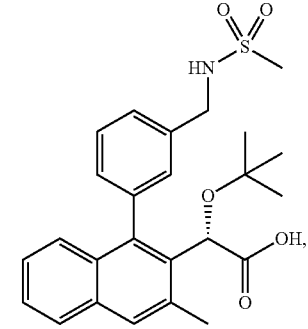
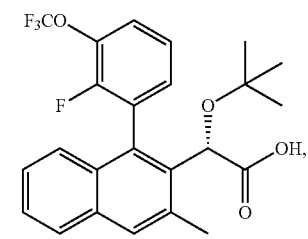
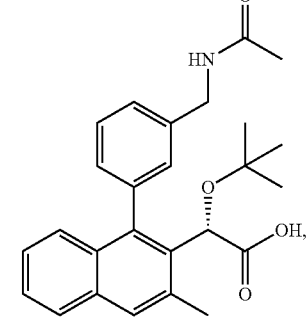
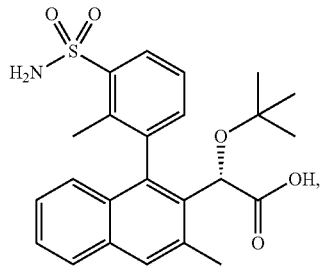

79
-continued
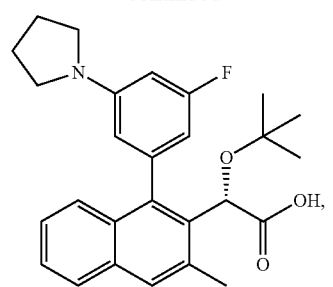
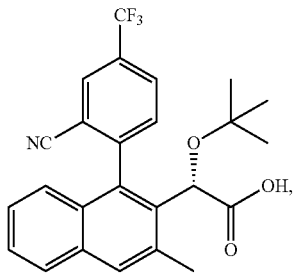
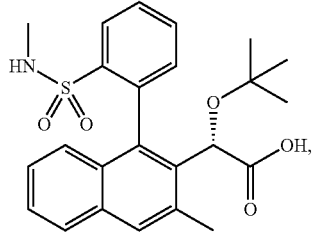
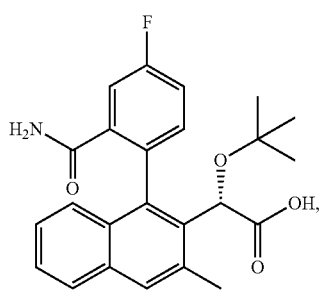
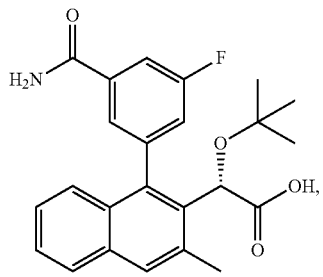
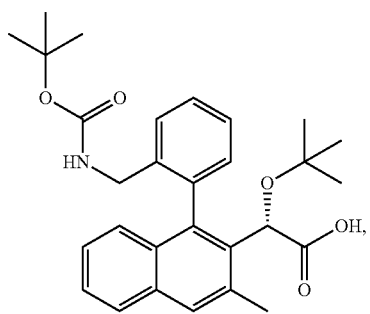
80
-continued
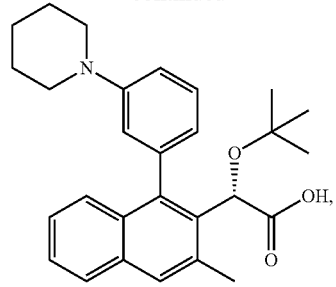
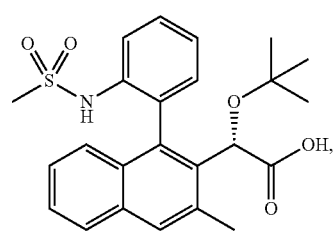
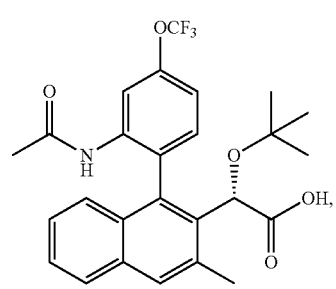
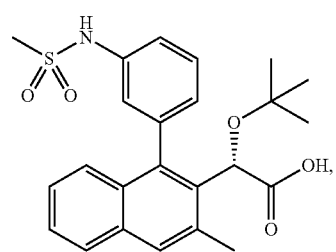
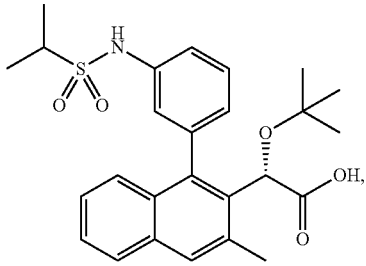
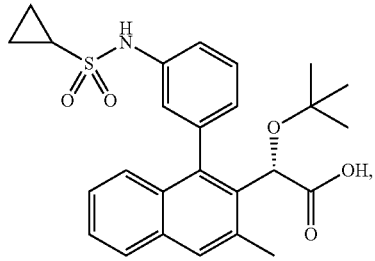

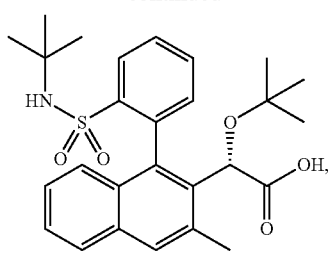
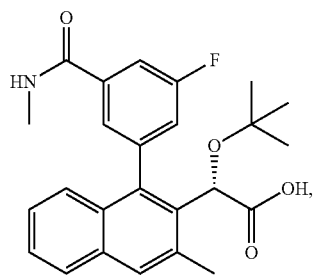
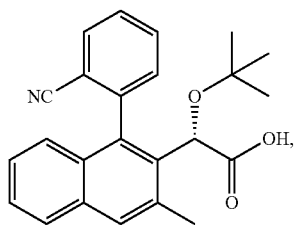
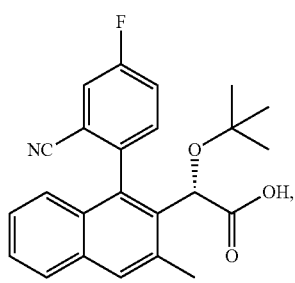
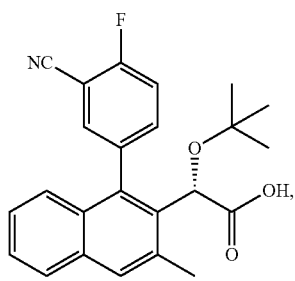
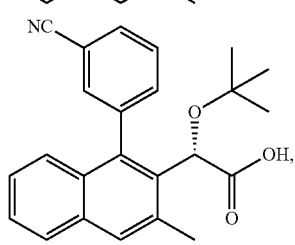
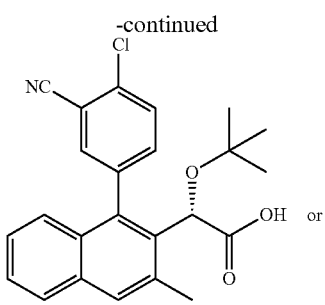
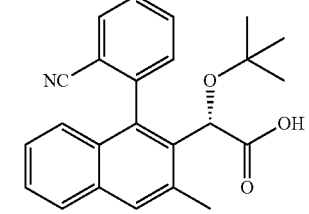
or a salt thereof.
In another embodiment, the compounds of formula I include:
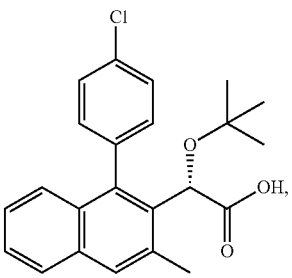
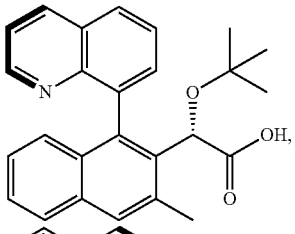
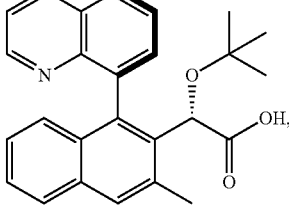
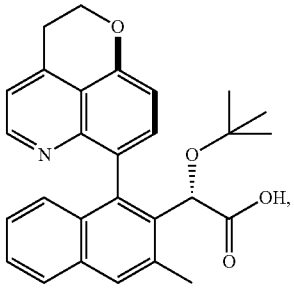

-continued
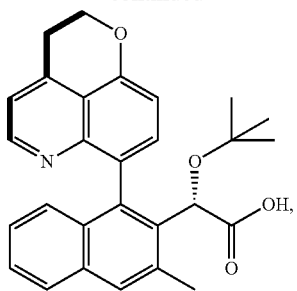
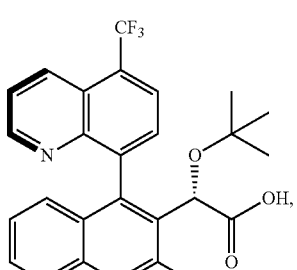
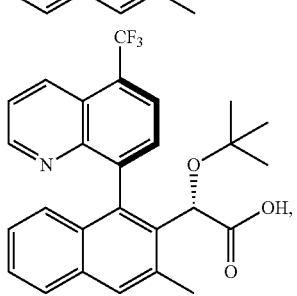
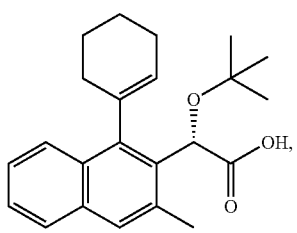
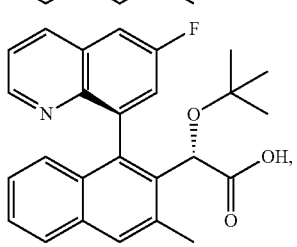
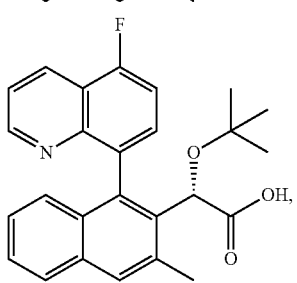
-continued
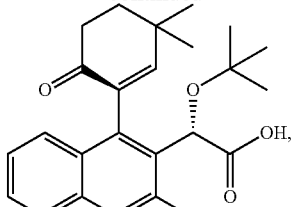
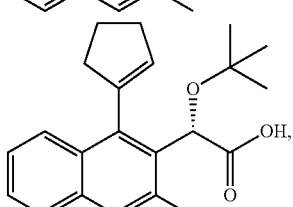
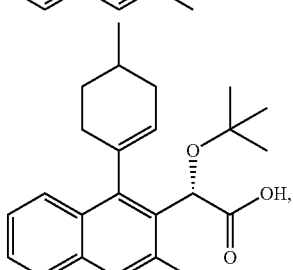
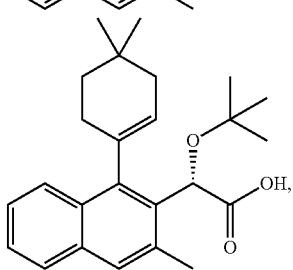
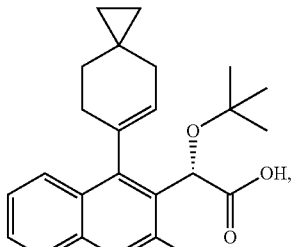
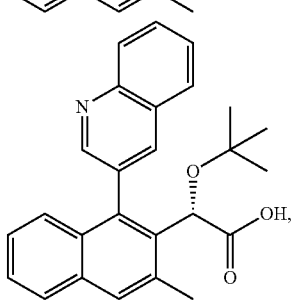
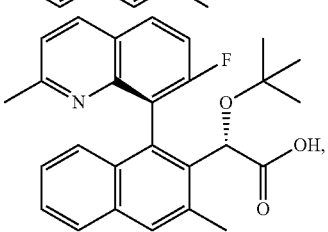

85
-continued
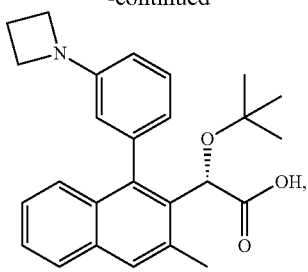
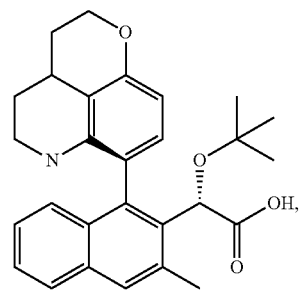
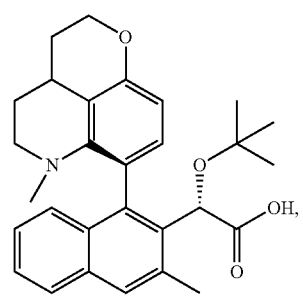
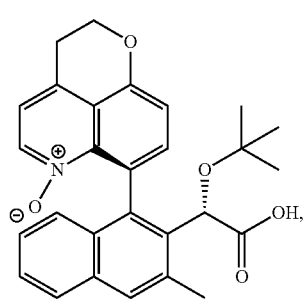
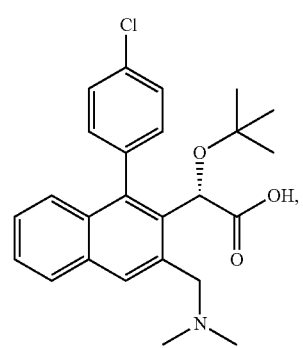
86
-continued
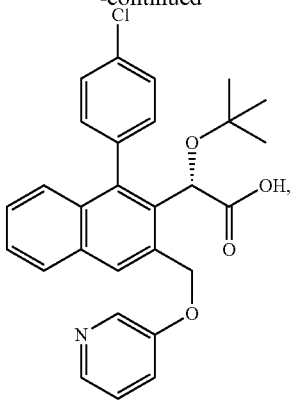
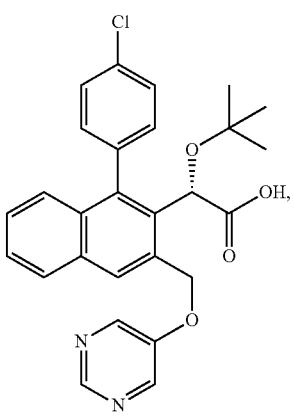
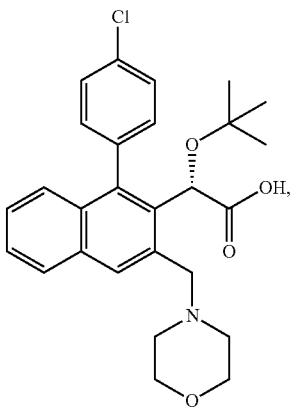
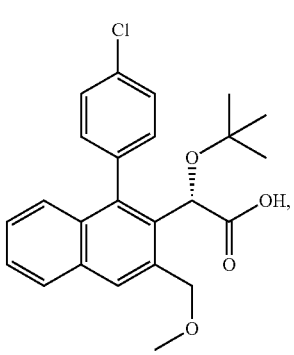

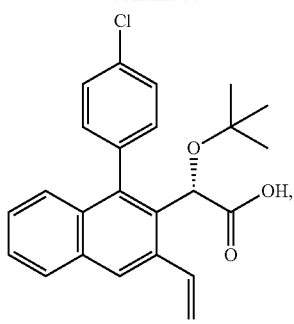
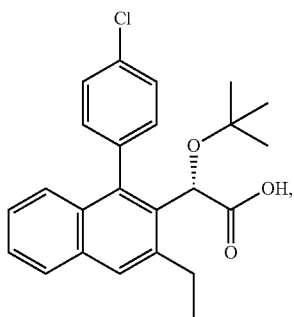
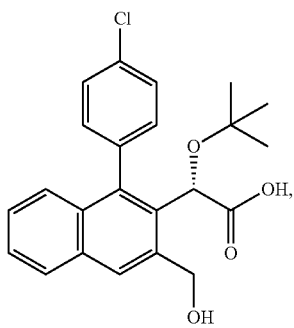
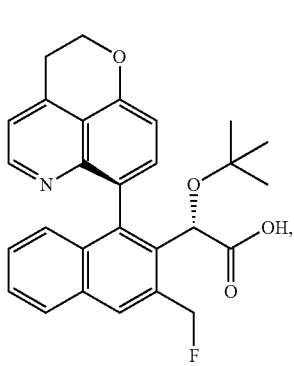
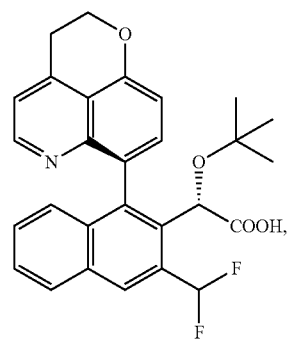
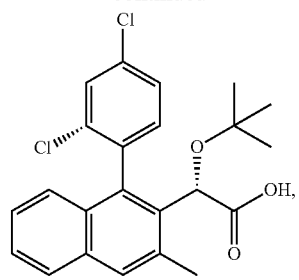
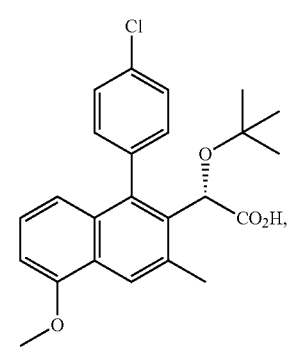
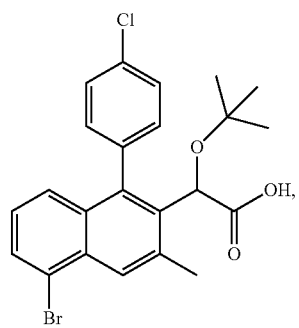
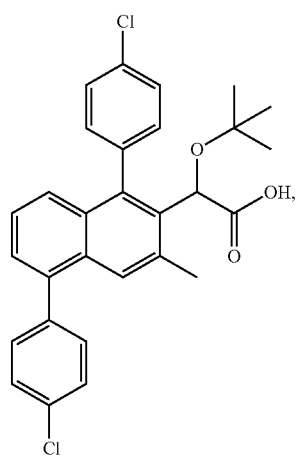

89
-continued
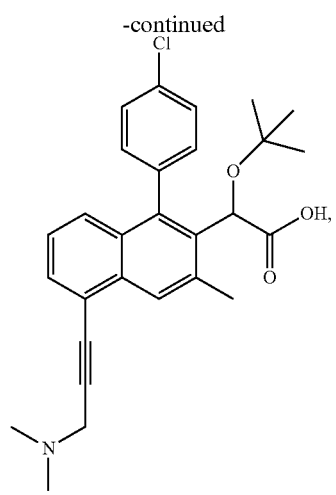
90
-continued
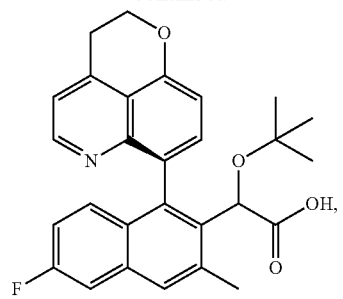
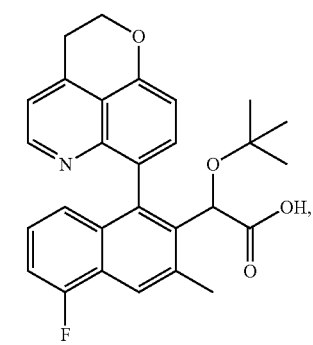
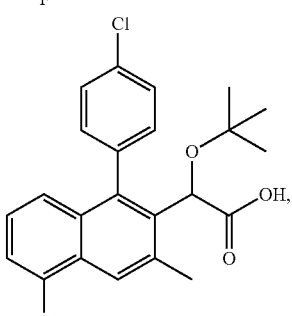
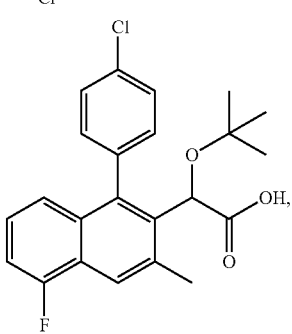
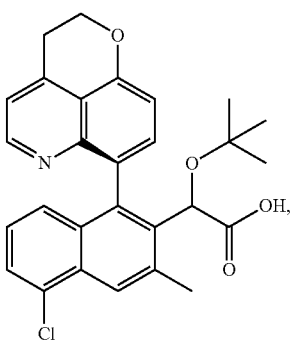

91
-continued
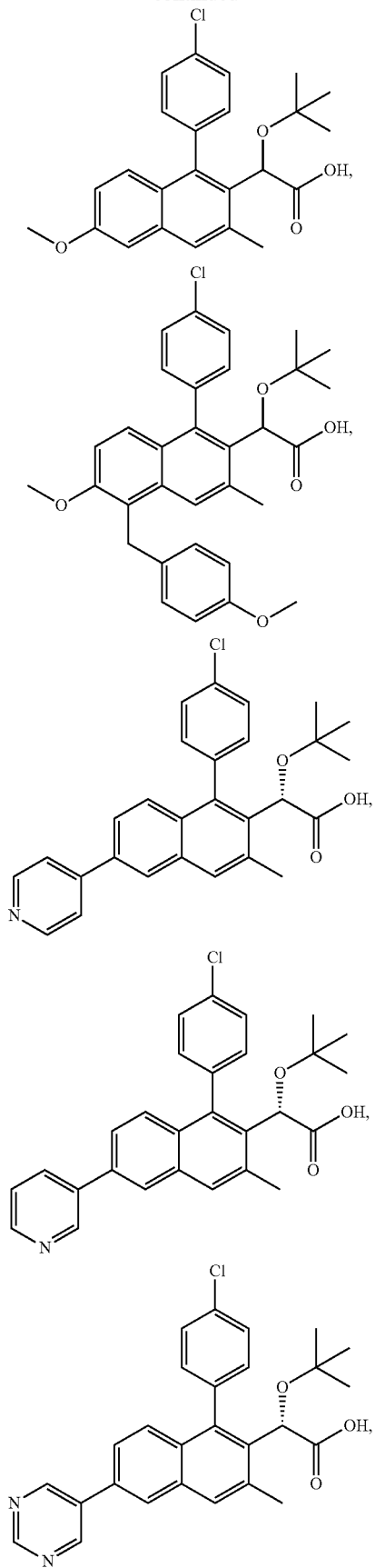
92
-continued
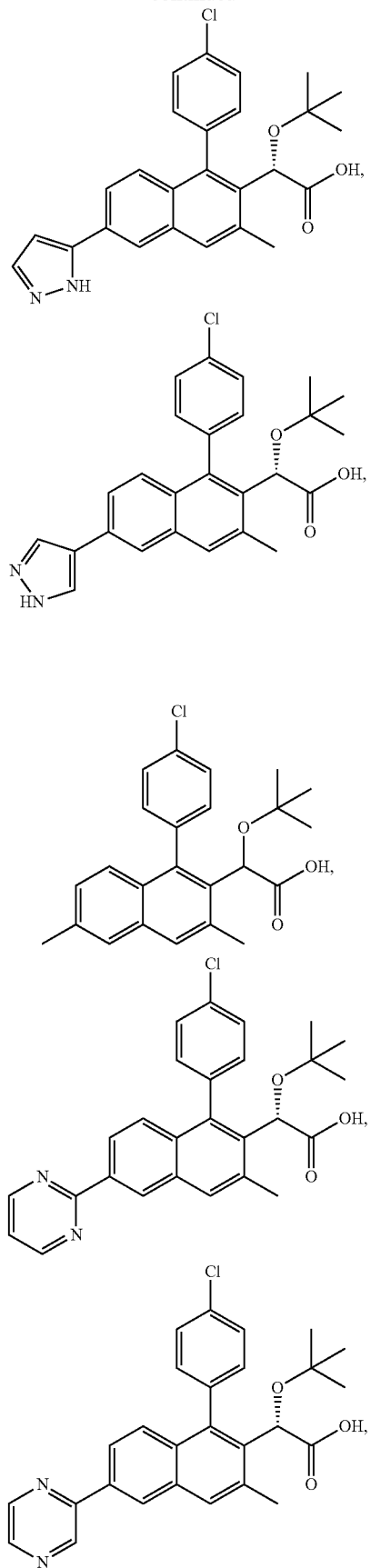

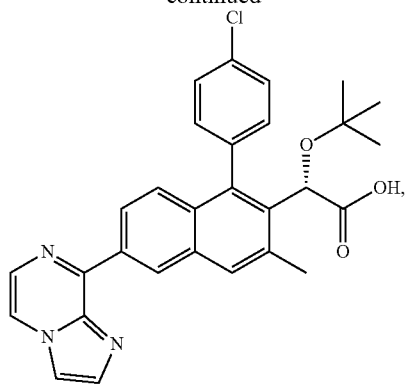
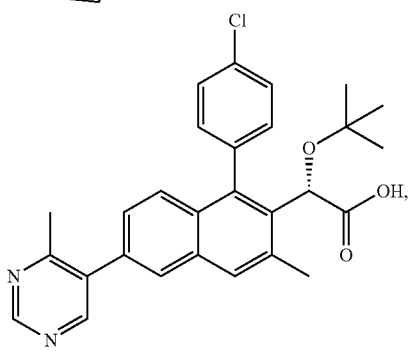
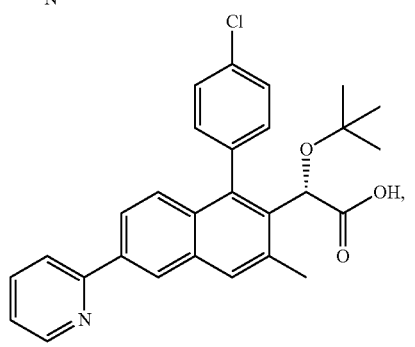
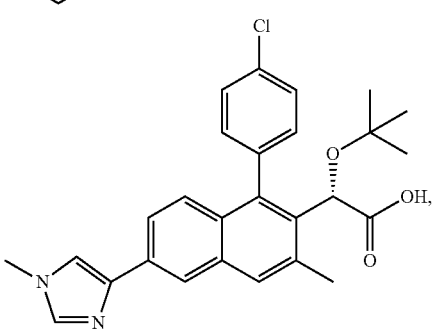
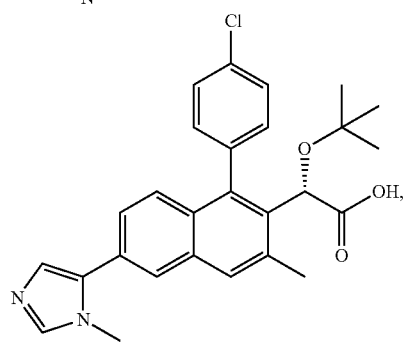
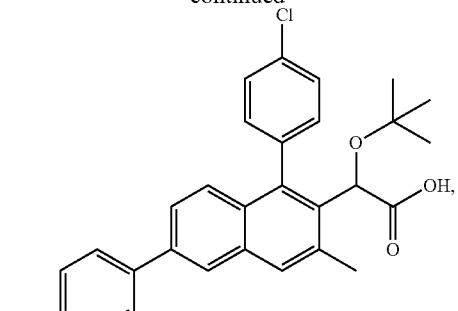
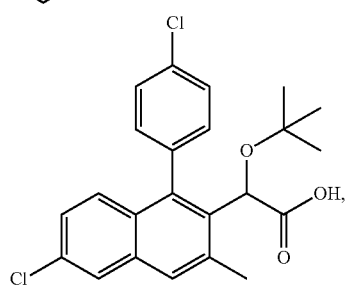
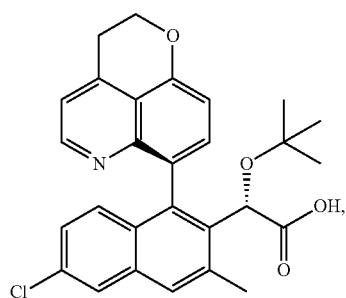
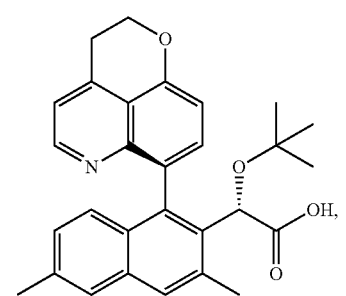
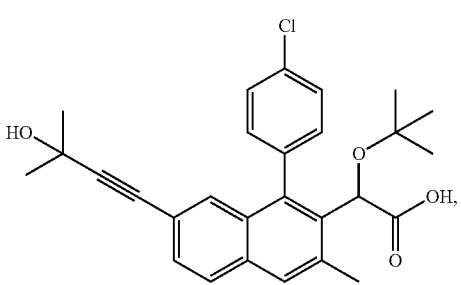

95
-continued
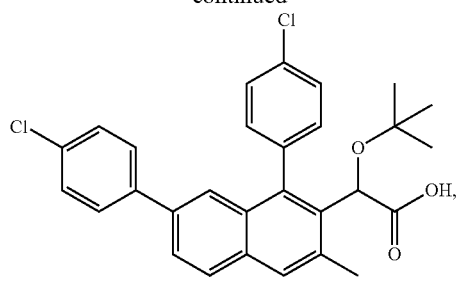
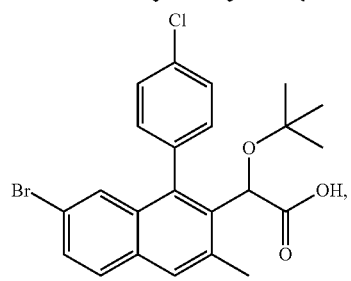
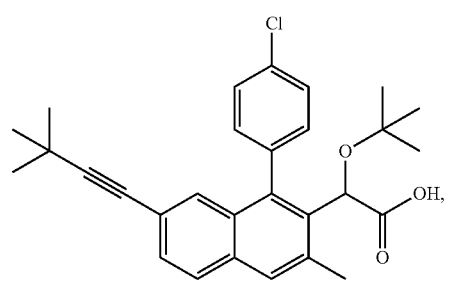
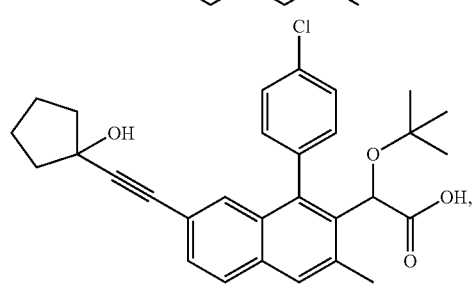
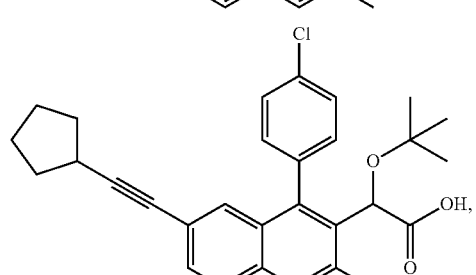
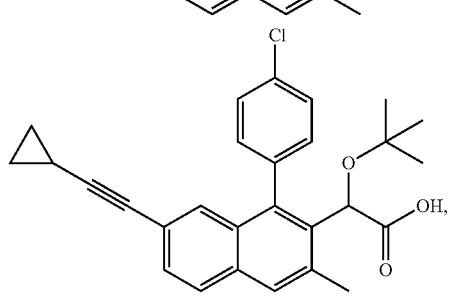
96
-continued
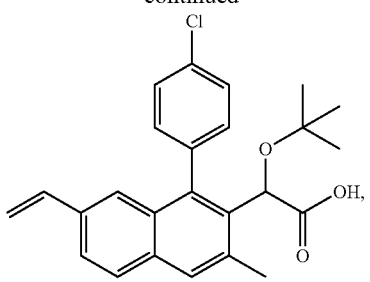
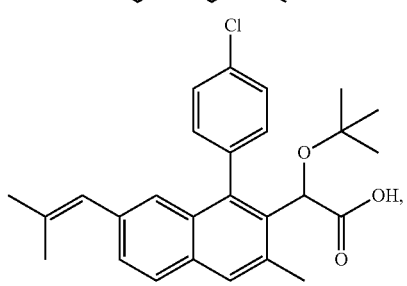
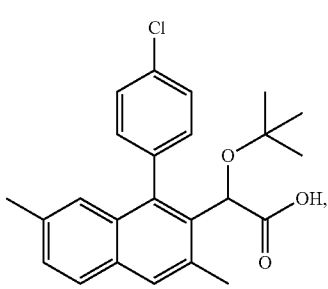
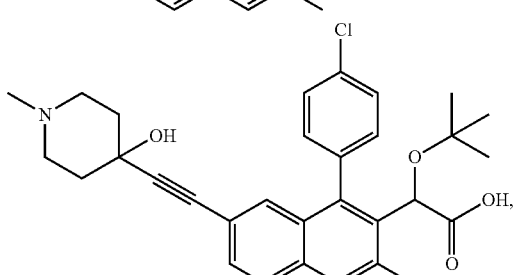
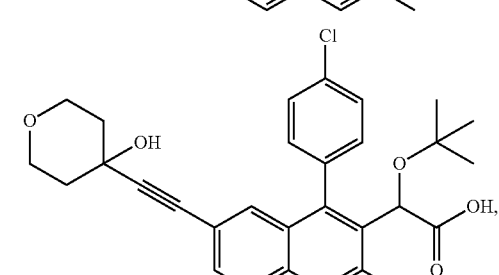
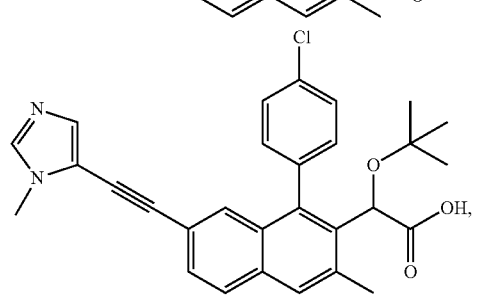

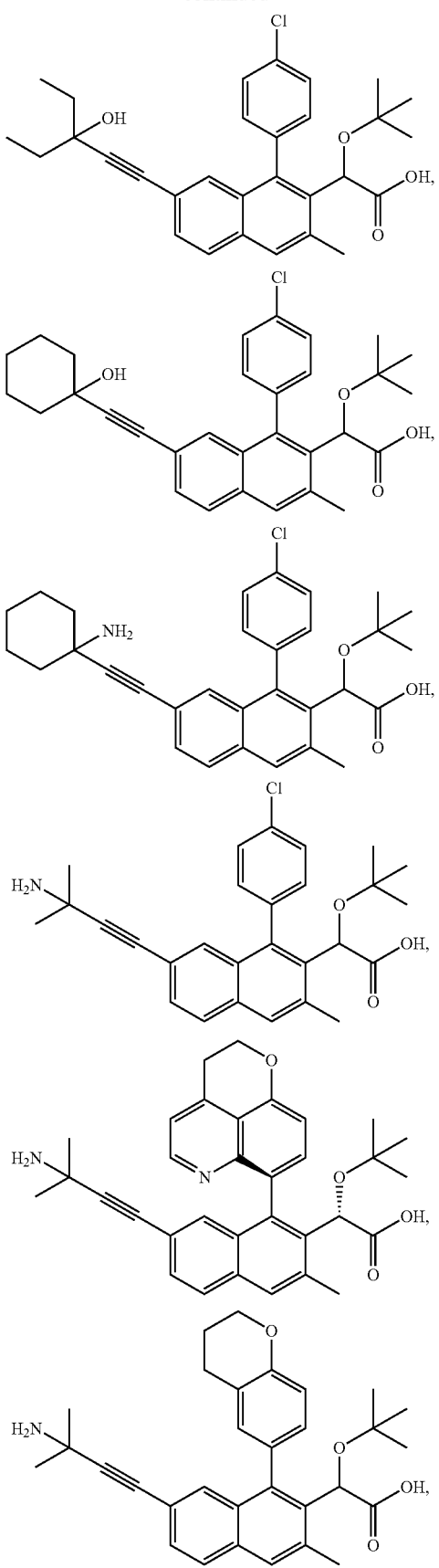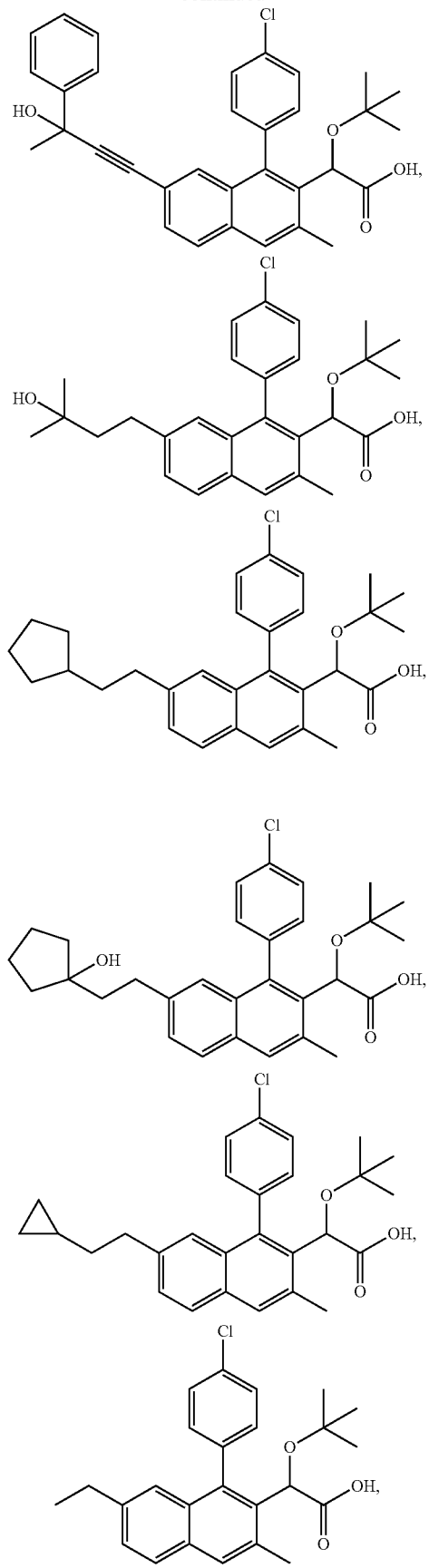

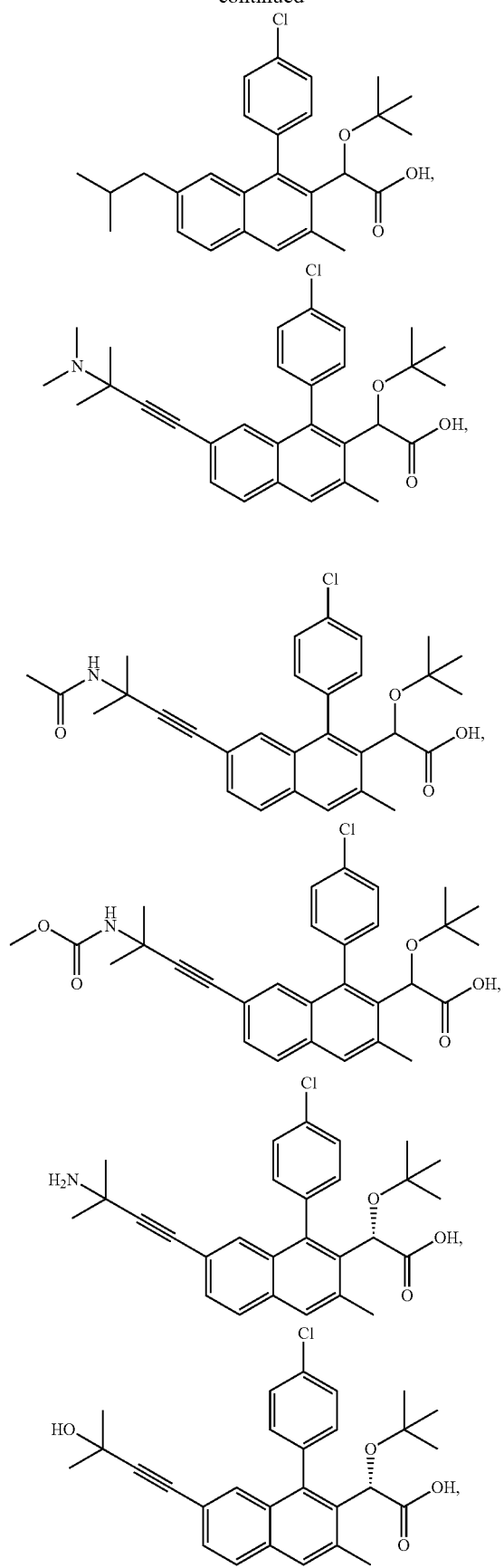
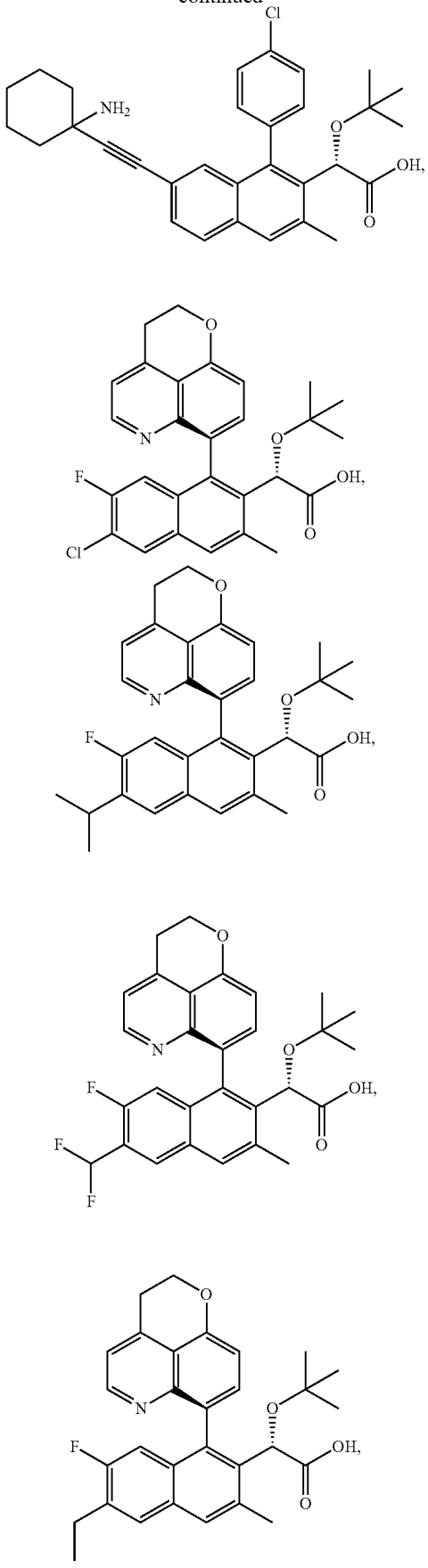

| 101 | 102 |
|---|---|
| -continued | -continued |
| 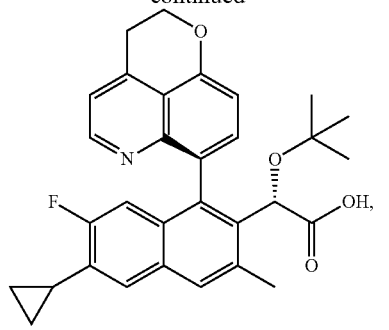 | 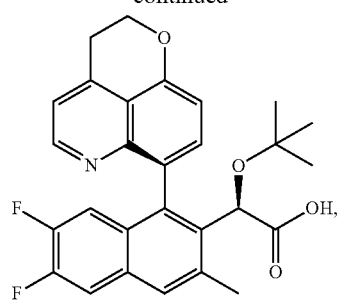 |
| 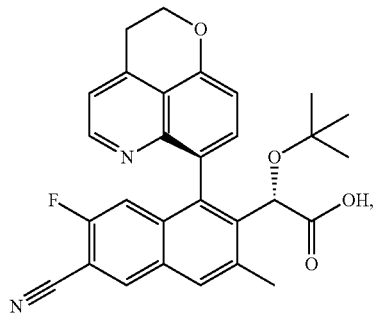 | 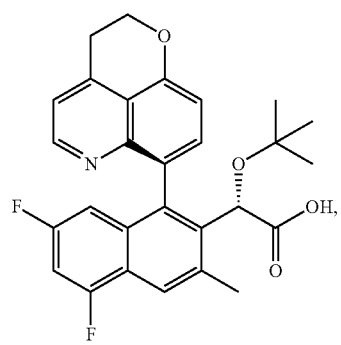 |
| 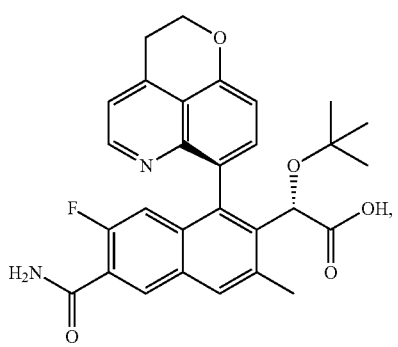 | 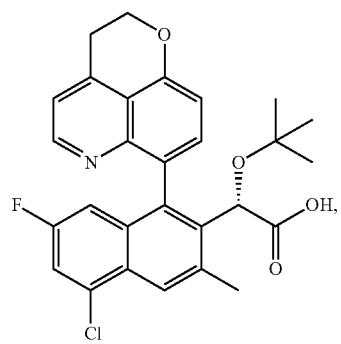 |
| 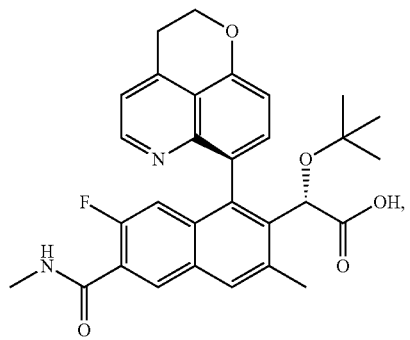 | 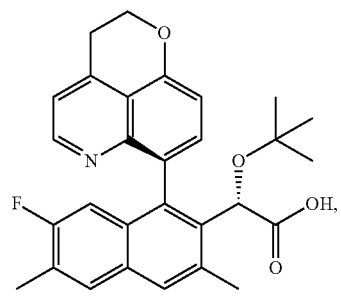 |
| 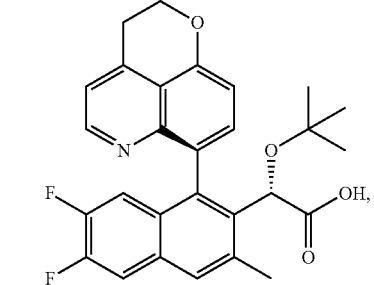 | 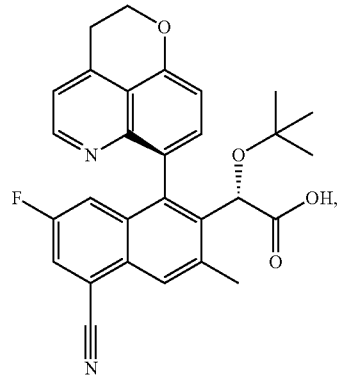 |

103
-continued
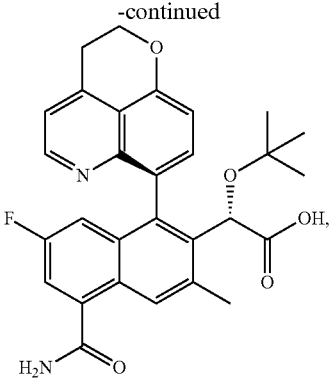
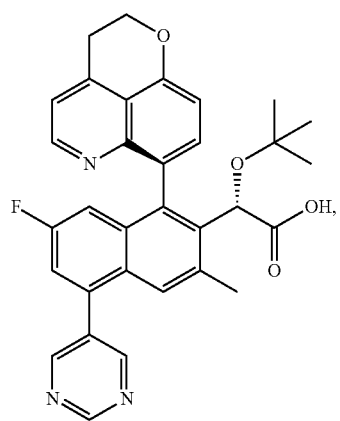
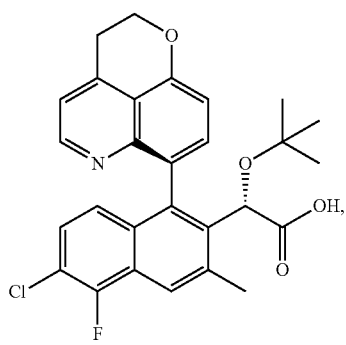
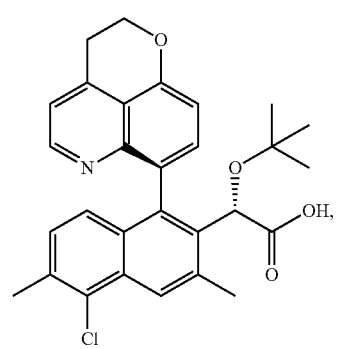
104
-continued
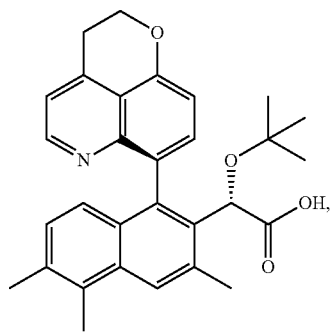
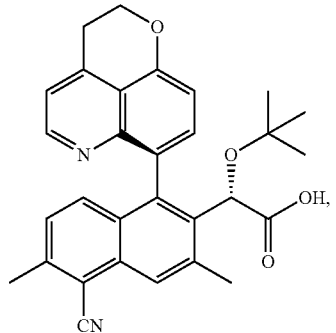
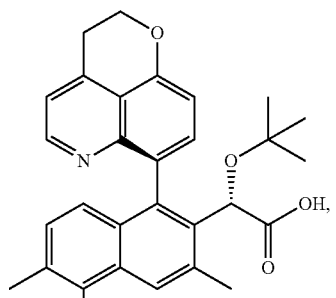
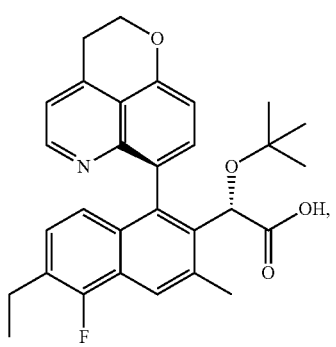
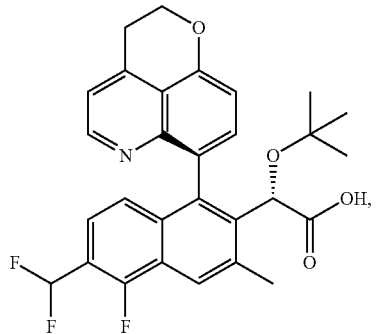

105
-continued
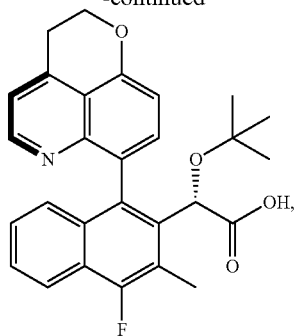
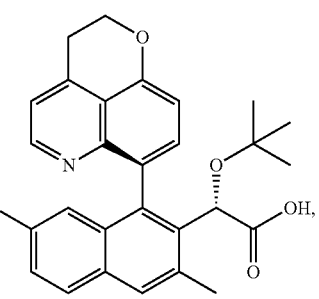
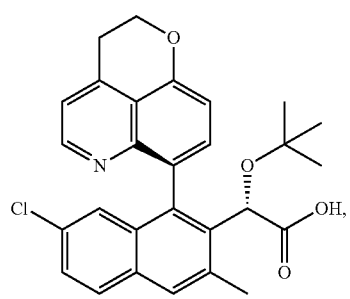
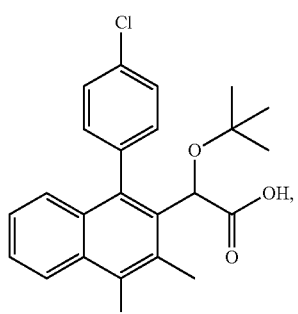
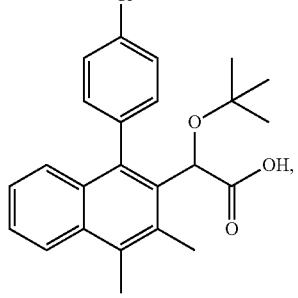
106
-continued
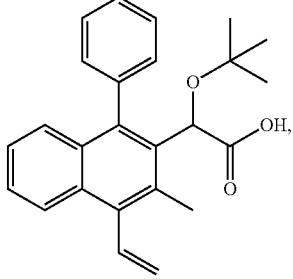
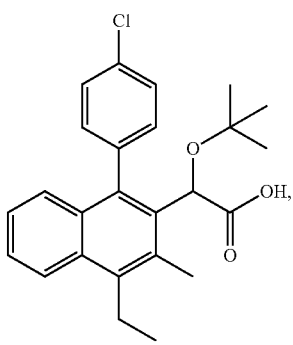
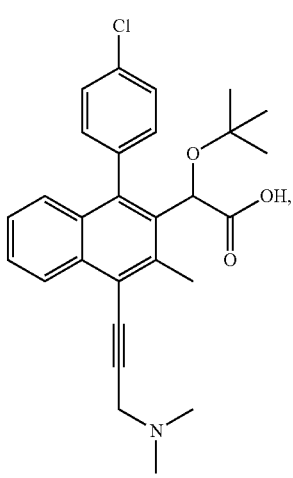
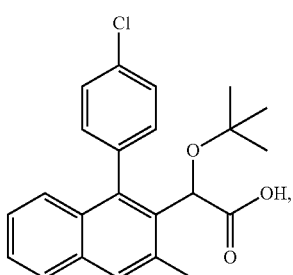

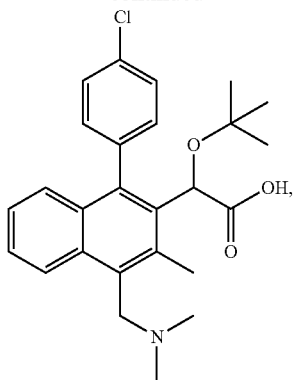
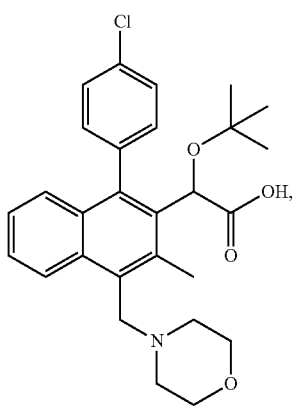
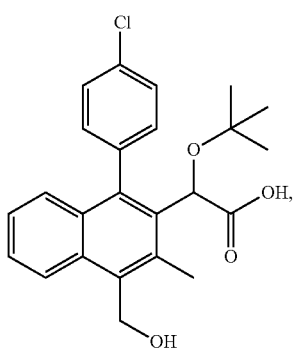
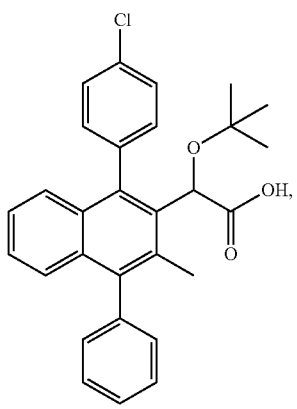
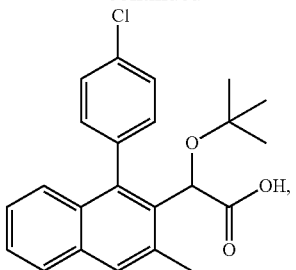
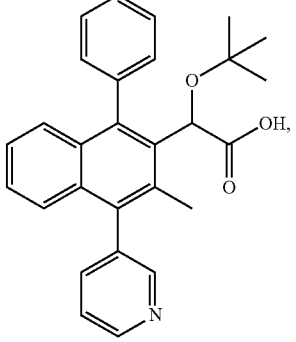
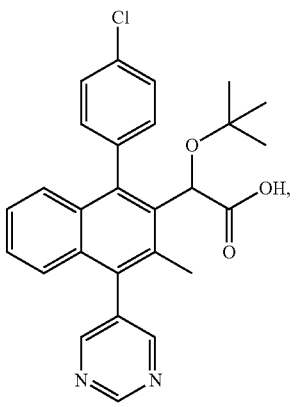
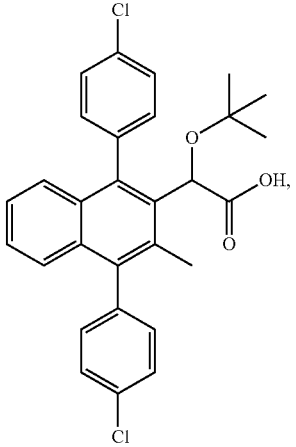

-continued
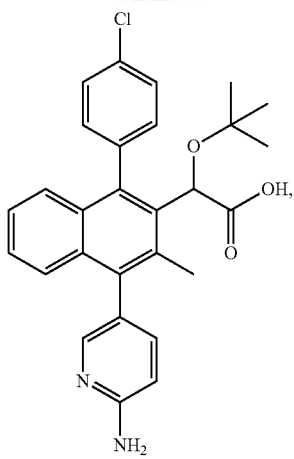
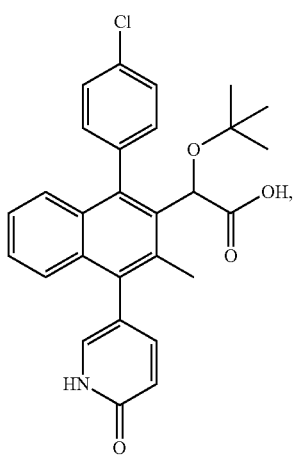
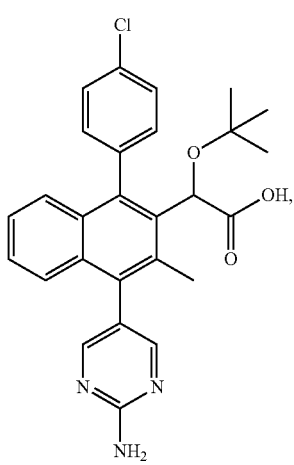
-continued
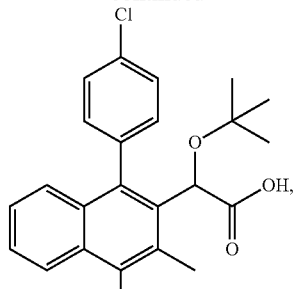
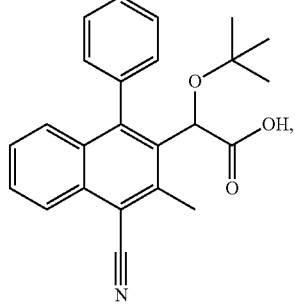
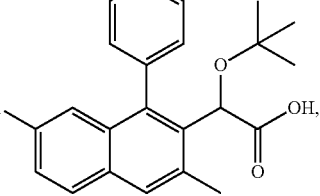
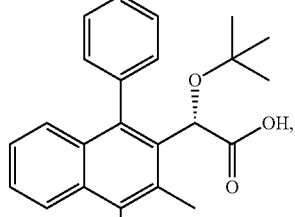
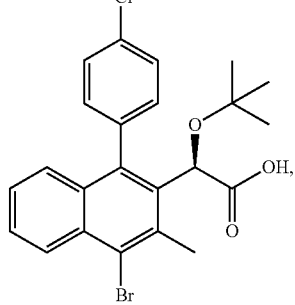

111
-continued
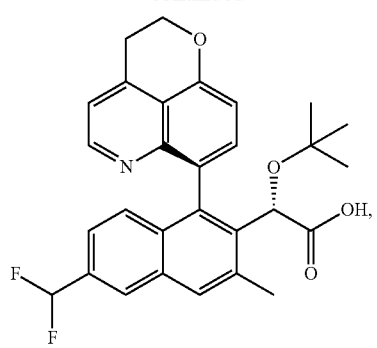
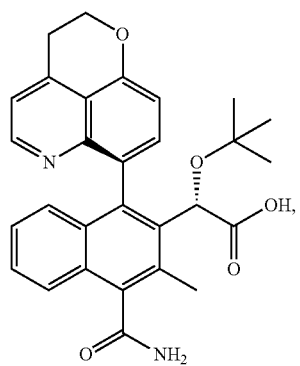
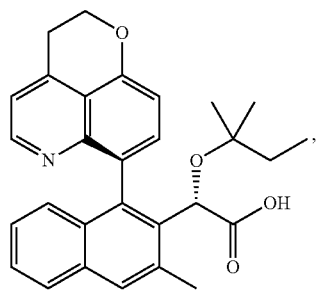
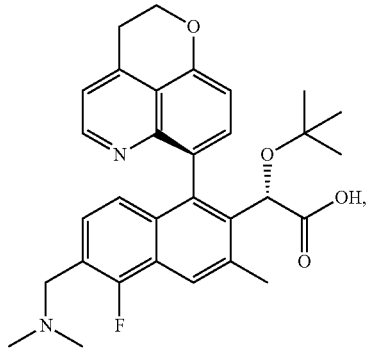
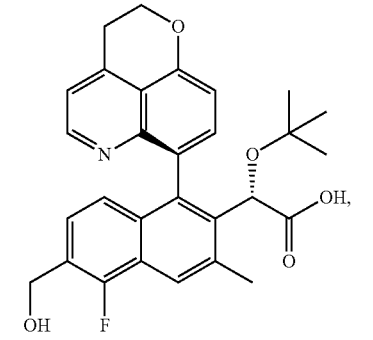
112
-continued
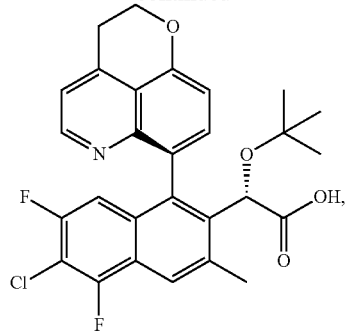
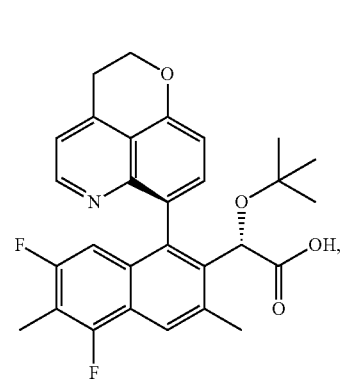
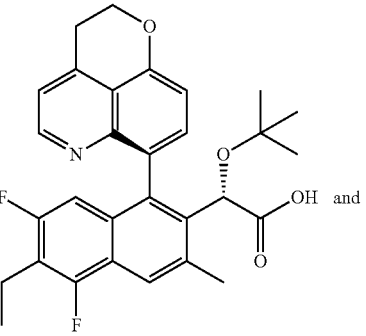
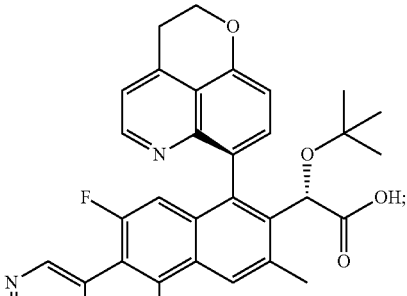
and salts thereof.

In another embodiment, the compounds of formula I include:

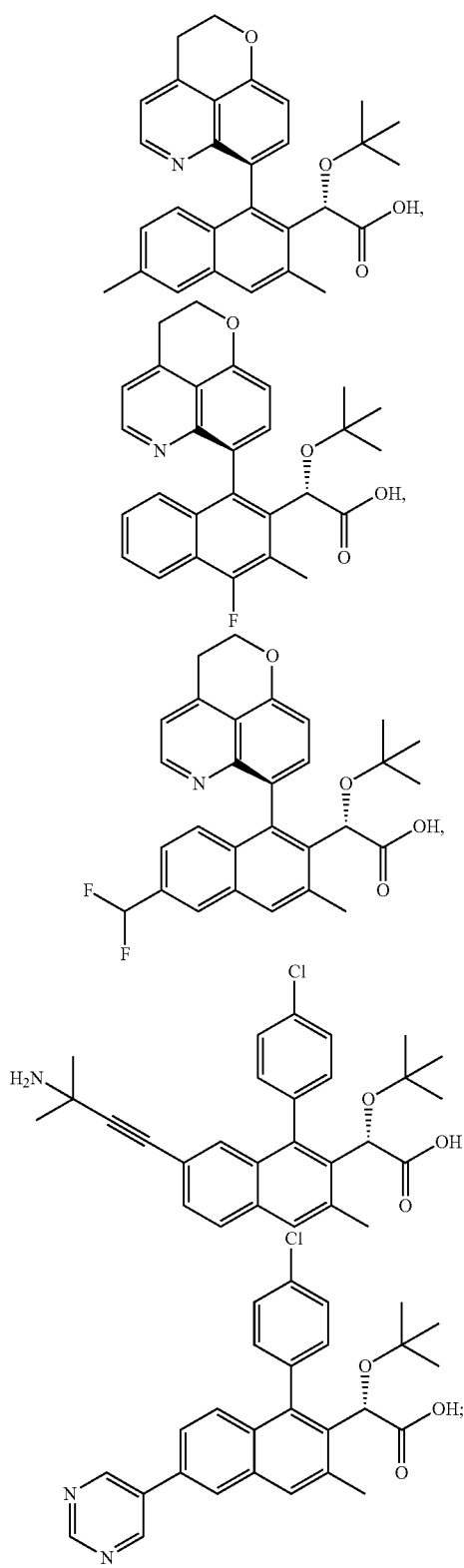

and salts thereof.

In another embodiment the compounds of formula I include compounds 151-180 as described in Example 149.

General Synthetic Procedures

Scheme 1 is provided as a further embodiment of the invention and illustrates a process that was used to prepare a compound of formula I and which can be used to prepare other compounds of formula I. Schemes 2-6 are also provided as further embodiments of the invention and illustrate processes that can be used to prepare compounds of formula I.

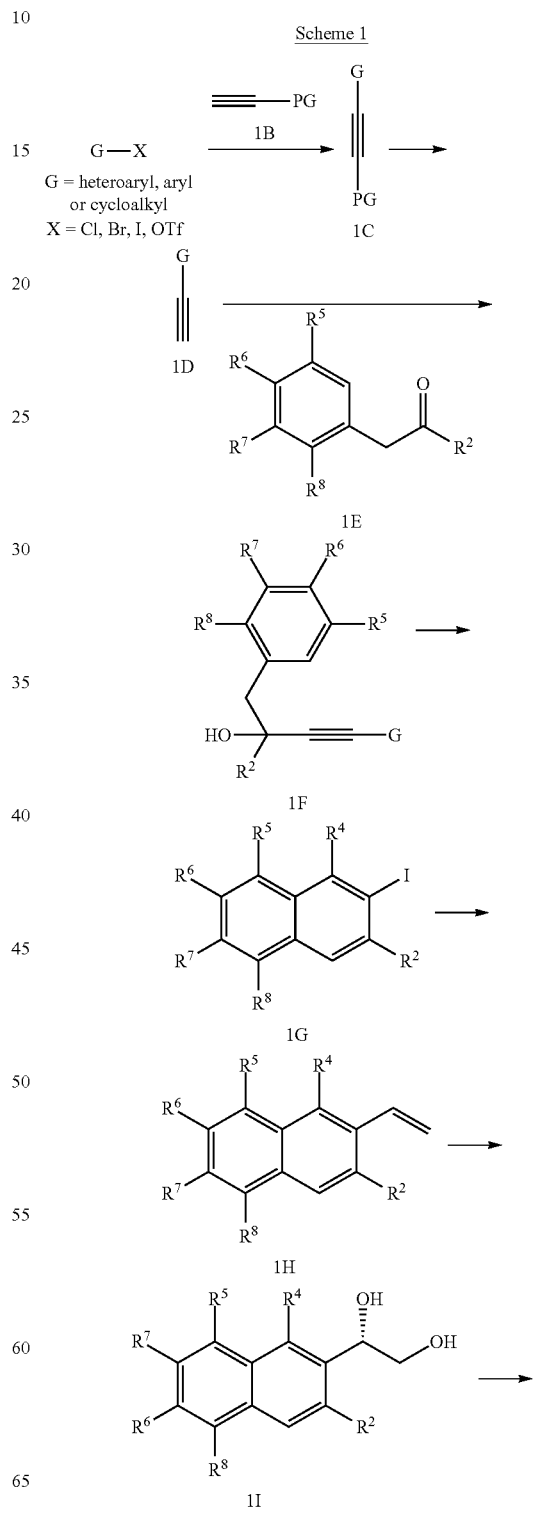

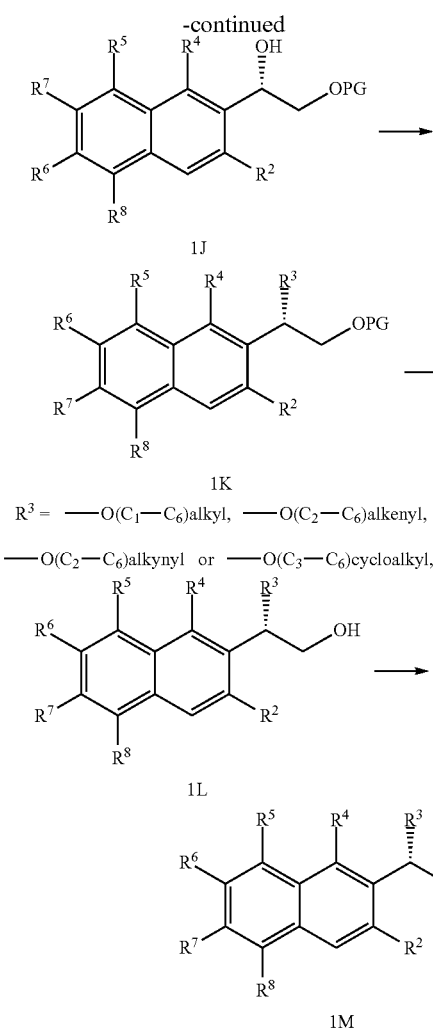

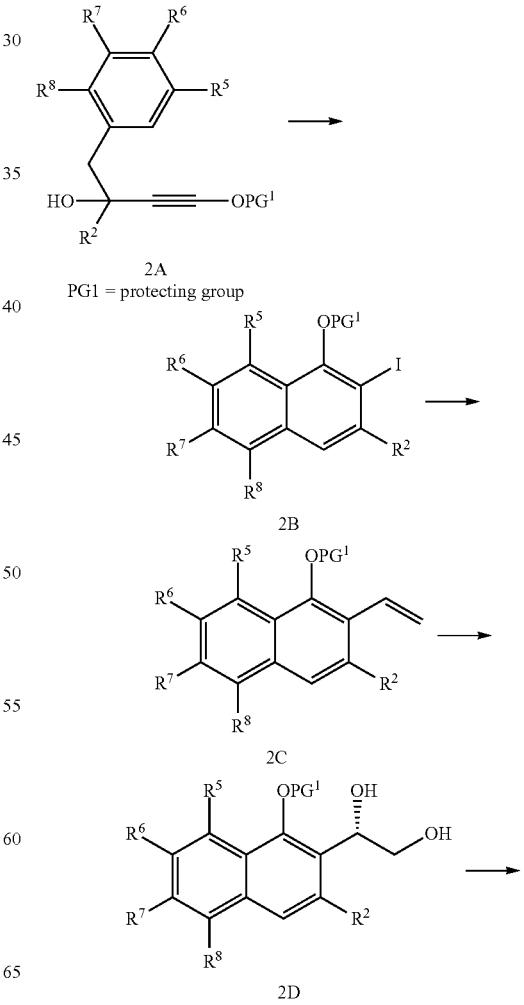

cross-coupling using a tin reagent such as tributyl(vinyl)tin and a palladium catalyst such as bis(triphenylphosphine) palladium(II) dichloride to give the corresponding cross-coupled naphthalene such as, for example, vinylnaphthalene 1H. The vinylnaphthalene 1H can be dihydroxylated by methods known to those skilled in the art such as, for example Sharpless asymmetric dihydroxylation using, for example, commercially available AD-mix-α.

The resulting diol 1I can be protected at the primary hydroxyl by suitable protecting groups such as, for example, pivalate ester using pivaloyl chloride and pyridine to provide 1J. The secondary hydroxyl can be converted to the corresponding ether 1K such as tert-butyl ether using methods known to those skilled in the art such as, for example, tert-butyl acetate and perchloric acid. The protected primary hydroxyl can be deprotected by methods known to those skilled in the art such as, for example the deprotection of a pivalate protecting group under basic conditions, such as, for example sodium hydroxide, to give the corresponding primary hydroxyl compound 1L. The primary hydroxyl can be oxidized to the corresponding carboxylic acid 1M by methods known to those skilled in the art such as, for example, periodic acid and chromium trioxide.

An aromatic or heteroaromatic halide or triflate (1A) can be crossed-coupled to a suitably protected alkyne (1B) such as ethynyl(trimethyl)silane using a palladium catalyst and copper halide salt such as, for example, copper(I) iodide, N,N-diisopropylethylamine, tetrakis(triphenylphosphine) palladium(0) and dimethylformamide or copper(I) iodide, diethylamine, and bis(triphenylphosphine) palladium(II) dichloride. Deprotection of cross-coupled alkyne (1C) yields the corresponding terminal alkyne (1D) such as, for example, deprotection of a trimethylsilyl-protected alkyne with a fluoride source such as, for example, tetrabutylammonium fluoride. Metalation of a terminal alkyl (1D) such as, for example, deprotonation with n-butyllithium, yields the corresponding metal acetylide such as, for example lithium acetylide, that undergoes nucleophilic addition to an appropriate electrophile (1E) to give the corresponding hydroxy alkyne addition product 1F. A suitably substituted phenyl electrophile such as phenyl-2-propanone can be purchased or prepared by those skilled in the art through, for example, Friedel-Crafts alkylation of benzene with chloroacetone.

The hydroxyl alkyne 1F can undergo 6-endo-dig electrophilic cyclization under suitable reaction conditions such as, for example iodine and sodium bicarbonate to give the corresponding substituted naphthalene such as, for example the iodonaphthalene 1G. The substituted naphthalene 1G, can undergo a cross-coupling reaction such as, for example Stille

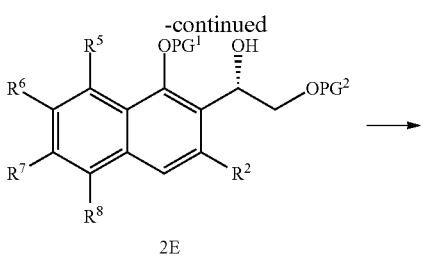

2E

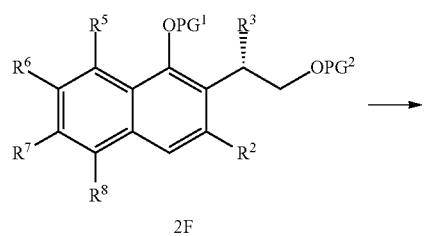

2F $R^3 =$ —$O(C_1$—$C_6)$alkyl, —$O(C_2$—$C_6)$alkenyl,

—$O(C_2$—$C_6)$alkynyl or —$O(C_3$—$C_6)$cycloalkyl,

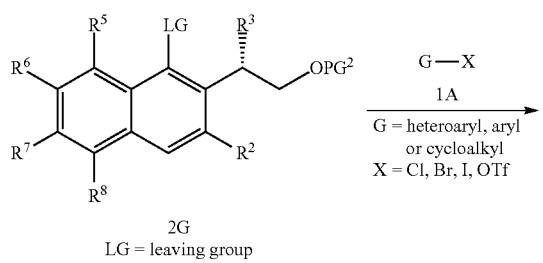

2G
LG = leaving group

G = heteroaryl, aryl or cycloalkyl
X = Cl, Br, I, OTf

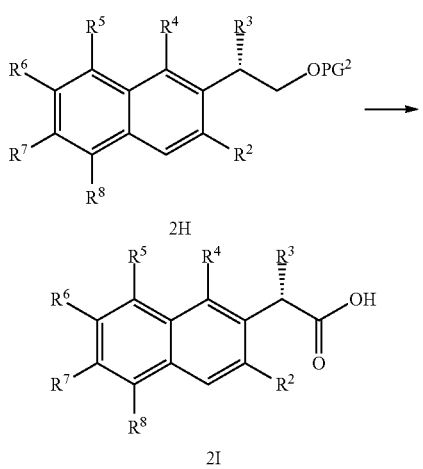

example iodonaphthalene 2B. The substituted naphthalene 2B, can undergo a cross-coupling reaction such as, for example Stille cross-coupling using a tin reagent such as, for example, tributyl(vinyl)tin and a palladium catalyst such as, for example, bis(triphenylphosphine)palladium(II) dichloride to give the corresponding cross-coupled naphthalene such as, for example, vinylnaphthalene 2C. The alkenylnaphthalene 2C can be dihydroxylated using methods known to those skilled in the art such as, for example Sharpless asymmetric dihydroxylation using, for example, commercially available AD-mix-α.

The resulting diol 2D can be protected at the primary hydroxyl by an orthogonal protecting groups, such as, for example, pivaloyl ester using pivaloyl chloride and pyridine. The secondary hydroxyl of 2E can be converted to the corresponding ether 2F, such as a tert-butyl ether using methods known to those skilled in the art for example, using tert-butyl acetate and perchloric acid. The naphthol protecting group can be differentially deprotected by methods known to those skilled in the art and converted to a leaving group (e.g. triflate) known to undergo cross-coupling reactions. The corresponding activated naphthalene 2G can undergo cross-coupling reactions such as but not limited to Suzuki reactions with boronic acids or esters, Stille reactions with trialkylstannane reagents, and Buchwald-Hartwig reactions with amines thus providing carbon linked and nitrogen linked $R^4$ groups of 2H. The protected primary hydroxyl can be deprotected by methods known to those skilled in the art such as, for example the deprotection of a pivalate protecting group under basic conditions, such as, for example sodium hydroxide, to give the corresponding primary hydroxyl. The primary hydroxyl can be oxidized to the corresponding carboxylic acid analog 2I by methods known to those skilled in the art such as, for example, periodic acid and chromium trioxide.

Scheme 3

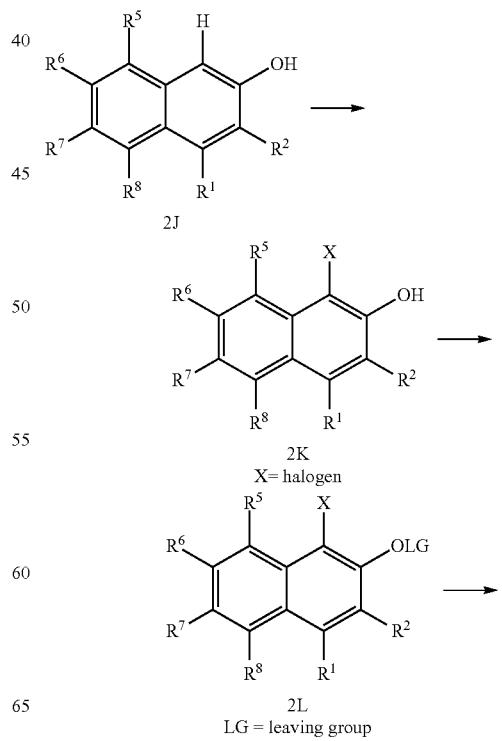

Metalation of a suitably functionalized and protected terminal alkyne such as, for example, deprotonation with n-butyllithium, can yield the corresponding metal acetylide such as, for example lithium acetylide, that undergoes nucleophilic addition to an appropriate electrophile, such as, for example 1E, to give the corresponding hydroxy alkyne addition product 2A. The hydroxyl alkyne 2A can undergo 6-endo-dig electrophilic cyclization under suitable reaction conditions such as, for example iodine and sodium bicarbonate to give the corresponding substituted naphthalene such as, for

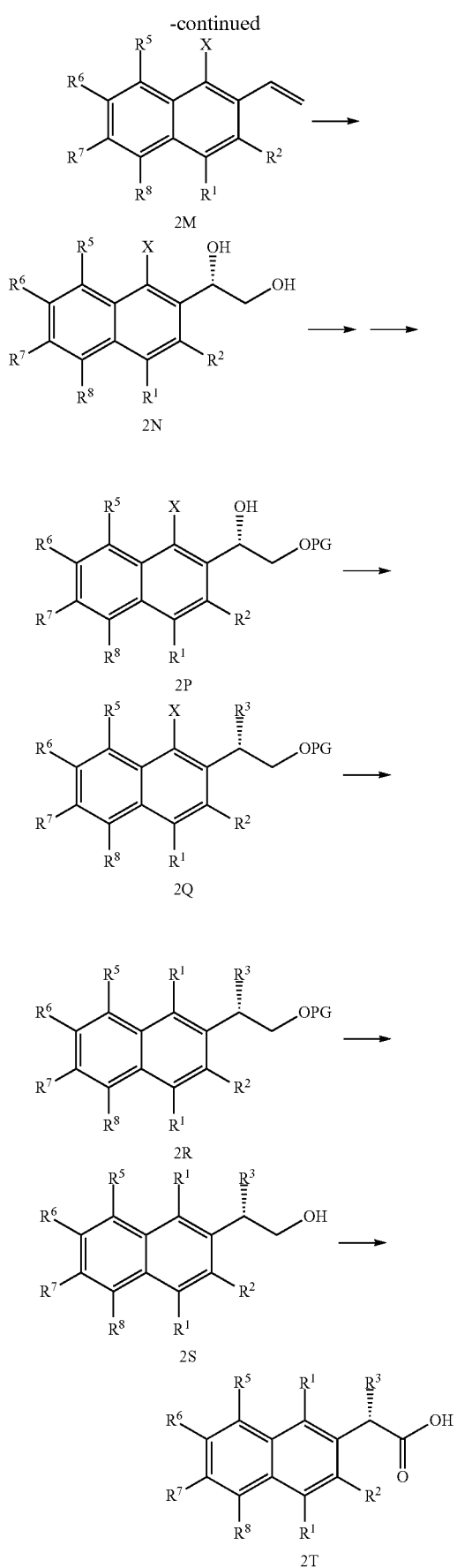

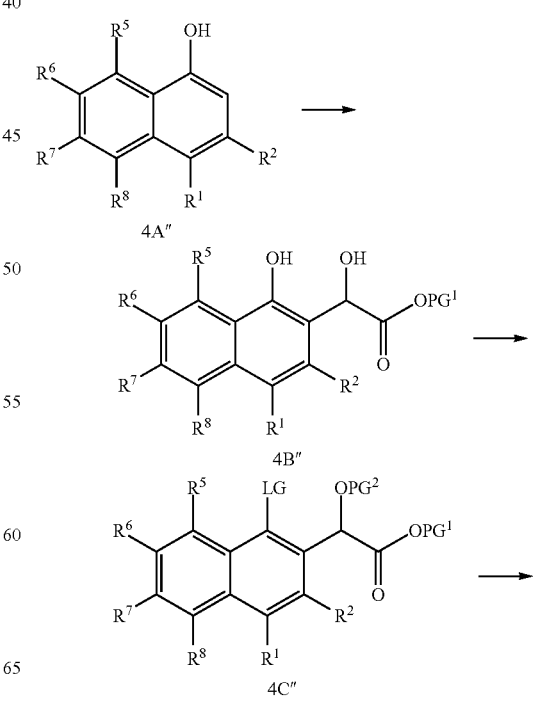

The substituted hydroxyl naphthalene 2J can undergo halogenation using an appropriate halogen source and catalyst such as, for example N-chlorosuccinimide and zirconium (IV) chloride to provide 2K. The hydroxyl naphthalene 2K can be converted to a leaving group such as, for example trifluoromethanesulfonate ester by treatment with trifluoromethanesulfonic anhydride and base such as, for example, 2,6-lutidine to provide 2L. Naphthalene 2L can undergo a selective cross-coupling reaction such as, for example Stille cross-coupling using a tin reagent such as tributyl(vinyl)tin and a palladium catalyst such as bis(triphenylphosphine) palladium(II) dichloride to give the corresponding cross-coupled naphthalene such as vinylnaphthalene 2M. The alkenylnaphthalene can be dihydroxylated to provide 2N by methods known to those skilled in the art such as, Sharpless asymmetric dihydroxylation using, for example, commercially available AD mix-α.

The resulting diol 2N can be protected at the primary hydroxyl by suitable protecting groups such as pivalate ester using pivaloyl chloride and pyridine to provide 2P. The secondary hydroxyl can be converted to the corresponding ether such as tert-butyl ether using methods known to those skilled in the art such as, tert-butyl acetate and perchloric acid to provide 2Q. The halogenated naphthalene 2Q can undergo cross-coupling reaction such as Suzuki cross-coupling using a boronic acid and a palladium catalyst such as palladium(II) acetate with SPhos to give the corresponding cross-coupled naphthalene 2R. The protected primary hydroxyl can be deprotected by methods known to those skilled in the art such as the deprotection of a pivalate protecting group under basic conditions for example, using sodium hydroxide, to give the corresponding primary hydroxyl compound 2R. The primary hydroxyl can be oxidized to the corresponding carboxylic acid 2S by methods known to those skilled in the art such as, for example, periodic acid and chromium trioxide.

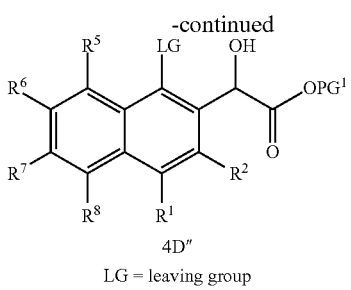

4D''

LG = leaving group

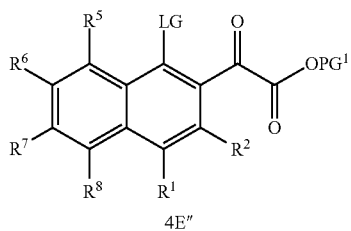

4E''

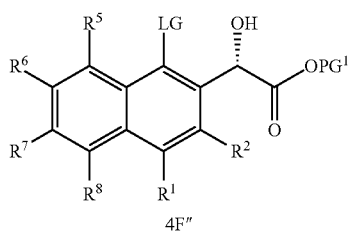

4F''

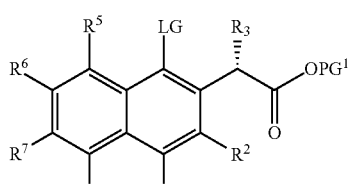

4G''

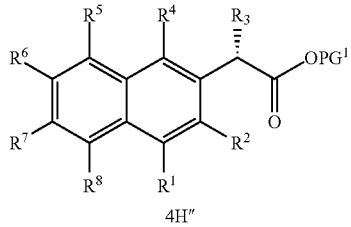

4H''

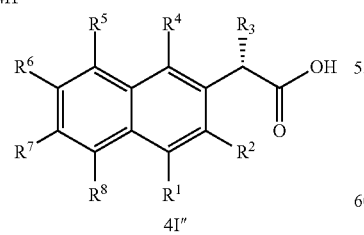

4I''

Electrophilic aromatic substitution with a suitably functionalized and protected naphthol such as, for example 4A'', with an electrophile such as, for example, ethyl glyoxylate under appropriate conditions such as, for example, titanium tetrachloride, can provide 4B''. The secondary alcohol can be protected with a protecting group and the naphthol converted to a leaving group (e.g. triflate) known to undergo cross-coupling reactions to provide 4C''. The alcohol protecting group can be removed and the resulting alcohol oxidized to the ketone using an oxidant such as Dess-Martin Periodinane, for example, to provide 4E''. The ketone can be reduced stereoselectively using an asymmetric reduction method such as, for example Corey-Bakshi-Shibata Reduction to provide 4F''.

The secondary hydroxyl can be converted to the corresponding ether such as tert-butyl ether using methods known to those skilled in the art such as, tert-butyl acetate and perchloric acid to provide 4G''. The functionalized naphthalene 4G'' can undergo can undergo cross-coupling reactions such as but not limited to Suzuki reactions with boronic acids or esters, Stille reactions with trialkylstannane reagents, and Buchwald-Hartwig reactions with amines thus providing carbon linked and nitrogen linked products using a palladium catalyst such as palladium(II) acetate with SPhos to give the corresponding cross-coupled naphthalene 4H''. The protected ester can be deprotected by methods known to those skilled in the art such as, for example the deprotection of a ethyl ester protecting group under basic conditions, such as, for example sodium hydroxide, to give the corresponding carboxylic acid 4I''.

It is known to those skilled in the art that the functionalized naphthalenes (e.g. 4E'', 4G'', or 4H1'') that contain a halogen or pseudohalogen (e.g. triflate), can undergo cross-coupling reactions such as but not limited to Suzuki reactions with boronic acids or esters, Stille reactions with trialkyltin reagents, Sonogashira reactions with alkynes, and Buchwald-Hartwig reactions with amines and carried forward in a similar manner to provide 4I''.

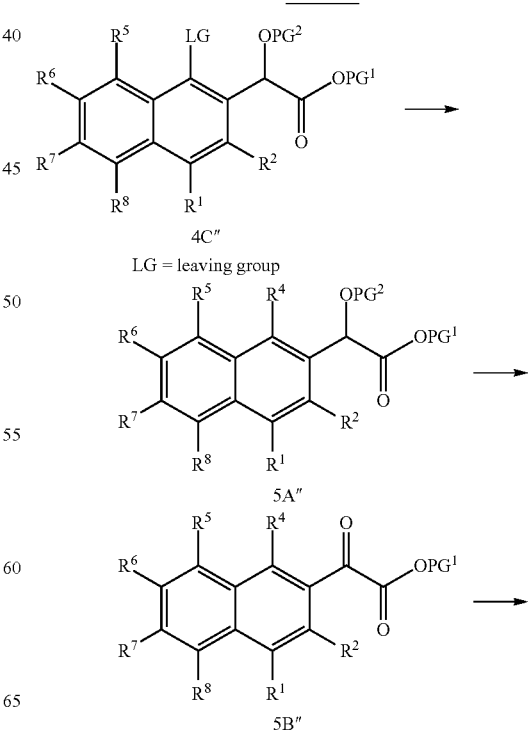

Scheme 5

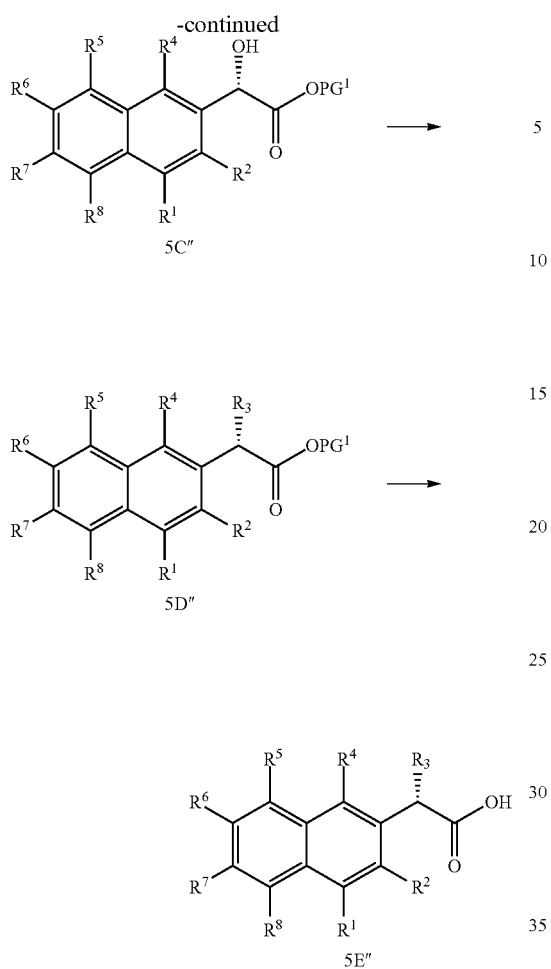

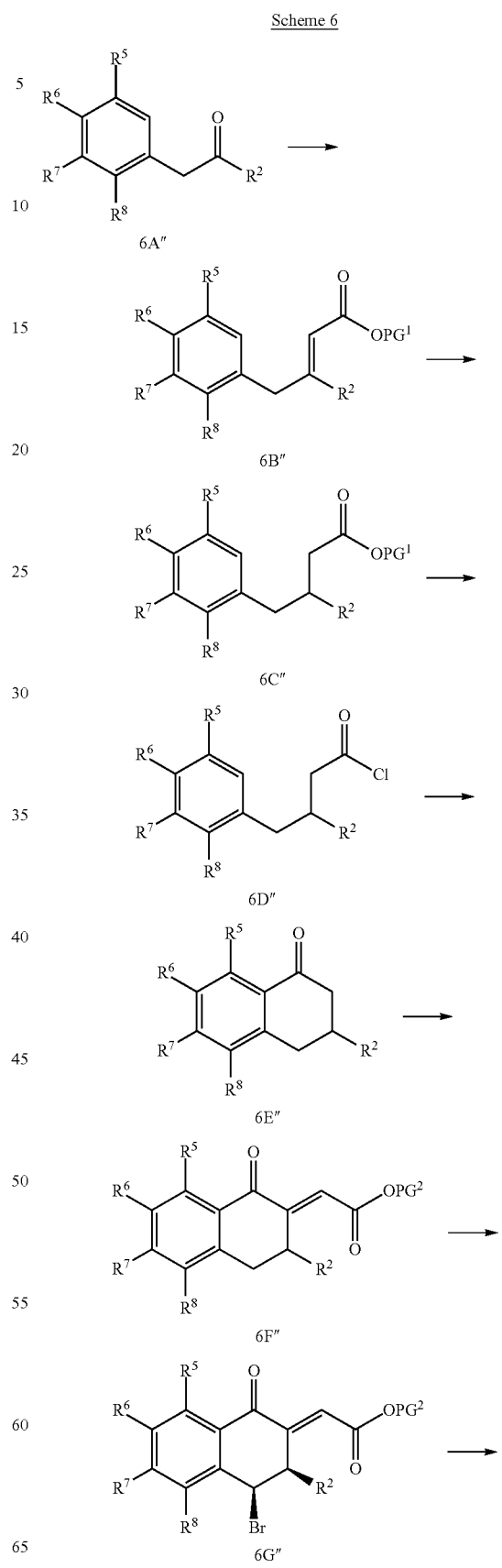

Scheme 6

The functionalized naphthalene 4C" can undergo can undergo cross-coupling reactions such as but not limited to Suzuki reactions with boronic acids or esters, Stille reactions with trialkyltin reagents, Sonogashira reactions with alkynes, and Buchwald-Hartwig reactions with amines thus providing carbon linked and nitrogen linked products using a palladium catalyst such as palladium tetrakis to give the corresponding cross-coupled naphthalene 5A". The alcohol protecting group can be removed and the resulting alcohol oxidized to the ketone using an oxidant such as Dess-Martin Periodinane, for example, to provide 5B". The ketone can be reduced stereoselectively using an asymmetric reduction method such as, for example Corey-Bakshi-Shibata Reduction to provide 5C". The secondary hydroxyl can be converted to the corresponding ether such as tert-butyl ether using methods known to those skilled in the art such as, tert-butyl acetate and perchloric acid to provide 5D". The protected ester can be deprotected by methods known to those skilled in the art such as, for example the deprotection of a ethyl ester protecting group under basic conditions, such as, for example sodium hydroxide, to give the corresponding carboxylic acid 5E".

It is known to those skilled in the art that the functionalized naphthalenes (e.g. 5A" or 5D") that contain a halogen or pseudohalogen (e.g. triflate), can undergo cross-coupling reactions such as but not limited to Suzuki reactions with boronic acids or esters, Stille reactions with trialkyltin reagents, Sonogashira reactions with alkynes, and Buchwald-Hartwig reactions with amines and carried forward in a similar manner to provide 5E".

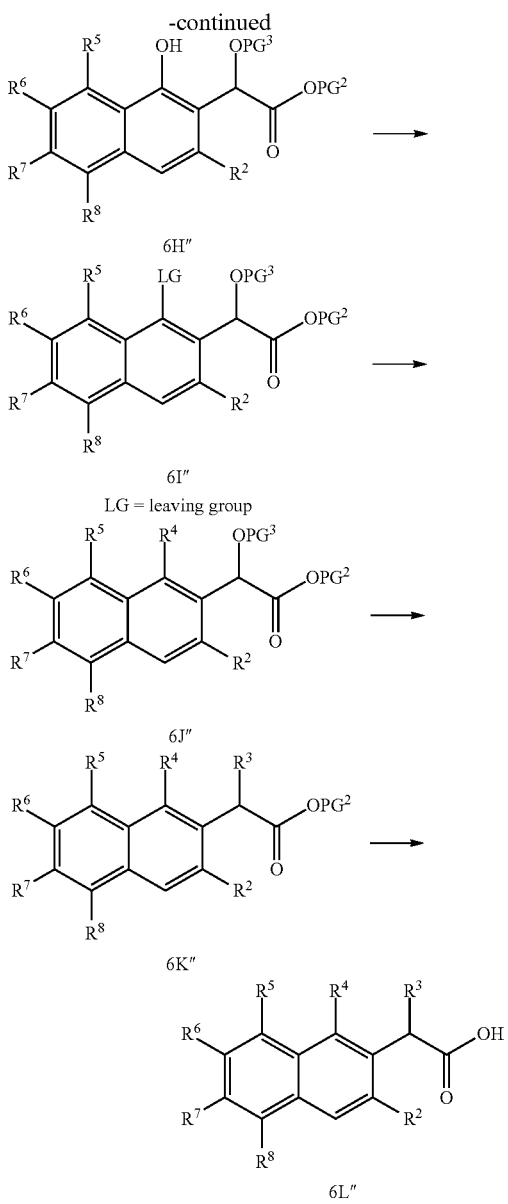

LG = leaving group

It is known to those skilled in the art that 6A" can undergo The Horner-Wadsworth-Emmons with stabilized phosphonate carbanions such as, for example (diethoxyphosphoryl) acetic acid ethyl ester and sodium hydride to provide 6B". The olefin can be reduced by hydrogenation with palladium on carbon, for example, to provide 6C". The protected ester can be deprotected by methods known to those skilled in the art such as, for example the deprotection of a ethyl ester protecting group under basic conditions, such as, for example lithium hydroxide, to give the corresponding carboxylic acid that can be converted to the corresponding acid chloride using oxalyl chloride to give 6D". Friedel Crafts reaction catalyzed by a Lewis acid such as, for example, aluminum trichloride provides tetralone 6E". Condensation of 6E" with, for example, ethyl glyoxylate under acid catalysis provides 6F" which can be brominated under radical conditions such as, for example, N-bromosuccinimide and AIBN, and converted to 6H" using an alkoxide such as that derived from reaction of 4-methoxybenzyl alcohol and LHMDS, for example.

The naphthol 6H" can be converted to a leaving group (e.g. triflate) known to undergo cross-coupling reactions by methods known to those skilled in the art. Compound 6I" can undergo cross-coupling reactions such as but not limited to Suzuki reactions with boronic acids or esters, Stille reactions with trialkyltin reagents, Sonogashira reactions with alkynes, and Buchwald-Hartwig reactions with amines thus providing carbon linked and nitrogen linked products using a palladium catalyst such as palladium tetrakis to give the corresponding cross-coupled naphthalene 6J".

The alcohol protecting group can be removed by methods known to those skilled in the art and the resulting hydroxyl can be converted to the corresponding ether such as tert-butyl ether using methods known to those skilled in the art such as, tert-butyl acetate and perchloric acid to provide 6K". The protected ester can be deprotected by methods known to those skilled in the art such as, for example the deprotection of a ethyl ester protecting group under basic conditions, such as, for example sodium hydroxide, to give the corresponding carboxylic acid 6L".

Prodrugs

In one embodiment, the invention provides for a prodrug of a compound of the invention. The term "prodrug" as used herein refers to any compound that when administered to a biological system generates a compound of the invention that inhibits the replication of HIV ("the active inhibitory compound"). The compound may be formed from the prodrug as a result of: (i) spontaneous chemical reaction(s), (ii) enzyme catalyzed chemical reaction(s), (iii) photolysis, and/or (iv) metabolic chemical reaction(s).

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2OC(=O)R^{99}$ and acyloxymethyl carbonates —$CH_2OC(=O)OR^{99}$ where $R^{99}$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968, 788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2C(=O)C(CH_3)_3$. An exemplary acyloxymethyl carbonate prodrug moiety is pivaloyloxymethylcarbonate (POC)—$CH_2C(=O)OC(CH_3)_3$.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to a phosphate have also been described (Khamnei and Torrence, (1996) *J. Med. Chem.* 39:4109-4115). Benzyl esters are reported to generate parent phosphonic acids. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate phosphoric acid and a quinone methide intermediate. Examples of this class of prodrugs are described by Mitchell et al. (1992) *J. Chem. Soc. Perkin Trans. II* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.*, 22: 155-174; Benzaria et al. (1996) *J. Med. Chem.* 39: 4958).

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween®60, Span®80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents.

Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable.

These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkyl oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provides compositions comprising one or more compounds of the invention formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

The antiviral properties of a compound of the invention may be determined using Test A described below.

Test A: Antiviral Assays in MT4 Cells

For the antiviral assay utilizing MT-4 cells, 0.4 µL of 189X test concentration of 3-fold serially diluted compound in DMSO was added to 40 µL of cell growth medium (RPMI 1640, 10% FBS, 1% penicillin/Streptomycin, 1% L-Glutamine, 1% HEPES) in each well of 384-well assay plates (10 concentrations) in quadruplicate.

1 mL aliquots of 2×10e6 MT-4 cells are pre-infected for 1 and 3 hrs respectively, @37° C. with 25 µL (MT4) or of either cell growth medium (mock-infected) or a fresh 1:250 dilution of an HIV-IIIb concentrated ABI stock (0.004 m.o.i. for MT4 cells). Infected and uninfected cells are diluted in cell growth medium and 35 uL of 2000 (for MT4) cells is added to each well of the assay plates.

Assay plates were then incubated in a 37° C. incubator. After 5 days of incubation, 25 µl of 2× concentrated CellTiter-Glo™ Reagent (catalog #G7573, Promega Biosciences, Inc., Madison, Wis.) was added to each well of the assay plate. Cell lysis was carried out by incubating at room temperature for 2-3 min and then chemiluminescence was read using the Envision reader (PerkinElmer).

Compounds of the present invention demonstrate antiviral activity in this assay (Test A) as depicted in the table below.

| Compound Number | EC50 (µM) |
|---|---|
| 3K | 0.056 |
| 4K | 0.301 |
| 4L | 22 |
| 5K | 4.6 |
| 6D | 0.014 |
| 7D | 1.7 |
| 7E | 20 |
| 8 | 0.025 |
| 9 | 1.3 |
| 10 | 36 |
| 11 | 8.9 |
| 12 | 0.11 |
| 13 | 0.010 |
| 14 | 0.011 |
| 15 | 0.015 |
| 16 | 7.0 |
| 17 | 7.7 |
| 19 | 5.4 |
| 20 | 0.093 |
| 22 | 0.54 |
| 23 | 0.024 |
| 24 | 29 |
| 25 | 26 |
| 26 | 0.84 |
| 27 | 3.5 |
| 28 | 0.40 |
| 29A | 0.13 |
| 29B | 0.50 |
| 30 | 0.044 |
| 31 | 0.11 |
| 32 | 0.086 |
| 33 | 0.12 |
| 34 | 0.35 |
| 37 | 1.2 |
| 38 | 3.4 |
| 39 | 0.70 |
| 40 | 0.21 |
| 41 | 0.40 |
| 42 | 0.11 |
| 43 | 0.022 |
| 44 | 0.12 |
| 45 | 1.8 |
| 46 | 1.4 |
| 47 | 0.11 |

| Compound Number | EC50 (μM) |
| --- | --- |
| 48 | 0.21 |
| 49 | 0.65 |
| 53 | 0.12 |
| 54 | 0.055 |
| 55 | 0.054 |
| 56 | 0.21 |
| 57 | 0.082 |
| 58 | 0.042 |
| 59 | 0.16 |
| 60 | 0.032 |
| 61 | 0.264 |
| 62 | 0.136 |
| 63 | 0.099 |
| 64 | 0.052 |
| 65 | 0.19 |
| 66 | 0.29 |
| 67 | 0.29 |
| 68A | 0.014 |
| 68B | 0.005 |
| 69 | 0.38 |
| 70 | 8.8 |
| 71 | 35 |
| 72 | 2.0 |
| 73 | 0.13 |
| 74 | 1.2 |
| 75 | 0.98 |
| 76 | 0.93 |
| 77 | 8.9 |
| 78 | 0.30 |
| 79 | 0.089 |
| 80 | 0.051 |
| 81 | 0.15 |
| 82 | 0.058 |
| 83 | 0.078 |
| 84 | 0.014 |
| 85 | 0.018 |
| 86 | 0.98 |
| 87 | 0.072 |
| 88 | 0.024 |
| 89 | 0.28 |
| 90 | 31 |
| 91 | 0.25 |
| 92 | 7.1 |
| 93 | 0.086 |
| 94 | 12 |
| 95 | 0.38 |
| 96 | 0.088 |
| 97 | 0.30 |
| 98 | 0.010 |
| 99 | 0.107 |
| 100 | 0.023 |
| 101 | 0.041 |
| 102 | 0.037 |
| 103 | 0.026 |
| 104 | 0.036 |
| 105 | 0.043 |
| 106A | 0.086 |
| 106B | 0.091 |
| 107 | 0.092 |
| 108 | 0.028 |
| 109 | 29 |
| 110 | 0.067 |
| 111 | 1.1 |
| 112 | 0.009 |
| 113A | 0.91 |
| 113B | 0.46 |
| 114 | 1.9 |
| 115 | 0.037 |
| 116 | 0.016 |
| 117 | 0.011 |
| 118 | 0.036 |
| 119 | 0.011 |
| 120 | 0.032 |
| 121 | 0.014 |
| 122 | 0.036 |
| 123 | 0.024 |
| 124 | 0.15 |
| 126 | 0.833 |
| 127 | 0.087 |
| 128 | 5.3 |
| 129 | 0.17 |
| 131 | 0.062 |
| 132 | 0.118 |
| 133 | 0.123 |
| 134 | 0.15 |
| 135 | 0.045 |
| 136 | 0.34 |
| 137 | 0.13 |
| 138 | 0.040 |
| 139 | 0.010 |
| 140 | 1.6 |
| 143 | 0.056 |
| 144 | 1.3 |
| 145 | 0.050 |
| 146 | 10 |
| 147 | 1.1 |
| 149 | 0.20 |
| 150A | 29.150 |
| 150B | 0.26 |
| 151 | 0.85 |
| 152 | 5.8 |
| 153 | 11 |
| 154 | 29 |
| 155 | 29 |
| 156 | 7.3 |
| 157 | 10 |
| 158 | 35 |
| 159 | 1.3 |
| 160 | 36 |
| 161 | 4.7 |
| 162 | 1.4 |
| 163 | 16 |
| 164 | 25 |
| 165 | 53 |
| 166 | 16 |
| 167 | 29 |
| 168 | 45 |
| 169 | 18 |
| 170 | 29 |
| 171 | 36 |
| 172 | 50 |
| 173 | 3.2 |
| 174 | 3.2 |
| 175 | 20 |
| 176 | 12 |
| 177 | 37 |
| 178 | 34 |
| 179 | 18.7 |
| 180 | 29 |
| 181 | 0.005 |
| 183 | 0.351 |
| 185 | 0.024 |
| 186A | 1.694 |
| 186B | 0.024 |

In certain embodiments, the compounds demonstrate an EC50 of <50 μM. In certain embodiments, the compounds demonstrate an EC50 of <30 μM. In certain embodiments, the compounds demonstrate an EC50 of <10 μM. In certain embodiments, the compounds demonstrate an EC50 of <1 μM.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

The invention has been described with reference to various specific and preferred embodiments and techniques. However, it should be understood that many variations and modifications may be made while remaining within the spirit and scope of the invention.

The invention will now be illustrated by the following non-limiting Examples. The Examples provided herein describe the synthesis of compounds of the invention (i.e. compounds of Formula I) as well as intermediates used to prepare compounds of the invention.

EXAMPLE 1

(S)-2-tert-butoxy-2-(1-(4-chlorophenyl)-3-methyl-naphthalen-2-yl)acetic acid (3K)

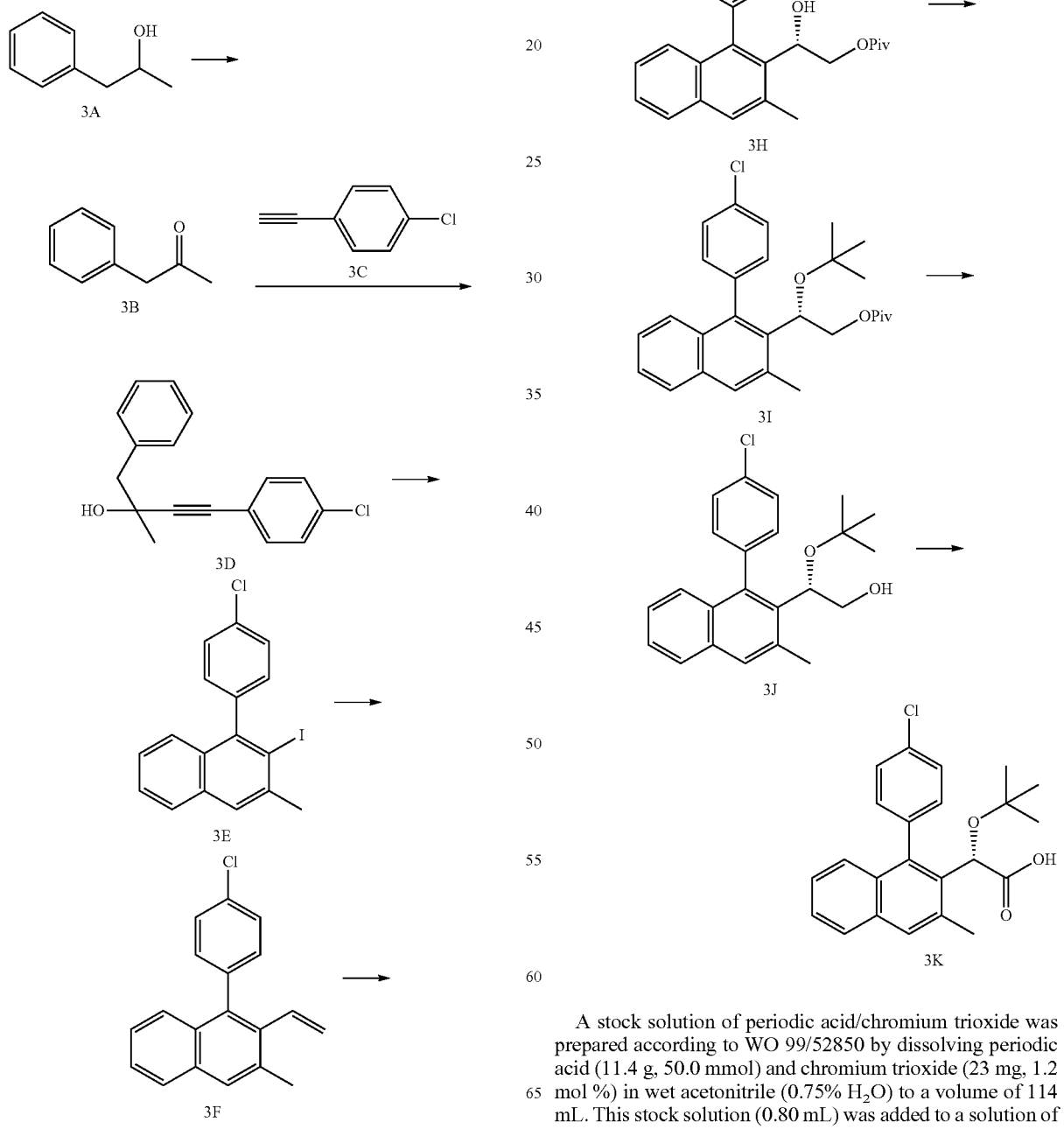

A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% $H_2O$) to a volume of 114 mL. This stock solution (0.80 mL) was added to a solution of (S)-2-tert-butoxy-2-(1-(4-chlorophenyl)-3-methylnaphthalen-2-yl)ethanol (3J) (51.7 mg, 0.14 mmol) in wet acetonitrile (2.0 mL), 0.75% H$_2$O) at 0° C. The reaction mixture was stirred for 30 minutes at 0° C. and quenched with 1.5 M K$_2$HPO$_4$ solution. Ethyl acetate was added and organic layer separated and washed with 1:1 brine/H$_2$O (2×), then saturated NaHSO$_3$/brine. The organic layer was dried (MgSO$_4$), filtered and concentrated and purified by reverse phase HPLC (Gemini, 50 to 95% ACN/H$_2$O+0.1% TFA) and the product lyophilized to give 3K as a white powder (27.8 mg). $^1$H-NMR: 300 MHz, (CDCl$_3$) δ 7.73 (d, J=7.8 Hz, 1H), 7.64 (s, 1H), 7.62 (d, J=7.8 Hz, 1H), 7.50-7.38 (m, 3H), 7.28-7.22 (m, 3H), 5.25 (s, 1H), 2.54 (s, 3 H), 0.98 (s, 9H). LCMS-ESI$^-$ (m/z): [M−H]$^-$ calcd for C$_{23}$H$_{22}$ClO$_3$: 381.88. Found: 380.9, 382.9.

Preparation of (S)-2-tert-butoxy-2-(1-(4-chlorophenyl)-3-methylnaphthalen-2-yl)ethanol (3J):

Preparation of 1-phenylpropan-2-one (3B): A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% H$_2$O) to a volume of 114 mL. This stock solution (104.5 mL) was added to a solution of 1-phenylpropan-2-ol (3A) (5.0 g, 36.71 mmol) in wet acetonitrile (150 mL, 0.75% H$_2$O) at 0° C. over 1 h, maintaining internal temperature below 5° C. The reaction was quenched with K$_2$HPO$_4$ (11.5 g, 50.5 mmol) in H$_2$O (60 mL). Dichloromethane was added and organic layer separated and washed with brine/H$_2$O (2×100 mL), followed by saturated NaHSO$_3$/brine. The organic layer was dried (MgSO$_4$), filtered and concentrated to give 3B as a yellow oil (5.1 g). $^1$H-NMR: 300 MHz, (CDCl$_3$) δ 7.35-7.10 (m, 5H), 3.65 (s, 2H), 2.11 (s, 3 H).

Preparation of 4-(4-chlorophenyl)-2-methyl-1-phenylbut-3-yn-2-ol (3D): To a solution of 1-chloro-4-ethynylbenzene (3C) (1.75 mL, 12.81 mmol) in THF (40 mL) at 0° C. was added n-butyllithium (2.5 M in hexanes, 5.13 mL, 12.81 mmol) and stirred for 1 h. A solution of 1-phenylpropan-2-one (3B) (1.38 g, 10.25 mmol) in THF (5 mL) was added and the reaction mixture was warmed to room temperature overnight. The reaction mixture was quenched with saturated NH$_4$Cl solution and extracted with diethyl ether (2×). The combined organic layer was dried (MgSO$_4$), filtered, concentrated and purified by flash column chromatography (silica gel, 0 to 10% ethyl acetate/hexanes) to give 3D as a yellow oil (2.29 g). $^1$H-NMR: 300 MHz, (CDCl$_3$) δ 7.35-7.20 (m, 9H), 3.0 (AB quart, J=13.2, 9.9 Hz, 2H), 1.59 (s, 3 H).

Preparation of 1-(4-chlorophenyl)-2-iodo-3-methylnaphthalene (3E): To a solution of 4-(4-chlorophenyl)-2-methyl-1-phenylbut-3-yn-2-ol (3D) (1.77 g, 6.53 mmol) in acetonitrile (50 mL) was added sodium bicarbonate (1.097 g, 13.06 mmol), followed by iodine (4.974 g, 19.60 mmol). The reaction mixture was stirred for 1.5 h, then diluted with diethyl ether. The organic layer was washed with 1 M sodium thiosulfate solution (50 mL). The aqueous layer was back-extracted with diethyl ether and the combined organic layer was dried (MgSO$_4$), filtered, concentrated, adsorbed onto silica gel and purified by flash column chromatography (silica gel, hexanes) to give 3E as an off-white solid (1.8733 g). $^1$H-NMR: 300 MHz, (CDCl$_3$) δ 7.74 (d, J=6.6 Hz, 1H), 7.73 (s, 1H), 7.48-7.40 (m, 3H), 7.24-7.20 (m, 2H), 7.13 (d, J=8.1 Hz, 2H), 2.64 (s, 3 H).

Preparation of 1-(4-chlorophenyl)-3-methyl-2-vinylnaphthalene (3F): A solution of 1-(4-chlorophenyl)-2-iodo-3-methylnaphthalene (3E) (1.50 g, 3.98 mmol), tributyl(vinyl)tin (1.28 mL, 4.37 mmol) and PdCl$_2$(PPh$_3$)$_2$ (0.279 g, 0.398 mmol) in DMF (20 mL) was stirred at 90° C. under argon overnight. The reaction mixture was cooled, diluted with ethyl acetate and washed with 5% LiCl solution (2×), brine and dried (MgSO$_4$). The mixture was filtered, concentrated and purified by flash column chromatography (silica gel, hexanes) to give 3F as a white solid (0.9894 g). $^1$H-NMR: 300 MHz, (CDCl$_3$) δ 7.74 (d, J=7.8 Hz, 1H), 7.66 (s, 1H), 7.40-7.13 (m, 5H), 7.15 (d, J=8.1 Hz, 2H), 6.50 (dd, J=18, 11.7 Hz, 1H), 5.27 (d, J=11.7 Hz, 1H), 5.03 (d, J=18 Hz, 1H), 2.50 (s, 3 H).

Preparation of (S)-1-(1-(4-chlorophenyl)-3-methylnaphthalen-2-yl)ethane-1,2-diol (3G): A biphasic mixture of AD-mix-α (4.928 g) in tert-butanol (17.5 mL)/H$_2$O (17.5 mL) was cooled to 0° C. and 1-(4-chlorophenyl)-3-methyl-2-vinylnaphthalene (3F) (0.980 g, 3.52 mmol) was added. The reaction mixture was stirred for 6 h at 0° C., then stored at −20° C. overnight. The reaction was resumed for 10 h at 0° C., then stored at −20° C. overnight. The reaction was resumed for 8 h at 0° C. until complete. Sodium sulfite (5.3 g) was added at 0° C., then warmed to room temperature and stirred for 30 min to give a white mixture. The mixture was diluted with dichloromethane and H$_2$O. The mixture was extracted with dichloromethane (3×) and the combined organic layer was dried (MgSO$_4$), filtered, concentrated and purified by flash column chromatography (silica gel, 0 to 100% ethyl acetate/hexanes) to give 3G as a white solid (0.9813 g). $^1$H-NMR: 300 MHz, (CDCl$_3$) δ 7.72 (d, J=8.1 Hz, 1H), 7.65 (s, 1H), 7.50-7.303 (m, 3H), 7.26-7.07 (m, 4H), 4.92 (dd, J=9.9, 3.6 Hz, 1H), 3.94 (dd, J=10.2, 10.2 Hz, 1H), 3.57 (dd, J=11.1, 3.6 Hz, 1H), 2.69 (s, 3 H).

Preparation of (S)-2-(1-(4-chlorophenyl)-3-methylnaphthalen-2-yl)-2-hydroxyethyl pivalate (3H): To a solution of (S)-1-(1-(4-chlorophenyl)-3-methylnaphthalen-2-yl)ethane-1,2-diol (3G) (0.981 g, 3.14 mmol) in pyridine (5.0 mL)/DCM (15.0 mL) was added pivaloyl chloride (0.463 mL, 3.77 mmol). The reaction mixture was stirred for 5 h at room temperature and diluted with ethyl acetate. The organic layer was washed with 1 N HCl, saturated sodium bicarbonate solution, dried (MgSO$_4$), filtered, concentrated and purified by flash column chromatography (silica gel, 0 to 30% ethyl acetate/hexanes) to give 3H as a white solid (1.296 g). $^1$H-NMR: 300 MHz, (CDCl$_3$): δ: 7.72 (d, J=8.1 Hz, 1H), 7.67 (s, 1H), 7.46-7.37 (m, 3H), 7.26-7.10 (m, 4H), 4.99 (dd, J=8.7, 3.0 Hz, 1H), 4.45 (dd, J=11.7, 9.7 Hz, 1H), 4.13 (dd, J=11.7, 3.3 Hz, 1H), 2.72 (s, 3H), 1.11 (s, 9H).

Preparation of (S)-2-tert-butoxy-2-(1-(4-chlorophenyl)-3-methylnaphthalen-2-yl)ethanol (3J): A solution of (S)-2-(1-(4-chlorophenyl)-3-methylnaphthalen-2-yl)-2-hydroxyethyl pivalate (3H) (0.4582 g, 1.15 mmol) and perchloric acid, (70%, 0.138 mL, 2.3 mmol) in tert-butyl acetate (10 mL) was stirred at room temperature for 3 h. The reaction mixture was quenched with solid sodium bicarbonate (0.5 g) for 1 h. Saturated sodium bicarbonate solution was added and extracted with ethyl acetate (3×). The combined organic layer was dried (MgSO$_4$), filtered and concentrated to give (S)-2-tert-butoxy-2-(1-(4-chlorophenyl)-3-methylnaphthalen-2-yl)ethyl pivalate (3I) that was used in next step without further purification. (S)-2-tert-butoxy-2-(1-(4-chlorophenyl)-3-methylnaphthalen-2-yl)ethyl pivalate (3I) from above reaction was dissolved in MeOH (1 mL) and THF (7 mL). Sodium hydroxide (2 M, 0.75 mL, 1.5 mmol) was added and the reaction mixture was stirred at room temperature overnight. Additional sodium hydroxide (2 M, 0.75 mL, 1.5 mmol) was added and reaction mixture was stirred for an additional 24 hours. The reaction mixture was then diluted with ethyl acetate and washed with brine. The aqueous layer was back-extracted with ethyl acetate and combined organic layer was dried (MgSO$_4$), filtered, concentrated and purified by flash column chromatography (silica gel, 0 to 10% ethyl acetate/ hexanes) to give 3J as a white solid (0.1889 g). ¹H-NMR: 300 MHz, (CDCl₃) δ 7.72 (d, J=8.1 Hz, 1H), 7.63 (s, 1H), 7.46-7.05 (m, 7H), 4.60 (dd, J=10.5, 4.5 Hz, 1H), 3.77 (dd, J=11.4, 4.2 Hz, 1H), 3.46 (dd, J=11.4, 4.2 Hz, 1H), 2.71 (s, 3H), 1.00 (s, 9H).

EXAMPLE 2

(S)-2-tert-butoxy-2-((R)-3-methyl-1-(quinolin-8-yl)naphthalen-2-yl)acetic acid (4K) and (S)-2-tert-butoxy-2-((S)-3-methyl-1-(quinolin-8-yl)naphthalen-2-yl)acetic acid (4L)

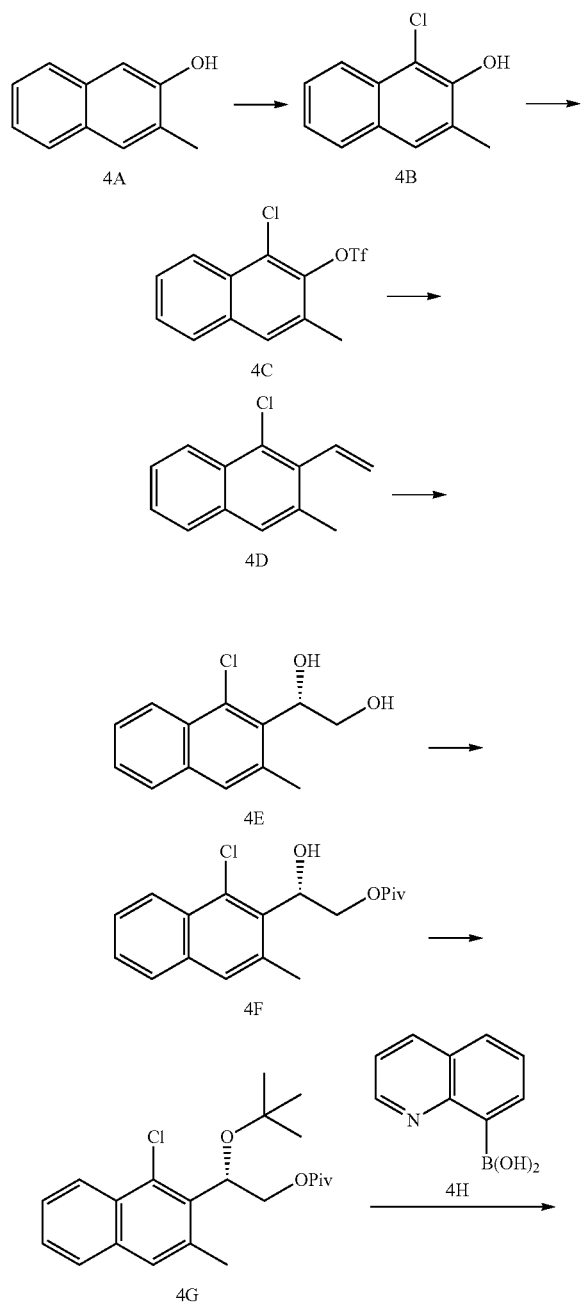

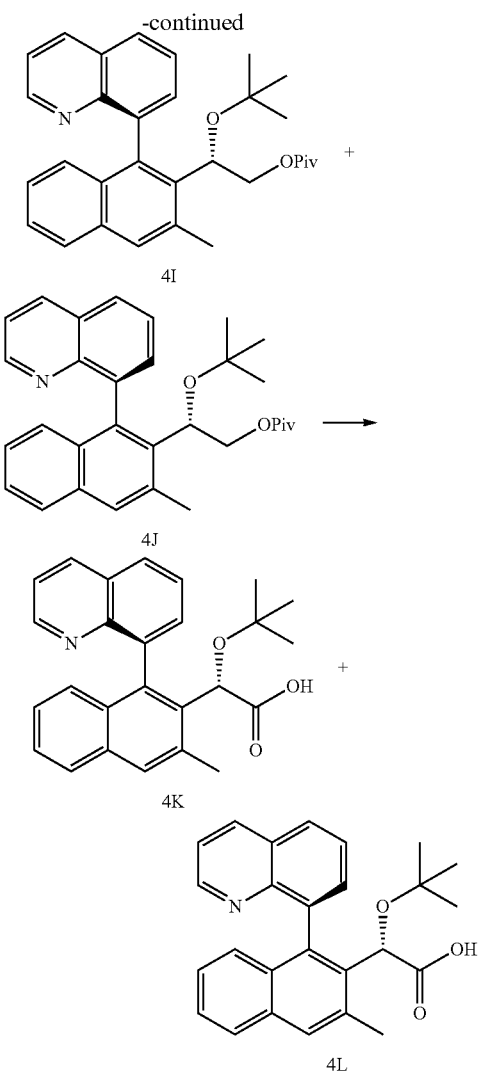

(S)-2-tert-butoxy-2-((R)-3-methyl-1-(quinolin-8-yl)naphthalen-2-yl)ethyl pivalate (4I) (22 mg, 0.0468 mmol) was dissolved in THF (1.0 mL) and MeOH (0.1 mL) and 2.0 M NaOH (94 µL) was added. The reaction mixture was stirred for 24 h and 2.0 M NaOH (94 µL) was added. After stirring for 60 h at room temperature, the reaction was heated at 55° C. for 1 h with little change in conversion. The reaction mixture was diluted with ethyl acetate and washed with brine, dried (MgSO₄), filtered, concentrated and used in next step without further purification. The residue from above was dissolved in wet acetonitrile (0.75% H₂O), and H₅IO₆/CrO₃ stock solution (0.439 M, 0.266 mL) was added at 0° C. The reaction mixture was stirred for 30 minutes and additional H₅IO₆/CrO₃ stock solution (0.439 M, 0.266 mL) was added. After stirring for 30 minutes, the reaction mixture was quenched with saturated NaHCO₃ solution and diluted with ethyl acetate. The organic layer was washed with H₂O/brine, dried (MgSO₄), filtered, concentrated and purified by reverse phase HPLC (Gemini, 5 to 100% acetonitrile/H₂O+0.1% TFA) to give 4K as a film (12.1 mg, 50%). ¹H-NMR: 400 MHz, (CD₃OD) δ 9.35 (dd, J=8.4, 1.6 Hz, 1 H), 8.86 (dd, J=5.6, 1.2 Hz, 1 H), 8.51 (dd, J=8.4, 1.2 Hz, 1 H), 8.13-8.07 (m, 2H), 8.01 (s, 1H), 7.95 (d, J=8.0 Hz, 1 H), 7.52-7.45 (m, 1H), 7.28-7.24 (m, 1H), 6.83 (d, J=8.4 Hz, 1 H), 5.23 (s, 1H), 2.80

(s, 3H), 0.84 (s, 9H). $^{19}$F-NMR: 376 MHz, (CD$_3$OD) δ: −77.87. LCMS-ESI$^+$ (m/z): [M+H]$^+$ calcd for C$_{26}$H$_{26}$NO$_3$: 400.5. Found: 400.1.

Compound 4L (1.8 mg, 32%) was prepared following the procedure used to prepare compound 4K except that compound 4J was used instead of compound 4I. $^1$H-NMR: 400 MHz, (CD$_3$OD) δ 9.23 (dd, J=8.4, 1.6 Hz, 1 H), 8.75 (dd, J=5.2, 1.6 Hz, 1 H), 8.48 (dd, J=8.8, 1.6 Hz, 1 H), 8.31 (dd, J=7.2, 1.2 Hz, 1 H), 8.13 (dd, J=7.6, 7.2 Hz, 1 H), 7.99 (dd, J=8.4, 5.2 Hz, 1 H), 7.96 (s, 1H), 7.94 (d, J=8.4 Hz, 1 H), 7.5-7.45 (m, 1H), 7.25-7.21 (m, 1H), 6.83 (d, J=8.8 Hz, 1 H), 5.16 (s, 1H), 2.75 (s, 3H), 0.83 (s, 9H). LCMS-ESI$^+$ (m/z): [M+H]$^+$ calcd for C$_{26}$H$_{26}$NO$_3$: 400.5. Found: 400.1.

Preparation of (S)-2-tert-butoxy-2-((R)-3-methyl-1-(quinolin-8-yl)naphthalen-2-yl)ethyl pivalate (4I) and (S)-2-tert-butoxy-2-((S)-3-methyl-1-(quinolin-8-yl)naphthalen-2-yl)ethyl pivalate (4J):

Preparation of 1-chloro-3-methylnaphthalen-2-ol (4B): To a solution of N-chlorosuccinimide (8.02 g, 60.05 mmol) in dichloromethane (475 mL) at −78° C. was added zirconium (IV)chloride (2.80 g, 12.01 mmol), followed by 3-methyl-naphthalen-2-ol (4A) (9.5 g, 60.05 mmol) under Ar. The reaction mixture was stirred at −78° C. for minutes, the cooling bath was removed and the reaction was stirred at room temperature for 5 h. The reaction was quenched with saturated sodium bicarbonate solution and stirred for 5 minutes. The mixture was diluted with H$_2$O, extracted with dichloromethane (3×) and the combined organic layer was dried (MgSO$_4$), filtered, concentrated and purified by flash column chromatography (silica gel, 0 to 10% ethyl acetate/hexanes) to give 4B as a white solid (9.05 g, 78%).

Preparation of 1-chloro-3-methylnaphthalen-2-yl trifluoromethanesulfonate (4C): To a solution of 1-chloro-3-methylnaphthalen-2-ol (4B) (9.05 g, 46.98 mmol) in dichloromethane (235 mL) at −78° C. was added trifluoromethanesulfonic anhydride (11.9 mL, 70.47 mmol), followed by 2,6-lutidine (8.2 mL, 70.47 mmol). The reaction mixture was stirred for 3 h to give a yellow solution, which was diluted with dichloromethane and washed with H$_2$O/brine. The organic layer was dried (MgSO$_4$), filtered, concentrated and purified by flash column chromatography (silica gel, 0 to 10% ethyl acetate/hexanes) to give 4C as a white solid (14.75 g, 97%).

Preparation of 1-chloro-3-methyl-2-vinylnaphthalene (4D): To a solution of 1-chloro-3-methylnaphthalen-2-yl trifluoromethanesulfonate (4C) (14.75 g, 45.43 mmol), tributyl(vinyl)tin (14.59 mL, 49.97 mmol) and lithium chloride (5.78 g, 136.29 mmol) was added bis(triphenylphosphine)palladium(II) dichloride under Ar. The reaction mixture was heated at 50° C. for 20 h, then heated at 90° C. for 8 h. The reaction mixture was than cooled to room temperature, diluted with ethyl acetate, washed with 5% lithium chloride solution (3×), brine and dried (MgSO$_4$), filtered and then concentrated and purified by flash column chromatography (silica gel, 0 to 10% ethyl acetate/hexanes) to give 4D contaminated by organotin. The residue was dissolved in dichloromethane and stirred with 10% KF solution overnight. The resulting white mixture was filtered through a pad of Celite and extracted with dichloromethane (2×). The organic layer was concentrated and purified by flash column chromatography (silica gel, 0 to 10% ethyl acetate/hexanes) to give 4D as a pale yellow oil (10.1 g).

Preparation of (S)-1-(1-chloro-3-methylnaphthalen-2-yl)ethane-1,2-diol (4E): A biphasic mixture of AD-mix-α (6.907 g) in tert-butanol (24.5 mL)/H$_2$O (24.5 mL) was cooled to 0° C. and 1-chloro-3-methyl-2-vinylnaphthalene (4D) (1.00 g, 4.93 mmol) was added. The reaction mixture was stirred for 8 h at 0° C. Sodium sulfite (7.4 g) was added at 0° C. and the reaction was stirred for 40 minutes to give a white mixture. The mixture was diluted with dichloromethane and H$_2$O. The mixture was extracted with dichloromethane (3×) and the combined organic layer was dried (MgSO$_4$), filtered, concentrated and purified by flash column chromatography (silica gel, 0 to 100% ethyl acetate/hexanes) to give 4E as a white solid (0.920 g).

Preparation of (S)-2-(1-chloro-3-methylnaphthalen-2-yl)-2-hydroxyethyl pivalate (4F): To a solution of (S)-1-(1-chloro-3-methylnaphthalen-2-yl)ethane-1,2-diol (4E) (0.920 g, 3.89 mmol) in pyridine (5.0 mL)/dichloromethane (15.0 mL) was added pivaloyl chloride (0.574 mL, 4.67 mmol). The reaction mixture was stirred for 18 h at room temperature. The reaction was incomplete and additional pivaloyl chloride (0.574 mL, 4.67 mmol) was added. After stirring for 1 h, the reaction mixture was quenched with 1 N HCl and diluted with ethyl acetate. The organic layer was washed with 1 N HCl, saturated sodium bicarbonate solution, dried (MgSO$_4$), filtered, concentrated and purified by flash column chromatography (silica gel, 0 to 30% ethyl acetate/hexanes) to give 4F as a colorless oil (1.139 g). LCMS-ESI$^+$ (m/z): [M—O]$^+$ calcd for C$_{18}$H$_{21}$ClO$_2$: 304.80. Found: 303.0, 305.0.

Preparation of (S)-2-tert-butoxy-2-(1-chloro-3-methylnaphthalen-2-yl)ethyl pivalate (4G): A solution of (S)-2-(1-chloro-3-methylnaphthalen-2-yl)-2-hydroxyethyl pivalate (4F) (1.13 g, 3.52 mmol) and perchloric acid, (70%, 0.605 mL, 7.04 mmol) in tert-butyl acetate (35 mL) was stirred at room temperature for 1.5 h. The reaction mixture was quenched with solid sodium bicarbonate (1.5 g) for 1 h. Saturated sodium bicarbonate solution was added and the reaction was extracted with ethyl acetate (3×). The combined organic layer was dried (MgSO$_4$), filtered, concentrated and purified by flash column chromatography (silica gel, 0 to 20% ethyl acetate/hexanes) to give 4G as a colorless oil (1.1889 g, 90%).

Preparation of (S)-2-tert-butoxy-2-((R)-3-methyl-1-(quinolin-8-yl)naphthalen-2-yl)ethyl pivalate (4I) and (S)-2-tert-butoxy-2-((S)-3-methyl-1-(quinolin-8-yl)naphthalen-2-yl)ethyl pivalate (4J): To a microwave vial was added (S)-2-tert-butoxy-2-(1-chloro-3-methylnaphthalen-2-yl)ethyl pivalate (4G) (0.100 g, 0.265 mmol), 8-quinoline boronic acid (4H) (0.069 g, 0.398 mmol), palladium(II) acetate (0.003 g, 0.013 mmol), SPhos (0.011 g, 0.0265 mmol) and potassium phosphate (0.169 g, 0.795 mmol). The vial was evacuated and backfilled with argon (3×). Anhydrous THF (0.53 mL) and H$_2$O (53 μL) were added and mixture stirred at room temperature for 2 h and then heated at 50° C. for 2 h. The reaction was charged with PdCl$_2$(CH$_3$CN)$_2$ (10 mg) and SPhos (20 mg) and heated overnight at 100° C. The reaction mixture was diluted with ethyl acetate, washed with brine, dried (MgSO$_4$), filtered, concentrated and purified by flash column chromatography (silica gel, 0 to 20% ethyl acetate/hexanes) to give the separated atropisomers; atropisomer 4I (22.0 mg) LCMS-ESI$^+$ (m/z): [M+H]$^+$ calcd for C$_{31}$H$_{36}$NO$_3$: 470.62. Found: 470.1; and atropisomer 4J (5.2 mg) LCMS-ESI (m/z): [M+H]$^+$ calcd for C$_{31}$H$_{36}$NO$_3$: 470.62; Found: 470.1.

EXAMPLE 3
(S)-2-tert-Butoxy-2-((S)-1-(2,3-dihydropyrano[4,3,2-de]quinolin-7-yl)-3-methylnaphthalen-2-yl)acetic acid (5K)
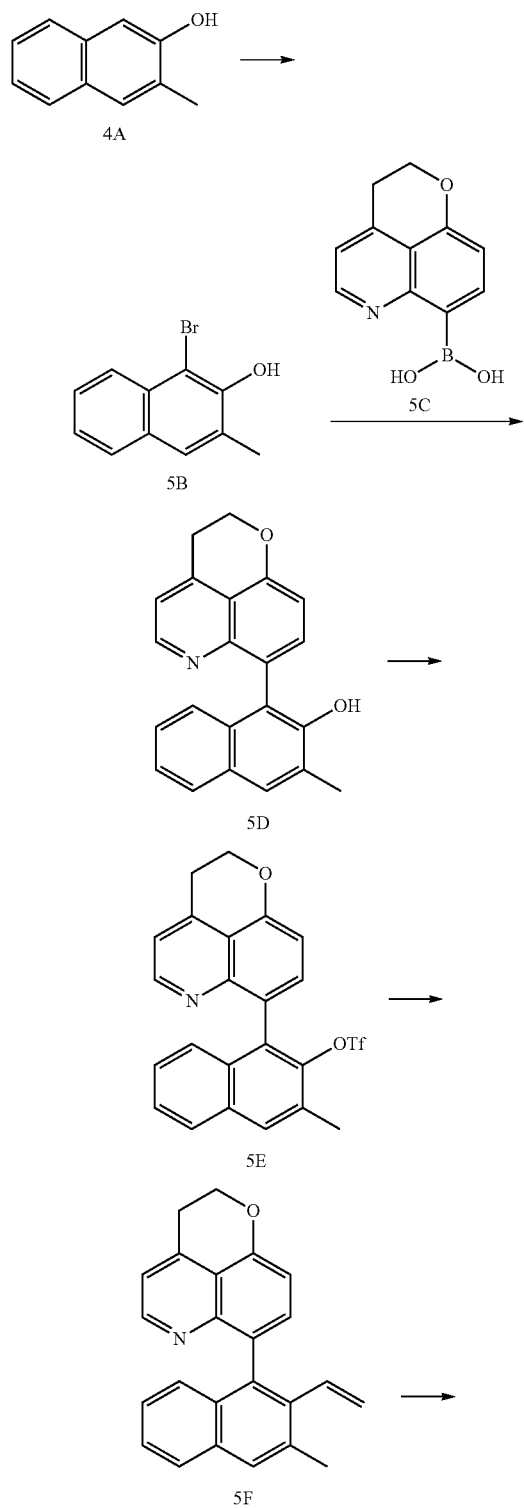
(S)-2-tert-Butoxy-2-((S)-1-(2,3-dihydropyrano[4,3,2-de]quinolin-7-yl)-3-methylnaphthalen-2-yl)acetic acid (5K)

was prepared in a similar manner as compound 3K of Example 1 except that compound 5J was used instead of compound 3J. $^1$H-NMR: 300 MHz, (CD$_3$OD) δ 8.54 (d, 1 H), 8.08 (d, 1 H), 7.86 (m, 2 H), 7.57 (m, 1 H), 7.40 (m, 2 H), 7.20 (m, 1 H), 6.88 (m, 1 H), 5.21 (s, 1H), 4.64 (dd, 2 H), 3.58 (dd, 2 H), 2.66 (s, 3 H), 0.84 (s, 9H). LCMS-ESI$^+$ (m/z): [M+H]$^+$ calcd for C$_{28}$H$_{28}$NO$_4$: 442.2; Found: 442.1.

Preparation of (S)-2-tert-butoxy-2-((S)-1-(2,3-dihydropyrano[4,3,2-de]quinolin-7-yl)-3-methylnaphthalen-2-yl)ethanol (5J)

Preparation of 1-bromo-3-methylnaphthalen-2-ol (5B): 3-Methylnaphthalen-2-ol (4A) (2.09 g, 13.2 mmol) was taken in acetic acid (50 mL) and bromine (2.11 g) was added to it. The mixture was stirred at room temperature for 20 minutes, concentrated and purified by flash chromatography (silica gel, ethyl acetate/hexanes) to give the desired product (2.7 g, 80%). $^1$H-NMR: 300 MHz, (CDCl$_3$) δ 7.98 (d, 1 H), 7.60 (d, 1 H), 7.58 (s, 1 H), 7.53 (dd, 1 H), 7.38 (dd, 1 H), 6.05 (s, 1 H), 2.48 (s, 3 H).

Preparation of 1-(2,3-dihydropyrano[4,3,2-de]quinolin-7-yl)-3-methylnaphthalen-2-ol (5D): 1-Bromo-3-methylnaphthalen-2-ol (5B) (340 mg, 1.43 mmol), 2,3-dihydropyrano[4,3,2-de]quinolin-7-ylboronic acid TFA salt (5C) (566 mg, 1.72 mmol), Pd(PPh$_3$)$_4$ (166 mg, 0.14 mmol) and K$_2$CO$_3$ (991 mg, 7.15 mmol) were added to a degassed solution of DMA (6 mL) and water (2 mL) and heated to 110° C. in a microwave for 1 h. The reaction mixture was cooled, diluted with ethyl acetate and washed with saturated sodium bicarbonate solution, brine and dried (MgSO$_4$), filtered, concentrated and purified by flash column chromatography (silica gel, ethyl acetate/hexanes) to give 5D (136 mg, 29%). LCMS-ESI$^+$ (m/z): [M+H]$^+$ calcd for C$_{22}$H$_{18}$NO$_2$: 328.38. Found: 328.2.

Preparation of 1-(2,3-dihydropyrano[4,3,2-de]quinolin-7-yl)-3-methylnaphthalen-2-yl trifluoromethanesulfonate (5E): 1-(2,3-Dihydropyrano[4,3,2-de]quinolin-7-yl)-3-methylnaphthalen-2-ol (5D) (136 mg, 0.415 mmol) was taken in 2 mL DCM at −78° C. and 2,6-lutidine (72 μL, 0.622 mmol) was added to it, followed by trifluoromethanesulfonic anhydride (210 μL, 1.24 mmol) and the reaction was stirred at −78° C. for 1 h. The reaction was quenched by adding saturated NaCl solution. The reaction was extracted with DCM, washed with brine, and concentrated. The crude product was purified by flash chromatography (silica gel, ethyl acetate/hexanes) to provide the desired product 5E (79 mg, 41%). LCMS-ESI$^+$ (m/z): [M+H]$^+$ calcd for C$_{23}$H$_{17}$F$_3$NO$_4$S: 460.45. Found: 460.0.

Preparation of 7-(3-methyl-2-vinylnaphthalen-1-yl)-2,3-dihydropyrano[4,3,2-de]quinoline (5F): A solution of 1-(2,3-dihydropyrano[4,3,2-de]quinolin-7-yl)-3-methylnaphthalen-2-yltrifluoromethanesulfonate (5E) (89 mg, 0.194 mmol), tributyl(vinyl)tin (0.23 mL, 0/776 mmol), Pd(PPh$_3$)$_4$ (34 mg, 0.029 mmol) and LiCl (16 mg, 0.39 mmol) in dioxane (3 mL) was stirred at 110° C. under Ar for 5 hours. The reaction mixture was cooled, diluted with ethyl acetate and washed with saturated NaHCO$_3$ solution (2×), brine and dried (MgSO$_4$), filtered, concentrated and purified by flash column chromatography (silica gel, hexanes) to give 5F as a white solid (74 mg, 91%). LCMS-ESI$^+$ (m/z): [M+H]$^+$ calcd for C$_{24}$H$_{20}$NO: 338.42. Found: 338.2.

Preparation of (1S)-1-(1-(2,3-dihydropyrano[4,3,2-de]quinolin-7-yl)-3-methylnaphthalen-2-yl)ethane-1,2-diol (5G): Compound 5G was prepared in a similar manner as compound 3G of Example 1, except that compound 5F was used instead of compound 3F: LCMS-ESI$^+$ (m/z): [M+H]$^+$ calcd for C$_{24}$H$_{22}$NO$_3$: 372.44. Found: 372.3.

Preparation of (S)-2-((S)-1-(2,3-dihydropyrano[4,3,2-de]quinolin-7-yl)-3-methylnaphthalen-2-yl)-2-hydroxyethyl pivalate (5H): Compound 5H was prepared in a similar manner as compound 3H of Example 1 except that compound 5G was used instead of compound 3G. The two atropisomers (compounds 5H and 6A) were separated at this stage and carried forward separately. LCMS-ESI$^+$ (m/z): [M+H]calcd for C$_{29}$H$_{30}$NO$_4$: 456.6. Found: 456.1.

Preparation of (S)-2-tert-butoxy-2-((S)-1-(2,3-dihydropyrano[4,3,2-de]quinolin-7-yl)-3-methylnaphthalen-2-yl)ethyl pivalate (5I): Compound 5I was prepared in a similar manner as compound 3I of Example 1 except that compound 5H was used instead of compound 3H. LCMS-ESI$^+$ (m/z): [M+H]$^+$ calcd for C$_{33}$H$_{38}$NO$_4$: 512.7. Found: 512.1.

Preparation of (S)-2-tert-butoxy-2-((S)-1-(2,3-dihydropyrano[4,3,2-de]quinolin-7-yl)-3-methylnaphthalen-2-yl)ethanol (5J): Compound 5J was prepared in a similar manner as compound 3J of Example 1 except that compound 5I was used instead of compound 3I. LCMS-ESI$^+$ (m/z): [M+H]$^+$ calcd for C$_{28}$H$_{30}$NO$_3$: 428.5. Found: 428.0.

EXAMPLE 4

(S)-2-tert-Butoxy-2-((R)-1-(2,3-dihydropyrano[4,3,2-de]quinolin-7-yl)-3-methylnaphthalen-2-yl)acetic acid (6D)

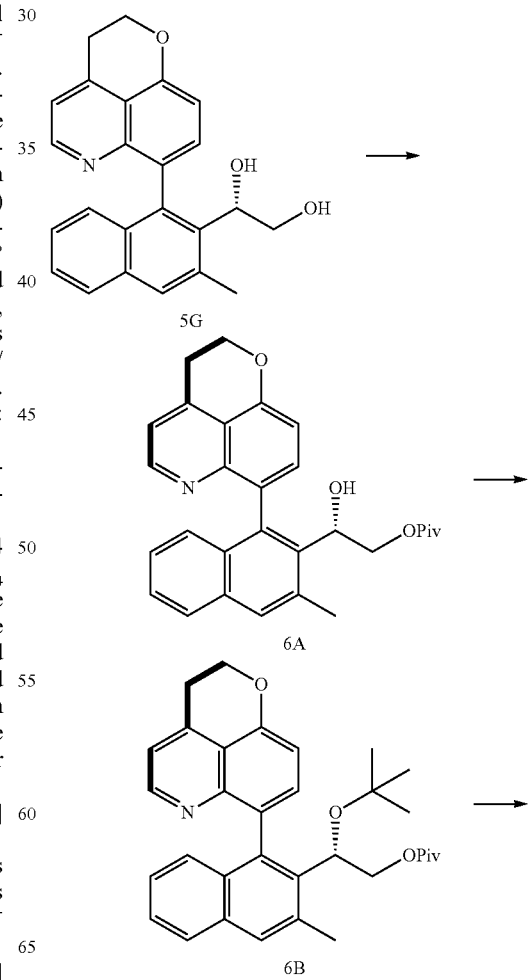

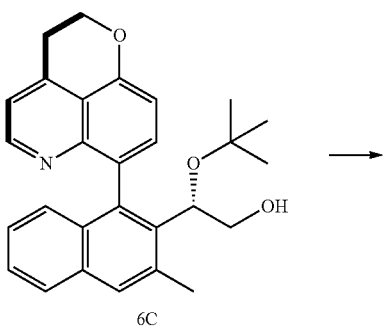

6C

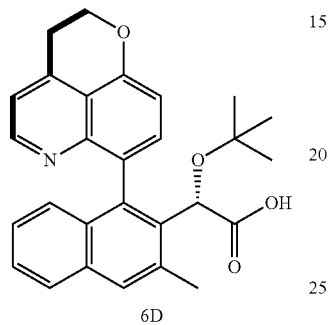

6D (2S)-2-tert-Butoxy-2-((R)-1-(2,3-dihydropyrano[4,3,2-de]quinolin-7-yl)-3-methylnaphthalen-2-yl)acetic acid (6D) was prepared in an analogous manner as used for the preparation of compound 5K of Example 3. $^1$H-NMR: 300 MHz, (CD$_3$OD) δ 8.58 (d, 1 H), 7.83 (m, 2 H), 7.66 (m, 2 H), 7.38 (m, 2 H), 7.17 (m, 1 H), 6.80 (m, 1 H), 5.18 (s, 1H), 4.61 (m, 2 H), 3.56 (dd, 2 H), 2.63 (s, 3 H), 0.84 (s, 9H). LCMS-ESI$^+$ (m/z): [M+H]$^+$ calcd for C$_{28}$H$_{28}$NO$_4$: 442.5. Found: 442.1.

EXAMPLe 5

(R)-2-tert-Butoxy-[3-methyl-1-(5-(trifluoromethyl)quinolin-8-yl)-naphthalen-2-yl]-acetic acid (7D) and (S)-2-tert-butoxy-2-((S)-3-methyl-1-(5-(trifluoromethyl)quinolin-8-yl)naphthalen-2-yl)acetic acid (7E).

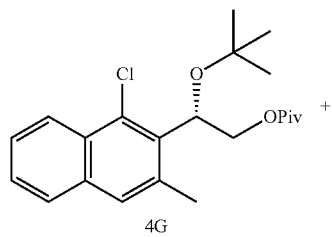

4G

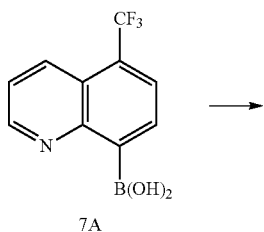

7A

7B

7C

7D

7E (S)-2-tert-butoxy-2-((R)-3-methyl-1-(5-(trifluoromethyl)quinolin-8-yl)naphthalen-2-yl)acetic acid (7D) was prepared in a similar manner as compound 4K of Example 2. $^1$H-NMR: 400 MHz, (CD$_3$OD) δ: 9.02 (d, J=8.8 Hz, 1 H), 8.83 (dd, J=4.8, 1.2 Hz, 1 H), 8.26 (d, J=7.6 Hz, 1 H), 7.99-7.88 (m, 3 H), 7.77 (d, J=7.6 Hz, 1 H), 7.45 (dd, J=8.0, 7.2 Hz, 1 H), 7.20 (dd, J=8.0, 7.2 Hz, 1 H), 6.83 (d, J=8.4 Hz, 1 H), 5.29 (s, 1H), 2.78 (s, 3H), 0.75 (s, 9H); $^{19}$F-NMR: 376 MHz, (CD$_3$OD) δ: −60.81; LCMS-ESI$^+$ (m/z): [M+H]$^+$ calcd for C$_{27}$H$_{25}$F$_3$NO$_3$: 468.5. Found: 468.0.

(S)-2-tert-butoxy-2-((S)-3-methyl-1-(5-(trifluoromethyl)quinolin-8-yl)naphthalen-2-yl)acetic acid (7E) was prepared in a similar manner as compound 4L of Example 2. $^1$H-NMR: 400 MHz, (CD$_3$OD) δ: 8.82 (d, J=8.4 Hz, 1 H), 7.72 (d, J=5.2, 1 H), 8.26 (d, J=7.6 Hz, 1 H), 8.12 (d, J=7.6 Hz, 1 H), 7.89-7.73 (m, 3 H), 7.40 (dd, J=7.6, 7.2 Hz, 1 H), 7.14 (dd, J=7.6, 7.2 Hz, 1 H), 6.76 (d, J=8.4 Hz, 1 H), 5.06 (s, 1H), 2.70

(s, 3H), 0.75 (s, 9H); $^{19}$F-NMR: 376 MHz, (CD$_3$OD) δ: −60.87; LCMS-ESI$^+$ (m/z): [M+H]$^+$ calcd for C$_{27}$H$_{25}$F$_3$NO$_3$: 468.5. Found: 468.0.

EXAMPLE 6

(S)-2-tert-Butoxy-2-(1-cyclohexenyl-3-methylnaphthalen-2-yl)acetic acid (8)

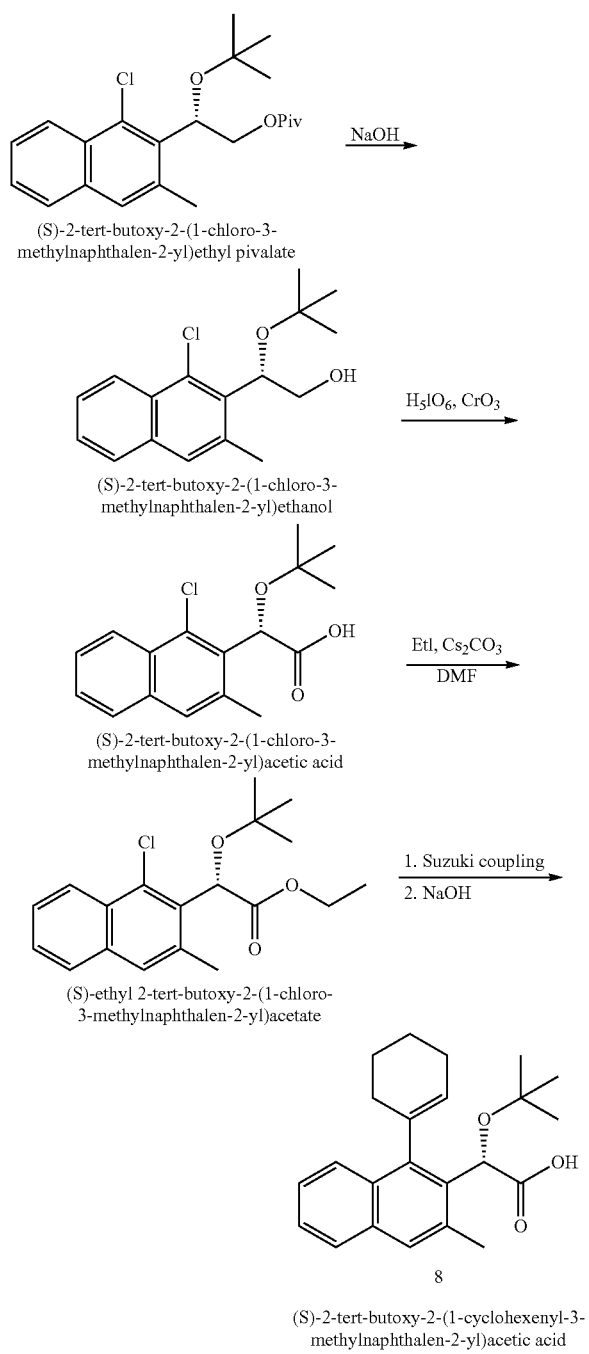

Preparation of (S)-2-tert-butoxy-2-(1-chloro-3-methylnaphthalen-2-yl)ethanol: (S)-2-tert-Butoxy-2-(1-chloro-3-methylnaphthalen-2-yl)ethyl pivalate (4G, 1.72 g, 4.56 mmol) was dissolved in MeOH (10 mL) and THF (10 mL). Sodium hydroxide (2 M, 9.13 mL) was added and the reaction mixture was stirred at room temperature overnight. The reaction mixture was diluted with ethyl acetate and washed with brine. The aqueous layer was back-extracted with ethyl acetate and the combined organics were dried (MgSO$_4$), concentrated in vacuo and purified by flash column chromatography (silica gel, 0 to 10% ethyl acetate/hexanes) to give a colorless liquid (1.12 g, 84%). $^1$H-NMR: 300 MHz, (CD$_3$OD) δ: 8.23 (d, 1H), 7.78 (d, 1H), 7.60 (s, 1H), 7.52 (dd, 2H), 5.69 (m, 1H), 3.83 (dd, 1H), 3.61 (m, 1H), 2.71 (s, 3H), 1.18 (s, 9H).

Preparation of (S)-2-tert-butoxy-2-(1-chloro-3-methylnaphthalen-2-yl)acetic acid: The periodic acid/chromium trioxide stock solution (26 mL) was added to a solution of (S)-2-tert-butoxy-2-(1-chloro-3-methylnaphthalen-2-yl) ethanol (1.12 g, 3.83 mmol) in wet acetonitrile (50 mL) (0.75% H$_2$O) at 0° C. The reaction mixture was stirred for 2 hours at 0° C. and quenched with 1.5 M K$_2$HPO$_4$ solution. Ethyl acetate was added and organic layer separated and washed with 1:1 brine/H$_2$O (2×), then saturated NaHSO$_3$/brine. The organic layer was dried (MgSO$_4$), and concentrated and purified by flash column chromatography (silica gel, 0 to 100% ethyl acetate/hexanes) to give a white solid (0.9 g, 78%). $^1$H-NMR: 300 MHz, (CDCl$_3$) δ: 8.24 (d, 1H), 7.73 (d, 1H), 7.56 (m, 3H), 6.22 (br, 1H), 2.57 (s, 3H), 1.23 (s, 9H). LCMS-ESI$^-$ (m/z): [M−H]$^-$ calcd for C$_{17}$H$_{18}$ClO$_3$: 305.78. Found: 304.9, 306.9.

Preparation of (S)-ethyl 2-tert-butoxy-2-(1-chloro-3-methylnaphthalen-2-yl)acetate: Ethyl iodide (0.35 mL, 1.5 eq.) was added to a mixture of (S)-2-tert-butoxy-2-(1-chloro-3-methylnaphthalen-2-yl)acetic acid (900 mg, 2.93 mmol, 1 eq.) and Cs$_2$CO$_3$ (1.91 g, 2 eq.) in DMF (920 mL) at room temperature. The reaction mixture was stirred for 1 hour at room temperature. Ethyl acetate was added and organic layer separated and washed with brine (2×). The organic layer was dried (MgSO$_4$) and concentrated and purified by flash column chromatography (silica gel, 0 to 100% ethyl acetate/hexanes) to give a colorless oil (0.911 g, 93%). $^1$H-NMR: 300 MHz, (CDCl$_3$) δ: 8.23 (d, 1H), 7.62 (d, 1H), 7.63 (s, 1H), 7.46 (m, 3H), 6.10 (s, 1H), 4.06 (dd, 2H), 2.42 (s, 3H), 1.18 (s, 9H), 1.08 (t, 3H).

Preparation of (S)-2-tert-butoxy-2-(1-cyclohexenyl-3-methylnaphthalen-2-yl)acetic acid (8): A Smith process vial was charged with (S)-ethyl 2-tert-butoxy-2-(1-chloro-3-methylnaphthalen-2-yl)acetate (15 mg, 0.045 mmol, 1 eq.), cyclohexenylboronic acid (9 mg, 1.5 eq.), Sphos precatalyst (5 mg, 15%) and potassium phosphate (29 mg, 3 eq.), THF (0.2 mL) and water (0.2 mL) was added and mixture sparged with nitrogen for 10 minutes and then heated in microwave at 110° C. for 1 hour. The reaction mixture was diluted with ethyl acetate and washed with brine, dried (MgSO$_4$), filtered, concentrated and purified by flash column chromatography (silica gel, 0 to 20% ethyl acetate/hexanes) to give (S)-ethyl 2-tert-butoxy-2-(1-cyclohexenyl-3-methylnaphthalen-2-yl) acetate (8 mg). Analytical HPLC (Gemini, 2-98% ACN/H$_2$O+0.05% TFA, 10 minutes run): t$_R$ (min)=7.06.

A solution of above intermediate (S)-ethyl 2-tert-butoxy-2-(1-cyclohexenyl-3-methylnaphthalen-2-yl)acetate (8 mg, 0.021 mmol, 1 eq.) in ethanol (1.5 mL) and 1 N sodium hydroxide (0.42 mL, 20 eq.) was heated at 60° C. overnight. The reaction mixture was diluted with ethyl acetate and washed with brine. The aqueous layer was back-extracted with ethyl acetate and the combined organic layer was dried (MgSO$_4$), filtered, concentrated and purified by reverse phase HPLC (Gemini, 5 to 100% ACN/H$_2$O+0.1% TFA). Product lyophilized to give 8 as a white powder (4.4 mg). Analytical HPLC (Gemini, 2-98% ACN/H$_2$O+0.05% TFA, 10 minutes run): $t_R$ (min)=6.10. $^1$H-NMR: 400 MHz, (CD$_3$OD) δ: 7.83 (m, 1H), 7.70 (m, 1H), 7.54 (m, 1H), 7.40 (m, 2H), 5.82, 5.62 (s, s, 1H), 2.58 (m, 3H), 2.62-2.16 (m, 4H), 1.92-1.80 (m, 4H), 1.03 (m, 9H). LCMS-ESI$^{31}$ (m/z): [M−H]$^-$ calcd for C$_{23}$H$_{27}$O$_3$: 351.46. Found: 351.1.

EXAMPLE 7

(S)-2-tert-Butoxy-2-(1-((R)-6-fluoroquinolin-8-yl)-3-methylnaphthalen-2-yl)acetic acid (9)

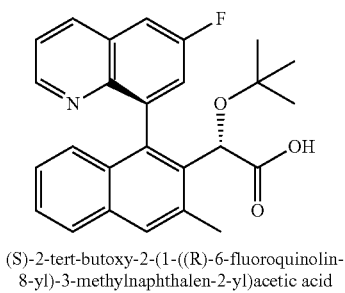

(S)-2-tert-butoxy-2-(1-((R)-6-fluoroquinolin-8-yl)-3-methylnaphthalen-2-yl)acetic acid Preparation of (S)-2-tert-butoxy-2-(1-((R)-6-fluoroquinolin-8-yl)-3-methylnaphthalen-2-yl)acetic acid (9): (S)-2-tert-butoxy-2-(1-((R)-6-fluoroquinolin-8-yl)-3-methylnaphthalen-2-yl)acetic acid (9) was prepared following the procedure to make (S)-2-tert-butoxy-2-(1-cyclohexenyl-3-methylnaphthalen-2-yl)acetic acid of Example 6 except that 6-fluoroquinolin-8-ylboronic acid was used instead of cyclohexenylboronic acid. Atropisomers were separated by flash column chromatography. $^1$H-NMR: 400 MHz, (CD$_3$OD) δ: 8.81 (d, J=8.2 Hz, 1H), 8.62 (dd, J=4.7 Hz, 1H), 8.02 (m, 1H), 7.96 (m, 1H), 7.82 (m, 2H), 7.76 (m, 1H), 7.42 (dd, J=7.5 Hz, 1H), 7.20 (dd, J=7.8 Hz, 1H), 6.84 (d, J=8.6 Hz, 1H), 5.18 (s, 1H), 2.72 (s, 3H), 0.82 (s, 9H). $^{19}$F-NMR: 377 MHz, (CD$_3$OD) δ: −77.9, −113.1. LCMS-ESI$^+$ (m/z): [M+H]$^+$ calcd for C$_{26}$H$_{25}$FNO$_3$: 418.48. found: 418.11.

EXAMPLE 8

(2S)-2-tert-Butoxy-2-(1-(5-fluoroquinolin-8-yl)-3-methylnaphthalen-2-yl)acetic acid (10)

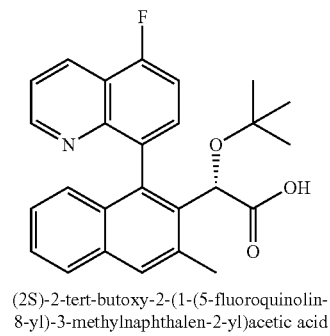

(2S)-2-tert-butoxy-2-(1-(5-fluoroquinolin-8-yl)-3-methylnaphthalen-2-yl)acetic acid Preparation of (2S)-2-tert-butoxy-2-(1-(5-fluoroquinolin-8-yl)-3-methylnaphthalen-2-yl)acetic acid (10): (2S)-2-tert-Butoxy-2-(1-(5-fluoroquinolin-8-yl)-3-methylnaphthalen-2-yl)acetic acid (10) was prepared following the procedure to make (S)-2-tert-butoxy-2-(1-cyclohexenyl-3-methylnaphthalen-2-yl)acetic acid of Example 6 except 5-fluoroquinolin-8-ylboronic acid was used instead of cyclohexenylboronic acid. $^1$H-NMR: 400 MHz, (CD$_3$OD) δ: 8.81 (d, J=8.2 Hz, 1H), 8.70 (dd, J=3.3 Hz, J=4.7 Hz, 1H), 8.09 (t, J=6.2 Hz, 1H), 7.92 (m, 2H), 7.78 (m, 1H), 7.63 (t, J=9.0 Hz, 1H), 7.42 (t, J=7.0 Hz, 1H), 7.18 (t, J=7.8 Hz, 1H), 6.84 (d, J=7.6 Hz, 1H), 5.18 (s, 1H), 2.68 (s, 3H), 0.80 (s, 9H). $^{19}$F-NMR: 377 MHz, (CD$_3$OD) δ: −77.9, −123.2. LCMS-ESI$^+$ (m/z): [M+H]$^+$ calcd for C$_{26}$H$_{25}$FNO$_3$: 418.47. found: 418.1.

EXAMPLE 9

(S)-2-tert-Butoxy-2-(1-(3,3-dimethyl-6-oxocyclohex-1-enyl)-3-methylnaphthalen-2-yl)acetic acid (11)

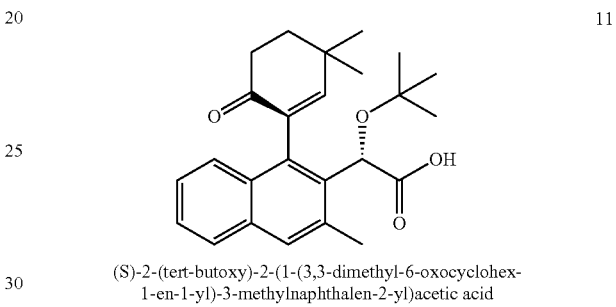

(S)-2-(tert-butoxy)-2-(1-(3,3-dimethyl-6-oxocyclohex-1-en-1-yl)-3-methylnaphthalen-2-yl)acetic acid Preparation of (S)-2-tert-butoxy-2-(1-(3,3-dimethyl-6-oxocyclohex-1-enyl)-3-methylnaphthalen-2-yl)acetic acid (11): (S)-2-tert-Butoxy-2-(1-(3,3-dimethyl-6-oxocyclohex-1-enyl)-3-methylnaphthalen-2-yl)acetic acid (11) was prepared following the procedure to make (S)-2-tert-butoxy-2-(1-cyclohexenyl-3-methylnaphthalen-2-yl)acetic acid of Example 6 except that 4,4-dimethyl-2-(4,4,5,5-tetramethyl-1,3,2-dioxaborolan-2-yl)cyclohex-2-enone was used instead of cyclohexenylboronic acid. Atropisomers were separated by flash column chromatography. $^1$H-NMR: 400 MHz, (CD$_3$OD) δ: 7.72 (d, J=8.2 Hz, 1H), 7.59 (s,1H), 7.39 (m, 2H), 7.37 (m, 1H), 7.02 (s, 1H), 5.42 (s,1H), 2.82 (m, 1H), 2.67 (m, 1H), 2.58 (s, 3H), 2.18 (m, 2H), 1.38 (s, 6H), 1.08 (s, 9H). LCMS-ESI$^+$ (m/z): [M−H]$^-$ calcd for C$_{25}$H$_{29}$O$_4$: 393.50. found: 393.0.

EXAMPLE 10

(S)-2-tert-Butoxy-2-(1-cyclopentenyl-3-methylnaphthalen-2-yl)acetic acid (12)

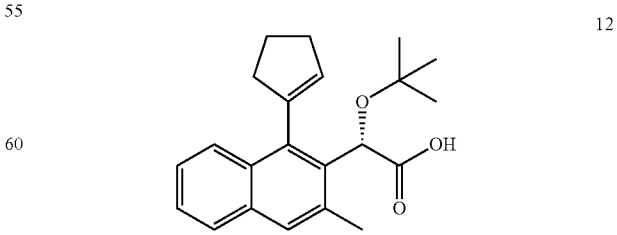

(S)-2-tert-butoxy-2-(1-cyclopentenyl-3-methylnaphthalen-2-yl)acetic acid

Preparation of (S)-2-tert-butoxy-2-(1-cyclopentenyl-3-methylnaphthalen-2-yl)acetic acid (12): (S)-2-tert-Butoxy-2-(1-cyclopentenyl-3-methylnaphthalen-2-yl)acetic acid (12) was prepared following the procedure to make (S)-2-tert-butoxy-2-(1-cyclohexenyl-3-methylnaphthalen-2-yl)acetic acid of Example 6, except that cyclopentenylboronic acid was used instead of cyclohexenylboronic acid. $^1$H-NMR: 400 MHz, (CD$_3$OD) δ: 7.78 (m, 1H), 7.53 (s,1H), 7.40 (m, 2H), 6.10-5.54 (m, 3H), 2.90 (m,1H), 2.65 (m, 5H), 2.57 (s, 3H), 1.18 (s, 9H). LCMS-ESI⁻ (m/z): [M−H]-calcd for C$_{22}$H$_{25}$O$_3$: 337.44. found: 337.1.

EXAMPLE 11

(2S)-2-tert-Butoxy-2-(3-methyl-1-(4-methylcyclohex-1-enyl)naphthalen-2-yl)acetic acid (13)

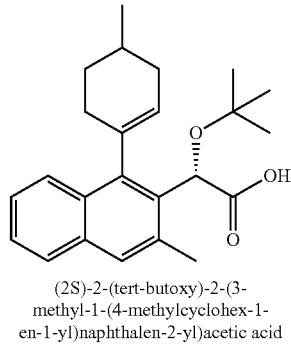

(2S)-2-(tert-butoxy)-2-(3-methyl-1-(4-methylcyclohex-1-en-1-yl)naphthalen-2-yl)acetic acid Preparation of (2S)-2-tert-butoxy-2-(3-methyl-1-(4-methylcyclohex-1-enyl)naphthalen-2-yl)acetic acid (13): (2S)-2-tert-Butoxy-2-(3-methyl-1-(4-methylcyclohex-1-enyl)naphthalen-2-yl)acetic acid was prepared following the procedure to make (S)-2-tert-butoxy-2-(1-cyclohexenyl-3-methylnaphthalen-2-yl)acetic acid of Example 6, except that 4-methylcyclohex-1-enylboronic acid was used instead of cyclohexenylboronic acid. $^1$H-NMR: 400 MHz, (CD$_3$OD) δ: 7.92-7.78 (m, 1H), 7.70 (m,1H), 7.52 (s, 1H), 7.39 (m, 2H), 6.10-5.58 (m, 2H), 2.56 (s,3H), 2.65-1.84 (m, 6H), 1.50 (m, 1H), 1.22 (s, 9H), 1.14 (t, 3H). LCMS-ESI⁻ (m/z): [M−H]⁻ calcd for C$_{24}$H$_{29}$O$_3$: 365.49. found: 365.1.

EXAMPLE 12

(S)-2-tert-Butoxy-2-(1-(4,4-dimethylcyclohex-1-enyl)-3-methylnaphthalen-2-yl)acetic acid (14)

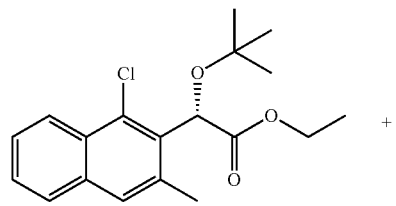

(S)-ethyl 2-(tert-butoxy)-2-(1-chloro-3-methylnaphthalen-2-yl)acetate

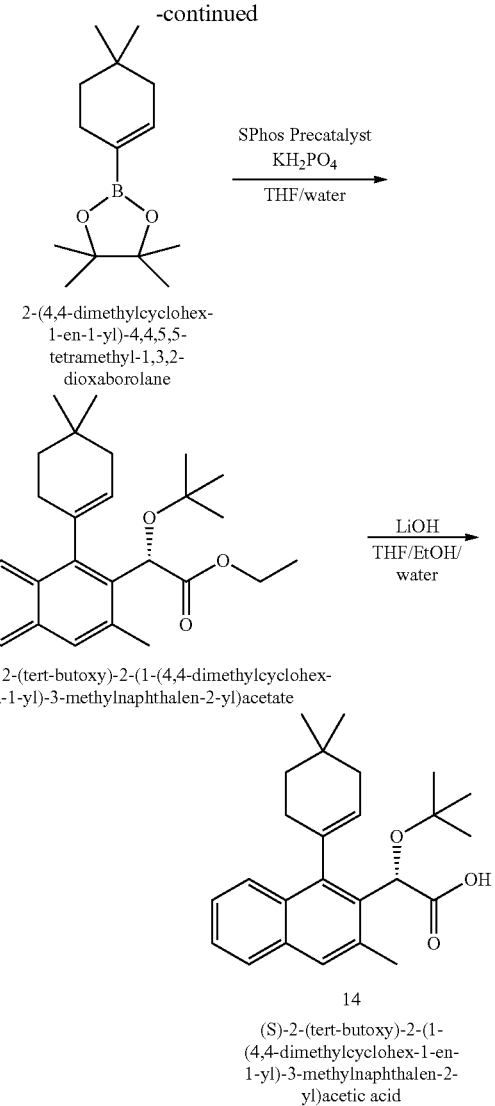

Preparation of (S)-ethyl 2-tert-butoxy-2-(1-(4,4-dimethylcyclohex-1-enyl)-3-methylnaphthalen-2-yl)acetate: To a solution of (S)-ethyl 2-tert-butoxy-2-(1-chloro-3-methylnaphthalen-2-yl)acetate (74 mg, 0.22 mmol) and 2-(4,4-dimethylcyclohex-1-enyl)-4,4,5,5-tetramethyl-1,3,2-dioxaborolane (78 mg, 0.33 mmol) in tetrahydrofuran (2 mL) was added potassium phosphate (153 mg, 0.66 mmol) and (2-dicyclohexyl-phosphino-2',6'-dimethoxy-1,1'-biphenyl)[2-(2-aminoethylphenyl)]palladium(II) chloride methyl-t-butyl ether adduct, (SPhos) palladium(II) phenethylamine chloride (15 mg, 0.022 mmol) and the reaction was degassed 10 minutes with argon. The reaction was heated to 110° C. for 1 hour in a microwave reactor. The crude reaction was absorbed onto silica and purified by flash column chromatography (silica gel, ethyl acetate/hexanes) to give a clear white oil (36 mg). $^1$H-NMR: 400 MHz, (CDCl$_3$) δ: 7.83-7.78 (m, 1H), 7.70 (d, J=7.6 Hz, 1H), 7.53 (s, 1H), 7.43-7.36 (m, 2H), 5.66-5.61 (m, 2H), 4.20-4.03 (m, 2H), 2.66-2.60 (m, 2H), 2.26-2.03 (m, 4H), 1.87-1.59 (m, 5H), 1.24-1.20 (m, 9H), 1.19-1.11 (m, 6H).

Preparation of (S)-2-tert-butoxy-2-(1-(4,4-dimethylcyclohex-1-enyl)-3-methylnaphthalen-2-yl)acetic acid (14): To a solution of (S)-ethyl 2-tert-butoxy-2-(1-(4,4-dimethylcyclohex-1-enyl)-3-methylnaphthalen-2-yl)acetate (36 mg, 0.087 mmol) in tetrahydrofuran:ethanol:water (2:2:1, 5 mL) was added lithium hydroxide (21 mg, 0.88 mmol) and the reaction was heated to 35° C. overnight. The reaction was then heated to 45° C. for 2 hours, and subsequently 5 equivalents of lithium hydroxide was added, and the reaction stirred at room temperature over 2 days. The reaction was then heated to 50° C. overnight. The crude reaction was purified by reverse phase HPLC (Gemini, 20-100% ACN/H$_2$O+0.1% TFA). Product was lyophilized to give a white powder (8.6 mg). $^1$H-NMR: 400 MHz, (CD$_3$OD) δ: 7.82 (d, J=8.0 Hz, 1H), 7.71 (d, J=7.6 Hz, 1H), 7.54 (s, 1H), 7.39 (m, 2H), 5.66 (m, 2H), 2.66 (m, 1H), 2.58 (s, 3H), 2.13 (m, 3H), 1.64 (m, 2H), 1.23 (s, 9H), 1.16 (s, 3H), 1.14 (s, 3H). LCMS-ESI$^-$ (m/z): [M−H]$^-$ calcd for C$_{25}$H$_{31}$O$_3$: 379.24. found: 379.27.

EXAMPLE 13

(S)-2-tert-Butoxy-2-(3-methyl-1-(spiro[2.5]oct-5-en-6-yl)naphthalen-2-yl)acetic acid (15)

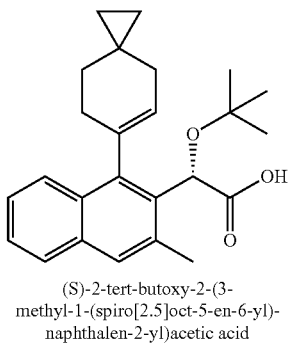

(S)-2-tert-butoxy-2-(3-methyl-1-(spiro[2.5]oct-5-en-6-yl)-naphthalen-2-yl)acetic acid Preparation of (S)-2-tert-butoxy-2-(3-methyl-1-(spiro [2.5]oct-5-en-6-yl)naphthalen-2-yl)acetic acid (15): (S)-2-tert-butoxy-2-(3-methyl-1-(spiro[2.5]oct-5-en-6-yl)naphthalen-2-yl)acetic acid was prepared following the procedure for (S)-2-tert-butoxy-2-(1-(4,4-dimethylcyclohex-1-enyl)-3-methylnaphthalen-2-yl)acetic acid of Example 12 except using 4,4,5,5-tetramethyl-2-(spiro[2.5]oct-5-en-6-yl)-1,3,2-dioxaborolane instead of 2-(4,4-dimethylcyclohex-1-enyl)-4,4,5,5-tetramethyl-1,3,2-dioxaborolane and that in the final step the reaction was heated to 50° C. overnight followed by an addition of 10 equivalents of lithium hydroxide and heating to 60° C. for four hours and then at 45° C. overnight. $^1$H-NMR: 400 MHz, (CD$_3$OD) δ: 7.90 (d, J=7.6 Hz, 1H), 7.71 (br d, J=7.2 Hz, 1H), 7.53 (d, J=8.0 Hz, 1H), 7.40 (m, 2H), 5.88 (s, 1H), 5.70 (s, 1H), 2.73 (m, 1H), 2.78 (s, 3H), 2.31 (m, 2H), 2.09 (m, 1H), 1.73 (m, 1H), 1.59 (m, 1H), 1.24 (s, 9H), 0.49 (m, 4H). LCMS-ESI$^-$ (m/z): [M−H]$^{-calcd\ for\ C}$$_{25}$H$_{29}$O$_3$: 377.22. found: 377.34.

EXAMPLE 14

(S)-2-tert-Butoxy-2-(3-methyl-1-(quinolin-3-yl) naphthalen-2-yl)acetic acid (16)

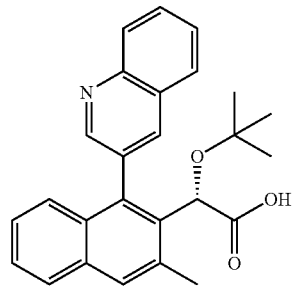

(S)-2-(tert-butoxy)-2-(3-methyl-1-(quinolin-3-yl)naphthalen-2-yl)acetic acid

Preparation of (S)-2-tert-butoxy-2-(3-methyl-1-(quinolin-3-yl)naphthalen-2-yl)acetic acid (16): (S)-2-tert-Butoxy-2-(3-methyl-1-(quinolin-3-yl)naphthalen-2-yl)acetic acid (16) was prepared following the procedure to make (S)-2-tert-butoxy-2-(1-cyclohexenyl-3-methylnaphthalen-2-yl)acetic acid of Example 6, using quinolin-3-ylboronic acid instead of cyclohexenylboronic acid. The compound is an atropisomer mixture. $^1$H-NMR: 400 MHz, (CD$_3$OD) δ: 9.20-8.50 (m, 2H), 8.18 (m, 1H), 8.08 (m, 1H), 7.95 (m, 1H), 7.80 (m, 3H), 7.40 (t. 1H), 7.25 (t, 1H), 7.06 (m, 1H), 5.19 (s, 1H), 2.62 (d, 3H), 0.95, 0.86 (s, 9H). LCMS-ESI$^+$ (m/z): [M+H]$^+$ calcd for C$_{26}$H$_{26}$NO$_3$: 400.48. found: 400.2.

EXAMPLE 15

(S)-2-(tert-Butoxy)-2-((S)-1-(7-fluoro-2-methylquinolin-8-yl)-3-methylnaphthalen-2-yl)acetic acid (17)

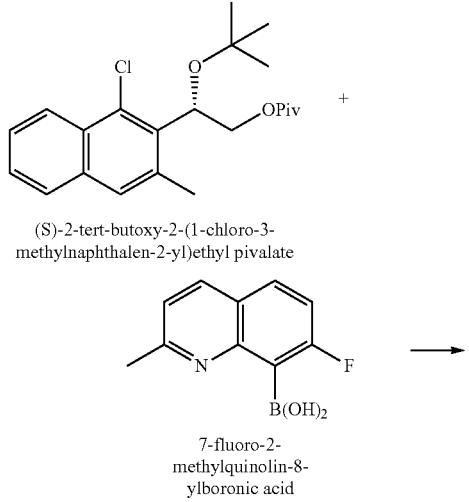

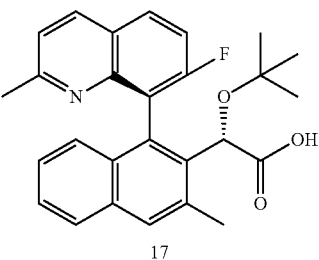

17

(S)-2-(tert-butoxy)-2-((S)-1-(7-fluoro-2-methylquinolin-8-yl)-3-methylnaphthalen-2-yl)acetic acid Preparation of (S)-2-(tert-butoxy)-2-((S)-1-(7-fluoro-2-methylquinolin-8-yl)-3-methylnaphthalen-2-yl)acetic acid (17): (S)-2-(tert-butoxy)-2-((S)-1-(7-fluoro-2-methylquinolin-8-yl)-3-methylnaphthalen-2-yl)acetic acid (17) was prepared following the procedure used to prepare compound 4K except that 7-fluoro-2-methylquinolin-8-ylboronic acid was used instead of compound 4H. $^1$H NMR (400 MHz, CD$_3$OD) δ 9.09 (d, J=8.5 Hz, 1H), 8.51 (dd, J=9.1, 5.6 Hz, 1H), 8.01 (s, 1H), 7.95 (d, J=8.1 Hz, 1H), 7.92-7.76 (m, 2H), 7.58-7.43 (m, 1H), 7.30 (ddd, J=8.2, 6.9, 1.2 Hz, 1H), 6.97 (d, J=8.6 Hz, 1H), 5.17 (s, 1H), 2.80 (s, 3H), 2.79 (s, 3H), 0.87 (s, 9H). LCMS-ESI$^+$ (m/z): [M+H]$^+$ calcd for C$_{27}$H$_{27}$FNO$_3$: 432.5. found: 432.1.

EXAMPLE 16

(S)-Ethyl 2-tert-butoxy-2-((R)-1-(2,3-dihydropyrano[4,3,2-de]quinolin-7-yl)-3-methylnaphthalen-2-yl)acetate (18)

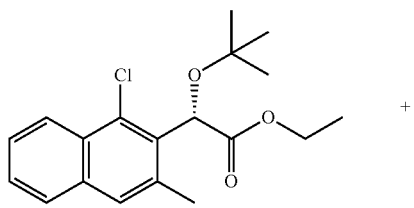

(S)-ethyl 2-(tert-butoxy)-2-(1-chloro-3-methylnaphthalen-2-yl)acetate

+

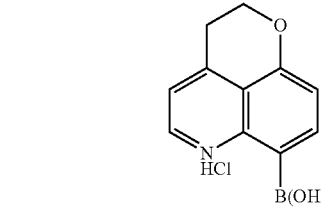

2,3-dihydropyrano[4,3,2-de]quinolin-7-ylboronic acid, HCl salt

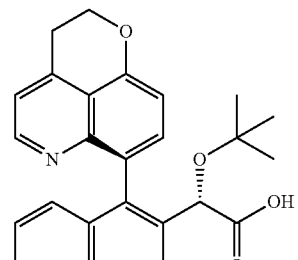

18

(S)-ethyl 2-(tert-butoxy)-2-((R)-1-(2,3-dihydropyrano[4,3,2-de]quinolin-7-yl)-3-methylnaphthalen-2-yl)acetate Preparation of (S)-ethyl 2-tert-butoxy-2-((R)-1-(2,3-dihydropyrano[4,3,2-de]quinolin-7-yl)-3-methylnaphthalen-2-yl)acetate (18): A Smith process vial was charged with (S)-ethyl 2-tert-butoxy-2-(1-chloro-3-methylnaphthalen-2-yl)acetate (compound of Example 6) (116 mg, 0.348 mmol), 2,3-dihydropyrano[4,3,2-de]quinolin-7-ylboronic acid, HCl salt (96 mg, 0.383 mmol), Sphos precatalyst (35 mg, 0.0522 mmol), cesium fluoride (233 mg, 1.54 mmol) and flushed with nitrogen. Dimethoxyethane (3.0 mL, distilled from Na/benzophenone) was added and mixture was heated in microwave at 120° C. for 1.5 hour. The reaction mixture was diluted with ethyl acetate and washed with brine. The aqueous layer was back-extracted and combined organic layer dried (MgSO$_4$), filtered, concentrated and purified by reverse phase HPLC (Gemini, 5 to 100% acetonitrile/H$_2$O+0.1% TFA) to give a yellow powder (16.8 mg). $^1$H-NMR: 400 MHz, (CD$_3$Cl) δ: 8.93 (d, J=4.4 Hz, 1H), 8.06 (d, J=8.0 Hz, 1H), 7.82 (s, 1H), 7.81 (d, J=8.8 Hz, 1H), 7.45-7.35 (m, 3H), 7.13 (dd, J=7.2, 7.2 Hz, 1H), 6.73 (d, J=8.8 Hz, 1H), 5.16 (s, 1H), 4.68-4.65 (m, 2H), 3.98-3.86 (m, 2H), 3.52 (q, J=5.6 Hz, 2H), 2.69 (s, 3H), 1.34 (t, J=7.2 Hz, 3H), 0.86 (s, 9H). LCMS-ESI$^+$ (m/z): [M+H]$^+$ calcd for C$_{30}$H$_{32}$NO$_4$: 470.5. found: 470.1.

EXAMPLE 17

(S)-2-(1-(3-(Azetidin-1-yl)phenyl)-3-methylnaphthalen-2-yl)-2-tert-butoxyacetic acid (19)

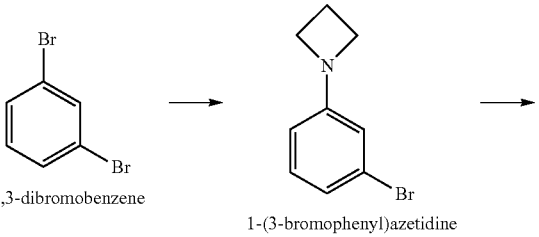

1,3-dibromobenzene     1-(3-bromophenyl)azetidine

-continued

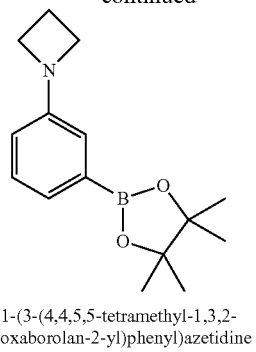

1-(3-(4,4,5,5-tetramethyl-1,3,2-
dioxaborolan-2-yl)phenyl)azetidine

+

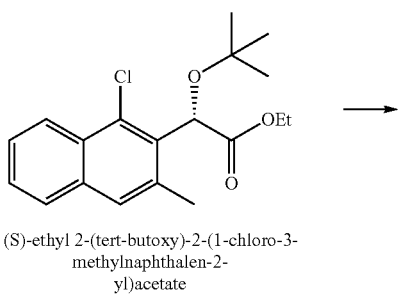

(S)-ethyl 2-(tert-butoxy)-2-(1-chloro-3-
methylnaphthalen-2-
yl)acetate

→

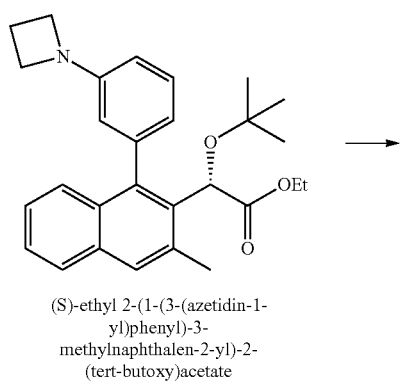

(S)-ethyl 2-(1-(3-(azetidin-1-
yl)phenyl)-3-
methylnaphthalen-2-yl)-2-
(tert-butoxy)acetate

→

19

(S)-2-(1-(3-(azetidin-1-yl)phenyl)-3-
methylnaphthalen-2-yl)-2-
(tert-butoxy)acetic acid Preparation of 1-(3-bromophenyl)azetidine: A mixture of 1,3-bromobenzene (1.0 g, 4.24 mmol), azetidine (0.19 mL, 2.83 mmol), Pd$_2$(dba)$_3$ (0.129 g, 0.142 mmol), Xantphos (0.164 g, 0.283 mmol), and sodium tert-butoxide (0.816 g, 8.49 mmol) in dioxane (20 mL) was sparged with nitrogen for 15 minutes. The reaction mixture was heated at 100° C. for 3 hours and then cooled to room temperature. The resulting mixture was diluted with water and ethyl acetate and washed with water (2×), brine, dried (MgSO$_4$), filtered, concentrated and purified by flash column chromatography (silica gel, 0 to 20% ethyl acetate/hexanes) to give a yellow oil (0.4474 g). LCMS-ESI$^+$ (m/z): [M+H]$^+$ calcd for C$_9$H$_{11}$BrN: 213.1. found: 212.0, 214.0.

Preparation of 1-(3-(4,4,5,5-tetramethyl-1,3,2-dioxaborolan-2-yl)phenyl)azetidine: A mixture of 1-(3-bromophenyl)azetidine (0.4474 g, 2.11 mmol), bis-pinacolatodiboron (0.803 g, 3.16 mmol), Pd(dppf)Cl$_2$ (0.172 g, 0.211 mmol), and potassium acetate (0.621 g, 6.33 mmol) in dioxane (21 mL) was sparged with nitrogen for 30 minutes. The reaction mixture was heated at 90° C. for 1.5 hours. The reaction was cooled to room temperature, diluted with ethyl acetate and washed with brine, dried (MgSO$_4$), filtered, concentrated and purified by flash column chromatography (silica gel, 0 to 20% ethyl acetate/hexanes) to give a yellow wax (0.6474 g). LCMS-ESI$^+$ (m/z): [M+H]$^+$ calcd for C$_{15}$H$_{23}$BNO$_2$: 260.2. found: 260.1.

Preparation of (S)-ethyl 2-(1-(3-(azetidin-1-yl)phenyl)-3-methylnaphthalen-2-yl)-2-tert-butoxyacetate: A Smith process vial was charged with (S)-ethyl 2-tert-butoxy-2-(1-chloro-3-methylnaphthalen-2-yl)acetate (60.5 mg, 0.181 mmol), 1-(3-(4,4,5,5-tetramethyl-1,3,2-dioxaborolan-2-yl)phenyl)azetidine (93.7 mg, 0.361 mmol), chloro(2-dicyclohexylphosphino-2',6'-dimethoxy-1,1'-biphenyl)[2-(2-aminoethylphenyl)]Pd(II)methyl-t-butyl ether adduct (12.2 mg, 0.0181 mmol) and potassium phosphate (153 mg, 0.543 mmol), THF (2 mL) and water (1 mL) was added and mixture sparged with nitrogen for 10 minutes and then heated in microwave at 110° C. for 1 hour. The reaction mixture was diluted with ethyl acetate and washed with brine, dried (MgSO$_4$), filtered, concentrated and purified by flash column chromatography (silica gel, ethyl acetate/hexanes) to the desired product containing some impurities that was used in the next step without further purification.

Preparation of (S)-2-(1-(3-(azetidin-1-yl)phenyl)-3-methylnaphthalen-2-yl)-2-tert-butoxyacetic acid (19): The above residue containing (S)-ethyl 2-(1-(3-(azetidin-1-yl)phenyl)-3-methylnaphthalen-2-yl)-2-tert-butoxyacetate in THF (1.0 mL), MeOH (0.1 mL) and 5 M NaOH (0.1 mL) was heated at 45° C. for 18 hours. The reaction mixture was concentrated, diluted with ethyl acetate and water and washed with saturated ammonium chloride solution. The aqueous layer was back-extracted with ethyl acetate and the combined organic layer was dried (MgSO$_4$), filtered, concentrated and purified by reverse phase HPLC (Gemini, 5 to 100% ACN/H$_2$O+0.1% TFA). The product was lyophilized to give a white powder (4.6 mg) which was resubjected to reverse phase HPLC (Gemini, 5 to 100% ACN/H$_2$O+0.1% TFA). Product containing fractions were stirred with saturated sodium bicarbonate solution for 30 minutes. The mixture was extracted with ethyl acetate (3×), dried (MgSO$_4$), filtered and lyophilized from acetonitrile/water to give an atropisomer mixture as a white powder (1.9 mg). $^1$H NMR (400 MHz, CD$_3$OD) δ 7.81-7.67 (m, 1H), 7.62 (s, 0.6H), 7.60 (s, 0.4H), 7.4-7.18 (m, 4H), 6.78 (s, 0.5H), 6.70 (d, J=7.7 Hz, 0.5H), 6.64-6.57 (m, 1H), 5.32 (s, 0.6H), 5.30 (s, 0.4H), 3.90-3.83 (m, 3H), 2.60 (s, 3H), 2.40-2.35 (m, 2H), 0.99 (s, 4H), 0.97 (s, 5H). LCMS-ESI$^+$ (m/z): [M+H]$^+$ calcd for C$_{26}$H$_{30}$NO$_3$: 404.5. found: 404.1.

EXAMPLE 18

(2S)-2-tert-Butoxy-2-(1-((7R)-2,3,3a,4,5,6-hexahydropyrano[4,3,2de]quinolin-7-yl)-3-methylnaphthalen-2-yl)acetic acid (20)

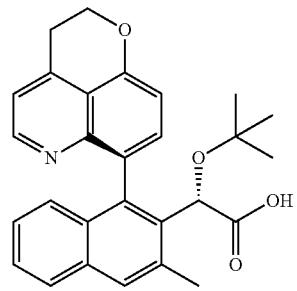

(S)-2-(tert-butoxy)-2-(1-((R)-2,3-dihydropyrano[4,3,2-de]quinolin-7-yl)-3-methylnaphthalen-2yl)acetic acid Pt/C, H₂ →

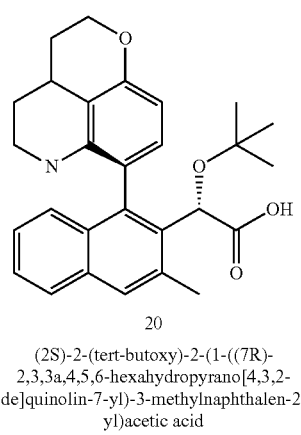

20

(2S)-2-(tert-butoxy)-2-(1-((7R)-2,3,3a,4,5,6-hexahydropyrano[4,3,2-de]quinolin-7-yl)-3-methylnaphthalen-2-yl)acetic acid Preparation of (2S)-2-tert-butoxy-2-(1-((7R)-2,3,3a,4,5,6-hexahydropyrano[4,3,2-de]quinolin-7-yl)-3-methylnaphthalen-2-yl)acetic acid (20): (S)-2-tert-Butoxy-2-(1-((R)-2,3-dihydropyrano[4,3,2-de]quinolin-7-yl)-3-methylnaphthalen-2-yl)acetic acid (130 mg) was dissolved in 20 mL EtOH and 1 drop of HOAc was added to the solution. 10% Pt/C (30 mg) was added the reaction was stirred at room temperature under one atmosphere of hydrogen (balloon) overnight. The reaction mixture was filtered, diluted with ethyl acetate and washed with brine, dried (MgSO₄), filtered, concentrated and purified by flash column chromatography (silica gel, 0 to 20% MeOH/DCM) to give (2S)-2-tert-butoxy-2-(1-((7R)-2,3,3a, 4,5,6-hexahydropyrano[4,3,2-de]quinolin-7-yl)-3-methylnaphthalen-2-yl)acetic acid (130 mg). 8 mg of the material was purified by reverse phase HPLC (Gemini, 5 to 100% ACN/H₂O+0.1% TFA). Product lyophilized to give a white powder (5.5 mg). ¹H-NMR: 400 MHz, (CD₃OD) δ: 7.78 (d, J=8.2 Hz, 1H), 7.63 (s, 1H), 7.40 (m, 2H), 7.27 (m, 1H), 6.70 (d, J=8.21 Hz, 1H), 6.22 (d, J=8.21 Hz, 1H), 5.26 (s, 1H), 4.41 (m, 1H), 4.22 (m, 1H), 3.18 (m, 2H), 2.83 (m, 1H), 2.59 (s, 3H), 2.12 (m, 1H), 1.98 (m, 1H), 1.70 (m, 1H), 1.32 (m, 1H), 1.05 (s, 9H). LCMS-ESI⁺ (m/z): [M+H]⁺ calcd for C₂₈H₃₂NO₄: 446.55. found: 446.1.

EXAMPLE 19

(2S)-Methyl 2-tert-butoxy-2-(1-((7R)-2,3,3a,4,5,6

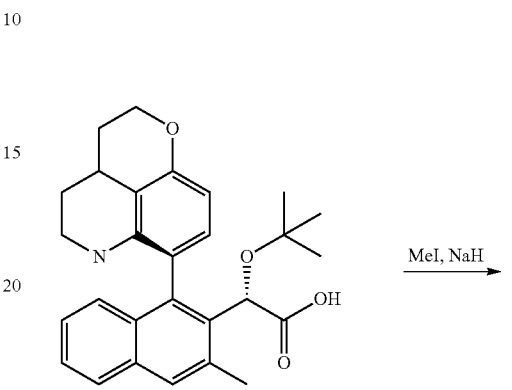

(2S)-2-tert-butoxy-2-(1-((7R)-2,3,3a,4,5,6-hexahydropyrano[4,3,2-de]quinolin-7-yl)-3-methylnaphthalen-2-yl)acetic acid MeI, NaH →

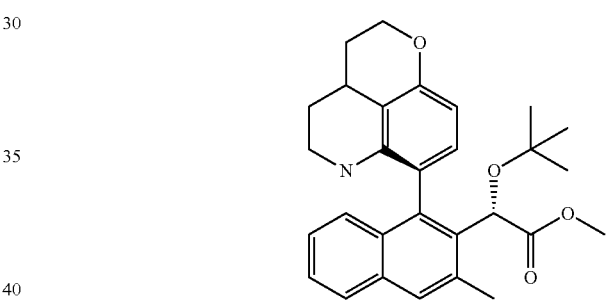

21

(2S)-methyl 2-(tert-butoxy)-2-(1-((7R)-2,3,3a,4,5,6-hexahydropyrano[4,3,2-de]quinolin-7-yl)-3-methylnaphthalen-2-yl)acetate Preparation of (2S)-methyl 2-tert-butoxy-2-(1-((7R)-2,3, 3a,4,5,6-hexahydropyrano[4,3,2-de]quinolin-7-yl)-3-methylnaphthalen-2-yl)acetate (21): At 0° C., NaH (60%, 5 mg) was added to (2S)-2-tert-butoxy-2-(1-((7R)-2,3,3a,4,5,6-hexahydropyrano[4,3,2-de]quinolin-7-yl)-3-methylnaphthalen-2-yl)acetic acid (26 mg, 0.06 mmol, 1 eq.) in 1.5 mL DMF at 0° C. After stirring for 30 minutes, MeI (50 μL, excess) was added to the solution. The reaction was stirred at 0° C. for 1 h. The reaction mixture was concentrated in vacuo and purified by reverse phase HPLC (Gemini, 5 to 100% ACN/H₂O+0.1% TFA). The product was lyophilized to give (2S)-methyl 2-tert-butoxy-2-(1-((7R)-2,3,3a,4,5,6-hexahydropyrano[4,3, 2-de]quinolin-7-yl)-3-methylnaphthalen-2-yl)acetate as white powder (11 mg). ¹H-NMR: 400 MHz, (CD₃OD) δ: 7.78 (d, J=8.2 Hz, 1H), 7.63 (s, 1H), 7.42 (m, 1H), 7.32 (m, 2H), 6.70 (m, 1H), 6.34 (d, 1H), 5.26 (s, 1H), 4.41 (m, 1H), 4.22 (m, 1H), 3.72 (s, 3H), 3.22 (m, 2H), 2.91 (m, 1H), 2.59 (s, 3H), 2.18 (m, 1H), 2.08 (m, 1H), 1.72 (m, 1H), 1.39 (m, 1H), 1.05 (s, 9H). LCMS-ESI+ (m/z): [M+H]+ calcd for C29H34NO4: 460.58. found: 460.1.

EXAMPLE 20

(2S)-2-tert-Butoxy-2-(3-methyl-1-((7R)-6-methyl-2,3,3a,4,5,6-hexahydropyrano[4,3,2-de]quinolin-7-yl)naphthalen-2-yl)acetic acid (22)

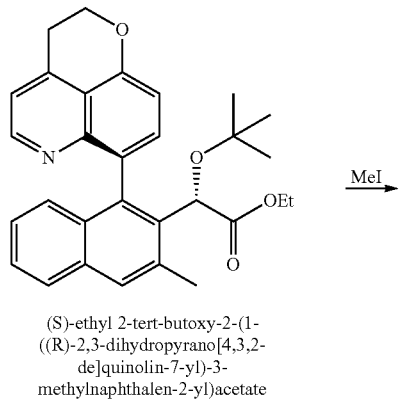

(S)-ethyl 2-tert-butoxy-2-(1-((R)-2,3-dihydropyrano[4,3,2-de]quinolin-7-yl)-3-methylnaphthalen-2-yl)acetate MeI →

(R)-7-(2-((S)-1-tert-butoxy-2-ethoxy-2-oxoethyl)-3-methylnaphthalen-1-yl)-6-methyl-2,3-dihydropyrano[4,3,2-de]quinolin-6-ium iodide Pt/C, H2 →

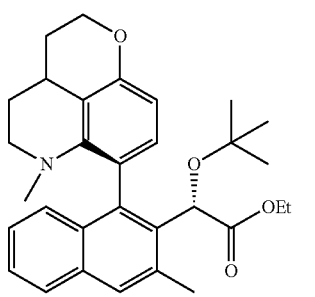

(2S)-ethyl 2-tert-butoxy-2-(3-methyl-1-((7R)-6-methyl-2,3,3a,4,5,6-hexahydropyrano[4,3,2-de]quinolin-7-yl)naphthalen-2-yl)acetate NaOH →

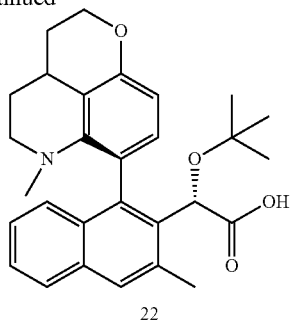

22

(2S)-tert-butoxy-2-(3-methyl-1-((7R)-6-methyl-2,3,3a,4,5,6-hexahydropyrano[4,3,2-de]quinolin-7-yl)naphthalen-2-yl)acetic acid Preparation of (R)-7-(2-((S)-1-tert-butoxy-2-ethoxy-2-oxoethyl)-3-methylnaphthalen-1-yl)-6-methyl-2,3-dihydropyrano[4,3,2-de]quinolin-6-ium iodide: A mixture of MeI (0.8 mL, large excess) and (S)-ethyl 2-tert-butoxy-2-(1-((R)-2,3-dihydropyrano[4,3,2-de]quinolin-7-yl)-3-methylnaphthalen-2-yl)acetate (37 mg). The reaction was heated at 50° C. for 2 days. The reaction mixture was diluted with ethyl acetate and washed with brine, dried over MgSO4, filtered, concentrated and purified by flash column chromatography (silica gel, 0 to 20% MeOH/DCM) to give the desired material as a green oil (50 mg). LCMS-ESI+ (m/z): [M]+ calcd for C34H34NO4: 484.61. found: 484.3.

Preparation of (2S)-ethyl 2-tert-butoxy-2-(3-methyl-1-((7R)-6-methyl-2,3,3a,4,5,6-hexahydropyrano[4,3,2-de]quinolin-7-yl)naphthalen-2-yl)acetate: (R)-7-(2-((S)-1-tert-butoxy-2-ethoxy-2-oxoethyl)-3-methylnaphthalen-1-yl)-6-methyl-2,3-dihydropyrano[4,3,2-de]quinolin-6-ium iodide (50 mg) was dissolved in 20 mL EtOH and 1 drop of HOAc was added to the solution. 10% Pt/C (30 mg) was added and the resulting reaction mixture was stirred under hydrogen (1 atm, balloon) at room temperature overnight. The reaction mixture was filtered and diluted with ethyl acetate and washed with brine, dried (MgSO4), filtered, concentrated and purified by flash column chromatography (silica gel, 0 to 20% MeOH/DCM) to give (2S)-ethyl 2-tert-butoxy-2-(3-methyl-1-((7R)-6-methyl-2,3,3a,4,5,6-hexahydropyrano[4,3,2-de]quinolin-7-yl)naphthalen-2-yl)acetate as a grey solid (15 mg). LCMS-ESI+ (m/z): [M+H]+ calcd for C31H38NO4: 488.63. found: 488.2.

Preparation of (2S)-2-tert-butoxy-2-(3-methyl-1-((7R)-6-methyl-2,3,3a,4,5,6-hexahydropyrano[4,3,2-de]quinolin-7-yl)naphthalen-2-yl)acetic acid (22): To a solution of (2S)-ethyl 2-tert-butoxy-2-(3-methyl-1-((7R)-6-methyl-2,3,3a,4,5,6-hexahydro-pyrano[4,3,2-de]quinolin-7-yl)naphthalen-2-yl)acetate (12 mg, 0.021 mmol) in ethanol (1 mL) was added 2 N sodium hydroxide (1 mL) and the resulting reaction mixture was heated at 80° C. overnight. The reaction mixture was then concentrated and purified by reverse phase HPLC (Gemini, 5 to 100% ACN/H2O+0.1% TFA). The product was lyophilized to give (2S)-2-tert-butoxy-2-(3-methyl-1-((7R)-6-methyl-2,3,3a,4,5,6-hexahydropyrano[4,3,2-de]quinolin-7-yl)naphthalen-2-yl)acetic acid (22) as a white powder (2.6 mg). 1H-NMR: 400 MHz, (CD3OD) δ: 7.82 (d, J=8.2 Hz, 1H), 7.67 (s, 1H), 7.43 (m, 2H), 7.38 (m, 1H), 6.92 (m, 1H), 6.71 (m, 1H), 5.06 (s, 1H), 4.41 (m, 1H), 4.28 (m, 1H), 3.52 (m, 1H), 3.04 (m, 2H), 2.67, 2.62 (s, s, 3H), 2.29 (s, 3H), 2.28

(m, 1H), 2.08 (m, 1H), 1.72 (m, 1H), 1.59 (m, 1H), 0.95 (s, 9H). LCMS-ESI+ (m/z): [M+H]+ calcd for $C_{29}H_{34}NO_4$: 460.58. Found: 461.3.

EXAMPLE 21

7-((R)-2-((S)-tert-Butoxy(carboxy)methyl)-3-methylnaphthalen-1-yl)-2,3-dihydropyrano[4,3,2-de]quinoline 6-oxide (23)

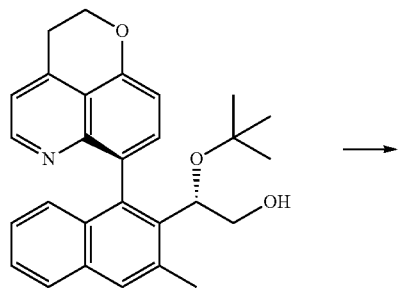

(S)-2-tert-butoxy-2-((R)-1-(2,3-dihydropyrano[4,3,2-de]quinolin-7-yl)-3-methylnaphthalen-2-yl)ethanol

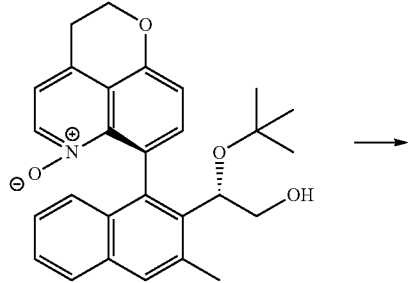

7-((R)-2-((S)-1-tert-butoxy-2-hydroxyethyl)-3-methylnaphthalen-1-yl)-2,3-dihydropyrano[4,3,2-de]quinoline 6-oxide

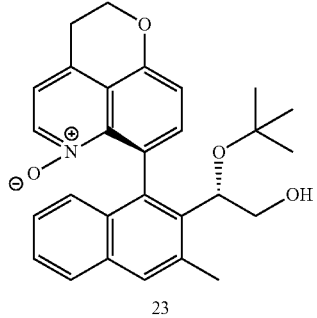

23

7-((R)-2-((S)-tert-butoxy(carboxy)methyl)-3-methylnaphthalen-1-yl)-2,3-dihydropyrano[4,3,2-de]quinoline 6-oxide Preparation of 7-((R)-2-((S)-1-tert-butoxy-2-hydroxyethyl)-3-methylnaphthalen-1-yl)-2,3-dihydropyrano[4,3,2-de]quinoline 6-oxide: To a solution of (S)-2-tert-butoxy-2-((R)-1-(2,3-dihydropyrano[4,3,2-de]quinolin-7-yl)-3-methylnaphthalen-2-yl)ethanol (6C, 31 mg, 0.727 mmol) in dichloromethane (1.3 mL) was added 3-chloroperoxybenzoic acid (77%, 36 mg, 0.161 mmol) and reaction mixture was stirred for 7 hours. Additional 3-chloroperoxybenzoic acid (26 mg, 0.116 mmol) was added and reaction mixture was stirred overnight and quenched with saturated sodium thiosulfate solution. The resulting mixture was extracted with ethyl acetate, washed with saturated sodium bicarbonate solution, brine, dried (MgSO₄), filtered, concentrated and purified by reverse phase HPLC (Gemini, 5 to 100% ACN/H₂O+0.1% TFA). The product was lyophilized to give a yellow powder (4.7 mg). LCMS-ESI+ (m/z): [M]+ calcd for $C_{28}H_{30}NO_4$: 443.5. found: 443.9.

Preparation of 7-((R)-2-((S)-tert-butoxy(carboxy)methyl)-3-methylnaphthalen-1-yl)-2,3-dihydropyrano[4,3,2-de]quinoline 6-oxide (23): To a solution of 7-((R)-2-((S)-1-tert-butoxy-2-hydroxyethyl)-3-methylnaphthalen-1-yl)-2,3-dihydropyrano[4,3,2-de]quinoline 6-oxide (4.7 mg, 0.0106 mol) in wet acetonitrile (0.75% H₂O, 1 mL) was added Hs₅₁₀dCrO₃ stock solution (0.439 M, 0.1 mL, 0.423 mmol) was added at 0° C. The reaction mixture was stirred for 90 minutes at room temperature and additional H₅IO₆/CrO₃ stock solution (0.439 M, 0.1 mL) was added. After stirring for 90 minutes, the reaction mixture was quenched with saturated NaHCO₃ solution and extracted with ethyl acetate (2×). The organic layer was washed with H₂O, saturated NaHSO₃ solution, dried (MgSO₄), filtered, concentrated and purified by reverse phase HPLC (Gemini, 5 to 100% acetonitrile/H₂O+ 0.1% TFA) to give a yellow powder (1.2 mg). ¹H NMR (400 MHz, CD₃OD) δ 8.51 (d, J=6.3 Hz, 1H), 7.79 (d, J=8.2 Hz, 1H), 7.69 (s, 1H), 7.57 (d, J=8.0 Hz, 1H), 7.44 (d, J=6.1 Hz, 1H), 7.43-7.37 (m, 1H), 7.34 (d, J=8.3 Hz, 1H), 7.25-7.13 (m, 1H), 6.87 (d, J=7.8 Hz, 1H), 5.06 (s, 1H), 4.67-4.55 (m, 2H), 3.52-3.46 (m, 2H), 2.61 (s, 3H), 0.97 (s, 9H). LCMS-ESI+ (m/z): [M+H]+ calcd for $C_{28}H_{28}NO_5$: 458.5. found: 458.1.

EXAMPLE 22

(S)-2-tert-Butoxy-2-(1-(4-chlorophenyl)-3-(dimethylaminomethyl) naphthalen-2-yl)acetic acid (24)

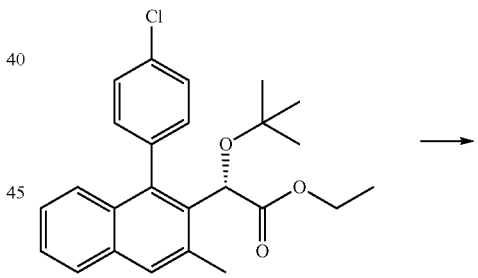

(S)-ethyl 2-tert-butoxy-2-(1-(4-chlorophenyl)-3-methylnaphthalen-2-yl)acetate

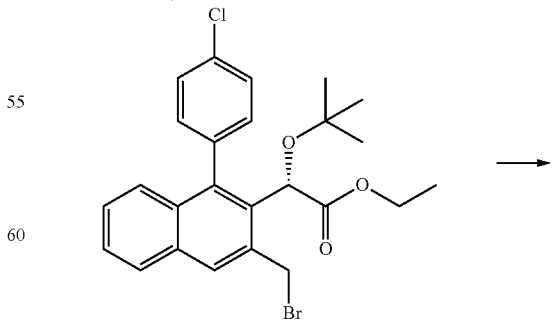

(S)-ethyl 2-(3-(bromomethyl)-1-(4-chlorophenyl)naphthalen-2-yl)-2-tert-butoxyacetate

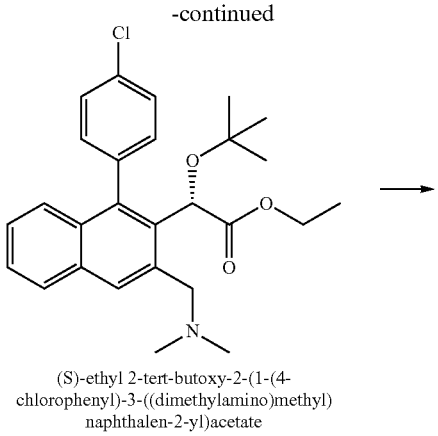

(S)-ethyl 2-tert-butoxy-2-(1-(4-chlorophenyl)-3-((dimethylamino)methyl)naphthalen-2-yl)acetate Preparation of (S)-2-tert-butoxy-2-(1-(4-chlorophenyl)-3-((dimethyl-amino)methyl)naphthalen-2-yl)acetic acid (24): To a solution of (S)-ethyl 2-tert-butoxy-2-(1-(4-chlorophenyl)-3-((dimethylamino)methyl)naphthalen-2-yl)acetate in THF (0.5 mL) and MeOH (0.5 mL), was added NaOH solution (2N, 100 µL). The reaction mixture was stirred at room temperature for 1 day. The reaction mixture was neutralized by HOAc and concentrated down. The residue was dissolved in MeOH and purified by reverse phase HPLC (Gemini, 5 to 100% ACN/H$_2$O+0.1% TFA) to provide the desired product (3.7 mg). $^1$H-NMR: 400 MHz, (CD$_3$OD) δ: 8.12 (s, 1H), 8.00 (d, J=4.2 Hz, 1H), 7.65-7.52 (m, 5H), 7.32-7.30 (m, 2H), 5.36 (s, 1H), 4.93 (d, J=6.8 Hz, 1H), 4.47 (d, J=7 Hz, 1H), 3.12 (s, 3H), 2.89 (s, 3H), 1.12 (s, 9H). LCMS-ESI$^+$ (m/z): [M+H]$^+$ calcd for C$_{25}$H$_{29}$ClNO$_3$: 426.2. Found: 426.1, 428.1.

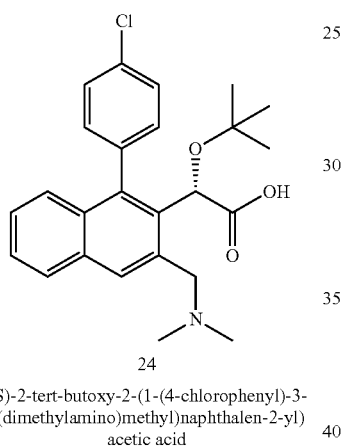

24

(S)-2-tert-butoxy-2-(1-(4-chlorophenyl)-3-((dimethylamino)methyl)naphthalen-2-yl) acetic acid Preparation of (S)-ethyl 2-(3-(bromomethyl)-1-(4-chlorophenyl)naphthalen-2-yl)-2-tert-butoxyacetate: To a solution of (S)-ethyl 2-tert-butoxy-2-(1-(4-chlorophenyl)-3-methylnaphthalen-2-yl)acetate (3K, 43 mg, 0.0105 mmol) in CCl$_4$ (2 mL) was added NBS (24 mg, 0.13 mmol) and AIBN (cat. amount). The reaction mixture was refluxed for 5 h. After cooling to room temperature, the reaction mixture was diluted by DCM, washed with sat. NaHCO$_3$, extracted with DCM and the organic layers were combined and dried over MgSO$_4$, filtered, concentrated and purified by flash column chromatography (silica gel, ethyl acetate/hexanes) to provide 12 mg of the desired product. $^1$H-MNR 400 MHz (CDCl$_3$) δ: 8.01 (s, 1H), 7.77 (d, J=4 Hz, 1H), 7.43-7.15 (m, 7H), 5.11 (d, J=5.2 Hz, 1H), 5.06 (s, 1H), 5.00 (d, J=5.2 Hz, 1H), 4.07-4.02 (m, 2H), 1.20-1.15 (m, 3H), 0.96 (s, 9H).

Preparation of (S)-ethyl 2-tert-butoxy-2-(1-(4-chlorophenyl)-3-((dimethyl-amino)methyl)naphthalen-2-yl)acetate: To a solution of (S)-ethyl 2-(3-(bromomethyl)-1-(4-chlorophenyl)naphthalen-2-yl)-2-tert-butoxyacetate (12 mg, 0.0245 mmol) in THF (1 mL) was added dimethylamine (2 M in THF, 0.12 µL). The reaction mixture was stirred at room temperature for 1 h. Removal of the solvent in vacuo followed by purification of the residue by flash chromatography (silica gel, ethyl acetate/hexanes) provided 8 mg of the desired product. LCMS-ESI$^+$ (m/z): [M+H]$^+$ calcd for C$_{27}$H$_{33}$ClNO$_3$: 454.2. Found: 454.2, 456.1.

EXAMPLE 23

(S)-2-tert-Butoxy-2-(1-(4-chlorophenyl)-3-((pyridin-3-yloxy)methyl)naphthalen-2-yl)acetic acid (25)

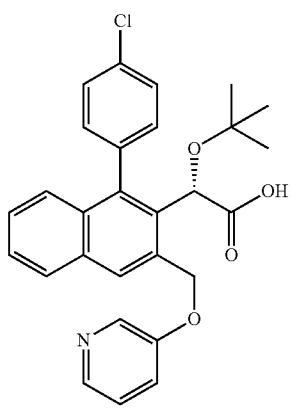

(S)-2-tert-butoxy-2-(1-(4-chlorophenyl)-3-((pyridin-3-yloxy)methyl)naphthalen-2-yl) acetic acid Preparation of (S)-2-tert-butoxy-2-(1-(4-chlorophenyl)-3-((pyridin-3-yloxy)methyl)naphthalen-2-yl)acetic acid (25): (S)-2-tert-Butoxy-2-(1-(4-chlorophenyl)-3-((pyridin-3-yloxy)methyl)naphthalen-2-yl)acetic acid (25) was prepared by the similar method of Example 22, except that K$_2$CO$_3$ and pyridin-3-ol were used instead of dimethylamine in step 2. $^1$H-NMR: 400 MHz, (CD$_3$OD) δ: 8.39 (d, J=2.8 Hz, 1H), 8.31 (s, 1H), 8.05 (s, 1H), 7.96-7.86 (m, 3H), 7.64-7.49 (m, 5H), 7.34-7.31 (m, 2H), 6.44 (d, J=7.4 Hz, 1H), 6.12 (d, J=7.6 Hz, 1H), 5.24 (s, 1H), 0.92 (s, 9H). LCMS-ESI$^+$ (m/z): [M+H]$^+$ calcd for C$_{28}$H$_{27}$ClNO$_4$: 476.2. Found: 476.0, 478.0.

Example 24

(S)-2-tert-Butoxy-2-(1-(4-chlorophenyl)-3-((pyrimidin-5-yloxy)methyl)naphthalen-2-yl)acetic acid (26)

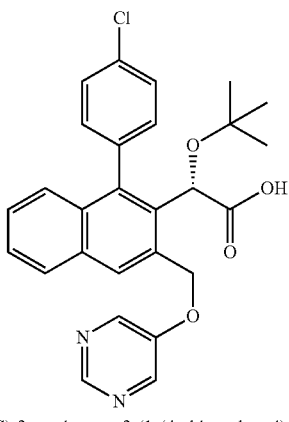

(S)-2-tert-butoxy-2-(1-(4-chlorophenyl)-3-
((pyrimidin-5-yloxy)methyl)naphthalen-2-yl)
acetic acid Preparation of (S)-2-tert-butoxy-2-(1-(4-chlorophenyl)-3-((pyrimidin-5-yloxy)methyl)naphthalen-2-yl)acetic acid (26): (S)-2-tert-Butoxy-2-(1-(4-chlorophenyl)-3-((pyrimidin-5-yloxy)methyl)naphthalen-2-yl)acetic acid (26) was prepared by the similar method of Example 22, except that $K_2CO_3$ and pyrimidin-5-ol were used instead of dimethylamine in step 2. $^1$H-NMR: 400 MHz, (CD$_3$OD) δ: 8.75 (s, 1H), 8.60 (s, 1H), 8.08 (s, 1H), 7.88 (d, J=3.8 Hz, 1H), 7.60 (s, 2H), 7.58-7.26 (m, 4H), 5.72-5.70 (m, 2H), 5.21 (s, 1H), 1.02 (s, 9H). LCMS-ESI$^+$ (m/z): [M+H]$^+$ calcd for $C_{27}H_{26}ClN_2O_4$: 477.2. Found: 477.1, 478.1.

EXAMPLE 25

(S)-2-tert-Butoxy-2-(1-(4-chlorophenyl)-3-(morpholinomethyl) naphthalen-2-yl)acetic acid (27)

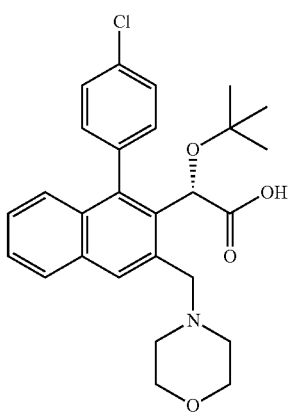

(S)-2-tert-butoxy-2-(1-(4-chlorophenyl)-3-
(morpholinomethyl)naphthalen-2-yl)
acetic acid Preparation of (S)-2-tert-butoxy-2-(1-(4-chlorophenyl)-3-(morpholinomethyl)naphthalen-2-yl)acetic acid (27): (S)-2-tert-Butoxy-2-(1-(4-chlorophenyl)-3-(morpholinomethyl)naphthalen-2-yl)acetic acid (27) was prepared by the similar method of Example 22, except that morpholine was used instead of dimethylamine in step 2. $^1$H-NMR: 400 MHz, (CD$_3$OD) δ: 8.14 (s, 1H), 7.99 (d, J=4 Hz, 1H), 7.64-7.60 (m, 3H), 7.53-7.49 (m, 2H), 7.29-7.27 (m, 2H), 5.38 (s, 1H), 4.81-4.78 (m, 2H), 4.11-4.08 (m, 2H), 3.81-3.78 (m, 2H), 3.55-3.41 (m, 4H), 1.16 (s, 9H). LCMS-ESI$^+$ (m/z): [M+H]$^+$ calcd for $C_{27}H_{31}ClNO_4$: 468.2. Found: 468.0, 470.1.

EXAMPLE 26

(S)-2-tert-Butoxy-2-(1-(4-chlorophenyl)-3-(methoxymethyl) naphthalen-2-yl)acetic acid (28)

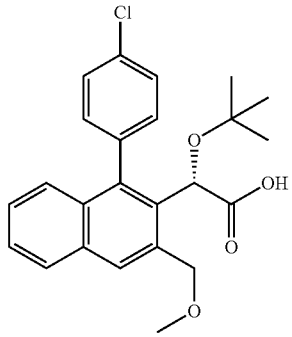

(S)-2-tert-butoxy-2-(1-(4-chlorophenyl)-3-
(methoxymethyl)naphthalen-2-yl)
acetic acid Preparation of (S)-2-tert-butoxy-2-(1-(4-chlorophenyl)-3-(methoxymethyl)naphthalen-2-yl)acetic acid (28): (S)-2-tert-Butoxy-2-(1-(4-chlorophenyl)-3-(methoxymethyl)naphthalen-2-yl)acetic acid (28) was prepared by the similar method of Example 22, except that sodium methoxide and methanol were used instead of dimethylamine and THF and the reaction was heated at 50° C. for 3 h. $^1$H-NMR: 400 MHz, (CD$_3$OD) δ: 7.91 (s, 1H), 7.77 (d, J=4.2 Hz, 1H), 7.50-7.13 (m, 7H), 5.06 (s, 1H), 4.84 (d, J=6.6 Hz, 2H), 4.71 (d, J=6.4 Hz, 2H), 3.32 (s, 3H), 0.90 (s, 9H). LCMS-ESI$^+$ (m/z): [M−H]$^+$ calcd for $C_{24}H_{24}ClO_4$: 411.1. Found: 411.0, 413.0.

EXAMPLE 27

(S)-2-tert-Butoxy-2-(1-(4-chlorophenyl)-3-vinyl-naphthalen-2-yl)acetic acid (29A) and (S)-2-tert-butoxy-2-(1-(4-chlorophenyl)-3-ethylnaphthalen-2-yl)acetic acid (29B)

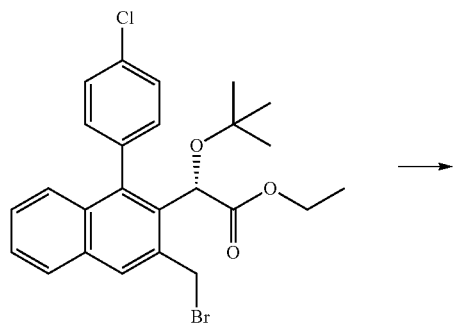

(S)-ethyl 2-(3-(bromomethyl)-1-(4-chlorophenyl)naphthalen-2-yl)-2-tert-butoxyacetate

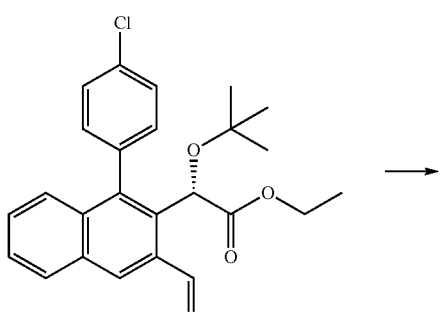

(S)-ethyl 2-tert-butoxy-2-(1-(4-chlorophenyl)-3-formylnaphthalen-2-yl)acetate

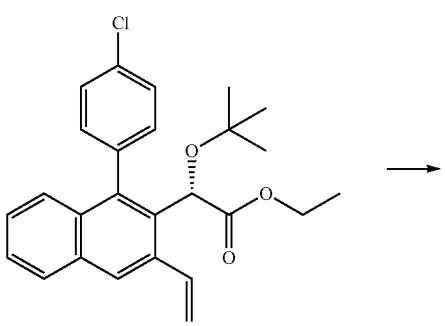

(S)-ethyl 2-tert-butoxy-2-(1-(4-chlorophenyl)-3-vinylnaphthalen-2-yl)acetate

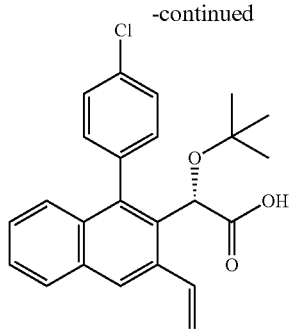

29A
(S)-2-tert-butoxy-2-(1-(4-chlorophenyl)-3-vinylnaphthalen-2-yl)acetic acid

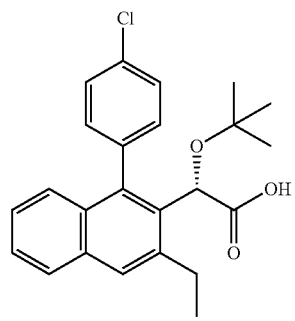

29B
(S)-2-tert-butoxy-2-(1-(4-chlorophenyl)-3-ethylnaphthalen-2-yl)acetic acid

Preparation of (S)-ethyl 2-tert-butoxy-2-(1-(4-chlorophenyl)-3-formylnaphthalen-2-yl)acetate: To a solution of (S)-ethyl 2-(3-(bromomethyl)-1-(4-chlorophenyl)naphthalen-2-yl)-2-tert-butoxyacetate from Example 22 (200 mg, 0.408 mmol) in acetonitrile (4 mL) was added N-methylmorpholine N-oxide (478 mg, 4.08 mmol) and 4 Å molecular sieves (200 mg). The reaction mixture was stirred at room temperature for 2 h. Additional N-methylmorpholine N-oxide (500 mg, 4.27 mmol) was added and the reaction mixture was stirred at room temperature for another 2 h. The reaction mixture was then filtered and the organics washed with sat. NaHCO$_3$, extracted by DCM, dried over MgSO$_4$. The organic layer was then filtered, concentrated down and purified by flash column chromatography (silica gel, ethyl acetate/hexanes) to provide 110 mg (64%) of the desired product. $^1$H-MNR 400 MHz (CDCl$_3$) δ: 10.82 (s, 1H), 8.55 (s, 1H), 8.01 (d, J=4 Hz, 1H), 7.55-7.23 (m, 7H), 5.19 (s, 1H), 4.17-4.13 (m, 2H), 1.22 (t, J=7 Hz, 3H), 1.04 (s, 9H).

Preparation of (S)-ethyl 2-tert-butoxy-2-(1-(4-chlorophenyl)-3-vinylnaphthalen-2-yl)acetate: To a suspension of methyltriphenylphosphonium bromide (60 mg, 0.168 mmol) in THF (1 mL) at −78° C. was added dropwise n-BuLi (1.6 M in hexanes, 90 µL), followed after 30 min by a solution of (S)-ethyl 2-tert-butoxy-2-(1-(4-chlorophenyl)-3-formylnaphthalen-2-yl)acetate (12 mg, 0.028 mmol) in THF (1 mL). The reaction mixture was allowed to warm to room temperature and stirred at room temperature for 2 hours. This mixture was added to another mixture, which was made by adding n-BuLi (1.6 M in hexanes, 300 µL) to a suspension of methyltriphenylphosphonium bromide (200 mg, 0.56 mmol) in THF (2 mL) and stirred at −78° C. for 15 min. Then the reaction mixture was allowed to warm to room temperature and stirred at room temperature for 1 h. The reaction mixture was diluted with EtOAc, washed with sat. NH₄Cl, and extracted with EtOAc. The organic layers were combined, dried over MgSO₄, filtered, concentrated in vacuo and purified by flash column chromatography (silica gel, ethyl acetate/hexanes) to provide 7.4 mg of the desired product. ¹H-MNR 400 MHz (CDCl₃) δ: 7.95 (s, 1H), 7.78 (d, J=4.2 Hz, 1H), 7.57-7.50 (m, 1H), 7.43-7.17 (m, 6H), 5.62 (dd, J=8.1, 2 Hz, 1H), 5.25 (dd, J=5.3, 1.8 Hz, 1H), 5.07 (s, 1H), 4.06-4.02 (m, 2H), 1.10 (t, J=7 Hz, 3H), 0.93 (s, 9H).

Preparation of (S)-2-tert-butoxy-2-(1-(4-chlorophenyl)-3-vinylnaphthalen-2-yl)acetic acid (29A): To a solution (S)-ethyl 2-tert-butoxy-2-(1-(4-chlorophenyl)-3-vinylnaphthalen-2-yl)acetate (7.4 mg, 0.0175 mmol) in THF/MeOH (1/1, 1 mL), was added NaOH (2 N, 280 L). The reaction mixture was stirred at room temperature overnight. Then the temperature was raised to 40° C. and the reaction mixture was stirred for 4 h. The reaction was then cooled down and neutralized by adding HOAc. The reaction mixture was concentrated in vacuo and the residue was purified by reverse phase HPLC (Gemini, 5 to 100% ACN/H₂O+0.1% TFA) to provide 5.3 mg of the desired product. ¹H-NMR: 400 MHz, (CD₃OD) δ: 8.07 (s, 1H), 7.89 (d, J=4.0 Hz, 1H), 7.60-7.54 (m, 4H), 7.48-7.44 (m, 1H), 7.35-7.31 (m, 2H), 7.25-7.22 (m, 1H), 5.76-5.71 (m, 1H), 5.29-5.26 (m, 1H), 5.21 (s, 1H), 0.98 (s, 9H). LCMS-ESI⁻ (m/z): [M−H]⁻ calcd for C₂₄H₂₃ClO₃: 393.1. Found: 393.0.

Preparation of (S)-2-tert-butoxy-2-(1-(4-chlorophenyl)-3-ethylnaphthalen-2-yl)acetic acid (29B): To a solution of (S)-2-tert-butoxy-2-(1-(4-chlorophenyl)-3-vinylnaphthalen-2-yl)acetic acid (4 mg, 0.010 mmol) in EtOH (1.5 mL) was added Rh/Al₂O₃ (cat. amount) and the resulting mixture stirred under hydrogen (1 atm, balloon) at room temperature for 2 h. The reaction mixture was filtered over Celite, concentrated in vacuo and the residue was purified by reverse phase HPLC (Gemini, 5 to 100% ACN/H₂O+0.1% TFA) to provide 0.8 mg of the desired product. ¹H-NMR: 400 MHz, (CD₃OD) δ: 7.81 (d, J=4.2 Hz, 1H), 7.77 (s, 1H), 7.58-7.53 (m, 3H), 7.44-7.41 (m, 1H), 7.33-7.20 (m, 3H), 5.20 (s, 1H), 3.14-3.08 (m, 1H), 2.93-2.87 (m, 1H), 1.34 (t, J=7.4 Hz, 3H), 0.98 (s, 9H). LCMS-ESI⁻ (m/z): [M−H]⁻ calcd for C₂₄H₂₄ClO₃: 395.1. Found: 395.0.

EXAMPLE 28

(S)-2-tert-Butoxy-2-(1-(4-chlorophenyl)-3-(hydroxymethyl)naphthalen-2-yl)acetic acid (30)

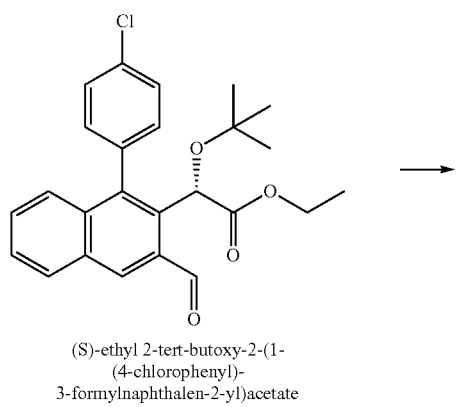

(S)-ethyl 2-tert-butoxy-2-(1-(4-chlorophenyl)-3-formylnaphthalen-2-yl)acetate

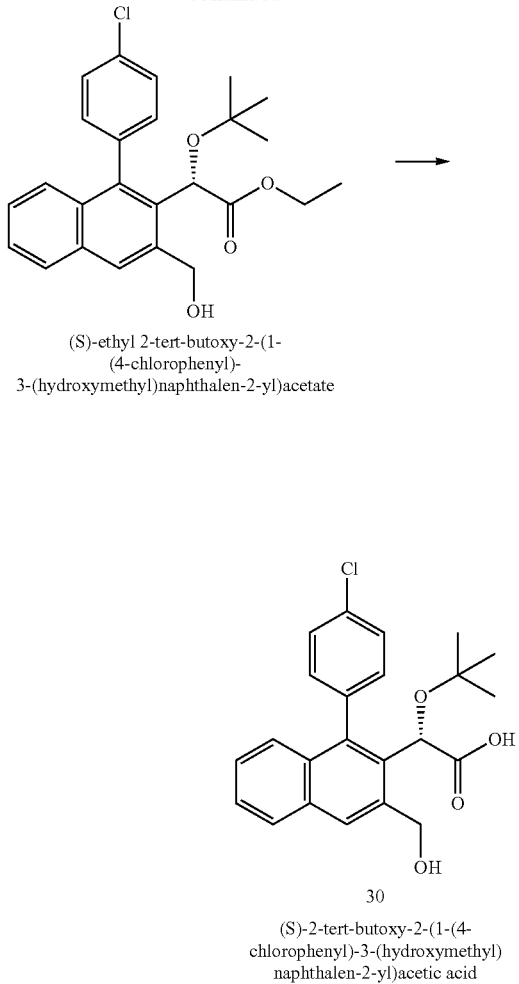

(S)-ethyl 2-tert-butoxy-2-(1-(4-chlorophenyl)-3-(hydroxymethyl)naphthalen-2-yl)acetate (S)-2-tert-butoxy-2-(1-(4-chlorophenyl)-3-(hydroxymethyl)naphthalen-2-yl)acetic acid
30

Preparation of (S)-ethyl 2-tert-butoxy-2-(1-(4-chlorophenyl)-3-(hydroxymethyl)naphthalen-2-yl)acetate: To a solution of (S)-ethyl 2-tert-butoxy-2-(1-(4-chlorophenyl)-3-formylnaphthalen-2-yl)acetate (12 mg, 0.0283 mmol) in DCM/EtOH (1/1, 1 mL) at 0° C., was added NaBH₄ (2 mg, 0.053 mmol) and the reaction mixture stirred at 0° C. for 2 h. The reaction was quenched by adding sat. NH₄Cl. The resulting mixture was extracted with DCM, dried over MgSO₄, filtered, concentrated in vacuo and purified by flash column chromatography (silica gel, ethyl acetate/hexanes) to provide 8 mg of the desired product. ¹H-MNR 400 MHz (CDCl₃) δ: 7.85 (s, 1H), 7.78 (d, J=4.0 Hz, 1H), 7.46-7.38 (m, 4H), 7.30-7.26 (m, 1H), 7.20-7.15 (m, 2H), 5.13 (s, 1H), 5.02 (d, J=6.2 Hz, 1H), 4.54 (d, J=6 Hz, 1H), 4.12-4.02 (m, 2H), 3.82 (bs, 1H), 1.14 (t, J=7 Hz, 3H), 1.01 (s, 9H).

Preparation of (S)-2-tert-butoxy-2-(1-(4-chlorophenyl)-3-(hydroxymethyl) naphthalen-2-yl)acetic acid (30): This compound was made using a method similar to that used for (S)-2-tert-butoxy-2-(1-(4-chlorophenyl)-3-(dimethylaminomethyl) naphthalen-2-yl)acetic acid in Example 22. The compound was purified by reverse phase HPLC (Gemini, 5 to 100% ACN/H₂O). ¹H-NMR: 400 MHz, (CD₃OD) δ: 7.98 (s, 1H), 7.78 (d, J=4.2 Hz, 1H), 7.52-7.44 (m, 3H), 7.39-7.35 (m, 1H), 7.26-7.13 (m, 3H), 5.09 (s, 1H), 5.05 (d, J=7.4 Hz, 1H), 4.73 (d, J=7.2 Hz, 1H), 0.92 (s, 9H). LCMS-ESI⁻ (m/z): [M−H]calcd for $C_{23}H_{22}ClO_4$: 397.1. Found: 396.9, 399.0.

EXAMPLE 29

(S)-2-tert-Butoxy-2-((R)-1-(2,3-dihydropyrano[4,3,2-de]quinolin-7-yl)-3-(fluoromethyl)naphthalen-2-yl)acetic acid (31)

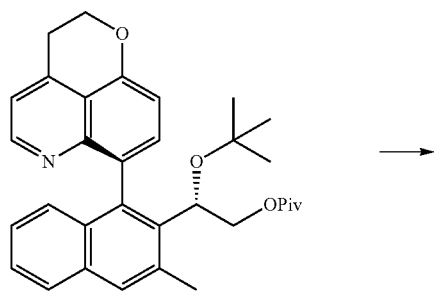

(S)-2-tert-butoxy-2-((R)-1-(2,3-dihydropyrano[4,3,2-de]quinolin-7-yl)-3-methylnaphthalen-2-yl)ethyl pivalate

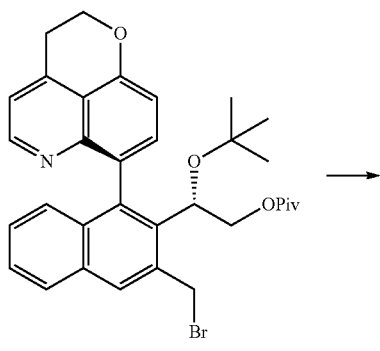

(S)-2-((R)-3-(bromomethyl)-1-(2,3-dihydropyrano[4,3,2-de]quinolin-7-yl)naphthalen-2-yl)-2-tert-butoxyethyl pivalate

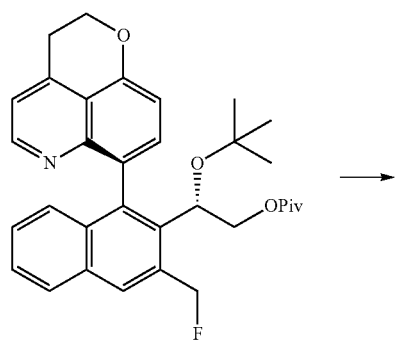

(S)-2-tert-butoxy-2-((R)-1-(2,3-dihydropyrano[4,3,2-de]quinolin-7-yl)-3-(fluoromethyl)naphthalen-2-yl)ethyl pivalate

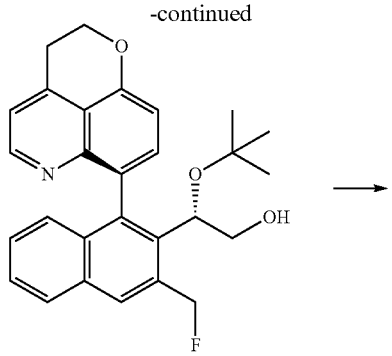

(S)-2-tert-butoxy-2-((R)-1-(2,3-dihydropyrano[4,3,2-de]quinolin-7-yl)-3-(fluoromethyl)naphthalen-2-yl)ethanol

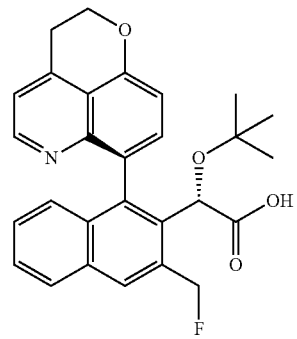

31
(S)-2-tert-butoxy-2-((R)-1-(2,3-dihydropyrano[4,3,2-de]quinolin-7-yl)-3-(fluoromethyl)naphthalen-2-yl)acetic acid Preparation of (S)-2-((R)-3-(bromomethyl)-1-(2,3-dihydropyrano[4,3,2-de]quinolin-7-yl)naphthalen-2-yl)-2-tert-butoxyethyl pivalate: The compound was made similarly to the method for making (S)-ethyl 2-(3-(bromomethyl)-1-(4-chloro-phenyl)naphthalen-2-yl)-2-tert-butoxyacetate of Example 22. LCMS-ESI⁺ (m/z): [M+H]⁺ calcd for $C_{33}H_{37}BrNO_4$: 590.2. Found: 590.0, 592.0.

Preparation of (S)-2-tert-butoxy-2-((R)-1-(2,3-dihydropyrano[4,3,2-de]quinolin-7-yl)-3-(fluoromethyl)naphthalen-2-yl)ethyl pivalate: To a solution of (S)-2-(3-(bromomethyl)-1-(2,3-dihydropyrano[4,3,2-de]quinolin-7-yl)naphthalen-2-yl)-2-tert-butoxyethyl pivalate (15 mg, 0.0255 mmol) in acetonitrile (1 mL), was added AgF (8 mg, 0.063 mmol). The reaction mixture was stirred at room temperature for 1 day. The reaction mixture was then washed by sat. NaHCO₃, extracted with EtOAc, dried over MgSO₄, filtered, concentrated in vacuo and purified by flash column chromatography (silica gel, 0 to 30% ethyl acetate/hexanes) to provide 13 mg of the desired product. LCMS-ESI⁺ (m/z): [M+H]⁺ calcd for $C_{33}H_{37}FNO_4$: 530.3. Found: 530.1.

Preparation of (S)-2-tert-butoxy-2-((R)-1-(2,3-dihydropyrano[4,3,2-de]quinolin-7-yl)-3-(fluoromethyl)naphthalen-2-yl)ethanol: To a solution of (S)-2-tert-butoxy-2-(1-(2,3-dihydropyrano[4,3,2-de]quinolin-7-yl)-3-(fluoromethyl)naphthalen-2-yl)ethyl pivalate (13 mg, 0.024 mol) in THF (1 mL) and MeOH (0.5 mL), was added NaOH (2 N, 240 μL). The reaction mixture was reacted at room temperature for 1 day. The reaction mixture was washed with sat. NaHCO₃ and extracted with EtOAc. The organic layers were combined, dried over MgSO₄, concentrated and purified by flash column chromatography (silica gel, ethyl acetate/hexanes) to provide 5 mg of the desired product. LCMS-ESI⁺ (m/z): [M+H]⁺ calcd for $C_{28}H_{29}FNO_3$: 446.2. Found: 446.0.

Preparation of (S)-2-tert-butoxy-2-((R)-1-(2,3-dihydropyrano[4,3,2-de]quinolin-7-yl)-3-(fluoromethyl)naphthalen-2-yl)acetic acid (31): To a solution of (2S)-2-tert-butoxy-2-(1-(2,3-dihydropyrano[4,3,2-de]quinolin-7-yl)-3-(fluoromethyl)naphthalen-2-yl)ethanol (5 mg, 0.0112 mmol) in wet acetonitrile (0.75% wt H₂O) was added $H_5IO_6/CrO_3$ (0.439 M stock solution in wet acetonitrile, 400 µL) at 0° C. The reaction mixture was stirred at 0° C. for 30 min. The reaction mixture was filtered and purified by reverse phase HPLC (Gemini, 5 to 100% ACN/H₂O+0.1% TFA) to provide 0.8 mg of the desired product. ¹H-NMR: 400 MHz, (CD₃OD) δ: 8.51 (d, J=2.4 Hz, 1H), 8.15 (s, 1H), 7.92 (d, J=4.0 Hz, 1H), 7.69 (d, J=4.2 Hz, 1H), 7.54 (d, J=2.6 Hz, 1H), 7.43 (t, J=7.6 Hz, 1H), 7.31 (d, J=4 Hz, 1H), 7.24-7.21 (m, 1H), 6.88 (d, J=4.4 Hz, 1H), 6.01-5.74 (m, 2H), 5.06 (s, 1H), 4.59 (t, J=6.2 Hz, 2H), 3.49 (t, J=6 Hz, 2H), 0.81 (s, 9H). ¹⁹F-NMR 400 MHz (CD₃OD) δ: −77.51 (s, 1F). LCMS-ESI⁺ (m/z): [M+H]⁺ calcd for $C_{28}H_{27}FNO_4$: 460.2. Found: 460.1.

EXAMPLE 30

(S)-2-tert-Butoxy-2-((R)-3-(difluoromethyl)-1-(2,3-dihydropyrano[4,3,2-de]quinolin-7-yl)naphthalen-2-yl)acetic acid (32)

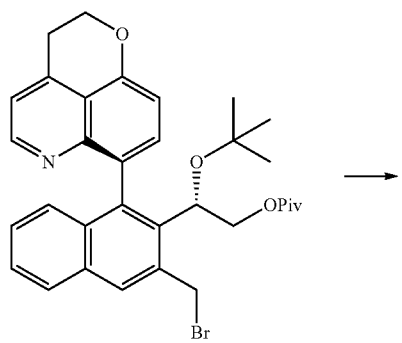

(S)-2-((R)-3-(bromomethyl)-1-(2,3-dihydropyrano[4,3,2-de]quinolin-7-yl)naphthalen-2-yl)-2-tert-butoxyethyl pivalate

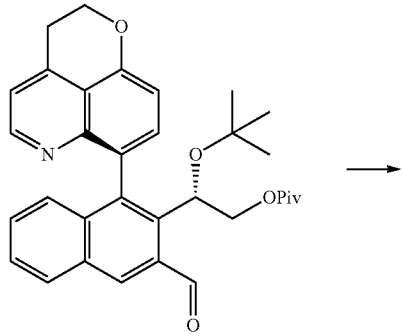

(S)-2-tert-butoxy-2-((R)-1-(2,3-dihydropyrano[4,3,2-de]quinolin-7-yl)-3-formylnaphthalen-2-yl)ethyl pivalate

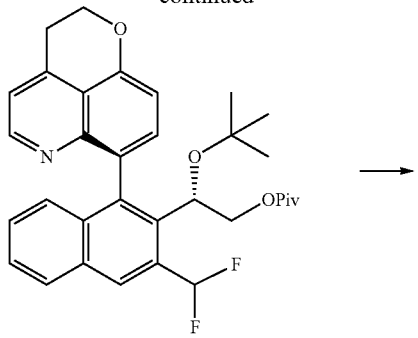

(S)-2-tert-butoxy-2-((R)-3-(difluoromethyl)-1-(2,3-dihydropyrano[4,3,2-de]quinolin-7-yl)naphthalen-2-yl)ethyl pivalate

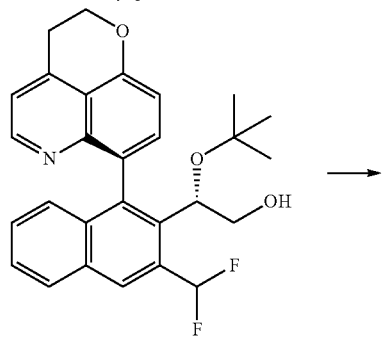

(S)-2-tert-butoxy-2-((R)-3-(difluoromethyl)-1-(2,3-dihydropyrano[4,3,2-de]quinolin-7-yl)naphthalen-2-yl)ethanol

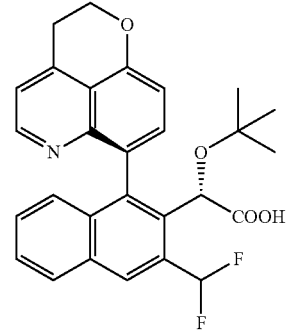

32
(S)-2-tert-butoxy-2-((R)-3-(difluoromethyl)-1-(2,3-dihydropyrano[4,3,2-de]quinolin-7-yl)naphthalen-2-yl)acetic acid Preparation of (S)-2-tert-butoxy-2-((R)-1-(2,3-dihydropyrano[4,3,2-de]quinolin-7-yl)-3-formylnaphthalen-2-yl)ethyl pivalate: The compound was made similarly to (S)-ethyl 2-tert-butoxy-2-(1-(4-chlorophenyl)-3-formylnaphthalen-2-yl)acetate of Example 27. LCMS-ESI⁺ (m/z): [M+H]⁺ calcd for $C_{33}H_{36}NO_5$: 526.2. Found: 526.1.

Preparation of (S)-2-tert-butoxy-2-((R)-3-(difluoromethyl)-1-(2,3-dihydropyrano[4,3,2-de]quinolin-7-yl)naphthalen-2-yl)ethyl pivalate: To a solution of (S)-2-tert-butoxy-2-(1-(2,3-dihydropyrano[4,3,2-de]quinolin-7-yl)-3-formylnaphthalen-2-yl)ethyl pivalate (18 mg, 0.0343 mmol) in DCM (1.5 mL) was added Deoxofluor (20 µL, 0.105 mmol). The reaction mixture was stirred at room temperature overnight. More Deoxofluor (300 µL, 1.6 mmol) was added and the reaction mixture was stirred at room temperature over weekend. The reaction mixture was washed by sat. NaHCO$_3$ and extracted with DCM. The organic layers were combined, concentrated in vacuo and purified by flash column chromatography (silica gel, 0 to 30% ethyl acetate/hexanes) to produce 20 mg of the desired product. LCMS-ESI$^+$ (m/z): [M+H]$^+$ calcd for C$_{33}$H$_{36}$F$_2$NO$_4$: 548.2. Found: 548.1.

Preparation of (S)-2-tert-butoxy-2-((R)-3-(difluoromethyl)-1-(2,3-dihydropyrano[4,3,2-de]quinolin-7-yl)naphthalen-2-yl)ethanol: The compound was made by the similar method to make (2S)-2-tert-butoxy-2-(1-(2,3-dihydropyrano[4,3,2-de]quinolin-7-yl)-3-(fluoromethyl)naphthalen-2-yl)ethanol of Example 29. LCMS-ESI$^+$ (m/z): [M+H]$^+$ calcd for C$_{28}$H$_{28}$F$_2$NO$_3$: 464.2. Found: 464.1.

Preparation of (S)-2-tert-butoxy-2-((R)-3-(difluoromethyl)-1-(2,3-dihydropyrano[4,3,2-de]quinolin-7-yl)naphthalen-2-yl)acetic acid (32): The compound was made by the similar method to make (2S)-2-tert-butoxy-2-(1-(2,3-dihydropyrano[4,3,2-de]quinolin-7-yl)-3-(fluoromethyl)naphthalen-2-yl)acetic acid of Example 29. $^1$H-NMR: 400 MHz, (CD$_3$OD) δ: 8.66 (d, J=2.8 Hz, 1H), 8.56 (s, 1H), 8.15 (d, J=4.2 Hz, 1H), 8.00-7.81 (m, 3H), 7.69-7.54 (m, 2H), 7.45 (t, J=7.8 Hz, 1H), 7.04 (d, J=4.2 Hz, 1H), 5.10 (s, 1H), 4.75 (t, J=6 Hz, 2H), 3.68 (t, J=6.2 Hz, 2H), 1.07 (s, 9H). $^{19}$F-NMR 400 MHz (CD$_3$OD) δ: −77.77 (s, 2F). LCMS-ESI$^+$ (m/z): [M+H]$^+$ calcd for C$_{28}$H$_{26}$F$_2$NO$_4$: 478.1; Found: 478.1.

EXAMPLE 31 tert-Butoxy-[1-(2,4-dichloro-phenyl)-3-methyl-naphthalen-2-yl]-acetic acid (33)

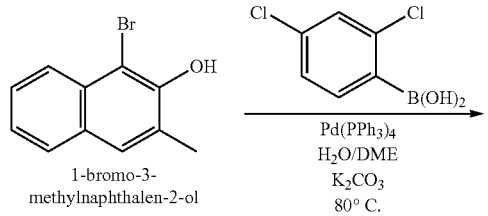

1-bromo-3-methylnaphthalen-2-ol

Pd(PPh$_3$)$_4$
H$_2$O/DME
K$_2$CO$_3$
80° C.

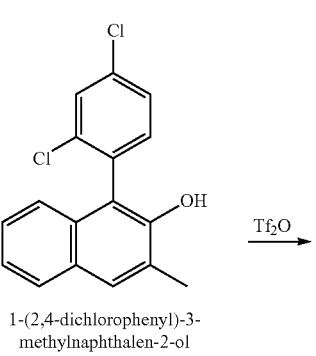

1-(2,4-dichlorophenyl)-3-methylnaphthalen-2-ol

Tf$_2$O →

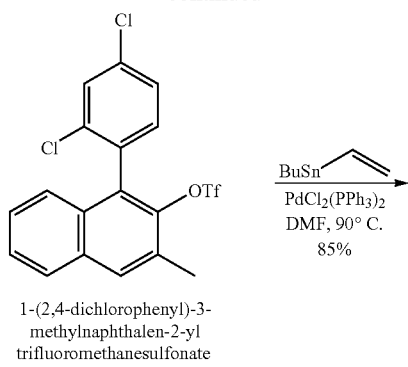

1-(2,4-dichlorophenyl)-3-methylnaphthalen-2-yl trifluoromethanesulfonate

BuSn⁀
PdCl$_2$(PPh$_3$)$_2$
DMF, 90° C.
85%

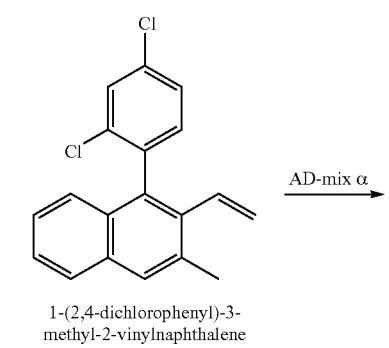

1-(2,4-dichlorophenyl)-3-methyl-2-vinylnaphthalene

AD-mix α →

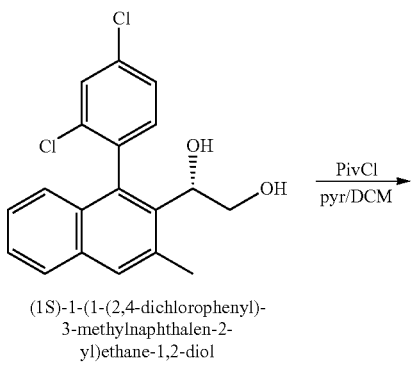

(1S)-1-(1-(2,4-dichlorophenyl)-3-methylnaphthalen-2-yl)ethane-1,2-diol

PivCl
pyr/DCM →

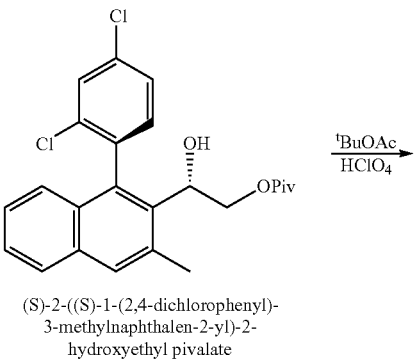

(S)-2-((S)-1-(2,4-dichlorophenyl)-3-methylnaphthalen-2-yl)-2-hydroxyethyl pivalate $^t$BuOAc
HClO$_4$ →

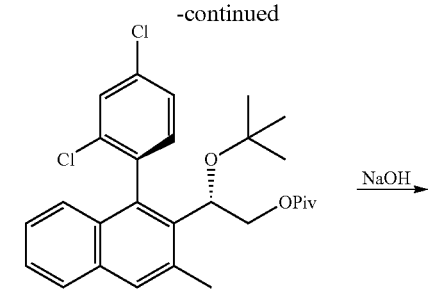

(S)-2-tert-butoxy-2-((S)-1-(2,4-dichlorophenyl)-3-methylnaphthalen-2-yl)-ethyl pivalate NaOH ↓

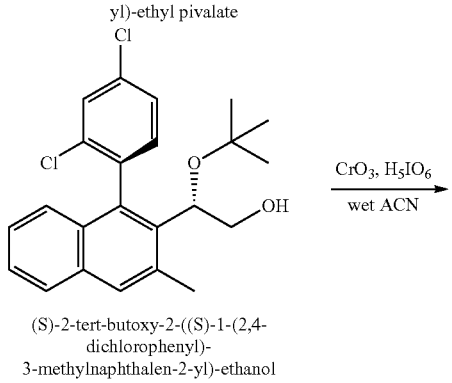

(S)-2-tert-butoxy-2-((S)-1-(2,4-dichlorophenyl)-3-methylnaphthalen-2-yl)-ethanol CrO₃, H₅IO₆ / wet ACN ↓

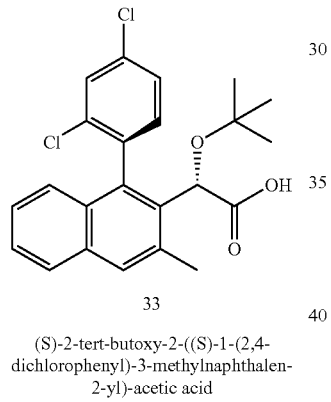

33
(S)-2-tert-butoxy-2-((S)-1-(2,4-dichlorophenyl)-3-methylnaphthalen-2-yl)-acetic acid Preparation of 1-(2,4-dichlorophenyl)-3-methylnaphthalen-2-ol: A mixture of 2,4-dichlorophenylboronic acid (1.0 g), tetrakis(triphenylphosphine)palladium(0) (300 mg), 1-bromo-3-methyl-naphthalen-2-ol (5B, 625 mg) in K₂CO₃ (2 M, 5.3 mL) and DME (26 mL) was degassed with argon and sealed in a Schlenk tube. The reaction was heated to 80° C. for 75 minutes, then cooled to room temperature. The reaction was diluted with EtOAc and filtered through a pad of silica gel. The silica was washed with EtOAc and the combined organics were concentrated. The crude residue was purified by flash column chromatography (0-18% EtOAc in hexanes) to yield 784 mg of desired product.

Preparation of 1-(2,4-dichlorophenyl)-3-methylnaphthalen-2-yl trifluoromethanesulfonate: 1-(2,4-dichlorophenyl)-3-methylnaphthalen-2-yl trifluoromethanesulfonate was prepared in a similar manner as compound 4C in Example 2, except starting from 1-(2,4-dichlorophenyl)-3-methylnaphthalen-2-ol instead of 4B. ¹H-NMR: 400 MHz, (CDCl₃) δ: 7.85-7.90 (m, 2H), 7.62 (d, 1H), 7.55 (app dt, 1H), 7.41-7.48 (m, 2H), 7.32-7.49 (m, 2H), 2.64 (s, 3H).

Preparation of tert-butoxy-[1-(2,4-dichloro-phenyl)-3-methyl-naphthalen-2-yl]-acetic acid (33): tert-butoxy-[1-(2,4-dichloro-phenyl)-3-methyl-naphthalen-2-yl]-acetic acid (33) was prepared in a similar manner as compound 3K in Example 1, except starting from 1-(2,4-dichlorophenyl)-3-methylnaphthalen-2-yl trifluoromethanesulfonate instead of 3E. ¹H-NMR: 400 MHz, (CD₃CN) δ: 7.84 (d, 1H), 7.78 (s, 1H), 7.69 (d, 1H), 7.63 (d, 1H), 7.47-7.54 (m, 2H), 7.37 (app dt, 1H), 7.16 (d, 1H), 5.17 (s, 1H), 2.60 (s, 3H), 1.06 (s, 9H).

EXAMPLE 32 tert-Butoxy-[1-(4-chloro-phenyl)-5-methoxy-3-methyl-naphthalen-2-yl]-acetic acid (34)

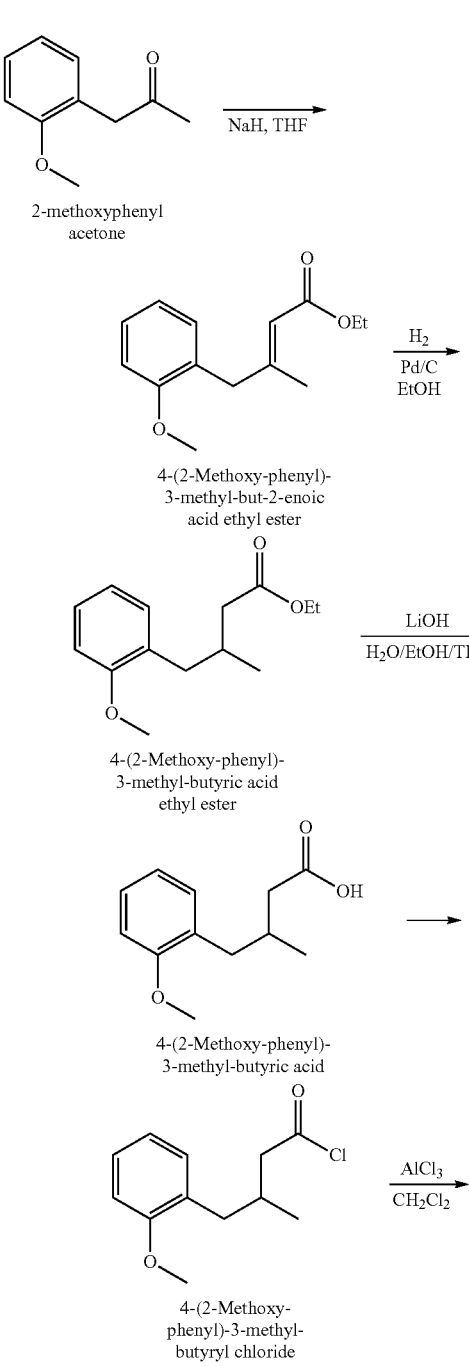

183
-continued

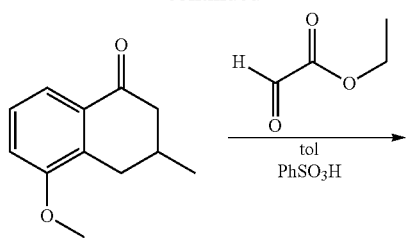

5-Methoxy-3-methyl-
3,4-dihydro-2H-
naphthalen-1-one

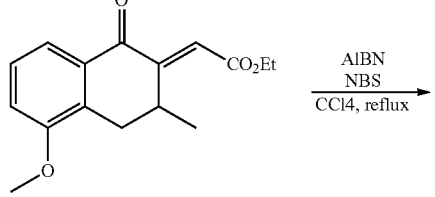

(5-Methoxy-3-methyl-1-
oxo-3,4-dihydro-1H-
naphthalen-2-ylidene)-
acetic acid ethyl ester

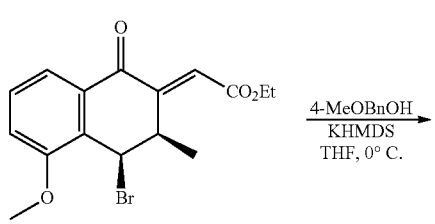

(4-Bromo-5-methoxy-3-
methyl-1-oxo-3,4-dihydro-
1H-naphthalen-2-ylidene)-
acetic acid ethyl ester

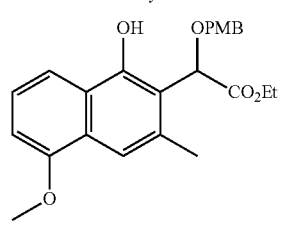

(1-Hydroxy-5-methoxy-3-
methyl-naphthalen-2-yl)
(4-methoxy-benzyloxy)-
acetic acid ethyl ester

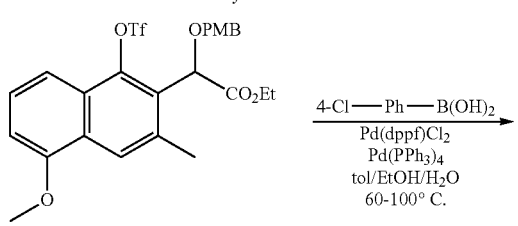

(4-Methoxy-benzyloxy)-(5-
methoxy-3-methyl-1-
trifluoromethanesulfonyloxy-
naphthalen-2-yl)-acetic
acid ethyl ester

184
-continued

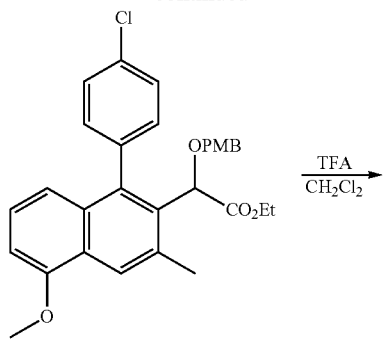

[1-(4-Chloro-phenyl)-5-
methoxy-3-methyl-
naphthalen-2-yl]-(4-methoxy-
benzyloxy)-acetic acid ethyl
ester

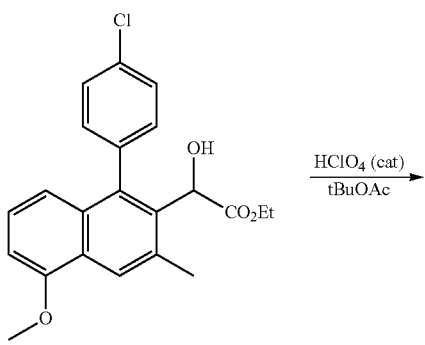

[1-(4-Chloro-phenyl)-5-methoxy-
3-methyl-naphthalen-2-yl]-
hydroxy-acetic acid ethyl ester

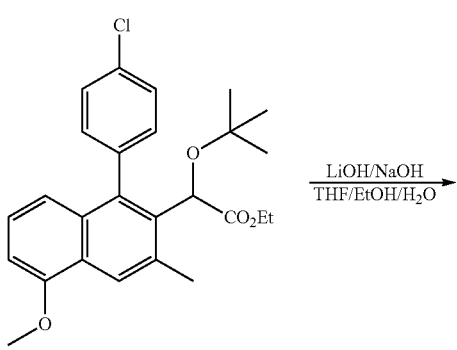

tert-Butoxy-[1-(4-chloro-phenyl)-
5-methoxy-3-methyl-naphthalen-
2-yl]-acetic acid ethyl ester -continued

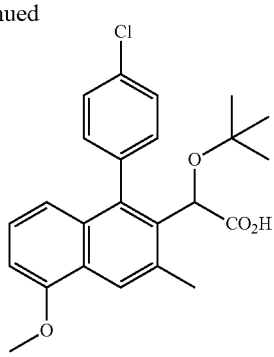

34
tert-Butoxy-[1-(4-chloro-phenyl)-5-methoxy-3-methyl-naphthalen-2-yl]-acetic acid Preparation of 4-(2-methoxyphenyl)-3-methyl-but-2-enoic acid ethyl ester: In a 3-neck round bottom flask, fitted with an internal thermometer and addition funnel, a mixture of sodium hydride (60% in mineral oil, 4.14 g) in THF (200 mL), under argon, was cooled to 10° C. (Diethoxyphosphoryl)acetic acid ethyl ester (21 mL) was added dropwise (heat and gas evolution), keeping the internal temperature below room temperature. After addition, the reaction mixture was stirred at room temperature for minutes, and then cooled to 0° C. A solution of 2-methoxyphenyl acetone (5 g) in THF (25 mL) was added dropwise over 5 minutes. The reaction was allowed to warm to room temperature overnight. With active cooling, the reaction was quenched with $H_2O$ (200 mL), then AcOH (to pH ~6) and extracted with EtOAc. The combined organics were washed with $NaHCO_3$, water, and brine, dried over $Na_2SO_4$, and concentrated. The crude residue was purified by flash column chromatography to give the desired compound (5.73 g). $^1$H-NMR: 400 MHz, ($CDCl_3$) δ: 7.24 (app dt, 1H), 7.10 (dd, 1H), 6.92 (d, 1H), 6.88 (d, 1H), 5.58 (s, 1H), 4.13 (q, 2H), 3.82 (s, 3H), 3.46 (s, 2H), 1.26 (t, 3H).

Preparation of 4-(2-methoxyphenyl)-3-methyl-butyric acid ethyl ester: Palladium on carbon (10%, wet Degussa, 300 mg) was degassed. Ethanol (60 mL), degassed with argon, was added followed by 4-(2-methoxyphenyl)-3-methyl-but-2-enoic acid ethyl ester (5.7 g, 24 mmol). Hydrogen was bubbled through the ethanol, and the reaction was stirred under 1 atm of $H_2$ (balloon)overnight. The balloon was removed, and the reaction was flushed with argon and the reaction was filtered through Celite. The Celite was washed with ethyl acetate and the filtrates dried over magnesium sulfate and concentrated. The crude residue was used without further purification. LCMS-ESI$^+$ (m/z): [M]$^+$ calcd for $C_{14}H_{20}O_3$: 236.14. Found: 236.96.

Preparation of 4-(2-methoxyphenyl)-3-methyl-butyric acid: A solution of 4-(2-methoxyphenyl)-3-methyl-butyric acid ethyl ester (24 mmol, crude from previous reaction) in THF (50 mL), EtOH (50 mL) and LiOH (1 M, 50 mL) was stirred at room temperature overnight. The reaction was acidified with 1 M HCl, and extracted with EtOAc. The combined extracts were washed with brine and dried over sodium sulfate. Concentration gave the desired product, which was used without further purification. LCMS-ESI$^+$ (m/z): [M]$^+$ calcd for $C_{12}H_{16}O_3$: 208.11. Found: 208.86.

Preparation of 4-(2-methoxyphenyl)-3-methyl-butyryl chloride: To a solution of 4-(2-methoxyphenyl)-3-methylbutyric acid (24 mmol, crude from previous reaction) in dichloromethane (36 mL) was added oxalyl chloride (2 M in DCM, 36 mL). The reaction was stirred for 1 h at room temperature. All volatiles were removed in vacuo and the crude residue used without further purification.

Preparation of 5-methoxy-3-methyl-3,4-dihydro-2H-naphthalen-1-one: A mixture of $AlCl_3$ (6.4 g) and $CH_2Cl_2$ (100 mL) was cooled to 0° C. To the mixture was added 4-(2-methoxyphenyl)-3-methylbutyryl chloride (24 mmol, crude from previous reaction). The reaction was allowed to warm slowly to room temperature and then quenched by slowly pouring over ice. The mixture was extracted with dichloromethane (3×) and the combined organics were washed with 1 M HCl, water, dried over sodium sulfate, and concentrated. Purification by flash column chromatography yielded the desired product (1.65 g, 36% yield from 4-(2-methoxy-phenyl)-3-methyl-but-2-enoic acid ethyl ester). LCMS-ESI$^+$ (m/z): [M+H]$^+$ calcd for $C_{12}H_{15}O_2$: 191.11. Found: 191.19.

Preparation of (5-methoxy-3-methyl-1-oxo-3,4-dihydro-1H-naphthalen-2-ylidene)-acetic acid ethyl ester: In a heavy walled sealed tube, 5-methoxy-3-methyl-3,4-dihydro-2H-naphthalen-1-one (1.3 g, 6.8 mmol), ethyl glyoxylate (3 mL, 50% solution in toluene), benzenesulfonic acid (100 mg), magnesium sulfate (5 g), and toluene (30 mL) were heated to 120° C. for 13 hours. The reaction was cooled to room temp, filtered, diluted with water, and extracted with ethyl acetate. The extracts were washed with brine, dried with sodium sulfate, and concentrated. The crude residue was purified by flash column chromatography to yield the desired product (960 mg, 51% yield). LCMS-ESI$^+$ (m/z): [M+H]$^+$ calcd for $C_{16}H_{19}O_4$: 275.13. Found: 275.26.

Preparation of (4-bromo-5-methoxy-3-methyl-1-oxo-3,4-dihydro-1H-naphthalen-2-ylidene)-acetic acid ethyl ester: A mixture of (5-methoxy-3-methyl-1-oxo-3,4-dihydro-1H-naphthalen-2-ylidene)-acetic acid ethyl ester (480 mg), NBS (420 mg), and AIBN (30 mg) in $CCl_4$ (18 mL) was refluxed for 3 hours. The reaction mixture was then cooled to room temperature, quenched with saturated sodium bicarbonate solution and extracted with dichloromethane (2×). The combined organics were washed with water, dried ($Na_2SO_4$), concentrated, and purified by flash column chromatography to give a light brown solid (420 mg) LCMS-ESI$^+$ (m/z): [M+H]$^+$ calcd for $C_{16}H_{18}BrO_4$: 353.03. Found: 352.91.

Preparation of (1-hydroxy-5-methoxy-3-methyl-naphthalen-2-yl)-(4-methoxy-benzyloxy)-acetic acid ethyl ester: To a solution of 4-methoxybenzyl alcohol (0.27 mL, 4 equiv) in THF (11 mL) at 0° C. was added KHMDS (0.5 M in toluene, 3.4 mL, 3 equiv) and the resulting mixture was allowed to stir for 10 min at 0° C. A solution of (4-bromo-5-methoxy-3-methyl-1-oxo-3,4-dihydro-1H-naphthalen-2-ylidene)-acetic acid ethyl ester (200 mg) in THF (1 mL) was added slowly. After stirring for 3 min at 0° C., the reaction was quenched with citric acid (1 M) and extracted with EtOAc. The organic extracts were washed with brine, dried over $Na_2SO_4$ and concentrated. The crude residue was purified by flash column chromatography (5-20% EtOAc/hexanes) to give 157 mg of pale orange oil (68% yield). LCMS-ESI$^+$ (m/z): [M+H]$^+$ calcd for $C_{24}H_{27}O_6$: 411.18. Found: 411.21.

Preparation of (4-methoxybenzyloxy)-(5-methoxy-3-methyl-1-trifluoromethanesulfonyloxy-naphthalen-2-yl)-acetic acid ethyl ester: A solution of (1-hydroxy-5-methoxy-3-methyl-naphthalen-2-yl)-(4-methoxy-benzyloxy)-acetic acid ethyl ester (157 mg, 0.38 mmol) in dichloromethane (3.8 mL) was cooled to −78° C. under Ar. To the solution was added 2,6-lutidine (0.1 mL) and triflic anhydride (0.1 mL) and stirred at −78° C. for 2.5 hours. Saturated sodium bicarbonate (3 mL) was added and the reaction mixture was warmed to room temperature and diluted with dichloromethane. The dichloromethane was separated, the aqueous layer extracted with $CH_2Cl_2$, and the combined organics dried over sodium sulfate and concentrated. The crude residue was purified by flash column chromatography to give the desired product (128 mg, 62% yield). LCMS-ESI$^+$ (m/z): [M+Na]$^+$ calcd for $C_{25}H_{25}F_3NaO_8S$: 565.11. Found: 565.23.

Preparation of [1-(4-chlorophenyl)-5-methoxy-3-methyl-naphthalen-2-yl]-(4-methoxybenzyloxy)acetic acid ethyl ester: A solution of (4-methoxy-benzyloxy)-(5-methoxy-3-methyl-1-trifluoromethanesulfonyloxy-naphthalen-2-yl)-acetic acid ethyl ester (128 mg, 0.236 mmol), 4-chlorophenylboronic acid (74 mg, 2 equiv), EtOH (0.5 mL), $K_2CO_3$ (2 M, 0.5 mL), and toluene (1.3 mL) were degassed with argon at room temperature in a Schlenk tube. Pd(dppf)$Cl_2$ was then added (17 mg) and the tube sealed. The reaction was heated to 60° C. for 14 hours. Analysis of the reaction mixture by LCMS showed 40% conversion, with visual analysis showing significant amount of palladium black. The crude mixture was filtered via syringe through a microfilter into a new sealable tube charged with Pd(PPh$_3$)$_4$. The tube was sealed and heated to 100° C. for 16 hours. The reaction was cooled to room temperature, diluted with EtOAc and filtered through Celite. The filtrate was concentrated, and the crude residue purified by flash column chromatography to give the desired product (60 mg, 50% yield). LCMS-ESI$^+$ (m/z): [M+Na]$^+$ calcd for $C_{30}H_{29}ClNaO_5$: 527.99. Found: 527.44.

Preparation of [1-(4-chloro-phenyl)-5-methoxy-3-methyl-naphthalen-2-yl]-hydroxy-acetic acid ethyl ester: To a solution of [1-(4-chloro-phenyl)-5-methoxy-3-methyl-naphthalen-2-yl]-(4-methoxy-benzyloxy)-acetic acid ethyl ester (58 mg, 0.115 mmol) in dichloromethane (3 mL) was added trifluoroacetic acid (58 µL). The reaction mixture was stirred for 2 h at room temperature and then quenched carefully with sat. NaHCO$_3$. The aqueous layer was extracted with dichloromethane twice, and then the combined organic layers were washed with water, dried (Na$_2$SO$_4$), concentrated and purified by flash column chromatography to give desired (23 mg).

Preparation of tert-butoxy-[1-(4-chloro-phenyl)-5-methoxy-3-methyl-naphthalen-2-yl]-acetic acid ethyl ester: A solution of [1-(4-chloro-phenyl)-5-methoxy-3-methyl-naphthalen-2-yl]-hydroxy-acetic acid ethyl ester (23 mg) and perchloric acid, 70% (3 µL) in tert-butyl acetate (1 mL) was stirred at room temperature for 2 h. After 2 h, the reaction had apparently stalled, so 3 µL additional perchloric acid was added. After 2 additional hours, no further conversion was observed (LCMS analysis). Saturated sodium bicarbonate solution was added and the mixture was extracted with ethyl acetate (3×). The combined organic layer was dried (Na$_2$SO$_4$), and concentrated. The crude mixture was purified by flash column chromatography to give tert-butoxy-[1-(4-chloro-phenyl)-5-methoxy-3-methyl-naphthalen-2-yl]-acetic acid ethyl ester (9 mg) plus 7 mg of recovered starting material. The recovered starting material was re-subjected to similar reaction conditions to yield an additional 3 mg of desired. $^1$H-NMR: 400 MHz, (CDCl$_3$) δ: 8.10 (s, 1H), 7.39-7.48 (m, 3H), 7.25 (s, 1H), 7.17 (app t, 1H), 6.78 (app t, 2H), 5.09 (s, 1H), 4.06-4.20 (m, 2H), 3.99 (s, 3H), 2.61 (s, 3H), 1.185 (t, 3H), 0.98 (s, 9H).

Preparation of tert-butoxy-[1-(4-chlorophenyl)-5-methoxy-3-methyl-naphthalen-2-yl]-acetic acid (34): To a solution of tert-butoxy-[1-(4-chloro-phenyl)-5-methoxy-3-methyl-naphthalen-2-yl]-acetic acid ethyl ester (12 mg) in THF (0.3 mL) and EtOH (0.1 mL) was added 0.1 mL of 1 M LiOH. The reaction was stirred for 30 min at room temperature, then 0.3 mL each of THF, EtOH, and 1 M NaOH were added. The reaction was heated to 70° C. for 2.5 hours, and then cooled to room temperature. Formic acid was added until pH ~5. The reaction mixture was directly purified by HPLC (Gemini, 50-100% MeCN/H$_2$O, with 0.1% TFA). The product was lyophilized to give a white powder (8 mg).

$^1$H-NMR: 400 MHz, (CD$_3$CN) δ: 8.09 (s, 1H), 7.49-7.58 (m, 3H), 7.32 (br d, 1H), 7.26 (app t, 1H), 6.91 (d, 1H), 6.81 (d, 1H), 5.19 (s, 1H), 3.99 (s, 3H), 2.57 (s, 3H), 0.99 (s, 9H). LCMS-ESI$^+$ (m/z): [M-OtBu]$^+$ calcd for $C_{20}H_{16}ClO_3$: 339.79; found: 339.07.

EXAMPLE 33

Ethyl 2-(5-bromo-3-methyl-1-(trifluoromethylsulfonyl-oxy) naphthalen-2-yl)-2-(4-methoxybenzyloxy) acetate (35)

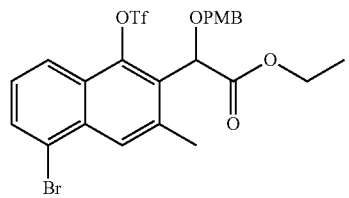

ethyl 2-(5-bromo-3-methyl-1-(((trifluoromethyl)sulfonyl)oxy)naphthalen-2-yl)-2-((4-methoxybenzyl)oxy)acetate Preparation of ethyl 2-(5-bromo-3-methyl-1-(trifluoromethylsulfonyl-oxy)naphthalen-2-yl)-2-(4-methoxybenzyloxy)acetate (35): Ethyl 2-(5-bromo-3-methyl-1-(trifluoromethylsulfonyloxy)naphthalen-2-yl)-2-(4-methoxybenzyl oxy)acetate (35) was prepared similarly to ethyl 2-(6-methoxy-3-methyl-1-(trifluoromethylsulfonyloxy)naphthalen-2-yl)-2-(4-methoxybenzyloxy)acetate of Example 32, using 1-(2-bromophenyl)propan-2-one as the starting material instead of 1-(3-methoxyphenyl)propan-2-one. $^1$H-NMR: 400 MHz, (CDCl$_3$) δ: 8.11 (s, 1H), 8.01 (d, J=8.8 Hz, 1H), 7.85 (d, J=7.6 Hz, 1H), 7.40 (t, J=7.6 Hz, 1H), 7.23 (d, J=8.4 Hz, 2H), 6.81 (d, J=7.6 Hz, 2H), 5.61 (s, 1H), 4.62 (q, J=11.2 Hz, 2H), 4.26-4.15 (m, 2H), 3.75 (s, 3H), 2.62 (s, 3H), 1.18 (t, J=6.8 Hz, 3H).

EXAMPLE 34

Ethyl 2-(5-bromo-1-(4-chlorophenyl)-3-methylnaphthalen-2-yl)-2-oxoacetate (36A) and Ethyl 2-(1,5-bis (4-chlorophenyl)-3-methylnaphthalen-2-yl)-2-oxoacetate (36B):

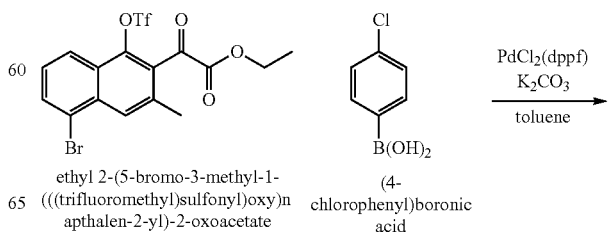

ethyl 2-(5-bromo-3-methyl-1-(((trifluoromethyl)sulfonyl)oxy)naphthalen-2-yl)-2-oxoacetate (4-chlorophenyl)boronic acid

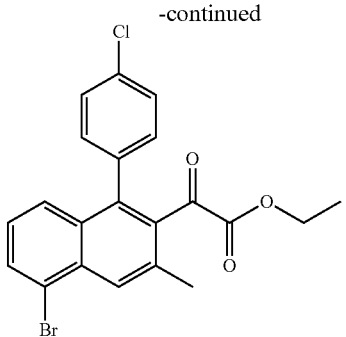

36A ethyl 2-(5-bromo-1-(4-chlorophenyl)-3-methylnaphthalen-2-yl)-2-oxoacetate

+

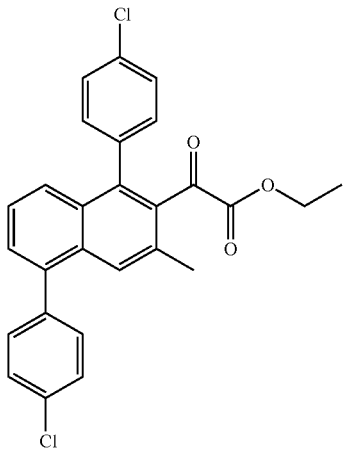

36B ethyl 2-(1,5bis(4-chlorophenyl)-3-methylnaphthalen-2-yl)-2-oxoacetate

Preparation of ethyl 2-(5-bromo-3-methyl-1-(trifluoromethylsulfonyloxy) naphthalen-2-yl)-2-oxoacetate: Prepared similarly to ethyl 2-(7-bromo-3-methyl-1-(trifluoromethylsulfonyloxy)naphthalen-2-yl)-2-oxoacetate of Example 67, using ethyl 2-(5-bromo-3-methyl-1-(trifluoromethylsulfonyloxy)naphthalen-2-yl)-2-(4-methoxybenzyloxy)acetate instead of ethyl 2-(7-bromo-3-methyl-1-(trifluoromethylsulfonyloxy)naphthalen-2-yl)-2-(4-methoxybenzyloxy)acetate. $^1$H-NMR: 400 MHz, (CDCl$_3$) δ: 8.20 (s, 1H), 8.08 (d, J=8.4 Hz, 1H), 7.95 (dd, J=7.4, 0.8 Hz, 1H), 7.48 (t, J=8.4 Hz, 1H), 4.42 (q, J=7.2 Hz, 2H), 2.54 (s, 3H), 1.40 t, J=7.6 Hz, 3H).

Preparation of ethyl 2-(5-bromo-1-(4-chlorophenyl)-3-methylnaphthalen-2-yl)-2-oxoacetate (36A) and ethyl 2-(1,5-bis(4-chlorophenyl)-3-methylnaphthalen-2-yl)-2-oxoacetate (36B): To a solution of ethyl 2-(5-bromo-3-methyl-1-(trifluoromethylsulfonyloxy)naphthalen-2-yl)-2-oxoacetate (1.2 g, 2.56 mmol) and 4-chlorophenylboronic acid (440 mg, 2.81 mmol) in toluene was added 2 M potassium carbonate (2.8 mL, 5.63 mmol) and PdCl$_2$(dppf) (187 mg, 0.256 mmol) and the reaction was degassed with argon 10 minutes. The reaction was stirred at room temperature for 4 hours. The reaction was filtered, diluted with water, extracted with ethyl acetate and concentrated. The crude reaction was purified by flash column chromatography (silica gel, ethyl acetate/hexanes) followed by reverse phase HPLC (Gemini, 40-100% ACN/H$_2$O+0.1% TFA). Product was lyophilized to give 670 mg of ethyl 2-(5-bromo-1-(4-chlorophenyl)-3-methylnaphthalen-2-yl)-2-oxoacetate (36A) as a yellow oil, $^1$H-NMR: 400 MHz, (CDCl$_3$) δ: 8.20 (s, 1H), 8.13 (d, J=8.8 Hz, 1H), 7.85 (d, J=6.8 Hz, 1H), 7.68 (t, J=7.2 Hz, 1H), 7.51 (d, J=8.8 Hz, 2H), 7.39 (d, J=8.4 Hz, 2H), 3.95 (q, J=6.8 Hz, 2H), 2.41 (s, 3H), 1.14 (t, J=7.2 Hz, 5H); and 109 mg of ethyl 2-(1,5-bis(4-chlorophenyl)-3-methylnaphthalen-2-yl)-2-oxoacetate (36B) as a white solid. $^1$H-NMR: 400 MHz, (CDCl$_3$) δ: 7.72 (s, 1H), 7.59-7.56 (m, 1H), 7.50 (t, J=8.0 Hz, 2H), 7.46-7.44 (m, 5H), 7.43 (d, J=2.4 Hz, 1H), 7.28 (d, J=8.0 Hz, 2H), 3.94 (q, J=7.2 Hz, 2H), 2.42 (s, 3H), 1.14 (t, J=7.2 Hz, 3H).

EXAMPLE 35

2-(5-Bromo-1-(4-chlorophenyl)-3-methylnaphthalen-2-yl)-2-tert-butoxyacetic acid (37)

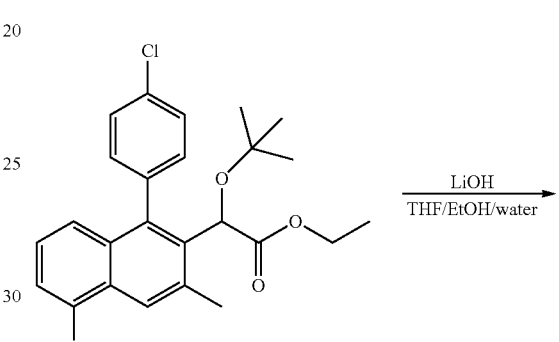

ethyl 2-(5-bromo-1-(4-chlorophenyl)-3-methylnaphthalen-2-yl)-2-(tert-butoxy)acetate → LiOH, THF/EtOH/water

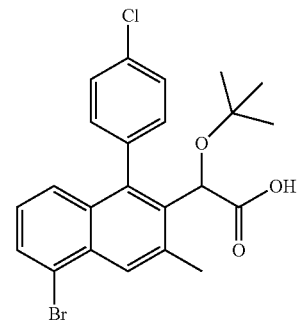

37

2-(5-bromo-1-(4-chlorophenyl)-3-methylnaphthalen-2-yl)-2-(tert-butoxy)acetic acid Preparation of ethyl 2-(5-bromo-1-(4-chlorophenyl)-3-methylnaphthalen-2-yl)-2-tert-butoxyacetate: Prepared similarly to ethyl 2-(7-bromo-1-(4-chlorophenyl)-3-methylnaphthalen-2-yl)-2-tert-butoxyacetate of Example 67 using ethyl 2-(5-bromo-1-(4-chlorophenyl)-3-methylnaphthalen-2-yl)-2-oxoacetate instead of ethyl 2-(7-bromo-1-(4-chlorophenyl)-3-methylnaphthalen-2-yl)-2-oxoacetate. Product was carried on crude to next reaction.

Preparation of 2-(5-bromo-1-(4-chlorophenyl)-3-methylnaphthalen-2-yl)-2-tert-butoxyacetic acid (37): To a solution of ethyl 2-(5-bromo-1-(4-chlorophenyl)-3-methylnaphthalen-2-yl)-2-tert-butoxyacetate (30 mg, 0.061 mmol) in tetrahydrofuran:ethanol:water (2:2:1, 3 mL) was added lithium hydroxide (7 mg, 0.31 mmol) and the reaction was heated to 50° C. overnight. Crude reaction purified by reverse phase HPLC (Gemini, 40-100% ACN/H$_2$O+0.1% TFA). Product lyophilized to give a white powder (5.9 mg). $^1$H-NMR: 400 MHz, (CD$_3$OD) δ: 8.07 (s, 1H), 7.77 (d, J=6.0 Hz, 1H), 7.58 (s, 2H), 7.55 (as, 1H), 7.32 (d, J=8.8 Hz, 1H), 7.26 (d, J=8.8 Hz, 1H), 7.18 (m, 1H), 5.17 (s, 1H), 2.67 (s, 3H), 0.99 (s, 9H). LCMS-ESI$^-$ (m/z): [M–H]$^-$ calcd for C$_{23}$H$_{21}$BrClO$_3$: 460.8. found; 460.2.

EXAMPLE 36

2-(1,5-Bis(4-chlorophenyl)-3-methylnaphthalen-2-yl)-2-tert-butoxyacetic acid (38)

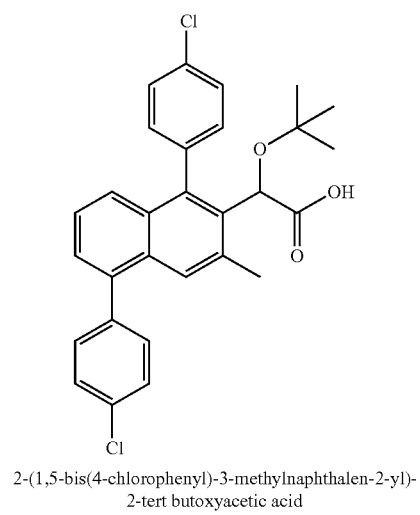

2-(1,5-bis(4-chlorophenyl)-3-methylnaphthalen-2-yl)-2-tert butoxyacetic acid

Preparation of 2-(1,5-bis(4-chlorophenyl)-3-methylnaphthalen-2-yl)-2-tert-butoxyacetic acid (38): 2-(1,5-Bis(4-chlorophenyl)-3-methylnaphthalen-2-yl)-2-tert-butoxyacetic acid (38) was prepared similarly to 2-(5-bromo-1-(4-chlorophenyl)-3-methylnaphthalen-2-yl)-2-tert-butoxyacetic acid of Example 35 using ethyl 2-(1,5-bis(4-chlorophenyl)-3-methylnaphthalen-2-yl)-2-oxoacetate instead of ethyl 2-(5-bromo-1-(4-chlorophenyl)-3-methylnaphthalen-2-yl)-2-oxoacetate. $^1$H-NMR: 400 MHz, (CD$_3$OD) δ: 7.59 (m, 4H), 7.53 (d, J=8.4 Hz, 2H), 7.45 (d, J=8.4 Hz, 2H), 7.35 (m, 3H), 7.28 (m, 1H), 5.18 (s, 1H), 2.51 (s, 3H), 0.99 (s, 9H). LCMS-ESI$^-$ (m/z): [M–H]$^-$ calcd for C$_{29}$H$_{26}$Cl$_2$O$_3$: 491.13; found: 491.42.

EXAMPLE 37

2-tert-Butoxy-2-(1-(4-chlorophenyl)-5-(3-(dimethylamino)prop-1-ynyl)-3-methylnaphthalen-2-yl)acetic acid (39)

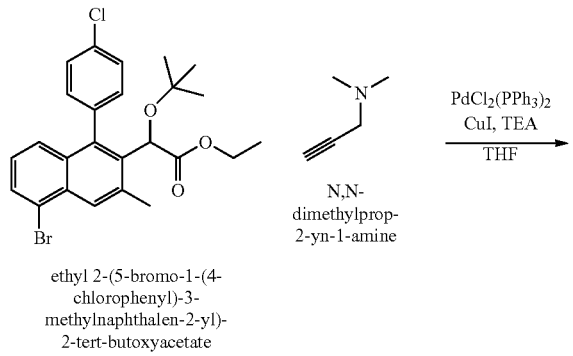

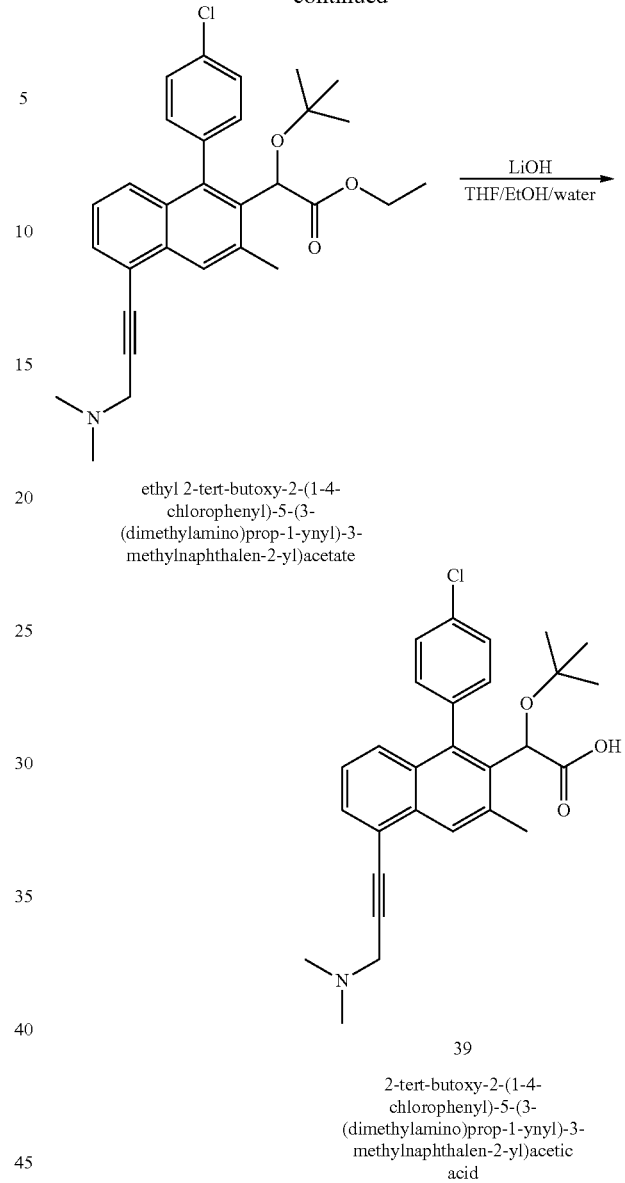

Preparation of ethyl 2-tert-butoxy-2-(1-(4-chlorophenyl)-5-(3-(dimethylamino)prop-1-ynyl)-3-methylnaphthalen-2-yl)acetate: To a solution of ethyl 2-(5-bromo-1-(4-chlorophenyl)-3-methylnaphthalen-2-yl)-2-tert-butoxyacetate (100 mg, 0.20 mmol) and N,N-dimethylprop-2-yn-1-amine (0.065 mL, 0.61 mmol) in anhydrous tetrahydrofuran was added copper iodide (8 mg, 0.04 mmol) and PdCl$_2$(PPh$_3$)$_2$ (14 mg, 0.02 mmol). The reaction was heated to 100° C. overnight. After cooling to room temperature the reaction was charged with PdCl$_2$(PPh$_3$)$_2$ (14 mg, 0.02 mmol), copper iodide (8 mg, 0.04 mmol), N,N-dimethylprop-2-yn-1-amine (0.065 mL, 0.61 mmol) and triethylamine (1 mL). The reaction was heated to 100° C. overnight. To the reaction was then added N,N-dimethylprop-2-yn-1-amine (0.065 mL, 0.61 mmol) and heated to 100° C. overnight. The crude reaction mixture was absorbed onto silica gel and purified by flash column chromatography (silica gel, ethyl acetate/hexanes, methanol/ethyl acetate) to give a yellow oil (6.5 mg). LCMS-ESI$^+$ (m/z): [M+H]$^+$ calcd for C$_{30}$H$_{35}$ClNO$_3$: 492.22; found: 492.15.

Preparation of 2-tert-butoxy-2-(1-(4-chlorophenyl)-5-(3-(dimethylamino)prop-1-ynyl)-3-methylnaphthalen-2-yl)acetic acid (39): To a solution of ethyl 2-tert-butoxy-2-(1-(4-chlorophenyl)-5-(3-(dimethylamino)prop-1-ynyl)-3-methylnaphthalen-2-yl)acetate (6.5 mg, 0.013 mmol) in tetrahydrofuran:ethanol:water (2:2:1, 4 mL) was added lithium hydroxide (2 mg, 0.066 mmol) and the reaction was heated to 50° C. overnight. The reaction was purified by reverse phase HPLC (Gemini, 40-60% ACN/H$_2$O+0.1% TFA). The product was lyophilized to give a white powder (1.2 mg). $^1$H-NMR: 400 MHz, (CD$_3$OD) δ: 8.14 (s, 1H), 7.74 (d, J=6.4 Hz, 1H), 7.58 (s, 2H), 7.56 (as, 1H), 7.33 (m, 3H), 5.18 (s, 1H), 4.42 (s, 2H), 3.04 (s, 6H), 2.67 (s, 3H), 0.99 (s, 9H). LCMS-ESI$^+$ (m/z): [M+H]$^+$ calcd for C$_{28}$H$_{31}$ClNO$_3$: 464.19; found: 464.51.

EXAMPLE 38

2-tert-Butoxy-2-(1-(4-chlorophenyl)-3,5-dimethyl-naphthalen-2-yl)acetic acid (40)

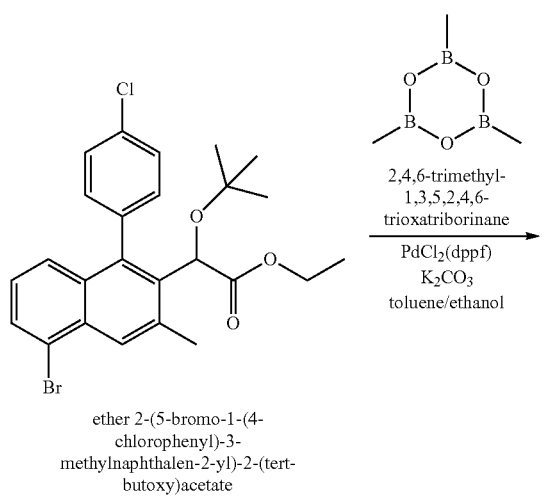

ether 2-(5-bromo-1-(4-chlorophenyl)-3-methylnaphthalen-2-yl)-2-(tert-butoxy)acetate 2,4,6-trimethyl-1,3,5,2,4,6-trioxatriborinane PdCl$_2$(dppf)
K$_2$CO$_3$
toluene/ethanol

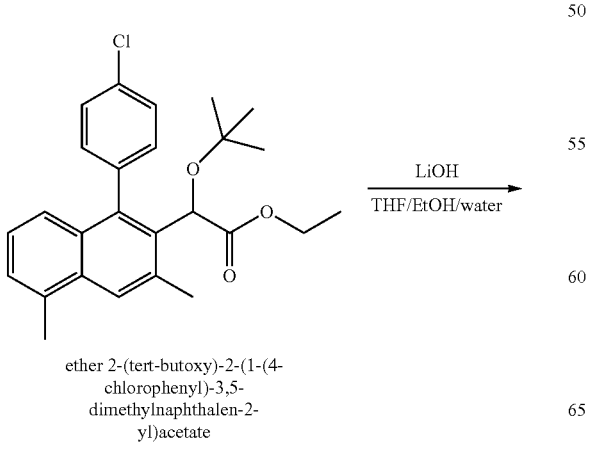

ether 2-(tert-butoxy)-2-(1-(4-chlorophenyl)-3,5-dimethylnaphthalen-2-yl)acetate

LiOH
THF/EtOH/water

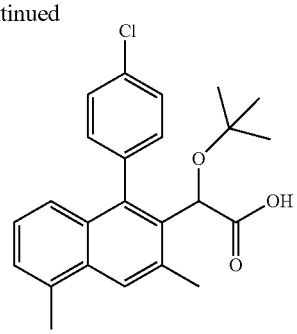

40
2-(tert-butoxy)-2-(1-(4-chlorophenyl)-3,5-dimethylnaphthalen-2-yl)acetic acid Preparation of ethyl 2-tert-butoxy-2-(1-(4-chlorophenyl)-3,5-dimethylnaphthalen-2-yl)acetate: To a solution of ethyl 2-(5-bromo-1-(4-chlorophenyl)-3-methylnaphthalen-2-yl)-2-tert-butoxyacetate (100 mg, 0.204 mmol) and 2,4,6-trimethyl-1,3,5,2,4,6-trioxatriborinane (0.086 mL, 0.61 mmol) in toluene:ethanol (2:1, 3 mL) and water (1 mL) was added potassium carbonate (282 mg, 2.04 mmol) and PdCl$_2$(dppf) (15 mg, 0.02 mmol) and the reaction was degassed with argon for 10 minutes. The reaction was heated to 100° C. for 20 minutes in a microwave reactor. The crude reaction was purified by flash column chromatography (silica gel, ethyl acetate/hexanes) to give a yellow oil (32 mg) $^1$H-NMR: 400 MHz, (CD$_3$OD) δ: 8.08-7.87 (m, 2H), 7.87 (s, 1H), 7.65-7.35 (m, 1H), 7.26 (m, 2H), 7.15 (d, J=7.2 Hz, 1H), 7.09 (d, J=8.0 Hz, 1H). 5.10 (s, 1H), 4.14 (m, 2H), 2.69 (s, 3H), 2.65 (s, 3H), 1.20 (t, J=6.8 Hz, 3H), 0.99 (s, 9H).

Preparation of 2-tert-butoxy-2-(1-(4-chlorophenyl)-3,5-dimethylnaphthalen-2-yl)acetic acid (40): To a solution of ethyl 2-tert-butoxy-2-(1-(4-chlorophenyl)-3,5-dimethylnaphthalen-2-yl)acetate (32 mg, 0.075 mmol) in tetrahydrofuran: ethanol:water (2:2:1, 3 mL) was added lithium hydroxide (9 mg, 0.377 mmol) and the reaction was heated to 50° C. overnight. The reaction was purified by reverse phase HPLC (Gemini, 40-100% ACN/H$_2$O+0.1% TFA). The product was lyophilized to give a white powder (16.8 mg). $^1$H-NMR: 400 MHz, (CD$_3$OD) δ: 7.86 (s, 1H), 7.54 (m, 3H), 7.29 (m, 2H), 7.16 (t, J=8.8 Hz, 1H), 7.08 (d, J=8.8 Hz, 1H), 5.17 (s, 1H), 2.69 (s, 3H), 2.65 (s, 3H), 0.98 (s, 9H). LCMS-ESI$^-$ (m/z): [M−H]$^-$ calcd for C$_{24}$H$_{24}$ClO$_3$: 395.15; found: 394.97.

EXAMPLE 39

2-tert-Butoxy-2-(1-(4-chlorophenyl)-3-methyl-5-(pyrimidin-5-yl)naphthalen-2-yl)acetic acid (41)

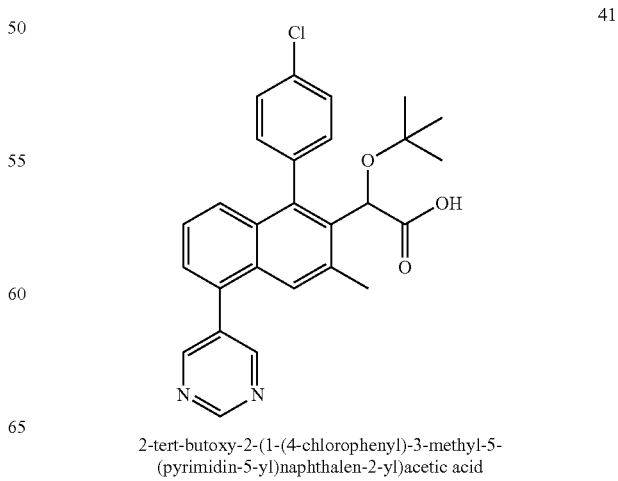

41

2-tert-butoxy-2-(1-(4-chlorophenyl)-3-methyl-5-(pyrimidin-5-yl)naphthalen-2-yl)acetic acid Preparation of 2-tert-butoxy-2-(1-(4-chlorophenyl)-3-methyl-5-(pyrimidin-5-yl)naphthalen-2-yl)acetic acid (41): 2-tert-Butoxy-2-(1-(4-chlorophenyl)-3-methyl-5-(pyrimidin-5-yl)naphthalen-2-yl)acetic acid (41) was prepared similarly to 2-tert-butoxy-2-(1-(4-chlorophenyl)-3,5-dimethylnaphthalen-2-yl)acetic acid of Example 38 using pyrimidin-5-ylboronic acid in place of 2,4,6-trimethyl-1,3,5,2,4,6-trioxatriborinane. $^1$H-NMR: 400 MHz, (CD$_3$OD) δ: 9.27 (s, 1H), 8.95 (s, 2H), 7.60 (s, 2H), 7.58 (s, 1H), 7.54 (s, 1H), 7.43 (m, 3H), 7.36 (d, J=8.4 Hz, 1H), 5.20 (s, 1H), 2.55 (s, 3H), 1.00 (s, 9H). LCMS-ESI$^+$ (m/z): [M+H]$^+$ calcd for C$_{27}$H$_{26}$ClN$_2$O$_3$: 461.16; found: 461.45.

EXAMPLE 40

2-tert-Butoxy-2-(1-(4-chlorophenyl)-6-fluoro-3-methylnaphthalen-2-yl)acetic acid (42

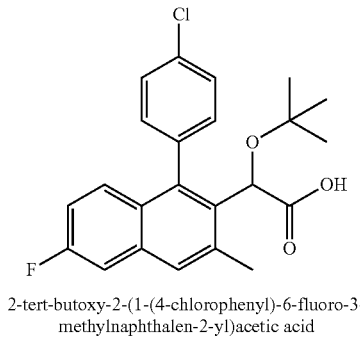

2-tert-butoxy-2-(1-(4-chlorophenyl)-6-fluoro-3-methylnaphthalen-2-yl)acetic acid Preparation of 2-tert-butoxy-2-(1-(4-chlorophenyl)-6-fluoro-3-methylnaphthalen-2-yl)acetic acid (42): 2-tert-Butoxy-2-(1-(4-chlorophenyl)-6-fluoro-3-methylnaphthalen-2-yl)acetic acid (42) was prepared similarly to 2-(5-bromo-1-(4-chlorophenyl)-3-methylnaphthalen-2-yl)-2-tert-butoxyacetic acid of Example 35, using 6-fluoro-3-methyl-3,4-dihydronaphthalen-1(2H)-one instead of 5-bromo-3-methyl-3,4-dihydronaphthalen-1(2H)-one. $^1$H-NMR: 400 MHz, (CD$_3$OD) δ: 7.67 (s, 1H), 7.57 (s, 2H), 7.55 (as, 1H), 7.45 (dd, J=9.8, 2.8 Hz, 1H), 7.32 (d, J=8.4 Hz, 1H), 7.27 (dd, J=9.4, 5.2 Hz, 1H), 7.11 (td, J=9.0, 2.4 Hz, 1H) 5.16 (s, 1H), 2.60 (s, 3H), 0.98 (s, 9H). $^{19}$F-NMR: 377 MHz, (CD$_3$OD) δ: −118.01 (s). LCMS-ESI$^-$ (m/z): [M—H]$^-$ calcd for C$_{23}$H$_{21}$ClFO$_3$: 399.12; found: 399.19.

EXAMPLE 41

2-tert-butoxy-2-((R)-1-(2,3-dihydropyrano[4,3,2-de]quinolin-7-yl)-6-fluoro-3-methylnaphthalen-2-yl)acetic acid (43)

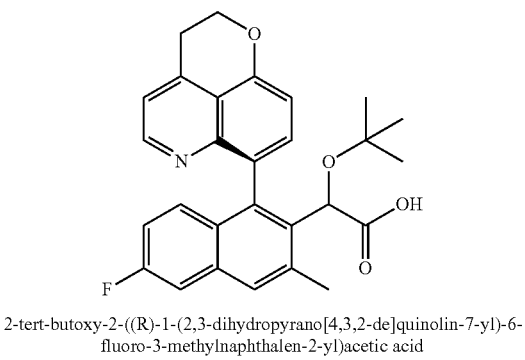

2-tert-butoxy-2-((R)-1-(2,3-dihydropyrano[4,3,2-de]quinolin-7-yl)-6-fluoro-3-methylnaphthalen-2-yl)acetic acid Preparation of 2-tert-butoxy-2-((R)-1-(2,3-dihydropyrano[4,3,2-de]quinolin-7-yl)-6-fluoro-3-methylnaphthalen-2-yl)acetic acid (43): 2-tert-Butoxy-2-((R)-1-(2,3-dihydropyrano[4,3,2-de]quinolin-7-yl)-6-fluoro-3-methylnaphthalen-2-yl)acetic acid (43) was prepared similarly to 2-tert-butoxy-2-(1-(4-chlorophenyl)-6-fluoro-3-methylnaphthalen-2-yl)acetic acid of Example 40 using 1-(3-fluorophenyl)propan-2-one instead of 1-(2-bromophenyl)propan-2-one and 2,3-dihydropyrano[4,3,2-de]quinolin-7-ylboronic acid instead of 4-chlorophenylboronic acid. $^1$H-NMR: 400 MHz, (CD$_3$OD) δ: 8.67 (d, J=5.6 Hz, 1H), 7.93 (s, 1H), 7.79 (d, J=8.0 Hz, 1H), 7.75 (d, J=5.2 Hz, 1H), 7.59 (dd, J=9.6, 2.8 Hz, 1H), 7.42 (d, J=8.4 Hz, 1H), 7.07 (td, J=9.2, 2.8 Hz, 1H), 6.98 (m, 1H), 5.21 (s, 1H), 4.71 (m, 2H), 3.64 (t, J=6.0 Hz, 2H), 2.77 (s, 3H), 0.93 (s, 9H). $^{19}$F-NMR: 377 MHz, (CD$_3$OD) δ: −116.92 (s). LCMS-ESI$^+$ (m/z): [M+H]$^+$ calcd for C$_{28}$H$_{27}$FNO$_4$: 460.18; found: 460.15.

EXAMPLE 42

2-tert-Butoxy-2-(1-(2,3-dihydropyrano[4,3,2-de]quinolin-7-yl)-5-fluoro-3-methylnaphthalen-2-yl)acetic acid (44)

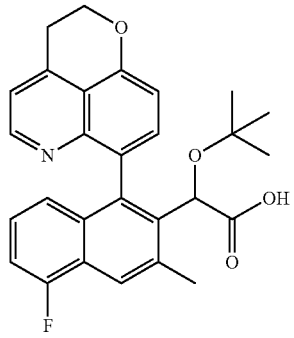

2-tert-butoxy-2-(1-(2,3-dihydropyrano[4,3,2-de]quinolin-7-yl)-5-fluoro-3-methylnaphthalen-2-yl)acetic acid Preparation of 2-tert-butoxy-2-(1-(2,3-dihydropyrano[4,3,2-de]quinolin-7-yl)-5-fluoro-3-methylnaphthalen-2-yl)acetic acid (44): 2-tert-Butoxy-2-(1-(2,3-dihydropyrano[4,3,2-de]quinolin-7-yl)-5-fluoro-3-methylnaphthalen-2-yl)acetic acid (44) was prepared similarly to 2-tert-butoxy-2-((R)-1-(2,3-dihydropyrano[4,3,2-de]quinolin-7-yl)-6-fluoro-3-methylnaphthalen-2-yl)acetic acid (43) using 1-(2-fluorophenyl)propan-2-one instead of 1-(3-fluorophenyl)propan-2-one. $^1$H-NMR: 400 MHz, (CD$_3$OD) δ: 8.68 (d, J=5.6 Hz, 1H), 8.56 (d, J=5.2 Hz, 1H), 8.10 (s, 1H), 7.78 (d, J=5.6 Hz, 1H), 7.43 m, 1H), 7.19 (m, 2H), 6.73 (M, 1H), 5.23 (s, 1H), 4.67 (m, 2H), 3.57 (t, J=5.6 Hz, 2H), 2.75 (s, 3H), 0.85 (s, 9H). $^{19}$F-NMR: 377 MHz, (CD$_3$OD) δ: −125.97 (t, J=7.54 Hz). LCMS-ESI$^-$ (m/z): [M–H]$^-$ calcd for C$_{28}$H$_{27}$FNO$_4$: 458.18; found: 457.76.

EXAMPLE 43

2-tert-Butoxy-2-(5-chloro-1-(4-chlorophenyl)-3-methylnaphthalen-2-yl)acetic acid (45)

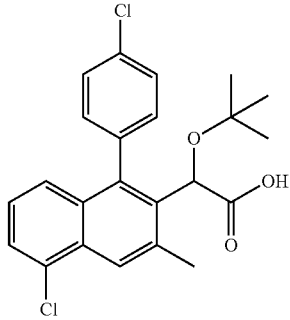

2-tert-butoxy-2-(5-chloro-1-(4-chlorophenyl)-3-methylnaphthalen-2-yl)acetic acid Preparation of 2-tert-butoxy-2-(5-chloro-1-(4-chlorophenyl)-3-methylnaphthalen-2-yl)acetic acid (45): 2-tert-Butoxy-2-(5-chloro-1-(4-chlorophenyl)-3-methylnaphthalen-2-yl)acetic acid (45) was prepared similarly to 2-tert-butoxy-2-(1-(4-chlorophenyl)-6-fluoro-3-methylnaphthalen-2-yl)acetic acid of Example 40 using 1-(2-chlorophenyl)propan-2-one instead of 1-(3-fluorophenyl)propan-2-one. $^1$H-NMR: 400 MHz, (CDCl$_3$) δ: 8.14 (s, 1H), 7.64 (m, 1H), 7.54 (m, 2H), 7.50 (d, J=7.6 Hz, 1H), 7.23 (m, 3H), 5.27 (s, 1H), 2.64 (s, 3H), 1.03 (s, 9H). LCMS-ESI$^-$ (m/z): [M–H]$^-$ calcd for C$_{23}$H$_{21}$Cl$_2$O$_3$: 415.09; found; 415.09.

EXAMPLE 44

2-tert-Butoxy-2-(1-(4-chlorophenyl)-5-fluoro-3-methylnaphthalen-2-yl)acetic acid (46)

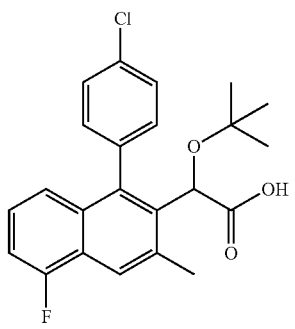

2-tert-butoxy-2-(1-(4-chlorophenyl)-5-fluoro-3-methylnaphthalen-2-yl)acetic acid Preparation of 2-tert-butoxy-2-(1-(4-chlorophenyl)-5-fluoro-3-methylnaphthalen-2-yl)acetic acid (46): 2-tert-Butoxy-2-(1-(4-chlorophenyl)-5-fluoro-3-methylnaphthalen-2-yl)acetic acid (46) was prepared similarly to 2-tert-butoxy-2-(1-(4-chlorophenyl)-6-fluoro-3-methylnaphthalen-2-yl)acetic acid of Example 40 using 1-(2-fluorophenyl)propan-2-one instead of 1-(3-fluorophenyl)propan-2-one. $^1$H-NMR: 400 MHz, (CD$_3$OD) δ: 7.94 (s, 1H), 7.59 (s, 2H), 7.57 (m, 1H), 7.35 (d, J=8.8 Hz, 1h), 7.27 (m, 1H), 7.16 (m, 1H), 7.07 (d, J=8.8 Hz, 1H), 5.21 (s, 1H), 2.66 (s, 3H), 1.01 (s, 9H). $^{19}$F-NMR: 377 MHz, (CD$_3$OD) δ: –126.85 (dd, J=10.2, 5.3 Hz). LCMS-ESI$^-$ (m/z):[M–H]$^-$ calcd for C$_{23}$H$_{21}$ClFO$_3$: 399.12; found: 399.14.

EXAMPLE 45

2-tert-Butoxy-2-((R)-5-chloro-1-(2,3-dihydropyrano[4,3,2-de]quinolin-7-yl)-3-methylnaphthalen-2-yl)acetic acid (47)

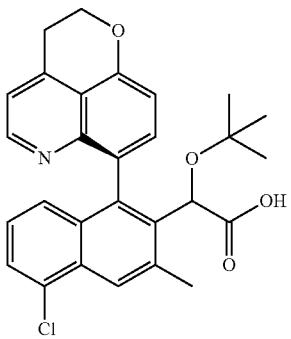

2-tert-butoxy-2-((R)-5-chloro-1-(2,3-dihydropyrano[4,3,2-de]quinolin-7-yl)-3-methylnaphthalen-2-yl)acetic acid Preparation of 2-tert-butoxy-2-((R)-5-chloro-1-(2,3-dihydropyrano[4,3,2-de]quinolin-7-yl)-3-methylnaphthalen-2-yl)acetic acid (47): 2-tert-Butoxy-2-((R)-5-chloro-1-(2,3-dihydropyrano[4,3,2-de]quinolin-7-yl)-3-methylnaphthalen-2-yl)acetic acid (47) was prepared similarly to 2-tert-butoxy-2-((R)-1-(2,3-dihydropyrano[4,3,2-de]quinolin-7-yl)-6-fluoro-3-methylnaphthalen-2-yl)acetic acid of Example 41 using 1-(2-chlorophenyl)propan-2-one instead of 1-(3-fluorophenyl)propan-2-one. $^1$H-NMR: 400 MHz, (CD$_3$OD) δ: 8.65 (d, J=5.2 Hz, 1H), 8.33 (s, 1H), 7.76 (d, J=8.4 Hz, 1H), 7.69 (d, J=5.2 Hz, 1H), 7.60 (d, J=7.6 Hz, 1H), 7.39 (d, J=8.0 Hz, 1H), 7.19 (t, J=8.4 Hz, 1H), 6.91 (d, J=8.4 Hz, 1H), 5.24 (s, 1H), 4.70 (m, 2H), 3.61 (t, J=6.0 Hz, 2H), 2.82 (s, 3H), 0.93 (s, 9H). LCMS-ESI$^-$ (m/z): [M–H]$^-$ calcd for C$_{28}$H$_{25}$ClNO$_4$: 474.16; found: 474.08.

EXAMPLE 46

2-tert-Butoxy-2-(1-(4-chlorophenyl)-6-methoxy-3-methylnaphthalen-2-yl)acetic acid (48)

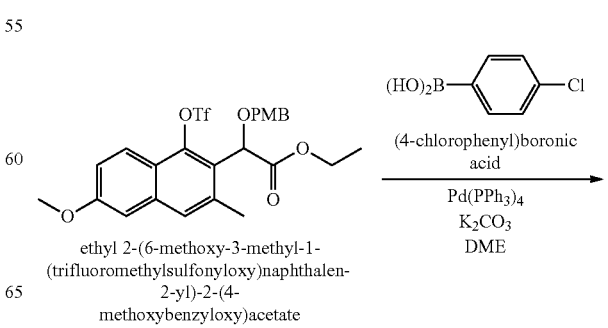

ethyl 2-(6-methoxy-3-methyl-1-(trifluoromethylsulfonyloxy)naphthalen-2-yl)-2-(4-methoxybenzyloxy)acetate (4-chlorophenyl)boronic acid Pd(PPh$_3$)$_4$
K$_2$CO$_3$
DME

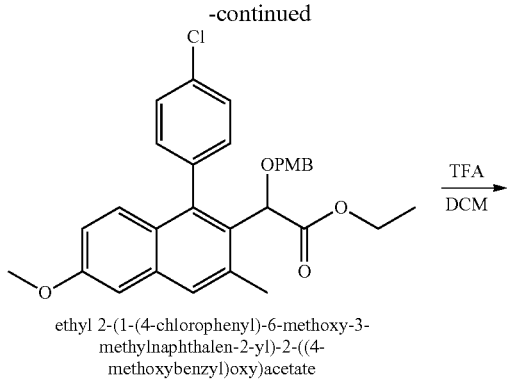

ethyl 2-(1-(4-chlorophenyl)-6-methoxy-3-methylnaphthalen-2-yl)-2-((4-methoxybenzyl)oxy)acetate

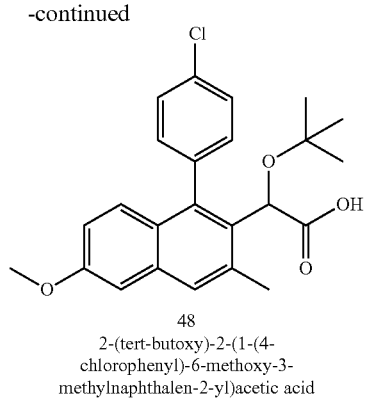

48
2-(tert-butoxy)-2-(1-(4-chlorophenyl)-6-methoxy-3-methylnaphthalen-2-yl)acetic acid

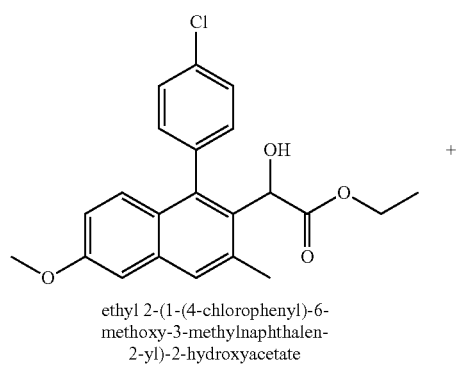

ethyl 2-(1-(4-chlorophenyl)-6-methoxy-3-methylnaphthalen-2-yl)-2-hydroxyacetate

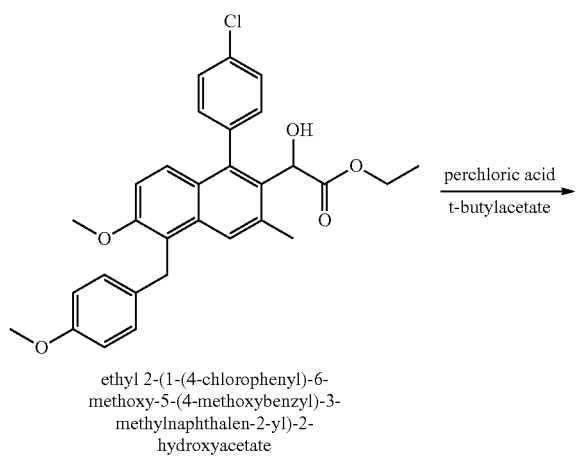

ethyl 2-(1-(4-chlorophenyl)-6-methoxy-5-(4-methoxybenzyl)-3-methylnaphthalen-2-yl)-2-hydroxyacetate

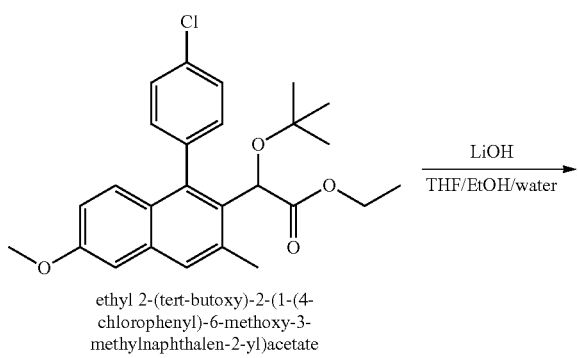

ethyl 2-(tert-butoxy)-2-(1-(4-chlorophenyl)-6-methoxy-3-methylnaphthalen-2-yl)acetate Preparation of ethyl 2-(6-methoxy-3-methyl-1-(trifluoromethylsulfonyl-oxy)naphthalen-2-yl)-2-(4-methoxybenzyloxy)acetate: Ethyl 2-(6-methoxy-3-methyl-1-(trifluoromethylsulfonyloxy)naphthalen-2-yl)-2-(4-methoxybenzyloxy)acetate was prepared similarly as the preparation of ethyl 2-(5-methoxy-3-methyl-1-(trifluoromethylsulfonyloxy)naphthalen-2-yl)-2-(4-methoxybenzyloxy)acetate of Example 32 using 6-methoxy-3-methyl-3,4-dihydronaphthalen-1(2H)-one instead of 5-methoxy-3-methyl-3,4-dihydronaphthalen-1(2H)-one. $^1$H-NMR: 400 MHz, (CDCl$_3$) δ: 7.93 (d, J=9.2 Hz, 1H), 7.56 (s, 1H), 7.25-7.21 (m, 3H), 7.07 (d, J=2.4 1H), 6.82 (d, J=8.8 Hz, 2H), 5.57 (s, 1H), 4.62-4.55 (m, 2H), 4.27-4.13 (m, 2H), 3.93 (s, 3H), 3.77 (s, 3H), 2.53 (s, 3H), 1.18 (t, J=6.8 Hz, 3H).

Preparation of ethyl 2-(1-(4-chlorophenyl)-6-methoxy-3-methylnaphthalen-2-yl)-2-(4-methoxybenzyloxy)acetate: To a solution of ethyl 2-(6-methoxy-3-methyl-1-(trifluoromethylsulfonyloxy)naphthalen-2-yl)-2-(4-methoxybenzyl-oxy)acetate (100 mg, 0.184 mmol) and 4-chlorophenylboronic acid (58 mg, 0.37 mmol) in 1,2-dimethoxyethane (2 mL) was added 2 M potassium carbonate (0.368 mL, 0.74 mmol) and Pd(PPh$_3$)$_4$ (21 mg, 0.018 mmol) and the reaction was degassed for 15 minutes with argon. The mixture was heated to 120° C. for 20 minutes in a microwave reactor. The crude reaction was absorbed onto silica and purified by flash column chromatography (silica gel, ethyl acetate/hexanes) to produce a yellow oil (66 mg). $^1$H-NMR: 400 MHz, (CDCl$_3$) δ: 7.58 (s, 1H), 7.39 (dd, J=8.2, 1.6 Hz, 1H), 7.31-7.26 (m, 2H), 7.13-7.07 (m, 4H), 7.01 (dd, J=8.2, 2.4 Hz, 1H), 6.94 (dd, J=9.2, 2.8 Hz, 1H), 6.78 (d, J=8.4 Hz, 1H), 6.77 (m, 1H), 4.50 (s, 1H), 4.42 (ABd, J=11.2 Hz, 1H), 4.34 (ABd, J=11.2 Hz, 1H), 4.20-4.15 (m, 2H), 3.91 (s, 3H), 3.81 (s, 3H), 2.60 (s, 3H), 1.21 (t, J=7.2 Hz, 3H).

Preparation of ethyl 2-(1-(4-chlorophenyl)-6-methoxy-3-methylnaphthalen-2-yl)-2-hydroxyacetate and ethyl 2-(1-(4-chlorophenyl)-6-methoxy-5-(4-methoxybenzyl)-3-methylnaphthalen-2-yl)-2-hydroxyacetate: To a solution of ethyl 2-(1-(4-chlorophenyl)-6-methoxy-3-methylnaphthalen-2-yl)-2-(4-methoxybenzyloxy)acetate (185 mg, 0.37 mmol) in dichloromethane at 0° C. was added trifluoroacetic acid (0.185 mL, 2.4 mmol) and the reaction was allowed to warm to room temperature over 2 hours. The reaction was quenched with saturated sodium bicarbonate with active cooling, extracted with dichloromethane and concentrated. The crude reaction was purified by flash column chromatography (silica gel, ethyl acetate/hexanes) and then further purified by reverse phase HPLC (Gemini, 20-100% ACN/H$_2$O+0.1% TFA) to give the two products: ethyl 2-(1-(4-chlorophenyl)-6-methoxy-3-methylnaphthalen-2-yl)-2-hydroxyacetate: 27 mg clear oil. LCMS-ESI$^+$ (m/z): [M+H—H$_2$O]$^+$ calcd for $C_{22}H_{19}ClO_3$: 367.09; found: 367.05: and ethyl 2-(1-(4-chlorophenyl)-6-methoxy-5-(4-methoxybenzyl)-3-methylnaphthalen-2-yl)-2-hydroxyacetate: 105 mg as a brown oil. LCMS-ESI$^+$ (m/z): [M+H—H$_2$O]$^+$ calcd for $C_{30}H_{27}ClO_4$: 487.15; found: 486.90.

Preparation of ethyl 2-tert-butoxy-2-(1-(4-chlorophenyl)-6-methoxy-3-methylnaphthalen-2-yl)acetate: To a solution of ethyl 2-(1-(4-chlorophenyl)-6-methoxy-3-methylnaphthalen-2-yl)-2-hydroxyacetate (27 mg, 0.07 mmol) in tert-butylacetate (1.0 mL) was added 70% perchloric acid (0.012 mL, 0.14 mmol) and the reaction was stirred at room temperature for 1.5 hours. The reaction was quenched with solid sodium bicarbonate, water (2 mL) added and stirred 1 hour. The product was extracted with ethyl acetate, concentrated and purified by flash column chromatography (silica gel, ethyl acetate/hexanes) to give a colorless oil (16.2 mg). $^1$H-NMR: 400 MHz, (CDCl$_3$) δ: 7.48 (s, 1H), 7.41-7.36 (m, 3H), 7.19 (d, J=6.4 Hz, 1H), 7.06 (d, J=9.2 Hz, 1H), 6.99 (br s, 1H), 6.86 (d, J=9.2 Hz, 1H), 5.00 (s, 1H), 4.12-4.02 (m, 2H), 3.82 (s, 3H), 2.52 (s, 3H), 1.13 (t, J=7.2 Hz, 3H), 0.91 (s, 9H).

Preparation of 2-tert-butoxy-2-(1-(4-chlorophenyl)-6-methoxy-3-methylnaphthalen-2-yl)acetic acid (48): To a solution of ethyl 2-tert-butoxy-2-(1-(4-chlorophenyl)-6-methoxy-3-methylnaphthalen-2-yl)acetate (16.2 mg, 0.037 mmol) in tetrahydrofuran:ethanol:water (2:2:1, 2.5 mL) was added lithium hydroxide (4 mg, 0.183 mmol) and the reaction was heated at 50° C. overnight. The reaction was purified by reverse phase HPLC (Gemini, 20-90% ACN/H$_2$O+0.1% TFA) to give a white powder (12 mg). $^1$H-NMR: 400 MHz, (CD$_3$OD) δ: 7.60 (s, 1H), 7.55 (m, 3H), 7.30 (m, 1H), 7.17 (d, J=2.8 Hz, 1H), 7.13 (d, J=9.6 Hz, 1H), 6.94 (dd, J=9.2, 2.8 Hz, 1H), 5.15 (s, 1H), 3.90 (s, 3H), 2.58 (s, 3H), 0.98 (s, 9H). LCMS-ESI$^-$ (m/z): [M–H]$^-$ calcd for $C_{24}H_{24}ClO_4$: 411.14; found: 411.14.

EXAMPLE 47

2-tert-Butoxy-2-(1-(4-chlorophenyl)-6-methoxy-5-(4-methoxybenzyl)-3-methylnaphthalen-2-yl)acetic acid (49)

49

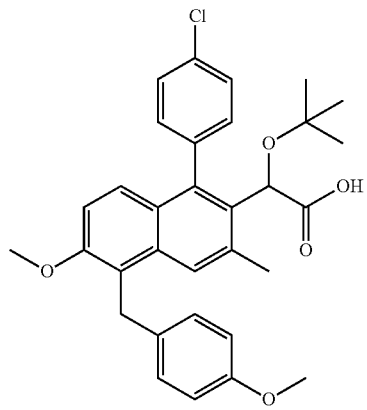

2-tert-butoxy-2-(1-(4-chlorophenyl)-6-methyoxy-5-(4-methoxybenzyl)-3-methylnaphthalen-2-yl)acetic acid Preparation of 2-tert-butoxy-2-(1-(4-chlorophenyl)-6-methoxy-5-(4-methoxybenzyl)-3-methylnaphthalen-2-yl)acetic acid (49): 2-tert-Butoxy-2-(1-(4-chlorophenyl)-6-methoxy-5-(4-methoxybenzyl)-3-methylnaphthalen-2-yl)acetic acid (49) was prepared following the procedure for 2-tert-butoxy-2-(1-(4-chlorophenyl)-6-methoxy-3-methylnaphthalen-2-yl)acetic acid of Example 46 using ethyl 2-(1-(4-chlorophenyl)-6-methoxy-5-(4-methoxybenzyl)-3-methylnaphthalen-2-yl)-2-hydroxyacetate in place of ethyl 2-(1-(4-chlorophenyl)-6-methoxy-3-methylnaphthalen-2-yl)-2-hydroxyacetate. $^1$H-NMR: 400 MHz, (CD$_3$OD) δ: 7.75 (s, 1H), 7.54 (m, 3H), 7.32 (d, J=6.8 Hz, 1H), 7.22 (m, 2H), 7.07 (d, J=8.4 Hz, 2H), 6.76 (d, J=8.4 Hz, 2H), 5.12 (s, 1H), 4.38 (s, 2H), 3.90 (s, 3H), 3.72 (s, 3H), 2.52 (s, 3H), 0.97 (s, 9H). LCMS-ESI$^-$ (m/z): [M–H]$^-$ calcd for $C_{32}H_{32}ClO_5$: 531.20; found: 531.01.

EXAMPLE 48

6-Bromo-3-methyl-3,4-dihydronaphthalen-1(2H)-one (50)

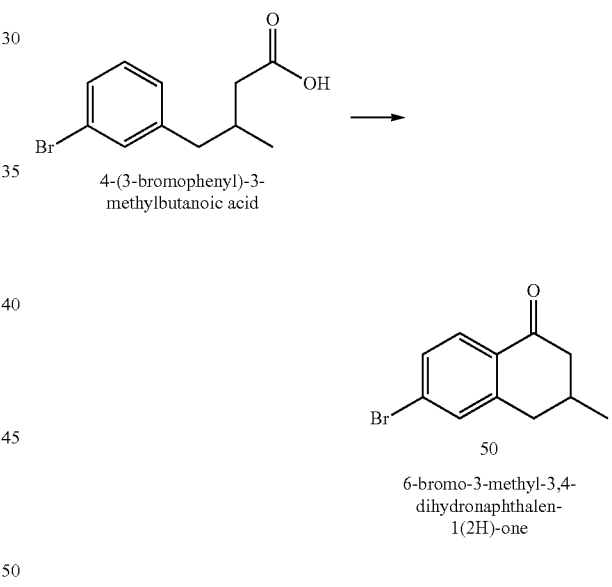

4-(3-bromophenyl)-3-methylbutanoic acid

50

6-bromo-3-methyl-3,4-dihydronaphthalen-1(2H)-one

Preparation of 6-bromo-3-methyl-3,4-dihydronaphthalen-1(2H)-one (50): A flask was charged with trifluoromethane sulfonic acid (450 g, 3 mol) and cooled to 0° C. with an ice-water bath. 4-(3-bromophenyl)-3-methylbutanoic acid, prepared in a similar manner as described in Example 32 (15.5 g, 60 mmol), was added as a solution in DCM (30 mL) slowly to produce a clear dark brown solution. After 15 min, the reaction was diluted with 500 mL of CHCl$_3$ and poured slowly onto approximately 1 L of crushed ice. The resulting slurry was allowed to stir until the solution warms to room temperature and became biphasic. Following separation of layers, the aqueous layer was extracted with CHCl$_3$. The combined organics were washed with brine and dried over anhydrous MgSO$_4$ prior to concentration in vacuo. Purification via Isco column chromatography (50% DCM/hex isocratic) provided a quantitative yield of the named compound as a pale yellow amorphous solid. LCMS-ESI+ (m/z): [M]+ calcd for $C_{11}H_{11}BrO$: 239.11; found: 239.20.

EXAMPLE 49

7-Bromo-3-methyl-3,4-dihydronaphthalen-1(2H)-one (51)

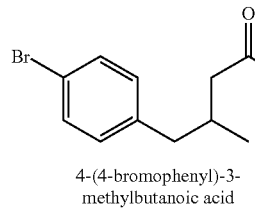

4-(4-bromophenyl)-3-methylbutanoic acid

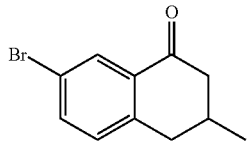

51
7-bromo-3-methyl-3,4-dihydronaphthalen-1(2H)-one

Preparation of 7-bromo-3-methyl-3,4-dihydronaphthalen-1(2H)-one (51): A solution of 4-(4-bromophenyl)-3-methylbutanoic acid, prepared in a similar manner as described in Example 32 (6.43 g, 25.0 mmol), in $H_2SO_4$ (25 mL) was stirred at 75° C. for 3 h. The mixture was slowly poured onto ice. The resulting slurry was extracted with EtOAc (2×100 mL). The combined organic layers were washed with brine, dried, filtered, and concentrated in vacuo. The crude material was purified by column chromatography (EtOAc/hexanes) to give 5.74 g (96%) of the title compound. $^1$H-NMR: 400 MHz, (CDCl$_3$) δ: 8.10 (d, J=2 Hz, 1H), 7.54 (dd, J=8, 2 Hz, 1H), 7.11 (d, J=8 Hz, 1H), 2.91 (d, J=16 Hz, 1H), 2.71 (d, J=13 Hz, 1H), 2.58 (m, 1H), 2.28 (m, 2H), 1.12 (d, J=6 Hz, 3H).

EXAMPLE 50

(6-Bromo-5-(4-chlorophenyl)-7-methylnaphthalen-2yloxy)triisopropylsilane (52)

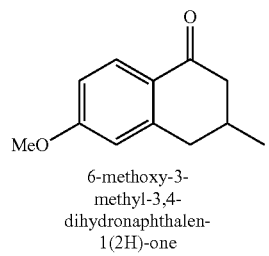

6-methoxy-3-methyl-3,4-dihydronaphthalen-1(2H)-one triflic anhydride
2,6-di-t-butyl pyridine
DCM

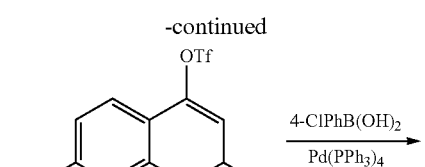

6-methoxy-3-methyl-3,4-dihydronaphthalen-1-yl trifluoromethanesulfonate

4-ClPhB(OH)$_2$
Pd(PPh$_3$)$_4$

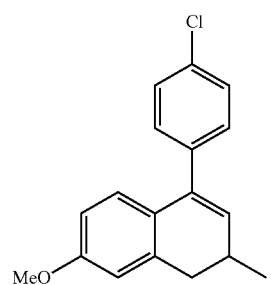

4-(4-chlorophenyl)-7-methoxy-2-methyl-1,2-dihydronaphthalene

PyrBr$_3$
DCM

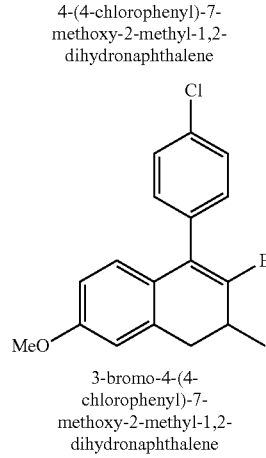

3-bromo-4-(4-chlorophenyl)-7-methoxy-2-methyl-1,2-dihydronaphthalene

DDQ

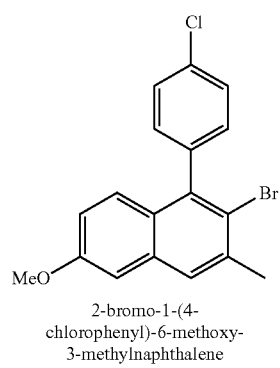

2-bromo-1-(4-chlorophenyl)-6-methoxy-3-methylnaphthalene

BBr$_3$

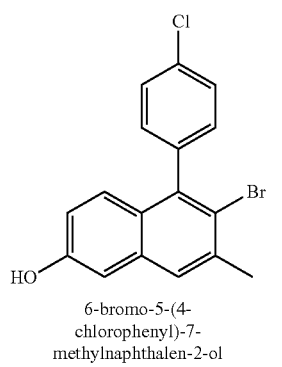

6-bromo-5-(4-chlorophenyl)-7-methylnaphthalen-2-ol

TIPSCl
DMAP, DBU

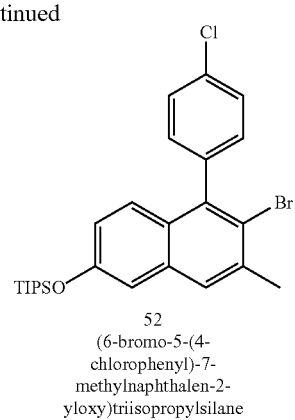

52
(6-bromo-5-(4-chlorophenyl)-7-methylnaphthalen-2-yloxy)triisopropylsilane

Preparation of (6-bromo-5-(4-chlorophenyl)-7-methylnaphthalen-2-yloxy)triisopropylsilane (52):

Step 1: Preparation of 6-methoxy-3-methyl-3,4-dihydronaphthalen-1-yl trifluoromethanesulfonate: To a solution of 6-methoxy-3-methyl-3,4-dihydronaphthalen-1(2H)-one (10.06 g, 53 mmol; prepared similarly to 6-bromo-3-methyl-3,4-dihydronaphthalen-1(2H)-one (50) of Example 48 beginning with 1-(3-methoxyphenyl)propan-2-one), cooled to 0° C. was added 2,6-di-tert-butyl-4-methylpyridine (19.6 g, 95.4 mmol) followed by trifluoromethanesulfonic anhydride (13.3 mL, 79.4 mmol). The resulting solution was allowed to warm slowly to room temperature over 1.5 h and then quenched by addition of 1 M HCl (100 mL). Following separation, the aqueous layer was extracted with DCM (3×100 mL) and the combined organics washed with brine. Following concentration in vacuo, the residue was taken up in hexanes. The resulting precipitated solids were removed via filtration and the mother liquor was dried over anhydrous MgSO₄ and then concentrated in vacuo. The resulting residue was purified by Yamazen column chromatography (3% to 35% EtOAc/Hex) to produce 9.88 g (57%) of the title compound as a colorless syrup. $^1$H-NMR: 400 MHz, (CDCl$_3$) δ: 7.28 (s, 1H); 6.75 (m, 2H); 5.74 (d, J=4 Hz, 1H); 3.82 (s, 3H); 2.77 (m, 1H) 2.89 (dd, J=15.2, 10 Hz; 1H); 2.61 (dd, J=15.2, 10 Hz; 1H); 1.14 (d, J=7.2 Hz, 3H).

Step 2: Preparation of 4-(4-chlorophenyl)-7-methoxy-2-methyl-1,2-dihydronaphthalene: 6-methoxy-3-methyl-3,4-dihydronaphthalen-1-yl trifluoromethanesulfonate (9.88 g, 30.7 mmol), 4-chlorophenylboronic acid (6.23 g, 39.9 mmol) and K$_2$CO$_3$ (12.7 g, 91.9 mmol) were combined in a mixture of toluene/ethanol/water (80 mL/40 mL/40 mL) at room temperature in a heavy walled pressure flask. Following sparging of the mixture with Ar for 30 minutes, PdCl$_2$(dppf) (1.12 g, 1.53 mmol) was added in one portion and the flask was sealed and heated to 50° C. for 2.5 h. After returning to room temperature, the layers were separated and the aqueous layer was extracted with EtOAc and Hex (2×50 mL each). The combined organics were washed with brine, filtered through a pad of Celite, and dried over anhydrous MgSO$_4$. The resulting solution was absorbed on silica gel in vacuo and purified via Yamazen column chromatography (0-15% EtOAc/Hex) to provide 7.7 g (88%) of the title compound as an amorphous white solid. $^1$H-NMR: 400 MHz, (CDCl$_3$) δ: 7.32 (d, J=8 Hz, 2H); 7.26 (d, J=8 Hz, 2H); 6.87 (d, J=8.4 Hz, 1H); 6.57 (d, J=2.8 Hz, 1H); 6.62 (dd, J=8.4, 2.8 Hz, 1H); 5.74 (d, J=2.8 Hz, 1H); 3.79 (s, 3H); 2.81 (ABq, J=20.8, 12.4 Hz, 1H); 2.60 (m, 1H); 2.59 (ABq, J=8.4, 2.8 Hz, 1H); 1.14 (d, J=6.4 Hz, 3H).

Step 3: Preparation of 3-bromo-4-(4-chlorophenyl)-7-methoxy-2-methyl-1,2-dihydronaphthalene: A solution of 4-(4-chlorophenyl)-7-methoxy-2-methyl-1,2-dihydronaphthalene (5 g, 17.6 mmol) in DCM (120 mL) was cooled in an ice-water bath prior to addition of solid pyridinium perbromide (6.2 g, 19.3 mmol) in one portion. The dark blue solution was allowed to stir for 30 min and was quenched by addition of saturated Na$_2$S$_2$O$_3$ (200 mL). The reaction was further diluted with water and DCM before separation and extraction of the aqueous layer with DCM. The combined pink organics were washed with brine and dried over anhydrous MgSO$_4$. Following filtration and concentration in vacuo, the resulting residue was purified by Yamazen column chromatography (0-10% EtOAc/Hex) to afford 5.5 g (86%) of the title compound as an orange colored gel. LCMS-ESI$^+$ (m/z): [M+H]$^+$ calcd for C$_{18}$H$_{17}$BrClO: 364.68; found: 364.89.

Step 4: Preparation of 2-bromo-1-(4-chlorophenyl)-6-methoxy-3-methylnaphthalene: A solution of 3-bromo-4-(4-chlorophenyl)-7-methoxy-2-methyl-1,2-dihydronaphthalene (5.5 g, 15.1 mmol) in toluene (100 mL) was vacuum flushed with Ar. DDQ (5.2 g, 22.7 mmol) was added and the mixture heated to reflux for 1.5 h. The heterogeneous red-brown mixture was cooled to room temperature and the toluene removed in vacuo. The resulting residue was taken up in DCM (300 mL) and filtered to remove precipitated DDHQ. The resulting mother liquor was absorbed on silica gel and purified by Yamazen column chromatography (15% DCM/Hex) to afford 5.21 g (95%) of the title compound as an amorphous yellow solid. $^1$H-NMR: 400 MHz, (CDCl$_3$) δ: 7.66 (s, 1H); 7.49 (br d, J=2 Hz, 2H); 7.24-7.18 (m, 3H); 7.07 (d, J=2 Hz, 1H); 6.97 (dd, J=9.2, 2 Hz, 1H); 3.91 (s, 3H); 2.60 (s, 3H).

Step 5: Preparation of 6-bromo-5-(4-chlorophenyl)-7-methylnaphthalen-2-ol: A vessel was charged with boron tribromide (1 M in DCM, 0.7 mL, 0.7 mmol) and cooled to −78° C. 2-bromo-1-(4-chlorophenyl)-6-methoxy-3-methylnaphthalene (0.1 g, 0.28 mmol) was added as a solution in DCM (0.5 mL). The reaction was allowed to slowly warm to room temperature over 3.5 h. This procedure was repeated twice on a scale of 1 g and 4.1 g of 2-bromo-1-(4-chlorophenyl)-6-methoxy-3-methylnaphthalene with appropriate adjustments in the scale of other reagents. The three lots were combined, cooled to 0° C. and the volume of the reaction was slowly doubled with MeOH. After warming to room temperature, the mixture was concentrated in vacuo and the residue was taken up in EtOAc (150 mL), treated with saturated NaHCO$_3$ (150 mL) and then small portions of solid NaHCO$_3$ until the solution was pH ~7. The layers were separated and the aqueous layer was extracted with EtOAc. The combined organics were washed with brine, dried over anhydrous MgSO$_4$, and concentrated in vacuo. The resulting residue was purified by Yamazen column chromatography (5-25% EtOAc/Hex) to afford 4.54 g (91%) of the title compound as a colorless syrup. LCMS-ESI$^+$ (m/z): [M+H]$^+$ calcd for C$_{17}$H$_{13}$BrClO: 348.64; found: 348.79.

Step 6: Preparation of (6-bromo-5-(4-chlorophenyl)-7-methylnaphthalen-2-yloxy)triisopropylsilane (52): 6-Bromo-5-(4-chlorophenyl)-7-methylnaphthalen-2-ol (4.5 g, 12.9 mmol) was taken up in DCM (65 mL). Added to this solution were TIPSCl (4.1 mL, 19.4 mmol), DBU (3.5 mL, 23.2 mmol), and DMAP (0.16 g, 1.3 mmol). After stirring at room temperature overnight, the DCM was removed in vacuo and the residue taken up in hexane (200 mL). This solution was washed with 1 M HCl (100 mL) and the layers separated. Following extraction of the aqueous layer with hexanes, the combined organics were washed with brine, dried over anhydrous MgSO$_4$ and concentrated in vacuo. The resulting residue was purified by Yamazen column chromatography (2-5%

DCM/Hex) to afford 5.12 g (79%) of the title compound as a colorless syrup. ¹H-NMR: 400 MHz, (CDCl₃) δ: 7.61 (s, 1H); 7.49 (br d, J=8.4 Hz, 2H); 7.23 (br d, J=8.4 Hz, 2H); 7.17 (d, J=8.8 Hz, 1H), 7.16 (d, J=2.4 Hz, 1H); 6.95 (dd, J=8.8, 2.4 Hz; 1H); 2.60 (s, 3H); 1.30 (hep, J=7.2 Hz, 3H); 1.12 (d, J=7.2 Hz, 18H).

EXAMPLE 51

(S)-2-tert-Butoxy-2-(1-(4-chlorophenyl)-3-methyl-6-(pyridin-4-yl)naphthalen-2-yl)acetic acid (53)

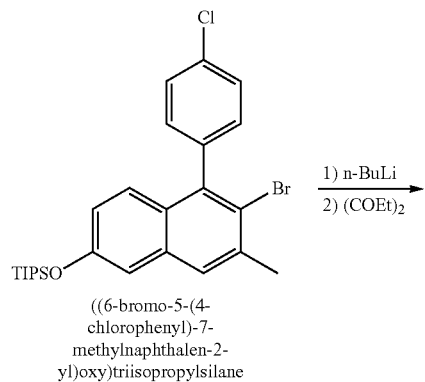

((6-bromo-5-(4-chlorophenyl)-7-methylnaphthalen-2-yl)oxy)triisopropylsilane 1) n-BuLi
2) (COEt)₂

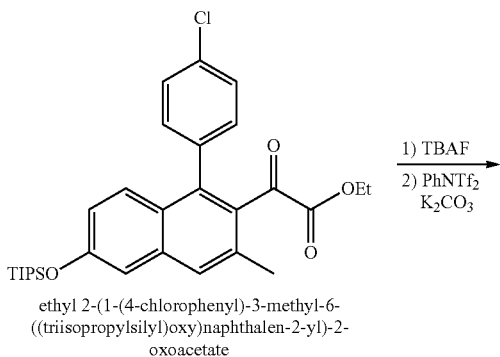

ethyl 2-(1-(4-chlorophenyl)-3-methyl-6-((triisopropylsilyl)oxy)naphthalen-2-yl)-2-oxoacetate 1) TBAF
2) PhNTf₂ K₂CO₃

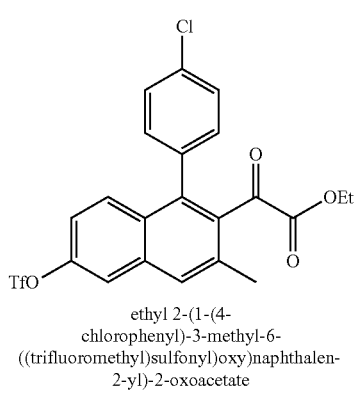

ethyl 2-(1-(4-chlorophenyl)-3-methyl-6-((trifluoromethyl)sulfonyl)oxy)naphthalen-2-yl)-2-oxoacetate (R)-2-MeCBS
catechol borane

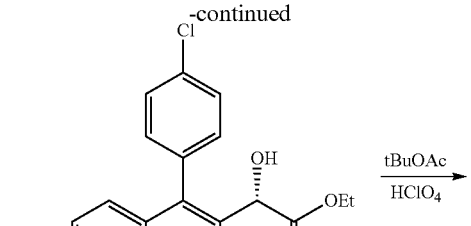

(S)-ethyl 2-(1-(4-chlorophenyl)-3-methyl-6-(trifluoromethylsulfonyloxy)naphthalen-2-yl)-2-hydroxyacetate tBuOAc
HClO₄

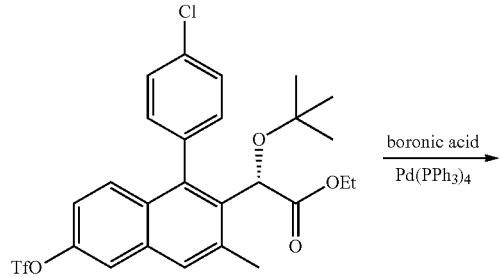

(S)-ethyl 2-(tert-butoxy)-2-(1-(4-chlorophenyl)-3-methyl-6-(((trifluoromethyl)sulfonyl)oxy)naphthalen-2-yl)acetate boronic acid
Pd(PPh₃)₄

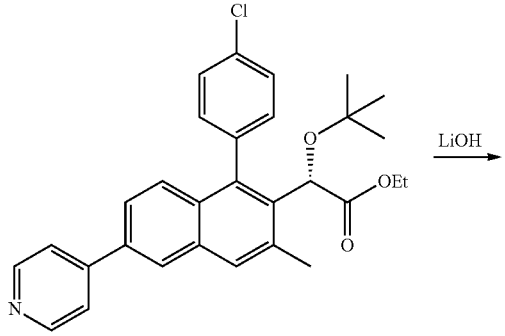

(S)-ethyl 2-(tert-butoxy)-2-(1-(4-chlorophenyl)-3-methyl-6-(pyridin-4-yl)naphthalen-2-yl)acetate LiOH

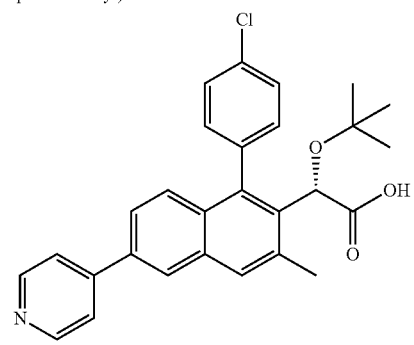

53
(S)-2-(tert-butoxy)-2-(1-(4-chlorophenyl)-3-methyl-6-(pyridin-4-yl)naphthalen-2-yl)acetic acid Step 1: Preparation of ethyl 2-(1-(4-chlorophenyl)-3-methyl-6-(triisopropyl-silyloxy)naphthalen-2-yl)-2-oxoacetate: To a solution of (6-bromo-5-(4-chlorophenyl)-7-methylnaphthalen-2-yloxy)triisopropylsilane (2.5 g, 4.9 mmol) in THF (50 mL) cooled to −78° C. was added n-BuLi (1.6 M in hexanes, 4.6 mL, 7.4 mmol) dropwise. The resulting solution was allowed to stir at −78° C. for 30 min before addition of diethyl oxalate (1.7 mL, 12.4 mmol). After 45 min at −78° C., the cold bath was removed and the reaction allowed to warm to room temperature over 1 h. 5% citric acid (50 mL) solution was added and the layers separated. Following extraction with EtOAc, the combined organics were washed with brine, dried over anhydrous MgSO$_4$ and concentrated in vacuo. The resulting residue was purified by Yamazen column chromatography (0-10% EtOAc/Hex) to afford 2.10 g (81%) of the title compound as a colorless syrup. LCMS-ESI$^+$ (m/z): [M+H]$^+$ calcd for $C_{30}H_{38}ClO_4Si$: 526.16; found: 526.89.

Step 2: Preparation of ethyl 2-(1-(4-chlorophenyl)-3-methyl-6-(trifluoromethylsulfonyloxy)naphthalen-2-yl)-2-oxoacetate: To a solution of ethyl 2-(1-(4-chlorophenyl)-3-methyl-6-(triisopropylsilyloxy)naphthalen-2-yl)-2-oxoacetate (5.11 g, 9.7 mmol) in THF (25 mL) cooled to 0° C. was added TBAF (1 M in THF, 10.7 mL, 10.7 mmol). After 15 min, a solution of N-Phenyl-bis(trifluoromethane-sulfonimide) (5.2 g, 14.6 mmol) in THF (20 mL) was added to produce a clear yellow solution. Solid potassium carbonate (2.7 g, 19.4 mmol) was added and the cold bath removed. After 4 h at room temperature, the reaction was diluted with EtOAc and 1 M NaOH (100 mL each) and shaken vigorously for 5 min. The layers were separated and the aqueous extracted with EtOAc. The combined organics were washed with brine, dried over anhydrous MgSO$_4$ and concentrated in vacuo. The resulting residue was purified by Yamazen column chromatography (0-20% EtOAc/Hex) to produce 3.12 g (64%) as an amorphous pale yellow solid. $^1$H-NMR: 400 MHz, (CDCl$_3$) δ: 7.80 (s, 1H); 7.76 (d, J=2.4 Hz, 1H); 7.67 (d, J=9.6 Hz, 1H); 7.48 (br d, J=8.4 Hz, 2H); 7.30 (dd, J=9.6, 2.4 Hz, 1H); 7.25 (br d, J=8.4 Hz, 2H); 3.95 (q, J=7.2 Hz, 2H); 2.53 (s, 3H); 1.15 (t, J=7.2 Hz, 3H).

Step 3: Preparation of (S)-ethyl 2-(1-(4-chlorophenyl)-3-methyl-6-(trifluoromethylsulfonyloxy)naphthalen-2-yl)-2-hydroxyacetate: To a solution of ethyl 2-(1-(4-chlorophenyl)-3-methyl-6-(trifluoromethylsulfonyloxy)naphthalen-2-yl)-2-oxoacetate (1 g, 2 mmol) and (R)-(+)-2-methyl-CBS-oxazaborolidine (0.11 g, 0.4 mmol) in toluene (7 mL) cooled to −20° C. was added a solution of freshly distilled catecholborane (0.29 mL, 2.6 mmol) in toluene (3 mL). After 3 h, saturated Na$_2$CO$_3$ (10 mL) was added, the mixture allowed to warm to room temperature and the layers separated. Following extraction with EtOAc, the combined organic layers were washed with additional saturated Na$_2$CO$_3$ (15 mL portions) until the washing was no longer colored and then once with saturated NH$_4$Cl (15 mL). After drying over anhydrous MgSO$_4$, the solution was absorbed onto silica gel in vacuo and purified by Yamazen column chromatography (10-65% EtOAc/Hex) to afford 0.61 g (61%, 98% ee) of the title compound as a colorless amorphous solid. $^1$H-NMR: 400 MHz, (CDCl$_3$) δ: 7.72 (s, 1H); 7.69 (d, J=2.4 Hz, 1H); 7.50 (m, 2H); 7.37 (d, J=9.2 Hz, 1H); 7.30 (m, 2H); 7.19 (dd, J=9.2, 2.4 Hz, 1H); 5.21 (d, J=2 Hz, 1H); 4.21 (m, 2H); 3.25 (d, J=2 Hz, 1H); 2.53 (s, 3H); 1.22 (t, J=7.2 Hz, 3H).

Step 4: Preparation of (S)-ethyl 2-tert-butoxy-2-(1-(4-chlorophenyl)-3-methyl-6-(trifluoromethylsulfonyloxy) naphthalen-2-yl)acetate: Perchloric acid (70%, 0.28 mL, 3.2 mmol) was added to a solution of (S)-ethyl 2-(1-(4-chlorophenyl)-3-methyl-6-(trifluoromethylsulfonyloxy) naphthalen-2-yl)-2-hydroxyacetate (0.82 g, 1.6 mmol) in tert-butyl acetate (5 mL) at room temperature. After 3 h, solid NaHCO$_3$ was added and the slurry stirred vigorously for 30 min. Saturated NaHCO$_3$ was added slowly until the mixture was pH ~8. Following extraction of the organic layer with EtOAc, the combined organics were washed with brine, dried over anhydrous MgSO$_4$ and concentrated in vacuo. The resulting residue was purified by Yamazen column chromatography (0-35% EtOAc/Hex) to produce 0.52 g (57%) of the title compound as an amorphous solid. $^1$H-NMR: 400 MHz, (CDCl$_3$) δ: 7.69 (s, 1H); 7.66 (d, J=2.4 Hz, 1H); 7.51 (m, 2H); 7.44 (m, 1H); 7.34 (d, J=9.4 Hz, 1H); 7.27 (m, 1H); 7.15 (dd, J=9.4, 2.4 Hz, 1H); 5.12 (s, 1H); 4.17 (m, 2H); 2.63 (s, 3H); 1.23 (t, J=7.2 Hz, 3H); 1.01 (s, 9H).

Step 5: Preparation of (S)-ethyl 2-tert-butoxy-2-(1-(4-chlorophenyl)-3-methyl-6-(pyridin-4-yl)naphthalen-2-yl) acetate: A solution of (S)-ethyl 2-tert-butoxy-2-(1-(4-chlorophenyl)-3-methyl-6-(trifluoromethylsulfonyloxy) naphthalen-2-yl)acetate (0.060 g, 0.11 mmol), pyridin-4-ylboronic acid (0.020 g, 0.16 mmol), and Pd(PPh$_3$)$_4$ (0.012 g, 0.011 mmol) in DME (1 mL) was treated with 2 M K$_2$CO$_3$ (0.16 mL, 0.32 mmol) and sparged with Ar for 10 min. Following microwave heating at 110° C. for 20 min, the reaction mixture was absorbed onto silica gel in vacuo and purified by Yamazen column chromatography (15-100% EtOAc/Hex) to afford 0.043 g (82%) as a colorless glass. LCMS-ESI$^+$ (m/z): [M+H]$^+$ calcd for $C_{30}H_{31}ClNO_3$: 488.20; found: 488.70.

Step 6: Preparation of (S)-2-tert-butoxy-2-(1-(4-chlorophenyl)-3-methyl-6-(pyridin-4-yl)naphthalen-2-yl)acetic acid (53): A solution (S)-ethyl 2-tert-butoxy-2-(1-(4-chlorophenyl)-3-methyl-6-(pyridin-4-yl)naphthalen-2-yl)acetate (0.043 g, 0.088 mmol) in THF/MeOH/H$_2$O (1 mL each) was treated with LiOH.H$_2$O (0.025 g, 0.59 mmol) and heated to 50° C. overnight. The resulting solution was diluted with DMF and purified by preparatory reverse phase HPLC (Gemini column, 15 to 100% MeCN/H$_2$O, 0.1% TFA). Lyophilization of appropriate fractions afforded 0.021 g of 53 as an off-white amorphous powder. $^1$H-NMR: 400 MHz, (CD$_3$CN) δ: 8.77 (br s, 2H); 8.37 (br s, 1H); 8.17 (br s, 2H); 7.91 (s, 1H); 7.76 (dd, J=8.8, 2.4 Hz, 1H); 7.62-7.54 (m, 3H); 7.46 (d, J=8.8 Hz, 1H); 7.38 (br d, J=8.8 Hz, 1H); 5.25 (s, 1H); 2.61 (s, 3H); 0.99 (s, 9H). LCMS-ESI$^-$ (m/z): [2M−H]$^-$ calcd for $C_{56}H_{51}Cl_2N_2O_6$: 917.31; found: 917.51.

EXAMPLE 52

(S)-2-tert-Butoxy-2-(1-(4-chlorophenyl)-3-methyl-6-(pyridin-3-yl)naphthalen-2-yl)acetic acid (54)

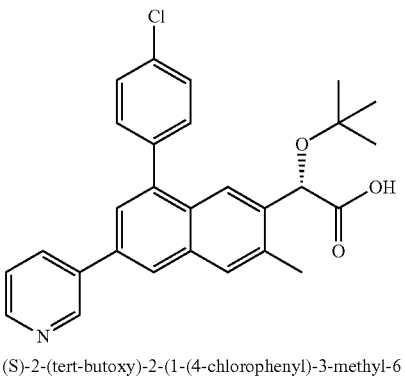

(S)-2-(tert-butoxy)-2-(1-(4-chlorophenyl)-3-methyl-6-(pyridin-3-yl)naphthalen-2-yl)acetic acid Preparation of (S)-2-tert-butoxy-2-(1-(4-chlorophenyl)-3-methyl-6-(pyridin-3-yl)naphthalen-2-yl)acetic acid (54): (S)-2-tert-butoxy-2-(1-(4-chlorophenyl)-3-methyl-6-(pyridin-3-yl)naphthalen-2-yl)acetic acid (54) was prepared in a similar fashion to compound 53 of Example 51 with the substitution of pyridin-3-ylboronic acid for pyridin-4-ylboronic acid in step 5. The title compound (0.024 g) was isolated as an amorphous white powder. LCMS-ESI⁻ (m/z): [2M–H]⁻ calcd for $C_{56}H_{51}Cl_2N_2O_6$: 917.31; found: 917.39. ¹H-NMR: 400 MHz, (CD₃CN) δ: 9.08 (s, 1H); 8.74 (d, J=5.2 Hz, 1H); 8.61 (d, J=8 Hz, 1H); 8.19 (s, 1H); 7.93-7.88 (m, 1H); 7.84 (s, 1H); 7.66-7.53 (m, 4H); 7.44-7.35 (m, 2H); 5.24 (s, 1H); 2.59 (s, 3H); 0.99 (s, 9H).

EXAMPLE 53

(S)-2-tert-Butoxy-2-(1-(4-chlorophenyl)-3-methyl-6-(pyrimidin-5-yl)naphthalen-2-yl)acetic acid (55)

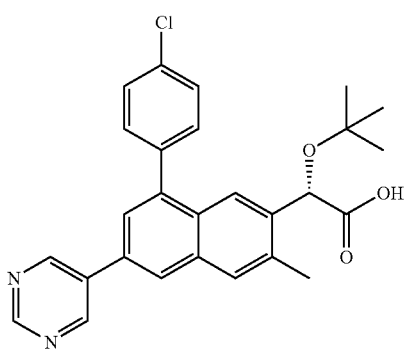

(S)-2-tert-butoxy-2-(1-(4-chlorophenyl)-3-methyl-6-(pyrimidin-5-yl)naphthalen-2-yl)acetic acid Preparation of (S)-2-tert-butoxy-2-(1-(4-chlorophenyl)-3-methyl-6-(pyrimidin-5-yl)naphthalen-2-yl)acetic acid (55): (S)-2-tert-butoxy-2-(1-(4-chlorophenyl)-3-methyl-6-(pyrimidin-5-yl)naphthalen-2-yl)acetic acid (55) was prepared in a similar fashion to compound 53 of Example 51 with the substitution of pyrimidin-5-ylboronic acid for pyridin-4-ylboronic acid in step 5. The title compound (0.004 g) was isolated as an amorphous white powder. LCMS-ESI⁻ (m/z): [2M–H]⁻ calcd for $C_{54}H_{49}Cl_2N_4O_6$: 919.30; found: 919.76. ¹H-NMR: 400 MHz, (CD₃CN) δ: 9.16 (s, 1H); 9.12 (br s, 2H); 8.19 (br s, 1H); 7.85 (br s, 1H); 7.67 (dd. J=9.2H, 1.6 Hz, 1H); 7.61-7.54 (m, 3H); 7.43 (d, J=9.2 Hz, 1H); 7.41-7.37 (m, 1H); 5.24 (s, 1H); 2.60 (s, 3H); 0.99 (s, 9H).

EXAMPLE 54

(S)-2-tert-Butoxy-2-(1-(4-chlorophenyl)-3-methyl-6-(1H-pyrazol-5-yl)naphthalen-2-yl)acetic acid (56)

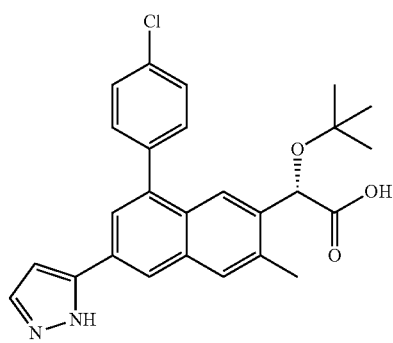

(S)-2-tert-butoxy-2-(1-(4-chlorophenyl)-3-methyl-6-(1H-pyrazol-5-yl) naphthalen-2-yl)acetic acid Preparation of (S)-2-tert-butoxy-2-(1-(4-chlorophenyl)-3-methyl-6-(1H-pyrazol-5-yl)naphthalen-2-yl)acetic acid (56): (S)-2-tert-butoxy-2-(1-(4-chlorophenyl)-3-methyl-6-(1H-pyrazol-5-yl)naphthalen-2-yl)acetic acid (56) was prepared in a similar fashion to compound 53 of Example 51 with the substitution of 1H-pyrazol-5-ylboronic acid for pyridin-4-ylboronic acid in step 5. The title compound (0.004 g) was isolated as an amorphous white powder. LCMS-ESI⁻ (m/z): [2M–H]⁻ calcd for $C_{52}H_{49}Cl_2N_4O_6$: 895.30; found: 895.45. ¹H-NMR: 400 MHz, (CD₃CN) δ: 8.23 (br s, 1H); 7.93 (d, J=9.6 Hz, 1H); 7.79 (s, 1H); 7.68 (s, 1H); 7.61-7.53 (m, 3H); 7.40-7.35 (m, 1H); 7.30 (d, J=9.6 Hz, 1H); 6.78 (s, 1H); 5.22 (s, 1H); 2.57 (s, 3H); 0.99 (s, 9H).

EXAMPLE 55

(S)-2-tert-Butoxy-2-(1-(4-chlorophenyl)-3-methyl-6-(1H-pyrazol-4-yl)naphthalen-2-yl)acetic acid (57)

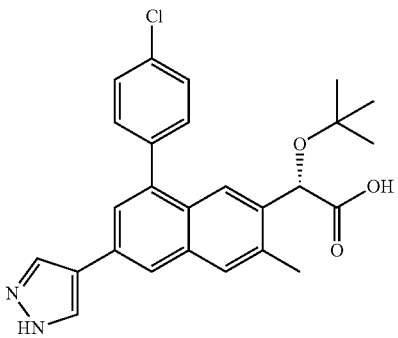

(S)-2-tert-butoxy-2-(1-(4-chlorophenyl)-3-methyl-6-(1H-pyrazol-4-yl) naphthalen-2-yl)acetic acid Preparation of (S)-2-tert-butoxy-2-(1-(4-chlorophenyl)-3-methyl-6-(1H-pyrazol-4-yl)naphthalen-2-yl)acetic acid (57): (S)-2-tert-butoxy-2-(1-(4-chlorophenyl)-3-methyl-6-(1H-pyrazol-4-yl)naphthalen-2-yl)acetic acid (57) was prepared in a similar fashion to compound 53 of Example 51 with the substitution of 4-(4,4,5,5-tetramethyl-1,3,2-dioxaborolan-2-yl)-1H-pyrazole for pyridin-4-ylboronic acid in step 5. The title compound (0.004 g) was isolated as an amorphous white powder. LCMS-ESI⁺ (m/z): [M+H]⁺ calcd for $C_{26}H_{26}ClN_2O_3$: 449.95; found: 449.57. ¹H-NMR: 400 MHz, (CD₃CN) δ: 8.03 (br s, 2H); 8.00 (br s, 1H); 7.71 (s, 1H); 7.59-7.52 (m, 4H); 7.38-7.34 (m, 1H); 7.26 (d, J=9.6 Hz, 1H); 5.20 (1H); 2.56 (3H); 0.98 (s, 9H).

EXAMPLE 56

2-tert-Butoxy-2-(1-(4-chlorophenyl)-3,6-dimethyl-naphthalen-2-yl)acetic acid (58)

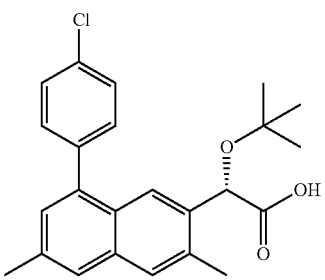

2-tert-butoxy-2-(1-(4-chlorophenyl)-3,6-dimethylnaphthalen-2-yl)acetic acid

Preparation of 2-tert-butoxy-2-(1-(4-chlorophenyl)-3,6-dimethylnaphthalen-2-yl)acetic acid (58): 2-tert-Butoxy-2-(1-(4-chlorophenyl)-3,6-dimethylnaphthalen-2-yl)acetic acid (58) was prepared with a route similar to that described for compound 53 of Example 51 beginning with 3,6-dimethyl-3,4-dihydronaphthalen-1(2H)-one (prepared from 1-(3-methylphenyl)propan-2-one) and omitting steps 5 and 6 of Example 50, and steps 2 and 5 of Example 51. Step 3 of Example 51 was replaced by treatment with NaBH$_4$ in EtOH at room temperature to afford racemic material. The title compound was isolated (0.075 g) as a white amorphous powder. LCMS-ESI$^-$ (m/z): [M–H]$^-$ calcd for $C_{24}H_{24}ClO_3$: 395.14; found: 394.96. $^1$H-NMR: 400 MHz, (CDCl$_3$) δ: 7.69-7.61 (m, 1H); 7.58 (s, 1H); 7.54 (s, 1H); 7.53-7.46 (m, 2H); 7.30-7.23 (m, 1H); 7.21 (d, J=8.4 Hz, 1H); 7.14 (d, J=8.4 Hz, 1H); 5.27 (s, 2H); 2.56 (s, 3H); 2.48 (s, 3H); 1.01 (s, 9H).

EXAMPLE 57

(S)-2-tert-butoxy-2-(1-(4-chlorophenyl)-3-methyl-6-(pyrimidin-2-yl)naphthalen-2-yl)acetic acid (59)

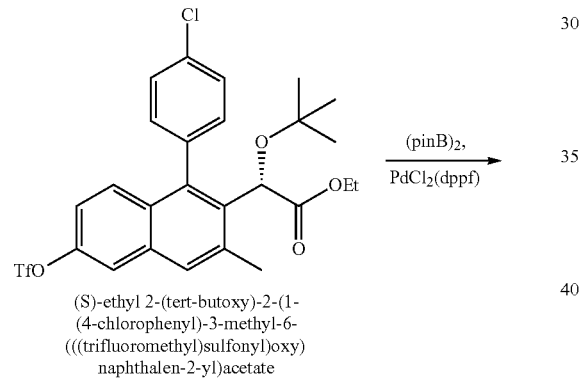
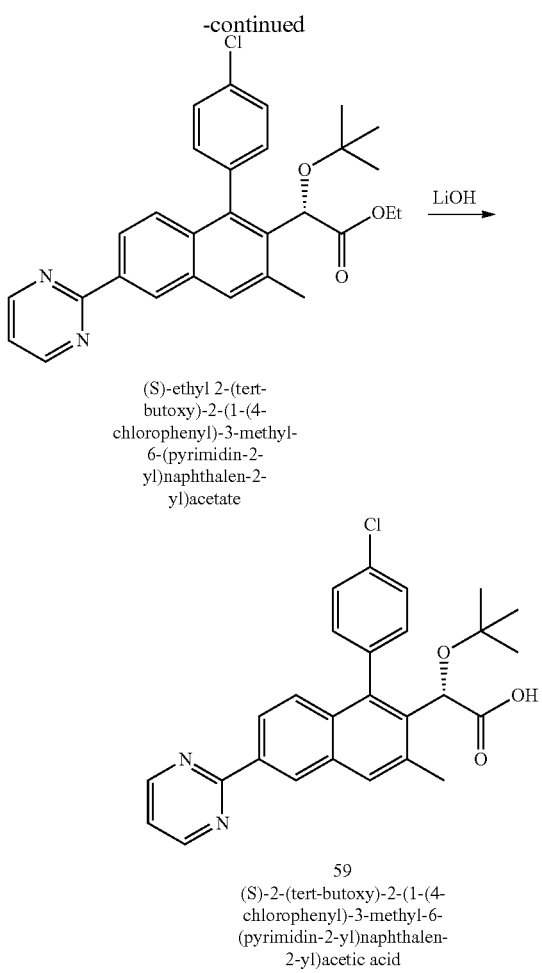

Step 1. Preparation of (S)-ethyl 2-tert-butoxy-2-(1-(4-chlorophenyl)-3-methyl-6-(4,4,5,5-tetramethyl-1,3,2-dioxaborolan-2-yl)naphthalen-2-yl)acetate: A solution of (S)-ethyl 2-tert-butoxy-2-(1-(4-chlorophenyl)-3-methyl-6-(trifluoromethylsulfonyloxy) naphthalen-2-yl)acetate (0.56 g, 1 mmol) in DME (6.5 mL) was treated with bis(pinacolato) diboron (0.51 g, 2 mmol), potassium acetate (0.20 g, 2 mmol) and PdCl$_2$(dppf) (0.073 g, 0.1 mmol) and sparged with Ar for 10 min. After heating at 100° C. in a sealed vessel for 3 h, the mixture was allowed to cool to room temperature and absorbed onto silica gel in vacuo. Purification by Yamazen column chromatography (2-35% EtOAc/Hex) produced 0.46 g (85%) of the title compound as a colorless oil that was contaminated with a small amount of pinacol. The material was used in subsequent reactions without further purification. $^1$H-NMR: 400 MHz, (CDCl$_3$) δ: 8.28 (s, 1H); 7.69 (s, 1H); 7.63 (br d, J=8.4 Hz, 1H); 7.51-7.42 (m, 3H); 7.29-7.26 (m, 1H); 7.22 (d, J=8.4 Hz, 1H); 5.13 (s, 1H); 4.15 (m, 2H); 2.61 (s, 3H); 1.38 (s, 2H); 1.21 (t, J=7.2 Hz, 3H); 0.99 (s, 9H).

Step 2: Preparation of (S)-ethyl 2-tert-butoxy-2-(1-(4-chlorophenyl)-3-methyl-6-(pyrimidin-2-yl)naphthalen-2-yl) acetate: (S)-Ethyl 2-tert-butoxy-2-(1-(4-chlorophenyl)-3-methyl-6-(4,4,5,5-tetramethyl-1,3,2-dioxaborolan-2-yl) naphthalen-2-yl)acetate (0.072 g, 0.13 mmol), 2-bromopyrimidine (0.032 g, 0.20 mmol), PdCl$_2$(dppf) (0.005 g, 0.007 mmol) were taken up in 3/1 PhMe/EtOH (1 mL). The resulting solution was treated with 2 M K$_2$CO$_3$ (0.35 mL, 0.70 mmol), sealed and sparged with Ar for 10 min. After 2.5 h of heating at 50° C. and cooling to room temperature, the crude reaction mixture was purified by Yamazen column chromatography (20-100% EtOAc/Hex) to produce 0.042 g (64%) of a colorless film. LCMS-ESI+ (m/z): [M]+ calcd for $C_{29}H_{29}ClN_2O_3$: 489.01; found: 489.51.

Step 3: Preparation of (S)-2-tert-butoxy-2-(1-(4-chlorophenyl)-3-methyl-6-(pyrimidin-2-yl)naphthalen-2-yl)acetic acid (59): (S)-2-tert-butoxy-2-(1-(4-chlorophenyl)-3-methyl-6-(pyrimidin-2-yl)naphthalen-2-yl)acetic acid (59) was prepared using a method similar to step 6 of Example 51 to afford 0.021 g of 59 as an off-white amorphous powder. LCMS-ESI+ (m/z): [M+H]+ calcd for $C_{27}H_{26}ClN_2O_3$: 461.96; found: 461.34. $^1$H-NMR: 400 MHz, (CD$_3$CN) δ: 8.92 (s, 1H); 8.87 (d, J=4.4 Hz, 2H); 8.36 (dd, J=9.2, 1.6 Hz, 1H); 7.94 (s, 1H); 7.61-7.55 (m, 3H); 7.43-7.36 (m, 2H); 7.34 (t, J=4.4 Hz, 1H); 5.24 (s, 1H); 2.59 (s, 3H); 1.0 (s, 9H).

EXAMPLE 58

(S)-2-tert-Butoxy-2-(1-(4-chlorophenyl)-3-methyl-6-(pyrazin-2-yl)naphthalen-2-yl)acetic acid (60)

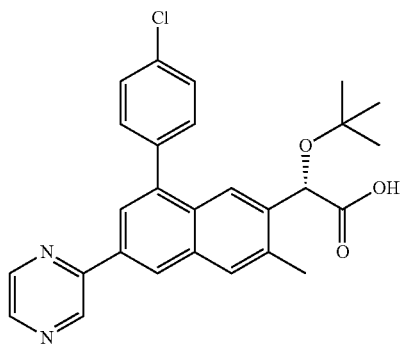

(S)-2-tert-butoxy-2-(1-(4-chlorophenyl)-3-methyl-6-(pyrazin-2-yl) naphthalen-2-yl)acetic acid Preparation of (S)-2-tert-butoxy-2-(1-(4-chlorophenyl)-3-methyl-6-(pyrazin-2-yl)naphthalen-2-yl)acetic acid (60): (S)-2-tert-butoxy-2-(1-(4-chlorophenyl)-3-methyl-6-(pyrazin-2-yl)naphthalen-2-yl)acetic acid was prepared in a similar fashion to compound 59 with the substitution of 2-chloropyrazine for 2-bromopyrimidine in step 2. The title compound (0.026 g) was isolated as an amorphous pale yellow powder. LCMS-ESI+ (m/z): [M+H]+ calcd for $C_{27}H_{26}ClN_2O_3$: 461.96; found: 461.30. $^1$H-NMR: 400 MHz, (CD$_3$CN) δ: 9.23 (s, 1H); 8.67 (s, 1H); 8.56 (s, 2H); 8.05 (d, J=8.8 Hz, 1H); 7.89 (s, 1H); 7.61-7.54 (m, 3H); 7.42 (d, J=8.8 Hz, 1H); 7.39 (br d, J=8.8 Hz, 1H); 5.23 (s, 1H); 2.60 (s, 3H); 1.00 (s, 9H).

EXAMPLE 59

(S)-2-tert-Butoxy-2-(1-(4-chlorophenyl)-6-(imidazo[1,2-a]pyrazin-8-yl)-3-methylnaphthalen-2-yl)acetic acid (61)

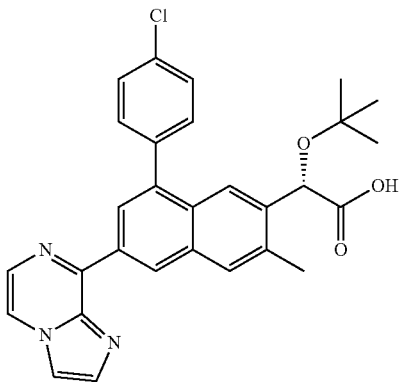

(S)-2-tert-butoxy-2-(1-(4-chlorophenyl)-6-(imidazo[1,2-a]pyrazin-8-yl)-3-methylnaphthalen-2-yl)acetic acid Preparation of (S)-2-tert-butoxy-2-(1-(4-chlorophenyl)-6-(imidazo[1,2-a]pyrazin-8-yl)-3-methylnaphthalen-2-yl)acetic acid (61): (S)-2-tert-butoxy-2-(1-(4-chlorophenyl)-6-(imidazo[1,2-a]pyrazin-8-yl)-3-methylnaphthalen-2-yl) acetic acid (61) was prepared in a similar fashion to compound 59 with the substitution of 8-chloroimidazo[1,2-a]pyrazine hydrobromide (See Guzi, T. J, Paruch, K., et. al. US 20070105864, p. 121) for 2-bromopyrimidine in step 2. The title compound (0.017 g) was isolated as an amorphous pale yellow powder. LCMS-ESI+ (m/z): [M+H]+ calcd for $C_{29}H_{27}ClN_3O_3$: 500.7; found: 500.0. $^1$H-NMR: 400 MHz, (CD$_3$CN) δ: 9.00 (d, J=1.2 Hz, 1H); 8.39 (d, J=4.4 Hz, 1H); 8.20 (dd, J=8.8, 1.2 Hz, 1H); 8.11 (d, J=4.4 Hz, 1H); 8.06 (d, J=1.2 Hz, 1H); 7.99 (s, 1H); 7.62-7.56 (m, 3H); 7.38 (d, J=8.8 Hz, 1H); 7.36 (br d, J=8.8 Hz, 1H); 5.25 (s, 1H); 2.58 (s, 3H); 0.99 (s, 9H).

EXAMPLE 60

(S)-2-tert-Butoxy-2-(1-(4-chlorophenyl)-3-methyl-6-(4-methylpyrimidin-5-yl)naphthalen-2-yl)acetic acid (62)

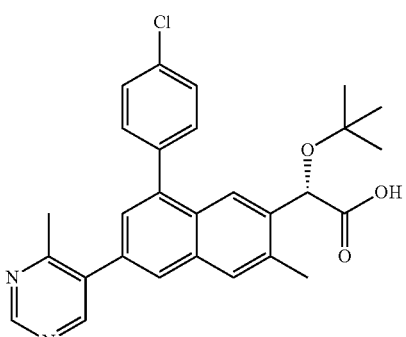

(S)-2-tert-butoxy-2-(1-(4-chlorophenyl)-3-methyl-6-(4-methylpyrimidin-5-yl) naphthalen-2-yl)acetic acid Preparation of (S)-2-tert-butoxy-2-(1-(4-chlorophenyl)-3-methyl-6-(4-methylpyrimidin-5-yl)naphthalen-2-yl)acetic acid (62): (S)-2-tert-Butoxy-2-(1-(4-chlorophenyl)-3-methyl-6-(4-methylpyrimidin-5-yl)naphthalen-2-yl)acetic acid (62) was prepared in a similar fashion to compound 59 with the substitution of 5-bromo-4-methylpyrimidine for 2-bromopyrimidine in step 2. The title compound (0.015 g) was isolated as an amorphous white powder. LCMS-ESI+ (m/z): [M+H]+ calcd for $C_{28}H_{28}ClN_2O_3$: 475.99; found: 475.69. $^1$H-NMR: 400 MHz, (CD$_3$CN) δ: 9.13 (br s, 1H); 8.77 (br s, 1H); 7.87 (s, 1H); 7.81 (s, 1H); 7.60-7.54 (m, 3H); 7.42-7.37 (m, 3H); 5.25 (s, 1H); 2.59 (s, 3H); 2.50 (s, 3H); 1.00 (s, 9H).

EXAMPLE 61

(S)-2-tert-Butoxy-2-(1-(4-chlorophenyl)-3-methyl-6-(pyridin-2-yl)naphthalen-2-yl)acetic acid (63)

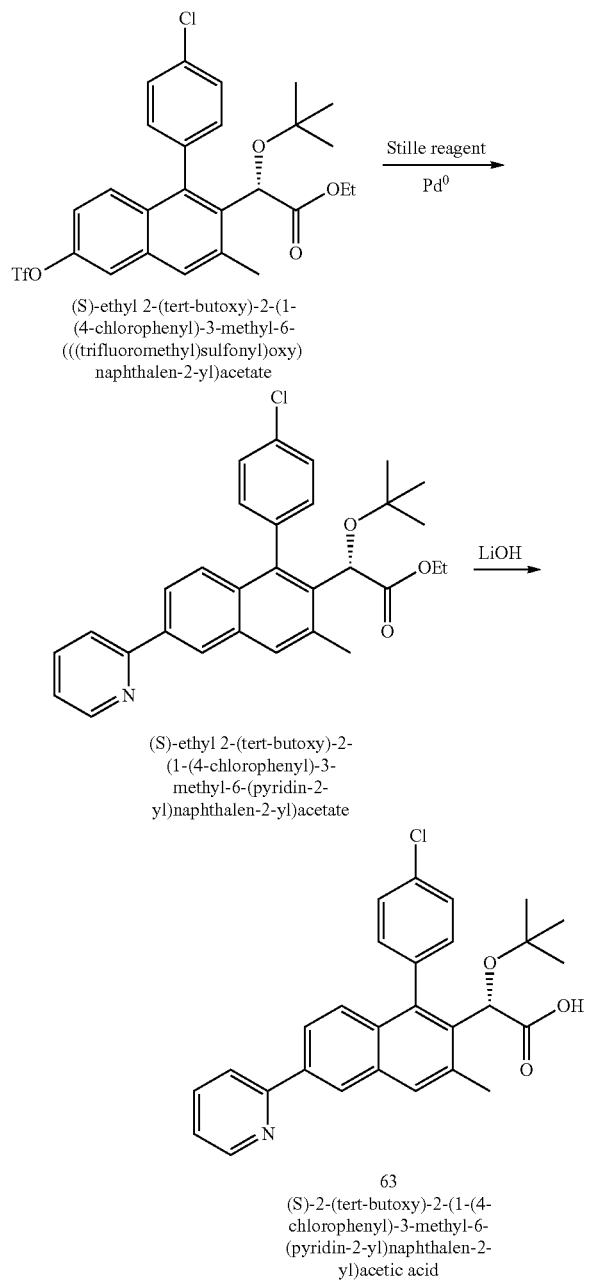

Step 1. Preparation of (S)-ethyl 2-tert-butoxy-2-(1-(4-chlorophenyl)-3-methyl-6-(pyridin-2-yl)naphthalen-2-yl)acetate: A solution of (S)-ethyl 2-tert-butoxy-2-(1-(4-chlorophenyl)-3-methyl-6-(trifluoromethylsulfonyloxy)naphthalen-2-yl)acetate (0.070 g, 0.13 mmol) in NMP (1 mL) was treated with LiCl (0.008 g, 0.19 mmol), Pd(PPh$_3$)$_4$ (0.014 g, 0.013 mmol) and 2-(tributylstannyl)pyridine (85%, 0.071 mL, 0.19 mmol). After sparging the mixture with Ar for 10 min and microwave heating at 100° C. for 10 min, the reaction mixture was allowed to cool to room temperature and loaded directly onto silica for purification by Yamazen column chromatography (20-100% EtOAc/Hex) to produce 0.015 g (25%) as a colorless film. LCMS-ESI+ (m/z): [M+H]+ calcd for $C_{30}H_{31}ClNO_3$: 488.20; found: 488.90.

Step 2. Preparation of (S)-2-tert-butoxy-2-(1-(4-chlorophenyl)-3-methyl-6-(pyridin-2-yl)naphthalen-2-yl)acetic acid (63): (S)-2-tert-Butoxy-2-(1-(4-chlorophenyl)-3-methyl-6-(pyridin-2-yl)naphthalen-2-yl)acetic acid (63) was prepared using a method similar to step 6 of Example 51 to afford 0.0041 g of 63 as an off-white amorphous powder. LCMS-ESI+ (m/z): [M+H]+ calcd for $C_{28}H_{27}ClNO_3$: 460.97; found: 460.70. $^1$H-NMR: 400 MHz, (CD$_3$CN) δ: 8.75 (d, J=4.4 Hz, 1H); 8.49 (br s, 1H); 8.07-7.96 (m, 3H); 7.87 (s, 3H); 7.60-7.53 (m, 3H); 7.46 (t, J=5.6 Hz, 1H); 7.40 (d, J=8.8 Hz, 1H); 7.39 (br s, 1H); 5.23 (s, 1H); 2.59 (s, 3H); 0.99 (s, 9H).

EXAMPLE 62

(S)-2-tert-Butoxy-2-(1-(4-chlorophenyl)-3-methyl-6-(1-methyl-1H-imidazol-4-yl)naphthalen-2-yl)acetic acid (64)

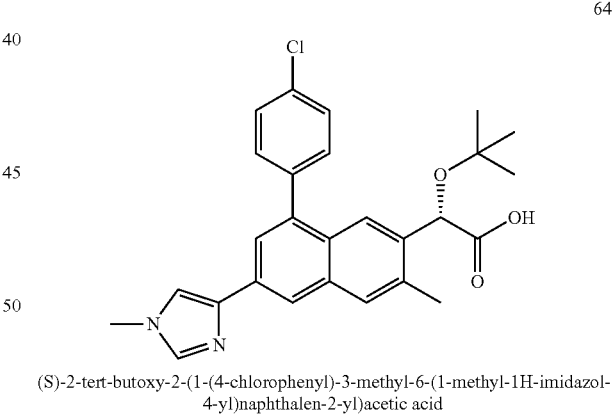

(S)-2-tert-butoxy-2-(1-(4-chlorophenyl)-3-methyl-6-(1-methyl-1H-imidazol-4-yl)naphthalen-2-yl)acetic acid Preparation of (S)-2-tert-butoxy-2-(1-(4-chlorophenyl)-3-methyl-6-(1-methyl-1H-imidazol-4-yl)naphthalen-2-yl)acetic acid (64): (S)-2-tert-butoxy-2-(1-(4-chlorophenyl)-3-methyl-6-(1-methyl-1H-imidazol-4-yl)naphthalen-2-yl)acetic acid (64) was prepared in a similar fashion to compound 63 with the substitution of 1-methyl-4-(tributylstannyl)-1H-imidazole for 2-(tributylstannyl)pyridine in step 1. The title compound (0.026 g) was isolated as an amorphous white powder. LCMS-ESI+ (m/z): [M+H]+ calcd for $C_{27}H_{28}ClN_2O_3$: 463.98; found: 463.86. $^1$H-NMR: 400 MHz, (CD$_3$CN) δ: 6.46 (br s, 1H); 8.24 (br s, 1H); 7.73 (br s, 1H); 7.65 (s, 1H);

7.62-7.51 (m, 4H); 7.36-7.25 (m, 2H); 5.21 (s, 1H): 3.85 (s, 3H); 2.56 (s, 3H); 0.97 (s, 9H).

EXAMPLE 63

(S)-2-tert-butoxy-2-(1-(4-chlorophenyl)-3-methyl-6-(1-methyl-1H-imidazol-5-yl)naphthalen-2-yl)acetic acid (65)

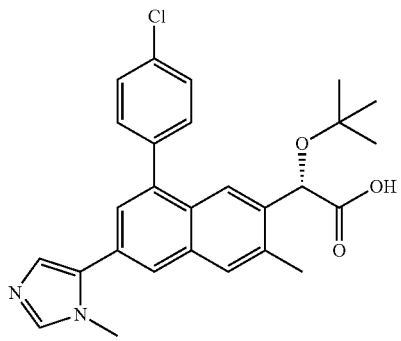

(S)-2-tert-butoxy-2-(1-(4-chlorophenyl)-3-methyl-6-(1-methyl-1H-imidazol-5-yl)naphthalen-2-yl)acetic acid Preparation of (S)-2-tert-butoxy-2-(1-(4-chlorophenyl)-3-methyl-6-(1-methyl-1H-imidazol-5-yl)naphthalen-2-yl)acetic acid (65): (S)-2-tert-Butoxy-2-(1-(4-chlorophenyl)-3-methyl-6-(1-methyl-1H-imidazol-5-yl)naphthalen-2-yl)acetic acid (65) was prepared in a similar fashion to compound 63 with the substitution of 1-methyl-5-(tributylstannyl)-1H-imidazole for 2-(tributylstannyl)pyridine in step 1. The title compound (0.026 g) was isolated as an amorphous white powder. LCMS-ESI+ (m/z): [M+H]+ calcd for $C_{27}H_{28}ClN_2O_3$: 463.98; found: 463.81. $^1$H-NMR: 400 MHz, (CD$_3$CN) δ: 8.54 (s, 1H); 7.99 (s, 1H); 7.84 (s, 1H): 7.62-7.50 (m, 3H); 7.45-7.32 (m, 3H), 5.24 (s, 1H); 3.80 (s, 3H); 2.60 (s, 3H); 0.99 (s, 9H).

EXAMPLE 64

2-(1,6-Bis(4-chlorophenyl)-3-methylnaphthalen-2-yl)-2-tert-butoxyacetic acid (66)

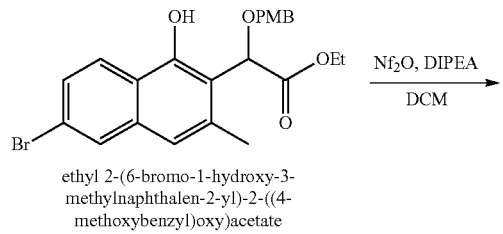

ethyl 2-(6-bromo-1-hydroxy-3-methylnaphthalen-2-yl)-2-((4-methoxybenzyl)oxy)acetate

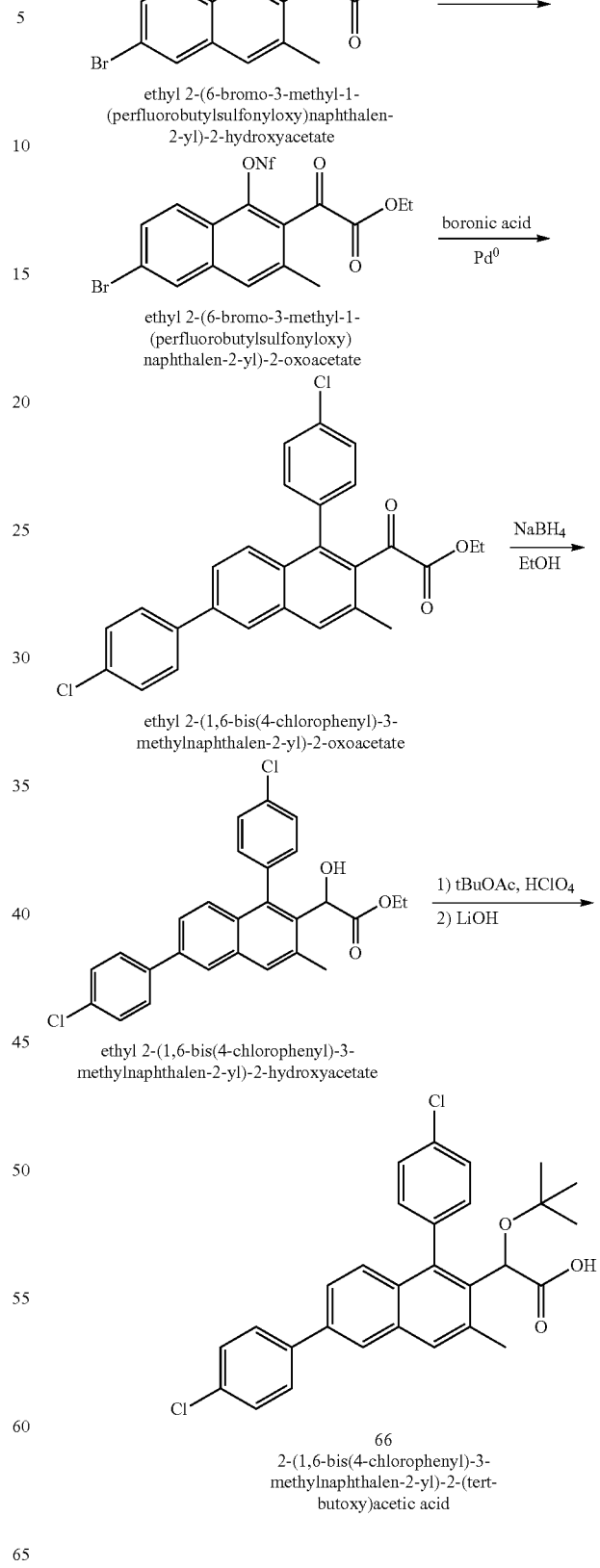

Step 1. Preparation of ethyl 2-(6-bromo-3-methyl-1-(per-fluorobutyl-sulfonyloxy)naphthalen-2-yl)-2-hydroxyacetate: A solution of ethyl 2-(6-bromo-1-hydroxy-3-methyl-naphthalen-2-yl)-2-(4-methoxybenzyloxy)acetate (0.78 g, 1.7 mmol; prepared similarly to (1-hydroxy-5-methoxy-3-methyl-naphthalen-2-yl)-(4-methoxybenzyloxy)acetic acid ethyl ester of Example 32 beginning with 1-(3-bromophenyl) propan-2-one) in DCM (17 mL) was cooled to −78° C. and treated with DIPEA (0.44 mL, 2.6 mmol) and perfluorobutanesulfonic anhydride (0.68 mL, 2.2 mmol). The resulting slurry was allowed to slowly warm to room temperature overnight. Saturated NaHCO$_3$ was added and the mixture extracted with EtOAc. The combined organics were washed with brine, dried over anhydrous MgSO$_4$ and concentrated in vacuo. The residue was purified via Yamazen column chromatography (0-15% EtOAc/Hex) to afford 0.52 g (95%) of the title compound as a yellow solid that was used without further purification. $^1$H-NMR: 400 MHz, (CDCl$_3$) δ: 7.97 (d, J=6.4 Hz, 1H); 7.94 (d, J=9.2 Hz, 1H); 7.66 (dd, J=9.2, 6.4 Hz, 1H); 7.59 (s, 1H); 5.78 (br s, 1H); 4.31 (m, 1H); 4.22 (m, 1H); 3.39 (br s, 1H): 2.50 (s, 3H); 1.20 (t, J=7.2 Hz, 3H).

Step 2. Preparation of ethyl 2-(6-bromo-3-methyl-1-(perfluorobutyl-sulfonyloxy)naphthalen-2-yl)-2-oxoacetate: A solution of ethyl 2-(6-bromo-3-methyl-1-(perfluorobutylsulfonyloxy)naphthalen-2-yl)-2-hydroxyacetate (0.52 g, 0.84 mmol) in DCM (8.5 mL) was treated with Dess-Martin periodinane (0.43 g, 1.01 mmol) at room temperature. After 1.5 h, a 1/1 mixture of saturated NaHCO$_3$ and saturated Na$_2$S$_2$O$_3$ (10 mL) was added and the slurry allowed to stir at room temperature for 10 min. The reaction was further diluted with water and DCM and the aqueous layer extracted with DCM. The combined organics were washed with water, brine, and dried over anhydrous MgSO$_4$. After concentration in vacuo, the residue was purified using Yamazen column chromatography (0-15% EtOAc/Hex) to produce 0.38 g (73%) of the title compound as an amorphous solid. $^1$H-NMR: 400 MHz, (CDCl$_3$) δ: 8.04 (s, 1H); 7.97 (d, J=9.2 Hz, 1H); 7.72 (d, J=9.2 Hz, 1H); 7.68 (s, 1H); 4.41 (q, J=7.2 Hz, 2H); 2.50 (s, 3H); 1.39 (t, J=7.2 Hz, 3H).

Step 3. Preparation of ethyl 2-(1,6-bis(4-chlorophenyl)-3-methylnaphthalen-2-yl)-2-oxoacetate: A solution of ethyl 2-(6-bromo-3-methyl-1-(perfluorobutylsulfonyl-oxy)naphthalen-2-yl)-2-oxoacetate (0.379 g, 0.612 mmol), 4-chlorophenylboronic acid (0.105 g, 0.67 mmol), potassium carbonate (0.254 g, 1.84 mmol), and Pd(dppf)Cl$_2$ (0.022 g, 0.031 mmol) was prepared in PhMe (3 mL), EtOH (1.5 mL) and water (1.5 mL). The dark brown solution was sparged with argon for 10 min, then allowed to stir at room temperature for 2.5 h. Following purification, the product was determined to be a mixture of mono and bis substitution. The mixture was resubmitted to reaction conditions and was heated to 50° C. for 2 h. After cooling to room temperature, the reaction was diluted with EtOAc, and washed with water. The organic layer was absorbed onto silica gel in vacuo and purified by Yamazen column chromatography (0-20% EtOAc/Hex) to afford 0.145 g (53%) of the title compound as an amorphous solid. $^1$H-NMR: 400 MHz, (CDCl$_3$) δ: 7.98 (s, 1H); 7.78 (s, 1H); 7.64-7.56 (m, 4H); 7.48-7.41 (m, 4H); 7.30-7.22 (m, 2H); 3.91 (q, J=7.2 Hz, 2H); 2.51 (s, 3H); 1.12 (t, J=7.2 Hz, 3H).

Step 4. Preparation of ethyl 2-(1,6-bis(4-chlorophenyl)-3-methylnaphthalen-2-yl)-2-hydroxyacetate: A solution of ethyl 2-(1,6-bis(4-chlorophenyl)-3-methylnaphthalen-2-yl)-2-oxoacetate (0.145 g, 0.31 mmol) in EtOH (2 mL) and DCM (1 mL) at 0° C. was treated with NaBH$_4$ (0.018 g, 0.048 mmol) in one portion. The reaction was allowed to warm to room temperature over 30 min and treated with saturated NaHCO$_3$ (3 mL). The mixture was stirred vigorously for 30 min and then diluted with EtOAc and water. Following extraction with EtOAc, the organics were washed with brine, dried over anhydrous Na$_2$SO$_4$ and concentrated to produce 0.121 g (84%) of the title compound as a white foam that was used in subsequent steps without further purification. $^1$H-NMR: 400 MHz, (CDCl$_3$) δ: 7.94 (s, 1H); 7.73 (s, 1H); 7.60 (d, J=8.4 Hz, 2H); 7.56-7.42 (m, 6H); 7.38-7.30 (m, 2H); 5.23 (s, 1H); 4.20 (m, 2H); 2.52 (s, 3H); 1.21 (t, J=7.2 Hz, 3H).

Steps 5 and 6. Preparation of 2-(1,6-bis(4-chlorophenyl)-3-methylnaphthalen-2-yl)-2-tert-butoxyacetic acid (66): Step 5 was performed similarly to step 4 of Example 51. Step 6 was performed similarly to Step 6 of Example 51 with heating at 60° C. overnight to produce 0.053 g of the title compound as an amorphous white powder. LCMS-ESI⁻ (m/z): [2M-2H+Na]⁻ calcd for C$_{58}$H$_{50}$Cl$_4$NaO$_6$: 1007.82; found: 1007.05. $^1$H-NMR: 400 MHz, (CDCl$_3$) δ: 7.93 (br s, 1H); 7.23 (s, 1H); 7.60 (br d, J=8.8 Hz, 2H); 7.58-7.49 (m, 3H); 7.43 (br d, J=8.8 Hz, 2H); 7.39 (br d, J=8.8 Hz, 1H); 7.32 (br s, 1H); 5.30 (s, 1H); 2.60 (s, 3H); 1.03 (s, 9H).

Example 65

2-tert-Butoxy-2-(6-chloro-1-(4-chlorophenyl)-3-methylnaphthalen-2-yl)acetic acid (67)

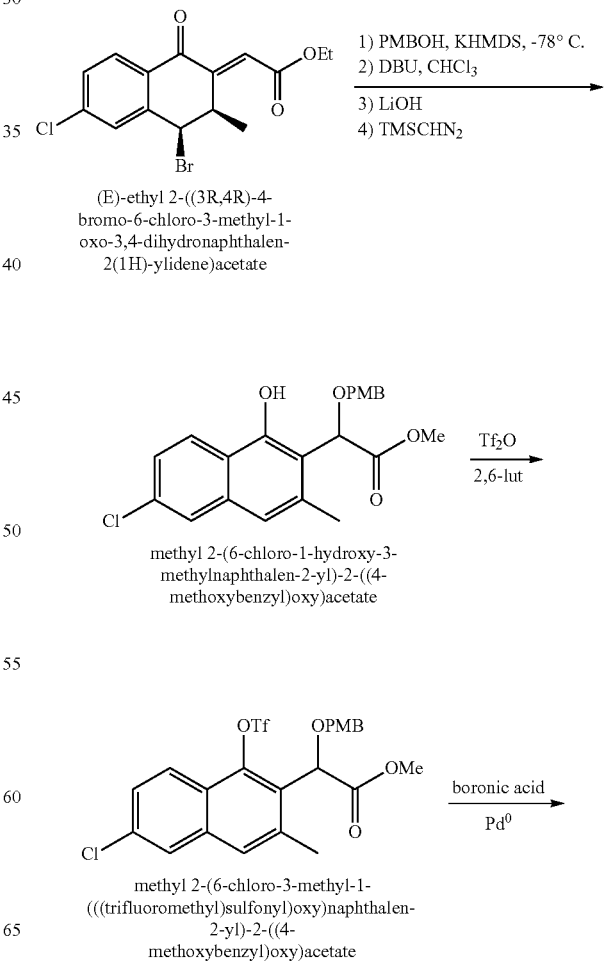

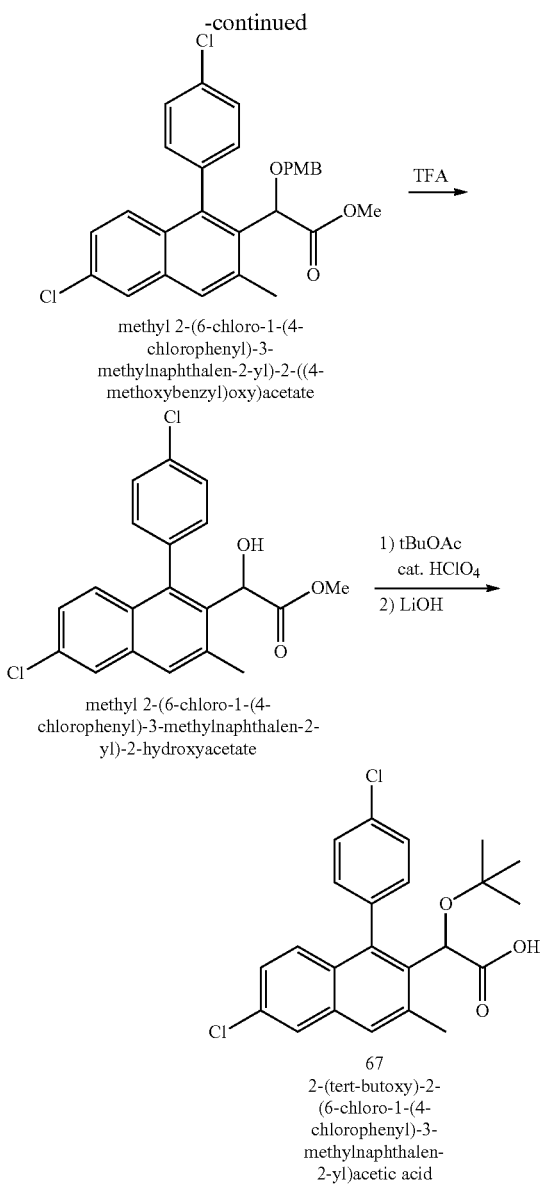

Steps 1-4. Preparation of methyl 2-(6-chloro-1-hydroxy-3-methylnaphthalen-2-yl)-2-(4-methoxybenzyloxy)acetate: p-methoxybenzyl alcohol (5.9 mL, 47.2 mmol) was diluted with THF (180 mL) and cooled to −78° C. under an Ar atmosphere. KHMDS (0.5 M PhMe solution, 71 mL, 35.4 mmol) was added dropwise over 20 min and the solution allowed to age for 20 min at this temperature to produce an opaque white suspension. A solution of (E)-ethyl 2-((3R,4R)-4-bromo-6-chloro-3-methyl-1-oxo-3,4-dihydronaphthalen-2(1H)-ylidene)acetate (4.22 g, 11.8 mmol; prepared similarly to (4-bromo-5-methoxy-3-methyl-1-oxo-3,4-dihydro-1H-naphthalen-2-ylidene)acetic acid ethyl ester of Example 32 beginning with 1-(3-chlorophenyl)propan-2-one) was prepared in THF (50 mL) and added to the reaction at a rate that maintained an internal temperature less than −65° C. After 5 min, propionic acid (10 mL, 134 mmol) was added and the reaction warmed to room temperature over 1.5 h prior to dilution with water (150 mL). Extraction of the aqueous layer with ethyl acetate was followed by washing of the combined organics with saturated NaHCO₃, water and brine. Following drying over anhydrous MgSO₄ and concentration in vacuo, the resulting residue was eluted on Yamazen column chromatography to produce an inseparable mixture of products (5.56 g) that included ethyl 2-(6-chloro-1-hydroxy-3-methylnaphthalen-2-yl)-2-(4-methoxybenzyloxy)acetate, 4-methoxybenzyl 2-(6-chloro-1-hydroxy-3-methylnaphthalen-2-yl)-2-(4-methoxybenzyloxy)acetate, ethyl 2-((3R,4R)-4-bromo-6-chloro-3-methyl-1-oxo-1,2,3,4-tetrahydronaphthalen-2-yl)-2-(4-methoxybenzyloxy)acetate, and 4-methoxybenzyl 2-((3R,4R)-4-bromo-6-chloro-3-methyl-1-oxo-1,2,3,4-tetrahydronaphthalen-2-yl)-2-(4-methoxybenzyloxy)acetate. This material was taken up in chloroform (60 mL) and treated with DBU (5.1 mL, 33.9 mmol) at room temperature. After 1 h, 5% citric acid solution was added and the aqueous phase extracted with DCM. The combined organics were washed with brine, dried over anhydrous MgSO₄, and concentrated in vacuo. Following elution by Yamazen column chromatography, 1.68 g of material was recovered that was primarily a mixture of ethyl 2-(6-chloro-1-hydroxy-3-methylnaphthalen-2-yl)-2-(4-methoxybenzyloxy)acetate and 4-methoxybenzyl 2-(6-chloro-1-hydroxy-3-methylnaphthalen-2-yl)-2-(4-methoxybenzyloxy)acetate. This material was taken up in THF/MeOH/H₂O (10/5/5 mL respectively) and treated with LiOH monohydrate (0.86 g, 20.5 mmol). The mixture was heated to 50° C. for 1.5 h and then allowed to cool before acidifying with 2 M HCl solution. The aqueous phase was extracted with EtOAc. The combined organics were washed with brine, dried over anhydrous Na₂SO₄ and concentrated in vacuo to afford 2-(6-chloro-1-hydroxy-3-methylnaphthalen-2-yl)-2-(4-methoxybenzyloxy)acetic acid (0.658 g) as a white foam that was used in the next step without further purification. 2-(6-chloro-1-hydroxy-3-methylnaphthalen-2-yl)-2-(4-methoxybenzyloxy)acetic acid (0.658 g, 1.7 mmol) was diluted in DCM and MeOH (20 mL each) and treated with TMSCHN₂ (2 M in hexanes) until the reaction remained a bright yellow color. After 45 min, glacial acetic acid was added dropwise until the reaction faded to a pale yellow color, indicating any remaining TMSCHN₂ had been destroyed. The reaction was absorbed onto silica gel in vacuo and was purified by Yamazen column chromatography to produce 0.649 g (14% over four steps) of the title compound as an amorphous white solid that was used without further purification. ¹H-NMR: 400 MHz, (CDCl₃) δ: 8.54 (s, 1H); 8.18 (d, J=8.8 Hz, 1H); 7.63 (d, J=1.6 Hz, 1H); 7.33 (dd, J=8.8, 1.6 Hz, 1H); 7.27 (d, J=8.8 Hz, 2H); 7.09 (s, 1H); 6.90 (s, J=8.8 Hz, 2H); 5.38 (s, 1H); 4.65 (AB d, J=11.2 Hz, 1H); 4.59 (AB d, J=11.2 Hz, 1H); 3.83 (s, 3H); 3.73 (s, 3H); 2.39 (s, 3H).

Step 5. Preparation of methyl 2-(6-chloro-3-methyl-1-(trifluoromethylsulfonyloxy)naphthalen-2-yl)-2-(4-methoxybenzyloxy)acetate: A solution of methyl 2-(6-chloro-1-hydroxy-3-methylnaphthalen-2-yl)-2-(4-methoxybenzyloxy)acetate (0.649 g, 1.62 mmol) in DCM (16 mL) under Ar was cooled to −78° C. and treated with 2,6-lutidine (0.56 mL, 4.9 mmol) and trifluoromethanesulfonic anhydride (1.15 mL, 2.4 mmol). After 4 h, saturated NaHCO₃ solution was added at −78° C. and the reaction warmed to room temperature with stirring. Following dilution with water and DCM, the aqueous layer was extracted with DCM and the combined organics were washed with brine, dried over anhydrous MgSO₄ and concentrated in vacuo. The residue was purified using Yamazen column chromatography (5-25% EtOAc/hex) to produce 0.765 g of the title compound as an amorphous solid. ¹H-NMR: 400 MHz, (CDCl₃) δ: 7.97 (d, J=9.2 Hz, 1H); 7.78 (d, J=1.6 Hz, 1H); 7.60 (s, 1H); 7.53 (dd, J=9.2, 1.6 Hz, 1H); 7.24 (d, J=8.8 Hz, 2H); 6.82 (d, J=8.8 Hz, 2H); 5.62 (s, 1H); 4.66 (ABd, J=11.2 Hz, 1H); 4.59 (ABd, J=11.2 Hz, 1H); 3.78 (s, 3H); 3.75 (s, 3H); 2.55 (s, 3H).

Step 6. Preparation of methyl 2-(6-chloro-1-(4-chlorophenyl)-3-methylnaphthalen-2-yl)-2-(4-methoxybenzyloxy)acetate: Methyl 2-(6-chloro-3-methyl-1-(trifluoromethylsulfonyloxy)naphthalen-2-yl)-2-(4-methoxybenzyloxy)acetate (0.106 g, 0.2 mmol), 4-chlorophenylboronic acid (0.038 g, 0.24 mmol), and Pd(PPh$_3$)$_4$ (0.23 g, 0.02 mmol) were combined in DME (1 mL) and treated with 2 M K$_2$CO$_3$ solution (1.2 mL, 0.6 mmol). The resulting mixture was sparged with Ar for 10 minutes and then heated in a microwave reactor at 100° C. for 20 min. The resulting mixture was loaded directly onto silica gel and purified with Yamazen column chromatography (3-25% EtOAc/Hex) to produce 0.051 g of the title compound as an amorphous foam. $^1$H-NMR: 400 MHz, (CDCl$_3$) δ: 7.67 (d, J=2.4 Hz, 1H); 7.60 (s, 1H); 7.42 (dd, J=8, 2.4 Hz, 1H); 7.32 (dd, J=8.2, 2.4 Hz, 1H); 7.28 (dd (obscured), J=8.2, 2.4 Hz, 1H); 7.22 (dd, J=8.8, 2 Hz, 1H); 7.15 (d, J=8.8 Hz, 1H); 7.08 (br d, J=8.4 Hz, 2H); 6.99 (dd, J=8, 2 Hz, 1H); 6.79 (br d, J=8.4 Hz, 2H); 5.05 (s, 1H); 4.46 (ABd, J=11.6 Hz, 1H); 4.35 (ABd, J=11.6 Hz, 1H); 3.82 (s, 3H); 3.72 (s, 3H); 2.57 (s, 3H).

Step 7. Preparation of methyl 2-(6-chloro-1-(4-chlorophenyl)-3-methylnaphthalen-2-yl)-2-hydroxyacetate: A solution of methyl 2-(6-chloro-1-(4-chlorophenyl)-3-methylnaphthalen-2-yl)-2-(4-methoxybenzyloxy)acetate in DCM (1 mL) was treated with trifluoroacetic acid (0.052 mL, 0.67 mmol) at room temperature. After 45 min, the reaction was diluted with DCM and treated with saturated NaHCO$_3$. After separation the organic layer was absorbed directly onto silica gel in vacuo. Purification via Yamazen column chromatography yielded 0.039 g of a colorless film. $^1$H-NMR: 400 MHz, (CDCl$_3$) δ: 7.76 (d, J=1.6 Hz, 1H); 7.60 (s, 1H); 7.52-7.45 (m, 2H); 7.34-7.27 (m, 2H); 7.25 (dd (obscured) J=8.8, 2 Hz, 1H); 7.20 (d, J=8.8 Hz, 1H); 5.23 (s, 1H); 3.74 (s, 3H), 2.49 (s, 3H).

Steps 8 and 9. Preparation of 2-tert-butoxy-2-(6-chloro-1-(4-chlorophenyl)-3-methylnaphthalen-2-yl)acetic acid (67): Step 8 was performed similarly to Step 4 of Example 51. Step 9 was performed similarly to Step 6 of Example 51 with appropriate adjustments for scale to produce 0.006 g of a racemic mixture of the title compound as an amorphous white powder. LCMS-ESI$^-$ (m/z): [M–H]$^-$ calcd for C$_{23}$H$_{21}$Cl$_2$O$_3$: 415.09; found: 415.56. $^1$H-NMR: 400 MHz, (CD$_3$CN) δ: 7.85 (d, J=2 Hz, 1H); 7.70 (s, 1H); 7.59-7.50 (m, 3H); 7.36-7.23 (m, 3H); 5.20 (s, 1H); 2.56 (s, 3H); 0.97 (s, 9H).

EXAMPLE 66

(S)-2-tert-Butoxy-2-((R)-6-chloro-1-(2,3-dihydropyrano[4,3,2-de]quinolin-7-yl)-3-methylnaphthalen-2-yl)acetic acid (68A) and (S)-2-tert-Butoxy-2-((R)-1-(2,3-dihydropyrano[4,3,2-de]quinolin-7-yl)-3,6-dimethylnaphthalen-2-yl)acetic acid (68B)

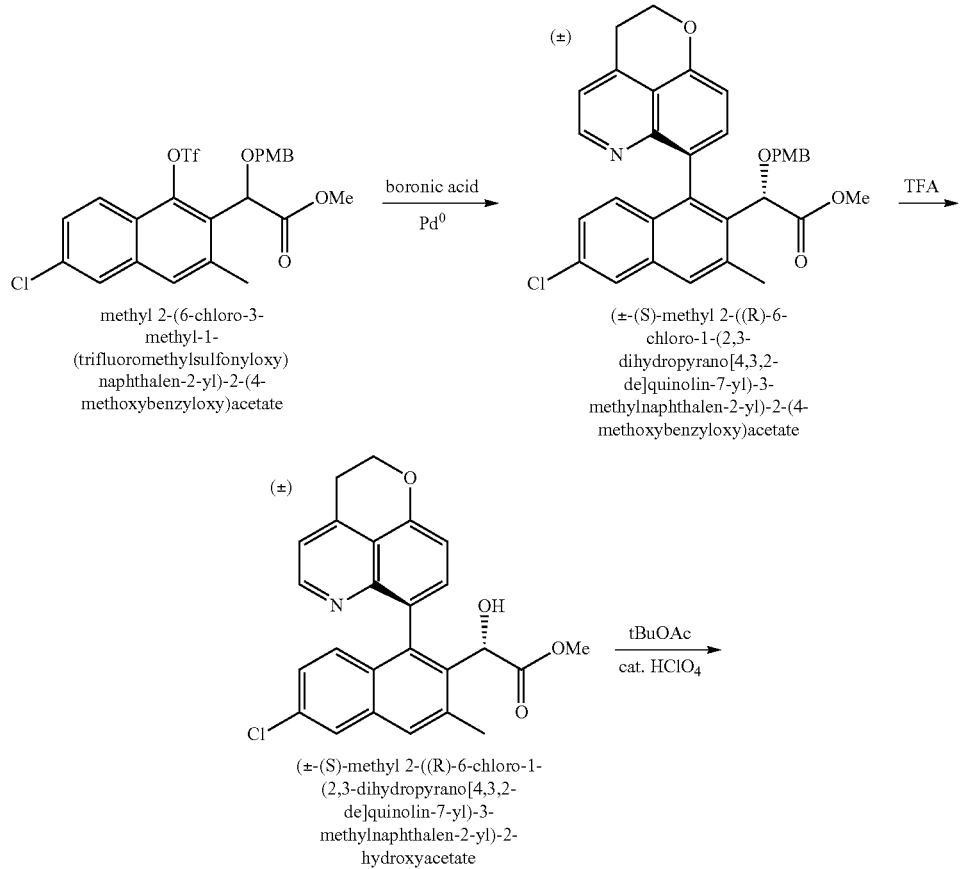

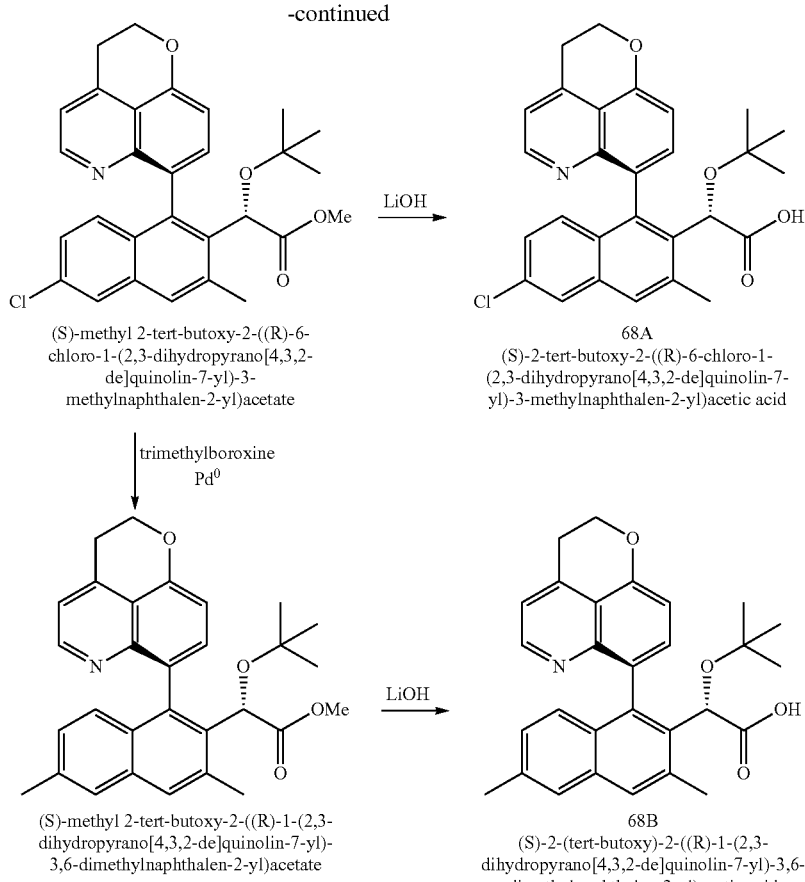

Step 1: Preparation of (±)-(S)-methyl 2-((R)-6-chloro-1-(2,3-dihydropyrano[4,3,2-de]quinolin-7-yl)-3-methylnaphthalen-2-yl)-2-(4-methoxybenzyloxy)acetate. Methyl 2-(6-chloro-3-methyl-1-(trifluoromethyl-sulfonyloxy) naphthalen-2-yl)-2-(4-methoxybenzyloxy)acetate (1.24 g, 2.32 mmol), 2,3-dihydropyrano[4,3,2-de]quinolin-7-ylboronic acid hydrochloride (0.70 g, 2.79 mmol) and Pd(PPh$_3$)$_4$ (0.27 g, 0.232 mmol) were combined in DME (6.2 mL) and treated with 2 M K$_2$CO$_3$ (4.6 mL, 9.3 mmol). After sparging for 10 min with Ar, the reaction was heated in a microwave reactor at 100° C. for 20 min. The reaction mixture was then absorbed directly onto silica gel and purified by Yamazen column chromatography (20-59% EtOAc/Hex) to provide two diastereomer pairs as white amorphous solids. Anti racemate: 0.348 g; $^1$H-NMR: 400 MHz, (CDCl$_3$) δ: 8.70 (d, J=4.4 Hz, 1H); 7.75 (d, J=2 Hz, 1H); 7.63 (s, 1H); 7.35 (d, J=8 Hz, 1H); 7.15 (d, J=8.8 Hz, 2H); 7.09 (d, J=4.4 Hz, 1H); 7.06 (dd, J=8, 2 Hz, 1H); 6.99 (d, J=8 Hz, 1H); 6.95 (d, J=8.8 Hz, 1H); 6.81 (d, J=8.8 Hz, 2H); 4.97 (s, 1H); 4.57 (t, J=5.6 Hz, 2H); 4.53 (AX d, J=11.2 Hz, 1H); 4.24 (AX d, J=11.2 Hz, 1H); 3.81 (s, 3H); 3.58 (s, 3H); 3.33 (t, J=5.6 Hz, 2H); 2.59 (s, 3H). Syn racemate: 0.166 g; $^1$H-NMR: 400 MHz, (CDCl$_3$) δ: 8.64 (d, J=4 Hz, 1H); 7.74 (d, J=2 Hz, 1H); 7.62 (s, 1H); 7.57 (d, J=8 Hz, 1H); 7.08 (br d, J=4 Hz, 1H); 7.04 (dd, J=8, 2 Hz, 1H); 7.03 (d, J=9 Hz, 1H); 6.87 (d, J=9 Hz, 1H); 6.77 (d, J=8.4 Hz, 2H); 6.57 (d, J=8.4 Hz, 2H); 5.04 (s, 1H); 4.52 (m, 2H); 4.23 (AM d, J=12.4 Hz, 1H); 3.99 (AM d, J=12.4 Hz, 1H); 3.71 (s, 3H); 3.67 (s, 3H); 3.31 (m, 2H); 2.56 (s, 3H).

Step 2. (±)-(S)-methyl 2-((R)-6-chloro-1-(2,3-dihydropyrano[4,3,2-de]quinolin-7-yl)-3-methylnaphthalen-2-yl)-2-hydroxyacetate was prepared similarly to Step 7 of Example 65 to produce 0.238 g as an amorphous foam. LCMS-ESI$^+$ (m/z): [M+H]$^+$ calcd for C$_{25}$H$_{21}$ClNO$_4$: 434.89; found: 434.53. The syn racemate was treated in the same fashion to produce 0.106 g of an amorphous foam. LCMS-ESI$^+$ (m/z): [M+H]$^+$ calcd for C$_{25}$H$_{21}$ClNO$_4$: 434.89; found: 434.57.

Step 3. (S)-methyl 2-tert-butoxy-2-((R)-6-chloro-1-(2,3-dihydropyrano[4,3,2-de]quinolin-7-yl)-3-methylnaphthalen-2-yl)acetate was prepared similarly to Step 4 of Example 51 with appropriate adjustments for scale to produce 0.154 g of the anti enantiomers as a colorless film, which were separated by preparatory HPLC on a Chiracel OJ-H column (4.6× 250 mm, 15 mL/min) with 100% MeOH elution to produce 0.063 g of (R)-methyl 2-tert-butoxy-2-((S)-6-chloro-1-(2,3-dihydropyrano[4,3,2-de]quinolin-7-yl)-3-methylnaphthalen-2-yl)acetate and 0.057 g of (S)-methyl 2-tert-butoxy-2-((R)-6-chloro-1-(2,3-dihydropyrano[4,3,2-de]quinolin-7-yl)-3-methylnaphthalen-2-yl)acetate as colorless films. LCMS-ESI$^+$ (m/z): [M+H]$^+$ calcd for C$_{29}$H$_{29}$ClNO$_4$: 490.99; found: 490.59. The syn enantiomers were treated in a similar fashion to produce 0.047 g of a colorless film as a racemic mixture. LCMS-ESI$^+$ (m/z): [M+H]$^+$ calcd for C$_{29}$H$_{29}$ClNO$_4$: 490.99; found: 490.62.

Step 4. (S)-2-tert-butoxy-2-((R)-6-chloro-1-(2,3-dihydropyrano[4,3,2-de]quinolin-7-yl)-3-methylnaphthalen-2-yl) acetic acid (68A) was prepared in a similar fashion to step 6 of Example 51 with appropriate adjustments for scale to produce 0.043 g of a pale yellow amorphous powder. LCMS-ESI$^-$ (m/z): [M−H]$^-$ calcd for C$_{28}$H$_{25}$ClNO$_4$: 474.96; found: 474.37. $^1$H-NMR: 400 MHz, (CD$_3$CN) δ: 8.58 (d, J=5.2 Hz, 1H); 7.93 (d, J=2 Hz, 1H); 7.75 (d, J=8.8 Hz, 1H); 7.60 (d, J=5.2 Hz, 1H); 7.34 (d, J=8 Hz, 1H); 7.20 (dd, J=8, 2 Hz, 1H); 6.88 (d, J=8.8 Hz, 1H); 5.16 (s, 1H); 4.64 (m, 2H); 3.52 (t, J=5.6 Hz, 2H); 2.68 (s, 3H); 0.92 (s, 9H).

Step 5 and 6. Preparation of (S)-2-tert-butoxy-2-((R)-1-(2,3-dihydropyrano[4,3,2-de]quinolin-7-yl)-3,6-dimethylnaphthalen-2-yl)acetic acid (68B): A solution of (S)-methyl 2-tert-butoxy-2-((R)-6-chloro-1-(2,3-dihydropyrano[4,3,2-de]quinolin-7-yl)-3-methylnaphthalen-2-yl)acetate (0.020 g, 0.041 mmol) in toluene (0.5 mL) and EtOH (0.25 mL) was treated with trimethylboroxine (0.021 mL, 0.123 mmol), S-Phos precatalyst (0.001 g, 0.002 mmol) and $K_2CO_3$ (2 M, 0.105 mL, 0.21 mmol). The mixture was sparged with Ar for 10 min and then heated in a microwave reactor at 100° C. for 30 min. The reaction mixture was loaded directly onto silica gel and eluted with Yamazen column chromatography. The collected material was taken up in THF/MeOH/$H_2O$ (1 mL each) and treated with LiOH.$H_2O$ (0.030 g, 0.72 mmol) at 50° C. overnight. Following purification by preparatory HPLC to produce 0.007 g of (S)-2-tert-butoxy-2-((R)-1-(2,3-dihydropyrano[4,3,2-de]quinolin-7-yl)-3,6-dimethylnaphthalen-2-yl)acetic acid (68B). LCMS-ESI$^+$ (m/z): [M+H]$^+$ calcd for $C_{29}H_{30}NO_4$: 456.55; found: 456.15. $^1$H-NMR: 400 MHz, (CD$_3$CN) δ: 8.56 (d, J=4.8 Hz, 1H); 7.79 (s, 1H); 7.72 (br d, J=8, 1H); 7.65 (s, 1H); 7.53 (br s, 1H); 7.30 (d, J=8 Hz, 1H); 7.08 (d, J=8 Hz, 1H); 6.76 (d, J=8 Hz, 1H); 5.15 (br s, 1H); 4.62 (m, 2H); 3.49 (t, J=6 Hz, 2H); 2.65 (s, 3H); 2.44 (s, 3H); 0.92 (s, 9H).

EXAMPLE 67

2-tert-butoxy-2-(1-(4-chlorophenyl)-7-(3-hydroxy-3-methylbut-1-ynyl)-3-methylnaphthalen-2-yl)acetic acid (69)

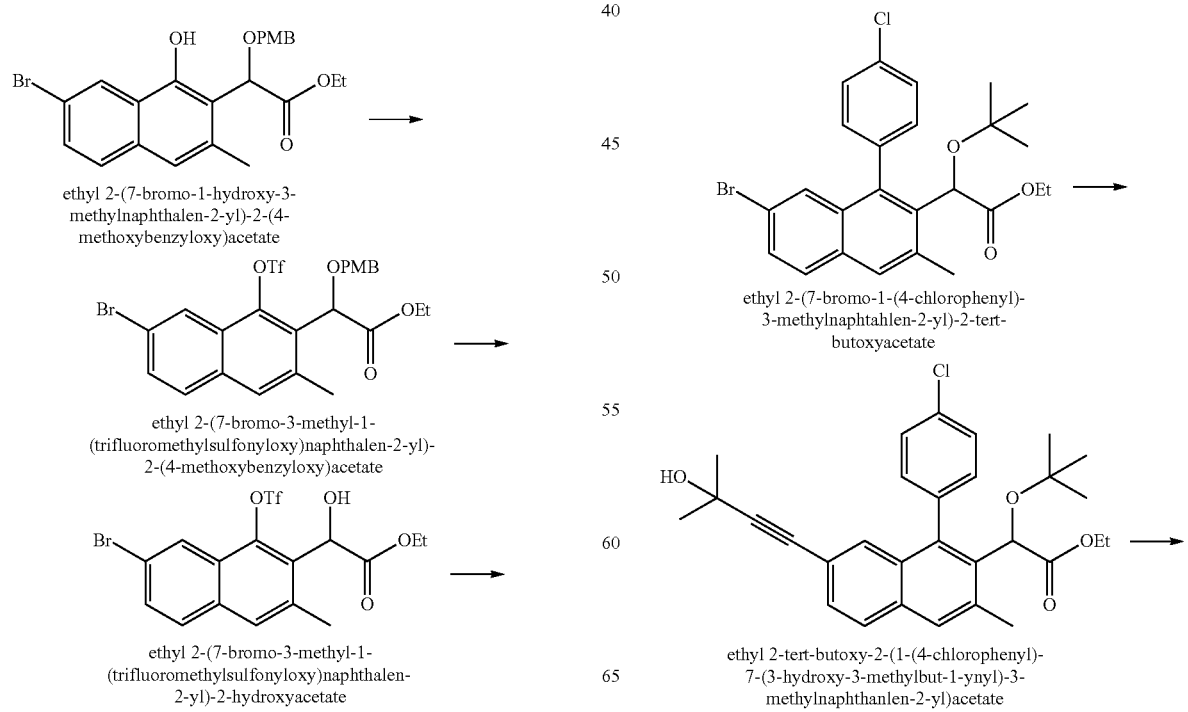

-continued

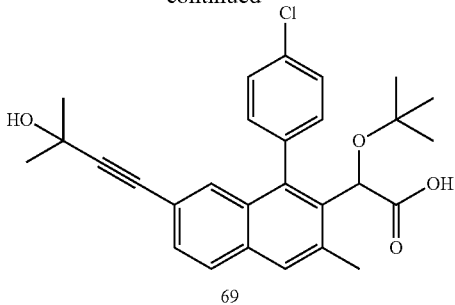

69

2-tert-butoxy-2-(1-(4-chlorophenyl)-7-
(3-hydroxy-3-methylbut-1-ynyl)-3-methylnaphthanlen-2-yl)acetic acid Step 1. Preparation of ethyl 2-(7-bromo-3-methyl-1-(trifluoromethylsulfonyloxy)naphthalen-2-yl)-2-(4-methoxybenzyloxy)acetate: To a solution of ethyl 2-(7-bromo-1-hydroxy-3-methylnaphthalen-2-yl)-2-(4-methoxybenzyloxy)acetate (4.0 g, 8.7 mmol) in $CH_2Cl_2$ (40 mL) at −78° C. was added triethylamine (1.46 mL, 10.5 mmol) and trifluoromethanesulfonic anhydride (1.0 M solution in $CH_2Cl_2$, 9.6 mL, 9.6 mmol). After 15 min, a saturated solution of $NH_4Cl$ was added. The mixture was warmed to room temperature. The layers were separated, dried, filtered, and concentrated in vacuo. The crude product was taken on without further purification. $^1$H-NMR: 400 MHz, ($CDCl_3$) δ: 8.30 (s, 1H), 7.77 (m, 3H), 7.35 (d, J=9 Hz, 2H), 6.94 (d, J=9 Hz, 2H), 5.73 (s, 1H), 4.73 (m, 2H), 4.36 (m, 2H), 3.89 (s, 3H), 2.67 (s, 3H), 1.32 (t, J=7 Hz, 3H).

Step 2. Preparation of ethyl 2-(7-bromo-3-methyl-1-(trifluoromethyl-sulfonyloxy)naphthalen-2-yl)-2-hydroxyacetate: To a solution of ethyl 2-(7-bromo-3-methyl-1-(trifluoromethylsulfonyloxy)naphthalen-2-yl)-2-(4-methoxybenzyl-oxy)acetate (8.7 mmol from previous step) in $CH_2Cl_2$ (40 mL) was added trifluoroacetic acid (TFA) (4 mL). After 1.5 h, water was added (40 mL). The layers were separated. The organic layer was washed with a saturated solution of $NaHCO_3$. The organic layer was dried, filtered, and concentrated in vacuo. The crude product was taken on without further purification. $^1$H-NMR: 400 MHz, ($CDCl_3$) δ: 8.21 (s, 1H), 7.65 (m, 3H), 5.79 (s, 1H), 4.27 (m, 2H), 2.48 (s, 3H), 1.20 (t, J=7 Hz, 3H). $^{19}$F-NMR: 377 MHz, ($CDCl_3$) δ: −73.0.

Step 3. Preparation of ethyl 2-(7-bromo-3-methyl-1-(trifluoromethylsulfonyloxy)naphthalen-2-yl)-2-oxoacetate: To a solution of ethyl 2-(7-bromo-3-methyl-1-(trifluoromethylsulfonyloxy)naphthalen-2-yl)-2-hydroxyacetate (~8.7 mmol) in $CH_2Cl_2$ (40 mL) was added Dess-Martin periodinane (4.07 g, 9.6 mmol). After 1.5 h, a saturated solution of $Na_2S_2O_4$ (20 mL) and water (20 mL) was added. The mixture was stirred vigorously for 30 min. The layers were separated, and the organic layer was dried, filtered, and concentrated in vacuo. The crude material was purified by column chromatography (EtOAc/hexanes) to give 3.22 g (79%) of the titled compound. $^1$H-NMR: 400 MHz, ($CDCl_3$) δ: 8.22 (s, 1H), 7.70 (m, 3H), 4.41 (q, J=7 Hz, 2H), 2.47 (s, 3H), 1.39 (t, J=7 Hz, 3H). $^{19}$F-NMR: 377 MHz, ($CDCl_3$) δ: −73.2.

Step 4. Preparation of ethyl 2-(7-bromo-1-(4-chlorophenyl)-3-methylnaphthalen-2-yl)-2-oxoacetate: To a solution of ethyl 2-(7-bromo-3-methyl-1-(trifluoromethylsulfonyloxy)naphthalen-2-yl)-2-oxoacetate (235 mg, 0.50 mmol) in $PhCH_3$ (1.2 mL), EtOH (0.6 mL), $H_2O$ (0.6 mL) was added 4-chlorophenylboronic acid (86 mg, 0.55 mmol), $K_2CO_3$ (207 mg, 1.5 mmol), and $PdCl_2$dppf (11 mg, 0.015 mmol). The reaction mixture was stirred at room temperature for 2 h and was then diluted with $H_2O$ and EtOAc. The layers were separated, and the organic layer was dried, filtered, and concentrated in vacuo. The crude material was purified by column chromatography (EtOAc/hexanes) to give 129 mg (60%) of the titled compound and 37 mg of the bis-coupled product (ethyl 2-(1,7-bis(4-chlorophenyl)-3-methylnaphthalen-2-yl)-2-oxoacetate). $^1$H-NMR: 400 MHz, ($CDCl_3$) δ: 7.60-7.72 (m, 4H), 7.45 (m, 2H), 7.23 (m, 2H), 3.93 (q, J=7 Hz, 2H), 2.48 (s, 3H), 1.13 (t, J=7 Hz, 3H).

Step 5. Preparation of ethyl 2-(7-bromo-1-(4-chlorophenyl)-3-methylnaphthalen-2-yl)-2-hydroxyacetate: To a solution of ethyl 2-(7-bromo-1-(4-chlorophenyl)-3-methylnaphthalen-2-yl)-2-oxoacetate (1.6 g, 2.78 mmol) in EtOH (10 mL) was added sodium borohydride ($NaBH_4$) (157 mg, 4.17 mmol). After 20 min, a saturated solution of $NH_4Cl$ was added and EtOAc. The layers were separated, and the organic layer was dried, filtered, and concentrated in vacuo. The crude material was taken on without further purification. $^1$H-NMR: 400 MHz, ($CDCl_3$) δ: 7.64 (m, 2H), 7.45 (m, 3H), 7.39 (s, 1H), 7.28 (m, 2H), 5.18 (s, 1H), 4.17 (m, 2H), 2.48 (s, 3H), 1.20 (t, J=7 Hz, 3H).

Step 6. Preparation of ethyl 2-(7-bromo-1-(4-chlorophenyl)-3-methylnaphthalen-2-yl)-2-tert-butoxyacetate: To a solution of ethyl 2-(7-bromo-1-(4-chlorophenyl)-3-methylnaphthalen-2-yl)-2-hydroxyacetate (~2.78 mmol) in t-BuOAc (14 mL) was added perchloric acid ($HClO_4$) (334 µL, 5.56 mmol). After 3 h, water was added. The layers were separated, and the organic layer was dried, filtered, and concentrated in vacuo. The crude material was purified by column chromatography (EtOAc/hexanes) to give 877 mg of the titled compound. $^1$H-NMR: 400 MHz, ($CDCl_3$) δ: 7.62 (m, 2H), 7.51 (m, 4H), 7.27 (m, 2H), 5.09 (s, 1H), 4.15 (m, 2H), 2.59 (s, 3H), 1.19 (t, J=7 Hz, 3H), 1.00 (s, 9H).

Step 7. Preparation of ethyl 2-tert-butoxy-2-(1-(4-chlorophenyl)-7-(3-hydroxy-3-methylbut-1-ynyl)-3-methylnaphthalen-2-yl)acetate: To a solution of ethyl 2-(7-bromo-1-(4-chlorophenyl)-3-methylnaphthalen-2-yl)-2-tert-butoxyacetate (30 mg, 0.061 mmol) in THF (1 mL) was added 2-methylbut-3-yn-2-ol (15 mg, 0.18 mmol), CuI (1 mg, 0.006 mmol), Pd($PPh_3$)$_4$ (3 mg, 0.003 mmol), and $Et_3N$ (50 µL, 0.36 mmol). The reaction mixture was stirred at 65° C. for 1 h. A saturated solution of $NH_4Cl$ was added. The layers were separated, and the organic layer was dried, filtered, and concentrated in vacuo. The crude material was purified by column chromatography (EtOAc/hexanes) to give 22 mg of the titled compound. $^1$H-NMR: 400 MHz, ($CD_3OD$) δ: 7.73 (d, J=9 Hz, 1H), 7.67 (s, 1H), 7.57 (m, 2H), 7.48 (m, 1H), 7.40 (d, J=9 Hz, 1H), 7.29 (d, J=9 Hz, 1H), 7.24 (s, 1H), 5.15 (s, 1H), 4.16 (m, 2H), 2.57 (s, 3H), 1.51 (s, 6H), 1.20 (t, J=7 Hz, 3H), 0.99 (s, 9H).

Step 8. Preparation of 2-tert-butoxy-2-(1-(4-chlorophenyl)-7-(3-hydroxy-3-methylbut-1-ynyl)-3-methylnaphthalen-2-yl)acetic acid (69): To a solution of ethyl 2-tert-butoxy-2-(1-(4-chlorophenyl)-7-(3-hydroxy-3-methylbut-1-ynyl)-3-methylnaphthalen-2-yl)acetate (22 mg, 0.045 mmol) in 2:2:1 THF/MeOH/$H_2O$ (1 mL total) was added a NaOH solution (4 M, 0.2 mL). The reaction mixture was stirred at 60° C. for 2 h. The mixture was partially concentrated and diluted with MeCN and $H_2O$ and purified by reverse phase HPLC (MeCN/$H_2O$) to give 12 mg of the titled compound. $^1$H-NMR: 400 MHz, ($CD_3OD$) δ: 7.73 (d, J=9 Hz, 1H), 7.67 (s, 1H), 7.57 (m, 3H), 7.38 (d, J=9 Hz, 1H), 7.30 (d, J=9 Hz, 1H), 7.26 (s, 1H), 5.16 (s, 1H), 2.60 (s, 3H), 1.51 (s, 6H), 0.98

(s, 9H). HPLC (Kinetex 2.6u, 50×4.6 mm, 2-100% MeCN/H₂O+0.05% HOAc, 5 min run): $t_R$ (min)=3.40.

EXAMPLE 68

2-(1,7-Bis(4-chlorophenyl)-3-methylnaphthalen-2-yl)-2-tert-butoxyacetic acid (70)

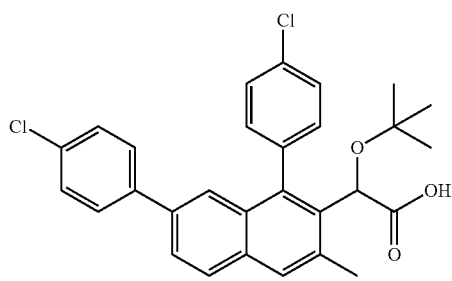

2-(1,7-bis(4-chlorophenyl)-3-methylnaphthanlen-2-yl)-2-tert-butoxyacetic acid

Preparation of 2-(1,7-bis(4-chlorophenyl)-3-methylnaphthalen-2-yl)-2-tert-butoxyacetic acid (70): 2-(1,7-Bis(4-chlorophenyl)-3-methylnaphthalen-2-yl)-2-tert-butoxyacetic acid (70)was prepared by the method of Example 67. Steps 5, 6 and 8 from ethyl 2-(1,7-bis(4-chlorophenyl)-3-methylnaphthalen-2-yl)-2-oxoacetate, which was a byproduct in Step 4. ¹H-NMR: 400 MHz, (CD₃OD) δ: 7.88 (d, J=8 Hz, 2H), 7.72 (m, 2H), 7.58 (m, 3H), 7.44 (m, 3H), 7.38 (d, J=8 Hz, 2H), 5.19 (s, 1H), 2.62 (s, 3H), 0.98 (s, 9H). HPLC (Kinetex 2.6u, 50×4.6 mm, 2-100% MeCN/H₂O+0.05% HOAc, 5 min run): $t_R$ (min)=3.83.

EXAMPLE 69

2-(7-Bromo-1-(4-chlorophenyl)-3-methylnaphthalen-2-yl)-2-tert-butoxyacetic acid (71)

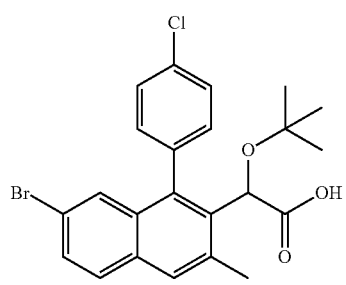

2-(1,7-bromo-1-(4-chlorophenyl)-3-methylnaphthanlen-2-yl)-2-tert-butoxyacetic acid Preparation of 2-(7-bromo-1-(4-chlorophenyl)-3-methylnaphthalen-2-yl)-2-tert-butoxyacetic acid (71): 2-(7-Bromo-1-(4-chlorophenyl)-3-methylnaphthalen-2-yl)-2-tert-butoxyacetic acid (71) was prepared by the method of Example 67 skipping step 7 from ethyl 2-(7-bromo-1-(4-chlorophenyl)-3-methylnaphthalen-2-yl)-2-tert-butoxyacetate. ¹H-NMR: 400 MHz, (CD₃OD) δ: 7.71 (m, 2H), 7.58 (m, 3H), 7.52 (dd, J=9, 2 Hz, 1H), 7.33 (m, 2H), 5.15 (s, 1H), 2.59 (s, 3H), 0.97 (s, 9H). HPLC (Kinetex 2.6u, 50×4.6 mm, 2-100% MeCN/H₂O+0.05% HOAc, 5 min run): $t_R$ (min)=3.67.

EXAMPLE 70

2-tert-Butoxy-2-(1-(4-chlorophenyl)-7-(3,3-dimethylbut-1-ynyl)-3-methylnaphthalen-2-yl)acetic acid (72)

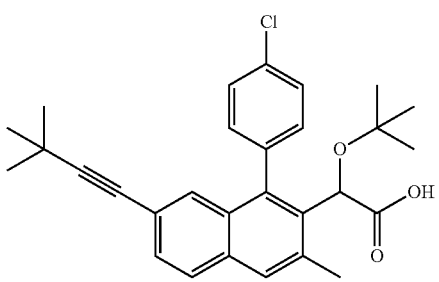

2-tert-butoxy-2-(1-(4-chlorophenyl)-7-(3,3-dimethylbut-1-ynyl)-3-methylnaphthalen-2-yl)acetic acid Preparation of 2-tert-butoxy-2-(1-(4-chlorophenyl)-7-(3,3-dimethylbut-1-ynyl)-3-methylnaphthalen-2-yl)acetic acid (72): 2-tert-Butoxy-2-(1-(4-chlorophenyl)-7-(3,3-dimethylbut-1-ynyl)-3-methylnaphthalen-2-yl)acetic acid (72) was prepared by the method of Example 67 from ethyl 2-(7-bromo-1-(4-chlorophenyl)-3-methylnaphthalen-2-yl)-2-tert-butoxyacetate using t-butylacetylene. ¹H-NMR: 400 MHz, (CD₃OD) δ: 7.70 (d, J=8 Hz, 1H), 7.65 (s, 1H), 7.57 (m, 3H), 7.33 (m, 2H), 7.19 (s, 1H), 5.16 (s, 1H), 2.59 (s, 3H), 1.27 (s, 9H), 0.97 (s, 9H). HPLC (Kinetex 2.6u, 50×4.6 mm, 2-100% MeCN/H₂O+0.05% HOAc, 5 min run): $t_R$ (min)=3.78.

EXAMPLE 71

2-tert-Butoxy-2-(1-(4-chlorophenyl)-7-((1-hydroxycyclo-pentyl)ethynyl)-3-methylnaphthalen-2-yl)acetic acid (73)

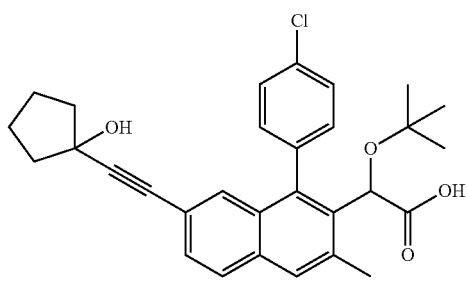

2-tert-butoxy-2-(1-(4-chlorophenyl)-7-((1-hydroxycyclopentyl)ethynyl)-3-methylnaphthalen-2-yl)acetic acid Preparation of 2-tert-butoxy-2-(1-(4-chlorophenyl)-7-((1-hydroxycyclopentyl)ethynyl)-3-methylnaphthalen-2-yl)acetic acid (73): 2-tert-Butoxy-2-(1-(4-chlorophenyl)-7-((1-hydroxycyclopentyl)ethynyl)-3-methylnaphthalen-2-yl)acetic acid (73) was prepared by the method of Example 67 from ethyl 2-(7-bromo-1-(4-chlorophenyl)-3-methylnaphthalen-2-yl)-2-tert-butoxyacetate using 1-ethynylcyclopentanol. $^1$H-NMR: 400 MHz, (CD$_3$OD) δ: 7.73 (d, J=9 Hz, 1H), 7.67 (s, 1H), 7.56 (m, 3H), 7.39 (d, J=8 Hz, 1H), 7.30 (d, J=8 Hz, 1H), 7.26 (s, 1H), 5.17 (s, 1H), 2.60 (s, 3H), 1.93 (m, 4H), 1.78 (m, 4H), 0.98 (s, 9H). HPLC (Kinetex 2.6u, 50×4.6 mm, 2-100% MeCN/H$_2$O+0.05% HOAc, 5 min run): t$_R$ (min)= 3.56.

EXAMPLE 72

2-tert-Butoxy-2-(1-(4-chlorophenyl)-7-(cyclopentylethynyl)-3-methylnaphthalen-2-yl)acetic acid (74)

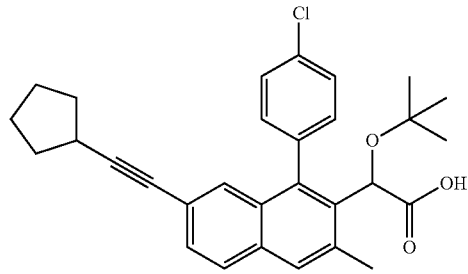

2-tert-butoxy-2-(1-(4-chlorophenyl)-
7-(cyclopentylethynyl)-3-
methylnaphthalen-2-yl)acetic acid 2-tert-Butoxy-2-(1-(4-chlorophenyl)-7-(cyclopentylethynyl)-3-methylnaphthalen-2-yl)acetic acid (74): 2-tert-Butoxy-2-(1-(4-chlorophenyl)-7-(cyclopentylethynyl)-3-methylnaphthalen-2-yl)acetic acid (74) was prepared by the method of Example 67 from ethyl 2-(7-bromo-1-(4-chlorophenyl)-3-methylnaphthalen-2-yl)-2-tert-butoxyacetate using ethynylcyclopentane.
$^1$H-NMR: 400 MHz, (CD$_3$OD) δ: 7.56-7.71 (m, 6H), 7.32 (m, 1H), 7.19 (s, 1H), 5.16 (s, 1H), 2.79 (m, 1H), 2.59 (s, 3H), 1.57-1.75 (m, 8H), 0.97 (s, 9H). HPLC (Kinetex 2.6u, 50×4.6 mm, 2-100% MeCN/H$_2$O+0.05% HOAc, 5 min run): t$_R$ (min)= 4.10.

EXAMPLE 73

2-tert-Butoxy-2-(1-(4-chlorophenyl)-7-(cyclopropylethynyl)-3-methylnaphthalen-2-yl)acetic acid (75)

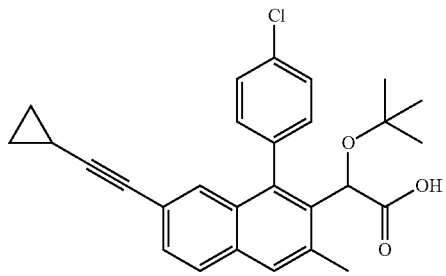

2-tert-butoxy-2-(1-(4-chlorophenyl)-
7-(cyclopropylethynyl)-3-
methylnaphthalen-2-yl)acetic acid Preparation of 2-tert-butoxy-2-(1-(4-chlorophenyl)-7-(cyclopropylethynyl)-3-methylnaphthalen-2-yl)acetic acid (75): 2-tert-Butoxy-2-(1-(4-chlorophenyl)-7-(cyclopropylethynyl)-3-methylnaphthalen-2-yl)acetic acid (75) was prepared by the method of Example 67 from ethyl 2-(7-bromo-1-(4-chlorophenyl)-3-methylnaphthalen-2-yl)-2-tert-butoxyacetate using ethynylcyclopropane. $^1$H-NMR: 400 MHz, (CD$_3$OD) δ: 7.69 (m, 2H), 7.57 (m, 3H), 7.32 (m, 2H), 7.18 (s, 1H), 5.16 (s, 1H), 2.59 (s, 3H), 1.42 (br m, 1H), 0.97 (s, 9H), 0.83 (br m, 2H), 0.68 (br m, 2H). HPLC (Kinetex 2.6u, 50×4.6 mm, 2-100% MeCN/H$_2$O+0.05% HOAc, 5 min run): t$_R$ (min)= 3.78.

EXAMPLE 74

2-tert-Butoxy-2-(1-(4-chlorophenyl)-3-methyl-7-vinylnaphthalen-2-yl)acetic acid (76)

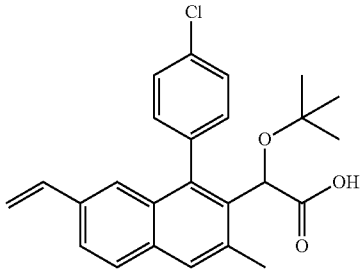

2-tert-butoxy-2-(1-(4-chlorophenyl)-
3-methyl-7-vinylnaphthalen-2-yl)
acetic acid Preparation of 2-tert-butoxy-2-(1-(4-chlorophenyl)-3-methyl-7-vinylnaphthalen-2-yl)acetic acid (76): 2-tert-Butoxy-2-(1-(4-chlorophenyl)-3-methyl-7-vinylnaphthalen-2-yl) acetic acid (76) was prepared by the method of Example 67 from ethyl 2-(7-bromo-1-(4-chlorophenyl)-3-methylnaphthalen-2-yl)-2-tert-butoxyacetate using tributyl(vinyl)tin and without triethylamine. $^1$H-NMR: 400 MHz, (CD$_3$OD) δ: 7.74 (d, J=9 Hz, 1H), 7.65 (m, 2H), 7.55 (m, 3H), 7.32 (d, J=9 Hz, 1H), 7.13 (s, 1H), 6.65 (dd, J=18, 11 Hz, 1H), 5.71 (d, J=18 Hz, 1H), 5.19 (d, J=11 Hz, 1H), 5.17 (s, 1H), 2.59 (s, 3H), 0.98 (s, 9H). HPLC (Kinetex 2.6u, 50×4.6 mm, 2-100% MeCN/H$_2$O+0.05% HOAc, 5 min run): t$_R$ (min)=3.99.

EXAMPLE 75

2-tert-Butoxy-2-(1-(4-chlorophenyl)-3-methyl-7-(2-methylprop-1enyl)naphthalen-2-yl)acetic acid (77)

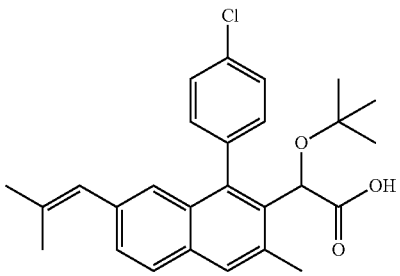

2-tert-butoxy-2-(1-(4-chlorophenyl)-
3-methyl-7-(2-methylprop-1-enyl)naphthalen-2-yl)
acetic acid Preparation of 2-tert-butoxy-2-(1-(4-chlorophenyl)-3-methyl-7-(2-methylprop-1-enyl)naphthalen-2-yl)acetic acid (77): 2-tert-Butoxy-2-(1-(4-chlorophenyl)-3-methyl-7-(2-methylprop-1-enyl)naphthalen-2-yl)acetic acid (77) was prepared by the method of Example 67 from ethyl 2-(7-bromo-1-(4-chlorophenyl)-3-methylnaphthalen-2-yl)-2-tert-butoxyacetate using 4,4,5,5-tetramethyl-2-(2-methylprop-1-enyl)-1,3,2-dioxaborolane and $K_2CO_3$ instead of triethylamine, and toluene, ethanol, water as a solvent mixture. $^1$H-NMR: 400 MHz, (CD$_3$OD) δ: 7.69 (d, J=8 Hz, 1H), 7.61 (s, 1H), 7.54 (m, 3H), 7.27 (m, 2H), 7.02 (s, 1H), 6.23 (s, 1H), 5.18 (s, 1H), 2.57 (s, 3H), 1.83 (s, 3H), 1.68 (s, 3H), 0.97 (s, 9H). HPLC (Kinetex 2.6u, 50×4.6 mm, 2-100% MeCN/H$_2$O+0.05% HOAc, 5 min run): $t_R$ (min)=3.98.

EXAMPLE 76

2-tert-Butoxy-2-(1-(4-chlorophenyl)-3,7-dimethylnaphthalen-2-yl)acetic acid (78)

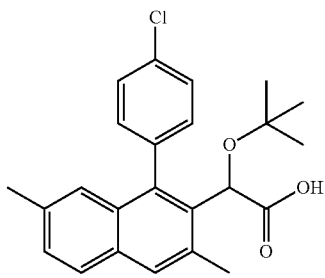

78

2-tert-butoxy-2-(1-(4-chlorophenyl)-3,7-dimethylnaphthalen-2-yl)
acetic acid

Preparation of 2-tert-butoxy-2-(1-(4-chlorophenyl)-3,7-dimethylnaphthalen-2-yl)acetic acid (78): 2-tert-Butoxy-2-(1-(4-chlorophenyl)-3,7-dimethylnaphthalen-2-yl)acetic acid (78) was prepared by the method of Example 67 from ethyl 2-(7-bromo-1-(4-chlorophenyl)-3-methylnaphthalen-2-yl)-2-tert-butoxyacetate using trimethylboroxine and $K_2CO_3$ instead of triethylamine, and toluene, ethanol, water as a solvent mixture. $^1$H-NMR: 400 MHz, (CD$_3$OD) δ: 7.65 (d, J=8 Hz, 1H), 7.61 (s, 1H), 7.53 (m, 3H), 7.27 (m, 2H), 6.98 (s, 1H), 5.15 (s, 1H), 2.56 (s, 3H), 2.30 (s, 3H), 0.96 (s, 9H). HPLC (Kinetex 2.6u, 50×4.6 mm, 2-100% MeCN/H$_2$O+ 0.05% HOAc, 5 min run): $t_R$ (min)=4.06.

EXAMPLE 77

2-tert-Butoxy-2-(1-(4-chlorophenyl)-7-((4-hydroxy-1-methylpiperidin-4-yl)ethynyl)-3-methylnaphthalen-2-yl)acetic acid (79)

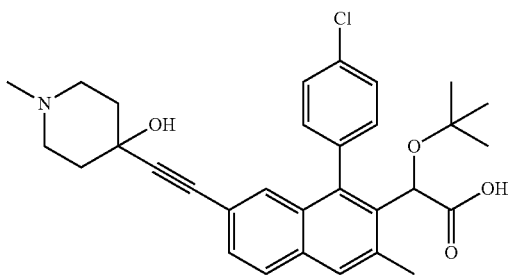

79

2-tert-butoxy-2-(1-(4-chlorophenyl)-7-
((4-hydroxy-1-methylpiperidin-4-yl)ethynyl)-
3-methylnaphthalen-2-yl)acetic acid Preparation of 2-tert-butoxy-2-(1-(4-chlorophenyl)-7-((4-hydroxy-1-methylpiperidin-4-yl)ethynyl)-3-methylnaphthalen-2-yl)acetic acid (79): 2-tert-Butoxy-2-(1-(4-chlorophenyl)-7-((4-hydroxy-1-methylpiperidin-4-yl)ethynyl)-3-methylnaphthalen-2-yl)acetic acid (79) was prepared by the method of Example 68 from ethyl 2-(7-bromo-1-(4-chlorophenyl)-3-methylnaphthalen-2-yl)-2-tert-butoxyacetate using 4-ethynyl-1-methylpiperidin-4-ol. $^1$H-NMR: 400 MHz, (CD$_3$OD) δ: 7.77 (d, J=9 Hz, 1H), 7.70 (br s, 1H), 7.58 (m, 3H), 7.41 (d, J=8 Hz, 1H), 7.30 (m, 2H), 5.16 (s, 1H), 3.35 (m, 4H), 2.89 (s, 3H), 2.60 (s, 3H), 2.15 (m, 4H), 0.98 (s, 9H). LCMS-ESI$^+$ (m/z): [M+H]$^+$ calcd for $C_{31}H_{35}ClNO_4$: 520.2; found: 520.1.

EXAMPLE 78

2-tert-Butoxy-2-(1-(4-chlorophenyl)-7-((4-hydroxytetrahydro-2H-pyran-4-yl)ethynyl)-3-methylnaphthalen-2-yl)acetic acid (80)

80

2-tert-butoxy-2-(1-(4-chlorophenyl)-7-
((4-hydroxytetrahydro-2H-pyran-4-yl)ethynyl)-
3-methylnaphthalen-2-yl)acetic acid Preparation of 2-tert-butoxy-2-(1-(4-chlorophenyl)-7-((4-hydroxytetrahydro-2H-pyran-4-yl)ethynyl)-3-methylnaphthalen-2-yl)acetic acid (80): 2-tert-Butoxy-2-(1-(4-chlorophenyl)-7-((4-hydroxytetrahydro-2H-pyran-4-yl)ethynyl)-3-methylnaphthalen-2-yl)acetic acid (80) was prepared by the method of Example 67 from ethyl 2-(7-bromo-1-(4-chlorophenyl)-3-methylnaphthalen-2-yl)-2-tert-butoxyacetate using 4-ethynyltetrahydro-2H-pyran-4-ol. $^1$H-NMR: 400 MHz, (CD$_3$OD) δ: 7.76 (d, J=8 Hz, 7.68 (s, 1H), 7.57 (m, 3H), 7.42 (d, J=9 Hz, 1H), 7.30 (m, 2H), 5.16 (s, 1H), 3.85 (br m, 2H), 3.65 (br m, 2H), 2.60 (s, 3H), 1.92 (br m, 2H), 1.77 (br m, 2H), 0.98 (s, 9H). HPLC (Kinetex 2.6u, 50×4.6 mm, 2-100% MeCN/H$_2$O+0.05% HOAc, 3.5 min run): t$_R$ (min)=2.41.

EXAMPLE 79

2-tert-Butoxy-2-(1-(4-chlorophenyl)-3-methyl-7-((1-methyl-1H-imidazol-5-yl)ethynyl)naphthalen-2-yl)acetic acid (81)

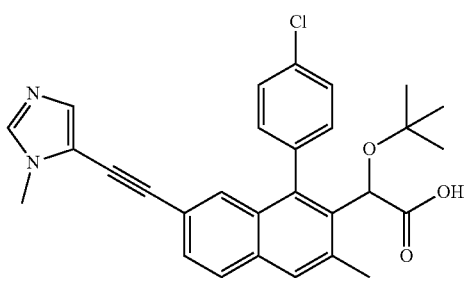

2-tert-butoxy-2-(1-(4-chlorophenyl)-3-methyl-7-((1-methyl-1H-imidazole-5-yl)ethynyl)naphthalen-2-yl)acetic acid Preparation of 2-tert-butoxy-2-(1-(4-chlorophenyl)-3-methyl-7-((1-methyl-1H-imidazol-5-yl)ethynyl)naphthalen-2-yl)acetic acid (81): 2-tert-Butoxy-2-(1-(4-chlorophenyl)-3-methyl-7-((1-methyl-1H-imidazol-5-yl)ethynyl)naphthalen-2-yl)acetic acid (81) was prepared by the method of Example 67 from ethyl 2-(7-bromo-1-(4-chlorophenyl)-3-methylnaphthalen-2-yl)-2-tert-butoxyacetate using 5-ethynyl-1-methyl-1H-imidazole. $^1$H-NMR: 400 MHz, (CD$_3$OD) δ: 8.80 (br s, 1H), 7.87 (d, J=8 Hz, 1H), 7.76 (s, 1H), 7.58 (m, 5H), 7.48 (s, 1H), 7.33 (d, J=8 Hz, 1H), 5.18 (s, 1H), 3.92 (s, 3H), 2.63 (s, 3H), 0.98 (s, 9H). LCMS-ESI$^+$ (m/z): [M+H]$^+$ calcd for C$_{29}$H$_{28}$ClN$_2$O$_3$: 487.2; found: 487.2.

EXAMPLE 80

2-tert-Butoxy-2-(1-(4-chlorophenyl)-7-(3-ethyl-3-hydroxypent-1-ynyl)-3-methylnaphthalen-2-yl)acetic acid (82)

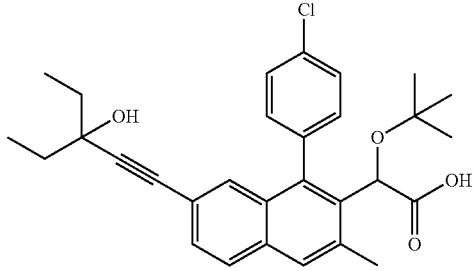

2-tert-butoxy-2-(1-(4-chlorophenyl)-7-(3-ethyl-3-hydroxypent-1-ynyl)-3-methylnaphthalen-2-yl)acetic acid Preparation of 2-tert-butoxy-2-(1-(4-chlorophenyl)-7-(3-ethyl-3-hydroxypent-1-ynyl)-3-methylnaphthalen-2-yl)acetic acid (82): 2-tert-Butoxy-2-(1-(4-chlorophenyl)-7-(3-ethyl-3-hydroxypent-1-ynyl)-3-methylnaphthalen-2-yl)acetic acid (82) was prepared by the method of Example 67 from ethyl 2-(7-bromo-1-(4-chlorophenyl)-3-methylnaphthalen-2-yl)-2-tert-butoxyacetate using 3-ethylpent-1-yn-3-ol. $^1$H-NMR: 400 MHz, (CD$_3$OD) δ: 7.74 (d, J=8 Hz, 1H), 7.67 (s, 1H), 7.58 (m, 3H), 7.40 (d, J=8 Hz, 1H), 7.30 (m, 2H), 5.17 (s, 1H), 2.59 (s, 3H), 1.69 (m, 4H), 1.01 (m, 6H), 0.98 (s, 9H). HPLC (Kinetex 2.6u, 50×4.6 mm, 2-100% MeCN/H$_2$O+0.05% HOAc, 3.5 min run): t$_R$ (min)=2.64.

EXAMPLE 81

2-tert-Butoxy-2-(1-(4-chlorophenyl)-7-((1-hydroxycyclohexyl)ethynyl)-3-methylnaphthalen-2-yl)acetic acid (83)

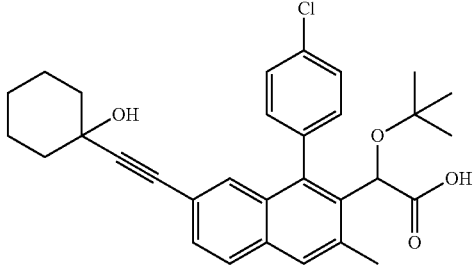

2-tert-butoxy-2-(1-(4-chlorophenyl)-7-((1-hydroxycyclohexyl)ethynyl)-3-methylnaphthalen-2-yl)acetic acid Preparation of 2-tert-butoxy-2-(1-(4-chlorophenyl)-7-((1-hydroxycyclohexyl)ethynyl)-3-methylnaphthalen-2-yl)acetic acid (83): 2-tert-Butoxy-2-(1-(4-chlorophenyl)-7-((1-hydroxycyclohexyl)ethynyl)-3-methylnaphthalen-2-yl)acetic acid (83) was prepared by the method of Example 67 from ethyl 2-(7-bromo-1-(4-chlorophenyl)-3-methylnaphthalen-2-yl)-2-tert-butoxyacetate using 1-ethynylcyclohexanol. $^1$H-NMR: 400 MHz, (CD$_3$OD) δ: 7.75 (d, J=8 Hz, 1H), 7.68 (s, 1H), 7.58 (m, 3H), 7.40 (d, J=8 Hz, 1H), 7.31 (d, J=8 Hz, 1H), 7.28 (s, 1H), 5.17 (s, 1H), 2.60 (s, 3H), 1.91 (m, 2H), 1.57-1.71 (m, 8H), 0.98 (s, 9H). HPLC (Kinetex 2.6u, 50×4.6 mm, 2-100% MeCN/H$_2$O+0.05% HOAc, 3.5 min run): t$_R$ (min)=2.66.

EXAMPLE 82

2-(7-((1-Aminocyclohexyl)ethynyl)-1-(4-chlorophenyl)-3-methylnaphthalen-2-yl)-2-tert-butoxyacetic acid (84)

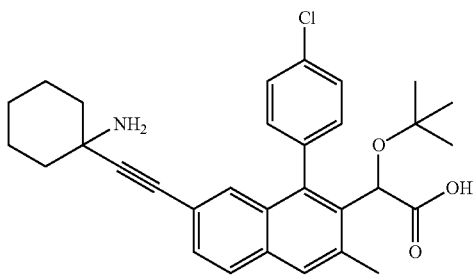

2-(7-((1-aminocyclohexyl)ethynyl)-1-
(4-chlorophenyl)-3-methylnaphthalen-2-yl)-
2-tert-butoxyacetic acid Preparation of 2-(7-((1-aminocyclohexyl)ethynyl)-1-(4-chlorophenyl)-3-methylnaphthalen-2-yl)-2-tert-butoxyacetic acid (84): 2-(7-((1-Aminocyclohexyl)ethynyl)-1-(4-chlorophenyl)-3-methylnaphthalen-2-yl)-2-tert-butoxyacetic acid (84) was prepared by the method of Example 67 from ethyl 2-(7-bromo-1-(4-chlorophenyl)-3-methylnaphthalen-2-yl)-2-tert-butoxyacetate using 1-ethynylcyclohexanamine. $^1$H-NMR: 400 MHz, (CD$_3$OD) δ: 7.82 (d, J=8 Hz, 1H), 7.72 (s, 1H), 7.56 (m, 3H), 7.47 (d, J=8 Hz, 1H), 7.37 (s, 1H), 7.31 (d, J=8 Hz, 1H), 5.20 (s, 1H), 2.60 (s, 3H), 2.11 (m, 2H), 1.63-1.85 (m, 8H), 0.99 (s, 9H). LCMS-ESI$^+$ (m/z): [M—NH$_2$]$^+$ calcd for C$_{31}$H$_{32}$ClO$_3$: 487.2; found: 487.2.

EXAMPLE 83

2-(7-(3-Amino-3-methylbut-1-ynyl)-1-(4-chlorophenyl)-3-methylnaphthalen-2-yl)-2-tert-butoxyacetic acid (85)

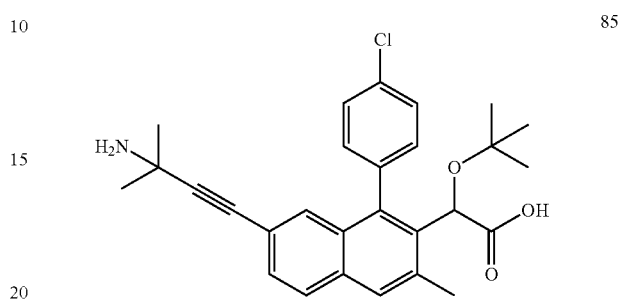

2-(7-(3-amino-3-methylbut-1-ynyl)-1-
(4-chlorophenyl)-3-methylnaphthalen-2-yl)-
2-tert-butoxyacetic acid Preparation of 2-(7-(3-amino-3-methylbut-1-ynyl)-1-(4-chlorophenyl)-3-methylnaphthalen-2-yl)-2-tert-butoxyacetic acid (85): 2-(7-(3-Amino-3-methylbut-1-ynyl)-1-(4-chlorophenyl)-3-methylnaphthalen-2-yl)-2-tert-butoxyacetic acid (85) was prepared by the method of Example 67 from ethyl 2-(7-bromo-1-(4-chlorophenyl)-3-methylnaphthalen-2-yl)-2-tert-butoxyacetate using 2-methylbut-3-yn-2-amine. $^1$H-NMR: 400 MHz, (CD$_3$OD) δ: 7.81 (d, J=8 Hz, 1H), 7.72 (s, 1H), 7.57 (m, 3H), 7.45 (d, J=8 Hz, 1H), 7.35 (s, 1H), 7.30 (d, J=8 Hz, 1H), 5.16 (s, 1H), 2.62 (s, 3H), 1.68 (s, 6H), 0.98 (s, 9H). LCMS-ESI$^+$ (m/z): [M—NH$_2$]$^+$ calcd for C$_{28}$H$_{28}$ClO$_3$: 447.2; found: 446.9.

EXAMPLE 84

(S)-2-((R)-7-(3-Amino-3-methylbut-1-ynyl)-1-(2,3-dihydropyrano[4,3,2-de]quinolin-7-yl)-3-methylnaphthalen-2-yl)-2-tert-butoxyacetic acid (86)

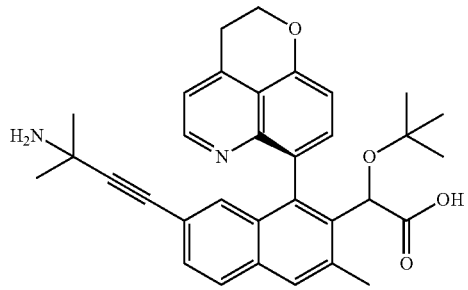

(S)-2-((R)-7-(3-amino-3-methylbut-1-ynyl)-1-
(2,3-dihydropyrano[4,3,2-de]quinolin-7-yl)-3-
methylnaphthalen-2-yl)-2-tert-butoxyacetic acid Preparation of (S)-2-((R)-7-(3-amino-3-methylbut-1-ynyl)-1-(2,3-dihydropyrano[4,3,2-de]quinolin-7-yl)-3-me-

EXAMPLE 85

2-(7-(3-Amino-3-methylbut-1-ynyl)-1-(chroman-6-yl)-3-methylnaphthalen-2-yl)-2-tert-butoxyacetic acid (87)

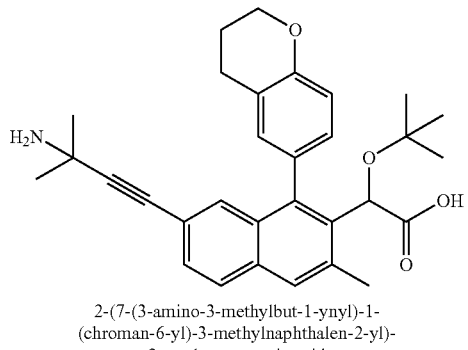

2-(7-(3-amino-3-methylbut-1-ynyl)-1-(chroman-6-yl)-3-methylnaphthalen-2-yl)-2-tert-butoxyacetic acid thylnaphthalen-2-yl)-2-tert-butoxyacetic acid (86): (S)-2-((R)-7-(3-Amino-3-methylbut-1-ynyl)-1-(2,3-dihydropyrano[4,3,2-de]quinolin-7-yl)-3-methylnaphthalen-2-yl)-2-tert-butoxyacetic acid (86) (racemic with relative stereochemistry) was prepared by the method of Example 67 from ethyl 2-(7-bromo-3-methyl-1-(trifluoromethylsulfonyloxy)naphthalen-2-yl)-2-oxoacetate using 2,3-dihydropyrano[4,3,2-de]quinolin-7-ylboronic acid. The remainder of the sequence follows the method of Example 67 using 2-methylbut-3-yn-2-amine was Step 7. $^1$H-NMR: 400 MHz, (CD$_3$OD) δ: 8.72 (d, J=6 Hz, 1H), 8.00 (s, 1H), 7.96 (d, J=8 Hz, 1H), 7.83 (m, 2H), 7.52 (dd, J=8, 2 Hz, 1H), 7.46 (d, J=8 Hz, 1H), 7.07 (s, 1H), 5.21 (s, 1H), 4.73 (m, 2H), 3.68 (t, J=6 Hz, 2H), 2.78 (s, 3H), 1.61 (s, 6H), 0.92 (s, 9H). LCMS-ESI$^+$ (m/z): [M+H]$^+$ calcd for C$_{33}$H$_{35}$N$_2$O$_4$: 523.3; found: 523.1.

Preparation of 2-(7-(3-amino-3-methylbut-1-ynyl)-1-(chroman-6-yl)-3-methylnaphthalen-2-yl)-2-tert-butoxyacetic acid (87): 2-(7-(3-Amino-3-methylbut-1-ynyl)-1-(chroman-6-yl)-3-methylnaphthalen-2-yl)-2-tert-butoxyacetic acid (87) was prepared by the method of Example 67 from ethyl 2-(7-bromo-3-methyl-1-(trifluoromethylsulfonyloxy)naphthalen-2-yl)-2-oxoacetate using chroman-6-ylboronic acid. The remainder of the sequence follows the method of Example 67 using 2-methylbut-3-yn-2-amine in Step 7. $^1$H-NMR: 400 MHz, (CD$_3$OD) δ: 7.77 (d, J=8 Hz, 1H), 7.66 (s, 1H), 7.48 (s, 1H), 7.45 (m, 1H), 7.23 (m, 1H), 6.90 (m, 2H), 5.31 (s, 1H), 4.28 (t, J=5 Hz, 1H), 2.87 (m, 2H), 2.58 (s, 3H), 2.08 (m, 2H), 1.68 (s, 6H), 0.99 (s, 9H). LCMS-ESI$^+$ (m/z): [M—NH$_2$]$^+$ calcd for C$_{31}$H$_{33}$O$_4$: 469.2; found: 469.2.

EXAMPLE 86

2-tert-Butoxy-2-(1-(4-chlorophenyl)-7-(3-hydroxy-3-phenylbut-1-ynyl)-3-methylnaphthalen-2-yl)acetic acid (88)

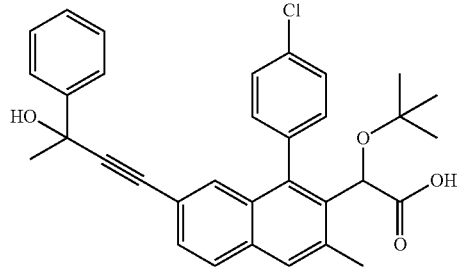

2-tert-butoxy-2-(1-(4-chlorophenyl)-7-(3-hydroxy-3-phenylbut-1-ynyl)-3-methylnaphthalen-2-yl)acetic acid Preparation of 2-tert-butoxy-2-(1-(4-chlorophenyl)-7-(3-hydroxy-3-phenylbut-1-ynyl)-3-methylnaphthalen-2-yl)acetic acid (88): 2-tert-Butoxy-2-(1-(4-chlorophenyl)-7-(3-hydroxy-3-phenylbut-1-ynyl)-3-methylnaphthalen-2-yl)acetic acid (88) was prepared by the method of Example 67 from ethyl 2-(7-bromo-1-(4-chlorophenyl)-3-methylnaphthalen-2-yl)-2-tert-butoxyacetate using 2-phenylbut-3-yn-2-ol. $^1$H-NMR: 400 MHz, (CD$_3$OD) δ: 7.76 (d, J=8 Hz, 1H), 7.69 (s, 1H), 7.64 (d, J=8 Hz, 2H), 7.57 (m, 3H), 7.46 (d, J=8 Hz, 1H), 7.33 (m, 5H), 5.18 (s, 1H), 2.61 (s, 3H), 1.75 (s, 3H), 0.98 (s, 9H). LCMS-ESI$^+$ (m/z): [M—OH]$^+$ calcd for C$_{33}$H$_{30}$ClO$_3$: 509.1; found: 508.8.

EXAMPLE 87

2-tert-Butoxy-2-(1-(4-chlorophenyl)-7-(3-hydroxy-3-methylbutyl)-3-methylnaphthalen-2-yl)acetic acid (89)

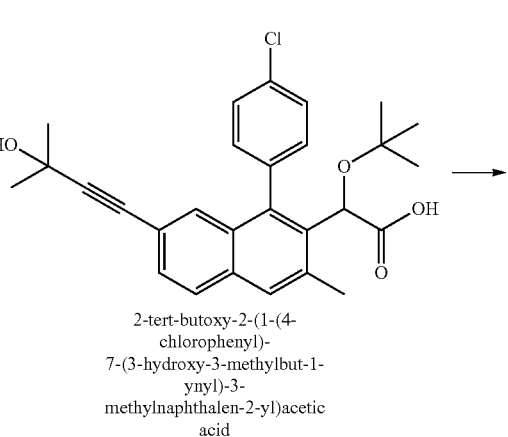

2-tert-butoxy-2-(1-(4-chlorophenyl)-7-(3-hydroxy-3-methylbut-1-ynyl)-3-methylnaphthalen-2-yl)acetic acid -continued

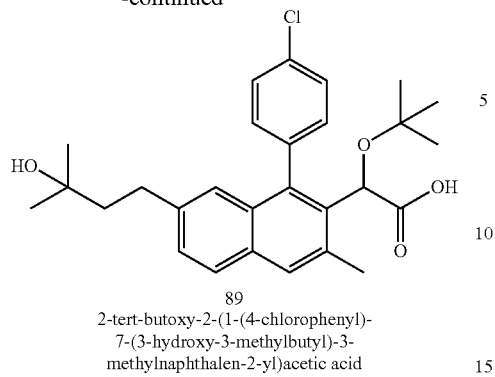

89
2-tert-butoxy-2-(1-(4-chlorophenyl)-
7-(3-hydroxy-3-methylbutyl)-3-
methylnaphthalen-2-yl)acetic acid Preparation of 2-tert-butoxy-2-(1-(4-chlorophenyl)-7-(3-hydroxy-3-methylbutyl)-3-methylnaphthalen-2-yl)acetic acid (89): To a solution of 2-tert-butoxy-2-(1-(4-chlorophenyl)-7-(3-hydroxy-3-methylbut-1-ynyl)-3-methylnaphthalen-2-yl)acetic acid (8 mg, 0.017 mmol) in EtOH (1 mL) was added rhodium on alumina (2 mg). The reaction was flushed with hydrogen gas and then stirred under and hydrogen atmosphere for 1 h. The reaction was filtered and concentrated in vacuo to give 7 mg of the titled compound. $^1$H-NMR: 400 MHz, (CD$_3$OD) δ: 7.68 (d, J=8 Hz, 1H), 7.63 (m, 1H), 7.61 (s, 1H), 7.53 (m, 2H), 7.30 (m, 2H), 7.05 (s, 1H), 5.12 (s, 1H), 2.65 (m, 2H), 2.59 (s, 3H), 1.66 (m, 2H), 1.19 (s, 6H), 0.96 (s, 9H). HPLC (Kinetex 2.6u, 50×4.6 mm, 2-100% MeCN/H$_2$O+0.05% HOAc, 4.0 min run): $t_R$ (min)=3.52.

EXAMPLE 88

2-tert-Butoxy-2-(1-(4-chlorophenyl)-7-(2-cyclopentylethyl)-3-methylnaphthalen-2-yl)acetic acid (90)

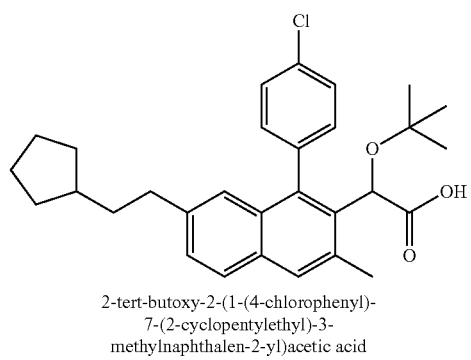

90

2-tert-butoxy-2-(1-(4-chlorophenyl)-
7-(2-cyclopentylethyl)-3-
methylnaphthalen-2-yl)acetic acid Preparation of 2-tert-butoxy-2-(1-(4-chlorophenyl)-7-(2-cyclopentylethyl)-3-methylnaphthalen-2-yl)acetic acid (90): 2-tert-Butoxy-2-(1-(4-chlorophenyl)-7-(2-cyclopentylethyl)-3-methylnaphthalen-2-yl)acetic acid (90) was prepared using the procedure of Example 87 from 2-tert-butoxy-2-(1-(4-chlorophenyl)-7-(cyclopentylethynyl)-3-methylnaphthalen-2-yl)acetic acid. $^1$H-NMR: 400 MHz, (CD$_3$OD) δ: 7.69 (d, J=9 Hz, 1H), 7.63 (s, 1H), 7.56 (m, 3H), 7.29 (m, 2H), 6.99 (s, 1H), 5.18 (s, 1H), 2.60 (m, 2H), 2.58 (s, 3H), 1.71 (m, 3H), 1.52 (m, 6H), 1.07 (m, 2H), 0.98 (s, 9H).

HPLC (Kinetex 2.6u, 50×4.6 mm, 2-100% MeCN/H$_2$O+0.05% HOAc, 5.0 min run): $t_R$ (min)=4.54.

EXAMPLE 89

2-tert-Butoxy-2-(1-(4-chlorophenyl)-7-(2-(1-hydroxycyclopentyl)ethyl)-methylnaphthalen-2-yl)acetic acid (91)

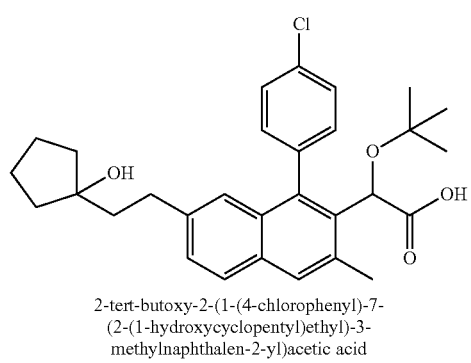

91

2-tert-butoxy-2-(1-(4-chlorophenyl)-7-
(2-(1-hydroxycyclopentyl)ethyl)-3-
methylnaphthalen-2-yl)acetic acid Preparation of 2-tert-butoxy-2-(1-(4-chlorophenyl)-7-(2-(1-hydroxycyclopentyl)ethyl)-3-methylnaphthalen-2-yl)acetic acid (91): 2-tert-Butoxy-2-(1-(4-chlorophenyl)-7-(2-(1-hydroxycyclopentyl)ethyl)-3-methylnaphthalen-2-yl)acetic acid (91) was prepared using the procedure of Example 87 from 2-tert-butoxy-2-(1-(4-chlorophenyl)-7-((1-hydroxycyclopentyl)ethynyl)-3-methylnaphthalen-2-yl)acetic acid. $^1$H-NMR: 400 MHz, (CD$_3$OD) δ: 7.78 (d, J=8 Hz, 1H), 7.67 (d, J=8 Hz, 1H), 7.58 (s, 1H), 7.51 (m, 2H), 7.29 (m, 2H), 7.07 (s, 1H), 5.05 (s, 1H), 2.70 (m, 2H), 2.62 (s, 3H), 1.75 (m, 4H), 1.61 (m, 6H), 0.94 (s, 9H). HPLC (Kinetex 2.6u, 50×4.6 mm, 2-100% MeCN/H$_2$O+0.05% HOAc, 4.0 min run): $t_R$ (min)=3.69.

EXAMPLE 90

2-tert-Butoxy-2-(1-(4-chlorophenyl)-7-(2-cyclopropylethyl)-3-methylnaphthalen-2-yl)acetic acid (92)

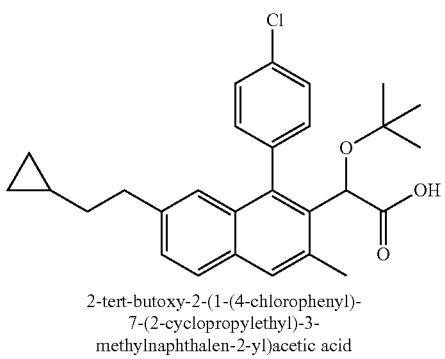

92

2-tert-butoxy-2-(1-(4-chlorophenyl)-
7-(2-cyclopropylethyl)-3-
methylnaphthalen-2-yl)acetic acid Preparation of 2-tert-butoxy-2-(1-(4-chlorophenyl)-7-(2-cyclopropylethyl)-3-methylnaphthalen-2-yl)acetic acid (92): 2-tert-Butoxy-2-(1-(4-chlorophenyl)-7-(2-cyclopropylethyl)-3-methylnaphthalen-2-yl)acetic acid (92) was prepared using the procedure of Example 87 from 2-tert-butoxy-2-(1-(4-chlorophenyl)-7-(cyclopropylethynyl)-3-methylnaphthalen-2-yl)acetic acid. ¹H-NMR: 400 MHz, (CD₃OD) δ: 7.73 (d, J=9 Hz, 1H), 7.67 (s, 1H), 7.60 (m, 3H), 7.35 (m, 2H), 7.06 (s, 1H), 5.21 (s, 1H), 2.72 (t, J=7 Hz, 2H), 2.62 (s, 3H), 1.48 (m, 2H), 0.94 (s, 9H), 0.65 (m, 1H), 0.37 (m, 2H), 0.01 (m, 2H). HPLC (Kinetex 2.6u, 50×4.6 mm, 2-100% MeCN/H₂O+0.05% HOAc, 5.0 min run): $t_R$ (min)=4.02.

EXAMPLE 91

2-tert-Butoxy-2-(1-(4-chlorophenyl)-7-ethyl-3-methylnaphthalen-2-yl)acetic acid (93)

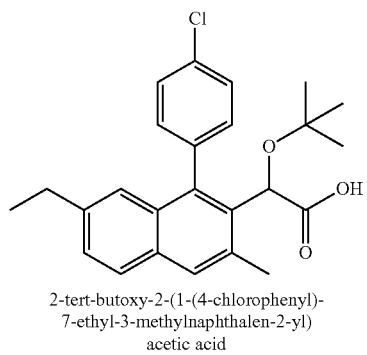

93

2-tert-butoxy-2-(1-(4-chlorophenyl)-7-ethyl-3-methylnaphthalen-2-yl)acetic acid

Preparation of 2-tert-butoxy-2-(1-(4-chlorophenyl)-7-ethyl-3-methylnaphthalen-2-yl)acetic acid (93): 2-tert-Butoxy-2-(1-(4-chlorophenyl)-7-ethyl-3-methylnaphthalen-2-yl)acetic acid (93) was prepared using the procedure of Example 87 from 2-tert-butoxy-2-(1-(4-chlorophenyl)-3-methyl-7-vinylnaphthalen-2-yl)acetic acid. ¹H-NMR: 400 MHz, (CD₃OD) δ: 7.74 (d, J=8 Hz, 1H), 7.67 (d, J=8 Hz, 1H), 7.59 (s, 1H), 7.53 (m, 2H), 7.29 (m, 2H), 7.04 (s, 1H), 5.07 (s, 1H), 2.60 (m, 5H), 1.15 (t, J=7 Hz, 3H), 0.94 (s, 9H). HPLC (Kinetex 2.6u, 50×4.6 mm, 2-100% MeCN/H₂O+0.05% HOAc, 4.0 min run): $t_R$ (min)=3.81.

EXAMPLE 92

2-tert-Butoxy-2-(1-(4-chlorophenyl)-7-isobutyl-3-methylnaphthalen-2-yl)acetic acid (94)

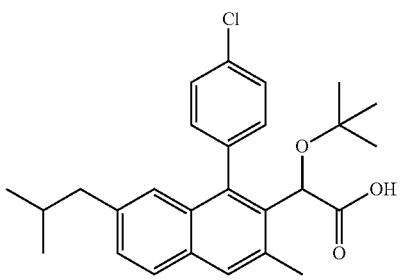

94

2-tert-butoxy-2-(1-(4-chlorophenyl)-7-isobutyl-3-methylnaphthalen-2-yl)acetic acid Preparation of 2-tert-butoxy-2-(1-(4-chlorophenyl)-7-isobutyl-3-methylnaphthalen-2-yl)acetic acid (94): 2-tert-Butoxy-2-(1-(4-chlorophenyl)-7-isobutyl-3-methylnaphthalen-2-yl)acetic acid (94) was prepared using the procedure of Example 87 from 2-tert-butoxy-2-(1-(4-chlorophenyl)-3-methyl-7-(2-methylprop-1-enyl)naphthalen-2-yl)acetic acid. ¹H-NMR: 400 MHz, (CD₃OD) δ: 7.66 (m, 3H), 7.55 (m, 2H), 7.28 (m, 2H), 6.97 (s, 1H), 5.13 (s, 1H), 2.59 (s, 3H), 2.44 (d, J=7 Hz, 2H), 0.96 (s, 9H), 0.83 (m, 6H). HPLC (Kinetex 2.6u, 50×4.6 mm, 2-100% MeCN/H₂O+0.05% HOAc, 4.0 min run): $t_R$ (min)=3.03.

EXAMPLE 93

2-tert-Butoxy-2-(1-(4-chlorophenyl)-7-(3-(dimethylamino)-3-methylbut-1-ynyl)-3-methylnaphthalen-2-yl)acetic acid (95)

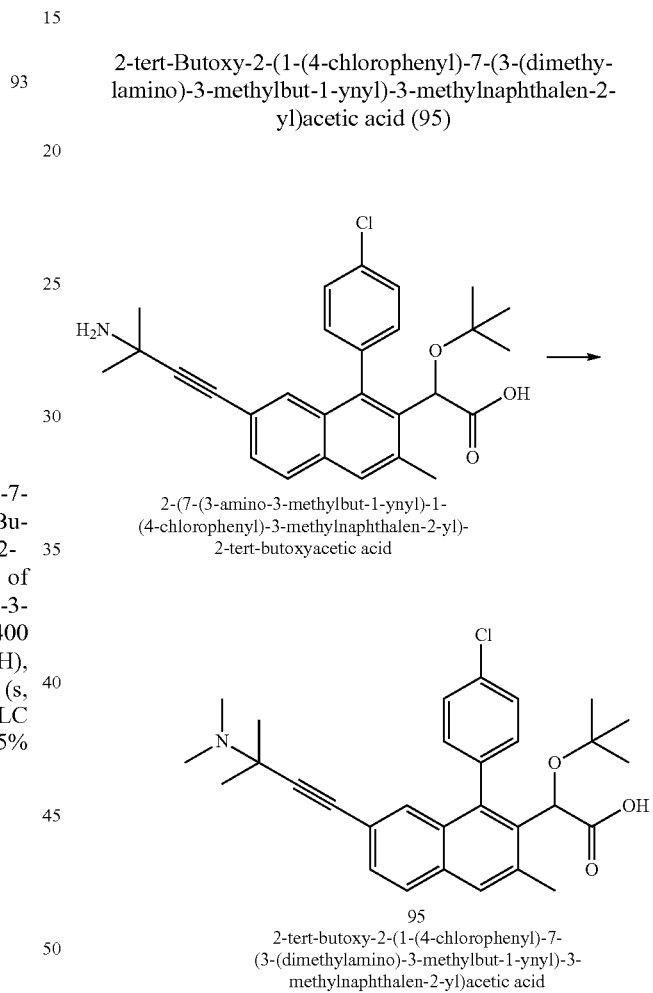

2-(7-(3-amino-3-methylbut-1-ynyl)-1-(4-chlorophenyl)-3-methylnaphthalen-2-yl)-2-tert-butoxyacetic acid 95
2-tert-butoxy-2-(1-(4-chlorophenyl)-7-(3-(dimethylamino)-3-methylbut-1-ynyl)-3-methylnaphthalen-2-yl)acetic acid Preparation of 2-tert-butoxy-2-(1-(4-chlorophenyl)-7-(3-(dimethylamino)-3-methylbut-1-ynyl)-3-methylnaphthalen-2-yl)acetic acid (95): To a solution of 2-(7-(3-amino-3-methylbut-1-ynyl)-1-(4-chlorophenyl)-3-methylnaphthalen-2-yl)-2-tert-butoxyacetic acid (12 mg, 0.026 mmol) in MeOH (1 mL) was added acetic acid (100 μL), formaldehyde (50 μL, 37% in water), and sodium triacetoxyborohydride (10 mg). After 30 min, the reaction mixture was filtered and purified by reverse phase HPLC (MeCN/H₂O w/0.1% TFA) to give 4 mg of the titled compound.

¹H-NMR: 400 MHz, (CD₃OD) δ: 7.85 (d, J=8 Hz, 1H), 7.74 (s, 1H), 7.57 (m, 3H), 7.51 (d, J=8 Hz, 1H), 7.40 (s, 1H), 7.31 (d, J=8 Hz, 1H), 5.16 (s, 1H), 2.97 (s, 6H), 2.62 (s, 3H), 1.75 (s, 6H), 0.98 (s, 9H). LCMS-ESI⁺ (m/z): [M+H]⁺ calcd for $C_{30}H_{35}ClNO_3$: 492.2; found: 492.0.

EXAMPLE 94

2-(7-(3-Acetamido-3-methylbut-1-ynyl)-1-(4-chlorophenyl)-3-methylnaphthalen-2-yl)-2-tert-butoxyacetic acid (96)

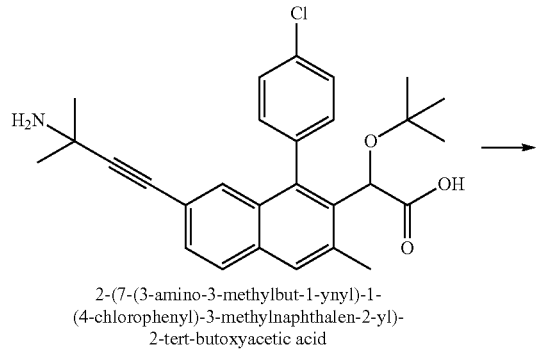

2-(7-(3-amino-3-methylbut-1-ynyl)-1-
(4-chlorophenyl)-3-methylnaphthalen-2-yl)-
2-tert-butoxyacetic acid

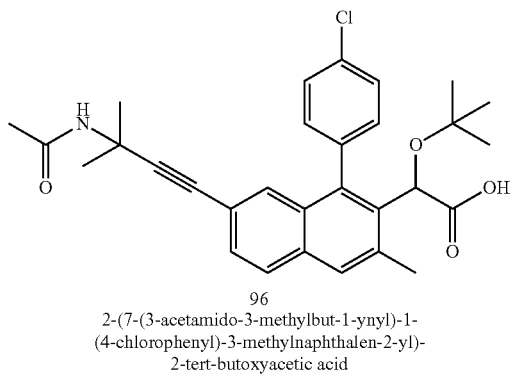

96
2-(7-(3-acetamido-3-methylbut-1-ynyl)-1-
(4-chlorophenyl)-3-methylnaphthalen-2-yl)-
2-tert-butoxyacetic acid Preparation of 2-(7-(3-acetamido-3-methylbut-1-ynyl)-1-(4-chlorophenyl)-3-methylnaphthalen-2-yl)-2-tert-butoxyacetic acid (96): To a solution of 2-(7-(3-amino-3-methylbut-1-ynyl)-1-(4-chlorophenyl)-3-methylnaphthalen-2-yl)-2-tert-butoxyacetic acid (12 mg, 0.026 mmol) in $CH_2Cl_2$ (1 mL) was added triethylamine (50 μL) and acetic anhydride (10 μL) and trace DMAP. After 30 min, the reaction mixture was filtered and purified by reverse phase HPLC (MeCN/$H_2O$ w/0.1% TFA) to give 10 mg of the titled compound. ¹H-NMR: 400 MHz, (CD₃OD) δ: 7.73 (d, J=9 Hz, 1H), 7.67 (s, 1H), 7.58 (m, 3H), 7.40 (d, J=9 Hz, 1H), 7.32 (d, J=9 Hz, 1H), 7.27 (s, 1H), 5.16 (s, 1H), 2.60 (s, 3H), 1.90 (s, 3H), 1.61 (s, 6H), 0.98 (s, 9H). LCMS-ESI⁺ (m/z): [M+H]⁺ calcd for $C_{30}H_{33}ClNO_4$: 506.2; found: 506.0.

EXAMPLE 95

2-tert-Butoxy-2-(1-(4-chlorophenyl)-7-(3-(methoxycarbonylamino)-3-methylbut-1-ynyl)-3-methylnaphthalen-2-yl)acetic acid (97)

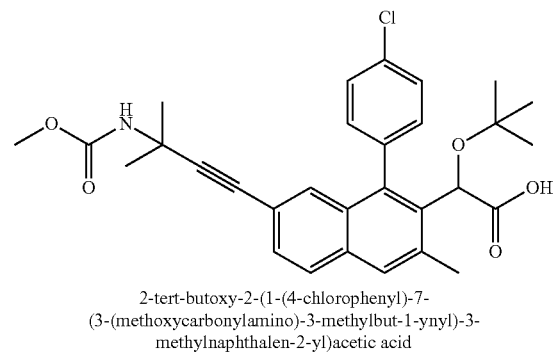

2-tert-butoxy-2-(1-(4-chlorophenyl)-7-
(3-(methoxycarbonylamino)-3-methylbut-1-ynyl)-3-
methylnaphthalen-2-yl)acetic acid Preparation of 2-tert-butoxy-2-(1-(4-chlorophenyl)-7-(3-(methoxycarbonylamino)-3-methylbut-1-ynyl)-3-methylnaphthalen-2-yl)acetic acid (97): 2-tert-Butoxy-2-(1-(4-chlorophenyl)-7-(3-(methoxycarbonylamino)-3-methylbut-1-ynyl)-3-methylnaphthalen-2-yl)acetic acid (97) was prepared by the method of Example 94 from 2-(7-(3-amino-3-methylbut-1-ynyl)-1-(4-chlorophenyl)-3-methylnaphthalen-2-yl)-2-tert-butoxyacetic acid using methyl chloroformate. ¹H-NMR: 400 MHz, (CD₃OD) δ: 7.72 (d, J=8 Hz, 1H), 7.67 (s, 1H), 7.57 (m, 3H), 7.40 (d, J=8 Hz, 1H), 7.31 (d, J=9 Hz, 1H), 7.26 (s, 1H), 5.16 (s, 1H), 3.60 (s, 3H), 2.60 (s, 3H), 1.58 (s, 6H), 0.98 (s, 9H). LCMS-ESI⁺ (m/z): [M+H]⁺ calcd for $C_{30}H_{33}ClNO_5$: 522.2. found: 522.1.

EXAMPLE 96

(S)-2-(7-(3-Amino-3-methylbut-1-ynyl)-1-(4-chlorophenyl)-3-methylnaphthalen-2-yl)-2-tert-butoxyacetic acid (98)

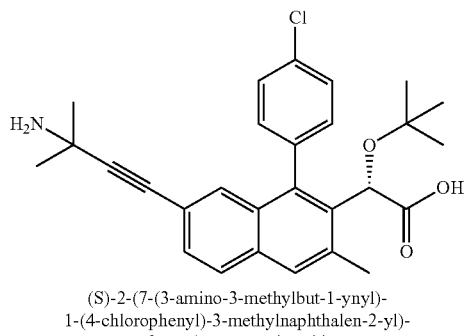

(S)-2-(7-(3-amino-3-methylbut-1-ynyl)-
1-(4-chlorophenyl)-3-methylnaphthalen-2-yl)-
2-tert-butoxyacetic acid Preparation of (S)-2-(7-(3-amino-3-methylbut-1-ynyl)-1-(4-chlorophenyl)-3-methylnaphthalen-2-yl)-2-tert-butoxyacetic acid (98): (S)-2-(7-(3-Amino-3-methylbut-1-ynyl)-1-(4-chlorophenyl)-3-methylnaphthalen-2-yl)-2-tert-butoxyacetic acid (98) was prepared by the method of Example 67 using the reduction method of Example 51, step 3, for (S)-ethyl 2-(1-(4-chlorophenyl)-3-methyl-6-(trifluoromethylsulfonyloxy) naphthalen-2-yl)-2-hydroxyacetate instead of step 5, NaBH$_4$ step, from ethyl 2-(7-bromo-1-(4-chlorophenyl)-3-methylnaphthalen-2-yl)-2-oxoacetate. The remainder of the sequence follows the method of Example 67 using 2-methylbut-3-yn-2-amine in Step 7. $^1$H-NMR: 400 MHz, (CD$_3$OD) δ: 7.81 (d, J=8 Hz, 1H), 7.72 (s, 1H), 7.57 (m, 3H), 7.45 (d, J=8 Hz, 1H), 7.35 (s, 1H), 7.30 (d, J=8 Hz, 1H), 5.16 (s, 1H), 2.62 (s, 3H), 1.68 (s, 6H), 0.98 (s, 9H). LCMS-ESI$^+$ (m/z): [M—NH$_2$]calcd for C$_{28}$H$_{28}$ClO$_3$: 447.2; found: 446.9.

EXAMPLE 97

(S)-2-tert-Butoxy-2-(1-(4-chlorophenyl)-7-(3-hydroxy-3-methylbut-1-ynyl)-3-methylnaphthalen-2-yl)acetic acid (99)

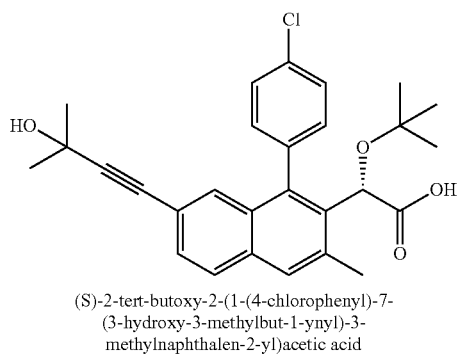

(S)-2-tert-butoxy-2-(1-(4-chlorophenyl)-7-(3-hydroxy-3-methylbut-1-ynyl)-3-methylnaphthalen-2-yl)acetic acid Preparation of (S)-2-tert-butoxy-2-(1-(4-chlorophenyl)-7-(3-hydroxy-3-methylbut-1-ynyl)-3-methylnaphthalen-2-yl) acetic acid (99): (S)-2-tert-Butoxy-2-(1-(4-chlorophenyl)-7-(3-hydroxy-3-methylbut-1-ynyl)-3-methylnaphthalen-2-yl) acetic acid (99) was prepared by the method of Example 67 using the reduction method of Example 51 step 3 for (S)-ethyl 2-(1-(4-chlorophenyl)-3-methyl-6-(trifluoromethylsulfonyloxy) naphthalen-2-yl)-2-hydroxyacetate instead of step 5, NaBH$_4$ step, from ethyl 2-(7-bromo-1-(4-chlorophenyl)-3-methylnaphthalen-2-yl)-2-oxoacetate. The remainder of the sequence follows the method of Example 67 using 2-methylbut-3-yn-2-ol in Step 7. $^1$H-NMR: 400 MHz, (CD$_3$OD) δ: 7.73 (d, J=9 Hz, 1H), 7.67 (s, 1H), 7.57 (m, 3H), 7.38 (d, J=9 Hz, 1H), 7.30 (d, J=9 Hz, 1H), 7.26 (s, 1H), 5.16 (s, 1H), 2.60 (s, 3H), 1.51 (s, 6H), 0.98 (s, 9H). HPLC (Kinetex 2.6u, 50×4.6 mm, 2-100% MeCN/H$_2$O+0.05% HOAc, 5 min run): $t_R$ (min)=3.40.

EXAMPLE 98

(S)-2-(7-((1-Aminocyclohexyl)ethynyl)-1-(4-chlorophenyl)-3-methylnaphthalen-2-yl)-2-tert-butoxyacetic acid (100)

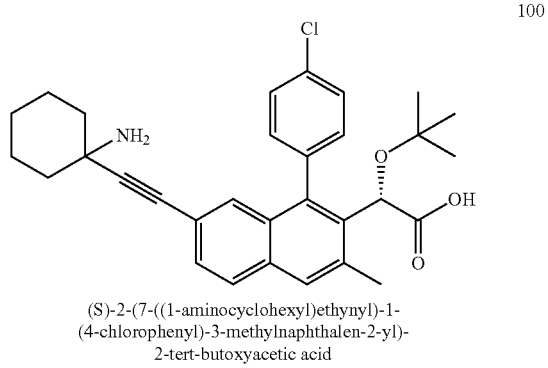 [SMILES: Cc1cc2ccc(C#CC3(N)CCCCC3)cc2c(-c2ccc(Cl)cc2)c1[C@H](OC(C)(C)C)C(=O)O]

(S)-2-(7-((1-aminocyclohexyl)ethynyl)-1-(4-chlorophenyl)-3-methylnaphthalen-2-yl)-2-tert-butoxyacetic acid Preparation of (S)-2-(7-((1-aminocyclohexyl)ethynyl)-1-(4-chlorophenyl)-3-methylnaphthalen-2-yl)-2-tert-butoxyacetic acid (100): (S)-2-(7-((1-Aminocyclohexyl)ethynyl)-1-(4-chlorophenyl)-3-methylnaphthalen-2-yl)-2-tert-butoxyacetic acid (100) was prepared by the method of Example 67 using the reduction method of Example 51 step 3 for (S)-ethyl 2-(1-(4-chlorophenyl)-3-methyl-6-(trifluoromethylsulfonyloxy) naphthalen-2-yl)-2-hydroxyacetate instead of step 5, NaBH$_4$ step, from ethyl 2-(7-bromo-1-(4-chlorophenyl)-3-methylnaphthalen-2-yl)-2-oxoacetate. The remainder of the sequence follows the method of Example 67 using 1-ethynylcyclohexanamine in Step 7. $^1$H-NMR: 400 MHz, (CD$_3$OD) δ: 7.82 (d, J=8 Hz, 1H), 7.72 (s, 1H), 7.56 (m, 3H), 7.47 (d, J=8 Hz, 1H), 7.37 (s, 1H), 7.31 (d, J=8 Hz, 1H), 5.20 (s, 1H), 2.60 (s, 3H), 2.11 (m, 2H), 1.63-1.85 (m, 8H), 0.99 (s, 9H). LCMS-ESI$^+$ (m/z): [M—NH$_2$]$^+$ calcd for C$_{31}$H$_{32}$ClO$_3$: 487.2; found: 487.2.

EXAMPLE 99

(S)-2-tert-Butoxy-2-((R)-6-chloro-1-(2,3-dihydropyrano[4,3,2-de]quinolin-7-yl)-7-fluoro-3-methylnaphthalen-2-yl)acetic acid (101)

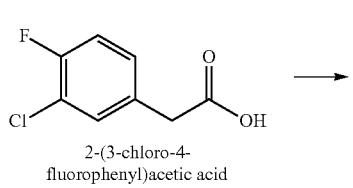

2-(3-chloro-4-fluorophenyl)acetic acid

253
-continued
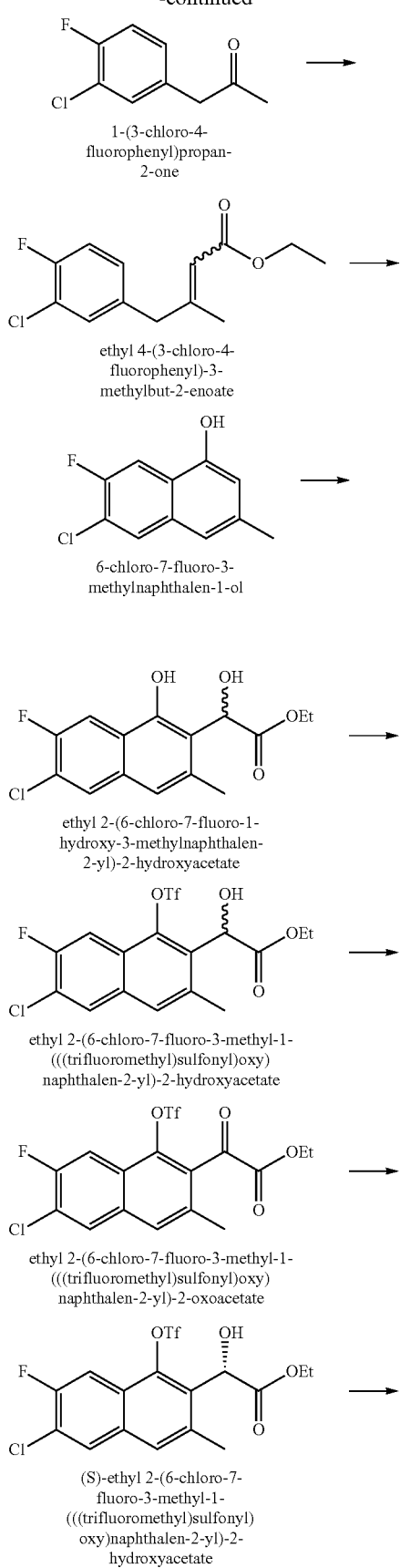
254
-continued
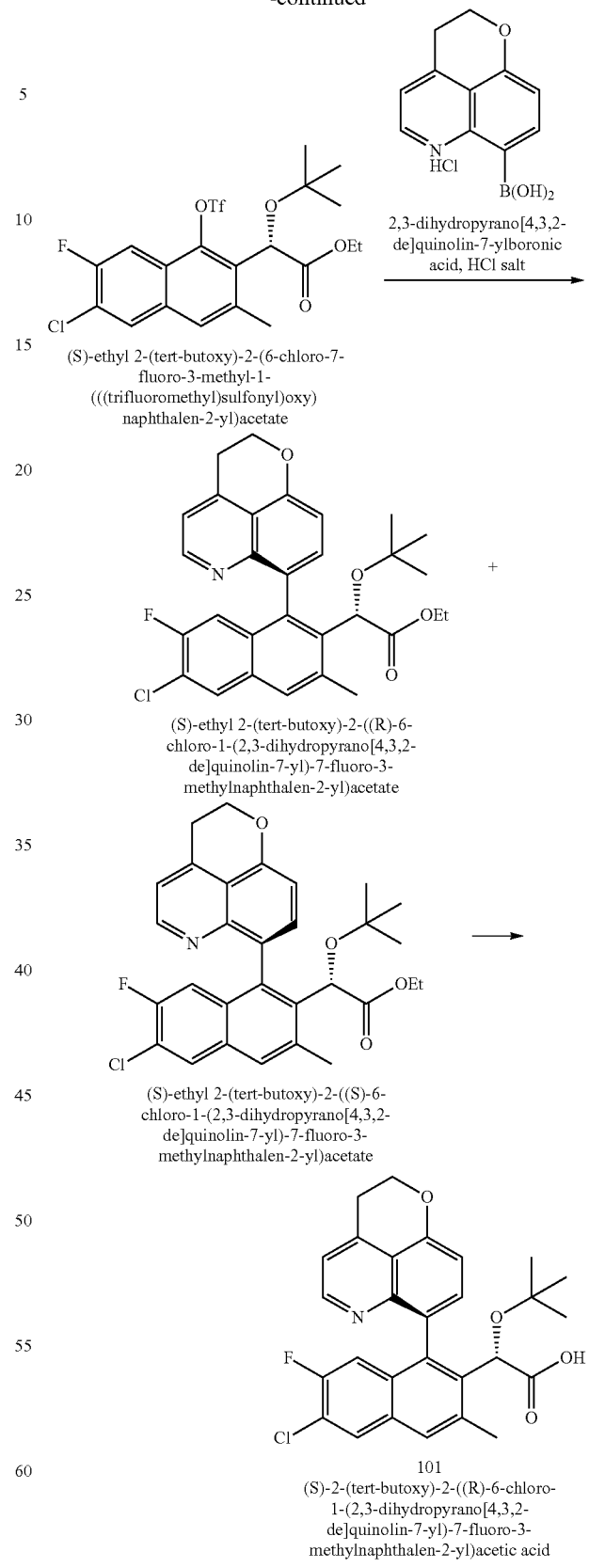
Preparation of 1-(3-chloro-4-fluorophenyl)propan-2-one:
To a solution of 2-(3-chloro-4-fluorophenyl)acetic acid (18.46 g, 97.89 mmol) in acetic anhydride (463 mL) was added N-methylimidazole (3.9 mL) and the reaction mixture was stirred overnight at room temperature. The reaction mixture was partitioned between ethyl acetate and saturated sodium bicarbonate solution and organic layer was concentrated and purified by flash column chromatography (silica gel, ethyl acetate/hexanes) to give a colorless oil (14.5 g, 79%). $^1$H NMR (400 MHz, CDCl$_3$) δ 7.23 (dd, J=6.9, 2.1 Hz, 1H), 7.14-7.00 (m, 2H), 3.66 (s, 2H), 2.19 (s, 3H).

Preparation of ethyl 4-(3-chloro-4-fluorophenyl)-3-methylbut-2-enoate: To a solution of triethylphosphonoacetate (25.3 mL, 126.2 mmol) in anhydrous tetrahydrofuran (250 mL) at 0° C. was added 60% sodium hydride (5.15 g, 126.2 mmol) and the resulting mixture stirred for 30 minutes. 1-(3-chloro-4-fluorophenyl)propan-2-one (15.7 g, 84.13 mmol) in tetrahydrofuran (10 mL) added and the reaction mixture was stirred for 2 hours and quenched with saturated sodium bicarbonate solution. The mixture was extracted with ethyl acetate and organic layer was concentrated and purified by flash column chromatography (silica gel, ethyl acetate/hexanes) to give mixture of E/Z isomers (17.2 g, 80%). E isomer: $^1$H NMR (400 MHz, CDCl$_3$): δ 7.19 (dd, J=7.0, 2.1 Hz, 1H), 7.12-6.97 (m, 2H), 5.64 (d, J=1.2 Hz, 1H), 4.13 (dq, J=14.4, 7.2 Hz, 3H), 3.36 (s, 2H), 2.03 (s, 3H), 1.26 (dd, J=15.9, 7.2 Hz, 3H); Z isomer: $^1$H NMR (400 MHz, CDCl$_3$): δ 7.28 (dd, J=7.1, 2.1 Hz, 1H), 7.15-6.98 (m, 2H), 5.79 (s, 1H), 4.17 (dq, J=14.3, 7.1 Hz, 2H), 3.37 (s, 2H), 1.79 (s, 3H), 1.29 (dd, J=15.1, 7.2 Hz, 3H).

Preparation of 6-chloro-7-fluoro-3-methylnaphthalen-1-ol: A solution of ethyl 4-(3-chloro-4-fluorophenyl)-3-methylbut-2-enoate (9.7 g, 37.8 mmol) in concentrated sulfuric acid (40 mL) was stirred at 50° C. overnight. The reaction mixture was poured onto ice and diluted with water and extracted with ethyl acetate. The organic layer was concentrated and purified by flash column chromatography (silica gel, ethyl acetate/hexanes) to give a pale yellow solid (1.57 g). $^1$H-NMR: 400 MHz, (CDCl$_3$) δ: 7.83 (d, J=10.4 Hz, 1H), 7.75 (d, J=7.2 Hz, 1H), 7.11 (s, 1H), 6.67 (s, 1H), 2.42 (s, 3H).

Preparation of ethyl 2-(6-chloro-7-fluoro-1-hydroxy-3-methylnaphthalen-2-yl)-2-hydroxyacetate: To a mixture of 6-chloro-7-fluoro-3-methylnaphthalen-1-ol (2.24 g, 13.78 mmol) in anhydrous dichloromethane (100 mL) at −40° C. was added a 1 M titanium(IV) chloride solution in dichloromethane (13.78 mL, 13.78 mmol) and stirred for 45 min. Ethyl glyoxylate (1.69 g, 16.54 mmol) dissolved in dichloromethane (5 mL) was added over 15 minutes and stirred for 1 hour at −40° C. The reaction was quenched by the addition of Rochelle's salt solution and stirred at room temperature for 2.5 hours. The resulting mixture was washed with water and aqueous layer back-extracted with dichloromethane (2×). The combined organic layer was dried (MgSO$_4$), filtered, concentrated and purified by flash column chromatography (silica gel, 5 to 30% ethyl acetate/hexanes) to give an off-white solid (2.53 g). $^1$H-NMR: 400 MHz, (CDCl$_3$) δ: 8.48 (s, 1H), 7.89 (d, J=10.5 Hz, 1H), 7.70 (d, J=7.2 Hz, 1H), 7.11 (s, 1H), 5.67 (s, 1H), 4.30 (dq, J=10.8, 7.1 Hz, 1H), 4.15 (dq, J=10.8, 7.1 Hz, 1H), 3.61 (s, 1H), 2.52 (s, 3H), 1.20 (t, J=7.1 Hz, 3H). LCMS-ESI$^+$ (m/z): [M+H]$^+$ calcd for C$_{15}$H$_{13}$ClFO$_4$: 311.7; found: 311.0.

Preparation of ethyl 2-(6-chloro-7-fluoro-3-methyl-1-(trifluoromethylsulfonyloxy)naphthalen-2-yl)-2-hydroxyacetate: To a solution of ethyl 2-(6-chloro-7-fluoro-1-hydroxy-3-methylnaphthalen-2-yl)-2-hydroxyacetate (4.13 g, 13.22 mmol) in anhydrous dichloromethane (120 mL) at 0° C. was added imidazole (1.215 g, 17.85 mmol), followed by chlorotriethylsilane (2.55 mL, 15.2 mmol). The cloudy reaction mixture was stirred for 1.5 hours, quenched with water and diluted with dichloromethane. The mixture was washed with 1 N HCl solution/brine and organic layer dried (MgSO$_4$), filtered, concentrated to give an orange oil that used in next step without further purification.

The above residue was dissolved in anhydrous dichloromethane (130 mL) containing triethylamine (2.21 mL, 15.86 mmol) and cooled in a dry ice/acetone bath. Trifluoromethanesulfonic anhydride (2.45 mL, 14.54 mmol) was added dropwise over 20 minutes and stirred for 1 hour. The reaction was quenched with brine and stirred for 15 minutes at room temperature. The mixture was diluted with dichloromethane, washed with 1 N HCl solution, saturated sodium bicarbonate solution/brine and dried (MgSO$_4$), filtered, concentrated to give an orange oil that used in next step without further purification.

The above residue was dissolved in tetrahydrofuran (100 mL) and 48% hydrofluoric acid (16.77 mL, 462.7 mmol) was added. The reaction mixture was stirred overnight at room temperature and quenched with solid sodium bicarbonate and stirred for 30 minutes. Water and saturated sodium bicarbonate were added and the mixture was extracted with ethyl acetate (2×). The combined organic layer was dried (MgSO$_4$), filtered, concentrated and purified by flash column chromatography (silica gel, 5 to 30% ethyl acetate/hexanes) to give an off-white solid (4.89 g). $^1$H-NMR: 400 MHz, (CDCl$_3$) δ: 7.87 (d, J=7.1 Hz, 1H), 7.76 (d, J=10.1 Hz, 1H), 7.59 (s, 1H), 5.76 (d, J=2.0 Hz, 1H), 4.36-4.18 (m, 2H), 3.42 (d, J=2.4 Hz, 1H), 2.48 (s, 3H), 1.20 (t, J=7.1 Hz, 3H).

Preparation of ethyl 2-(6-chloro-7-fluoro-3-methyl-1-(trifluoromethyl-sulfonyloxy)naphthalen-2-yl)-2-oxoacetate: To a solution of ethyl 2-(6-chloro-7-fluoro-3-methyl-1-(trifluoromethylsulfonyloxy)naphthalen-2-yl)-2-hydroxyacetate (4.89 g, 10.99 mmol) in anhydrous dichloromethane (100 mL) at 0° C. was added Dess-Martin periodinane (5.59 g, 13.18 mmol) portion-wise over 5 minutes. The reaction mixture was stirred at 0° C. for 1 hour and quenched with sodium thiosulfate solution and saturated sodium bicarbonate solution and stirred for 30 minutes. The mixture was diluted with ethyl ether and washed with saturated sodium bicarbonate solution (3×), brine and dried (MgSO$_4$), filtered, concentrated to give a yellow oil with a white precipitate. The mixture was suspended in diethyl ether, washed with brine, dried (MgSO$_4$), filtered, concentrated and purified by flash column chromatography (silica gel, 0 to 10% ethyl acetate/hexanes) to give an off-white solid (4.60 g). $^1$H NMR (400 MHz, CDCl$_3$) δ: 7.93 (d, J=7.0 Hz, 1H), 7.78 (d, J=9.6 Hz, 1H), 7.67 (s, 1H), 4.41 (q, J=7.1 Hz, 2H), 2.47 (s, 3H), 1.40 (t, J=7.1 Hz, 3H).

Preparation of (S)-ethyl 2-(6-chloro-7-fluoro-3-methyl-1-(trifluoromethyl-sulfonyloxy)naphthalen-2-yl)-2-hydroxyacetate: To a solution of ethyl 2-(6-chloro-7-fluoro-3-methyl-1-(trifluoromethylsulfonyloxy)naphthalen-2-yl)-2-oxoacetate (4.60 g, 10.79 mmol) and (R)-2-methyl-CBS-oxazaborolidine (0.598 g, 2.16 mmol) in anhydrous toluene at −40° C. was added a solution of catecholborane (1.55 mL, 14.67 mmol) in toluene (10 mL) over 40 minutes. The reaction mixture was stirred for 1 hour and quenched with sodium carbonate solution, diluted with ethyl acetate and stirred vigorously for 20 minutes at −20° C., then at room temperature for 45 minutes. The aqueous layer was removed and the organic layer was washed with sodium carbonate solution (4×), saturated ammonium chloride solution, dried (MgSO$_4$), filtered, concentrated and purified by flash column chromatography (silica gel, 0 to 20% ethyl acetate/hexanes) to give an off-white solid (4.44 g). $^1$H NMR (400 MHz, CDCl$_3$) δ: 7.87 (d, J=7.1 Hz, 1H), 7.76 (d, J=10.0 Hz, 1H), 7.59 (s, 1H), 5.76 (d, J=1.7 Hz, 1H), 4.38-4.17 (m, 2H), 3.43 (d, J=2.3 Hz, 1H), 2.48 (s, 3H), 1.20 (t, J=7.1 Hz, 3H). The enantiomeric excess was determined by chiral column analysis (Chiralpak AD-H, heptane:ethanol (80:20)) to be 95%.

Preparation of (S)-ethyl 2-tert-butoxy-2-(6-chloro-7-fluoro-3-methyl-1-(trifluoromethylsulfonyloxy)naphthalen-2-yl)acetate: To a solution of (S)-ethyl 2-(6-chloro-7-fluoro-3-methyl-1-(trifluoromethylsulfonyloxy)naphthalen-2-yl)-2-hydroxyacetate (4.44 g, 9.99 mmol) in tert-butylacetate (100 mL) was added 70% perchloric acid (1.20 mL, 19.98 mmol). The reaction mixture was stirred for 2.5 hours and quenched with solid sodium bicarbonate and stirred for 45 minutes. Water and solid sodium bicarbonate were carefully added and stirred for another 15 minutes. The mixture was diluted with ethyl acetate, washed with saturated bicarbonate solution (2×), brine, dried (MgSO$_4$), filtered, concentrated and purified by flash column chromatography (silica gel, 0 to 20% ethyl acetate/hexanes) to give an pale orange oil (4.26 g). $^1$H NMR (400 MHz, CDCl$_3$) δ: 7.86 (d, J=7.2 Hz, 4H), 7.74 (d, J=10.2 Hz, 4H), 7.58 (s, 4H), 7.26 (s, 3H), 5.69 (s, 4H), 4.26-4.08 (m, 9H), 2.53 (s, 12H), 1.20 (s, 34H), 1.17 (t, J=7.1 Hz, 13H).

Preparation of (S)-ethyl 2-tert-butoxy-2-((R)-6-chloro-1-(2,3-dihydropyrano[4,3,2-de]quinolin-7-yl)-7-fluoro-3-methylnaphthalen-2-yl)acetate: A Smith process vial was charged with (S)-ethyl 2-tert-butoxy-2-(6-chloro-7-fluoro-3-methyl-1-(trifluoromethylsulfonyloxy)naphthalen-2-yl)acetate (110 mg, 0.199 mmol), 2,3-dihydropyrano[4,3,2-de]quinolin-7-ylboronic acid, HCl salt (55 mg, 0.220 mmol), PdCl$_2$(dppf) (16 mg, 0.02 mmol), cesium fluoride (133 mg, 0.876 mmol) and flushed with nitrogen. Dimethoxyethane (1.0 mL, distilled from Na/benzophenone) was added and mixture sparged with nitrogen for 10 minutes and then heated in microwave at 110° C. for 1 hour. The reaction mixture was diluted with ethyl acetate and washed with brine, dried (MgSO$_4$), filtered, concentrated and purified by flash column chromatography (silica gel, 0 to 20% ethyl acetate/hexanes) to give (S)-ethyl 2-tert-butoxy-2-((R)-6-chloro-1-(2,3-dihydropyrano[4,3,2-de]quinolin-7-yl)-7-fluoro-3-methylnaphthalen-2-yl)acetate (9.7 mg). $^1$H NMR (400 MHz, CD$_3$OD): δ 8.49 (d, J=4.4 Hz, 1H), 7.97 (d, J=7.5 Hz, 1H), 7.74 (s, 1H), 7.46 (d, J=7.9 Hz, 1H), 7.27 (d, J=4.4 Hz, 1H), 7.14 (d, J=7.9 Hz, 1H), 6.66 (d, J=11.5 Hz, 1H), 5.13 (s, 1H), 4.56 (dd, J=9.9, 5.9 Hz, 2H), 3.96 (dd, J=10.8, 7.1 Hz, 1H), 3.76 (dd, J=10.7, 7.1 Hz, 1H), 3.38 (t, J=5.8 Hz, 2H), 2.74 (s, 3H), 0.98-0.85 (m, 12H). LCMS-ESI$^+$ (m/z): [M+H]$^+$ calcd for C$_{30}$H$_{30}$ClFNO$_4$: 523.0; found: 522.1, 524.1.

The other atropisomer, (S)-ethyl 2-tert-butoxy-2-((S)-6-chloro-1-(2,3-dihydropyrano[4,3,2-de]quinolin-7-yl)-7-fluoro-3-methylnaphthalen-2-yl)acetate, was also isolated (16.4 mg). $^1$H NMR (400 MHz, CD$_3$OD): δ 8.47 (d, J=4.4 Hz, 1H), 7.94 (d, J=7.6 Hz, 1H), 7.77 (d, J=8.0 Hz, 1H), 7.70 (s, 1H), 7.25 (d, J=4.4 Hz, 1H), 7.18 (d, J=8.0 Hz, 1H), 6.56 (d, J=11.4 Hz, 1H), 5.15 (s, 2H), 4.52 (t, J=5.4 Hz, 2H), 4.22-4.04 (m, 2H), 3.37 (t, J=5.8 Hz, 2H), 2.61 (s, 3H), 1.20 (t, J=5.9 Hz, 3H), 0.70 (s, 9H). LCMS-ESI$^+$ (m/z): [M+H]$^+$ calcd for C$_{30}$H$_{30}$ClFNO$_4$: 523.0; found: 522.1, 524.1.

Preparation of (S)-2-tert-butoxy-2-((R)-6-chloro-1-(2,3-dihydropyrano[4,3,2-de]quinolin-7-yl)-7-fluoro-3-methylnaphthalen-2-yl)acetic acid (101): A solution of (S)-ethyl 2-tert-butoxy-2-((R)-6-chloro-1-(2,3-dihydropyrano[4,3,2-de]quinolin-7-yl)-7-fluoro-3-methylnaphthalen-2-yl)acetate (9.7 mg, 0.186 mmol) and 5 M sodium hydroxide (74 µL, 0.372 mmol) in tetrahydrofuran (1.0 mL) and methanol (0.2 mL) was heated at 50° C. overnight. The reaction mixture was diluted with ethyl acetate and washed with brine. The aqueous layer was back-extracted with ethyl acetate and the combined organic layer was dried (MgSO$_4$), filtered, concentrated and purified by reverse phase HPLC (Gemini, 5 to 100% ACN/H$_2$O+0.1% TFA). Product lyophilized to give a yellow powder (6.7 mg). $^1$H-NMR: 400 MHz, (CD$_3$OD): δ 8.69 (d, J=5.2 Hz, 1H), 8.12 (d, J=7.6 Hz, 1H), 7.96 (s, 1H), 7.81 (d, J=7.6 Hz, 1H), 7.80 (d, J=5.6 Hz, 1H), 7.45 (d, J=8.0 Hz, 1H), 6.73 (d, J=11.2 Hz, 1H), 5.21 (s, 1H), 4.75-4.70 (m, 2H), 3.66 (t, J=6 Hz, 2H), 2.76 (s, 3H) 0.92 (s, 9H). $^{19}$F-NMR: 377 MHz, (CD$_3$OD) δ: −77.7 (s, 3F), −119.2 (dd, J=10.6, 7.9 Hz, 1F). LCMS-ESI$^+$ (m/z): [M+H]$^+$ calcd for C$_{28}$H$_{26}$ClFNO$_4$: 494.95; found: 494.4, 496.1. The other atropisomer, (S)-2-tert-butoxy-2-((S)-6-chloro-1-(2,3-dihydropyrano[4,3,2-de]quinolin-7-yl)-7-fluoro-3-methylnaphthalen-2-yl)acetic acid, was prepared in a similar manner. $^1$H NMR (400 MHz, CD$_3$OD): δ 8.59 (d, J=5.3 Hz, 1H), 8.10 (d, J=8.5 Hz, 1H), 8.07 (d, J=8.5 Hz, 1H), 7.88 (s, 1H), 7.63 (d, J=5.2 Hz, 1H), 7.43 (d, J=8.1 Hz, 1H), 6.68 (d, J=11.2 Hz, 1H), 5.20 (s, 1H), 4.68 (t, J=6.0 Hz, 2H), 3.58 (t, J=5.9 Hz, 2H), 2.71 (s, 3H), 0.85 (s, 9H). $^{19}$F-NMR: 377 MHz, (CD$_3$OD) δ: −77.7 (s, 3F), −120.0 (br s, 1F). LCMS-ESI$^+$ (m/z): [M+H]$^+$ calcd for C$_{28}$H$_{26}$ClFNO$_4$: 494.95; found: 494.4, 496.1.

EXAMPLE 100

(S)-2-tert-Butoxy-2-((R)-1-(2,3-dihydropyrano[4,3,2-de]quinolin-7-yl)-7-fluoro-6-isopropyl-3-methylnaphthalen-2-yl)acetic acid (102)

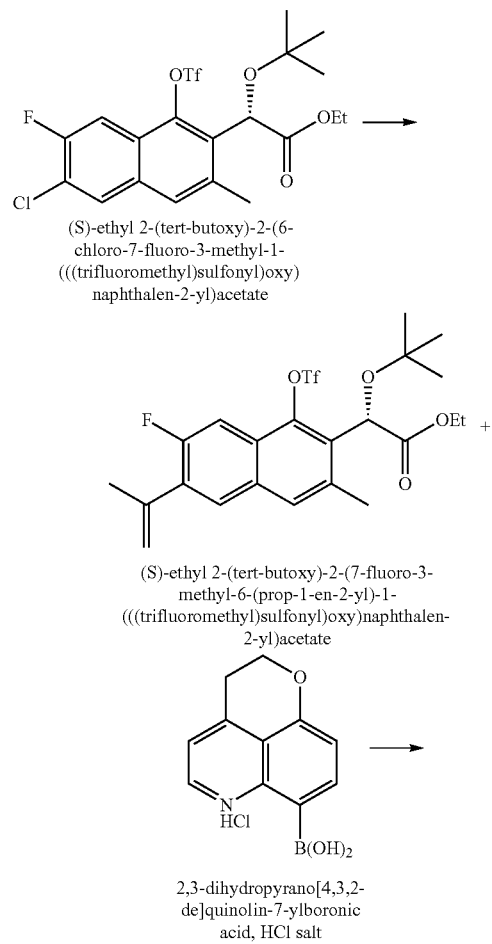

(S)-ethyl 2-(tert-butoxy)-2-(6-chloro-7-fluoro-3-methyl-1-(((trifluoromethyl)sulfonyl)oxy)naphthalen-2-yl)acetate (S)-ethyl 2-(tert-butoxy)-2-(7-fluoro-3-methyl-6-(prop-1-en-2-yl)-1-(((trifluoromethyl)sulfonyl)oxy)naphthalen-2-yl)acetate 2,3-dihydropyrano[4,3,2-de]quinolin-7-ylboronic acid, HCl salt

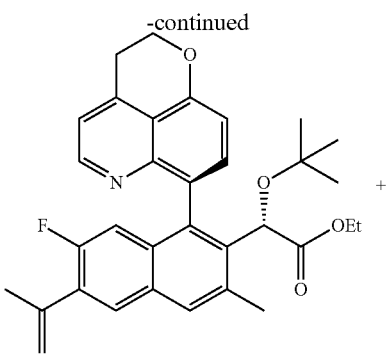

(S)-ethyl 2-(tert-butoxy)-2-((S)-1-(2,3-dihydropyrano[4,3,2-de]quinolin-7-yl)-7-fluoro-3-methyl-6-(prop-1-en-2-yl)naphthalen-2-yl)acetate

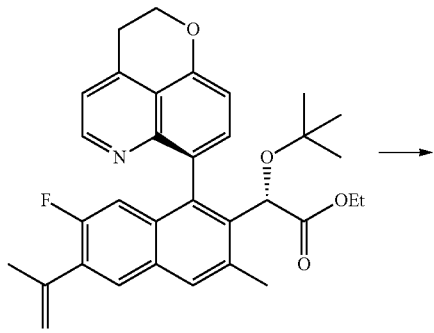

(S)-ethyl 2-(tert-butoxy)-2-((R)-1-(2,3-dihydropyrano[4,3,2-de]quinolin-7-yl)-7-fluoro-3-methyl-6-(prop-1-en-2-yl)naphthalen-2-yl)acetate

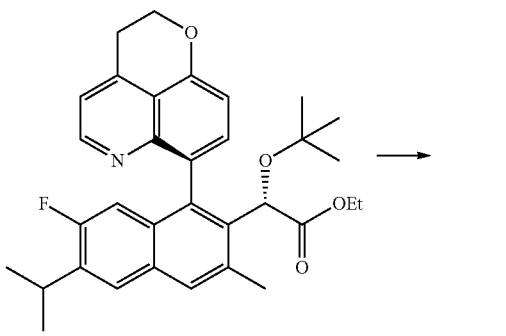

(S)-ethyl 2-(tert-butoxy)-2-((R)-1-(2,3-dihydropyrano[4,3,2-de]quinolin-7-yl)-7-fluoro-6-isopropyl-3-methylnaphthalen-2-yl)acetate

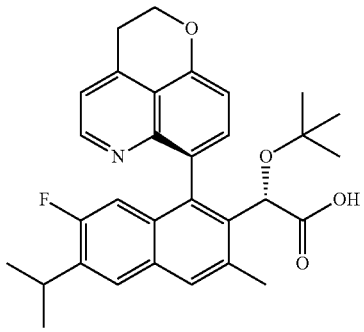

(S)-2-(tert-butoxy)-2-((R)-1-(2,3-dihydropyrano[4,3,2-de]quinolin-7-yl)-7-fluoro-6-isopropyl-3-methylnaphthalen-2-yl)acetate acid Preparation of (S)-ethyl 2-tert-butoxy-2-(7-fluoro-3-methyl-6-(prop-1-en-2-yl)-1-(trifluoromethylsulfonyloxy)naphthalen-2-yl)acetate: A Smith process vial was charged with (S)-ethyl 2-tert-butoxy-2-(6-chloro-7-fluoro-3-methyl-1-(trifluoromethylsulfonyloxy)naphthalen-2-yl)acetate (184.2 mg, 0.368 mmol), potassium isopropenyltrifluoroborate (60 mg, 0.405 mmol), BrettPhos Palladacycle (41 mg, 0.0552 mmol), cesium fluoride (623 mg, 0.405 mmol) and flushed with nitrogen. Dimethoxyethane (1.0 mL, distilled from Na/benzophenone) was added and mixture sparged with nitrogen for 10 minutes and then heated in microwave at 120° C. for 1.5 hour. The reaction mixture was diluted with ethyl acetate and washed with water, brine, dried (MgSO$_4$), filtered, concentrated and purified by flash column chromatography (silica gel, 0 to 20% ethyl acetate/hexanes) to give a colorless oil (60 mg). $^1$H NMR (400 MHz, CDCl$_3$) δ 7.85 (d, J=7.1 Hz, 13H), 7.71 (d, J=7.5 Hz, 1H), 5.70 (s, 1H), 5.35 (s, 1H), 5.32 (s, 1H), 4.18 (dt, J=19.3, 11.4 Hz, 2H), 2.53 (s, 3H), 2.21 (s, 3H), 1.24-1.12 (m, 12H).

Preparation of(S)-ethyl 2-tert-butoxy-2-((R)-1-(2,3-dihydropyrano[4,3,2-de]quinolin-7-yl)-7-fluoro-3-methyl-6-(prop-1-en-2-yl)naphthalen-2-yl)acetate: A Smith process vial was charged with (S)-ethyl 2-tert-butoxy-2-(7-fluoro-3-methyl-6-(prop-1-en-2-yl)-1-(trifluoromethylsulfonyloxy)naphthalen-2-yl)acetate (92.3 mg, 0.182 mmol), 2,3-dihydropyrano[4,3,2-de]quinolin-7-ylboronic acid, HCl salt (50 mg, 0.200 mmol), Sphos Palladacycle (18.4 mg, 0.0273 mmol), cesium fluoride (122 mg, 0.801 mmol) and flushed with nitrogen. Dimethoxyethane (1.5 mL, distilled from Na/benzophenone) was added and mixture sparged with nitrogen for 10 minutes and then heated in microwave at 120° C. for 1.5 hour. The reaction mixture was diluted with ethyl acetate and washed with brine. Aqueous layer back-extracted and combined organic layer dried (MgSO$_4$), filtered, concentrated and purified by flash column chromatography (silica gel, 0 to 20% ethyl acetate/hexanes) to give impure (S)-ethyl 2-tert-butoxy-2-((R)-1-(2,3-dihydropyrano[4,3,2-de]quinolin-7-yl)-7-fluoro-3-methyl-6-(prop-1-en-2-yl)naphthalen-2-yl)acetate (10 mg). Repurified by reverse phase HPLC (Gemini, 5 to 100% ACN/H$_2$O+0.1% TFA) and lyophilized to give an impure yellow powder (4.3 mg). LCMS-ESI$^+$ (m/z): [M+H]$^+$ calcd for C$_{33}$H$_{35}$FNO$_4$: 528.6; found: 528.1, 529.1.

The other atropisomer, (S)-ethyl 2-tert-butoxy-2-((S)-1-(2,3-dihydropyrano[4,3,2-de]quinolin-7-yl)-7-fluoro-3-methyl-6-(prop-1-en-2-yl)naphthalen-2-yl)acetate, was also isolated (4.3 mg). LCMS-ESI$^+$ (m/z): [M+H]$^+$ calcd for C$_{33}$H$_{35}$FNO$_4$: 528.6; found: 528.1, 529.1

Preparation of (S)-ethyl 2-tert-butoxy-2-((R)-1-(2,3-dihydropyrano[4,3,2-de]quinolin-7-yl)-7-fluoro-6-isopropyl-3-methylnaphthalen-2-yl)acetate: A mixture of (S)-ethyl 2-tert-butoxy-2-((R)-1-(2,3-dihydropyrano[4,3,2-de]quinolin-7-yl)-7-fluoro-3-methyl-6-(prop-1-en-2-yl)naphthalen-2-yl)acetate (4.3 mg, 0.007 mmol) and 10% Palladium/carbon (5.0 mg) in ethanol (1.5 mL) was stirred under a hydrogen atmosphere (1 atm) for 2 hours. The reaction mixture was filtered through a pad of Celite and concentrated to give a film that was used in the next step without further purification (4.2 mg). LCMS-ESI$^+$ (m/z): [M+H]$^+$ calcd for C$_{33}$H$_{37}$FNO$_4$: 530.6; found: 530.2.

Preparation of (S)-2-tert-butoxy-2-((R)-1-(2,3-dihydropyrano[4,3,2-de]quinolin-7-yl)-7-fluoro-6-isopropyl-3-methylnaphthalen-2-yl)acetic acid (102): A solution of (S)-ethyl 2-tert-butoxy-2-((R)-1-(2,3-dihydropyrano[4,3,2-de]quinolin-7-yl)-7-fluoro-6-isopropyl-3-methylnaphthalen-2-yl)acetate (4.2 mg, 0.007 mmol) and 5 M sodium hydroxide (31 μL, 0.16 mmol) in tetrahydrofuran (1.0 mL) and methanol (0.1 mL) was heated at 50° C. overnight. The reaction mixture was acidified with acetic acid, concentrated, dissolved in DMF and purified by reverse phase HPLC (Gemini, 5 to 100% ACN/H$_2$O+0.1% TFA). Product lyophilized to give a yellow powder (2.6 mg). $^1$H-NMR: 400 MHz, (CD$_3$OD) δ: 8.67 (d, J=5.6 Hz, 1H), 7.94 (s, 1H), 7.84 (d, J=7.6 Hz, 1H), 7.80 (d, J=6.0 Hz, 1H), 7.78 (d, J=6.0 Hz, 1H), 7.43 (d, J=8.0 Hz, 1H), 6.47 (d, J=12.4 Hz, 1H), 5.21 (s, 1H), 4.75-4.70 (m, 2H), 3.66 (t, J=6 Hz, 2H), 3.3-2.2 (m, 1H), 2.75 (s, 3H), 1.33 (d, J=8.4 Hz, 3H), 1.31 (d, J=8.8 Hz, 3H), 0.92 (s, 9H). $^{19}$F-NMR: 377 MHz, (CD$_3$OD) δ: −77.6 (s, 3F), −121.4 (dd, J=10.6, 7.9 Hz, 1F). LCMS-ESI$^+$ (m/z): [M+H]$^+$ calcd for C$_{31}$H$_{33}$FNO$_4$: 502.69; found: 502.1 (M+H$^+$).

EXAMPLE 101

(S)-2-tert-Butoxy-2-((R)-6-(difluoromethyl)-1-(2,3-dihydropyrano[4,3,2-de]quinolin-7-yl)-7-fluoro-3-methylnaphthalen-2-yl)acetic acid (103)

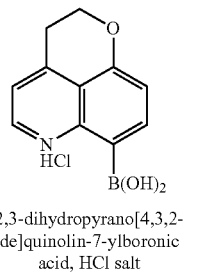

2,3-dihydropyrano[4,3,2-de]quinolin-7-ylboronic acid, HCl salt

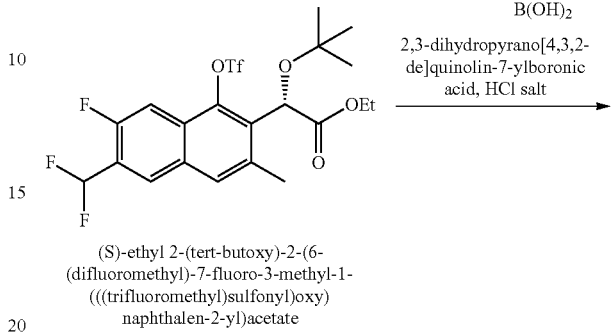

(S)-ethyl 2-(tert-butoxy)-2-(6-(difluoromethyl)-7-fluoro-3-methyl-1-(((trifluoromethyl)sulfonyl)oxy)naphthalen-2-yl)acetate

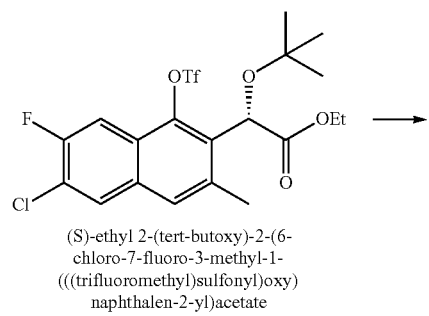

(S)-ethyl 2-(tert-butoxy)-2-(6-chloro-7-fluoro-3-methyl-1-(((trifluoromethyl)sulfonyl)oxy)naphthalen-2-yl)acetate

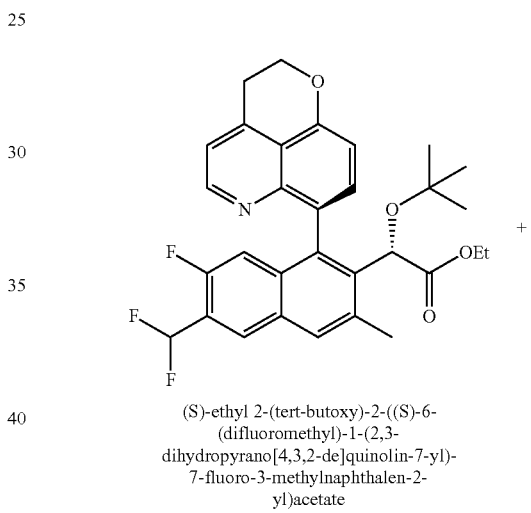

(S)-ethyl 2-(tert-butoxy)-2-((S)-6-(difluoromethyl)-1-(2,3-dihydropyrano[4,3,2-de]quinolin-7-yl)-7-fluoro-3-methylnaphthalen-2-yl)acetate

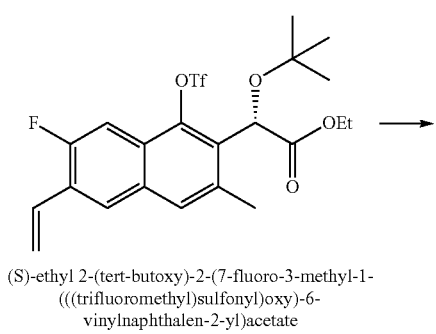

(S)-ethyl 2-(tert-butoxy)-2-(7-fluoro-3-methyl-1-(((trifluoromethyl)sulfonyl)oxy)-6-vinylnaphthalen-2-yl)acetate

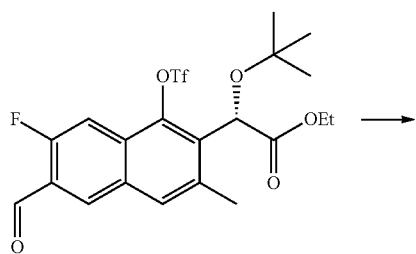

(S)-ethyl 2-(tert-butoxy)-2-(7-fluoro-6-formyl-3-methyl-1-(((trifluoromethyl)sulfonyl)oxy)-naphthalen-2-yl)acetate

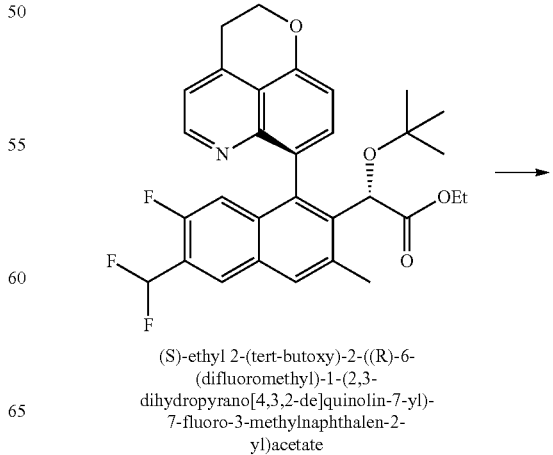

(S)-ethyl 2-(tert-butoxy)-2-((R)-6-(difluoromethyl)-1-(2,3-dihydropyrano[4,3,2-de]quinolin-7-yl)-7-fluoro-3-methylnaphthalen-2-yl)acetate

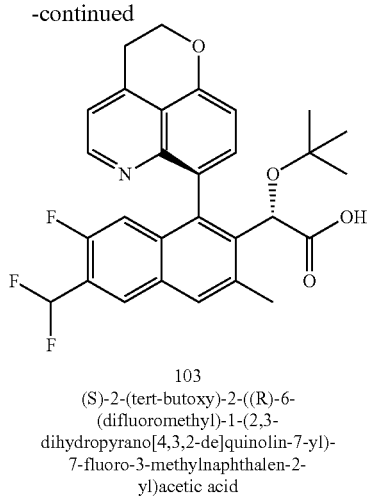

103
(S)-2-(tert-butoxy)-2-((R)-6-
(difluoromethyl)-1-(2,3-
dihydropyrano[4,3,2-de]quinolin-7-yl)-
7-fluoro-3-methylnaphthalen-2-
yl)acetic acid Preparation of (S)-ethyl 2-tert-butoxy-2-(7-fluoro-3-methyl-1-(trifluoromethylsulfonyloxy)-6-vinylnaphthalen-2-yl)acetate: A Smith process vial was charged with (S)-ethyl 2-tert-butoxy-2-(6-chloro-7-fluoro-3-methyl-1-(trifluoromethylsulfonyloxy)naphthalen-2-yl)acetate (213.6 mg, 0.426 mmol), tributyl(vinyl)tin (0.137 mL, 0.469 mmol), BrettPhos Palladacycle (47 mg, 0.0639 mmol) and flushed with nitrogen. DMF (2.0 mL) and sodium carbonate (5.0 mg, 0.0639 mmol) were added and heated in microwave at 120° C. for 1.5 hour. The reaction mixture was diluted with ethyl acetate and washed with 5% lithium chloride solution (2×), brine, dried (MgSO$_4$), filtered, concentrated and purified by flash column chromatography (silica gel, 0 to 10% ethyl acetate/hexanes) to give a colorless oil (149.5 mg). $^1$H NMR (400 MHz, CDCl$_3$) δ 7.64 (d, J=5.1 Hz, 1H), 7.62 (d, 1H), 6.95 (dd, J=17.7, 11.3 Hz, 1H), 6.00 (d, J=17.7 Hz, 1H), 5.52 (d, J=11.3 Hz, 1H), 4.33-4.03 (m, 2H), 2.53 (s, 3H), 1.20 (s, 9H), 1.17 (t, J=7.1 Hz, 3H).

Preparation of(S)-ethyl 2-tert-butoxy-2-(7-fluoro-6-formyl-3-methyl-1-(trifluoromethylsulfonyloxy)naphthalen-2-yl)acetate: A 3-neck round-bottom flask was charged with (S)-ethyl 2-tert-butoxy-2-(7-fluoro-3-methyl-1-(trifluoromethylsulfonyloxy)-6-vinylnaphthalen-2-yl)acetate (95 mg, 0.193 mmol), methanol (1 mL) and dichloromethane (1 mL) and cooled to −78° C. Ozone was bubbled into the reaction mixture until blue color persisted (2 minutes). The reaction was sparged with oxygen until blue color faded and quenched with methyl sulfide (0.06 mL, 0.828 mmol). The mixture was stirred at room temperature for 1 h, concentrated and purified by flash column chromatography (silica gel, 0 to 10% ethyl acetate/hexanes) to give a colorless oil (74 mg). $^1$H NMR (400 MHz, CDCl$_3$) δ 10.45 (s, 1H), 8.37 (d, J=6.8 Hz, 1H), 7.80 (s, 1H), 7.75 (d, J=11.7 Hz, 1H), 5.72 (s, 1H), 4.39-4.00 (m, 2H), 2.56 (s, 3H), 1.20 (s, 9H), 1.17 (t, J=7.1 Hz, 3H).

Preparation of (S)-ethyl 2-tert-butoxy-2-(6-(difluoromethyl)-7-fluoro-3-methyl-1-(trifluoromethylsulfonyloxy)naphthalen-2-yl)acetate: To a solution of S)-ethyl 2-tert-butoxy-2-(7-fluoro-6-formyl-3-methyl-1-(trifluoromethylsulfonyloxy)naphthalen-2-yl)acetate (37.3 mg, 0.075 mmol) in dichloromethane (0.5 mL) at 0° C. was added Deoxo-Fluor (28 μL, 0.151 mmol). The reaction mixture was stirred for 2.5 hours at 0° C., then loaded directly onto a silica gel column and purified by flash column chromatography (silica gel, 0 to 10% ethyl acetate/hexanes) to give a colorless oil (32.7 mg). $^1$H NMR (400 MHz, CDCl$_3$) δ 8.06 (d, J=6.8 Hz, 1H), 7.75 (s, 1H), 7.73 (d, J=10.7 Hz, 1H), 6.99 (t, J=54.8 Hz, 1H), 5.72 (s, 1H), 4.36-3.93 (m, 2H), 2.56 (s, 3H), 1.20 (s, 9H), 1.17 (t, J=7.1 Hz, 3H).

Preparation of(S)-ethyl 2-tert-butoxy-2-((R)-6-(difluoromethyl)-1-(2,3-dihydropyrano[4,3,2-de]quinolin-7-yl)-7-fluoro-3-methylnaphthalen-2-yl)acetate: A Smith process vial was charged with (S)-ethyl 2-tert-butoxy-2-(6-(difluoromethyl)-7-fluoro-3-methyl-1-(trifluoromethylsulfonyloxy)naphthalen-2-yl)acetate (53.6 mg, 0.104 mmol), 2,3-dihydropyrano[4,3,2-de]quinolin-7-ylboronic acid, HCl salt (31.3 mg, 0.125 mmol), Sphos Palladacycle (10.5 mg, 0.0156 mmol), cesium fluoride (69.5 mg, 0.458 mmol) and flushed with nitrogen. Dimethoxyethane (1.0 mL, distilled from Na/benzophenone) was added and mixture sparged with nitrogen for 10 minutes and then heated in microwave at 120° C. for 1.5 hour. The reaction mixture was diluted with ethyl acetate and washed with brine. Aqueous layer back-extracted and combined organic layer dried (MgSO$_4$), filtered, concentrated and purified by flash column chromatography (silica gel, 0 to 20% ethyl acetate/hexanes) to give (S)-ethyl 2-tert-butoxy-2-((R)-6-(difluoromethyl)-1-(2,3-dihydropyrano[4,3,2-de]quinolin-7-yl)-7-fluoro-3-methylnaphthalen-2-yl)acetate (10 mg). LCMS-ESI$^+$ (m/z): [M+H]$^+$ calcd for C$_{31}$H$_{31}$F$_3$NO$_4$: 538.6; found: 538.1.

The other atropisomer, (S)-ethyl 2-tert-butoxy-2-((S)-6-(difluoromethyl)-1-(2,3-dihydropyrano[4,3,2-de]quinolin-7-yl)-7-fluoro-3-methylnaphthalen-2-yl)acetate, was also isolated (12.0 mg). LCMS-ESI$^+$ (m/z): [M+H]$^+$ calcd for C$_{31}$H$_{31}$F$_3$NO$_4$: 538.6. found: 538.1.

Preparation of (S)-2-tert-butoxy-2-((R)-6-(difluoromethyl)-1-(2,3-dihydropyrano[4,3,2-de]quinolin-7-yl)-7-fluoro-3-methylnaphthalen-2-yl)acetic acid (103): A solution of (S)-ethyl 2-tert-butoxy-2-((R)-6-(difluoromethyl)-1-(2,3-dihydropyrano[4,3,2-de]quinolin-7-yl)-7-fluoro-3-methylnaphthalen-2-yl)acetate (10.0 mg, 0.0186 mmol) and 5 M sodium hydroxide (74 μL, 0.372 mmol) in tetrahydrofuran (1.0 mL) and methanol (0.1 mL) was heated at 50° C. overnight. The reaction mixture was re-suspended in methanol and concentrated to ~1 mL. DMF (0.3 mL) was added and concentrated to ~0.3 mL. Acetic acid was added, further diluted with DMF and purified by reverse phase HPLC (Gemini, 5 to 100% ACN/H$_2$O+0.1% TFA). Product lyophilized to give a yellow powder (9.8 mg). $^1$H NMR (400 MHz, CD$_3$OD) δ 8.70 (d, J=5.7 Hz, 1H), 8.24 (d, J=7.2 Hz, 1H), 8.10 (s, 1H), 7.82 (t, J=7.1 Hz, 2H), 7.46 (d, J=8.1 Hz, 1H), 7.04 (t, J=54.5 Hz, 1H), 6.71 (d, J=12.2 Hz, 1H), 5.24 (s, 1H), 4.81-4.64 (m, 2H), 3.67 (t, J=6.0 Hz, 2H), 2.79 (s, 3H), 0.93 (s, 9H). $^{19}$F NMR (377 MHz, CD$_3$OD) δ−77.77 (s), −114.82--118.07 (m), −123.29 (m). LCMS-ESI$^+$ (m/z): [M+H]$^+$ calcd for C$_{29}$H$_{27}$F$_3$NO$_4$: 510.5; found: 510.1.

EXAMPLE 102

(S)-2-tert-Butoxy-2-((R)-1-(2,3-dihydropyrano[4,3,2-de]quinolin-7-yl)-6-ethyl-7-fluoro-3-methylnaphthalen-2-yl)acetic acid (104)

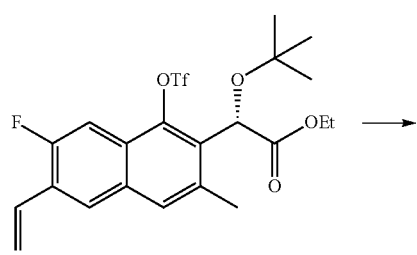

(S)-ethyl 2-(tert-butoxy)-2-(7-fluoro-3-methyl-1-(((trifluoromethyl)sulfonyl)oxy)-6-vinylnaphthalen-2-yl)acetate

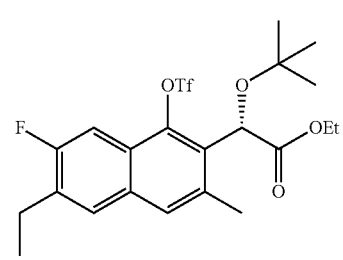

(S)-ethyl 2-(tert-butoxy)-2-(6-ethyl-7-fluoro-3-methyl-1-(((trifluoromethyl)sulfonyl)oxy)naphthalen-2-yl)acetate 2,3-dihydropyrano[4,3,2-de]quinolin-7-ylboronic acid, HCl salt

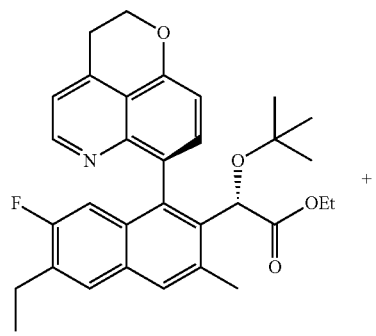

(S)-ethyl 2-(tert-butoxy)-2-((S)-1-(2,3-dihydropyrano[4,3,2-de]quinolin-7-yl)-6-ethyl-7-fluoro-3-methylnaphthalen-2-yl)acetate

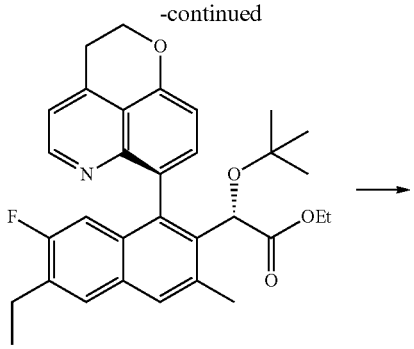

(S)-ethyl 2-(tert-butoxy)-2-((R)-1-(2,3-dihydropyrano[4,3,2-de]quinolin-7-yl)-6-ethyl-7-fluoro-3-methylnaphthalen-2-yl)acetate

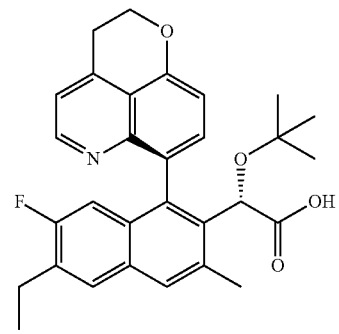

104
(S)-2-(tert-butoxy)-2-((R)-1-(2,3-dihydropyrano[4,3,2-de]quinolin-7-yl)-6-ethyl-7-fluoro-3-methylnaphthalen-2-yl)acetic acid Preparation of (S)-ethyl 2-tert-butoxy-2-(6-ethyl-7-fluoro-3-methyl-1-(trifluoromethylsulfonyloxy)naphthalen-2-yl)acetate: A mixture of (S)-ethyl 2-tert-butoxy-2-(7-fluoro-3-methyl-1-(trifluoromethylsulfonyloxy)-6-vinylnaphthalen-2-yl)acetate (23 mg, 0.050 mmol) and 10% Palladium on carbon (5 mg) in ethanol (2.0 mL) was stirred under a hydrogen atmosphere for 4 hours, then filtered through a pad of Celite. Filtrate was concentrated to give a thin film (23 mg) that was used in the next step without further purification.

Preparation of (S)-ethyl 2-tert-butoxy-2-((R)-1-(2,3-dihydropyrano[4,3,2-de]quinolin-7-yl)-6-ethyl-7-fluoro-3-methylnaphthalen-2-yl)acetate: A Smith process vial was charged with (S)-ethyl 2-tert-butoxy-2-(6-ethyl-7-fluoro-3-methyl-1-(trifluoromethylsulfonyloxy)naphthalen-2-yl)acetate (23.4 mg, 0.0473 mmol), 2,3-dihydropyrano[4,3,2-de]quinolin-7-ylboronic acid, HCl salt (14.3 mg, 0.568 mmol), Sphos Palladacycle (4.8 mg, 0.0071 mmol), cesium fluoride (31.6 mg, 0.208 mmol) and flushed with nitrogen. Dimethoxyethane (1.0 mL, distilled from Na/benzophenone) was added and mixture sparged with nitrogen for 10 minutes and then heated in microwave at 120° C. for 1.5 hour. The reaction mixture was diluted with ethyl acetate and washed with brine. Aqueous layer back-extracted and combined organic layer dried (MgSO$_4$), filtered, concentrated and purified by flash column chromatography (silica gel, 0 to 20% ethyl acetate/hexanes) to give (S)-ethyl 2-tert-butoxy-2-((R)-1-(2,3-dihydropyrano[4,3,2-de]quinolin-7-yl)-6-ethyl-7-fluoro-3-methylnaphthalen-2-yl)acetate (1.7 mg). LCMS-ESI$^+$ (m/z): [M+H]$^+$ calcd for $C_{32}H_{35}FNO_4$: 516.6; found: 516.1. The other atropisomer, (S)-ethyl 2-tert-butoxy-2-((S)-1-(2,3-dihydropyrano[4, 3,2-de]quinolin-7-yl)-6-ethyl-7-fluoro-3-methylnaphthalen-2-yl)acetate, was also isolated (2.6 mg). LCMS-ESI+ (m/z): [M+H]+ calcd for $C_{32}H_{35}FNO_4$: 516.6; found: 516.1.

Preparation of (S)-2-tert-butoxy-2-((R)-1-(2,3-dihydropyrano[4,3,2-de]quinolin-7-yl)-6-ethyl-7-fluoro-3-methylnaphthalen-2-yl)acetic acid (104): A solution of (S)-ethyl 2-tert-butoxy-2-((R)-1-(2,3-dihydropyrano[4,3,2-de]quinolin-7-yl)-6-ethyl-7-fluoro-3-methylnaphthalen-2-yl)acetate (1.7 mg, 0.005 mmol) and 5 M sodium hydroxide (21 µL, 0.101 mmol) in tetrahydrofuran (1.0 mL) and methanol (0.1 mL) was heated at 50° C. overnight. The reaction mixture was acidified with acetic acid, concentrated, dissolved in DMF and purified by reverse phase HPLC (Gemini, 5 to 100% ACN/H$_2$O+0.1% TFA). Product lyophilized to give a yellow powder (1.3 mg). $^1$H NMR (400 MHz, CD$_3$OD) δ 8.68 (d, J=5.6 Hz, 1H), 7.93 (s, 1H), 7.87-7.77 (m, J=7.0 Hz, 3H), 7.46 (d, J=8.1 Hz, 1H), 6.49 (d, J=12.1 Hz, 1H), 5.21 (s, 1H), 4.73 (d, J=6.3 Hz, 2H), 3.67 (t, J=6.0 Hz, 2H), 2.83-2.72 (m, 6H), 1.28 (t, J=7.5 Hz, 4H), 0.92 (s, 9H). $^{19}$F NMR (377 MHz, CD$_3$OD) δ −77.86 (s), −121.37 (d, J=7.9 Hz). LCMS-ESI+ (m/z): [M+H]+ calcd for $C_{30}H_{31}FNO_4$: 488.6; found: 488.1.

EXAMPLE 103

(S)-2-tert-Butoxy-2-((R)-6-cyclopropyl-1-(2,3-dihydropyrano[4,3,2de]quinolin-7-yl)-7-fluoro-3-methylnaphthalen-2-yl)acetic acid (105)

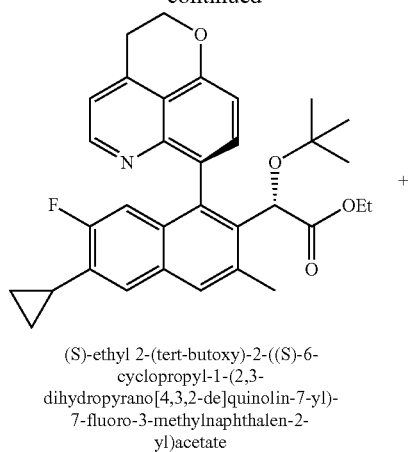

(S)-ethyl 2-(tert-butoxy)-2-((S)-6-cyclopropyl-1-(2,3-dihydropyrano[4,3,2-de]quinolin-7-yl)-7-fluoro-3-methylnaphthalen-2-yl)acetate

+

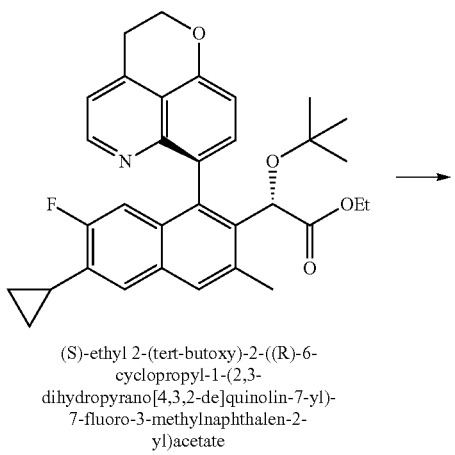

(S)-ethyl 2-(tert-butoxy)-2-((R)-6-cyclopropyl-1-(2,3-dihydropyrano[4,3,2-de]quinolin-7-yl)-7-fluoro-3-methylnaphthalen-2-yl)acetate

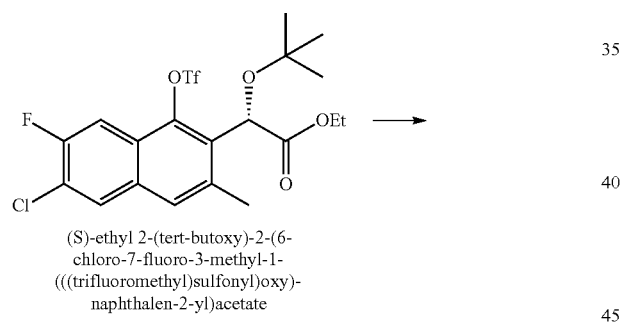

(S)-ethyl 2-(tert-butoxy)-2-(6-chloro-7-fluoro-3-methyl-1-(((trifluoromethyl)sulfonyl)oxy)-naphthalen-2-yl)acetate

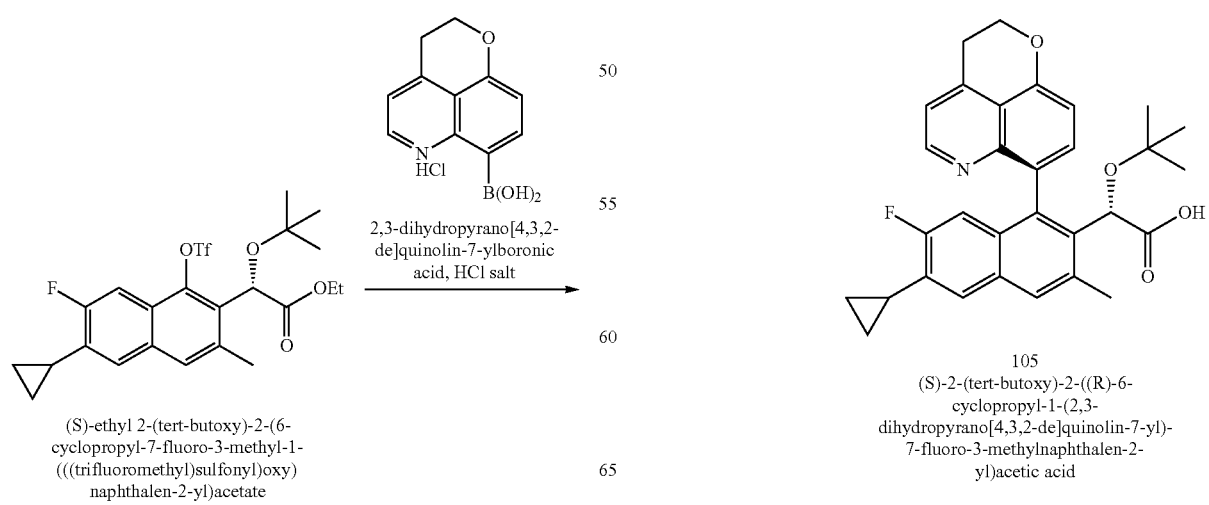

2,3-dihydropyrano[4,3,2-de]quinolin-7-ylboronic acid, HCl salt (S)-ethyl 2-(tert-butoxy)-2-(6-cyclopropyl-7-fluoro-3-methyl-1-(((trifluoromethyl)sulfonyl)oxy) naphthalen-2-yl)acetate 105
(S)-2-(tert-butoxy)-2-((R)-6-cyclopropyl-1-(2,3-dihydropyrano[4,3,2-de]quinolin-7-yl)-7-fluoro-3-methylnaphthalen-2-yl)acetic acid Preparation of (S)-ethyl 2-tert-butoxy-2-(6-cyclopropyl-7-fluoro-3-methyl-1-(trifluoromethylsulfonyloxy)naphthalen-2-yl)acetate: A Smith process vial was charged with (S)-ethyl 2-tert-butoxy-2-(6-chloro-7-fluoro-3-methyl-1-(trifluoromethylsulfonyloxy)naphthalen-2-yl)acetate (122.5 mg, 0.245 mmol), cyclopropylboronic acid (23 mg, 0.269 mmol), BrettPhos Palladacycle (27 mg, 0.0368 mmol), cesium fluoride (164 mg, 1.08 mmol) and flushed with nitrogen.

Dimethoxyethane (1.5 mL, distilled from Na/benzophenone) was added and mixture sparged with nitrogen for 15 minutes and then heated in microwave at 120° C. for 1.5 hour. The reaction mixture was diluted with ethyl acetate and washed with brine. Aqueous layer back-extracted with ethyl acetate and the combined organic layer was dried ($MgSO_4$), filtered, concentrated and purified by flash column chromatography (silica gel, 0 to 10% ethyl acetate/hexanes) to give an impure colorless oil (83.1 mg). Analytical HPLC (Gemini, 2-98% $ACN/H_2O$+0.05% TFA): $t_R$ (min)=5.53.

Preparation of (S)-ethyl 2-tert-butoxy-2-((R)-6-cyclopropyl-1-(2,3-dihydropyrano[4,3,2-de]quinolin-7-yl)-7-fluoro-3-methylnaphthalen-2-yl)acetate: A Smith process vial was charged with (S)-ethyl 2-tert-butoxy-2-(6-cyclopropyl-7-fluoro-3-methyl-1-(trifluoromethylsulfonyloxy)naphthalen-2-yl)acetate (83.1 mg, 0.164 mmol), 2,3-dihydropyrano[4,3,2-de]quinolin-7-ylboronic acid, HCl salt (45.4 mg, 0.180 mmol), Sphos Palladacycle (16.5 mg, 0.0246 mmol), cesium fluoride (110 mg, 0.722 mmol) and flushed with nitrogen. Dimethoxyethane (1.5 mL, distilled from Na/benzophenone) was added and mixture sparged with nitrogen for 15 minutes and then heated in microwave at 120° C. for 1.5 hour. The reaction mixture was diluted with ethyl acetate and washed with brine. Aqueous layer back-extracted and combined organic layer dried ($MgSO_4$), filtered, concentrated and purified by flash column chromatography (silica gel, 0 to 30% ethyl acetate/hexanes) to give (S)-ethyl 2-tert-butoxy-2-((R)-6-cyclopropyl-1-(2,3-dihydropyrano[4,3,2-de]quinolin-7-yl)-7-fluoro-3-methylnaphthalen-2-yl)acetate (2.2 mg).

LCMS-ESI$^+$ (m/z): [M+H]$^+$ calcd for $C_{33}H_{35}FNO_4$: 528.6; found: 528.1, 529.1. The other atropisomer, (S)-ethyl 2-tert-butoxy-2-((S)-6-cyclopropyl-1-(2,3-dihydropyrano[4,3,2-de]quinolin-7-yl)-7-fluoro-3-methylnaphthalen-2-yl)acetate, was also isolated (2.8 mg). LCMS-ESI$^+$ (m/z): [M+H]$^+$ calcd for $C_{33}H_{34}FNO_4$: 528.6; Found: 528.1, 529.1

Preparation of (S)-2-tert-butoxy-2-((R)-6-cyclopropyl-1-(2,3-dihydropyrano[4,3,2-de]quinolin-7-yl)-7-fluoro-3-methylnaphthalen-2-yl)acetic acid (105): A solution of (S)-ethyl 2-tert-butoxy-2-((R)-6-cyclopropyl-1-(2,3-dihydropyrano[4,3,2-de]quinolin-7-yl)-7-fluoro-3-methylnaphthalen-2-yl)acetate (2.2 mg, 0.0042 mmol) and 5 M sodium hydroxide (171 μL, 0.083 mmol) in tetrahydrofuran (0.5 mL) and methanol (0.1 mL) was heated at 45° C. overnight. The reaction mixture was concentrated, acidified with acetic acid, diluted in DMF and purified by reverse phase HPLC (Gemini, 5 to 100% $ACN/H_2O$+0.1% TFA). Product lyophilized to give a yellow powder (2.2 mg). $^1$H-NMR: 400 MHz, ($CD_3OD$) δ: 8.67 (d, J=5.6 Hz, 1H), 7.89 (s, 1H), 7.82-7.78 (m, 2H), 7.54 (d, J=7.6 Hz, 1H), 7.44 (d, J=8.0 Hz, 1H), 6.47 (d, J=12.4 Hz, 1H), 5.20 (s, 1H), 4.76-4.49 (m, 2H), 3.66 (t, J=6 Hz, 2H), 2.73 (s, 3H), 2.15-2.10 (m, 1H), 1.04 (d, J=8.4 Hz, 2H), 0.92 (s, 9H), 0.86-0.83 (m, 2H). $^{19}$F-NMR: 377 MHz, ($CD_3OD$) δ: −77.7 (s, 3F), −121.8 (dd, 1F). LCMS-ESI$^+$ (m/z): [M+H]$^+$ calcd for $C_{31}H_{31}FNO_4$: 500.6; found: 500.1.

EXAMPLE 104

(S)-2-tert-Butoxy-2-((R)-6-cyano-1-(2,3-dihydropyrano[4,3,2-de]quinolin-7-yl)-7-fluoro-3-methylnaphthalen-2-yl)acetic acid (106A) and (S)-2-tert-Butoxy-2-((R)-6-carbamoyl-1-(2,3-dihydropyrano[4,3, 2-de]quinolin-7-yl)-7-fluoro-3-methylnaphthalen-2-yl)acetic acid (106B)

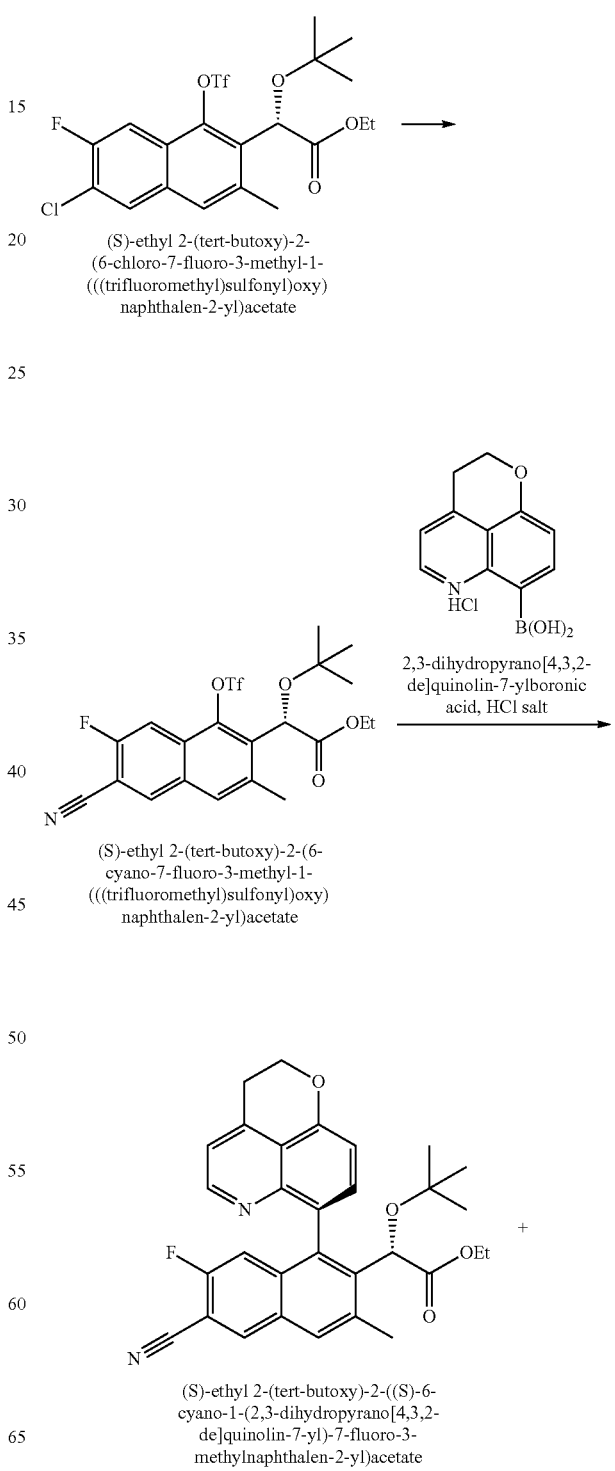

(S)-ethyl 2-(tert-butoxy)-2-(6-chloro-7-fluoro-3-methyl-1-(((trifluoromethyl)sulfonyl)oxy)naphthalen-2-yl)acetate (S)-ethyl 2-(tert-butoxy)-2-(6-cyano-7-fluoro-3-methyl-1-(((trifluoromethyl)sulfonyl)oxy)naphthalen-2-yl)acetate 2,3-dihydropyrano[4,3,2-de]quinolin-7-ylboronic acid, HCl salt (S)-ethyl 2-(tert-butoxy)-2-((S)-6-cyano-1-(2,3-dihydropyrano[4,3,2-de]quinolin-7-yl)-7-fluoro-3-methylnaphthalen-2-yl)acetate

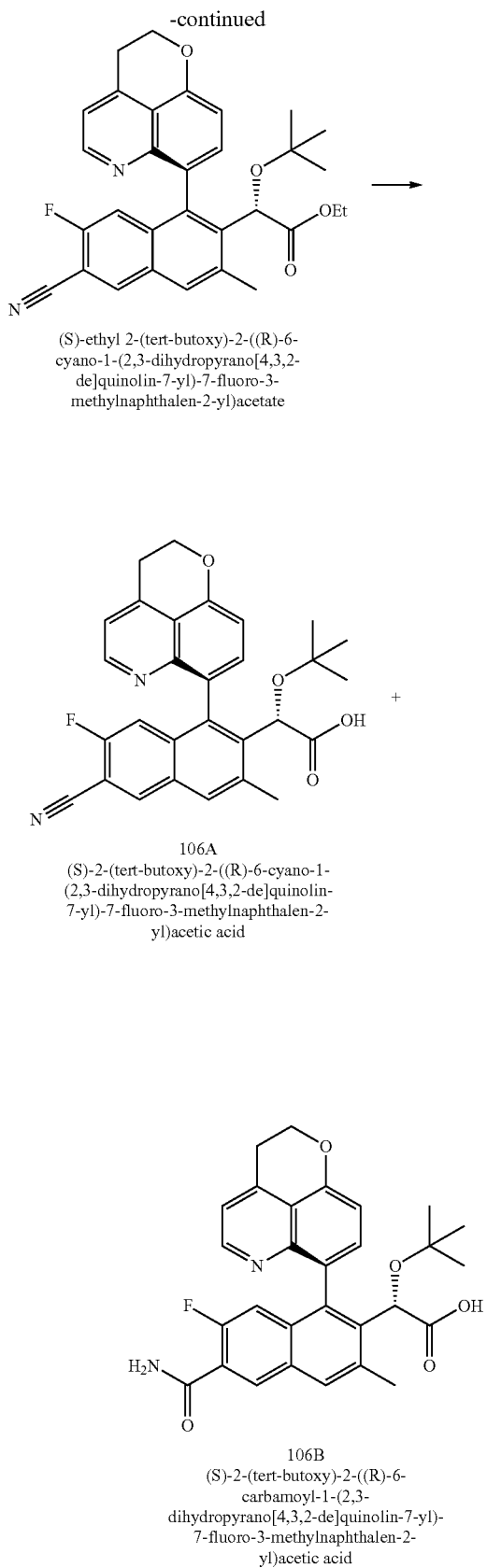

(S)-ethyl 2-(tert-butoxy)-2-((R)-6-cyano-1-(2,3-dihydropyrano[4,3,2-de]quinolin-7-yl)-7-fluoro-3-methylnaphthalen-2-yl)acetate 106A
(S)-2-(tert-butoxy)-2-((R)-6-cyano-1-(2,3-dihydropyrano[4,3,2-de]quinolin-7-yl)-7-fluoro-3-methylnaphthalen-2-yl)acetic acid 106B
(S)-2-(tert-butoxy)-2-((R)-6-carbamoyl-1-(2,3-dihydropyrano[4,3,2-de]quinolin-7-yl)-7-fluoro-3-methylnaphthalen-2-yl)acetic acid Preparation of (S)-ethyl 2-tert-butoxy-2-(6-cyano-7-fluoro-3-methyl-1-(trifluoromethylsulfonyloxy)naphthalen-2-yl)acetate: A Smith process vial was charged with (S)-ethyl 2-tert-butoxy-2-(6-chloro-7-fluoro-3-methyl-1-(trifluoromethylsulfonyloxy)naphthalen-2-yl)acetate (180 mg, 0.359 mmol), zinc(II) cyanide (25 mg, 0.215 mmol), BrettPhos Palladacycle (26 mg, 0.0359 mmol), sodium bicarbonate (3 mg, 0.0359 mmol). DMF (1.5 mL) was added and mixture was heated in microwave at 110° C. for 1.0 hour. The reaction mixture was diluted with ethyl acetate and washed with 5% lithium chloride solution (2×), brine, dried (MgSO$_4$), filtered, concentrated and purified by flash column chromatography (silica gel, 0 to 10% ethyl acetate/hexanes) to give a colorless oil (129 mg). Analytical HPLC (Gemini, 2-98% ACN/H$_2$O+ 0.05% TFA): $t_R$ (min)=5.01.

Preparation of (S)-ethyl 2-tert-butoxy-2-((R)-6-cyano-1-(2,3-dihydropyrano[4,3,2-de]quinolin-7-yl)-7-fluoro-3-methylnaphthalen-2-yl)acetate: A Smith process vial was charged with (S)-ethyl 2-tert-butoxy-2-(6-cyano-7-fluoro-3-methyl-1-(trifluoromethylsulfonyloxy)naphthalen-2-yl)acetate (129 mg, 0.262 mmol), 2,3-dihydropyrano[4,3,2-de]quinolin-7-ylboronic acid, HCl salt (72.6 mg, 0.289 mmol), Sphos Palladacycle (26 mg, 0.0393 mmol), cesium fluoride (175 mg, 1.15 mmol) and flushed with nitrogen. Dimethoxyethane (1.5 mL, distilled from Na/benzophenone) was added and mixture sparged with nitrogen for 15 minutes and then heated in microwave at 120° C. for 1.5 hour. The reaction mixture was diluted with ethyl acetate and washed with brine. Aqueous layer back-extracted and combined organic layer dried (MgSO$_4$), filtered, concentrated and purified by flash column chromatography (silica gel, 0 to 30% ethyl acetate/hexanes) to give impure (S)-ethyl 2-tert-butoxy-2-((R)-6-cyano-1-(2,3-dihydropyrano[4,3,2-de]quinolin-7-yl)-7-fluoro-3-methylnaphthalen-2-yl)acetate (36.6 mg). LCMS-ESI$^+$ (m/z): [M+H]$^+$ calcd for C$_{31}$H$_{30}$FN$_2$O$_4$: 513.6; found: 513.1. The other atropisomer, (S)-ethyl 2-tert-butoxy-2-((S)-6-cyano-1-(2,3-dihydropyrano[4,3,2-de]quinolin-7-yl)-7-fluoro-3-methylnaphthalen-2-yl)acetate, was also isolated (36.8 mg). LCMS-ESI$^+$ (m/z): [M+H]$^+$ calcd for C$_{31}$H$_{30}$FN$_2$O$_4$: 513.6; found: 513.1.

Preparation of (S)-2-tert-butoxy-2-((R)-6-cyano-1-(2,3-dihydropyrano[4,3,2-de]quinolin-7-yl)-7-fluoro-3-methylnaphthalen-2-yl)acetic acid (106A): A solution of (S)-ethyl 2-tert-butoxy-2-((R)-6-cyano-1-(2,3-dihydropyrano[4,3,2-de]quinolin-7-yl)-7-fluoro-3-methylnaphthalen-2-yl)acetate (36.8 mg, 0.0718 mmol) and 5 M sodium hydroxide (290 μL, 1.44 mmol) in tetrahydrofuran (1.5 mL) and methanol (0.3 mL) was heated at 35° C. overnight. The reaction mixture was concentrated, acidified with acetic acid, diluted in DMF and purified by reverse phase HPLC (Gemini, 5 to 100% ACN/H$_2$O+0.1% TFA). Product lyophilized to give a yellow powder (26.9 mg). $^1$H-NMR: 400 MHz, (CD$_3$OD) δ: 8.70 (d, J=5.6 Hz, 1H), 8.53 (d, J=6.8 Hz, 1H), 8.11 (s, 1H), 7.82-7.75 (m, 2H), 7.44 (d, J=8.0 Hz, 1H), 6.83 (d, J=11.2 Hz, 1H), 5.24 (s, 1H), 4.76-4.68 (m, 2H), 3.66 (t, J=6 Hz, 2H), 2.79 (s, 3H), 0.92 (s, 9H). $^{19}$F-NMR: 377 MHz, (CD$_3$OD) δ: −77.8 (s, 3F), −115.5 (br s, 1F).

LCMS-ESI$^+$ (m/z): [M+H]$^+$ calcd for C$_{29}$H$_{26}$FN$_2$O$_4$: 485.5; found: 485.1. A side-product, (S)-2-tert-butoxy-2-((R)-6-carbamoyl-1-(2,3-dihydropyrano[4,3,2-de]quinolin-7-yl)-7-fluoro-3-methylnaphthalen-2-yl)acetic acid (106B), was also isolated (2.8 mg). $^1$H-NMR: 400 MHz, (CD$_3$OD) δ: 8.70 (d, J=5.6 Hz, 1H), 8.44 (d, J=7.2 Hz, 1H), 8.09 (s, 1H), 7.82-7.80 (m, 2H), 7.44 (d, J=8.0 Hz, 1H), 6.68 (d, J=13.2 Hz, 1H), 5.24 (s, 1H), 4.76-4.70 (m, 2H), 3.66 (t, J=6.0 Hz, 2H), 2.78 (s, 3H), 0.93 (s, 9H). $^{19}$F-NMR: 377 MHz, (CD$_3$OD) δ:

−77.7 (s, 3F), −118.4 (br s, 1F). LCMS-ESI⁺ (m/z): [M+H]⁺ calcd for $C_{29}H_{28}FN_2O_5$: 503.5; found: 503.1.

EXAMPLE 105

(S)-2-tert-Butoxy-2-((R)-1-(2,3-dihydropyrano[4,3,2-de]quinolin-7-yl)-7-fluoro-3-methyl-6-(methylcarbamoyl)naphthalen-2-yl)acetic acid (107)

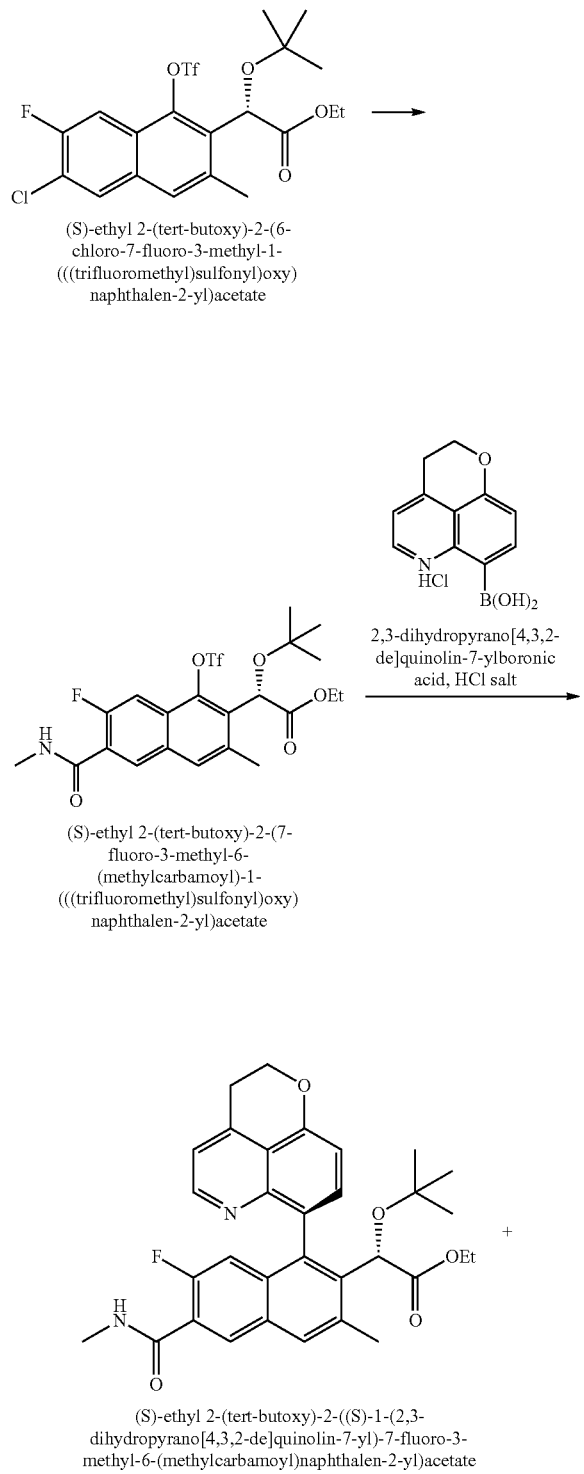

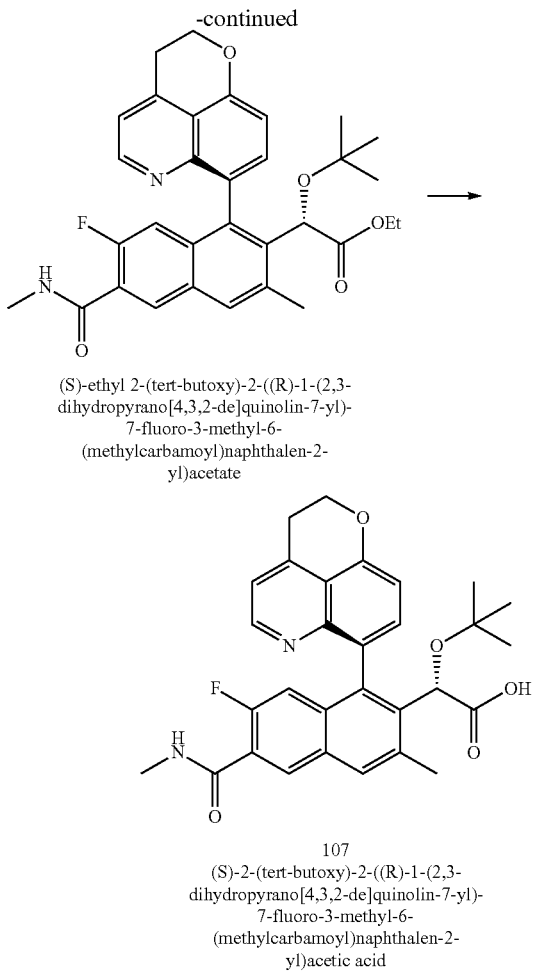

Preparation of (S)-ethyl 2-tert-butoxy-2-(7-fluoro-3-methyl-6-(methylcarbamoyl)-1-(trifluoromethylsulfonyloxy)naphthalen-2-yl)acetate: A Smith process vial was charged with (S)-ethyl 2-tert-butoxy-2-(6-chloro-7-fluoro-3-methyl-1-(trifluoromethylsulfonyloxy)naphthalen-2-yl)acetate (131.8 mg, 0.263 mmol), 2 M methylamine in THF (0.66 mL, 1.32 mmol), molybdenum hexacarbonyl (0.069 g, 0.263 mmol), BrettPhos Palladacycle (29 mg, 0.0395 mmol), and triethylamine (0.128 mL, 0.921 mmol). Toluene (1.5 mL) was added and mixture was heated in microwave at 140° C. for 1.5 hour. The reaction mixture was diluted with ethyl acetate, washed brine, dried (MgSO₄), filtered, concentrated and purified by flash column chromatography (silica gel, 0 to 50% ethyl acetate/hexanes) to give an off-white solid (19.2 mg). LCMS-ESI⁺ (m/z): [M+H]⁺ calcd for $C_{22}H_{26}F_4NO_7S$: 524.5; Found: 524.0.

Preparation of (S)-ethyl 2-tert-butoxy-2-((R)-1-(2,3-dihydropyrano[4,3,2-de]quinolin-7-yl)-7-fluoro-3-methyl-6-(methylcarbamoyl)naphthalen-2-yl)acetate: A Smith process vial was charged with (S)-ethyl 2-tert-butoxy-2-(7-fluoro-3-methyl-6-(methylcarbamoyl)-1-(trifluoromethylsulfonyloxy)naphthalen-2-yl)acetate (19.2 mg, 0.0367 mmol), 2,3-dihydropyrano[4,3,2-de]quinolin-7-ylboronic acid, HCl salt (11.1 mg, 0.044 mmol), Sphos Palladacycle (3.7 mg, 0.0055 mmol), cesium fluoride (25 mg, 0.161 mmol) and flushed with nitrogen. Dimethoxyethane (0.5 mL, distilled from Na/benzophenone) was added and mixture sparged with nitrogen for 10 minutes and then heated in microwave at 120°

C. for 1.5 hour. The reaction mixture was diluted with ethyl acetate and washed with brine. Aqueous layer back-extracted and combined organic layer dried (MgSO$_4$), filtered, concentrated and purified by flash column chromatography (silica gel, 30 to 80% ethyl acetate/hexanes) to give (S)-ethyl 2-tert-butoxy-2-((R)-1-(2,3-dihydropyrano[4,3,2-de]quinolin-7-yl)-7-fluoro-3-methyl-6-(methylcarbamoyl)naphthalen-2-yl)acetate (6.6 mg). LCMS-ESI$^+$ (m/z): [M+H]$^+$ calcd for C$_{32}$H$_{34}$FN$_2$O$_5$: 545.6; found: 545.1.

The other atropisomer, (S)-ethyl 2-tert-butoxy-2-((S)-1-(2,3-dihydropyrano[4,3,2-de]quinolin-7-yl)-7-fluoro-3-methyl-6-(methylcarbamoyl)naphthalen-2-yl)acetate, was also isolated (7.5 mg). LCMS-ESI$^+$ (m/z): [M+H]$^+$ calcd for C$_{32}$H$_{34}$FN$_2$O$_5$: 545.6; found: 545.1.

Preparation of (S)-2-tert-butoxy-2-((R)-1-(2,3-dihydropyrano[4,3,2-de]quinolin-7-yl)-7-fluoro-3-methyl-6-(methylcarbamoyl)naphthalen-2-yl)acetic acid (107): A solution of (S)-ethyl 2-tert-butoxy-2-((R)-1-(2,3-dihydropyrano[4,3,2-de]quinolin-7-yl)-7-fluoro-3-methyl-6-(methylcarbamoyl)naphthalen-2-yl)acetate (6.6 mg, 0.012 mmol) and 5 M lithium hydroxide (48 µL, 0.242 mmol) in tetrahydrofuran (1.0 mL) and methanol (0.3 mL) was heated at 55° C. for 3 hours, then overnight at 48° C. Additional 5 M lithium hydroxide solution (60 µL) was added and the reaction mixture stirred for 2 hours at 60° C. The reaction mixture was acidified with acetic acid, concentrated, diluted in DMF and purified by reverse phase HPLC (Gemini, 5 to 100% ACN/H$_2$O+0.1% TFA). Product lyophilized to give a yellow powder (5.0 mg). $^1$H-NMR: 400 MHz, (CD$_3$OD) δ: 8.70 (d, J=5.6 Hz, 1H), 8.35 (d, J=7.2 Hz, 1H), 8.07 (s, 1H), 7.82-7.80 (m, 2H), 7.44 (d, J=8.4 Hz, 1H), 6.66 (d, J=12.8 Hz, 1H), 5.24 (s, 1H), 4.76-4.70 (m, 2H), 3.66 (t, J=6 Hz, 2H), 2.94 (s, 3H), 2.78 (s, 3H), 0.92 (s, 9H). $^{19}$F-NMR: 377 MHz, (CD$_3$OD) δ: −77.6 (s, 3F), −115.5 (dd, J=12.4, 7.16 Hz, 1F). LCMS-ESI$^+$ (m/z): [M+H]$^+$ calcd for C$_{30}$H$_{30}$FN$_2$O$_5$: 517.6; found: 517.1.

EXAMPLE 106

(S)-2-tert-Butoxy-2-((R)-1-(2,3-dihydropyrano[4,3,2-de]quinolin-7-yl)-6,7-difluoro-3-methylnaphthalen-2-yl)acetic acid (108)

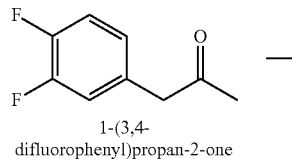

1-(3,4-difluorophenyl)propan-2-one

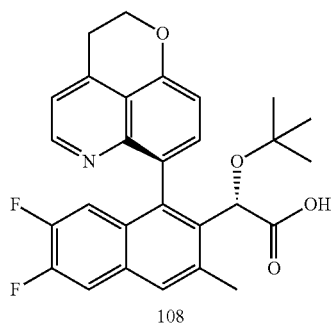

108
(S)-2-(tert-butoxy)-2-((R)-1(2-3-dihydropyrano[4,3,2-de]quinolin-7-yl)-6,7-difluoro-3-methylnaphthalen-2-yl)acetic acid Preparation of (S)-2-tert-butoxy-2-((R)-1-(2,3-dihydropyrano[4,3,2-de]quinolin-7-yl)-6,7-difluoro-3-methylnaphthalen-2-yl)acetic acid (108): (S)-2-tert-Butoxy-2-((R)-1-(2,3-dihydropyrano[4,3,2-de]quinolin-7-yl)-6,7-difluoro-3-methylnaphthalen-2-yl)acetic acid (108) was prepared in a similar manner as (S)-2-tert-butoxy-2-((R)-6-chloro-1-(2,3-dihydropyrano[4,3,2-de]quinolin-7-yl)-7-fluoro-3-methylnaphthalen-2-yl)acetic acid of Example 99 except starting with 1-(3,4-difluorophenyl)propan-2-one instead of 1-(3-chloro-4-fluorophenyl)propan-2-one.

$^1$H-NMR: 400 MHz, (CD$_3$OD) δ: 8.69 (d, J=5.6 Hz, 1H), 7.96 (s, 1H), 7.83-7.78 (m, 3H), 7.45 (d, J=8.4 Hz, 1H), 6.77 (d, J=8.0 Hz, 1H), 6.74 (d, J=8.0 Hz, 1H), 5.20 (s, 1H), 4.75-4.70 (m, 2H), 3.66 (t, J=5.6 Hz, 2H), 2.76 (s, 3H) 0.92 (s, 9H).

$^{19}$F-NMR: 377 MHz, (CD$_3$OD) δ: −77.9 (s, 3F), −138.8—138.9 (m, 1F), −139.8—139.9 (m, 1F). LCMS-ESI$^+$ (m/z): [M+H]$^+$ calcd for C$_{28}$H$_{26}$F$_2$NO$_4$: 478.5; found: 478.1. The other atropisomer, (S)-2-tert-butoxy-2-((S)-1-(2,3-dihydropyrano[4,3,2-de]quinolin-7-yl)-6,7-difluoro-3-methylnaphthalen-2-yl)acetic acid, was prepared in a similar manner. $^1$H NMR (400 MHz, CD$_3$OD) δ 8.60 (d, J=5.4 Hz, 1H), 8.12 (d, J=8.2 Hz, 1H), 7.89 (s, 1H), 7.77 (dd, J=11.1, 8.2 Hz, 1H), 7.66 (d, J=5.4 Hz, 1H), 7.45 (d, J=8.2 Hz, 1H), 6.71 (dd, J=12.3, 7.9 Hz, 1H), 5.19 (s, 1H), 4.69 (t, J=6.0 Hz, 2H), 3.60 (t, J=6.0 Hz, 2H), 2.71 (s, 3H), 0.86 (s, 9H). $^{19}$F NMR (377 MHz, CD$_3$OD) δ −78.04 (s), −139.49 (s), −140.31 (s). LCMS-ESI$^+$ (m/z): [M+H]$^+$ calcd for C$_{28}$H$_{26}$F$_2$NO$_4$: 478.5; Found: 478.1.

EXAMPLE 107

(R)-2-tert-Butoxy-2-((R)-1-(2,3-dihydropyrano[4,3,2-de]quinolin-7-yl)-6,7-difluoro-3-methylnaphthalen-2-yl)acetic acid (109)

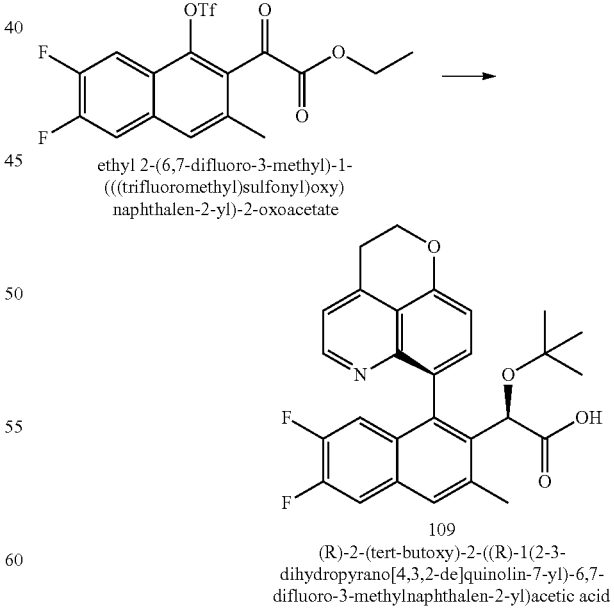

ethyl 2-(6,7-difluoro-3-methyl)-1-(((trifluoromethyl)sulfonyl)oxy)naphthalen-2-yl)-2-oxoacetate 109
(R)-2-(tert-butoxy)-2-((R)-1(2-3-dihydropyrano[4,3,2-de]quinolin-7-yl)-6,7-difluoro-3-methylnaphthalen-2-yl)acetic acid Preparation of (R)-2-tert-butoxy-2-((R)-1-(2,3-dihydropyrano[4,3,2-de]quinolin-7-yl)-6,7-difluoro-3-methylnaphthalen-2-yl)acetic acid (109): (R)-2-tert-butoxy-2-((R)-1-(2,3-dihydropyrano[4,3,2-de]quinolin-7-yl)-6,7-difluoro-3- methylnaphthalen-2-yl)acetic acid (109) was prepared in a similar manner as (S)-2-tert-butoxy-2-((R)-1-(2,3-dihydropyrano[4,3,2-de]quinolin-7-yl)-6,7-difluoro-3-methylnaphthalen-2-yl)acetic acid of Example 106 except using (S)-2-methyl-CBS-oxazaborolidine instead of (R)-2-methyl-CBS-oxazaborolidine. $^1$H NMR (400 MHz, CD$_3$OD) δ 8.59 (d, J=5.3 Hz, 1H), 8.10 (d, J=8.2 Hz, 1H), 7.88 (s, 1H), 7.76 (dd, J=11.1, 8.2 Hz, 1H), 7.63 (d, J=5.3 Hz, 1H), 7.44 (d, J=8.1 Hz, 1H), 6.71 (dd, J=12.4, 7.9 Hz, 1H), 5.19 (s, 1H), 4.68 (t, J=6.0 Hz, 2H), 3.59 (t, J=6.0 Hz, 2H), 2.70 (s, 3H), 0.85 (s, 8H). $^{19}$F NMR (377 MHz, CD$_3$OD) δ –77.84 (s), –139.69 (s), –140.48 (s). LCMS-ESI$^+$ (m/z): [M+H]$^+$ calcd for C$_{28}$H$_{26}$F$_2$NO$_4$: 478.5; Found: 478.1. The other atropisomer, (R)-2-tert-butoxy-2-((S)-1-(2,3-dihydropyrano[4,3,2-de]quinolin-7-yl)-6,7-difluoro-3-methylnaphthalen-2-yl)acetic acid, was prepared in a similar manner. $^1$H NMR (400 MHz, CD$_3$OD) δ 8.70 (d, J=5.7 Hz, 1H), 7.96 (s, 1H), 7.86-7.76 (m, 3H), 7.45 (d, J=8.1 Hz, 1H), 6.76 (dd, J=12.2, 7.9 Hz, 1H), 5.20 (s, 1H), 4.74 (dt, J=12.4, 6.3 Hz, 2H), 3.66 (t, J=5.9 Hz, 2H), 2.76 (s, 3H), 0.92 (s, 9H). $^{19}$F NMR (377 MHz, CD$_3$OD) δ –77.78 (s, 3F), –138.70--139.02 (m, 1F), –139.80--139.99 (m, 1F). LCMS-ESI$^+$ (m/z): [M+H]$^+$ calcd for C$_{28}$H$_{26}$F$_2$NO$_4$: 478.5; Found: 478.1.

EXAMPLE 108

(S)-2-tert-Butoxy-2-((R)-1-(2,3-dihydropyrano[4,3,2-de]quinolin-7-yl)-5,7-difluoro-3-methylnaphthalen-2-yl)acetic acid (110)

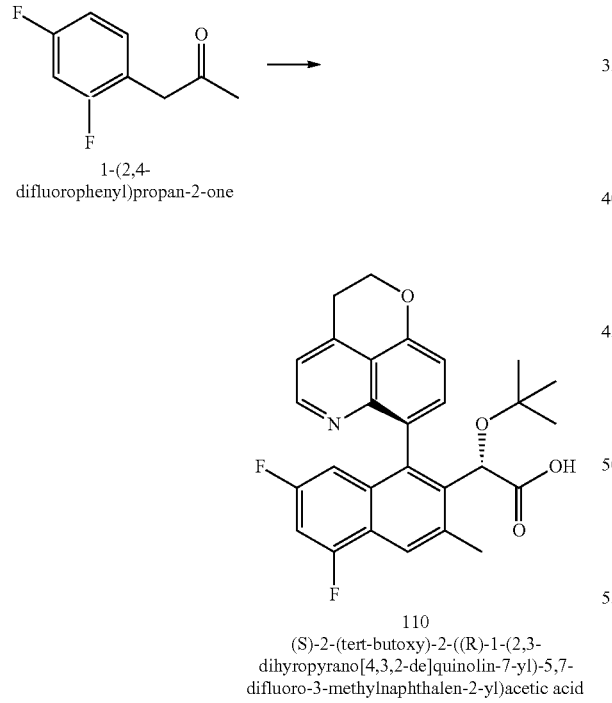

110
(S)-2-(tert-butoxy)-2-((R)-1-(2,3-dihyropyrano[4,3,2-de]quinolin-7-yl)-5,7-difluoro-3-methylnaphthalen-2-yl)acetic acid Preparation of (S)-2-tert-butoxy-2-((R)-1-(2,3-dihydropyrano[4,3,2-de]quinolin-7-yl)-5,7-difluoro-3-methylnaphthalen-2-yl)acetic acid (110): (S)-2-tert-Butoxy-2-((R)-1-(2,3-dihydropyrano[4,3,2-de]quinolin-7-yl)-5,7-difluoro-3-methylnaphthalen-2-yl)acetic acid (110) was prepared in a similar manner as (S)-2-tert-butoxy-2-((R)-6-chloro-1-(2,3-dihydropyrano[4,3,2-de]quinolin-7-yl)-7-fluoro-3-methyl-naphthalen-2-yl)acetic acid of Example 99 except starting with 1-(2,4-difluorophenyl)propan-2-one instead of 1-(3-chloro-4-fluorophenyl)propan-2-one.

$^1$H-NMR: 400 MHz, (CD$_3$OD) δ: 8.70 (d, J=6.0 Hz, 1H), 8.16 (s, 1H), 7.82 (d, J=8.0 Hz, 1H), 7.80 (d, J=6.0 Hz, 1H), 7.45 (d, J=8.4 Hz, 1H), 7.17 (ddd, J=8.0, 8.0, 2.4 Hz, 1H), 6.43 (d, J=10.0 Hz, 1H), 5.23 (s, 1H), 4.71-4.70 (m, 2H), 3.66 (t, J=6.0 Hz, 2H), 2.76 (s, 3H) 0.93 (s, 9H). $^{19}$F-NMR: 377 MHz, (CD$_3$OD) δ: –77.9 (s, 3F), –112.86 (d, J=7.9 Hz, 1F), –120.76 (dd, J=9.0, 9.0 Hz, 1F). LCMS-ESI$^+$(m/z): [M+H]$^+$ calcd for C$_{28}$H$_{26}$F$_2$NO$_4$: 478.5; Found: 478.1.

Example 109

(2S)-2-tert-Butoxy-2-(5-chloro-1-(2,3-dihydropyrano[4,3,2-de]quinolin-7-yl)-7-fluoro-3-methylnaphthalen-2-yl)acetic acid (111)

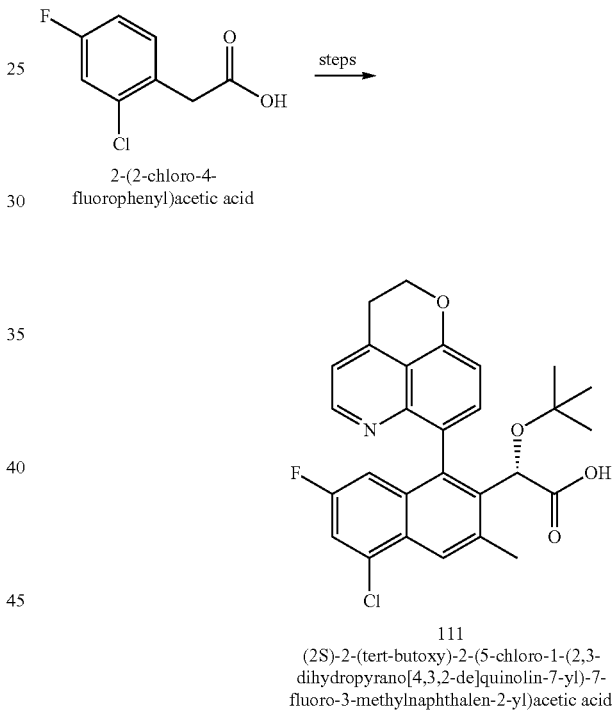

111
(2S)-2-(tert-butoxy)-2-(5-chloro-1-(2,3-dihydropyrano[4,3,2-de]quinolin-7-yl)-7-fluoro-3-methylnaphthalen-2-yl)acetic acid Preparation of (2S)-2-tert-butoxy-2-(5-chloro-1-(2,3-dihydropyrano[4,3,2-de]quinolin-7-yl)-7-fluoro-3-methylnaphthalen-2-yl)acetic acid (111): (2S)-2-tert-Butoxy-2-(5-chloro-1-(2,3-dihydropyrano[4,3,2-de]quinolin-7-yl)-7-fluoro-3-methylnaphthalen-2-yl)acetic acid (111) was prepared following the procedure to make (S)-2-tert-butoxy-2-((R)-6-chloro-1-(2,3-dihydropyrano[4,3,2-de]quinolin-7-yl)-7-fluoro-3-methylnaphthalen-2-yl)acetic acid of Example 99, except 2-(2-chloro-4-fluorophenyl)acetic acid was used instead of 2-(3-chloro-4-fluorophenyl)acetic acid. $^1$H-NMR: 400 MHz, (CDCl$_3$) δ: 8.59 (s, 1H), 8.30 (s, 1H), 8.11 (d, J=8.21 Hz, 1H), 7.46 (d, J=5.47 Hz, 1H), 7.19 (m, 2H), 6.35 (m. 1H), 5.38 (s, 1H), 4.64 (m, 2H), 3.57 (m, 2H), 2.78 (s, 3H), 1.16, 0.98 (s, 9H)

LCMS-ESI$^+$ (m/z): [M+H]$^+$ calcd for C$_{28}$H$_{26}$ClFNO$_4$: 494.95; found: 494.11. .

EXAMPLE 110

(S)-2-tert-Butoxy-2-((R)-1-(2,3-dihydropyrano[4,3,2-de]quinolin-7-yl)-7-fluoro-3,6-dimethylnaphthalen-2-yl)acetic acid (112)

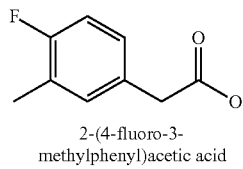

2-(4-fluoro-3-methylphenyl)acetic acid

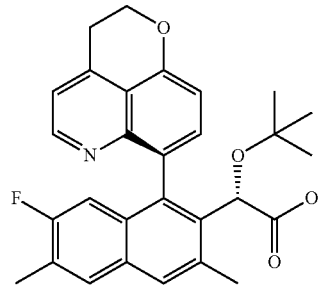

112
(S)-2-(tert-butoxy)-2-((R)-1-(2,3-dihydropyrano[4,3,2-de]quinolin-7-yl)-7-fluoro-3,6-dimethylnaphthalen-2-yl)acetic acid Preparation of (S)-2-tert-butoxy-2-((R)-1-(2,3-dihydropyrano[4,3,2-de]quinolin-7-yl)-7-fluoro-3,6-dimethylnaphthalen-2-yl)acetic acid (112): (S)-2-tert-butoxy-2-((R)-1-(2,3-dihydropyrano[4,3,2-de]quinolin-7-yl)-7-fluoro-3,6-dimethylnaphthalen-2-yl)acetic acid (112) was prepared following the procedure to make (S)-2-tert-butoxy-2-((R)-6-chloro-1-(2,3-dihydropyrano[4,3,2-de]quinolin-7-yl)-7-fluoro-3-methylnaphthalen-2-yl)acetic acid of Example 99, except 2-(4-fluoro-3-methylphenyl)acetic acid was used instead of 2-(3-chloro-4-fluorophenyl)acetic acid. $^1$H-NMR: 400 MHz, (CD$_3$OD) δ: 8.66 (d, J=5.76 Hz, 1H), 7.90 (s, 1H), 7.80 (d, J=6.65 Hz, 3H), 7.42 (d, J=7.82 Hz, 1H), 6.46 (d, J=11.73 Hz, 1H), 5.21 (s, 1H), 4.71 (m, 2H), 3.63 (t, J=6.26 Hz, 2H), 2.75 (s, 3H), 2.39 (s, 3H), 0.92 (s, 9H). LCMS-ESI$^+$ (m/z): [M+H]$^+$ calcd for C$_{29}$H$_{29}$FNO$_4$: 474.54; found: 474.14.

EXAMPLE 111

(S)-2-tert-Butoxy-2-((R)-5-cyano-1-(2,3-dihydropyrano[4,3,2-de]quinolin-7-yl)-7-fluoro-3-methylnaphthalen-2-yl)acetic acid (113A) and (S)-2-tert-Butoxy-2-((R)-5-carbamoyl-1-(2,3-dihydropyrano[4,3,2-de]quinolin-7-yl)-7-fluoro-3-methylnaphthalen-2-yl)acetic acid (113B)

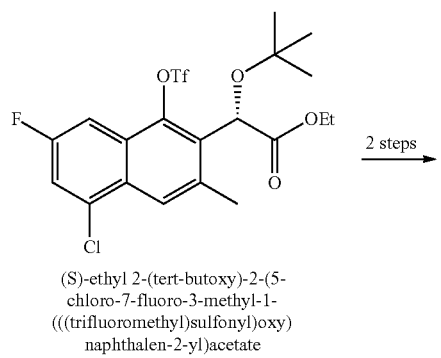

(S)-ethyl 2-(tert-butoxy)-2-(5-chloro-7-fluoro-3-methyl-1-(((trifluoromethyl)sulfonyl)oxy)naphthalen-2-yl)acetate

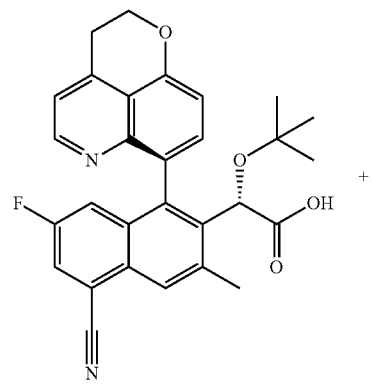

113A
(S)-2-(tert-butoxy)-2-((R)-5-cyano-1-(2,3-dihydropyrano[4,3,2-de]quinolin-7-yl)-7-fluoro-3-methylnaphthalen-2-yl)acetic acid

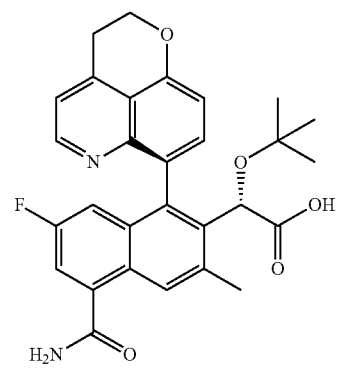

113B
(S)-2-(tert-butoxy)-2-((R)-5-carbamoyl-1-(2,3-dihydropyrano[4,3,2-de]quinolin-7-yl)-7-fluoro-3-methylnaphthalen-2-yl)acetic acid Preparation of (S)-2-tert-butoxy-2-((R)-5-cyano-1-(2,3-dihydropyrano[4,3,2-de]quinolin-7-yl)-7-fluoro-3-methylnaphthalen-2-yl)acetic acid (113A): (S)-2-tert-butoxy-2-((R)-5-cyano-1-(2,3-dihydropyrano[4,3,2-de]quinolin-7-yl)-7-fluoro-3-methylnaphthalen-2-yl)acetic acid (113A) was prepared following the procedure to make (S)-2-tert-butoxy-2-((R)-6-cyano-1-(2,3-dihydropyrano[4,3,2-de]quinolin-7-yl)-7-fluoro-3-methylnaphthalen-2-yl)acetic acid of Example 104, except (S)-ethyl 2-tert-butoxy-2-(5-chloro-7-fluoro-3-methyl-1-(trifluoromethylsulfonyloxy)naphthalen-2-yl)acetate was used instead of (S)-ethyl 2-tert-butoxy-2-(6-chloro-7-fluoro-3-methyl-1-(trifluoromethylsulfonyloxy)naphthalen-2-yl)acetate.
$^1$H-NMR: 400 MHz, (CD$_3$OD) δ: 8.64 (d, J=5.48 Hz, 1H), 8.22 (s, 1H), 7.92 (t, J=7.75 Hz, 1H), 7.76 (d, J=7.82 Hz, 1H), 7.68 (t, J=10.56 Hz, 1H), 7.38 (d, J=7.72 Hz, 1H), 6.98 (m, 1H), 5.21 (s, 1H), 4.71 (m. 2H), 3.60 (t, J=5.86 Hz, 2H), 2.82 (s, 3H), 0.92 (s, 9H).
$^{19}$F-NMR: 377 MHz, (CD$_3$OD) δ: −77.8 (s, 3F), −115.5 (br s, 1F). LCMS-ESI$^+$ (m/z): [M+H]$^+$ calcd for C$_{29}$H$_{26}$FN$_2$O$_4$: 485.52; found: 485.09.

Preparation of (S)-2-tert-butoxy-2-((R)-5-carbamoyl-1-(2,3-dihydropyrano[4,3,2-de]quinolin-7-yl)-7-fluoro-3-methylnaphthalen-2-yl)acetic acid (113B): Following the procedure to make (S)-2-tert-butoxy-2-((R)-6-carbamoyl-1-(2,3-dihydropyrano[4,3,2-de]quinolin-7-yl)-7-fluoro-3-methylnaphthalen-2-yl)acetic acid of Example 104, except (S)-ethyl 2-tert-butoxy-2-(5-chloro-7-fluoro-3-methyl-1-(trifluoromethylsulfonyloxy)naphthalen-2-yl)acetate was used instead of (S)-ethyl 2-tert-butoxy-2-(6-chloro-7-fluoro-3-methyl-1-(trifluoromethylsulfonyloxy)naphthalen-2-yl)acetate. $^1$H-NMR: 400 MHz, (CD$_3$OD) δ: 8.64 (d, J=5.48 Hz, 1H), 8.32 (s, 1H), 7.78 (d, J=7.82, 1H), 7.72 (d, J=5.87 Hz, 1H), 7.50 (t, J=8.21 Hz, 1H), 7.40 (d, J=8.22 Hz, 1H), 6.68 (m, 1H), 5.21 (s, 1H), 4.75 (m. 2H), 3.60 (t, J=5.87 Hz, 2H), 2.82 (s, 3H), 0.92 (s, 9H).

LCMS-ESI$^+$ (m/z): [M+H]$^+$ calcd for C$_{29}$H$_{28}$FN$_2$O$_5$: 503.53; found: 503.12.

EXAMPLE 112

(S)-2-tert-butoxy-2-((R)-1-(2,3-dihydropyrano[4,3,2-de]quinolin-7-yl)-7-fluoro-3-methyl-5-(pyrimidin-5-yl)naphthalen-2-yl)acetic acid (114)

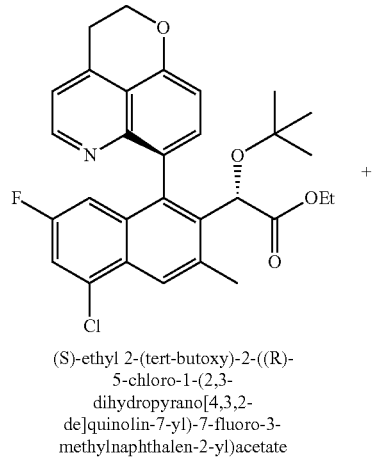

(S)-ethyl 2-(tert-butoxy)-2-((R)-5-chloro-1-(2,3-dihydropyrano[4,3,2-de]quinolin-7-yl)-7-fluoro-3-methylnaphthalen-2-yl)acetate

+

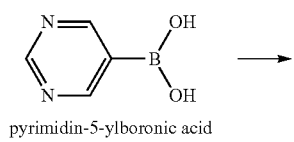

pyrimidin-5-ylboronic acid

→

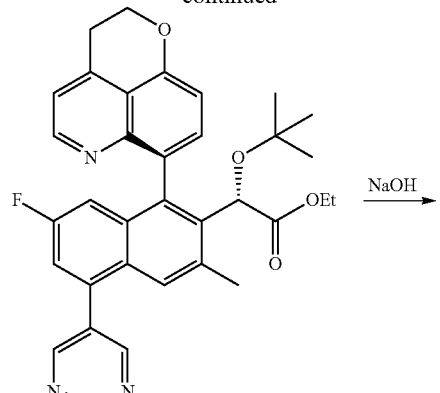

(S)-ethyl 2-(tert-butoxy)-2-((R)-1-(2,3-dihydropyrano[4,3,2-de]quinolin-7-yl)-7-fluoro-3-methyl-5-(pyrimidin-5-yl)naphthalen-2-yl)acetate NaOH →

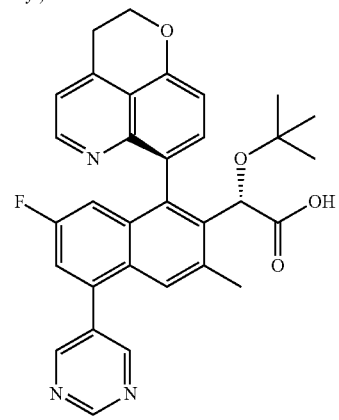

114
(S)-2-(tert-butoxy)-2-((R)-1-(2,3-dihydropyrano[4,3,2-de]quinolin-7-yl)-7-fluoro-3-methyl-5-(pyrimidin-5-yl)naphthalen-2-yl)acetic acid Preparation of (S)-ethyl 2-tert-butoxy-2-((R)-1-(2,3-dihydropyrano[4,3,2-de]quinolin-7-yl)-7-fluoro-3-methyl-5-(pyrimidin-5-yl)naphthalen-2-yl)acetate: A Smith process vial was charged with (S)-ethyl 2-tert-butoxy-2-((R)-5-chloro-1-(2,3-dihydropyrano[4,3,2-de]quinolin-7-yl)-7-fluoro-3-methylnaphthalen-2-yl)acetate (12 mg, 0.023 mmol, 1 eq.), pyrimidin-5-ylboronic acid (5 mg, 1.5 eq.), Sphos Palladacycle (3 mg, 0.1 eq.), cesium fluoride (12 mg, 3 eq.) and flushed with nitrogen. Dimethoxyethane (0.5 mL, distilled from Na/benzophenone) was added and mixture sparged with nitrogen for 10 minutes and then heated in microwave at 120° C. for 1 hour. The reaction mixture was diluted with ethyl acetate and washed with brine, dried (MgSO$_4$), filtered, concentrated and purified by flash column chromatography (silica gel, 0 to 20% ethyl acetate/hexanes) to give (S)-ethyl 2-tert-butoxy-2-((R)-1-(2,3-dihydropyrano[4,3,2-de]quinolin-7-yl)-7-fluoro-3-methyl-5-(pyrimidin-5-yl)naphthalen-2-yl)acetate (4 mg). LCMS-ESI$^+$ (m/z): [M+H]$^+$ calcd for C$_{34}$H$_{33}$FN$_3$O$_4$: 566.63; Found: 566.3.

Preparation of (S)-2-tert-butoxy-2-((R)-1-(2,3-dihydropyrano[4,3,2-de]quinolin-7-yl)-7-fluoro-3-methyl-5-(pyrimidin-5-yl)naphthalen-2-yl)acetic acid (114): A solution of (S)-ethyl 2-tert-butoxy-2-((R)-1-(2,3-dihydropyrano[4,3,2-de]quinolin-7-yl)-7-fluoro-3-methyl-5-(pyrimidin-5-yl)

naphthalen-2-yl)acetate (4 mg) and 2 M sodium hydroxide (0.5 mL) in tetrahydrofuran (0.5 mL) and ethanol (0.5 mL) was heated at 50° C. for 3 hours. The reaction mixture was diluted with ethyl acetate and washed with brine. The aqueous layer was back-extracted with ethyl acetate and the combined organic layer was dried (MgSO$_4$), filtered, concentrated and purified by reverse phase HPLC (Gemini, 5 to 100% ACN/H$_2$O+0.1% TFA). Product lyophilized to give a yellow powder (1.2 mg). $^1$H-NMR: 400 MHz, (CD$_3$OD): δ 9.23 (d, J=5.09 Hz, 1H), 8.82 (s, 1H), 7.96 (s, 1H), 8.60 (m, 1H), 7.80 (m, 1H), 7.52 (d, J=5.08 Hz, 1H), 7.32 (m, 2H), 7.19 (s, 1 H), 6.82 (m, 1 H), 5.02 (m, 1H), 4.76 (m, 2H), 3.50 (t, J=6 Hz, 2H), 2.37 (s, 3H) 0.92 (s, 9H).

$^{19}$F-NMR: 377 MHz, (CD$_3$OD) δ: −77.7 (s, 6F), −115.9 (m, 1F). LCMS-ESI$^+$ (m/z): [M+H]$^+$ calcd for C$_{32}$H$_{39}$FN$_3$O$_4$: 538.58; Found: 538.03.

EXAMPLE 113

(S)-2-tert-Butoxy-2-((R)-6-chloro-1-(2,3-dihydropyrano[4,3,2-de]quinolin-7-yl)-5-fluoro-3-methylnaphthalen-2-yl)acetic acid (115)

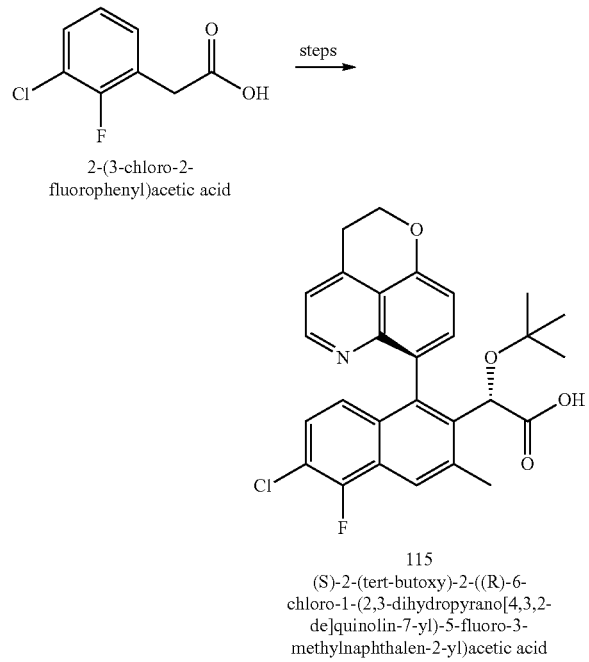

2-(3-chloro-2-fluorophenyl)acetic acid 115
(S)-2-(tert-butoxy)-2-((R)-6-chloro-1-(2,3-dihydropyrano[4,3,2-de]quinolin-7-yl)-5-fluoro-3-methylnaphthalen-2-yl)acetic acid Preparation of (S)-2-tert-butoxy-2-((R)-6-chloro-1-(2,3-dihydropyrano[4,3,2-de]quinolin-7-yl)-5-fluoro-3-methylnaphthalen-2-yl)acetic acid (115): (S)-2-tert-Butoxy-2-((R)-6-chloro-1-(2,3-dihydropyrano[4,3,2-de]quinolin-7-yl)-5-fluoro-3-methylnaphthalen-2-yl)acetic acid (115) was prepared following the procedure to make (S)-2-tert-butoxy-2-((R)-6-chloro-1-(2,3-dihydropyrano[4,3,2-de]quinolin-7-yl)-7-fluoro-3-methylnaphthalen-2-yl)acetic acid of Example 99, except 2-(3-chloro-2-fluorophenyl)acetic acid was used instead of 2-(3-chloro-4-fluorophenyl)acetic acid. $^1$H-NMR: 400 MHz, (CD$_3$OD) δ: 8.69 (d, J=5.87 Hz, 1H), 8.18 (s ,1H), 7.80 (m ,2H), 7.42 (d, J=7.72 Hz, 1H), 7.26 (t, J=7.43 Hz, 1H), 6.78 (d, J=9.38 Hz, 1H), 5.22 (s, 1H), 4.64 (m, 2H), 3.62 (t, J=5.86 Hz, 2H), 2.80 (s, 3H), 0.98 (s, 9H).

$^{19}$F-NMR: 377 MHz, (CD$_3$OD) δ: −77.7 (s, 3F), −127.87 (d, 1F). LCMS-ESI$^+$ (m/z): [M+H]$^+$ calcd for C$_{28}$H$_{26}$ClFNO$_4$: 494.95; found: 494.07.

EXAMPLE 114

(S)-2-tert-Butoxy-2-((R)-5-chloro-1-(2,3-dihydropyrano[4,3,2-de]quinolin-7-yl)-3,6-dimethylnaphthalen-2-yl)acetic acid (116)

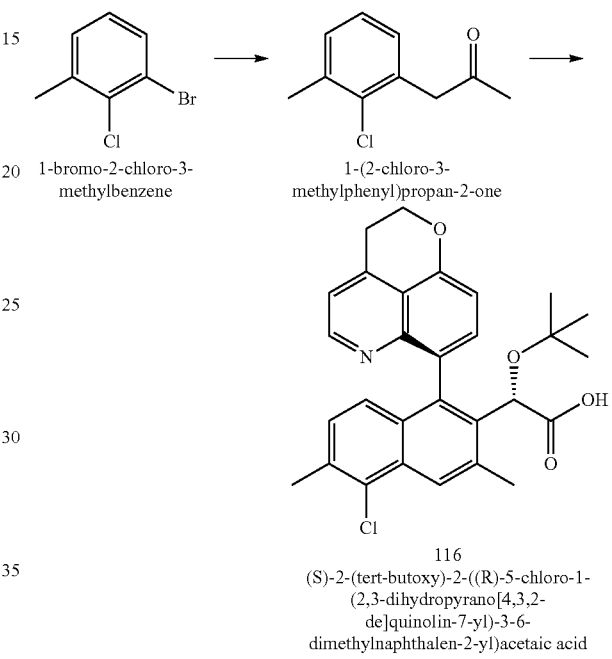

1-bromo-2-chloro-3-methylbenzene 1-(2-chloro-3-methylphenyl)propan-2-one 116
(S)-2-(tert-butoxy)-2-((R)-5-chloro-1-(2,3-dihydropyrano[4,3,2-de]quinolin-7-yl)-3-6-dimethylnaphthalen-2-yl)acetaic acid Preparation of 1-(2-chloro-3-methylphenyl)propan-2-one: A Smith process vial was charged with 1-bromo-2-chloro-3-methylbenzene (528 mg, 2.57 mmol, 1 eq.), tributylmethoxytin (1.11 mL, 1.5 eq.), 4-methylpent-4-en-2-one (0.42 mL, 1.5 eq.), PdCl$_2$ (23 mg, 5%) and tri(o-tolyl)phosphine (79 mg, 10%), toluene (1 mL) was added and mixture sparged with nitrogen for 10 minutes and then heated in oil bath at 100° C. for 5 hours. The reaction mixture was diluted with ethyl acetate and washed with brine, dried (MgSO$_4$), filtered, concentrated and purified by flash column chromatography (silica gel, 0 to 20% ethyl acetate/hexanes) to 1-(2-chloro-3-methylphenyl)propan-2-one (375 mg, 80% yield). $^1$H-NMR: 400 MHz, (CDCl$_3$) δ: 7.19-7.02 (m, 3H), 3.82 (s, 2H), 2.38 (s, 3H), 2.18 (s, 3H).

Preparation of (S)-2-tert-butoxy-2-((R)-5-chloro-1-(2,3-dihydropyrano[4,3,2-de]quinolin-7-yl)-3,6-dimethylnaphthalen-2-yl)acetic acid (116): (S)-2-tert-butoxy-2-((R)-5-chloro-1-(2,3-dihydropyrano[4,3,2-de]quinolin-7-yl)-3,6-dimethylnaphthalen-2-yl)acetic acid (116) was prepared following the procedure to make (S)-2-tert-butoxy-2-((R)-6-chloro-1-(2,3-dihydropyrano[4,3,2-de]quinolin-7-yl)-7-fluoro-3-methylnaphthalen-2-yl)acetic acid, used 1-bromo-2-chloro-3-methylbenzene instead of 2-(3-chloro-4-fluorophenyl)acetic acid. $^1$H-NMR: 400 MHz, (CD$_3$OD) δ: 8.59 (d, J=5.08 Hz, 1H), 8.26 (s ,1H), 7.68 (m ,2H), 7.34 (d, J=8.21 Hz, 1H), 7.08 (d, J=8.60 Hz, 1H), 6.72 (d, J=8.50 Hz, 1H), 5.16(s, 1H), 4.62 (m, 2H), 3.56 (t, J=6.26 Hz, 2H), 2.72(s, 3H), 2.42(s, 3H), 0.92 (s, 9H). LCMS-ESI+ (m/z): [M+H]+ calcd for $C_{29}H_{29}ClNO_4$: 490.99; found: 490.33.

EXAMPLE 115

(S)-2-tert-Butoxy-2-((R)-1-(2,3-dihydropyrano[4,3,2-de]quinolin-7-yl)-3,5,6-trimethylnaphthalen-2-yl)acetic acid (117)

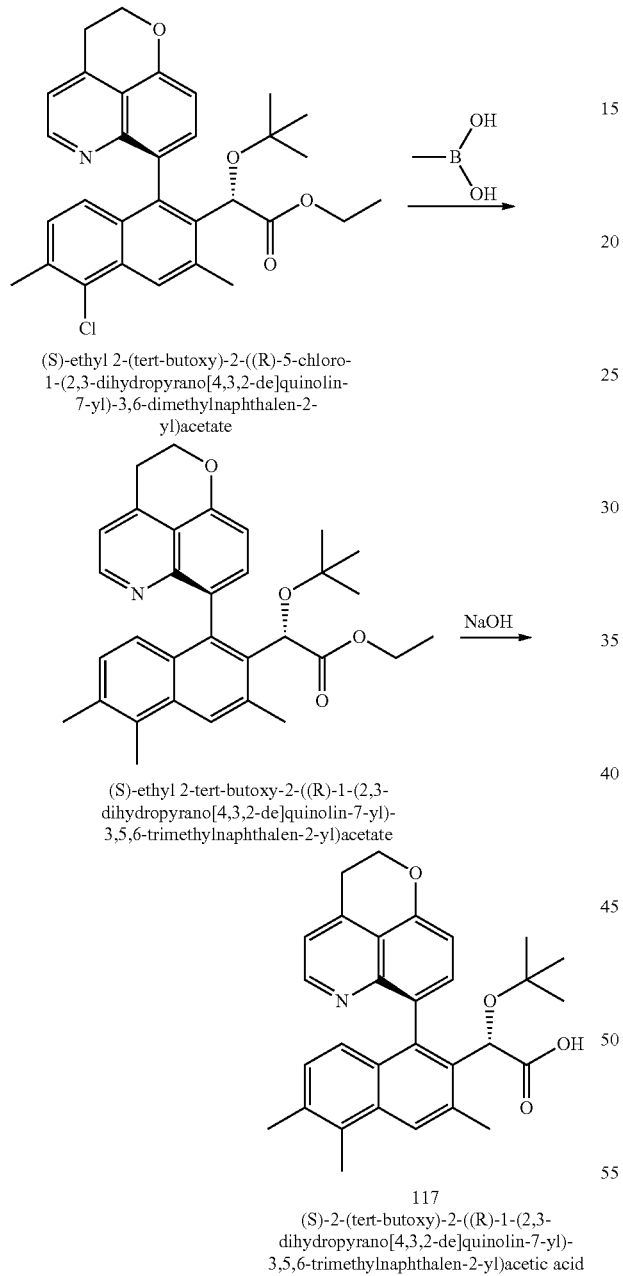

(S)-ethyl 2-(tert-butoxy)-2-((R)-5-chloro-1-(2,3-dihydropyrano[4,3,2-de]quinolin-7-yl)-3,6-dimethylnaphthalen-2-yl)acetate (S)-ethyl 2-tert-butoxy-2-((R)-1-(2,3-dihydropyrano[4,3,2-de]quinolin-7-yl)-3,5,6-trimethylnaphthalen-2-yl)acetate 117
(S)-2-(tert-butoxy)-2-((R)-1-(2,3-dihydropyrano[4,3,2-de]quinolin-7-yl)-3,5,6-trimethylnaphthalen-2-yl)acetic acid Preparation (S)-ethyl 2-tert-butoxy-2-((R)-1-(2,3-dihydropyrano[4,3,2-de]quinolin-7-yl)-3,5,6-trimethylnaphthalen-2-yl)acetate: A Smith process vial was charged with (S)-ethyl 2-tert-butoxy-2-((R)-5-chloro-1-(2,3-dihydropyrano[4,3,2-de]quinolin-7-yl)-3,6-dimethylnaphthalen-2-yl)acetate (16 mg, 0.031 mmol, 1 eq.), methylboronic acid (4 mg, 2 eq.), Sphos Palladacycle (2 mg, 0.1 eq.), cesium fluoride (19 mg, 4 eq.) and flushed with nitrogen. Dimethoxyethane (0.5 mL, distilled from Na/benzophenone) was added and mixture sparged with nitrogen for 10 minutes and then heated in microwave at 120° C. for 1 hour. The reaction mixture was diluted with ethyl acetate and washed with brine, dried (MgSO$_4$), filtered, concentrated and purified by flash column chromatography (silica gel, 0 to 20% ethyl acetate/hexanes) to give (S)-ethyl 2-tert-butoxy-2-((R)-1-(2,3-dihydropyrano[4,3,2-de]quinolin-7-yl)-3,5,6-trimethylnaphthalen-2-yl)acetate (7 mg). LCMS-ESI+ (m/z): [M+H]+ calcd for $C_{32}H_{36}NO_4$: 498.62; found: 498.1.

Preparation of (S)-2-tert-butoxy-2-((R)-1-(2,3-dihydropyrano[4,3,2-de]quinolin-7-yl)-3,5,6-trimethylnaphthalen-2-yl)acetic acid (117): A solution of (S)-ethyl 2-tert-butoxy-2-((R)-1-(2,3-dihydropyrano[4,3,2-de]quinolin-7-yl)-3,5,6-trimethylnaphthalen-2-yl)acetate (7 mg) and 2 M sodium hydroxide (0.5 mL) in tetrahydrofuran (0.5 mL) and ethanol (0.5 mL) was heated at 50° C. for 3 hours. The reaction mixture was diluted with ethyl acetate and washed with brine. The aqueous layer was back-extracted with ethyl acetate and the combined organic layer was dried (MgSO$_4$), filtered, concentrated and purified by reverse phase HPLC (Gemini, 5 to 100% ACN/H$_2$O+0.1% TFA). Product lyophilized to give a yellow powder (4.7 mg). $^1$H-NMR: 400 MHz, (CD$_3$OD): δ 8.64 (d, J=5.86 Hz, 1H), 8.15 (s, 1H), 7.76 (t, J=8.90 Hz, 2H), 7.43 (d, J=8.99 Hz, 1H), 7.07 (d, J=8.99 Hz, 1H), 6.65 (d, J=8.60 Hz, 1H), 5.21 (s, 1H), 4.70 (m, 2H), 3.64 (t, J=7.77 Hz, 2H), 2.79 (s, 3H), 2.67 (s, 3H), 2.43 (s, 3H), 0.92 (s, 9H). LCMS-ESI+ (m/z): [M+H]+ calcd for $C_{30}H_{32}NO_4$: 470.57; Found: 470.39.

EXAMPLE 116

(S)-2-tert-Butoxy-2-((R)-5-cyano-1-(2,3-dihydropyrano[4,3,2-de]quinolin-7-yl)-3,6-dimethylnaphthalen-2-yl)acetic acid (118)

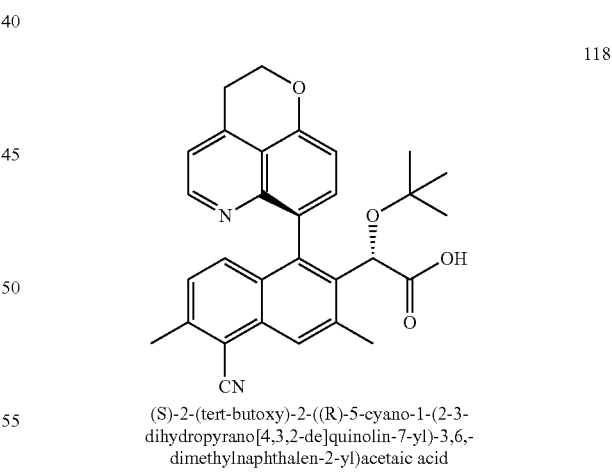

118

(S)-2-(tert-butoxy)-2-((R)-5-cyano-1-(2-3-dihydropyrano[4,3,2-de]quinolin-7-yl)-3,6,-dimethylnaphthalen-2-yl)acetaic acid Preparation of (S)-2-tert-butoxy-2-((R)-5-cyano-1-(2,3-dihydropyrano[4,3,2-de]quinolin-7-yl)-3,6-dimethylnaphthalen-2-yl)acetic acid (118): (S)-2-tert-butoxy-2-((R)-5-cyano-1-(2,3-dihydropyrano[4,3,2-de]quinolin-7-yl)-3,6-dimethylnaphthalen-2-yl)acetic acid (118) was prepared following the procedure to make (S)-2-tert-butoxy-2-((R)-1-(2,3-dihydropyrano[4,3,2-de]quinolin-7-yl)-3,5,6-trimethylnaphthalen-2-yl)acetic acid of Example 115, except used Zn(CN)$_2$ was used instead of methylboronic acid, and DMF was used instead of DME. Analytical HPLC (Gemini, 2-98% ACN/H$_2$O+0.05% TFA, 7 minutes run): t$_R$ (min)=4.00.

$^1$H-NMR: 400 MHz, (CD$_3$OD) δ: 8.59 (d, J=5.48 Hz, 1H), 8.09 (s, 1H), 7.64 (d, J=8.21 Hz, 1H), 7.62 (d, J=4.08 Hz, 1H), 7.36 (d, J=8.21 Hz, 1H), 7.19 (d, J=8.61 Hz, 1H), 7.12 (d, J=8.98 Hz, 1H), 5.16 (s, 1H), 4.62 (m, 2H), 3.56 (t, J=5.86 Hz, 2H), 2.72 (s, 3H), 2.62 (s, 3H), 0.92 (s, 9H). LCMS-ESI$^+$ (m/z): [M+H]$^+$ calcd for C$_{30}$H$_{29}$N$_4$O$_4$: 481.55; found: 481.32.

EXAMPLE 117

(S)-2-tert-Butoxy-2-((R)-1-(2,3-dihydropyrano[4,3,2-de]quinolin-7-yl)-5-fluoro-3,6-dimethylnaphthalen-2-yl)acetic acid (119)

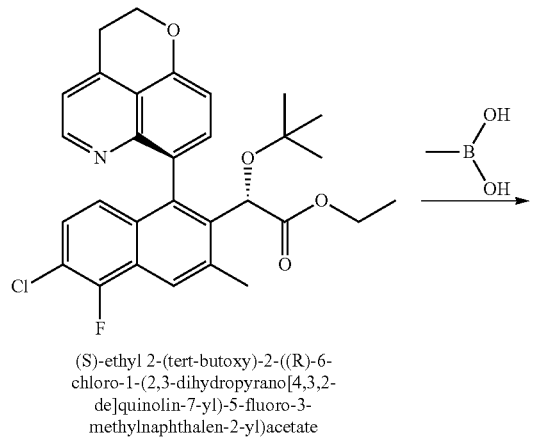

(S)-ethyl 2-(tert-butoxy)-2-((R)-6-chloro-1-(2,3-dihydropyrano[4,3,2-de]quinolin-7-yl)-5-fluoro-3-methylnaphthalen-2-yl)acetate

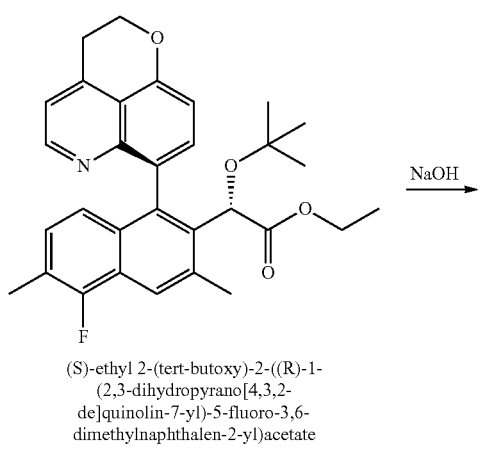

(S)-ethyl 2-(tert-butoxy)-2-((R)-1-(2,3-dihydropyrano[4,3,2-de]quinolin-7-yl)-5-fluoro-3,6-dimethylnaphthalen-2-yl)acetate

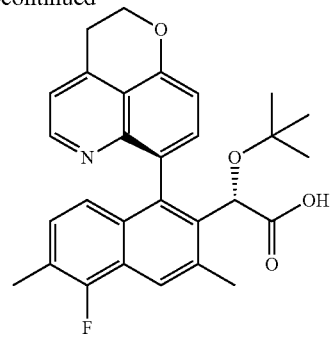

119
(S)-2-(tert-butoxy)-2-((R)-1-(2,3-dihydropyrano[4,3,2-de]quinolin-7-yl)-5-fluoro-3,6-dimethylnaphthalen-2-yl)acetic acid Preparation (S)-ethyl 2-tert-butoxy-2-((R)-1-(2,3-dihydropyrano[4,3,2-de]quinolin-7-yl)-5-fluoro-3,6-dimethylnaphthalen-2-yl)acetate: A Smith process vial was charged with (S)-ethyl 2-tert-butoxy-2-((R)-6-chloro-1-(2,3-dihydropyrano[4,3,2-de]quinolin-7-yl)-5-fluoro-3-methylnaphthalen-2-yl)acetate (10 mg, 0.019 mmol, 1 eq.), methylboronic acid (2 mg, 1.5 eq.), Sphos Palladacycle (1.3 mg, 0.1 eq.), cesium fluoride (14 mg, 4 eq.) and flushed with nitrogen. Dimethoxyethane (0.5 mL, distilled from Na/benzophenone) was added and mixture sparged with nitrogen for 10 minutes and then heated in microwave at 120° C. for 1 hour. The reaction mixture was diluted with ethyl acetate and washed with brine, dried (MgSO$_4$), filtered, concentrated and purified by flash column chromatography (silica gel, 0 to 20% ethyl acetate/hexanes) to give (S)-ethyl 2-tert-butoxy-2-((R)-1-(2,3-dihydropyrano[4,3,2-de]quinolin-7-yl)-5-fluoro-3,6-dimethylnaphthalen-2-yl)acetate (6 mg). LCMS-ESI$^+$ (m/z): [M+H]$^+$ calcd for C$_{31}$H$_{33}$FNO$_4$: 502.59; Found: 502.1.

Preparation of (S)-2-tert-butoxy-2-((R)-1-(2,3-dihydropyrano[4,3,2-de]quinolin-7-yl)-5-fluoro-3,6-dimethylnaphthalen-2-yl)acetic acid (119): A solution of (S)-ethyl 2-tert-butoxy-2-((R)-1-(2,3-dihydropyrano[4,3,2-de]quinolin-7-yl)-5-fluoro-3,6-dimethylnaphthalen-2-yl)acetate (6 mg) and 2 M sodium hydroxide (0.5 mL) in tetrahydrofuran (0.5 mL) and ethanol (0.5 mL) was heated at 50° C. for overnight. The reaction mixture was diluted with ethyl acetate and washed with brine. The aqueous layer was back-extracted with ethyl acetate and the combined organic layer was dried (MgSO$_4$), filtered, concentrated and purified by reverse phase HPLC (Gemini, 5 to 100% ACN/H$_2$O+0.1% TFA). Product lyophilized to give a yellow powder (4.7 mg). $^1$H-NMR: 400 MHz, (CD$_3$OD): δ 8.67 (d, J=5.47 Hz, 1H), 8.12 (s, 1H), 7.78 (t, J=5.87 Hz, 2H), 7.43 (d, J=8.82 Hz, 1H), 7.11 (t, J=8.21 Hz, 1H), 6.63 (d, J=8.60 Hz, 1H), 5.22 (s, 1H), 4.70 (m, 2H), 3.64 (t, J=5.86 Hz, 2H), 2.79 (s, 3H), 2.38 (d, J=1.47 Hz, 3H), 0.92 (s, 9H). $^{19}$F-NMR: 377 MHz, (CD$_3$OD) δ: −77.7 (s, 3F), −131.6 (d, 1F). LCMS-ESI$^+$ (m/z): [M+H]$^+$ calcd for C$_{29}$H$_{29}$FNO$_4$: 474.54; found: 474.33.

EXAMPLE 118

(S)-2-tert-Butoxy-2-((R)-1-(2,3-dihydropyrano[4,3,2-de]quinolin-7-yl)-6-ethyl-5-fluoro-3-methylnaphthalen-2-yl)acetic acid (120)

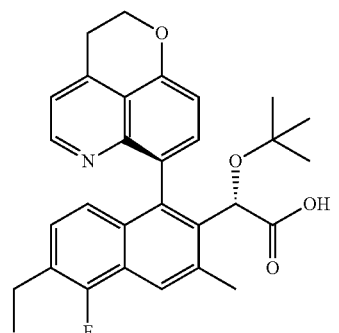

(S)-2-(tert-butoxy)-2-((R)-1-(2-3-dihydropyrano[4,3,2-de]quinolin-7-yl)-6-ethyl-5-fluoro-3-methylnaphthalen-2-yl)acetaic acid Preparation of (S)-2-tert-butoxy-2-((R)-1-(2,3-dihydropyrano[4,3,2-de]quinolin-7-yl)-6-ethyl-5-fluoro-3-methylnaphthalen-2-yl)acetic acid (120): (S)-2-tert-Butoxy-2-((R)-1-(2,3-dihydropyrano[4,3,2-de]quinolin-7-yl)-6-ethyl-5-fluoro-3-methylnaphthalen-2-yl)acetic acid (120) was prepared following the procedure to make (S)-2-tert-butoxy-2-((R)-1-(2,3-dihydropyrano[4,3,2-de]quinolin-7-yl)-5-fluoro-3,6-dimethylnaphthalen-2-yl)acetic acid of Example 117, except that ethylboronic acid was used instead of methylboronic acid. Analytical HPLC (Gemini, 2-98% ACN/H$_2$O+0.05% TFA, 7 minutes run): t$_R$ (min)=4.00.

$^1$H-NMR: 400 MHz, (CD$_3$OD): δ 8.67 (d, J=5.47 Hz, 1H), 8.14 (s, 1H), 7.81 (t, J=8.21 Hz, 2H), 7.46 (d, J=8.21 Hz, 1H), 7.16 (t, J=8.23 Hz, 1H), 6.67 (d, J=9.0 Hz, 1H), 5.22 (s, 1H), 4.71 (m, 2H), 3.66 (t, J=5.86 Hz, 2H), 2.79 (m, s, 5H), 1.23 (t, J=7.82 Hz, 3H), 0.93 (s, 9H). $^{19}$F-NMR: 377 MHz, (CD$_3$OD) δ: −77.7 (s, 3F), −133.06 (d, 1F). LCMS-ESI$^+$ (m/z): [M+H]$^+$ calcd for C$_{30}$H$_{31}$FNO$_4$: 488.56 (M+H$^+$); Found: 488.37.

EXAMPLE 119

(S)-2-tert-Butoxy-2-((R)-6-(difluoromethyl)-1-(2,3-dihydropyrano[4,3,2-de]quinolin-7-yl)-5-fluoro-3-methylnaphthalen-2-yl)acetic acid (121)

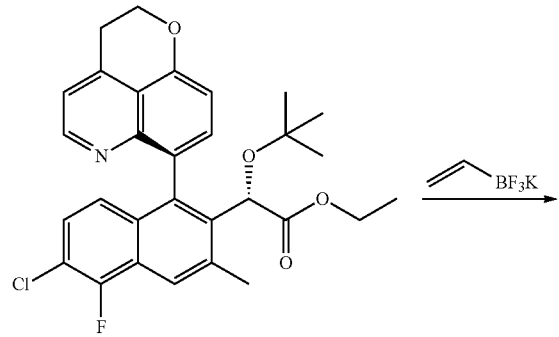

(S)-ethyl 2-(tert-butoxy)-2-((R)-6-chloro-1-(2,3-dihydropyrano[4,3,2-de]quinolin-7-yl)-5-fluoro-3-methylnaphthalen-2-yl)acetate

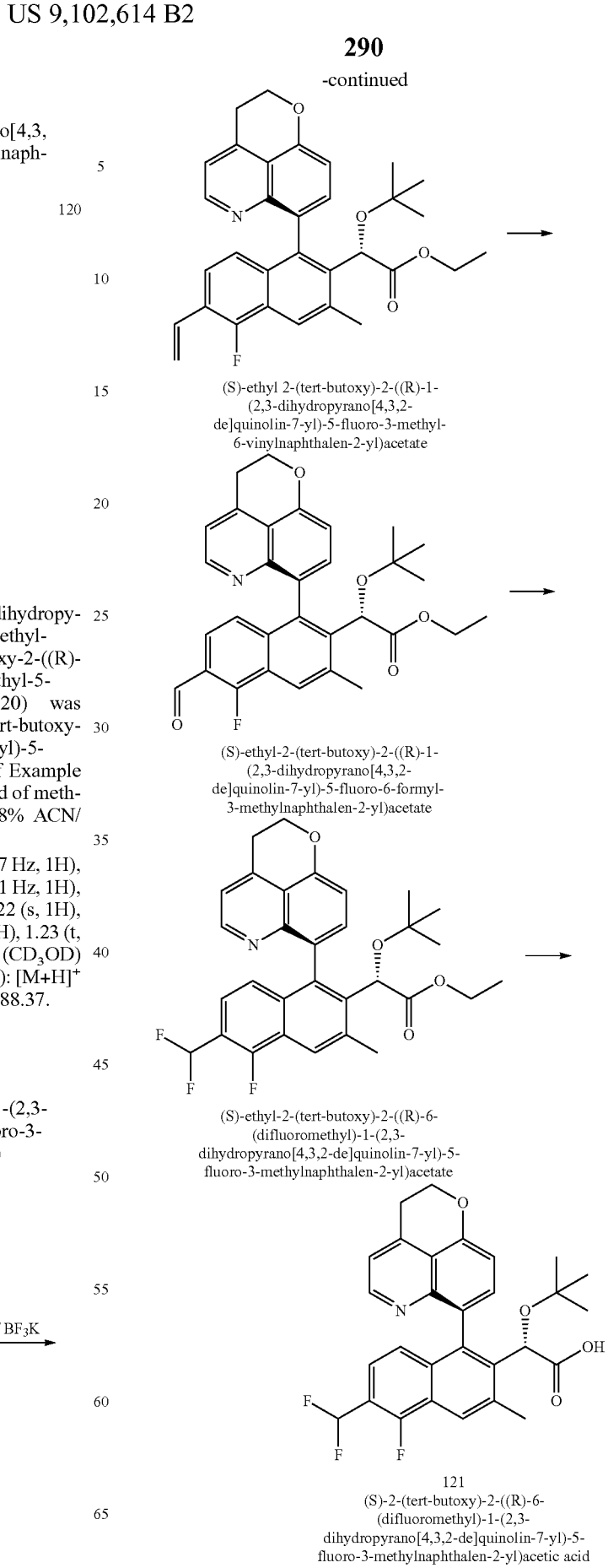

(S)-ethyl 2-(tert-butoxy)-2-((R)-1-(2,3-dihydropyrano[4,3,2-de]quinolin-7-yl)-5-fluoro-3-methyl-6-vinylnaphthalen-2-yl)acetate (S)-ethyl-2-(tert-butoxy)-2-((R)-1-(2,3-dihydropyrano[4,3,2-de]quinolin-7-yl)-5-fluoro-6-formyl-3-methylnaphthalen-2-yl)acetate (S)-ethyl-2-(tert-butoxy)-2-((R)-6-(difluoromethyl)-1-(2,3-dihydropyrano[4,3,2-de]quinolin-7-yl)-5-fluoro-3-methylnaphthalen-2-yl)acetate 121
(S)-2-(tert-butoxy)-2-((R)-6-(difluoromethyl)-1-(2,3-dihydropyrano[4,3,2-de]quinolin-7-yl)-5-fluoro-3-methylnaphthalen-2-yl)acetic acid Preparation (S)-ethyl 2-tert-butoxy-2-((R)-1-(2,3-dihydropyrano[4,3,2-de]quinolin-7-yl)-5-fluoro-3-methyl-6-vinylnaphthalen-2-yl)acetate: A Smith process vial was charged with (S)-ethyl 2-tert-butoxy-2-((R)-6-chloro-1-(2,3-dihydropyrano[4,3,2-de]quinolin-7-yl)-5-fluoro-3-methylnaphthalen-2-yl)acetate (99 mg, 0.19 mmol, 1 eq.), potassium vinyltrifluoroborate (28 mg, 1.1 eq.), Sphos Palladacycle (13 mg, 0.1 eq.), cesium fluoride (114 mg, 4 eq.) and flushed with nitrogen. Dimethoxyethane (2 mL, distilled from Na/benzophenone) was added and mixture sparged with nitrogen for 10 minutes and then heated in microwave at 110° C. for 1 hour. The reaction mixture was diluted with ethyl acetate and washed with brine, dried (MgSO$_4$), filtered, concentrated and purified by flash column chromatography (silica gel, 0 to 20% ethyl acetate/hexanes) to give (S)-ethyl 2-tert-butoxy-2-((R)-1-(2,3-dihydropyrano[4,3,2-de]quinolin-7-yl)-5-fluoro-3-methyl-6-vinylnaphthalen-2-yl)acetate (69 mg, 71% yield). LCMS-ESI$^+$ (m/z): [M+H]$^+$ calcd for C$_{32}$H$_{33}$FNO$_4$: 514.60; Found: 514.1.

Preparation (S)-ethyl 2-tert-butoxy-2-((R)-1-(2,3-dihydropyrano[4,3,2-de]quinolin-7-yl)-5-fluoro-6-formyl-3-methylnaphthalen-2-yl)acetate: (S)-ethyl 2-tert-butoxy-2-((R)-1-(2,3-dihydropyrano[4,3,2-de]quinolin-7-yl)-5-fluoro-3-methyl-6-vinylnaphthalen-2-yl)acetate (32 mg, 0.062 mmol, 1 eq.) was dissolved in 2 mL THF. This solution was added to the mixture of NaIO$_4$ (40 mg, 3 eq.) and K$_2$OsO$_4$.2H$_2$O (2.3 mg, 0.1 eq.) in 1 mL water at room temperature. The reaction was complete after stirring at room temperature for 30 minutes. The reaction mixture was filtered, the filtrate was diluted with ethyl acetate and washed with brine, dried (MgSO$_4$), filtered, concentrated and purified by flash column chromatography (silica gel, 0 to 20% ethyl acetate/hexanes) to give (S)-ethyl 2-tert-butoxy-2-((R)-1-(2,3-dihydropyrano[4,3,2-de]quinolin-7-yl)-5-fluoro-6-formyl-3-methylnaphthalen-2-yl)acetate as a light yellow oil (26 mg, 81% yield). LCMS-ESI$^+$ (m/z): [M+H]$^+$ calcd for C$_{31}$H$_{31}$FNO$_5$: 516.57; Found: 516.1.

Preparation (S)-ethyl 2-tert-butoxy-2-((R)-6-(difluoromethyl)-1-(2,3-dihydropyrano[4,3,2-de]quinolin-7-yl)-5-fluoro-3-methylnaphthalen-2-yl)acetate: (S)-ethyl 2-tert-butoxy-2-((R)-1-(2,3-dihydropyrano[4,3,2-de]quinolin-7-yl)-5-fluoro-6-formyl-3-methylnaphthalen-2-yl)acetate (8 mg) was dissolved in 0.5 mL DCM. Deoxofluor (50 μL, excess) was added to the solution. The reaction was stirred at room temperature for 1 hour. The reaction mixture was diluted with ethyl acetate and washed with brine, dried (MgSO$_4$), filtered, concentrated and purified by flash column chromatography (silica gel, 0 to 20% ethyl acetate/hexanes) to give (S)-ethyl 2-tert-butoxy-2-((R)-6-(difluoromethyl)-1-(2,3-dihydropyrano[4,3,2-de]quinolin-7-yl)-5-fluoro-3-methylnaphthalen-2-yl)acetate as a light yellow oil (6 mg, 76% yield). LCMS-ESI$^+$ (m/z): [M+H]$^+$ calcd for C$_{31}$H$_{31}$F$_3$NO$_5$: 538.57; Found: 538.34.

Preparation of (S)-2-tert-butoxy-2-((R)-6-(difluoromethyl)-1-(2,3-dihydropyrano[4,3,2-de]quinolin-7-yl)-5-fluoro-3-methylnaphthalen-2-yl)acetic acid (121): A solution of(S)-ethyl 2-tert-butoxy-2-((R)-6-(difluoromethyl)-1-(2,3-dihydropyrano[4,3,2-de]quinolin-7-yl)-5-fluoro-3-methylnaphthalen-2-yl)acetate (6 mg) in tetrahydrofuran (0.5 mL) and ethanol (0.5 mL) and 2 M sodium hydroxide (0.5 mL) was heated at 50° C. for 2 hours. The reaction mixture was diluted with ethyl acetate and washed with brine. The aqueous layer was back-extracted with ethyl acetate and the combined organic layer was dried (MgSO$_4$), filtered, concentrated and purified by reverse phase HPLC (Gemini, 5 to 100% ACN/H$_2$O+0.1% TFA). Product lyophilized to give a yellow powder (4.7 mg). $^1$H-NMR: 400 MHz, (CD$_3$OD): δ 8.69 (d, J=5.48 Hz, 1H), 8.26 (s, 1H), 7.84 (d, J=8.22 Hz, 1H), 7.80 (d, J=5.87 Hz, 1H), 7.43 (m, 2H), 7.34, 7.21, 7.07 (t, J=54.74 Hz, 1H), 6.90 (d, J=9.38 Hz, 1H), 5.25 (s, 1H), 4.73 (m, 2H), 3.64 (t, J=5.86 Hz, 2H), 2.83 (s, 3H), 0.93 (s, 9H). $^{19}$F-NMR: 377 MHz, (CD$_3$OD) δ: −77.7 (s, 3F), −113.97 to −116.29 (m, 2F), −131.6 (s, 1F). LCMS-ESI$^+$ (m/z): [M+H]$^+$ calcd for C$_{29}$H$_{27}$F$_3$NO$_4$: 510.52; Found: 510.36.

EXAMPLE 120

(2S)-2-tert-butoxy-2-(1-(2,3-dihydropyrano[4,3,2-de]quinolin-7-yl)-4-fluoro-3-methylnaphthalen-2-yl) acetic acid (122)

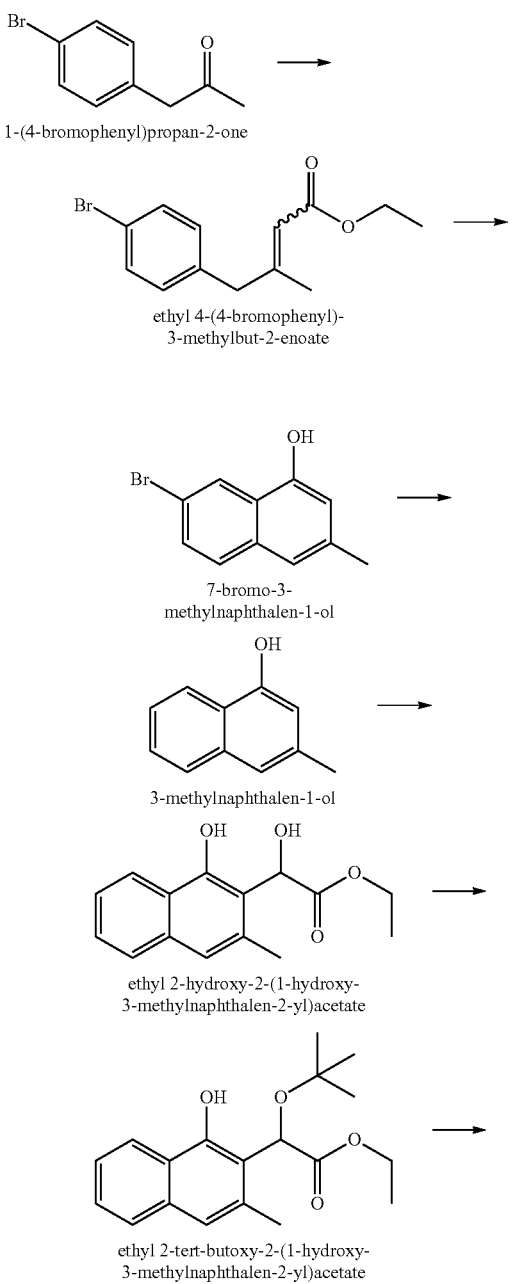

1-(4-bromophenyl)propan-2-one ethyl 4-(4-bromophenyl)-3-methylbut-2-enoate 7-bromo-3-methylnaphthalen-1-ol 3-methylnaphthalen-1-ol ethyl 2-hydroxy-2-(1-hydroxy-3-methylnaphthalen-2-yl)acetate ethyl 2-tert-butoxy-2-(1-hydroxy-3-methylnaphthalen-2-yl)acetate

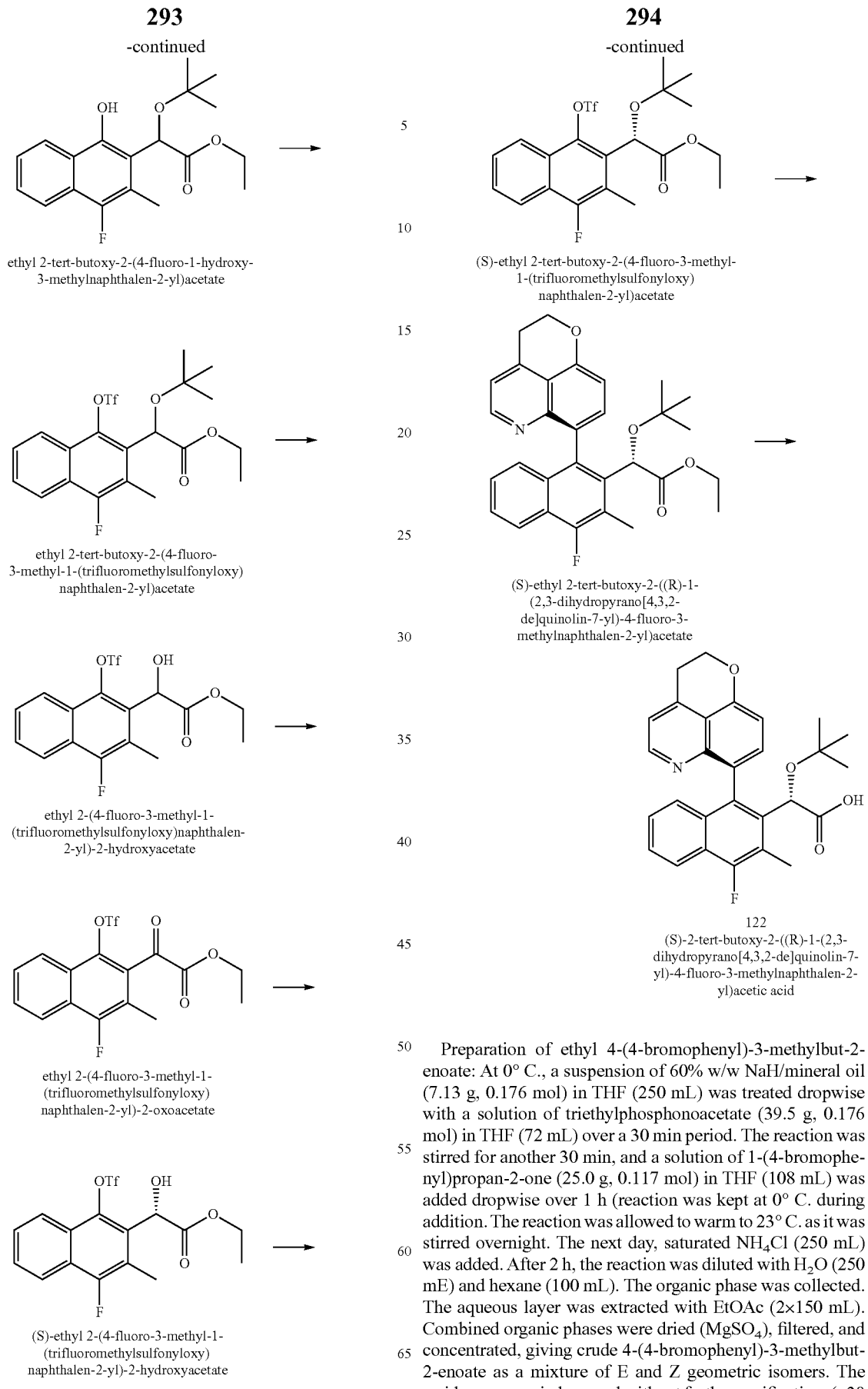

Preparation of ethyl 4-(4-bromophenyl)-3-methylbut-2-enoate: At 0° C., a suspension of 60% w/w NaH/mineral oil (7.13 g, 0.176 mol) in THF (250 mL) was treated dropwise with a solution of triethylphosphonoacetate (39.5 g, 0.176 mol) in THF (72 mL) over a 30 min period. The reaction was stirred for another 30 min, and a solution of 1-(4-bromophenyl)propan-2-one (25.0 g, 0.117 mol) in THF (108 mL) was added dropwise over 1 h (reaction was kept at 0° C. during addition. The reaction was allowed to warm to 23° C. as it was stirred overnight. The next day, saturated NH₄Cl (250 mL) was added. After 2 h, the reaction was diluted with H₂O (250 mE) and hexane (100 mL). The organic phase was collected. The aqueous layer was extracted with EtOAc (2×150 mL). Combined organic phases were dried (MgSO₄), filtered, and concentrated, giving crude 4-(4-bromophenyl)-3-methylbut-2-enoate as a mixture of E and Z geometric isomers. The residue was carried onward without further purification. (~30 grams; yield was not determined). The ¹H NMR reported below was from a crude mixture containing both the E and Z isomer.

¹H NMR (400 MHz, CDCl₃) δ 7.43 (d, J=8.6 Hz, 1.6H), 7.39 (d, J=8.6 Hz, 0.4H), 7.12 (d, J=8.2 Hz, 0.4H), 7.04 (d, J=8.2 Hz, 1.6H), 4.42-4.21 (m, 2H), 3.96 (s, 0.4H), 3.38 (s, 1.6H), 2.10 (s, 2.4H), 1.77 (s, 0.6H), 1.37-1.23 (m, 3H).

Preparation of 7-bromo-3-methylnaphthalen-1-ol: A flask containing the crude ethyl 4-(4-bromophenyl)-3-methylbut-2-enoate from above (~30 grams) was treated with concentrated H₂SO₄ (120 mL) and warmed to 50° C. for 2.5 h. The reaction was poured onto ~500 mL of crushed ice. Once the ice had thawed, the brown suspension was extracted with two portions of EtOAc (500 mL and 100 mL, respectively). The two extracts were combined, washed with saturated NaHCO₃, dried (MgSO₄), filtered, and concentrated to ~55 mL. The residue was treated with DCM and wet-loaded onto a silica gel column and purified by flash chromatography (ethyl acetate/hexanes) giving the desired product (16.6 g, 60% yield over 2 steps from 1-(4-bromophenyl)propan-2-one. ¹H NMR (400 MHz, CDCl₃) δ 8.29 (d, J=1.9 Hz, 1H), 7.57 (d, J=8.6 Hz, 1H), 7.50 (dd, J=8.6, 2.0 Hz, 1H), 7.17 (s, 1H), 6.67 (s, 1H), 2.42 (s, 3H).

Preparation of 3-methylnaphthalen-1-ol: A slurry of 7-bromo-3-methylnaphthalen-1-ol (100 mg, 0.421 mmol), 10% w/w Pd/C (45 mg, 42.1 μmol Pd), and absolute EtOH (2.0 mL) was purged under vacuum and backfilled with H₂ from a balloon several times. The suspension was stirred under a balloon of H₂ at 23° C. overnight. The reaction was filtered over Celite, the cake was washed with EtOAc. The filtrate was concentrated and dissolved in DCM. The solution was wet-loaded onto a 12 g "gold" ISCO silica gel column and purified by flash chromatography (ethyl acetate/hexanes) giving the desired product (yield was not found). ¹H NMR (400 MHz, CDCl₃) δ 8.10 (d, J=7.8 Hz, 1H), 7.72 (d, J=7.8 Hz, 1H), 7.47-7.39 (m, 2H), 7.22 (s, 1H), 6.67 (s, 1H), 2.45 (s, 3H).

Preparation of ethyl 2-hydroxy-2-(1-hydroxy-3-methylnaphthalen-2-yl)acetate: A flask containing DCM (5.0 mL) was charged with TiCl₄ (1.0 M in DCM, 3.16 mL, 3.16 mmol). After cooling to −40° C. (dry ice/CH₃CN bath), a solution of 3-methylnaphthalen-1-ol (500 mg, 3.16 mmol) in DCM (5.0 mL) was added dropwise over a 5 min period. The reaction turned deep violet. After 30 min, a solution of ethyl glyoxylate (323 mg, 3.16 mmol, distilled freshly from P₂O₅under N₂ from the 50% w/w toluene solution of ethyl glyoxylate) in DCM (2.0 mL) was added quickly. The reaction was warmed to 0° C. After 1 h, glacial AcOH (1.0 mL) was added. 5 min later, CH₃CN (5.0 mL) was introduced, followed by H₂O (10 mL). The reaction transitioned from violet to yellow-orange. The reaction was warmed to 23° C. and stirred for 30 min. The reaction was diluted with H₂O (15 mL) and extracted with DCM (3×20 mL). The combined extracts were washed with saturated NaHCO₃ (20 mL) (this decolorized the organic phase from orange to yellow), dried (Na₂SO₄), filtered, concentrated, treated with DCM (10 mL), and concentrated again. The residue was dissolved in DCM and loaded onto a 24 g "gold" ISCO silica gel column and purified by flash chromatography (ethyl acetate/hexanes) giving the desired product (622 mg, 76% yield). ¹H NMR (400 MHz, CDCl₃) δ 8.41 (s, 1H), 8.20 (d, J=8.2 Hz, 1H), 7.67 (d, J=8.8 Hz, 1H), 7.46 (dd, J=8.8, 8.0 Hz, 1H), 7.40 (dd, J=8.2, 8.0, Hz, 1H), 7.20 (s, 1H), 5.68 (s, 1H), 4.31-4.08 (m, 2H), 3.94 (s, broad, 1H), 2.52 (s, 3H), 1.18 (t, J=7.0 Hz, 3H).

Preparation of ethyl 2-tert-butoxy-2-(1-hydroxy-3-methylnaphthalen-2-yl)acetate: A solution of ethyl 2-hydroxy-2-(1-hydroxy-3-methylnaphthalen-2-yl)acetate (622 mg, 2.39 mmol) in tert-butyl acetate (12 mL) was treated with 70% HClO₄ (20 μL) at 23° C.). After 3 h, the reaction was added slowly over 5 min to saturated NaHCO₃ (25 mL). The resulting system was extracted with DCM (3×15 mL). The combined organic layers were dried (Na₂SO₄), filtered, and concentrated. Hexane (10 mL) was added, and the mixture was concentrated again. The residue was dissolved in benzene. The solution was wet-loaded onto a 24 g "gold" ISCO silica gel column and purified by flash chromatography (hexane→ethyl acetate) giving the desired product (286 mg, 38% yield). ¹H NMR (400 MHz, CDCl₃) δ 9.00 (s, 1H), 8.26 (d, J=8.2 Hz, 1H), 7.65 (d, J=8.8 Hz, 1H), 7.44 (dd, J=8.2, 8.0 Hz, 1H), 7/39 (dd, J=8.8, 8.0 Hz, 1H), 7.17 (s, 1H), 5.52 (s, 1H), 4.25-4.06 (m, 2H), 2.59 (s, 3H), 1.33 (s, 9H), 1.20 (t, J=7.0 Hz, 3H).

Preparation of ethyl 2-tert-butoxy-2-(4-fluoro-1-hydroxy-3-methylnaphthalen-2-yl)acetate: A solution of ethyl 2-tert-butoxy-2-(1-hydroxy-3-methylnaphthalen-2-yl)acetate (1.50 g, 4.74 mmol) in CH₃CN (37.5 mL) was cooled to 0° C. Selectfluor (1.70 g, 4.74 mmol) was added, and the reaction was allowed to warm to 23° C. After 2 h, the reaction was added slowly to a mixture of saturated Na₂HPO₄ (70 mL) and H₂O (30 mL) at 23° C. More H₂O (40 mL) was added, and the system was extracted with DCM (3×40 mL). The combined organic phases were treated with hexane (20 mL). The phase that separated was removed. The remaining organic phase was dried (Na₂SO₄), filtered, and concentrated. The filtrate was concentrated and dissolved in benzene. The solution was wet-loaded onto a 24 g "gold" ISCO silica gel column and purified by flash chromatography (ethyl acetate/hexanes) giving the desired product (1.26 g, 79%). ¹H NMR (400 MHz, CDCl₃) δ 8.83 (s, 1H), 8.23 (d, J=8.2 Hz, 1H), 7.93 (d, J=8.4 Hz, 1H), 7.51 (dd, J=6.9, 6.9 Hz, 1H), 7.45 (dd, J=6.9, 6.9 Hz, 1H), 5.46 (s, 1H), 4.23-4.14 (m, 2H), 2.49 (d, $J_{HF}$=3.2 Hz, 3H), 1.31 (s, 9H), 1.20 (t, J=7.1 Hz, 3H). ¹⁹F NMR (377 MHz, CDCl₃) δ−137.3 (app. s).

Preparation of ethyl 2-tert-butoxy-2-(4-fluoro-3-methyl-1-(trifluoromethylsulfonyloxy)naphthalen-2-yl)acetate: A flask was charged with Cs₂CO₃ (2.45 g, 7.53 mmol) and N-phenyltriflimide (2.69 g, 7.53 mmol). A solution of ethyl 2-tert-butoxy-2-(4-fluoro-1-hydroxy-3-methylnaphthalen-2-yl)acetate (1.26 g, 3.76 mmol) in THF (38 mL) was added at 23° C. After 30 min, the reaction was added slowly to a pre-stirred mixture of 2 M NaHSO₄ (30 mL) and saturated Na₂HPO₄ (100 mL) at 23° C. The system was extracted with a mixture of ethyl acetate/hexane (10:1)(3×50 mL). Combined organic layers were dried (Na₂SO₄), filtered, and concentrated. The residue was concentrated once more from hexane. The residue was dissolved in benzene. The solution was wet-loaded onto a 40 g "gold" ISCO silica gel column and purified by flash chromatography (hexane→ethyl acetate/hexanes 1:4) giving the desired product (1.75 g, >99%). ¹H NMR (400 MHz, CDCl₃) δ 8.11-8.02 (m, 2H), 7.66-7.60 (m, 2H), 5.72 (s, 1H), 4.27-4.10 (m, 2H), 2.44 (d, $J_{HF}$=3.2 Hz, 3H), 1.21 (s, 9H), 1.18 (t, J=7.0 Hz, 3H). ¹⁹F NMR (377 MHz, CDCl₃) δ−123.1 (app. s, 1F), −73.4 (s, 3F)

Preparation of ethyl 2-(4-fluoro-3-methyl-1-(trifluoromethylsulfonyl-oxy)naphthalen-2-yl)-2-hydroxyacetate: A solution of ethyl 2-tert-butoxy-2-(4-fluoro-3-methyl-(trifluoromethylsulfonyloxy)naphthalen-2-yl)acetate (1.75 g, 3.76 mmol) in DCM (30 mL) was treated dropwise with TFA (3.0 mL) over 3 min at 23° C. After 16 h, the reaction was diluted with H₂O (60 mL) and the system was extracted with DCM (3×20 mL). Combined organic layers were dried (Na₂SO₄), filtered, and concentrated giving the crude desired product (~1.54 g obtained), which was used in the next reaction. ¹H NMR (400 MHz, CDCl₃) δ 8.11-8.06 (m, 1H), 7.67-7.64 (m, 1H), 7.61-7.52 (m, 2H), 7.41 (d, J=7.8 Hz, 1H), 5.79 (s, 1H), 4.34-4.22 (m, 2H), 2.40 (d, $J_{HF}$=3.2 Hz, 3H), 1.22 (t, J=7.4 Hz, 3H). $^{19}$F NMR (377 MHz, CDCl$_3$) δ–122.6 (app. s, 1F), –73.3 (s, 3F).

Preparation of ethyl 2-(4-fluoro-3-methyl-1-(trifluoromethylsulfonyl-oxy)naphthalen-2-yl)-2-oxoacetate: A solution of ethyl 2-(4-fluoro-3-methyl-1-(trifluoromethylsulfonyloxy)naphthalen-2-yl)-2-hydroxyacetate (~1.54 g, 3.76 mmol) in DCM (60 mL) was treated with Dess-Martin periodinane (1.91 g, 4.51 mmol) at 23° C. After 4 h, the orange reaction was slowly added to 10% Na$_2$S$_2$O$_3$ (28 mL) at 23° C. After 5 min of stirring, the reaction was diluted with H$_2$O (40 mL) and extracted with DCM (3×20 mL). Combined organic layers were dried (Na$_2$SO$_4$), filtered, and concentrated. The residue was dissolved in benzene. The solution was wet-loaded onto a 40 g "gold" ISCO silica gel column and purified by flash chromatography (hexane→ethyl acetate/hexanes 1:4) giving the desired product (1.08 g, 70% yield over 2 steps from ethyl 2-tert-butoxy-2-(4-fluoro-3-methyl-1-(trifluoromethylsulfonyloxy)naphthalen-2-yl)acetate). $^1$H NMR (400 MHz, CDCl$_3$) δ 8.16-8.08 (m, 2H), 7.76-7.68 (m, 2H), 4.41 (q, J=7.1 Hz, 2H), 2.39 (d, $J_{HF}$=3.2 Hz, 3H), 1.40 (t, J=7.1 Hz, 3H). $^{19}$F NMR (377 MHz, CDCl$_3$) δ–122.3 (app. s, 1F), –73.3 (s, 3F).

Preparation of (S)-ethyl 2-(4-fluoro-3-methyl-1-(trifluoromethylsulfonyloxy)naphthalen-2-yl)-2-hydroxyacetate: A solution of ethyl 2-(4-fluoro-3-methyl-1-(trifluoromethylsulfonyloxy)naphthalen-2-yl)-2-oxoacetate (1.08 g, 2.64 mmol) in PhMe (20 mL) was cooled to –40° C. (dry ice/CH$_3$CN bath). (R)—CBS catalyst (146 mg, 0.528 mmol) was introduced. Distilled catecholborane (423 µL) was added dropwise over a 5 min period. After 30 min, the reaction was warmed to –20° C. and treated with EtOAc (20 mL). Then 15% Na$_2$CO$_3$ (10 mL) was added. The reaction was warmed to 23° C. and stirred vigorously. The organic phase was collected after 30 min. It was washed (vigorous stirring) with 10 mL portions of 15% Na$_2$CO$_3$ for 30 min each until the layer was colorless. (Early washes tended to be dark greenish-brown). After six such washings, the organic phase was treated with saturated NH$_4$Cl (20 mL) for 30 min. The organic phase was dried (MgSO$_4$), filtered, and concentrated. The residue was treated with hexanes and concentrated again. The material was dissolved in benzene. The solution was wet-loaded onto a 40 g "gold" ISCO silica gel column and purified by flash chromatography (hexane→ethyl acetate) giving the desired product (1.02 g, 94% yield). $^1$H NMR (400 MHz, CDCl$_3$) δ 8.11-8.06 (m, 2H), 7.67-7.64 (m, 2H), 5.79 (s, 1H), 4.33-4.22 (m, 2H), 2.40 (d, $J_{HF}$=3.2 Hz, 3H), 1.22 (t, J=7.4 Hz, 3H). $^{19}$F NMR (377 MHz, CDCl$_3$) δ–122.6 (app. s, 1F), –73.1 (s, 3F).

Preparation of (S)-ethyl 2-tert-butoxy-2-(4-fluoro-3-methyl-1-(trifluoromethylsulfonyloxy)naphthalen-2-yl)acetate: A solution of (S)-ethyl 2-(4-fluoro-3-methyl-1-(trifluoromethylsulfonyloxy)naphthalen-2-yl)-2-hydroxyacetate (1.02 g, 2.49 mmol) in tert-butyl acetate (20 mL) was treated with 70% HClO$_4$ (20 µL) at 23° C.). After 5 h, the reaction was added slowly over 5 min to saturated NaHCO$_3$ (40 mL). The resulting system was extracted with DCM (3×30 mL). The combined organic layers were dried (Na$_2$SO$_4$), filtered, and concentrated. The residue was dissolved in benzene. The solution was wet-loaded onto a 40 g "gold" ISCO silica gel column and purified by flash chromatography (hexane→ethyl acetate/hexane 1:4) giving the desired product (942 mg, 81% yield). $^1$H NMR (400 MHz, CDCl$_3$) δ 8.11-8.02 (m, 2H), 7.65-7.60 (m, 2H), 5.72 (s, 1H), 4.25-4.13 (m, 2H), 2.45 (d, $J_{HF}$=3.2 Hz, 3H), 1.21 (s, 9H), 1.18 (t, J=7.0 Hz, 3H). $^{19}$F NMR (377 MHz, CDCl$_3$) δ–123.1 (ap s, 1F), –73.3 (s, 3F).

Preparation of (2S)-ethyl 2-tert-butoxy-2-((R)-1-(2,3-dihydropyrano[4,3,2-de]quinolin-7-yl)-4-fluoro-3-methylnaphthalen-2-yl)acetate: The following reaction was run in triplicate: A sealable tube was charged with 2,3-dihydropyrano[4,3,2-de]quinolin-7-ylboronic acid monohydrochloride (160 mg, 0.636 mmol), S-Phos palladacycle (71.3 mg, 0.106 mmol), and CsF (354 mg, 2.33 mmol). The tubes were placed under vacuum, then backfilled with argon. A solution of (S)-ethyl 2-tert-butoxy-2-(4-fluoro-3-methyl-1-(trifluoromethylsulfonyloxy)naphthalen-2-yl)acetate (247 mg, 0.530 mmol) in 1,2-dimethoxyethane (distilled from Na°/benzophenone, 1.25 mL) was added. The system was stirred for 1 min to dislodge any clumps of solid, then wrapped in foil. The reaction was heated with vigorous stirring to 120° C. for 1.5 h. The three reactions were cooled to 23° C. and combined by adding to a mixture of brine (30 mL) and H$_2$O (30 mL). The system was extracted with EtOAc (3×30 mL). Combined organic layers were dried (Na$_2$SO$_4$), filtered, and concentrated. Hexane was added, and the system was concentrated again. The residue was dissolved in DCM/PhH 1:1. The solution was wet-loaded onto a 24 g "gold" ISCO silica gel column and purified by flash chromatography (hexane→ethyl acetate) giving the desired product (2S)-ethyl 2-tert-butoxy-2-((R)-1-(2,3-dihydropyrano[4,3,2-de]quinolin-7-yl)-4-fluoro-3-methylnaphthalen-2-yl)acetate (163 mg, 21% yield). $^1$H NMR (400 MHz, CDCl$_3$) δ 8.16 (d, J=8.6 Hz, 1H), 7.61-7.18 (m, 6H), 6.92 (d, broad, J=8 Hz, 1H), 5.25 (s, broad, 1H), 4.75-4.60 (m, 2H), 4.30-4.00 (m, 2H), 3.55-3.40 (m, 2H), 2.68 (d, $J_{HF}$=3.2 Hz, 3H), 1.20-1.00 (m, 3H), 0.90 (s, 9H). $^{19}$F NMR (377 MHz, CDCl$_3$) δ–122 (s, broad) LCMS-ESr (m/z): calcd for C$_{30}$H$_{30}$FNO$_4$: 488.2 (M+H$^+$); Found: 488.3 (M+H$^+$). The other diastereomer was also obtained; (2S)-ethyl 2-tert-butoxy-2-((S)-1-(2,3-dihydropyrano[4,3,2-de]quinolin-7-yl)-4-fluoro-3-methylnaphthalen-2-yl)acetate (208 mg, 27% yield):

$^1$H NMR (400 MHz, CDCl$_3$) δ 8.13 (d, J=8.6 Hz, 1H), 7.50-7.16 (m, 6H), 6.88 (d, J=8.2 Hz, 1H), 5.15 (s, 1H), 4.72-4.60 (m, 2H), 4.30-4.00 (m, 2H), 3.49-3.38 (m, 2H), 2.61 (d, $J_{HF}$=3.2 Hz, 3H), 1.27-1.19 (m, 3H), 0.83 (s, 9H). $^{19}$F NMR (377 MHz, CDCl$_3$) δ–124 (app. s, broad). LCMS-ESI$^+$ (m/z): [M+H]$^+$ calcd for C$_{30}$H$_{31}$FNO$_4$: 488.2; Found: 488.3.

Preparation of (2S)-2-tert-butoxy-2-((R)-1-(2,3-dihydropyrano[4,3,2-de]quinolin-7-yl)-4-fluoro-3-methylnaphthalen-2-yl)acetic acid (122): A solution of (2S)-ethyl 2-tert-butoxy-2-((R)-1-(2,3-dihydropyrano[4,3,2-de]quinolin-7-yl)-4-fluoro-3-methylnaphthalen-2-yl)acetate (163 mg, 0.334 mmol) in THF (6.0 mL) and EtOH (absolute, 2.0 mL) was treated with LiOH monohydrate (400 mg, 9.48 mmol) in H$_2$O (2.0 mL). The mixture was stirred vigorously at 100° C. for 2 h. More LiOH monohydrate (600 mg, 14.2 mmol) and H$_2$O (500 µL) were added, and heating was continued for another 4 h. The reaction was cooled to 23° C. and filtered through a 0.45 micron filter pad. The filtrate was purified on a C18 Gemini column (Eluent: H$_2$O/CH$_3$CN 95:5→0:100 spiked with 0.1% v/v TFA), giving (2S)-2-tert-butoxy-2-((R)-1-(2,3-dihydropyrano[4,3,2-de]quinolin-7-yl)-4-fluoro-3-methylnaphthalen-2-yl)acetic acid as the mono-trifluoroacetic acid salt (124 mg, 64%). $^1$H NMR (400 MHz, CD$_3$OD) δ 8.68 (d, J=5.8 Hz, 1H), 8.20 (d, J=8.2 Hz, 1H), 7.87 (d, J=7.8 Hz, 1H), 7.81 (d, J=5.4 Hz, 1H), 7.60 (dd, J=7.9, 7.4 Hz, 1H), 7.48 (d, J=8.2 Hz, 1H), 7.36 (dd, J=7.9, 7.4 Hz, 1H), 6.98 (d, J=8.6 Hz, 1H), 5.19 (s, 1H), 4.77-4.70 (m, 2H), 3.67 (dd, J=7.2, 5.9 Hz, 2H), 2.67 (d, JH$_F$=3.2 Hz, 3H), 0.97 (s, 9H). $^{19}$F NMR (377 MHz, CD$_3$OD) δ–77.7 (s).

LCMS-ESI⁺ (m/z): [M+H]⁺ calcd for $C_{28}H_{27}FNO_4$: 460.2; Found: 460.2. The other diastereomer, (2S)-2-tert-butoxy-2-((S)-1-(2,3-dihyropyrano[4,3,2-de]quinolin-7-yl)-4-fluoro-3-methylnaphthalen-2-yl)acetic acid, was prepared in a similar manner from (2S)-ethyl 2-tert-butoxy-2-((S)-1-(2,3-dihyropyrano[4,3,2-de]quinolin-7-yl)-4-fluoro-3-methylnaphthalen-2-yl)acetate: ¹H NMR (400 MHz, CD₃OD) δ 8.56 (d, J=5.1 Hz, 1H), 8.05 (d, J=8.2 Hz, 1H), 7.94 (dd, J=9.0, 5.9 Hz, 1H), 7.88 (s, 1H), 7.54 (d, J=5.6 Hz, 1H), 7.38 (d, J=7.8 Hz, 1H), 7.25 (ddd, J=8.7, 8.6, 2.4 Hz, 1H), 6.49 (dd, J=10.3, 2.4 Hz, 1H), 5.22 (s, 1H), 4.67 (dd, J=5.8, 5.8 Hz, 2H), 3.55 (dd, J=5.8, 5.8 Hz, 2H), 2.70 (s, 3H), 0.83 (s, 9H). ¹⁹F NMR (377 MHz, CD₃OD) δ −105.6 (s, 1F), −77.6 (s, 3F).

LCMS-ESI⁺ (m/z): [M+H]⁺ calcd for $C_{28}H_{27}FNO_4$: 460.2; Found: 460.5.

EXAMPLE 121

(±)-(2S)-2-tert-Butoxy-2-((R)-1-(2,3-dihydropyrano[4,3,2-de]quinolin-7-yl)-7-fluoro-3-methylnaphthalen-2-yl)acetic acid (123)

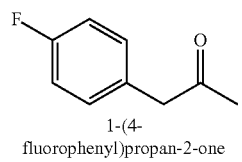
1-(4-fluorophenyl)propan-2-one

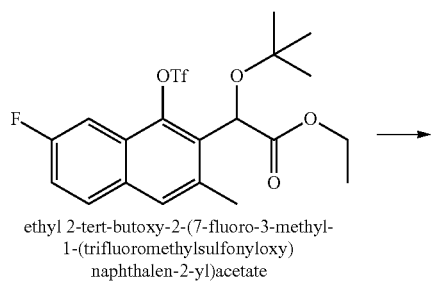
ethyl 2-tert-butoxy-2-(7-fluoro-3-methyl-1-(trifluoromethylsulfonyloxy)naphthalen-2-yl)acetate

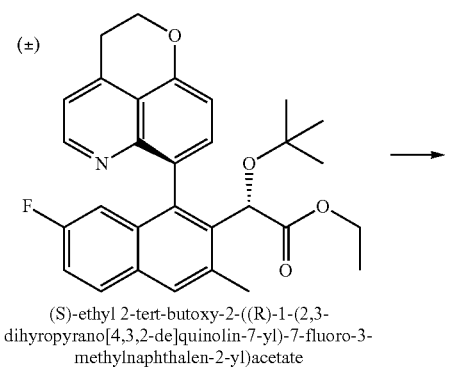
(S)-ethyl 2-tert-butoxy-2-((R)-1-(2,3-dihyropyrano[4,3,2-de]quinolin-7-yl)-7-fluoro-3-methylnaphthalen-2-yl)acetate

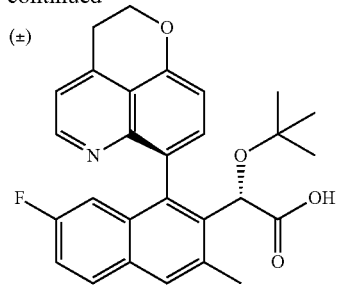
123
(S)-2-tert-butoxy-2-((R)-1-(2,3-dihyropyrano[4,3,2-de]quinolin-7-yl)-7-fluoro-3-methylnaphthalen-2-yl)acetic acid Preparation of ethyl 2-tert-butoxy-2-(7-fluoro-3-methyl-1-(trifluoromethyl-sulfonyloxy)naphthalen-2-yl)acetate: Prepared in a similar manner as 2-tert-butoxy-2-(7-chloro-3-methyl-1-(trifluoromethylsulfonyloxy)naphthalen-2-yl)acetate of Example 146 except using 1-(4-fluorophenyl)propan-2-one. ¹H NMR (400 MHz, CDCl₃) δ 7.79 (dd, $J_{HH}$=9.0 Hz, $J_{HF}$=5.4 Hz, 1H), 7.66 (s, 1H), 7.65 (dd, $J_{HH}$=9.0 Hz, $J_{HH}$=2.3 Hz, 1H), 7.38 (ddd, $J_{HH}$=9.0 Hz, $J_{HF}$=8.0 Hz, $J_{HH}$=2.3 Hz, 1H), 5.72 (s, 1H), 4.25-4.10 (m, 2H), 2.54 (s, 3H), 1.20 (s, 9H), 1.18 (t, J=7.0 Hz, 3H). ¹⁹F NMR (377 MHz, CDCl₃) δ −112.0 (ddd, $J_{HF}$=9.0, 8.0, 5.4 Hz, 1F), −73.4 (s, 3F).

Preparation of (±)-(S)-ethyl 2-tert-butoxy-2-((R)1-(2,3-dihydropyrano[4,3,2-de]quinolin-7-yl)-7-fluoro-3-methylnaphthalen-2-yl)acetate: Prepared in a manner similar to (S)-ethyl 2-tert-butoxy-2-((R)-6-chloro-1-(2,3-dihydropyrano[4,3,2-de]quinolin-7-yl)-7-fluoro-3-methylnaphthalen-2-yl)acetate of Example 99 expect using ethyl 2-tert-butoxy-2-(7-fluoro-3-methyl-1-(trifluoromethylsulfonyloxy)naphthalen-2-yl)acetate as starting material and S-Phos-palladacycle as the catalyst, giving the product as a racemate. LCMS-ESI⁺ (m/z): calcd for $C_{30}H_{30}FNO_4$: 488.2 (M+H⁺); Found: 488.2 (M+H⁺). The other diastereomer (±)-(2S)-ethyl 2-tert-butoxy-2-((S)1-(2,3-dihydropyrano[4,3,2-de]quinolin-7-yl)-7-fluoro-3-methylnaphthalen-2-yl)acetate was also isolated via silica gel chromatography. LCMS-ESI⁺ (m/z): [M+H]⁺ calcd for $C_{30}H_{31}FNO_4$: 488.2; Found: 488.2.

Preparation of (±)-(S)-2-tert-butoxy-2-((R)-1-(2,3-dihydropyrano[4,3,2-de]quinolin-7-yl)-7-fluoro-3-methylnaphthalen-2-yl)acetic acid (123): Prepared in a similar manner as (S)-2-tert-butoxy-2-((R)-6-chloro-1-(2,3-dihydropyrano[4,3,2-de]quinolin-7-yl)-7-fluoro-3-methylnaphthalen-2-yl)acetic acid of Example 99, except using (±)-(S)-ethyl 2-tert-butoxy-2-((R)-1-(2,3-dihydropyrano[4,3,2-de]quinolin-7-yl)-7-fluoro-3-methylnaphthalen-2-yl)acetate as the starting material, giving the racemate of the desired product as the mono-trifluoroacetic acid salt. ¹H NMR (400 MHz, CD₃OD) δ 8.68 (d, J=5.5 Hz, 1H), 8.02-7.97 (m, 2H), 7.81-7.75 (m, 2H), 7.43 (d, J=8.2 Hz, 1H), 7.32 (ddd, J=5.4, 5.4, 2.4 Hz, 1H), 6.54 (dd, J=10.0, 2.3 Hz, 1H), 5.24 (s, 1H), 4.78-4.67 (m, 2H), 3.67-3.62 (m, 2H), 2.77 (s, 3H), 0.93 (s, 9H). ¹⁹F NMR (377 MHz, CD₃OD) δ −105.6 (s, 1F), −77.6 (s, 3F). LCMS-ESI⁺ (m/z): [M+H]⁺ calcd for $C_{28}H_{27}FNO_4$: 460.2; Found: 460.4.

The other racemate, (±)-(S)-2-tert-butoxy-2-((S)-1-(2,3-dihydropyrano[4,3,2-de]quinolin-7-yl)-7-fluoro-3-methyl-naphthalen-2-yl)acetic acid, was prepared in a similar manner. ¹H NMR (400 MHz, CD₃OD) δ 8.61 (d, J=5.8 Hz, 1H), 8.18 (d, J=8.2 Hz, 1H), 7.71 (d, J=5.5 Hz, 1H), 7.58 (dd, J=7.0, 6.8 Hz, 1H), 7.51 (d, J=8.2 Hz, 1H), 7.34 (dd, J=7.0, 6.8 Hz, 1H), 6.96 (d, J=8.6 Hz, 1H), 5.20 (s, 1H), 4.72 (dd, J=6.2, 6.2 Hz, 2H), 3.64 (dd, J=6.2, 6.2 Hz, 2H), 2.64 (d, $J_{HF}$=3.2 Hz, 3H), 0.86 (s, 9H). $^{19}$F NMR (377 MHz, CD$_3$OD) δ −77.8 (s).

LCMS-ESI$^+$ (m/z): [M+H]$^+$ calcd for C$_{28}$H$_{27}$FNO$_4$: 460.2; Found: 460.4.

EXAMPLE 122

(2S)-2-tert-Butoxy-2-((R)-7-chloro-1-(2,3-dihydro-pyrano[4,3,2-de]quinolin-7-yl)-3-methylnaphthalen-2-yl)acetic acid (124)

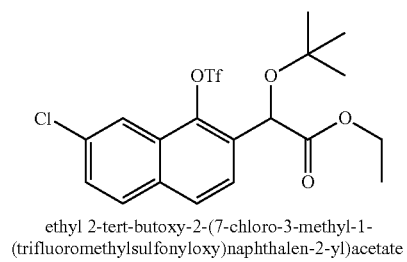

ethyl 2-tert-butoxy-2-(7-chloro-3-methyl-1-(trifluoromethylsulfonyloxy)naphthalen-2-yl)acetate (±)

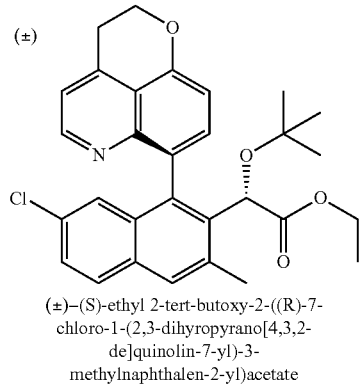

(±)-(S)-ethyl 2-tert-butoxy-2-((R)-7-chloro-1-(2,3-dihyropyrano[4,3,2-de]quinolin-7-yl)-3-methylnaphthalen-2-yl)acetate (±)

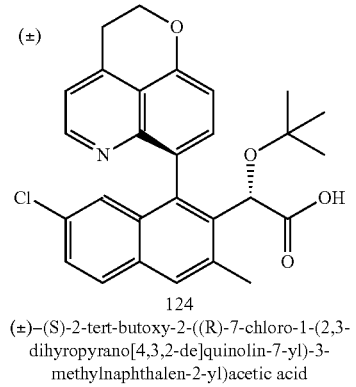

124
(±)-(S)-2-tert-butoxy-2-((R)-7-chloro-1-(2,3-dihyropyrano[4,3,2-de]quinolin-7-yl)-3-methylnaphthalen-2-yl)acetic acid Preparation of (±)-(2S)-ethyl 2-tert-butoxy-2-((R)-(7-chloro-1-(2,3-dihydropyrano[4,3,2-de]quinolin-7-yl)-3-methylnaphthalen-2-yl)acetate: Prepared in a manner similar to (S)-ethyl 2-tert-butoxy-2-((R)-6-chloro-1-(2,3-dihydropyrano[4,3,2-de]quinolin-7-yl)-7-fluoro-3-methylnaphthalen-2-yl)acetate of Example 99 except using ethyl 2-tert-butoxy-2-(7-chloro-3-methyl-1-(trifluoro-methylsulfonyloxy)naphthalen-2-yl)acetate as the starting material. LCMS-ESI$^+$ (m/z): [M+H]$^+$ calcd for C$_{30}$H$_{31}$ClNO$_4$: 504.2; Found: 504.2. The other racemate (±)-(2S)-ethyl 2-tert-butoxy-2-((S)(7-chloro-1-(2,3-dihydropyrano[4,3,2-de]quinolin-7-yl)-3-methylnaphthalen-2-yl)acetate was also isolated via silica gel chromatography. LCMS-ESI$^+$ (m/z): [M+H]$^+$ calcd for C$_{30}$H$_{31}$ClNO$_4$: 504.2; Found: 504.2.

Preparation of (±)-(S)-2-tert-butoxy-2-((R)-7-chloro-1-(2,3-dihydropyrano[4,3,2-de]quinolin-7-yl)-3-methylnaphthalen-2-yl)acetic acid (124): (±)-(S)-2-tert-butoxy-2-((R)-7-chloro-1-(2,3-dihydropyrano[4,3,2-de]quinolin-7-yl)-3-methylnaphthalen-2-yl)acetic acid (124) was prepared in a similar manner as (S)-2-tert-butoxy-2-((R)-6-chloro-1-(2,3-dihydropyrano[4,3,2-de]quinolin-7-yl)-7-fluoro-3-methyl-naphthalen-2-yl)acetic acid of Example 99, except using (±)-(S)-ethyl 2-tert-butoxy-2-((R)-7-chloro-1-(2,3-dihydropyrano[4,3,2-de]quinolin-7-yl)-3-methylnaphthalen-2-yl)acetate as the starting material, giving the racemate of the desired product as the mono-trifluoroacetic acid salt. $^1$H NMR (400 MHz, CD$_3$OD) δ 8.69 (d, J=5.5 Hz, 1H), 7.99-7.93 (m, 2H), 7.81-7.75 (m, 2H), 7.48-7.43 (m, 2H), 6.90 (d, J=2.0 Hz, 1H), 5.22 (s, 1H), 4.77-4.67 (m, 2H), 3.67-3.62 (m, 2H), 2.77 (s, 3H), 0.93 (s, 9H). $^{19}$F NMR (377 MHz, CD$_3$OD) δ −77.6 (s). LCMS-ESI$^+$ (m/z): calcd for C$_{28}$H$_{26}$ClNO$_4$: 476.2 (M+H$^+$); Found: 476.1 (M+H$^+$). The other racemate, (±)-(S)-2-tert-butoxy-2-((S)-7-chloro-1-(2,3-dihydropyrano[4,3,2-de]quinolin-7-yl)-3-methylnaphthalen-2-yl)acetic acid, was prepared in a similar manner. $^1$H NMR (400 MHz, CD$_3$OD) δ 8.55 (d, J=5.1 Hz, 1H), 8.00 (d, J=6.8 Hz, 1H), 7.88-7.84 (m, 2H), 7.48 (d, broad, J=4 Hz, 1H), 7.40 (dd, J=8.6, 1.8 Hz, 1H), 7.34 (d, J=8.2 Hz, 1H), 6.85 (d, J=1.8 Hz, 1H), 5.20 (s, 1H), 4.68-4.62 (m, 2H), 3.54-3.47 (m, 2H), 2.69 (s, 3H), 0.80 (s, 9H). LCMS-ESI$^+$ (m/z): [M+H]$^+$ calcd for C$_{28}$H$_{27}$ClNO$_4$: 476.2; Found: 476.4.

EXAMPLE 123

Ethyl 2-(4-bromo-1-(4-chlorophenyl)-3-methylnaphthalen-2-yl)-2-tert-butoxyacetate (125)

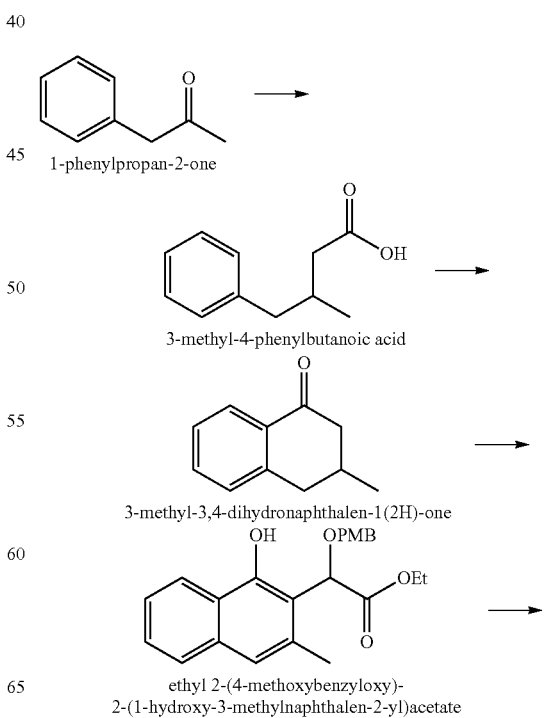

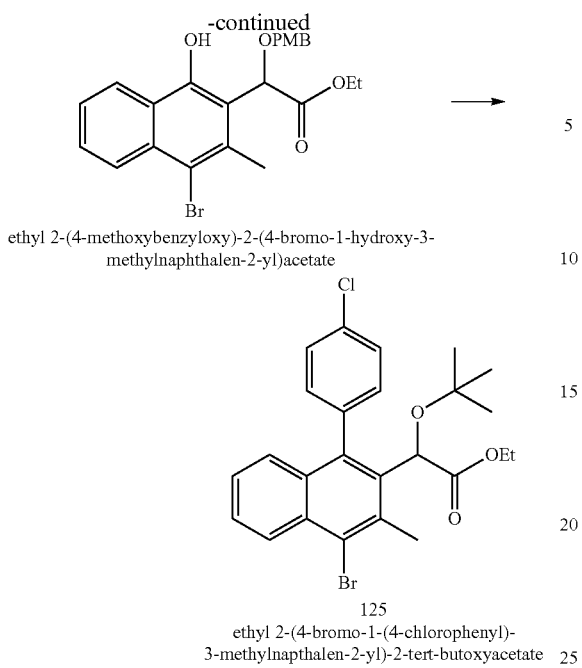

ethyl 2-(4-methoxybenzyloxy)-2-(4-bromo-1-hydroxy-3-methylnaphthalen-2-yl)acetate

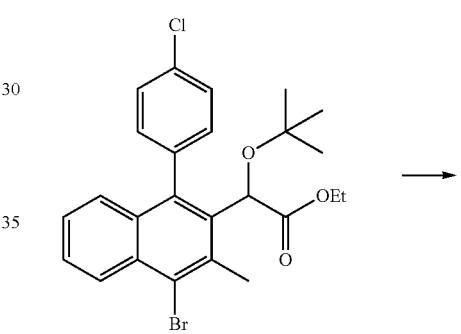

125
ethyl 2-(4-bromo-1-(4-chlorophenyl)-3-methylnapthalen-2-yl)-2-tert-butoxyacetate Preparation of 3-methyl-4-phenylbutanoic acid: 3-Methyl-4-phenylbutanoic acid was prepared in a similar manner as 4-(2-methoxy-phenyl)-3-methyl-butyric acid of Example 32 except using 1-phenylpropan-2-one. ¹H NMR (400 MHz, CDCl₃) δ 7.31-7.14 (m, 5H), 2.65 (dd, J=13.3, 6.7 Hz, 1H), 2.53 (dd, J=13.3, 7.4 Hz, 1H), 2.38 (dd, 14.9, 5.5 Hz, 1H), 2.28 (app. sext. J=6.7 Hz, 1H), 2.17 (dd, 14.5, 7.8 Hz, 1H), 0.98 (d, J=6.6 Hz, 3H).

Preparation of 3-methyl-3,4-dihydronaphthalen-1(2H)-one: 3-Methyl-3,4-dihydronaphthalen-1(2H)-one was prepared in a similar manner as 6-bromo-3-methyl-3,4-dihydronaphthalen-1(2H)-one of Example 48, except using 3-methyl-4-phenylbutanoic acid. ¹H NMR (400 MHz, CDCl₃) δ 8.02 (d, J=7.9 Hz, 1H), 7.47 (dd, J=7.4, 7.4 Hz, 1H), 7.31 (dd, J=7.4, 7.4 Hz, 1H), 7.24 (d, J=7.4 Hz, 1H), 3.01-2.95 (m, 1H), 2.76-2.66 (m, 2H), 2.37-2.27 (m, 2H), 1.15 (d, J=7.2 Hz, 3H).

Preparation of ethyl 2-(4-methoxybenzyloxy)-2-(1-hydroxy-3-methylnaphthalen-2-yl)acetate: Ethyl 2-(4-methoxybenzyloxy)-2-(1-hydroxy-3-methylnaphthalen-2-yl)acetate was prepared in a similar manner as (1-hydroxy-5-methoxy-3-methyl-naphthalen-2-yl)-(4-methoxy-benzyloxy)-acetic acid ethyl ester of Example 32, except using 3-methyl-3,4-dihydronaphthalen-1(2H)-one. ¹H NMR (400 MHz, CDCl₃) δ 8.51 (s, 1H), 8.24 (d, J=8.2 Hz, 1H), 7.65 (d, J=7.8 Hz, 1H), 7.48-7.36 (m, 2H), 7.27 (d, 8.5 Hz, 2H), 7.18 (s, 1H), 6.89 (d, J=8.4 Hz, 2H), 5.30 (s, 1H), 4.67-4.55 (m, 2H), 4.27-4.08 (m, 2H), 3.82 (s, 3H), 2.40 (s, 3H), 1.19 (t, J=7.0 Hz, 3H).

Preparation of ethyl 2-(4-methoxybenzyloxy)-2-(4-bromo-1-hydroxy-3-methylnaphthalen-2-yl)acetate: A solution of ethyl 2-(4-methoxybenzyloxy)-2-(1-hydroxy-3-methylnaphthalen-2-yl)acetate (102 mg, 0.268 mmol) in CHCl₃ (5.0 mL) was treated with solid NaHCO₃ (46 mg, 0.281 mmol). Br₂ (45 mg) in CHCl₃ (1.0 mL) was added dropwise over 5 min at 23° C. After 15 min, 10% Na₂S₂O₃ (10 mL) was added. The reaction was extracted two times with CHCl₃. Combined organic phases were dried (Na₂SO₄), filtered, and concentrated. The residue was dissolved in DCM. The solution was wet-loaded onto a 12 g "gold" ISCO silica gel column and purified by flash chromatography (ethyl acetate/hexanes) giving the desired product (83 mg, 67%). ¹H NMR (400 MHz, CDCl₃) δ 8.69 (s, 1H), 8.29 (d, J=8.2 Hz, 1H), 8.22 (d, J=8.6 Hz, 1H), 7.59 (dd, J=7.4, 7.4 Hz, 1H), 7.47 (dd, J=7.8, 7.8 Hz, 1H), 7.26 (d, J=8.2 Hz, 2H), 6.91 (d, J=8.6 Hz, 2H), 5.47 (s, 1H), 4.67-4.56 (m, 2H), 4.26-4.08 (m, 2H), 3.81 (s, 3H), 2.60 (s, 3H), 1.20 (t, J=7.1 Hz, 3H).

Preparation of ethyl 2-(4-bromo-1-(4-chlorophenyl)-3-methylnaphthalen-2-yl)-2-tert-butoxyacetate (125): Ethyl 2-(4-bromo-1-(4-chlorophenyl)-3-methylnaphthalen-2-yl)-2-tert-butoxyacetate (125) was prepared in a similar manner as ethyl 2-(7-bromo-1-(4-chlorophenyl)-3-methylnaphthalen-2-yl)-2-tert-butoxyacetate of Example 67 except using ethyl 2-(4-methoxybenzyloxy)-2-(4-bromo-1-hydroxy-3-methylnaphthalen-2-yl)acetate. ¹H NMR (400 MHz, CDCl₃) δ 8.39 (d, J=8.6 Hz, 1H), 7.57-7.42 (m, 4H), 7.36-7.24 (m, 3H), 5.16 (s, 1H), 4.24-4.09 (m, 2H), 2.75 (s, 3H), 1.23 (t, J=7.1 Hz, 3H), 1.00 (s, 9H).

EXAMPLE 124

2-(4-Bromo-1-(4-chlorophenyl)-3-methylnaphthalen-2-yl)-2-tert-butoxyacetic acid (126)

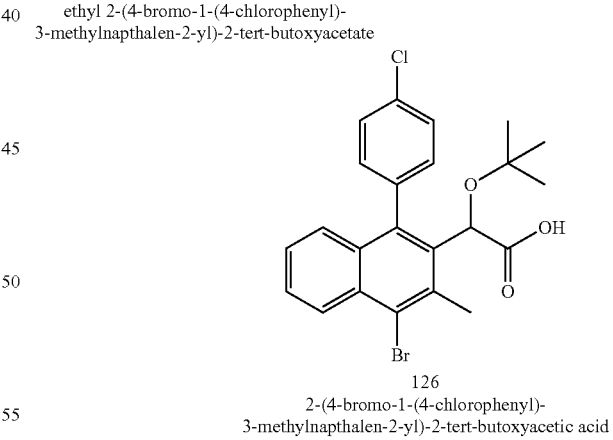

ethyl 2-(4-bromo-1-(4-chlorophenyl)-3-methylnapthalen-2-yl)-2-tert-butoxyacetate 126
2-(4-bromo-1-(4-chlorophenyl)-3-methylnapthalen-2-yl)-2-tert-butoxyacetic acid Preparation of 2-(4-bromo-1-(4-chlorophenyl)-3-methylnaphthalen-2-yl)-2-tert-butoxyacetic acid (126): A solution of ethyl 2-(4-bromo-1-(4-chlorophenyl)-3-methylnaphthalen-2-yl)-2-tert-butoxyacetate (30 mg, 71.4 μmol), LiOH monohydrate (15 mg, 0.357 mmol), H₂O (500 μL), EtOH (absolute, 500 μL), and THF (500 μL) was placed in a sealed tube and heated to 100° C. Once the reaction was complete, it was cooled to 23° C., filtered through a 0.45 micron filter, and directly purified by reverse phase HPLC (Gemini, 5 to 100% ACN/H₂O+0.1% TFA). The product-containing fractions were combined and lyophilized, giving the title compound (parent form) (11.5 mg, 40%). $^1$H NMR (400 MHz, CD$_3$OD) δ 8.38 (d, J=8.6 Hz, 1H), 7.63-7.47 (m, 4H), 7.38-7.20 (m, 3H), 5.30 (s, 1H), 2.69 (s, 3H), 1.00 (s, 9H). LCMS-ESI$^-$ (m/z): [M—CO$_2$—H]$^-$ calcd for C$_{22}$H$_{21}$BrClO: 415.2; Found: 415.0.

EXAMPLE 125

2-tert-Butoxy-2-(1-(4-chlorophenyl)-3,4-dimethyl-naphthalen-2-yl)acetic acid (127)

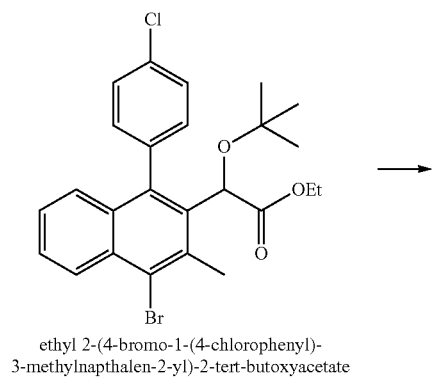

ethyl 2-(4-bromo-1-(4-chlorophenyl)-3-methylnapthalen-2-yl)-2-tert-butoxyacetate

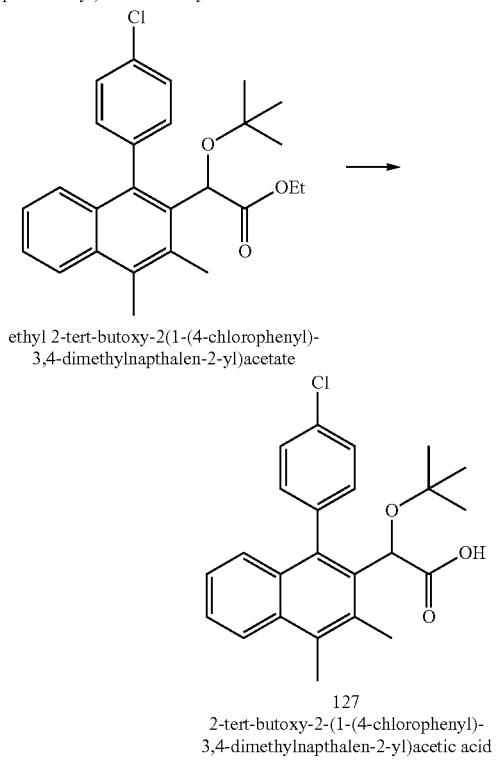

ethyl 2-tert-butoxy-2(1-(4-chlorophenyl)-3,4-dimethylnapthalen-2-yl)acetate 127
2-tert-butoxy-2-(1-(4-chlorophenyl)-3,4-dimethylnapthalen-2-yl)acetic acid Preparation of ethyl 2-tert-butoxy-2-(1-(4-chlorophenyl)-3,4-dimethylnaphthalen-2-yl)acetate: A suspension of ethyl 2-(4-bromo-1-(4-chlorophenyl)-3-methylnaphthalen-2-yl)-2-tert-butoxyacetate (25 mg, 51 μmol), trimethylboroxine (21 μL, 0.153 mmol), PdCl$_2$(dppf) (3.7 mg, 5.1 μmol), K$_2$CO$_3$ (70 mg, 0.510 mmol), PhMe (500 μL), EtOH (absolute, 250 μL), and H$_2$O (250 μL) was stirred in a sealed vessel at 100° C. for 3 h. The reaction was cooled to 23° C., diluted with H$_2$O and extracted with EtOAc (3×). Combined organic phases were dried (Na$_2$SO$_4$), filtered, and concentrated, giving crude product. (Yield was not found). $^1$H NMR (400 MHz, CD$_3$OD) δ 8.08 (d, J=8.2 Hz, 1H), 7.48-7.44 (m, 3H), 7.29-7.26 (m, 4H), 5.15 (s, 1H), 4.20-4.12 (m, 2H), 2.65 (s, 3H), 2.55 (s, 3H), 1.21 (t, J=7 Hz, 3H), 1.00 (s, 9H).

Preparation of 2-tert-butoxy-2-(1-(4-chlorophenyl)-3,4-dimethylnaphthalen-2-yl)acetic acid (127): A solution of the crude ethyl 2-tert-butoxy-2-(1-(4-chlorophenyl)-3,4-dimethylnaphthalen-2-yl)acetate in THF (500 μL), EtOH (Absolute, 250 μL), and H$_2$O (250 μL) was treated with LiOH monohydrate (61 mg, 1.45 mmol) and heated to 100° C. in a sealed vessel for 4 h. The reaction was cooled to 23° C., filtered through a 0.45 micron filter, and directly purified by reverse phase HPLC (Gemini, 5 to 100% ACN/H$_2$O+0.1% TFA). The product-containing fractions were combined and lyophilized, giving the title compound (parent form) (8.0 mg, 40% over 2 steps). $^1$H NMR (400 MHz, DMSO-d$_6$) δ 12.73 (s, broad, 1H), 8.15 (d, J=8.2 Hz, 1H), 7.72-7.62 (m, 2H), 7.57-7.47 (m, 2H), 7.39-7.32 (m, 2H), 7.19 (d, J=8.2 Hz, 1H), 5.07 (s, 1H), 2.63 (s, 3H), 2.51 (s, 3H), 0.93 (s, 9H).
LCMS-ESI$^-$ (m/z): [M–H]$^-$ calcd for C$_{48}$H$_{48}$Cl$_2$NaO$_6$: 813.3; Found: 813.2.

EXAMPLE 126

2-tert-Butoxy-2-(1-(4-chlorophenyl)-3-methyl-4-vinylnaphthalen-2-yl)acetic acid (128)

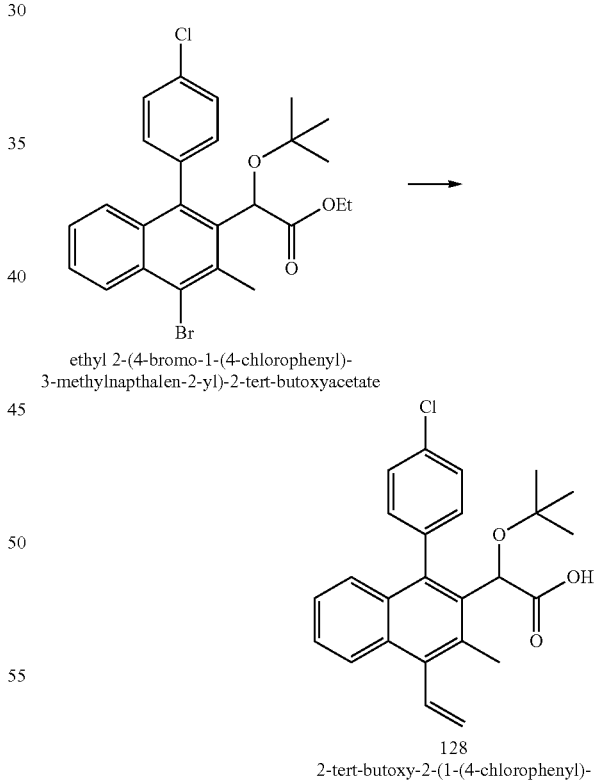

ethyl 2-(4-bromo-1-(4-chlorophenyl)-3-methylnapthalen-2-yl)-2-tert-butoxyacetate 128
2-tert-butoxy-2-(1-(4-chlorophenyl)-3-methyl-4-vinylnapthalen-2-yl)acetic acid Preparation of 2-tert-butoxy-2-(1-(4-chlorophenyl)-3-methyl-4-vinylnaphthalen-2-yl)acetic acid (128): 2-tert-butoxy-2-(1-(4-chlorophenyl)-3-methyl-4-vinylnaphthalen-2-yl) acetic acid (128) was prepared in a similar manner as 2-(4-bromo-1-(4-chlorophenyl)-3-methylnaphthalen-2-yl)-2-tert-butoxyacetic acid of Example 125, except using potassium vinyltrifluoroborate in the Suzuki coupling reaction, giving the title compound (parent form). $^1$H NMR (400 MHz, DMSO-d$_6$) δ 12.78 (s, broad, 1H), 8.13 (d, J=8.2 Hz, 1H), 7.73-7.65 (m, 2H), 7.54-7.48 (m, 2H), 7.41-7.36 (m, 2H), 7.20 (d, J=8.2 Hz, 1H), 7.11 (dd, J=18.0, 11.7 Hz, 1H), 5.87 (d, J=11.4 Hz, 1H), 5.41 (d, J=18.0 Hz, 1H), 5.09 (s, 1H), 2.50 (s, 3H), 0.94 (s, 9H). LCMS-ESI$^-$ (m/z): [2M-2H+Na]$^-$ calcd for C$_{50}$H$_{48}$Cl$_2$NaO$_6$: 839.3; Found: 839.2.

Example 127

2-tert-Butoxy-2-(1-(4-chlorophenyl)-4-ethyl-3-methylnaphthalen-2-yl)acetic acid (129)

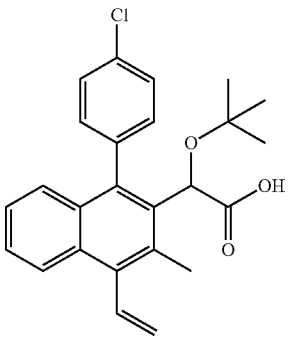

2-tert-butoxy-2-(1-(4-chlorophenyl)-
3-methyl-4-vinylnapthalen-2-yl)acetic acid

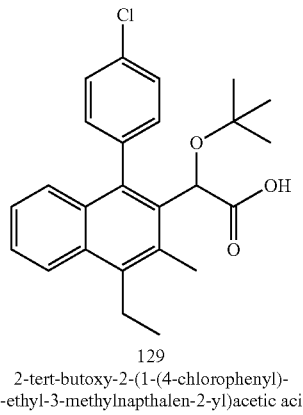

129
2-tert-butoxy-2-(1-(4-chlorophenyl)-
4-ethyl-3-methylnapthalen-2-yl)acetic acid Preparation of 2-tert-butoxy-2-(1-(4-chlorophenyl)-4-ethyl-3-methylnaphthalen-2-yl)acetic acid (129): A suspension of 2-tert-butoxy-2-(1-(4-chlorophenyl)-3-methyl-4-vinylnaphthalen-2-yl)acetic acid (5.0 mg, 12 µmol), 5% w/w Rh/Al$_2$O$_3$ (10 mg), and EtOH (absolute, 2.0 mL) was evacuated and purged several times (vaccuum/H$_2$ balloon). The suspension was rapidly stirred under a balloon of H$_2$ for 6 h. H$_2$O (500 µL) was added and the reaction was filtered through a 0.45 micron filter. The filtrate was directly purified by reverse phase HPLC (Gemini, 5 to 100% ACN/H$_2$O+0.1% TFA). The product-containing fractions were combined and lyophilized, giving the title compound (parent form) $^1$H NMR (400 MHz, DMSO-d$_6$) δ 12.71 (s, broad, 1H), 8.13 (d, J=8.2 Hz, 1H), 7.70-7.62 (m, 2H), 7.60-7.47 (m, 2H), 7.34-7.33 (m, 2H), 7.20 (d, J=8.2 Hz, 1H), 5.06 (s, 1H), 3.40-3.20 (m, 2H), 1.25 (t, J=7.4 Hz, 3H), 0.93 (s, 9H). LCMS-ESI$^-$ (m/z): [2M-2H+Na]$^-$ calcd for C$_{50}$H$_{52}$Cl$_2$NaO$_6$: 841.3; Found: 841.3.

EXAMPLE 128

Ethyl 2-tert-butoxy-2-(1-(4-chlorophenyl)-4-formyl-3-methylnaphthalen-2-yl)acetate (130)

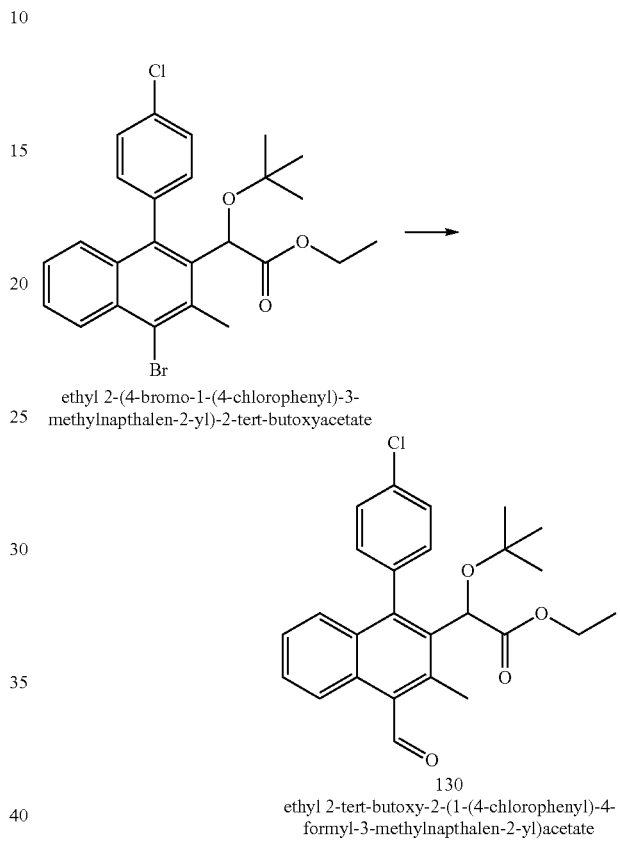

Preparation of ethyl 2-tert-butoxy-2-(1-(4-chlorophenyl)-4-formyl-3-methylnaphthalen-2-yl)acetate (130): A solution of ethyl 2-(4-bromo-1-(4-chlorophenyl)-3-methylnaphthalen-2-yl)-2-tert-butoxyacetate (75 mg, 0.153 mmol), K$_2$CO$_3$ (317 mg, 2.29 mmol), PdCl$_2$(dppf) (11.2 mg, 15.3 µmol), and potassium vinyltrifluoroborate (103 mg, 0.766 mmol) in H$_2$O (500 µL), EtOH (absolute, 500 µL), and PhMe (1.0 mL) was heated to 100° C. for 4 h in a sealed vessel. The reaction was cooled to 23° C., diluted with H$_2$O (30 mL), and extracted with EtOAc (3×). Combined organic phases were dried (Na$_2$SO$_4$), filtered, concentrated, and evaporated from MeOH in vacuo (2×). The residue was treated with MeOH (3.0 mL), and DCM (3.0 mL), and cooled to −78° C. The solution was sparged with ozone in O$_2$ for 5 min. After min past the end of the sparge, the reaction was treated with DMS (100 µL) and warmed to 0° C. 10% Na$_2$S$_2$O$_3$ (2.0 mL) was added, and the reaction was stirred at 23° C. for several minutes. The reaction was diluted with H$_2$O and DCM, then filtered over Celite. The filtrate was extracted with DCM (2×). Organic phases were combined, dried (Na$_2$SO$_4$), filtered, and concentrated. DCM was added, and the solution was wet-loaded onto a 12 g "gold" ISCO silica gel column and purified by flash chromatography (ethyl acetate/hexanes 3:97 isocratic) giving the desired product (34 mg, 51% yield). $^1$H NMR (400 MHz, DMSO-$d_6$) δ 11.01 (s, 1H), 8.73 (d, J=8.2 Hz, 1H), 7.56-7.22 (m, 7H), 5.16 (s, 1H), 4.24-4.12 (m, 2H), 2.81 (s, 3H), 1.23 (t, J=7.0 Hz, 3H), 1.00 (s, 9H).

EXAMPLE 129

2-tert-Butoxy-2-(1-(4-chlorophenyl)-4-(3-(dimethylamino)prop-1-ynyl)-3-methylnaphthalen-2-yl)acetic acid (131)

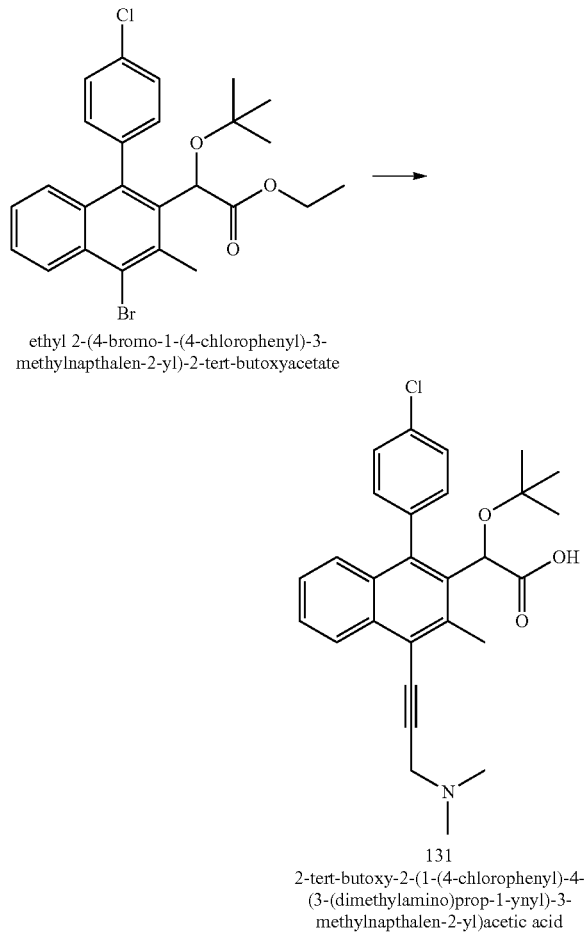

ethyl 2-(4-bromo-1-(4-chlorophenyl)-3-methylnapthalen-2-yl)-2-tert-butoxyacetate 131
2-tert-butoxy-2-(1-(4-chlorophenyl)-4-(3-(dimethylamino)prop-1-ynyl)-3-methylnapthalen-2-yl)acetic acid Preparation of 2-tert-butoxy-2-(1-(4-chlorophenyl)-4-(3-(dimethylamino)prop-1-ynyl)-3-methylnaphthalen-2-yl) acetic acid (131): A solution of ethyl 2-(4-bromo-1-(4-chlorophenyl)-3-methylnaphthalen-2-yl)-2-tert-butoxyacetate (40 mg, 81.7 μmol), N,N-dimethylpropargylamine (26 μL, 0.245 mmol), PdCl$_2$(PPh$_3$)$_2$ (5.7 mg, 16.3 μmol), CuI (3.1 mg, 16.3 μmol) and THF (1.00 mL) was heated to 70° C. for 18 h in a sealed vessel. Conversion was incomplete, so the vessel was charged with more PdCl$_2$(PPh$_3$)$_2$ (5.7 mg, 16.3 μmol) and CuI (3.1 mg, 16.3 μmol) and heated to 100° C. for an additional 26 h. The reaction was cooled to 23° C. THF (1.0 mL), EtOH (absolute, 500 μL), and H$_2$O (500 μL) were added followed by LiOH monohydrate (100 mg, 2.37 mmol). The reaction was heated to 100° C. for 4 h. After cooling to 23° C., the crude reaction was filtered through a 0.45 micron filter, and directly purified by reverse phase HPLC (Gemini, 5 to 100% ACN/H$_2$O+0.1% TFA). The product-containing fractions were combined and lyophilized, giving the title compound (mono trifluoroacetic acid salt) (6.8 mg, 15%). $^1$H NMR (400 MHz, DMSO-$d_6$) δ 12.92 (s, broad, 1H), 10.26 (s, broad, 1H), 8.30 (d, J=8.6 Hz, 1H), 7.71-7.62 (m, 3H), 7.47-7.43 (m, 2H), 7.34 (d, J=8.2 Hz, 1H), 7.22 (d, J=8.6 Hz, 1H), 5.03 (s, 1H), 4.56 (s, 2H), 2.96 (s, 6H), 2.72 (s, 3H), 0.90 (s, 9H). $^{19}$F NMR (377 MHz, DMSO-$d_6$) δ−74.1 (s) LCMS-ESI$^+$ (m/z): [M+H]$^+$ calcd for C$_{28}$H$_{31}$ClNO$_3$: 464.2; Found: 464.0.

EXAMPLE 130

2-tert-Butoxy-2-(1-(4-chlorophenyl)-4-(3-(dimethylamino)propyl)-3-methylnaphthalen-2-yl)acetic acid (132)

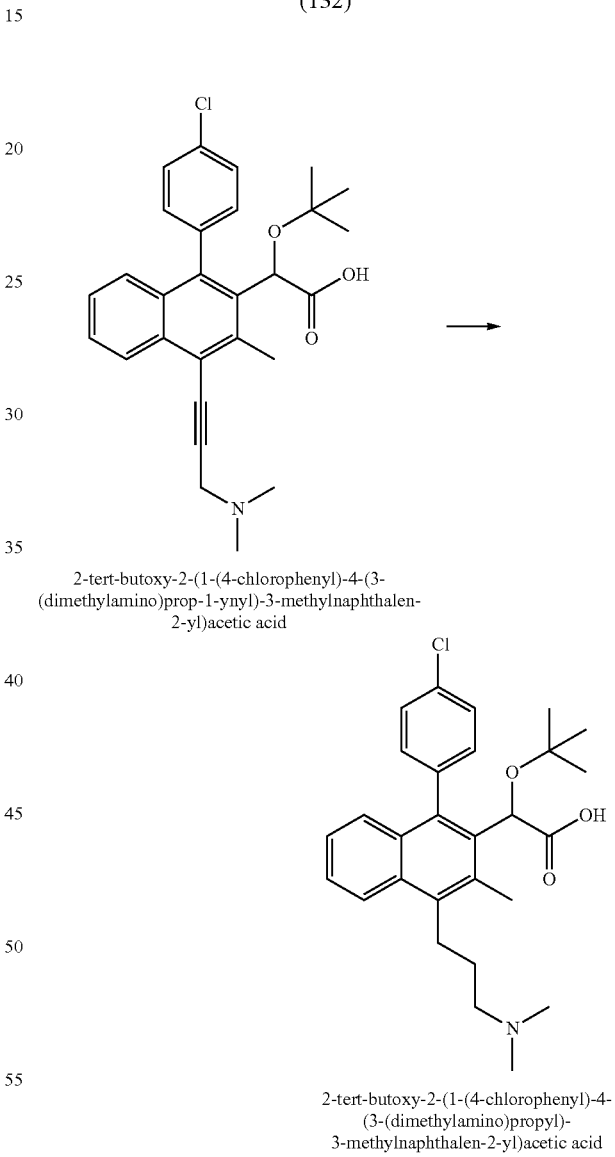

2-tert-butoxy-2-(1-(4-chlorophenyl)-4-(3-(dimethylamino)prop-1-ynyl)-3-methylnaphthalen-2-yl)acetic acid 2-tert-butoxy-2-(1-(4-chlorophenyl)-4-(3-(dimethylamino)propyl)-3-methylnaphthalen-2-yl)acetic acid Preparation of 2-tert-butoxy-2-(1-(4-chlorophenyl)-4-(3-(dimethylamino)propyl)-3-methylnaphthalen-2-yl)acetic acid (132): 2-tert-butoxy-2-(1-(4-chlorophenyl)-4-(3-(dimethylamino)propyl)-3-methylnaphthalen-2-yl)acetic acid (132) was prepared in a manner similar to 2-tert-butoxy-2-(1-(4-chlorophenyl)-4-ethyl-3-methylnaphthalen-2-yl)acetic acid of Example 127, except using 2-tert-butoxy-2-(1-(4-chlorophenyl)-4-(3-(dimethylamino)prop-1-ynyl)-3- methylnaphthalen-2-yl)acetic acid. LCMS-ESI⁺ (m/z): [M+H]⁺ calcd for $C_{28}H_{35}ClNO_3$: 468.2; Found: 468.2.

EXAMPLE 131

2-tert-Butoxy-2-(1-(4-chlorophenyl)-4-((dimethylamino)methyl)-3-methylnaphthalen-2-yl)acetic acid (133)

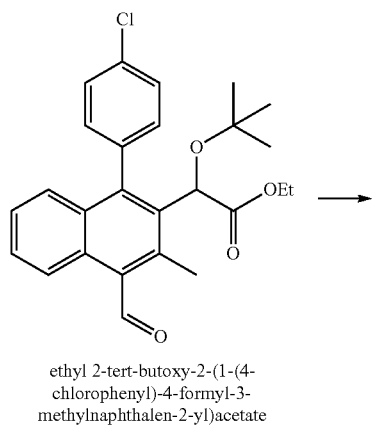

ethyl 2-tert-butoxy-2-(1-(4-chlorophenyl)-4-formyl-3-methylnaphthalen-2-yl)acetate

↓

2-tert-butoxy-2-(1-(4-chlorophenyl)-4-((dimethylamino)methyl)-3-methylnaphthalen-2-yl)acetic acid Preparation of 2-tert-butoxy-2-(1-(4-chlorophenyl)-4-((dimethylamino)methyl)-3-methylnaphthalen-2-yl)acetic acid (133): A suspension of ethyl 2-tert-butoxy-2-(1-(4-chlorophenyl)-4-formyl-3-methylnaphthalen-2-yl)acetate (6.0 mg, 13.9 μmol), EtOH (absolute, 500 μL), NaBH(OAc)₃ (8.8 mg, 41.7 μmol), and glacial AcOH (4 μL, 70 μmol) was treated with a solution of N,N-dimethylamine in MeOH (2 M, 35 μL, 69.5 μmol). DCM (50 μL) was added to improve solubility. The reaction was sealed and heated to 70° C. Conversion was limited, so more N,N-dimethylamine in MeOH (2 M, 170 μL, 0.337 mmol), glacial AcOH (20 μL, 0.35 mmol), NaBH(OAc)₃ (50 mg, 0.236 mmol), and DMF (500 μL) were added. Heating was continued. Once conversion was achieved, LiOH monohydrate (200 mg, 4.7 mmol) and H₂O (1.0 mL) were added. The reaction was sealed and heated to 100° C. overnight. Afterward, the reaction was filtered through a 0.45 micron filter, and directly purified by reverse phase HPLC (Gemini, 5 to 100% ACN/H₂O+0.1% TFA). The product-containing fractions were combined and lyophilized, giving the title compound (mono trifluoroacetic acid salt) (1.0 mg, 13%). LCMS-ESI⁺ (m/z): [M+H]⁺ calcd for $C_{26}H_{31}ClNO_3$: 440.2; Found: 440.0.

EXAMPLE 132

2-tert-Butoxy-2-(1-(4-chlorophenyl)-3-methyl-4-(morpholinomethyl)naphthalen-2-yl)acetic acid (134)

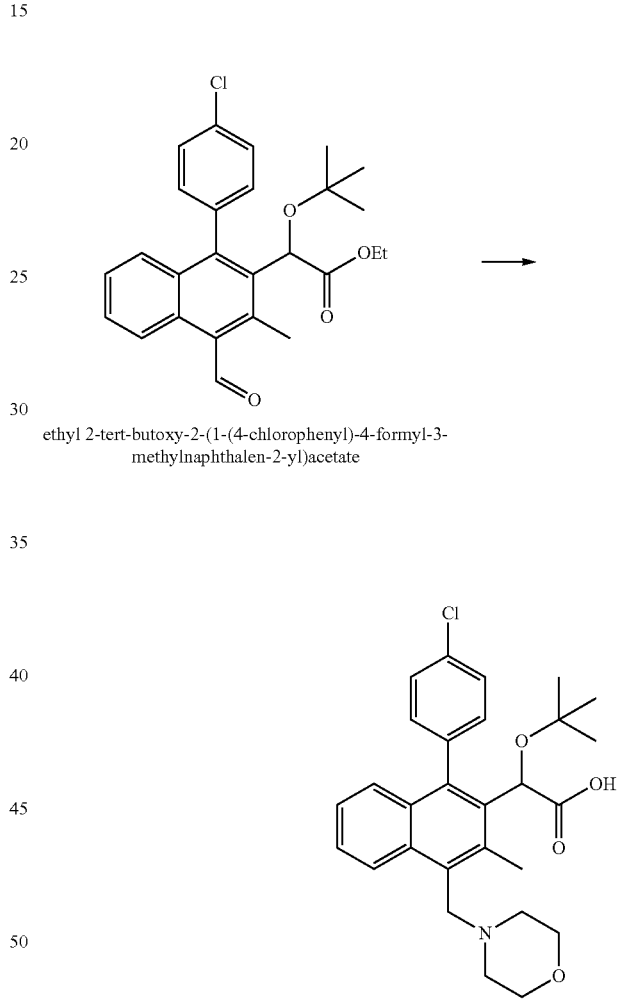

Preparation of 2-tert-butoxy-2-(1-(4-chlorophenyl)-3-methyl-4-(morpholinomethyl)naphthalen-2-yl)acetic acid (134): 2-tert-Butoxy-2-(1-(4-chlorophenyl)-3-methyl-4-(morpholinomethyl)naphthalen-2-yl)acetic acid (134) was prepared in a manner similar to 2-tert-butoxy-2-(1-(4-chlorophenyl)-4-((dimethylamino)methyl)-3-methylnaphthalen-2-yl)acetic acid of Example 131, except using morpholine in the reductive amination step. LCMS-ESI⁺ (m/z): [M+H]⁺ calcd for $C_{28}H_{33}ClNO_4$: 482.2; Found: 482.0.

EXAMPLE 133

2-tert-Butoxy-2-(1-(4-chlorophenyl)-4-(hydroxymethyl)-3-methylnaphthalen-2-yl)acetic acid (135)

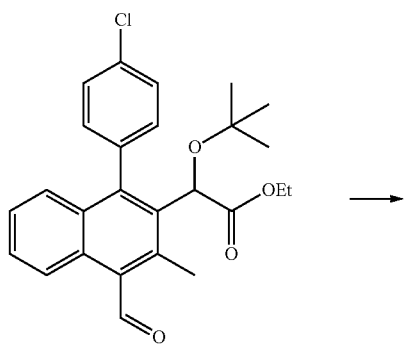

ethyl 2-tert-butoxy-2-(1-(4-chlorophenyl)-4-formyl-3-methylnaphthalen-2-yl)acetate

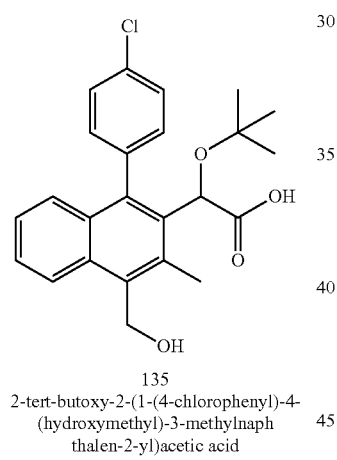

135
2-tert-butoxy-2-(1-(4-chlorophenyl)-4-(hydroxymethyl)-3-methylnaphthalen-2-yl)acetic acid Preparation of 2-tert-butoxy-2-(1-(4-chlorophenyl)-4-(hydroxymethyl)-3-methylnaphthalen-2-yl)acetic acid (135): A solution of ethyl 2-tert-butoxy-2-(1-(4-chlorophenyl)-4-formyl-3-methylnaphthalen-2-yl)acetate (6.0 mg, 14 µmol), NaBH$_4$ (1.5 mg, 40 µmol), THF (250 µL), and EtOH (absolute, 500 µL) was stirred at 23° C. for 1 h. H$_2$O (500 µL) and LiOH monohydrate (50 mg, 1.18 mmol) were added. The reaction was sealed and heated to 100° C. After 2 h, the reaction cooled to 23° C., filtered through a 0.45 micron filter, and directly purified by reverse phase HPLC (Gemini, 5 to 100% ACN/H$_2$O+0.1% TFA). The product-containing fractions were combined and lyophilized, giving the title compound (parent form) (2.6 mg, 43%). $^1$H NMR (400 MHz, DMSO-d$_6$) δ 12.76 (s, 1H), 8.27 (d, J=8.6 Hz, 1H), 7.72-7.65 (m, 2H), 7.58-7.48 (m, 2H), 7.39-7.33 (m, 2H), 7.18 (d, J=8.6 Hz, 1H), 5.07 (s, 1H), 5.01 (d, broad, J=2.7 Hz, 2H), 2.62 (s, 3H), 0.94 (s, 9H).
LCMS-ESI$^-$ (m/z): [M–H]$^-$ calcd for C$_{24}$H$_{24}$ClO$_4$: 411.1; Found: 410.9.

EXAMPLE 134

2-tert-Butoxy-2-(1-(4-chlorophenyl)-3-methyl-4-phenylnaphthalen-2-yl)acetic acid (136)

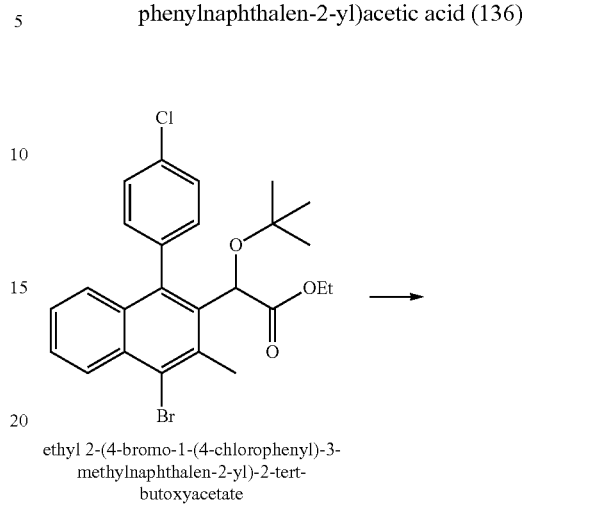

ethyl 2-(4-bromo-1-(4-chlorophenyl)-3-methylnaphthalen-2-yl)-2-tert-butoxyacetate

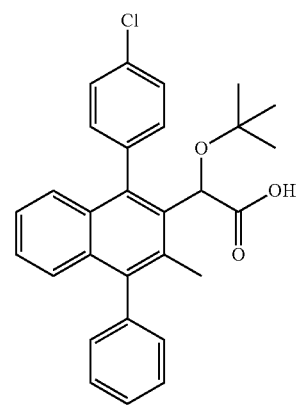

136
2-tert-butoxy-2-(1-(4-chlorophenyl)-3-methyl-4-phenylnaphthalen-2-yl)acetic acid Preparation of 2-tert-butoxy-2-(1-(4-chlorophenyl)-3-methyl-4-phenylnaphthalen-2-yl)acetic acid (136): 2-tert-Butoxy-2-(1-(4-chlorophenyl)-3-methyl-4-phenylnaphthalen-2-yl)acetic acid (136) was prepared in a manner similar to 2-tert-butoxy-2-(1-(4-chlorophenyl)-3,4-dimethylnaphthalen-2-yl)acetic acid of Example 125, except using benzeneboronic acid in the Suzuki reaction, giving the title compound (parent form). $^1$H-NMR: (400 MHz, MeOH-d$^4$): δ 7.67-7.55 (m, 5H); 7.50-7.48 (m, 1H); 7.41-7.39 (m, 1H); 7.33-7.23 (m, 6H); 5.31 (s, 1H); 2.28 (s, 3H); 1.02 (s, 9H). LCMS-ESI$^-$ (m/z): [M–H]$^-$ calcd for C$_{29}$H$_{26}$ClO$_3$: 457.2; Found: 457.2.

EXAMPLE 135

2-tert-Butoxy-2-(1-(4-chlorophenyl)-4-(6-(dimethylamino)pyridin-3-yl)-3-methylnaphthalen-2-yl)acetic acid (137)

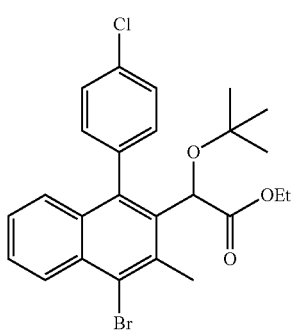

ethyl 2-(4-bromo-1-(4-chlorophenyl)-3-methylnaphthalen-2-yl)-2-tert-butoxyacetate

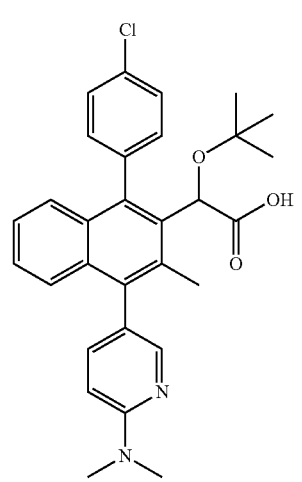

137
2-tert-butoxy-2-(1-(4-chlorophenyl)-4-(6-(dimethylamino)pyridin-3-yl)-3-methylnaphthalen-2-yl)acetic acid Preparation of 2-tert-butoxy-2-(1-(4-chlorophenyl)-4-(6-(dimethylamino)pyridin-3-yl)-3-methylnaphthalen-2-yl)acetic acid (137): 2-tert-Butoxy-2-(1-(4-chlorophenyl)-4-(6-(dimethylamino)pyridin-3-yl)-3-methylnaphthalen-2-yl)acetic acid (137) was prepared in a manner similar to 2-tert-butoxy-2-(1-(4-chlorophenyl)-3,4-dimethylnaphthalen-2-yl)acetic acid of Example 125, except using 2-(N,N-dimethylamino)-pyridin-5-yl-boronic acid in the Suzuki reaction, giving the title compound. $^1$H-NMR: (400 MHz, DMSO-d$^6$): δ 8.02-8.00 (m, 1H); 7.78 (m, broad, 1H); 7.72-7.69 (m, 1H); 7.67-7.65 (m, 1H); 7.52-7.49 (m, 1H); 7.45-7.36 (m, 4H); 7.23 (d, J=8.0 Hz, 2H); 5.11 (s, 1H); 2.29 (d, J=1.2 Hz, 3H); 0.93 (d, J=1.2 Hz, 9H). LCMS-ESI$^+$ (m/z): [M+H]$^+$ calcd for C$_{30}$H$_{32}$ClN$_2$O$_3$: 503.2; Found: 503.3.

EXAMPLE 136

2-tert-butoxy-2-(1-(4-chlorophenyl)-3-methyl-4-(pyridin-3-yl)naphthalen-2-yl)acetic acid (138)

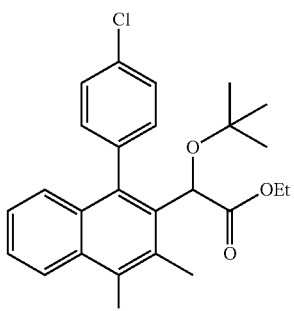

ethyl 2-(4-bromo-1-(4-chlorophenyl)-3-methylnaphthalen-2-yl)-2-tert-butoxyacetate

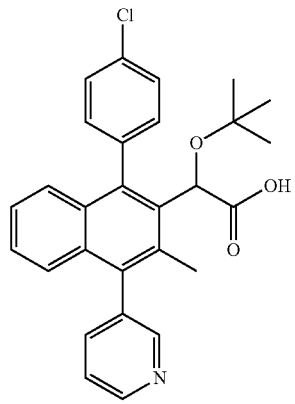

138
2-tert-butoxy-2-(1-(4-chlorophenyl)-3-methyl-4-(pyridin-3-yl)naphthalen-2-yl)acetic acid Preparation of 2-tert-butoxy-2-(1-(4-chlorophenyl)-3-methyl-4-(pyridin-3-yl)naphthalen-2-yl)acetic acid (138): 2-tert-butoxy-2-(1-(4-chlorophenyl)-3-methyl-4-(pyridin-3-yl)naphthalen-2-yl)acetic acid (138) was prepared in a manner similar to 2-tert-butoxy-2-(1-(4-chlorophenyl)-3,4-dimethylnaphthalen-2-yl)acetic acid of Example 125, except using pyridin-3-yl-boronic acid in the Suzuki reaction, giving the title compound (mono trifluoroacetic acid salt). $^1$H-NMR: (400 MHz, DMSO-d$^6$): δ 12.8 (s, broad, 1H), 8.80 (d, J=5.1 Hz, 1H), 8.62 (d, J=12.9 Hz, 1H), 7.97-7.92 (m, 1H), 7.76-7.69 (m, 3H), 7.60-7.54 (m, 1H), 7.47-7.40 (m, 3H), 7.28 (d, J=9.2 Hz, 1H), 7.18 (d, J=9.4 Hz, 1H), 5.15 (s, 1H), 2.25 (s, 3H), 0.96 (s, 9H). $^{19}$F-NMR: (377 MHz, DMSO-d$^6$): δ−74.7 (s) LCMS-ESI$^+$ (m/z): [M+H]$^+$ calcd for C$_{28}$H$_{27}$ClNO$_3$: 460.2; Found: 460.2.

EXAMPLE 137

2-tert-Butoxy-2-(1-(4-chlorophenyl)-3-methyl-4-(pyrimidin-5-yl)naphthalen-2-yl)acetic acid (139)

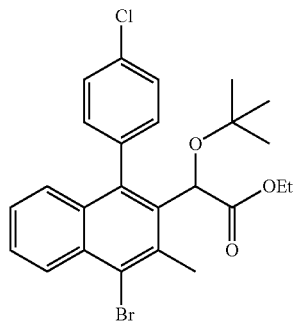

ethyl 2-(4-bromo-1-(4-chlorophenyl)-3-methylnaphthalen-2-yl)-2-tert-butoxyacetate

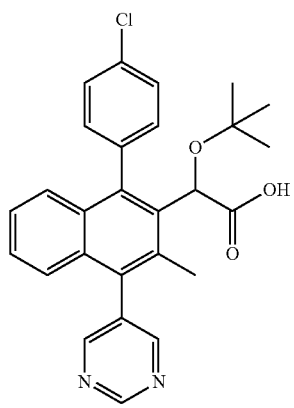

139
2-tert-butoxy-2-(1-(4-chlorophenyl)-3-methyl-4-(pyrimidin-5-yl)naphthalen-2-yl)acetic acid Preparation of 2-tert-butoxy-2-(1-(4-chlorophenyl)-3-methyl-4-(pyrimidin-5-yl)naphthalen-2-yl)acetic acid (139): 2-tert-Butoxy-2-(1-(4-chlorophenyl)-3-methyl-4-(pyrimidin-5-yl)naphthalen-2-yl)acetic acid (139) was prepared in a manner similar to 2-tert-butoxy-2-(1-(4-chlorophenyl)-3,4-dimethylnaphthalen-2-yl)acetic acid of Example 125, except using pyrimidin-5-yl-boronic acid in the Suzuki reaction, giving the title compound (mono trifluoroacetic acid salt). $^1$H-NMR: (400 MHz, DMSO-d$^6$): δ 12.87 (s, broad, 1H), 9.39 (s, 1H), 8.89-8.86 (m, 2H), 7.76-7.68 (m, 2H), 7.58-7.55 (s, 1H), 7.49-7.44 (m, 3H), 7.28 (d, J=8.2 Hz, 1H), 7.20 (d, J=8.2 Hz, 1H), 5.15 (s, 1H), 2.27 (s, 3H), 0.97 (s, 9H). $^{19}$F-NMR: (377 MHz, DMSO-d$^6$): δ −73.9 (s) LCMS-ESI$^+$ (m/z): [M+H]$^+$ calcd for $C_{27}H_{26}ClN_2O_3$: 461.2; Found: 461.2.

EXAMPLE 138

2-(1,4-Bis(4-chlorophenyl)-3-methylnaphthalen-2-yl)-2-tert-butoxyacetic acid (140)

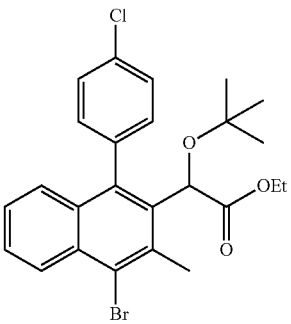

ethyl 2-(4-bromo-1-(4-chlorophenyl)-3-methylnaphthalen-2-yl)-2-tert-butoxyacetate

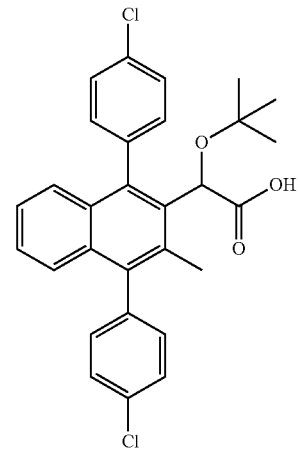

140
2-(1,4-bis(4-chlorophenyl)-3-methylnaphthalen-2-yl)-2-tert-butoxyacetic acid Preparation of 2-(1,4-bis(4-chlorophenyl)-3-methylnaphthalen-2-yl)-2-tert-butoxyacetic acid (140): 2-(1,4-bis(4-chlorophenyl)-3-methylnaphthalen-2-yl)-2-tert-butoxyacetic acid (140) was prepared in a manner similar to 2-tert-butoxy-2-(1-(4-chlorophenyl)-3,4-dimethylnaphthalen-2-yl)acetic acid of Example 125, except using 4-chlorobenzene boronic acid in the Suzuki reaction, giving the title compound (mono trifluoroacetic acid salt). $^1$H-NMR: (400 MHz, DMSO-d$^6$): δ 12.82 (s, 1H), 7.75-7.63 (m, 4H), 7.55 (dd, J=8.2, 2.4 Hz, 1H), 7.46-7.31 (m, 5H), 7.26-7.21 (m, 2H), 5.14 (s, 1H), 2.24 (s, 3H), 0.96 (s, 9H). LCMS-ESI$^-$ (m/z): [2M-2H+Na]$^-$ calcd for $C_{58}H_{50}Cl_4NaO_6$: 1007.2; Found: 1007.1.

EXAMPLE 139

1-(4-Bromo-1-(4-chlorophenyl)-3-methylnaphthalen-2-yl)prop-2-en-1-ol (141)

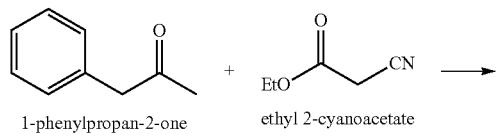

1-phenylpropan-2-one    ethyl 2-cyanoacetate

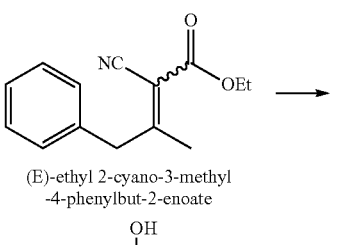

(E)-ethyl 2-cyano-3-methyl-4-phenylbut-2-enoate

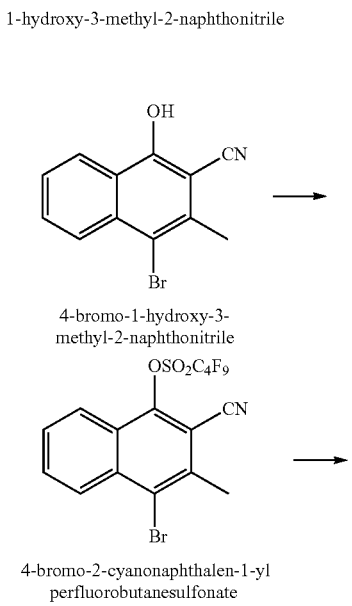

1-hydroxy-3-methyl-2-naphthonitrile 4-bromo-1-hydroxy-3-methyl-2-naphthonitrile 4-bromo-2-cyanonaphthalen-1-yl perfluorobutanesulfonate

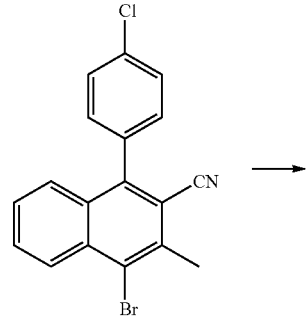

4-bromo-1-(4-chlorophenyl)-3-methyl-2-naphthonitrile

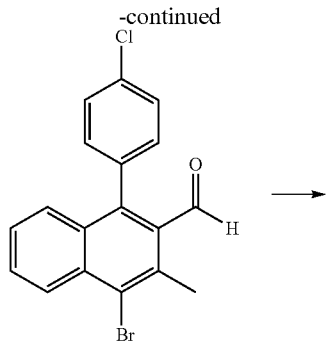

4-bromo-1-(4-chlorophenyl)-3-methyl-2-naphthaldehyde

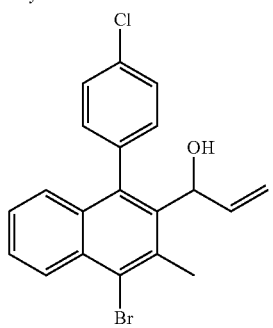

141
1-(4-bromo-1-(4-chlorophenyl)-3-methylnaphthalen-2-yl)prop-2-en-1-ol

Preparation of 1-hydroxy-3-methyl-2-naphthonitrile: Phenyl-2-propanone (24.93 g, 0.178 mol) was combined with ethylcyanoacetate (19.8 mL, 0.180 mol), acetic acid (8.0 mL, 0.14 mol), ammonium acetate (2.82 g, 0.0370 mol) and 80 mL of benzene in a round bottom flask equipped with a Dean-Stark trap and condenser cooled by a chiller. The reaction was heated to 160° C. for 4 h. The mixture was removed from heat and the trap drained so that the mixture could be concentrated by distilling off excess (~50 mL) benzene. The solution contained crude (E)-ethyl 2-cyano-3-methyl-4-phenylbut-2-enoate. The concentrated mixture was removed from heat and heat adjusted to 240° C. Acetamide (50.9483 g, 0.862 mol) was added, and a Claisen head attached to distill any ethanol resulting while the mixture was heated at 240° C. for 60-90 minutes. The mixture was cooled to ~100° C., and poured into room temperature water to quench the reaction. A clumpy orange solid was formed, removed by filtration and triturated with ice cold absolute EtOH. The solid was filtered off and the process repeated 4 times to harvest additional material. The resulting product was a pale yellow fine powder (13.20 g, 36% yield). $^1$H-NMR: (300 MHz, DMSO-d$^6$): δ 11.28 (s, 1H); 8.24 (d, J=8.4 Hz, 1H); 7.80 (d, J=8.0 Hz, 1H); 7.62-7.58 (m, 1H); 7.52-7.48 (m, 1H); 7.34 (s, 1H); 2.47 (s, 3H).

Preparation of 4-bromo-1-hydroxy-3-methyl-2-naphthonitrile: 1-hydroxy-3-methyl-2-naphthonitrile (1.065 g, 5.8 mmol) was dissolved CHCl$_3$ (24 mL) and combined with sodium bicarbonate (952 mg, 11.3 mmol) and bromine (330 µL, 6.43 mmol) and allowed to stir at room temperature overnight. The reaction was quenched by adding 10 mL of 10% sodium thiosulfate and the mixture stirred until decolorization was maximal. The solids were removed by filtration as crude product (1.47 g, 97% yield.) $^1$H-NMR: (300 MHz, DMSO-d$^6$): δ 8.334 (d, J=8.0 Hz, 1H); 8.166 (d, J=8.4 Hz, 1H); 7.81-7.77 (m, 1H); 7.65-7.61 (m, 1H); 2.65 (s, 3H).

Preparation of 4-bromo-2-cyanonaphthalen-1-yl perfluorobutanesulfonate: A dichloromethane solution (20 mL) of 4-bromo-1-hydroxy-3-methyl-2-naphthonitrile (518 mg, 1.97 mmol) was treated with triethylamine (800 µL, 5.37 mmol) at −78° C. To this cooled solution was added nonafluorobutanesulfonic anhydride (1.10 g, 1.97 mmol) dropwise as a DCM emulsion. After 15 min reaction was allowed warm to room temp. Reaction was quenched with saturated sodium bicarbonate and allowed to stir at 23° C. overnight. The mixture diluted with DCM, washed with brine and chromatographed on silica gel using EtOAc and hexanes to give desired product (330 mg, 31% yield) as well as recovered starting material (245 mg, 47% yield). $^1$H-NMR: (400 MHz, DMSO-$d^6$): δ 8.42 (d, J=8.4 Hz, 1H); 8.11 (d, J=8.8 Hz, 1H); 8.05-8.01 (m, 1H); 7.99-7.95 (m, 1H); 2.81 (s, 3H).

Preparation of 4-bromo-1-(4-chlorophenyl)-3-methyl-2-naphthonitrile: To a 50-50 (v/v) EtOH-toluene solution (4 mL) of 4-bromo-2-cyanonaphthalen-1-yl perfluorobutanesulfonate (3.99 g, 7.33 mmol) in a 2-5 mL microwave vial was added 4-chlorophenylboronic acid (1.65 g, 10.55 mmol) and dichloro[1,1'-bis(diphenylphosphino)ferrocene]palladium (II) dichloromethane adduct (165 mg, 0.171 mmol) and 6 mL of 2 M $K_2CO_3$. The vial was sealed, and heated thermally at 60° C. for 30 minutes. The mixture was concentrated in vacuo, redissolved in EtOAc and washed with saturated $NH_4Cl$ and brine then dried with sodium sulfate and concentrated. The residue was chromatographed on silica gel using EtOAc and hexanes to give a mixture of products. This mixture was then purified by hot filtration using neat hexanes (50 mL) to give rise to desired pure product (731 mg, 28% yield). A second crop (600 mg) was obtained by repeating the hot filtration that was contaminated with starting material. $^1$H-NMR: (400 MHz, MeOH-$d^4$): δ 8.361 (d, J=8.4 Hz, 1H); 7.89-7.85 (m, 1H); 7.69-7.62 (m, 3H); 7.56-7.49 (m, 3H); 2.81 (s, 3H).

Preparation of 4-bromo-1-(4-chlorophenyl)-3-methyl-2-naphthaldehyde: DIBAL-H (11.2 ml, 1.0 M in DCM) was added to a −40° C. DCM solution of 4-bromo-1-(4-chlorophenyl)-3-methyl-2-naphthonitrile (2.01 g, 5.63 mmol) slowly. The mixture was allowed to stir and gradually rise to 23° C. over 3-4 hours. The mixture was then cooled back to 0° C. and quenched with the addition of EtOAc (15 mL, 18.9 mmol) and stirred with vigor for 20-30 minutes. This mixture was poured into 30 mL of saturated $NH_4Cl$, and stirred 10-15 minutes. After being filtered though a short pad of Celite followed by extraction with DCM, the extracts were dried with sodium sulfate and concentrated in vacuo. Chromatography on silica gel using EtOAc in hexanes gave rise to desired aldehyde (1.56 g, 77% yield). $^1$H-NMR: (400 MHz, DMSO-$d^6$): δ 9.81 (s, 1H); 8.36 (d, J=8.8 Hz, 1H); 7.83-7.79 (m, 1H); 7.64-7.62 (m, 1H); 7.60-7.56 (m, 2H); 7.44-7.39 (m, 3H); 2.775 (s, 3H).

Preparation 1-(4-bromo-1-(4-chlorophenyl)-3-methyl-naphthalen-2-yl)prop-2-en-1-ol (141): To a 0° C. THF (15 mL) solution of 4-bromo-1-(4-chlorophenyl)-3-methyl-2-naphthaldehyde (500 mg, 1.39 mmol) was added vinyl magnesium bromide (1.40 mL, 1 M in THF, 1.4 mmol) and the mixture allowed to stir and warm to 23° C. for 4 hours. Reaction was quenched by the addition of 10 mL of saturated aqueous $NH_4Cl$ and extracted with ethyl acetate. Extracts were dried with sodium sulfate, concentrated in vacuo and chromatographed on silica gel using EtOAc in hexanes to give desired product (401.8 mg, 75% yield). $^1$H-NMR: (400 MHz, $CDCl_3$): δ 8.40 (d, J=8.8 Hz, 1H); 7.57-7.53 (m, 1H); 7.50-7.44 (m, 2H); 7.36-7.32 (m, 1H); 7.25-7.15 (m, 4H); 6.18-6.10 (m, 1H); 5.42-5.40 (m, 1H); 5.19-5.03 (m, 2H); 2.79 (s, 3H).

EXAMPLE 140

Methyl 2-(4-bromo-1-(4-chlorophenyl)-3-methyl-naphthalen-2-1)-2-tert-butoxyacetate (142)

141
1-(4-bromo-1-(4-chlorophenyl)-3-methylnaphthalen-2-yl)prop-2-en-1-ol (1-(4-bromo-1-(4-chlorophenyl)-3-methylnaphthalen-2-yl)allyloxy)(tert-butyl)dimethylsilane 2-(4-bromo-1-(4-chlorophenyl)-3-methyl naphthalen-2-yl)-2-(tert-butyldimethyl silyloxy)acetaldehyde

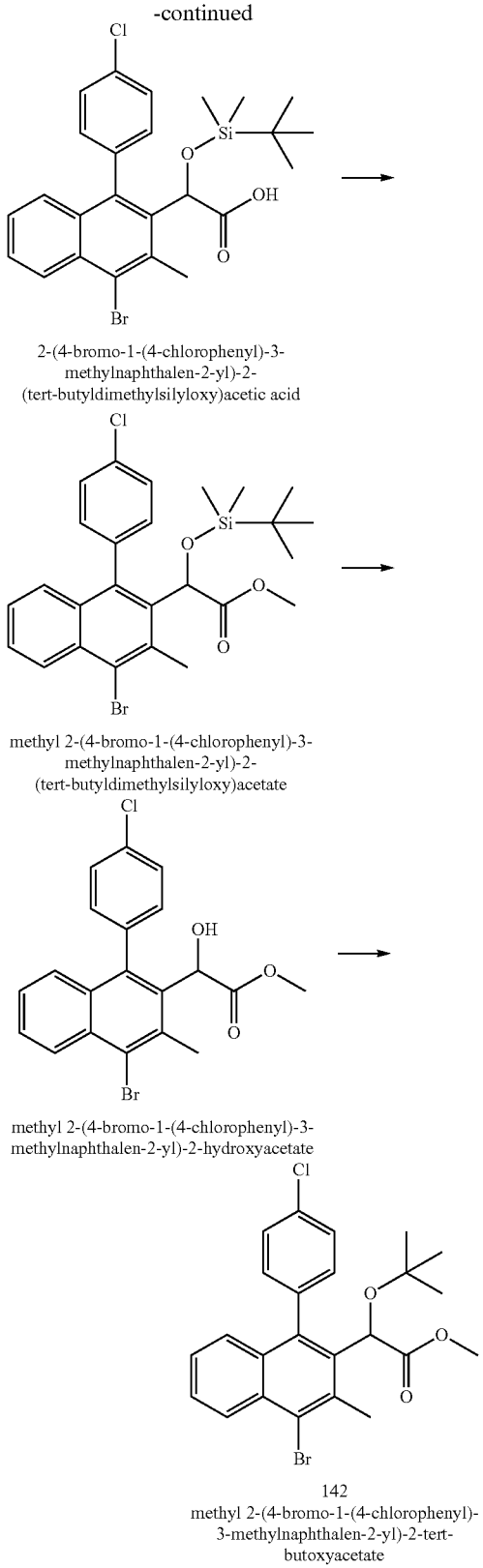

2-(4-bromo-1-(4-chlorophenyl)-3-methylnaphthalen-2-yl)-2-(tert-butyldimethylsilyloxy)acetic acid methyl 2-(4-bromo-1-(4-chlorophenyl)-3-methylnaphthalen-2-yl)-2-(tert-butyldimethylsilyloxy)acetate methyl 2-(4-bromo-1-(4-chlorophenyl)-3-methylnaphthalen-2-yl)-2-hydroxyacetate 142
methyl 2-(4-bromo-1-(4-chlorophenyl)-3-methylnaphthalen-2-yl)-2-tert-butoxyacetate Preparation of (1-(4-bromo-1-(4-chlorophenyl)-3-methylnaphthalen-2-yl)allyloxy)(tert-butyl)dimethylsilane: To a stirring 23° C. DCM solution (32 mL) of 1-(4-bromo-1-(4-chlorophenyl)-3-methylnaphthalen-2-yl)prop-2-en-1-ol (1.47 g, 3.79 mmol) and triethylamine (2.3 mL, 16.5 mmol) was added TBDMS-OTf (2.0 mL, 11.65 mmol) and the reaction was stirred and monitored by TLC. After 45 minutes, an additional 2 mL of TBDMSOTf was added and the mixture allowed to stir overnight. The dark mixture was then quenched 10% NaHCO$_3$ and the color dissipated. The mixture was washed with brine, dried with sodium sulfate and concentrated in vacuo. Column chromatography using silica gel with EtOAc in hexanes gave desired silylated product (1.60 g, 84% yield). $^1$H-NMR: (400 MHz, CDCl$_3$): δ 8.39 (d, J=8.4 Hz, 1H); 7.55-745 (m, 3H); 7.34-7.30 m, 1H); 7.26-7.24 (m, 1H); 7.24-7.18 (d, J=8.0 Hz, 1H); 7.16-7.14 (m, 1H); 6.09-6.01 (m, 1H); 5.32-5.30 (m, 1H); 5.13-5.03 (m, 2H); 2.77 (s, 3H); 0.87 (s, 6H); 0.83 (s, 9H).

Preparation of 2-(4-bromo-1-(4-chlorophenyl)-3-methylnaphthalen-2-yl)-2-(tert-butyldimethylsilyloxy)acetaldehyde: A −78° C. 50-50 (v/v) (MeOH/DCM) solution of (1-(4-bromo-1-(4-chlorophenyl)-3-methylnaphthalen-2-yl)allyloxy)(tert-butyl)dimethylsilane (1.6 g, 3.19 mmol) was ozonolyzed for 5-10 minutes. The mixture was quenched with the addition of 1 mL of DMS to and then allowed to warm to 23° C. After being diluted with DCM, the mixture was washed with 10% aqueous Na$_2$S$_2$O$_3$ (5×20 mL), dried with sodium sulfate and concentrated in vacuo. Silica gel chromatography using EtOAc in Hexanes gave rise to desired aldehyde (1.27 g, 79% yield). $^1$H-NMR: 400 MHz, (CDCl$_3$): δ: 9.94 (s, 1H); 8.41-8.36 (d, J=8.0 Hz, 1H); 7.60-7.55 (m, 1H); 7.53-7.45 (m, 2H); 7.39-7.32 (m, 2H); 7.29-7.24 (m, 2H); 5.16 (s, 1H); 2.63 (s, 3H); 0.86 (m, 15H).

Preparation of 2-(4-bromo-1-(4-chlorophenyl)-3-methylnaphthalen-2-yl)-2-(tert-butyldimethylsilyloxy)acetic acid: A DCM solution (8.0 mL) of 2-(4-bromo-1-(4-chlorophenyl)-3-methylnaphthalen-2-yl)-2-(tert-butyldimethylsilyloxy)acetaldehyde (0.65 g, 1.29 mmol) was combined with 2-methyl-2-butene (1.5 mL, 14.1 mmol), sodium dihydrogen phosphate (8.0 mL, 1.0 M) and sodium chlorite (1.37 g, 14.46 mmol) and stirred vigorously overnight. The mixture was diluted 200% with DCM, the acidity adjusted to pH<5 with 2 M NaHSO$_4$ and extracted with DCM (3×20 mL). The extracts were combined dried and concentrated under vacuo. The crude mixture was observed to contain the desired carboxylic acid (0.741 g) according to $^1$H NMR analysis and was used without purification. $^1$H-NMR: (400 MHz, CD$_3$OD): δ 8.35 (d, J=8.4 Hz, 1H); 7.58-7.51 (m, 3H); 7.46-7.44 (m, 1H); 7.39-7.33 (m, 1H); 7.31-7.22 (m, 2H); 5.33 (s, 1H); 2.72 (s, 3H); 0.825 (s, 9H); −0.03 (s, 3H); −0.26 (s, 3H).

Preparation of methyl 2-(4-bromo-1-(4-chlorophenyl)-3-methylnaphthalen-2-yl)-2-(tert-butyldimethylsilyloxy)acetate: Crude 2-(4-bromo-1-(4-chlorophenyl)-3-methylnaphthalen-2-yl)-2-(tert-butyldimethylsilyloxy)acetic acid 0.740 g, 1.4 mmol)was dissolved in 20 mL DCM-MeOH (50-50, v/v) and combined with TMS-diazomethane solution (7.0 mL, 2.0 M in hexanes) and allowed to stir 6 hrs at 23° C. The reaction was cooled on ice and quenched by the slow addition of TFA (500 μL) which simultaneously removed the yellow color from the reaction mixture. Mixture was diluted with DCM and washed with brine, then dried and concentrated in vacuo. Purification by silica gel chromatography with EtOAc in hexanes provided purified material (537.8 mg, 78% yield) from the 2-(4-bromo-1-(4-chlorophenyl)-3-methylnaphthalen-2-yl)-2-(tert-butyldimethylsilyloxy)acetaldehyde.
$^1$H-NMR: (400 MHz, MeOH-d$^4$): δ 8.39 (d, J=8.0 Hz, 1H); 7.58-7.54 (m, 1H); 7.50-7.47 (m, 2H); 7.37-7.33 (m, 2H); 7.27-7.21 (m, 2H); 5.31 (s, 1H); 3.69 (s, 3H); 2.67 (s, 3H); 0.83 (s, 9H); −0.04 (s, 3H); −0.27 (s, 3H).

Preparation of methyl 2-(4-bromo-1-(4-chlorophenyl)-3-methylnaphthalen-2-yl)-2-hydroxyacetate: Methyl 2-(4- bromo-1-(4-chlorophenyl)-3-methylnaphthalen-2-yl)-2-(tert-butyldimethylsilyloxy)acetate (537.8 mg, 1.01 mmol) was dissolved in 4.0 mL TFA and heated to 60° C. The reaction was monitored by HPLC and turned dark quickly after addition of TFA. The reaction was completed after 1 h by HPLC, was removed from heat and diluted with toluene (20 mL) and concentrated in vacuo. This dilution/concentration was repeated twice more and the color was observed to diminished on each cycle. Purification via column chromatography using silica gel with EtOAc and heptane gave rise to desired product (297.9 mg, 0.71 mmol). $^1$H-NMR: (400 MHz, CDCl$_3$): δ 10.34 (s, broad, 1H); 8.40 (d, J=8.0 Hz, 1H); 7.60-7.56 (m, 1H); 7.52-7.46 (m, 2H); 7.38-7.35 (m, 1H); 7.32-7.28 (m, 2H); 5.26 (s, 1H); 3.74 (s, 3H); 2.62 (s, 3H).

Preparation of methyl 2-(4-bromo-1-(4-chlorophenyl)-3-methylnaphthalen-2-yl)-2-tert-butoxyacetate (142): Methyl 2-(4-bromo-1-(4-chlorophenyl)-3-methylnaphthalen-2-yl)-2-hydroxyacetate (298 mg, 0.71 mmol) was dissolved in t-BuOAc (18.0 mL, 134 mmol) and 7 drops of perchloric acid were added. The reaction was monitored by HPLC and TLC for progress. After 4.5 hours, the mixture was added to icy saturated NaHCO$_3$ and stirred for 10-15 minutes. This mixture was extracted with EtOAc, extracts dried with sodium sulfate and concentrated in vacuo. Purification on silica gel using EtOAc in hexanes gave desired product as well as some starting material. $^1$H-NMR: (400 MHz, CDCl$_3$): δ 8.39 (d, J=8.8 Hz, 1H); 7.57-7.48 (m, 3H); 7.45-7.42 (m, 1H); 7.35-7.31 (m, 1H); 7.28-7.18 (m, 2H); 5.20 (s, 1H); 3.70 (s, 3H); 2.72 (s, 3H); 0.99 (s, 9H).

EXAMPLE 141

2-(4-(6-Aminopyridin-3-yl)-1-(4-chlorophenyl)-3-methylnaphthalen-2-yl)-2-tert-butoxyacetic acid (143)

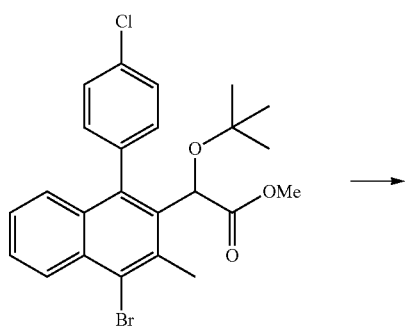

methyl 2-(4-bromo-1-(4-chlorophenyl)-3-methylnaphthalen-2-yl)-2-tert-butoxyacetate

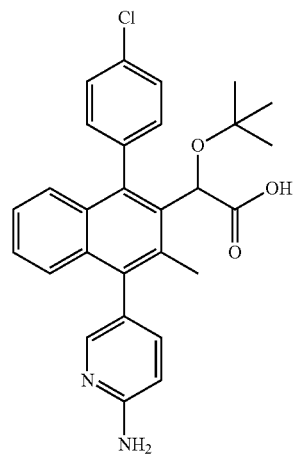

143
2-(4-(6-aminopyridin-3-yl)-1-(4-chlorophenyl)-3-methylnaphthalen-2-yl)-2-tert-butoxyacetic acid Preparation of 2-(4-(6-aminopyridin-3-yl)-1-(4-chlorophenyl)-3-methylnaphthalen-2-yl)-2-tert-butoxyacetic acid (143): 2-(4-(6-Aminopyridin-3-yl)-1-(4-chlorophenyl)-3-methylnaphthalen-2-yl)-2-tert-butoxyacetic acid (143) was prepared in a manner similar to 2-tert-butoxy-2-(1-(4-chlorophenyl)-3,4-dimethylnaphthalen-2-yl)acetic acid of Example 125, except using methyl 2-(4-bromo-1-(4-chlorophenyl)-3-methylnaphthalen-2-yl)-2-tert-butoxyacetate as the starting material and 2-aminopyridin-5-yl-boronic acid pinacolate ester in the Suzuki reaction, giving the title compound (mono trifluoroacetic acid salt). $^1$H-NMR: (400 MHz, DMSO-d$^6$): δ 8.06-7.86 (m, 4H), 7.76-7.68 (m, 2H), 7.56-7.37 (m, 5H), 7.26 (d, J=8.6 Hz, 1H), 7.17-7.13 (m, 1H), 5.13 (s, 1H), 2.33 (s, 3H), 0.96 (s, 9H). $^{19}$F-NMR: (377 MHz, DMSO-d$^6$): δ-74.2 (s). LCMS-ESI$^+$ (m/z): [M+H]$^+$ calcd for C$_{28}$H$_{28}$ClN$_2$O$_3$: 475.2; Found: 475.2.

EXAMPLE 142

2-tert-Butoxy-2-(1-(4-chlorophenyl)-3-methyl-4-(6-oxo-1,6-dihydropyridin-3-yl)naphthalen-2-yl)acetic acid (144)

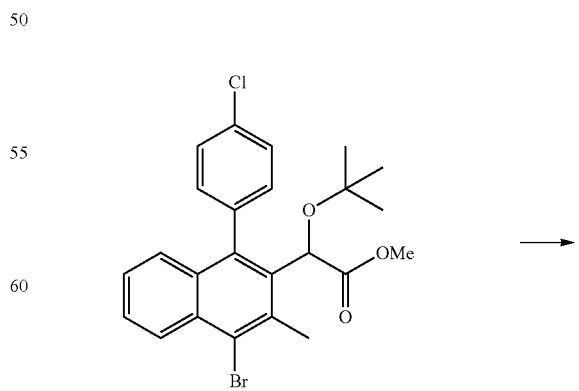

methyl 2-(4-bromo-1-(4-chlorophenyl)-3-methylnaphthalen-2-yl)-2-tert-butoxyacetate

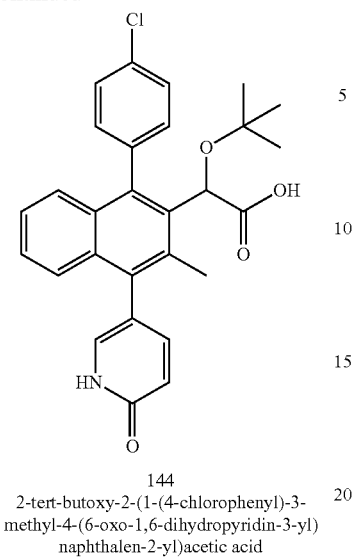

144
2-tert-butoxy-2-(1-(4-chlorophenyl)-3-methyl-4-(6-oxo-1,6-dihydropyridin-3-yl)naphthalen-2-yl)acetic acid Preparation of 2-tert-butoxy-2-(1-(4-chlorophenyl)-3-methyl-4-(6-oxo-1,6-dihydropyridin-3-yl)naphthalen-2-yl)acetic acid (144): 2-tert-Butoxy-2-(1-(4-chlorophenyl)-3-methyl-4-(6-oxo-1,6-dihydropyridin-3-yl)naphthalen-2-yl)acetic acid (144) was prepared in a manner similar to 2-tert-butoxy-2-(1-(4-chlorophenyl)-3,4-dimethylnaphthalen-2-yl)acetic acid of Example 125, except using methyl 2-(4-bromo-1-(4-chlorophenyl)-3-methylnaphthalen-2-yl)-2-tert-butoxyacetate as the starting material and 2-(1H)pyridone-5-yl-boronic acid pinacolate ester in the Suzuki reaction, giving the title compound (parent form). $^1$H-NMR: (400 MHz, DMSO-d$^6$): δ 12.8 (s, broad, 1H), 11.8 (app. s, broad, 1H), 7.67-7.30 (m, 10H), 7.23 (d, J=8.2 Hz, 1H), 5.11 (s, 1H), 2.36 (s, 3H), 0.95 (s, 9H). LCMS-ESI$^+$ (m/z): [M+H]$^+$ calcd for $C_{28}H_{27}ClNO_4$: 476.2; Found: 476.2.

EXAMPLE 143

2-(4-(2-Aminopyrimidin-5-yl)-1-(4-chlorophenyl)-3-methylnaphthalen-2-yl)-2-tert-butoxyacetic acid (145)

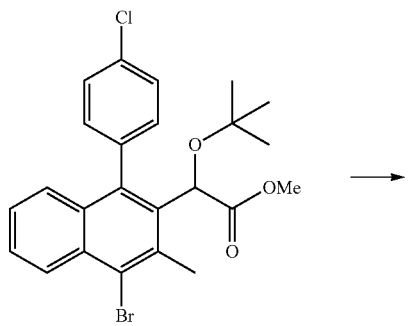

methyl 2-(4-bromo-1-(4-chlorophenyl)-3-methylnaphthalen-2-yl)-2-tert-butoxyacetate

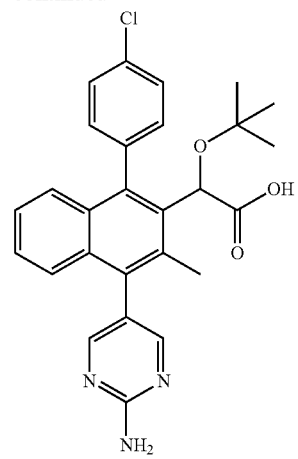

145
2-(4-(2-aminopyrimidin-5-yl)-1-(4-chlorophenyl)-3-methylnaphthalen-2-yl)-2-tert-butoxyacetic acid Preparation of 2-(4-(2-aminopyrimidin-5-yl)-1-(4-chlorophenyl)-3-methylnaphthalen-2-yl)-2-tert-butoxyacetic acid (145): 2-(4-(2-Aminopyrimidin-5-yl)-1-(4-chlorophenyl)-3-methylnaphthalen-2-yl)-2-tert-butoxyacetic acid (145) was prepared in a manner similar to 2-tert-butoxy-2-(1-(4-chlorophenyl)-3,4-dimethylnaphthalen-2-yl)acetic acid of Example 125, except using methyl 2-(4-bromo-1-(4-chlorophenyl)-3-methylnaphthalen-2-yl)-2-tert-butoxyacetate as the starting material and 2-aminopyrimidine-5-yl-boronic acid pinacolate ester in the Suzuki reaction, giving the title compound (mono trifluoroacetic acid salt form).

$^1$H-NMR: (400 MHz, DMSO-d$^6$): δ 12.8 (s, broad, 1H), 8.26-8.24 (m, 2H), 7.75-7.67 (m, 2H), 7.55 (dd, J=7.8, 2.0 Hz, 1H), 7.53-7.41 (m, 4H), 7.24 (d, J=8.2 Hz, 1H), 7.16 (s, broad, 2H), 5.13 (s, 1H), 2.34 (s, 3H), 0.95 (s, 9H). $^{19}$F-NMR: (400 MHz, DMSO-d$^6$): δ –74.9 (s). LCMS-ESI$^+$ (m/z): [M+H]$^+$ calcd for $C_{27}H_{27}ClN_3O_3$: 476.2; Found: 476.2.

EXAMPLE 144

2-tert-Butoxy-2-(1-(4-chlorophenyl)-3-methyl-4-(2-oxo-1,2-dihydropyrimidin-5-yl)naphthalen-2-yl)acetic acid (146)

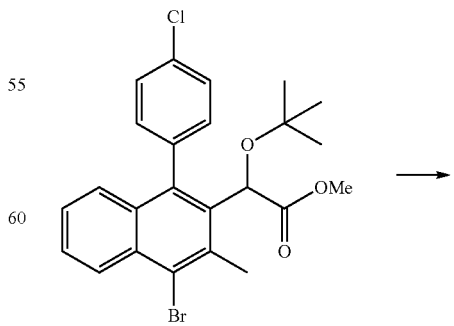

methyl 2-(4-bromo-1-(4-chlorophenyl)-3-methylnaphthalen-2-yl)-2-tert-butoxyacetate

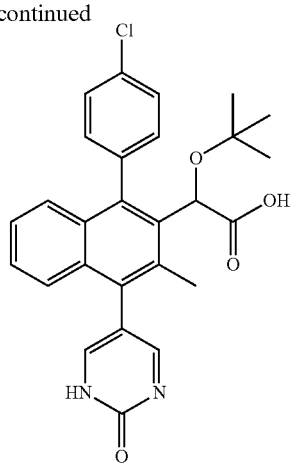

146
2-tert-butoxy-2-(1-(4-chlorophenyl)-3-methyl-
4-(2-oxo-1,2-dihydropyrimidin-
5-yl)naphthalen-2-yl)acetic acid Preparation of 2-tert-butoxy-2-(1-(4-chlorophenyl)-3-methyl-4-(2-oxo-1,2-dihydropyrimidin-5-yl)naphthalen-2-yl) acetic acid (146): A suspension methyl 2-(4-bromo-1-(4-chlorophenyl)-3-methylnaphthalen-2-yl)-2-tert-butoxyacetate (10.5 mg, 22.1 μmol), [1H]pyrimidin-2-one-5-yl-boronic acid (25 mg, 0.11 mmol), PdCl$_2$(dppf) (3.2 mg, 4.4 μmol), K$_2$CO$_3$ (46 mg, 0.33 mmol), PhMe (500 μL), EtOH (absolute, 250 μL), and H$_2$O (250 μL) was heated to 100° C. for 30 min, but conversion was poor. The reaction was treated with glacial AcOH (60 μL, 1.05 mmol) and KF (40 mg, 0.688 mmol). More PdCl$_2$(dppf) (3.2 mg, 4.4 μmol) and [1H]pyrimidin-2-one-5-yl-boronic acid (7 mg, 30 μmol) were added and the reaction was heated to 100° C. After 2 h, the reaction was added to H$_2$O (15 mL) and glacial AcOH (0.2 mL). The system was extracted with EtOAc (3×10 mL). Combined organic phases were dried (Na$_2$SO$_4$), filtered, and concentrated. The crude material was treated with THF (750 μL), EtOH (absolute, 750 μL), H$_2$O (500 μL), and LiOH monohydrate (50 mg 1.2 mmol). The suspension was heated to 100° C. for 30 min. The reaction was cooled to 23° C., filtered through a 0.45 micron filter, and directly purified by reverse phase HPLC (Gemini, 5 to 100% ACN/H$_2$O+0.1% TFA). The product-containing fractions were combined and lyophilized, giving the title compound (parent form) (3.8 mg, 36% over 2 steps). $^1$H-NMR: (400 MHz, DMSO-d$^6$): δ 12.8 (s, broad, 1H), 8.29 (app. s, broad, 1H), 7.75-7.68 (m, 2H), 7.58-7.44 (m, 4H), 7.43-7.38 (m, 2H), 7.25 (d, J=8.2 Hz, 1H), 5.12 (s, 1H), 2.38 (s, 3H), 0.96 (s, 9H). LCMS-ESI$^+$ (m/z): [M+H]$^+$ calcd for C$_{27}$H$_{26}$ClN$_2$O$_4$: 477.2; Found: 477.2.

EXAMPLE 145

2-tert-Butoxy-2-(1-(4-chlorophenyl)-4-cyano-3-methylnaphthalen-2-yl)acetic acid (147)

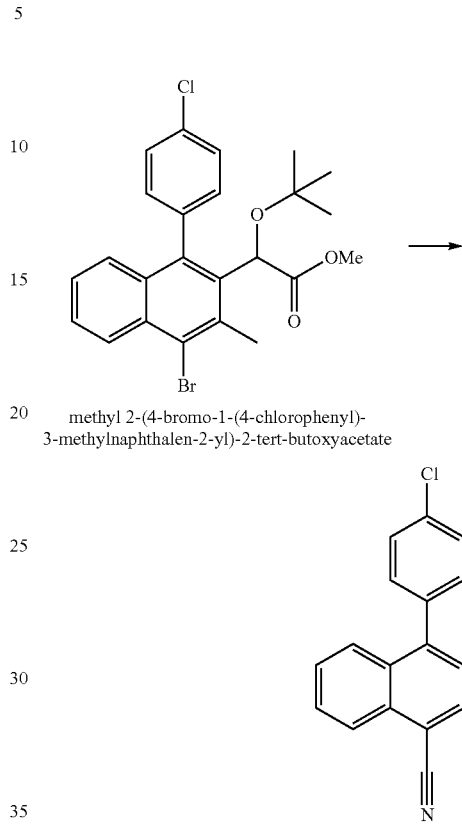

methyl 2-(4-bromo-1-(4-chlorophenyl)-
3-methylnaphthalen-2-yl)-2-tert-butoxyacetate 147
2-tert-butoxy-2-(1-(4-chlorophenyl)-4-
cyano-3-methylnaphthalen-2-yl)acetic acid Preparation of 2-tert-butoxy-2-(1-(4-chlorophenyl)-4-cyano-3-methylnaphthalen-2-yl)acetic acid (147): A suspension of methyl 2-(4-bromo-1-(4-chlorophenyl)-3-methylnaphthalen-2-yl)-2-tert-butoxyacetate (10.5 mg, 22.1 μmol), CuCN (9.8 mg, 0.11 mmol), and NMP (500 μL) was heated to 200° C. in a microwave. The reaction was cooled to 23° C., treated with EtOH (2.5 mL), filtered through a 0.45 micron filter, and directly purified by reverse phase HPLC (Gemini, 5 to 100% ACN/H$_2$O+0.1% TFA). The product-containing fractions were combined and treated with LiOH monohydrate until the pH was distinctly basic. The mixture was concentrated with warming to remove most of the water and all of the CH$_3$CN. The solution was treated with EtOH (absolute, 500 μL) and THF (1.0 mL). The suspension was stirred at 23° C. for 1 h. It was filtered through a 0.45 micron filter, and directly purified by reverse phase HPLC (Gemini, 5 to 100% ACN/H$_2$O+0.1% TFA). The product-containing fractions were combined and lyophilized, giving the title compound (parent form) (5.2 mg, 55% over 2 steps).

$^1$H-NMR: (400 MHz, DMSO-d$^6$): δ 13.12 (s, 1H), 8.16 (d, J=8.2 Hz, 1H), 7.82 (dd, J=7.8, 7.7 Hz, 1H), 7.77-7.70 (m, 2H), 7.60 (dd, J=8.0, 80 Hz, 1H), 7.48 (d, J=8.2 Hz, 1H), 7.43 (d, J=8.2 Hz, 1H), 7.33 (d, J=8.2 Hz, 1H), 5.07 (s, 1 h), 2.83 (s, 3H), 0.95 (s, 9H). LCMS-ESI$^-$ (m/z): [M–H]$^-$ calcd for C$_{48}$H$_{43}$Cl$_2$N$_2$O$_4$: 813.3; Found: 813.3.

EXAMPLE 146

Ethyl 2-(7-chloro-1-(4-chlorophenyl)-3-methylnaphthalen-2-yl)-2oxoacetate (148)

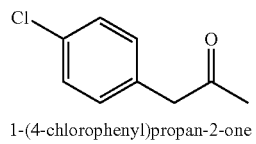

1-(4-chlorophenyl)propan-2-one

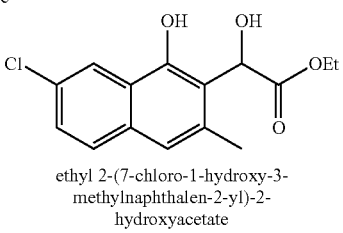

ethyl 2-(7-chloro-1-hydroxy-3-methylnaphthalen-2-yl)-2-hydroxyacetate

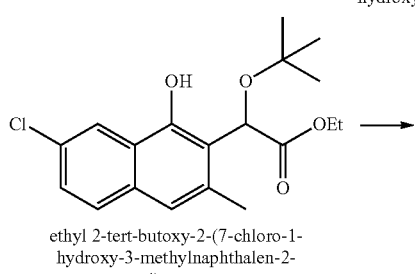

ethyl 2-tert-butoxy-2-(7-chloro-1-hydroxy-3-methylnaphthalen-2-yl)acetate

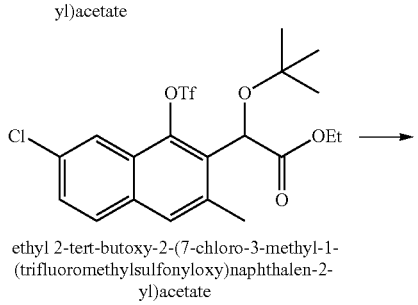

ethyl 2-tert-butoxy-2-(7-chloro-3-methyl-1-(trifluoromethylsulfonyloxy)naphthalen-2-yl)acetate

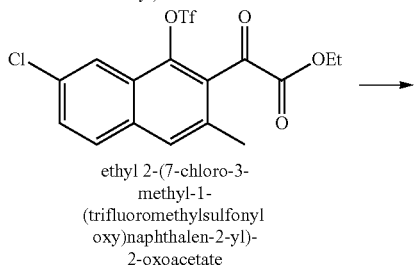

ethyl 2-(7-chloro-3-methyl-1-(trifluoromethylsulfonyloxy)naphthalen-2-yl)-2-oxoacetate

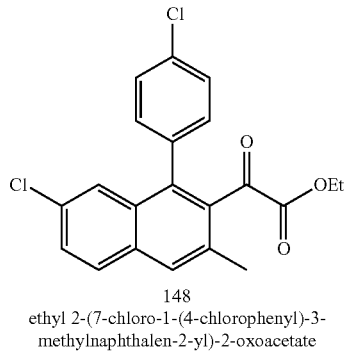

148
ethyl 2-(7-chloro-1-(4-chlorophenyl)-3-methylnaphthalen-2-yl)-2-oxoacetate

Preparation of ethyl 2-(7-chloro-1-hydroxy-3-methyl-naphthalen-2-yl)-2-hydroxyacetate: Prepared in a manner similar to ethyl 2-(6-chloro-7-fluoro-1-hydroxy-3-methyl-naphthalen-2-yl)-2-hydroxyacetate of Example 99 except using 1-(4-chlorophenyl)propan-2-one. $^1$H-NMR: (400 MHz, CDCl$_3$): δ 8.42 (s, broad, 1H), 8.18 (d, J=2.0 Hz, 1H), 7.59 (d, J=8.6 Hz, 1H), 7.38 (dd, J=8.6, 2.0 Hz, 1H), 7.18 (s, 1H), 5.68 (s, 1H), 4.33-4.10 (m, 2H), 2.53 (s, 3H), 1.20 (t, J=7.0 Hz, 3H).

Preparation of ethyl 2-tert-butoxy-2-(7-chloro-1-hydroxy-3-methyl-naphthalen-2-yl)acetate: Prepared in a similar manner to ethyl 2-tert-butoxy-2-(1-hydroxy-3-methylnaphthalen-2-yl)acetate of Example 120, except using ethyl 2-(7-chloro-1-hydroxy-3-methylnaphthalen-2-yl)-2-hydroxyacetate. $^1$H-NMR: (400 MHz, CDCl$_3$): δ 9.01 (s, 1H), 8.22 (d, J=2.0 Hz, 1H), 7.56 (d, J=8.6 Hz, 1H), 7.35 (dd, J=8.6, 2.0 Hz, 1H), 7.13 (s, 1H), 5.49 (s, 1H), 4.22-4.08 (m, 2H), 2.56 (s, 3H), 1.31 (s, 9H), 1.19 (t, J=7.0 Hz, 3H).

Preparation of ethyl 2-tert-butoxy-2-(7-chloro-3-methyl-1-(trifluoromethylsulfonyloxy)naphthalen-2-yl)acetate:
Ethyl 2-tert-butoxy-2-(7-chloro-3-methyl-1-(trifluoromethylsulfonyloxy)naphthalen-2-yl)acetate was prepared in a similar manner to ethyl 2-(7-bromo-3-methyl-1-(trifluoromethylsulfonyloxy)-naphthalen-2-yl)-2-(4-methoxybenzyloxy)acetate of Example 67, except using ethyl 2-tert-butoxy-2-(7-chloro-1-hydroxy-3-methylnaphthalen-2-yl)acetate.
$^1$H-NMR: (400 MHz, CDCl$_3$): δ 8.00 (d, J=2.0 Hz, 1H), 7.73 (d, J=8.6 Hz, 1H), 7.65 (s, 1H), 7.49 (dd, J=8.6, 2.0 Hz, 1H), 5.72 (s, 1H), 4.26-4.08 (m, 2H), 2.54 (s, 3H), 1.20 (s, 9H), 1.17 (t, J=7.0 Hz, 3H).
$^{19}$F-NMR: (377 MHz, CDCl$_3$): δ 73.2 (s)

Preparation of ethyl 2-(7-chloro-1-(4-chlorophenyl)-3-methylnaphthalen-2-yl)-2-oxoacetate: Ethyl 2-(7-chloro-1-(4-chlorophenyl)-3-methylnaphthalen-2-yl)-2-oxoacetate was prepared in a similar manner to 2-(6-chloro-7-fluoro-3-methyl-1-(trifluoromethylsulfonyloxy)naphthalen-2-yl)-2-oxoacetate of Example 99, except using ethyl 2-tert-butoxy-2-(7-chloro-3-methyl-1-(trifluoromethylsulfonyloxy) naphthalen-2-yl)acetate. $^1$H-NMR: (400 MHz, CDCl$_3$): δ 8.05 (d, J=2.0 Hz, 1H), 7.79 (d, J=8.6 Hz, 1H), 7.74 (s, 1H), 7.58 (dd, J=8.6, 2.0 Hz, 1H), 4.41 (q, J=7.0 Hz, 2H), 2.48 (s, 3H), 1.40 (t, J=7.0 Hz, 3H). $^{19}$F-NMR: (377 MHz, CDCl$_3$): δ−73.2 (s)

Preparation of ethyl 2-(7-chloro-1-(4-chlorophenyl)-3-methylnaphthalen-2-yl)-2-oxoacetate (148): Ethyl 2-(7-chloro-1-(4-chlorophenyl)-3-methylnaphthalen-2-yl)-2-oxoacetate (148) was prepared in a manner similar to ethyl 2-(7-bromo-1-(4-chlorophenyl)-3-methylnaphthalen-2-yl)-2-oxoacetate of Example 67, except using ethyl 2-(7-chloro-1-(4-chlorophenyl)-3-methylnaphthalen-2-yl)-2-oxoacetate. $^1$H-NMR: (400 MHz, CDCl$_3$): δ 7.78 (d, J=8.6 Hz, 1H), 7.73 (s, 1H), 7.50-7.22 (m, 6H), 4.12 (q, J=7.0 Hz, 2H), 2.49 (s, 3H), 1.13 (t, J=7.0 Hz, 3H).

EXAMPLE 147

2-tert-Butoxy-2-(7-chloro-1-(4-chlorophenyl)-3-methylnaphthalen-2-yl)acetic acid (149)

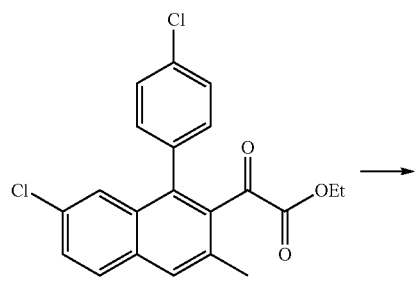

ethyl 2-(7-chloro-1-(4-chlorophenyl)-3-methylnaphthalen-2-yl)-2-oxoacetate

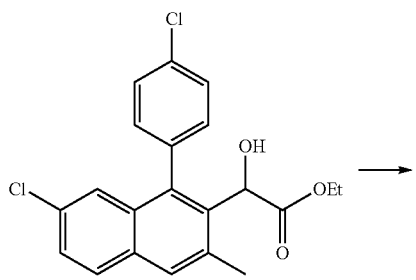

ethyl 2-(7-chloro-1-(4-chlorophenyl)-3-methylnaphthalen-2-yl)-2-hydroxyacetate

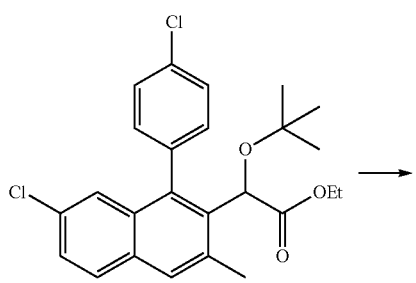

ethyl 2-tert-butoxy-2-(7-chloro-1-(4-chlorophenyl)-3-methylnaphthalen-2-yl)acetate

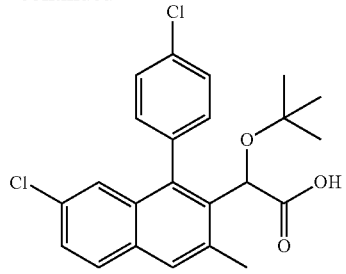

149
2-tert-butoxy-2-(7-chloro-1-(4-chlorophenyl)-3-methylnaphthalen-2-yl)acetic acid Preparation of ethyl 2-(7-chloro-1-(4-chlorophenyl)-3-methylnaphthalen-2-yl)-2-hydroxyacetate: A solution of ethyl 2-(7-chloro-1-(4-chlorophenyl)-3-methyl-naphthalen-2-yl)-2-oxoacetate (26 mg, 67 μmol) in EtOH (absolute, 1.0 mL) and DCM (1.0 mL) was treated with NaBH$_4$ (5.1 mg, 0.134 mmol) at 23° C. After 1 h, saturated NH$_4$Cl (1.0 mL) was added. The reaction was stirred overnight, then diluted with H$_2$O (10 mL). The mixture was extracted with DCM (3×), and the combined organics dried (Na$_2$SO$_4$), filtered, and concentrated, giving the title compound (28 mg, >99% yield). $^1$H-NMR: (400 MHz, CDCl$_3$): δ 7.72 (d, J=8.6 Hz, 1H), 7.65 (s, 1H), 7.51-7.22 (m, 6H), 5.19 (s, 1H), 4.35-4.17 (m, 2H), 2.49 (s, 3H), 1.20 (t, J=7.0 Hz, 3H).

Preparation of ethyl 2-tert-butoxy-2-(7-chloro-1-(4-chlorophenyl)-3-methylnaphthalen-2-yl)acetate: Ethyl 2-tert-butoxy-2-(7-chloro-1-(4-chlorophenyl)-3-methylnaphthalen-2-yl)acetate was prepared in a manner similar to (S)-ethyl 2-tert-butoxy-2-(1-(4-chlorophenyl)-3-methyl-6-(trifluoromethylsulfonyl-oxy)naphthalen-2-yl)acetate of Example 51, except using racemic ethyl 2-(7-chloro-1-(4-chlorophenyl)-3-methylnaphthalen-2-yl)-2-hydroxyacetate. Material was carried on crude without further characterization.

Preparation of 2-tert-butoxy-2-(7-chloro-1-(4-chlorophenyl)-3-methylnaphthalen-2-yl)acetic acid (149): 2-tert-Butoxy-2-(7-chloro-1-(4-chlorophenyl)-3-methylnaphthalen-2-yl)acetic acid (149) was prepared in a similar manner to 2-(4-bromo-1-(4-chlorophenyl)-3-methylnaphthalen-2-yl)-2-tert-butoxyacetic acid of Example 124, except using ethyl 2-tert-butoxy-2-(7-chloro-1-(4-chlorophenyl)-3-methyl-naphthalen-2-yl)acetate, giving the title compound (parent form) $^1$H-NMR: (400 MHz, DMSO-d$^6$): δ 12.86 (s, broad, 1H), 7.94 (d, J=8.0 Hz, 1H), 7.83 (s, 1H), 7.73-7.67 (m, 2H), 7.56-7.49 (m, 2H), 7.40 (d, J=8.2 Hz, 1H), 7.11 (d, J=1.6 Hz, 1H), 5.00 (s, 1H), 2.57 (s, 3H), 0.93 (s, 9H). LCMS-ESI$^-$ (m/z): [M−H]$^-$ calcd for C$_{23}$H$_{21}$Cl$_2$O$_3$: 415.1; Found: 415.3.

EXAMPLE 148

(R)-2-(4-Bromo-1-(4-chlorophenyl)-3-methylnaphthalen-2-yl)-2-tert-butoxyacetic acid (150A) and
(S)-2-(4-bromo-1-(4-chlorophenyl)-3-methylnaphthalen-2-yl)-2-tert-butoxyacetic acid (150B)

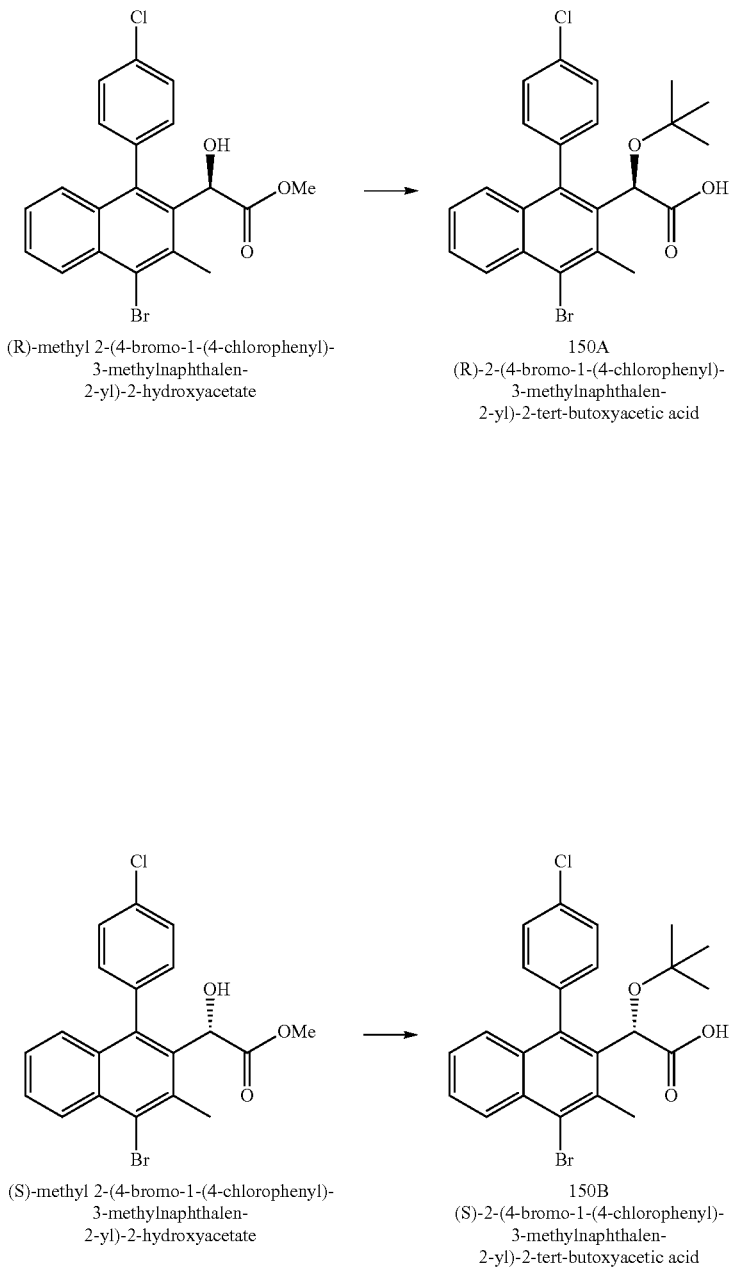

Chiral chromatographic separation of the two enantiomers of methyl 2-(4-bromo-1-(4-chlorophenyl)-3-methylnaphthalen-2-yl)-2-hydroxyacetate: A solution of the racemate (36 mg) in MeOH/EtOH 1:1 v/v (1.8 mL total) was separated preparatively into its two enantiomers on an OJ-H packed chiral column, (R)-methyl 2-(4-bromo-1-(4-chlorophenyl)-3-methylnaphthalen-2-yl)-2-hydroxyacetate (6.1 mg).

$^1$H-NMR: (400 MHz, CDCl$_3$): δ 10.34 (s, broad, 1H); 8.40 (d, J=8.0 Hz, 1H); 7.60-7.56 (m, 1H); 7.52-7.46 (m, 2H); 7.38-7.35 (m, 1H); 7.32-7.28 (m, 2H); 5.26 (s, 1H); 3.74 (s, 3H); 2.62 (s, 3H). (S)-methyl 2-(4-bromo-1-(4-chlorophenyl)-3-methylnaphthalen-2-yl)-2-hydroxyacetate (4.8 mg)

Preparation of (R)-2-(4-bromo-1-(4-chlorophenyl)-3-methylnaphthalen-2-yl)-2-tert-butoxyacetic acid (150A): (R)-2-(4-Bromo-1-(4-chlorophenyl)-3-methylnaphthalen-2-yl)-2-tert-butoxyacetic acid (150A) was prepared in a similar manner to 2-(4-bromo-1-(4-chlorophenyl)-3-methylnaphthalen-2-yl)-2-tert-butoxyacetic acid of Example 124, except using (R)-methyl 2-(4-bromo-1-(4-chlorophenyl)-3-methylnaphthalen-2-yl)-2-hydroxyacetate, giving the title compound (parent form). $^1$H NMR (400 MHz, CD$_3$OD) δ 8.38 (d, J=8.6 Hz, 1H), 7.63-7.47 (m, 4H), 7.38-7.20 (m, 3H), 5.30 (s, 1H), 2.69 (s, 3H), 1.00 (s, 9H). LCMS-ESI$^-$ (m/z): [M—CO$_2$—H]$^-$ calcd for C$_{22}$H$_{21}$BrClO: 415.2; Found: 415.0.

Preparation of (S)-2-(4-bromo-1-(4-chlorophenyl)-3-methylnaphthalen-2-yl)-2-tert-butoxyacetic acid (150B): (S)-2-(4-Bromo-1-(4-chlorophenyl)-3-methylnaphthalen-2-yl)-2-tert-butoxyacetic acid (150B) was prepared in a similar manner to 2-(4-bromo-1-(4-chlorophenyl)-3-methylnaphthalen-2-yl)-2-tert-butoxyacetic acid of Example 124, except using (S)-methyl 2-(4-bromo-1-(4-chlorophenyl)-3-methylnaphthalen-2-yl)-2-hydroxyacetate, giving the title compound (parent form). $^1$H NMR (400 MHz, CD$_3$OD) δ 8.38 (d, J=8.6 Hz, 1H), 7.63-7.47 (m, 4H), 7.38-7.20 (m, 3H), 5.30 (s, 1H), 2.69 (s, 3H), 1.00 (s, 9H). LCMS-ESI$^-$ (m/z): [M—CO$_2$—H]$^-$ calcd for C$_{22}$H$_{21}$BrClO: 415.2; Found: 415.0.

EXAMPLE 149

Compounds 151-180

Compounds 151-180 were prepared by similar methods as described in the above Examples.

| Compound Number | Compound | Mass | Measured mass |
|---|---|---|---|
| 151 | | 490 | 490.33 |
| 152 | | 493.96 | 494.07 |
| 153 | | 537.59 | 538.03 |

-continued

| Compound Number | Compound | Mass | Measured mass |
|---|---|---|---|
| 154 | | 484.53 | 485.1 |
| 155 | | 502.54 | 503.1 |
| 156 | | 473.54 | 474.14 |
| 157 | | 394.51 | 393.0 9(M − H) |
| 158 | | 417.48 | 418.1 |

-continued

| Compound Number | Compound | Mass | Measured mass |
|---|---|---|---|
| 159 | | 417.48 | 418.1 |
| 160 | | 417.48 | 418.1 |
| 161 | | 441.53 | 442.1 |
| 162 | | 459.52 | 460.16 |
| 163 | | 475.97 | 473.91/475.48 |

-continued
| Compound Number | Compound | Mass | Measured mass |
|---|---|---|---|
| 164 | 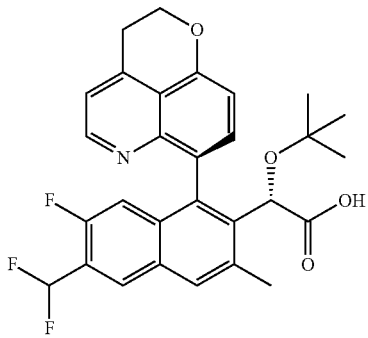 | 509.5 | 506.1 |
| 165 | 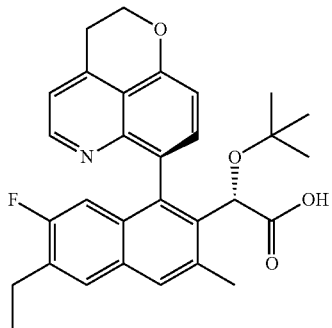 | 488.6 | 489.1 |
| 166 | 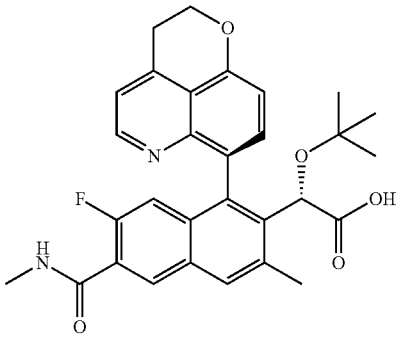 | 516.57 | 517.1 |
| 167 | 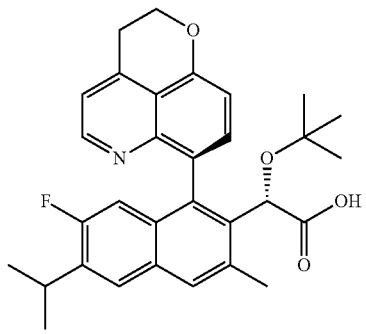 | 501.6 | 502.1 |

-continued
| Compound Number | Compound | Mass | Measured mass |
|---|---|---|---|
| 168 | 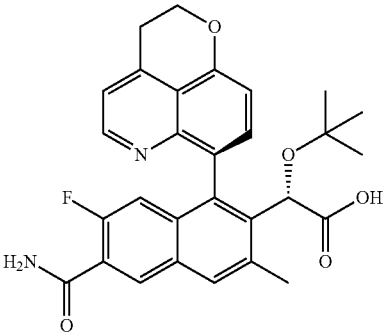 | 502.54 | 503.1 |
| 169 | 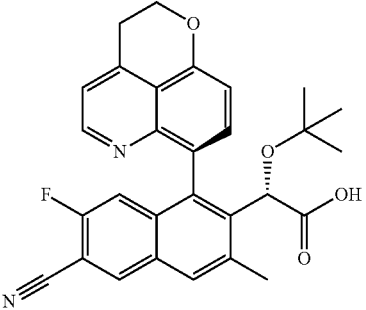 | 484.53 | 485.1 |
| 170 | 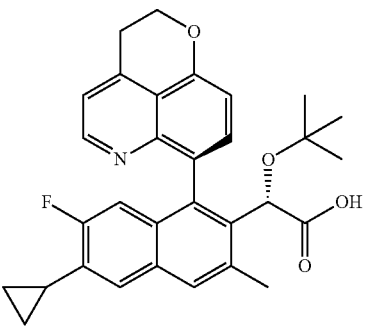 | 499.58 | 500.2 |
| 171 | 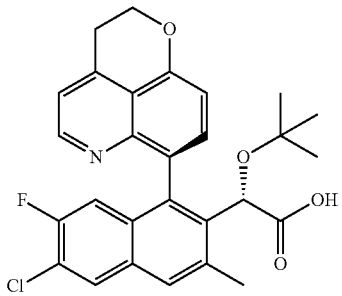 | 494.96 | 494.4/496.1 |

-continued

| Compound Number | Compound | Mass | Measured mass |
|---|---|---|---|
| 172 | | 477.51 | 478.1 |
| 173 | | 477.51 | 478.1 |
| 174 | | 477.51 | 478.1 |
| 175 | | 467.49 | 468.1 |
| 176 | | 522.64 | 523.1 |

-continued

| Compound Number | Compound | Mass | Measured mass |
|---|---|---|---|
| 177 | | 475.97 | 474.37 |
| 178 | | 459.52 | 460.5 |
| 179 | | 459.52 | 460.4 |
| 180 | | 475.97 | 476.4 |

EXAMPLE 150

Preparation of (S)-2-tert-butoxy-2-((R)-6-(difluoromethyl)-1-(2,3-dihydropyrano[4,3,2-de]quinolin-7-yl)-3-methynaphthalen-2-yl)acetic acid (181)

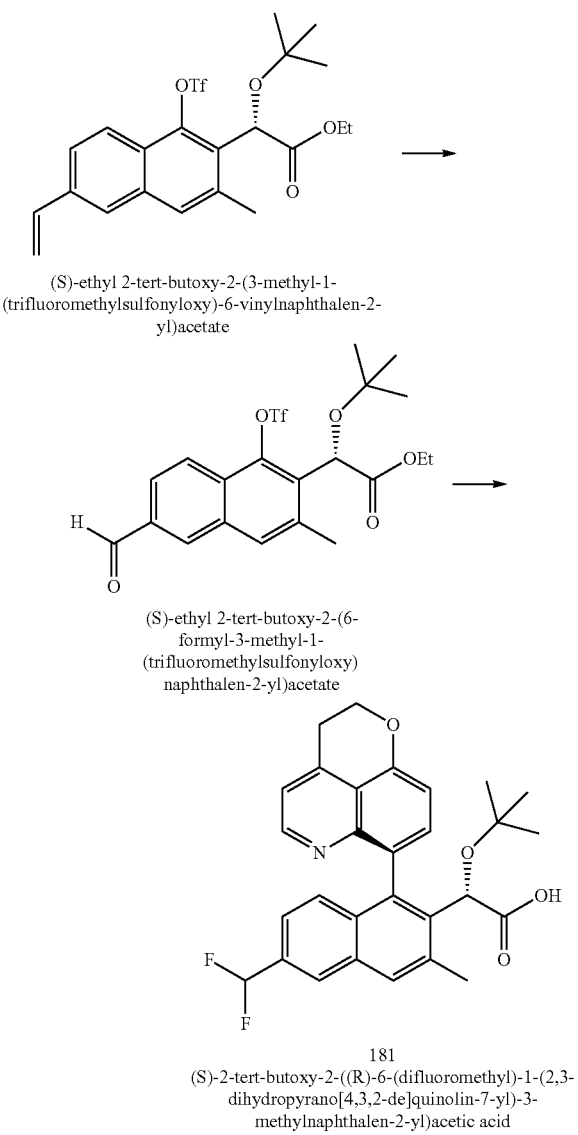

(S)-ethyl 2-tert-butoxy-2-(3-methyl-1-(trifluoromethylsulfonyloxy)-6-vinylnaphthalen-2-yl)acetate (S)-ethyl 2-tert-butoxy-2-(6-formyl-3-methyl-1-(trifluoromethylsulfonyloxy)naphthalen-2-yl)acetate 181
(S)-2-tert-butoxy-2-((R)-6-(difluoromethyl)-1-(2,3-dihydropyrano[4,3,2-de]quinolin-7-yl)-3-methylnaphthalen-2-yl)acetic acid Preparation of (S)-ethyl 2-tert-butoxy-2-(6-formyl-3-methyl-1-(trifluoromethyl-sulfonyloxy)naphthalen-2-yl)acetate: A solution of (S)-ethyl 2-tert-butoxy-2-(3-methyl-1-(trifluoromethylsulfonyloxy)-6-vinylnaphthalen-2-yl)acetate (0.60 g, 1.3 mmol, prepared similarly to (S)-ethyl 2-tert-butoxy-2-(7-fluoro-3-methyl-1-(trifluoromethylsulfonyloxy)-6-vinylnaphthalen-2-yl)acetate from Example 101) in THF (7 mL) at rt was treated with a previously prepared mixture of $K_2OsO_4 \cdot 2H_2O$ (0.023 g, 0.063 mmol) and $NaIO_4$ (0.81 g, 3.8 mmol) in water (5 mL). The resulting suspension becomes thick and opaque. After vigorous stirring for 20 min, the suspension is filtered through a pad of Celite, and the filtrate is washed with batches of EtOAc until white in color. The collected mother liquor is further diluted with water and EtOAc. Following separation, the aqueous layer is extracted with EtOAc until colorless. The combined organics are washed with brine, dried over anhydrous $MgSO_4$ and concentrated in vacuo. The residue is purified by Yamazen column chromatography (15-35% EtOAc/hex) to afford 0.348 g (60%) of the desired material as a pale yellow amorphous solid. $^1$H-NMR: 400 MHz, (CDCl$_3$) δ: 10.19 (s, 1H); 8.31 (br s, 1H); 8.16 (d, J=8.8 Hz, 1H); 8.05 (dd, J=8.8, 1.6 Hz, 1H); 7.85 (s, 1H); 5.76 (s, 1H); 4.28-4.10 (m, 2H); 2.61 (s, 3H); 1.22 (s, 9H); 1.18 (t, J=7.2 Hz, 3H).

Preparation of (S)-2-tert-butoxy-2-((R)-6-(difluoromethyl)-1-(2,3-dihydropyrano[4,3,2-de]quinolin-7-yl)-3-methylnaphthalen-2-yl)acetic acid (181): (S)-ethyl 2-tert-butoxy-2-(6-formyl-3-methyl-1-(trifluoromethylsulfonyl-oxy)naphthalen-2-yl)acetate was treated to a sequence of synthetic steps with appropriate adjustments for scale similar to the conversion of (S)-ethyl 2-tert-butoxy-2-(7-fluoro-6-formyl-3-methyl-1-(trifluoromethylsulfonyloxy)naphthalen-2-yl)acetate to (S)-2-tert-butoxy-2-((R)-6-(difluoromethyl)-1-(2,3-dihydropyrano[4,3,2-de]quinolin-7-yl)-7-fluoro-3-methylnaphthalen-2-yl)acetic acid in Example 101 to produce 0.039 g of the title compound (TFA salt) as an amorphous pale yellow powder. LCMS-ESI$^+$ (m/z): [M+H]$^+$ calcd for $C_{29}H_{28}F_2NO_4$: 492.2; found: 492.1. $^1$H-NMR: 400 MHz, (CD$_3$OD) δ: 8.67 (d, J=4.4 Hz, 1H); 8.13 (s, 1H); 8.08 (s, 1H); 7.85-7.99 (m, 2H); 7.46 (d, J=8.8 Hz, 1H); 7.40 (d, J=8.8 Hz, 1H); 7.07 (d, 8.8 Hz, 1H); 6.90 (t, J$_{HF}$=56 Hz, 1H); 5.26 (s, 1H); 4.77-4.69 (m, 2H); 3.67 (t, J=6 Hz, 2H); 2.80 (s, 3H); 0.93 (s, 9H).

EXAMPLE 151

Preparation of (S)-ethyl 2-tert-butoxy-2-(4-carbamoyl-3-methyl-1-(trifluoromethylsulfonyloxy)naphthalen-2-yl)acetate (182)

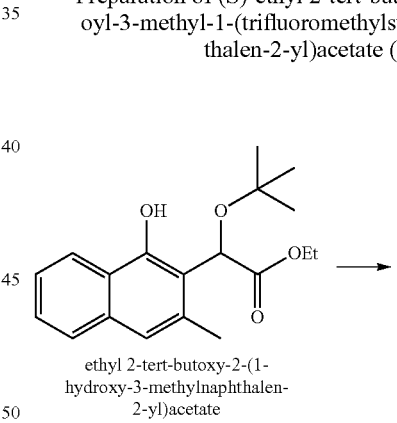

ethyl 2-tert-butoxy-2-(1-hydroxy-3-methylnaphthalen-2-yl)acetate

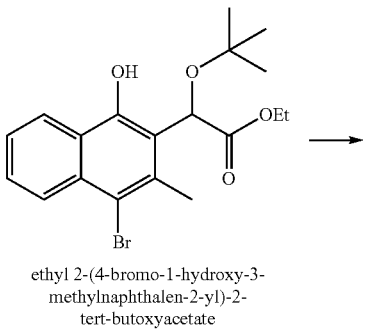

ethyl 2-(4-bromo-1-hydroxy-3-methylnaphthalen-2-yl)-2-tert-butoxyacetate

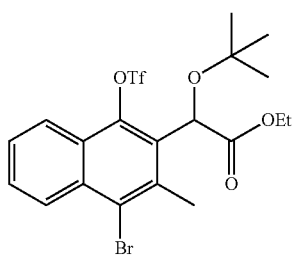

ethyl 2-(4-bromo-3-methyl-1-
(trifluoromethylsulfonyloxy)naphthalen-
2-yl)-2-tert-butoxyacetate

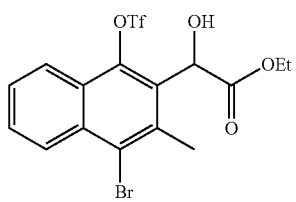

ethyl 2-(4-bromo-3-methyl-1-
(trifluoromethylsulfonyloxy)naphthalen-
2-yl)-2-hydroxyacetate

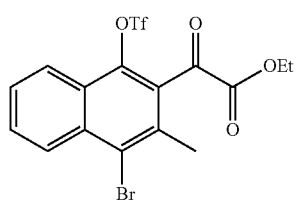

ethyl 2-(4-bromo-3-methyl-1-
(trifluoromethylsulfonyloxy)naphthalen-
2-yl)-2-oxoacetate

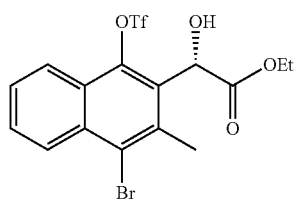

(S)-ethyl 2-(4-bromo-3-methyl-1-
(trifluoromethylsulfonyloxy)naphthalen-
2-yl)-2-hydroxyacetate

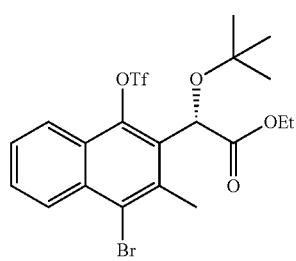

(S)-ethyl 2-(4-bromo-3-methyl-1-
(trifluoromethylsulfonyloxy)naphthalen-2-yl)-2-
tert-butoxyacetate

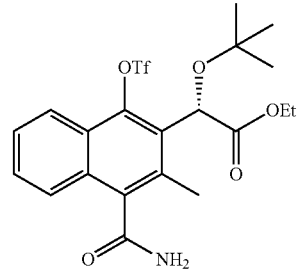

182
(S)-ethyl 2-tert-butoxy-2-(4-
carbamoyl-3-methyl-1-(trifluoro
methylsulfonyloxy)naphthalen-2-yl)acetate Preparation of ethyl 2-(4-bromo-1-hydroxy-3-methyl-naphthalen-2-yl)-2-tert-butoxyacetate: A solution of ethyl 2-tert-butoxy-2-(1-hydroxy-3-methylnaphthalen-2-yl)acetate (1.24 g, 3.92 mmol) in CHCl$_3$ (20 mL) was treated with solid NaHCO$_3$ (843 mg, 9.80 mmol). Then a solution of Br$_2$ (750 mg, 4.70 mmol) in CHCl$_3$ (5.0 mL) was added dropwise over 2 min at 23° C. After 30 min, the reaction was treated with 10% Na$_2$S$_2$O$_3$ solution (10 mL). After maximum decolorization was achieved, the reaction was diluted with H$_2$O (10 mL) and extracted with DCM (3×10 mL). Combined organic phases were dried (Na$_2$SO$_4$), filtered, and concentrated. The residue was treated with DCM and wet-loaded onto a silica gel column and purified by flash chromatography (ethyl acetate/hexanes) giving the desired product (1.50 g, 97% yield). $^1$H NMR (400 MHz, CDCl$_3$) δ 9.18 (s, 1H), 8.28 (d, J=8.6 Hz, 1H), 8.20 (d, J=8.6 Hz, 1H), 7.56 (dd, J=8.6, 8.6 Hz, 1H), 7.45 (dd, J=8.6, 8.6 Hz, 1H), 5.60 (s, 1H), 4.24-4.06 (m, 2H), 2.77 (s, 3H), 1.31 (s, 9H), 1.20 (t, J=7.0 Hz, 3H).

Preparation of ethyl 2-(4-bromo-3-methyl-1-(trifluoromethylsulfonyloxy) naphthalen-2-yl)-2-tert-butoxyacetate: A flask was charged with N-phenyl-trifluoromethanesulfonimide (2.70 g, 7.57 mmol), Cs$_2$CO$_3$ (2.47 g, 7.57 mmol), and THF (20 mL). A solution of ethyl 2-(4-bromo-1-hydroxy-3-methylnaphthalen-2-yl)-2-tert-butoxyacetate (1.50 g, 3.78 mmol) in THF (25 mL) was added with stirring at 23° C. After 30 min, the reaction was added over 5 min to a premixed solution of 2 M NaHSO$_4$ (30 mL) and saturated aq. Na$_2$HPO$_4$ (100 mL) at 23° C. The system was extracted with EtOAc/hexane (10:1, 3×50 mL). Combined organic phases were dried (Na$_2$SO$_4$), filtered, concentrated, dissolved in hexane, and concentrated again. The residue was treated with benzene and wet-loaded onto a silica gel column and purified by flash chromatography (hexanes→ethyl acetate/hexanes 1:4) giving the desired product (1.37 g, 69% yield). $^1$H NMR (400 MHz, CDCl$_3$) δ 8.41 (d, J=8.8 Hz, 1H), 8.06 (d, J=8.8 Hz, 1H), 7.70 (dd, J=8.8, 8.8 Hz, 1H), 7.64 (dd, J=8.8, 8.8 Hz, 1H), 5.77 (s, 1H), 4.28-4.02 (m, 2H), 2.66 (s, 3H), 1.21 (s, 9H), 1.20 (t, J=7.0 Hz, 3H). $^{19}$F NMR (377 MHz, CDCl$_3$) δ−73.2 (s).

Preparation ethyl 2-(4-bromo-3-methyl-1-(trifluoromethylsulfonyloxy) naphthalen-2-yl)-2-hydroxyacetate: A solution of ethyl 2-(4-bromo-3-methyl-1-(trifluoromethylsulfonyloxy)naphthalen-2-yl)-2-tert-butoxyacetate (1.37 g, 2.60 mmol) in DCM (30 mL) was treated with TFA (3.0 mL) at 23° C. After 2 h, the reaction was diluted with H$_2$O (30 mL). The organic phase was collected and the aqueous layer was extracted with DCM (2×20 mL). Combined organic layers were dried (Na$_2$SO$_4$), filtered, and concentrated giving the desired product as a crude residue (1.22 g), which was immediately used in the next reaction without further purification.

¹H NMR (400 MHz, CDCl₃) δ 8.41 (d, J=8.2 Hz, 1H), 8.09 (d, J=8.2 Hz, 1H), 7.71 (dd, J=8.2, 8.2 Hz, 1H), 7.66 (dd, J=8.2, 8.2 Hz, 1H), 5.84 (s, 1H), 4.34-4.20 (m, 2H), 2.63 (s, 3H), 1.22 (t, J=7.0 Hz, 3H). ¹⁹F NMR (377 MHz, CDCl₃) δ −73.0 (s).

Preparation of ethyl 2-(4-bromo-3-methyl-1-(trifluoromethyl-sulfonyloxy) naphthalen-2-yl)-2-oxoacetate: A solution of ethyl 2-(4-bromo-3-methyl-1-(trifluoromethylsulfonyloxy)naphthalen-2-yl)-2-hydroxyacetate (crude, 1.22 g, ~2.60 mmol) in DCM (60 mL) was treated with Dess-Martin periodinane (1.32 g, 3.12 mmol) at 23° C. After 30 min, 10% Na₂S₂O₃ (30 mL) was added at 23° C. The system was diluted with H₂O (20 mL) and extracted with DCM (3×30 mL). Combined organic layers were dried (Na₂SO₄), filtered, and concentrated. The residue was treated with benzene, filtered, and wet-loaded onto a silica gel column and purified by flash chromatography (ethyl acetate/hexanes) giving the desired product (1.18 g, 98% yield over 2 steps from ethyl 2-(4-bromo-3-methyl-1-(trifluoromethylsulfonyloxy)naphthalen-2-yl)-2-tert-butoxyacetate). ¹H NMR (400 MHz, CDCl₃) δ 8.43 (d, J=8.6 Hz, 1H), 8.13 (d, J=8.2 Hz, 1H), 7.77 (dd, J=8.6, 8.2 Hz, 1H), 7.71 (dd, J=8.6, 8.6 Hz, 1H), 4.42 (q, J=7.0 Hz, 2H), 2.57 (s, 3H), 1.39 (t, J=7.0 Hz, 3H). ¹⁹F NMR (377 MHz, CDCl₃) δ −73.3 (s).

Preparation of (S)-ethyl 2-(4-bromo-3-methyl-1-(trifluoromethylsulfonyl-oxy)naphthalen-2-yl)-2-hydroxyacetate:
A solution of ethyl 2-(4-bromo-3-methyl-1-(trifluoromethylsulfonyloxy)naphthalen-2-yl)-2-oxoacetate (1.18 g, 2.52 mmol) in PhMe (20 mL) was cooled to −40° C. (dry ice/CH₃CN). (R)—CBS catalyst (140 mg, 0.504 mmol) was introduced, followed by distilled catecholborane (neat, 402 μL, 3.77 mmol) over a 5 min period. After 30 min, the reaction was warmed to ~−20° C. EtOAc (20 mL) was added. Then 15% Na₂CO₃ (10 mL) was added. The reaction was stirred vigorously as it was warmed to 23° C. overnight. The next day, the organic phase was washed (with vigorous stirring) with more 15% Na₂CO₃ (10 mL portions for 30 min each) until the washes were colorless. After the fifth wash, the organic phase was washed once with saturated NH₄Cl (10 mL) for 10 min, then dried (MgSO₄), filtered, and concentrated. The residue was dissolved in hexane and re-concentrated. The residue was treated with benzene, filtered, and wet-loaded onto a silica gel column and purified by flash chromatography (ethyl acetate/hexanes) giving the desired product (886 mg, 75% yield). ¹H NMR (400 MHz, CDCl₃) δ 8.41 (d, J=8.2 Hz, 1H), 8.09 (d, J=8.6 Hz, 1H), 7.71 (dd, J=8.6, 8.2 Hz, 1H), 7.66 (dd, J=8.6, 8.6 Hz, 1H), 5.84 (d, J=2.4 Hz, 1H), 4.34-4.20 (m, 2H), 3.41 (d, J=2.4 Hz, 1H), 2.63 (s, 3H), 1.22 (t, J=7.0 Hz, 3H). ¹⁹F NMR (377 MHz, CDCl₃) δ −73.0 (s).

Preparation of (S)-ethyl 2-(4-bromo-3-methyl-1 (trifluoromethylsulfonyloxy naphthalen-2-yl)-2-tert-butoxyacetate:
A solution of (S)-ethyl 2-(4-bromo-3-methyl-1-(trifluoromethylsulfonyloxy)naphthalen-2-yl)-2-hydroxyacetate (880 mg, 1.87 mmol) in tert-butyl acetate (20 mL) was treated with 70% HClO₄ (40 μL) at 23° C. After 5 h, the reaction was added slowly over 5 min to saturated NaHCO₃ (50 mL) at 23° C. The system was stirred for 10 min, then extracted with DCM (3×20 mL). Combined organic layers were dried (Na₂SO₄), filtered, and concentrated. The residue was treated with hexane and concentrated once more. The residue was treated with benzene, filtered, and wet-loaded onto a silica gel column and purified by flash chromatography (ethyl acetate/hexanes) giving the desired product (816 mg, 83% yield). ¹H NMR (400 MHz, CDCl₃) δ 8.40 (d, J=7.8 Hz, 1H), 8.06 (d, J=7.8 Hz, 1H), 7.70-7.58 (m, 2H), 5.77 (s, 1H), 4.27-4.09 (m, 2H), 2.66 (s, 3H), 1.21 (s, 9H), 1.20 (t, J=7.0 Hz, 3H). ¹⁹F NMR (377 MHz, CDCl₃) δ −73.2 (s).

Preparation of (S)-ethyl 2-tert-butoxy-2-(4-carbamoyl-3-methyl-1-(trifluoromethylsulfonyloxy)naphthalen-2-yl)acetate (182): A solution of (S)-ethyl 2-(4-bromo-3-methyl-1 (trifluoromethylsulfonyloxy)naphthalen-2-yl)-2-tert-butoxyacetate (200 mg, 0.380 mmol) in dry THF (7.6 mL) was cooled to −78° C. tert-butyllithium (1.7 M in pentane, 446 μL, 0.759 mmol) was added dropwise under N₂ over 3 min. 10 min later, trimethylsilylisocyanate (62.0 μL, 0.456 mmol) was quickly added. The reaction was warmed to 23° C. After 1 h, the system was treated with glacial AcOH (87.0 μL, 1.52 mmol) followed by EtOH (absolute, 1.9 mL). The reaction was stirred for 30 min then diluted with saturated NaHCO₃ (20 mL) and H₂O (10 mL). The system was extracted with DCM (3×15 mL). Combined organic phases were dried (Na₂SO₄), filtered, and concentrated. The residue was treated with benzene and wet-loaded onto a silica gel column and purified by flash chromatography (ethyl acetate/hexanes) giving the desired product (75 mg, 40% yield.) ¹H NMR (400 MHz, CDCl₃) δ 8.10-8.05 (m, 1H), 7.96-7.86 (m, 1H), 7.64-7.58 (m, 2H), 6.19 (s, broad, 1H), 6.06 (s, broad, 1H), 5.75 (s, 1H), 4.30-4.07 (m, 2H), 2.53 (s, 3H), 1.21 (s, 9H), 1.20 (t, J=7.0 Hz, 3H). ¹⁹F NMR (377 MHz, CDCl₃) δ −73.2 (s).

EXAMPLE 153

Preparation of (S)-2-tert-butoxy-2-((R)-4-carbamoyl-1-(2,3-dihydropyrano[4,3,2-de]quinolin-7-yl)-3-methylnaphthalen-2-yl)acetic acid (183)

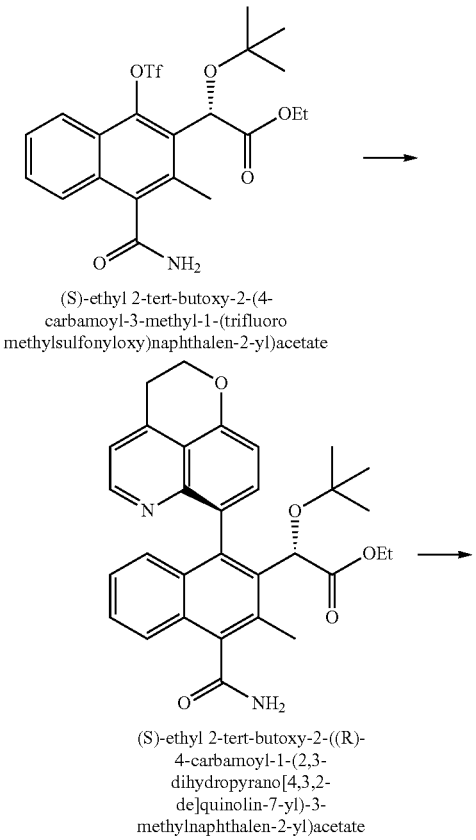

(S)-ethyl 2-tert-butoxy-2-(4-carbamoyl-3-methyl-1-(trifluoromethylsulfonyloxy)naphthalen-2-yl)acetate (S)-ethyl 2-tert-butoxy-2-((R)-4-carbamoyl-1-(2,3-dihydropyrano[4,3,2-de]quinolin-7-yl)-3-methylnaphthalen-2-yl)acetate

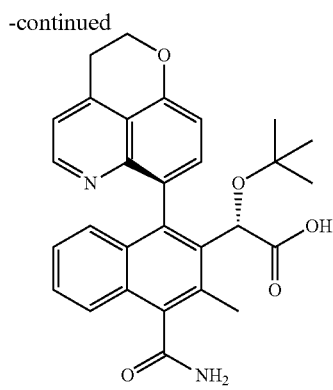

183
(S)-2-tert-butoxy-2-((R)-4-carbamoyl-1-
(2,3-dihydropyrano[4,3,2-de]quinolin-7-
yl)-3-methylnaphthalen-2-yl)acetic acid Preparation of(S)-ethyl 2-tert-butoxy-2-((R)-4-carbamoyl-1-(2,3-dihydropyrano[4,3,2-de]quinolin-7-yl)-3-methylnaphthalen-2-yl)acetate: A vessel was charged with 2,3-dihydropyrano[4,3,2-de]quinolin-7-ylboronic acid, monohydrochloride (49 mg, 0.193 mmol), S-Phos-palladacycle (22 mg, 32.2 µmol), and CsF (108 mg, 0.708 mmol). The vessel was evacuated under vacuum and backfilled with argon. A solution of (S)-ethyl 2-tert-butoxy-2-(4-carbamoyl-3-methyl-1-(trifluoromethylsulfonyloxy)naphthalen-2-yl)acetate (182, 79 mg, 0.161 mmol) in 1,2-DME (distilled from Na⁰/benzophenone, 1.4 mL) was added. The vessel was sealed and heated with vigorous stirring to 120° C. for 3 h. The reaction was cooled to 23° C. and diluted with brine (8 mL) and H₂O (8 mL). The system was extracted with DCM (3×mL). Combined organic layers were dried (Na₂SO₄), filtered, and concentrated. The residue was dissolved in DCM and concentrated once more. The residue was treated with benzene and wet-loaded onto a silica gel column and purified by flash chromatography (ethyl acetate/hexanes) giving (2S)-ethyl 2-tert-butoxy-2-((R)-4-carbamoyl-1-(2,3-dihydropyrano[4,3,2-de]quinolin-7-yl)-3-methylnaphthalen-2-yl)acetate (3.4 mg) in semipure form. LCMS-ESI⁺ (m/z): [M+H]⁺ calcd for $C_{31}H_{33}N_2O_5$: 513.2; Found: 513.1. The other diastereomer, (2S)-ethyl 2-tert-butoxy-2-((S)-4-carbamoyl-1-(2,3-dihydropyrano[4,3,2-de]quinolin-7-yl)-3-methylnaphthalen-2-yl)acetate, was also obtained from the flash column in semipure form (1.3 mg, yield not found). LCMS-ESI⁺ (m/z): [M+H]⁺ calcd for $C_{31}H_{33}N_2O_5$: 513.2; Found: 513.1.

Preparation of (S)-2-tert-butoxy-2-((R)-4-carbamoyl-1-(2,3-dihydropyrano[4,3,2-de]quinolin-7-yl)-3-methylnaphthalen-2-yl)acetic acid (183): A solution of (2S)-ethyl 2-tert-butoxy-2-((R)-4-carbamoyl-1-(2,3-dihydro pyrano[4,3,2-de]quinolin-7-yl)-3-methylnaphthalen-2-yl)acetate (3.4 mg, semipure) in THF (1.0 mL) and EtOH (absolute, 500 µL) was added to LiOH.H₂O (100 mg) predissolved in H₂O (500 µL). The mixture was stirred vigorously at 60° C. for 4 days. The reaction was cooled to 23° C., diluted with EtOH (absolute, 1.0 mL), and filtered (0.45 micron filter). The filtrate was purified on a C18 Gemini column (eluent: H₂O/CH₃CN 95:5→0:100 spiked with 0.1% v/v TFA), giving (S)-2-tert-butoxy-2-((R)-4-carbamoyl-1-(2,3-dihydropyrano[4,3,2-de]quinolin-7-yl)-3-methylnaphthalen-2-yl)acetic acid as the mono-trifluoroacetic acid salt (1.5 mg, yield not found). ¹H NMR (400 MHz, CD₃OD) δ 8.72-8.69 (m, 1H), 8.06-7.26 (m, 6H), 6.98 (d, J=8.6 Hz, 1H), 5.25 (s, 1H), 3.66-3.32 (m, 2H), 3.30-3.16 (m, 2H), 2.78 (s, 3H), 0.94 (s, 9H). ¹⁹F NMR (377 MHz, CDCl₃) δ-77.5 (s). LCMS-ESI⁺ (m/z): [M+H]⁺ calcd for $C_{29}H_{29}N_2O_5$: 485.2; Found: 485.1. The other diastereomer, (2S)-2-tert-butoxy-2-((S)-4-carbamoyl-1-(2,3-dihydropyrano[4,3,2-de]quinolin-7-yl)-3-methylnaphthalen-2-yl)acetic acid, was prepared in a similar manner from (2S)-ethyl 2-tert-butoxy-2-((S)-4-carbamoyl-1-(2,3-dihydropyrano[4,3,2-de]quinolin-7-yl)-3-methylnaphthalen-2-yl)acetate: ¹H NMR (400 MHz, CD₃OD) δ 8.66-7.19 (m, 7H), 6.96 (d, J=8.6 Hz, 1H), 5.25 (s, 1H), 3.67-3.32 (m, 2H), 3.30-3.14 (m, 2H), 2.72 (s, 3H), 0.77 (s, 9H). ¹⁹F NMR (377 MHz, CD₃OD) δ-77.6 (s). LCMS-ESI⁺ (m/z): [M+H]⁺ calcd for $C_{29}H_{29}N_2O_5$: 485.2; Found: 485.1.

EXAMPLE 154

Preparation of (S)-ethyl 2-tert-butoxy-2-((R)-1-(2,3-dihydropyrano[4,3,2-de]quinolin-7-yl)-3-methylnaphthalen-2-yl)acetate (184)

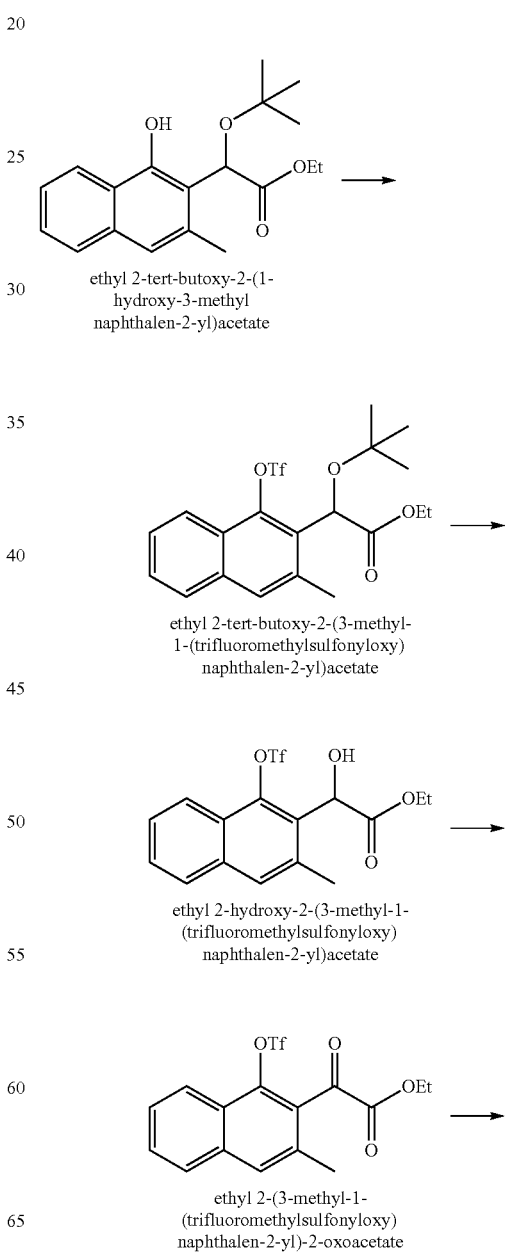

ethyl 2-tert-butoxy-2-(1-hydroxy-3-methyl naphthalen-2-yl)acetate ethyl 2-tert-butoxy-2-(3-methyl-1-(trifluoromethylsulfonyloxy) naphthalen-2-yl)acetate ethyl 2-hydroxy-2-(3-methyl-1-(trifluoromethylsulfonyloxy) naphthalen-2-yl)acetate ethyl 2-(3-methyl-1-(trifluoromethylsulfonyloxy) naphthalen-2-yl)-2-oxoacetate

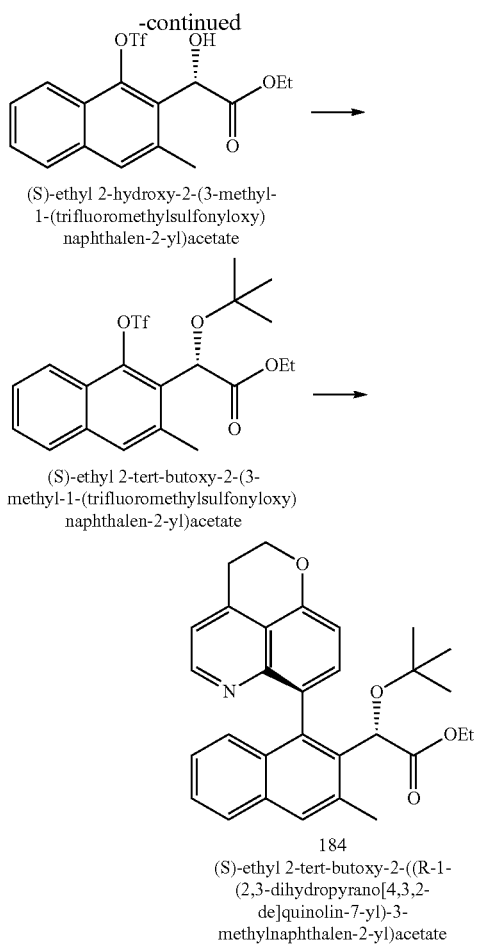

(S)-ethyl 2-hydroxy-2-(3-methyl-1-(trifluoromethylsulfonyloxy)naphthalen-2-yl)acetate (S)-ethyl 2-tert-butoxy-2-(3-methyl-1-(trifluoromethylsulfonyloxy)naphthalen-2-yl)acetate 184
(S)-ethyl 2-tert-butoxy-2-((R-1-(2,3-dihydropyrano[4,3,2-de]quinolin-7-yl)-3-methylnaphthalen-2-yl)acetate Preparation of ethyl 2-tert-butoxy-2-(3-methyl-1-(trifluoromethylsulfonyloxy) naphthalen-2-yl)acetate: Ethyl 2-tert-butoxy-2-(3-methyl-1-(trifluoromethylsulfonyloxy) naphthalen-2-yl)acetate was prepared in a similar fashion to ethyl 2-tert-butoxy-2-(4-fluoro-3-methyl-1-(trifluoromethylsulfonyloxy)naphthalen-2-yl)acetate in Example 120 with appropriate adjustments to scale to afford an amorphous white solid that was contaminated with a small amount of PhNH(Tf). LCMS-ESI$^+$ (m/z): [M—C$_4$H$_9$+H]$^+$ calcd for C$_{16}$H$_{15}$F$_3$O$_6$S: 392.4; Found: 392.6.

Preparation of ethyl 2-hydroxy-2-(3-methyl-1-(trifluoromethylsulfonyl-oxy)naphthalen-2-yl)acetate: A solution of ethyl 2-tert-butoxy-2-(3-methyl-1-(trifluoromethylsulfonyloxy)naphthalen-2-yl)acetate (6.0 grams, ~13 mmol, semipure) in DCM (60 mL) was treated with TFA (6.0 mL) at 23° C. The reaction was diluted with H$_2$O (60 mL) and the organic phase collected. The aqueous layer was extracted with DCM (2×30 mL). The combined organic layers were dried (Na$_2$SO$_4$), filtered, and concentrated. The residue (5.5 grams) was used in the next reaction without further purification. $^1$H NMR (400 MHz, CDCl$_3$): δ 8.08-8.06 (m, 1H), 7.81-7.78 (m, 1H), 7.69 (s, 1H), 7.62-7.55 (m, 2H), 5.81 (app. s, 1H), 4.35-4.21 (m, 2H), 3.26 (app. s, broad, 1H), 2.50 (s, 3H), 1.21 (t, J=7.0 Hz, 3H).

Preparation of ethyl 2-(3-methyl-1-(trifluoromethylsulfonyloxy)naphthalen-2-yl)-2-oxoacetate: A solution of ethyl 2-hydroxy-2-(3-methyl-1-(trifluoromethylsulfonyloxy) naphthalen-2-yl)acetate (5.5 g, crude) in DCM (160 mL) was treated with Dess-Martin periodinane (7.18 g, 16.9 mmol) at 23° C. After 1 h, the reaction was added slowly over 5 min to 10% Na$_2$S$_2$O$_3$ (100 mL). After 30 min, the reaction was extracted with DCM (3×50 mL). The combined organic layers were dried (Na$_2$SO$_4$), filtered, and concentrated. The residue was treated with benzene, filtered, and wet-loaded onto a silica gel column and purified by flash chromatography (ethyl acetate/hexanes) giving the desired product in semipure form (3.9 g). $^1$H NMR (400 MHz, CDCl$_3$): δ 8.11-8.08 (m, 1H), 7.86-7.83 (m, 1H), 7.76 (s, 1H), 7.66-7.60 (m, 2H), 4.41 (q, J=7.4 Hz, 2H), 2.50 (s, 3H), 1.40 (t, J=7.4 Hz, 3H). $^{19}$F NMR (377 MHz, CDCl$_3$) δ−73.3 (s).

Preparation of (S)-ethyl 2-hydroxy-2-(3-methyl-1-(trifluoromethylsulfonyloxy) naphthalen-2-yl)acetate: Ethyl 2-(3-methyl-1-(trifluoromethylsulfonyloxy)naphthalen-2-yl)-2-oxoacetate (1.31 g, 3.3 mmol) was dissolved in toluene (20 mL) and cooled to −40° C. After stirring for 20 minutes, (R)-(+)-2-Methyl-CBS-oxazaborolidine (219 mg, 7.5 mmol) and catechol borane (750 μL, 7.04 mmol) were added and the mixture stirred at −40° C. After 2 hrs at −40° C. the reaction was quenched by the addition of 15% Na$_2$CO$_3$ (12 mL) and the mixture was allowed to warm to room temperature. The mixture was washed with 15% Na$_2$CO$_3$ (8×12 mL) and saturated NH$_4$Cl (24 mL), organic layer was dried with sodium sulfate and concentrated in vacuo. Chromatography using silica gel using EtOAc in hexanes produced the desired (S)-ethyl 2-hydroxy-2-(3-methyl-1-(trifluoromethylsulfonyloxy)naphthalen-2-yl)acetate (976 mg, 1.8 mmol) in 74% yield. $^1$H-NMR: 400 MHz, (CDCl$_3$): δ 8.08-8.06 (m, 1H); 7.81-7.79 (m, 1H); 7.69 (s, 1H); 7.60-7.57 (m, 2H); 5.81-5.80 (m, 1H); 4.35-4.19 (m, 2H); 3.42 (d, J=2.4 Hz, 1H); 2.50 (s, 3H); 1.21 (t, J=7.0 Hz, 3H).

Preparation of (S)-ethyl 2-tert-butoxy-2-(3-methyl-1-(trifluoromethylsulfonyloxy) naphthalen-2-yl)acetate: To a stirring solution of (560 mg, 1.42 mmol) in t-BuOAc (32.0 mL, 381 mmol) was added 4 drops (catalytic) of 70% HClO$_4$ and the mixture allowed to stir at room temperature for 2 hours. The mixture was quenched by pouring it into an ice-cold solution of saturated NaHCO$_3$. Extraction with EtOAc (3×20 mL), drying with sodium sulfate and column chromatography on silica gel using EtOAc in hexanes produced the desired product (S)-ethyl 2-tert-butoxy-2-(3-methyl-1-(trifluoromethyl-sulfonyloxy)naphthalen-2-yl)acetate (455 mg, 71%). $^1$H-NMR: 400 MHz, (CDCl$_3$): δ 8.06-8.03 (m, 1H); 7.81-7.78 (m, 1H); 7.67 (s, 1H); 7.59-7.53 (m, 2H); 5.73 (s, 1H); 4.25-4.10 (m, 2H); 2.55 (s, 3H); 1.21 (s, 9H); 1.17 (t, J=7.2 Hz, 3H).

Preparation of (S)-ethyl 2-tert-butoxy-2-((R)-1-(2,3-dihydropyrano[4,3,2-de]quinolin-7-yl)-3-methylnaphthalen-2-yl)acetate (184): (S)-ethyl 2-tert-butoxy-2-(3-methyl-1-(trifluoromethylsulfonyloxy)naphthalen-2-yl)acetate (555 mg, 1.23 mmol) in freshly distilled DME (5.0 mL) was added to a 5-10 mL microwave vial charged with a mixture of 2,3-dihydropyrano[4,3,2-de]quinolin-7-ylboronic acid, HCl salt (368 mg, 1.46 mmol); S-Phos palladacycle (155 mg, 0.23 mmol), and CsF (743 mg, 4.89 mmol). This heterogeneous mixture was then microwaved at 125° C. for 60 minutes. The mixture was then diluted 400% with EtOAc, extracted with saturated NH$_4$Cl, brine, and dried with sodium sulfate. Chromatography via ISCO using a 15 μm particle size silica gel column separated the desired atropisomer (S)-ethyl 2-tert-butoxy-2-((R)-1-(2,3-dihydropyrano[4,3,2-de]quinolin-7-yl)-3-methylnaphthalen-2-yl)acetate (184) (79.7 mg, 0.17 mmol, 14%) and the undesired atropisomer (S)-ethyl 2-tert-butoxy-2-((S)-1-(2,3-dihydropyrano[4,3,2-de]quinolin-7-yl)-3-methylnaphthalen-2-yl)acetate (109.9 mg, 0.234 mmol). $^1$H-NMR: 400 MHz, (CDCl$_3$): δ 8.66 (d, J=4.4 Hz, 1H); 7.77 (d, J=8.0 Hz, 1H); 7.72 (s, 1H); 7.50 (d, J=8.0 Hz, 1H); 7.36-7.33 (m, 1H); 7.13-7.01 (m, 4H); 5.09 (s, 1H);

4.58-4.52 (m, 2H); 4.03-3.78 (m, 2H); 3.38-3.23 (m, 2H); 2.79 (s, 3H); 0.97 (s, 9H); 0.96 (t, J=7.6 Hz, 3H).

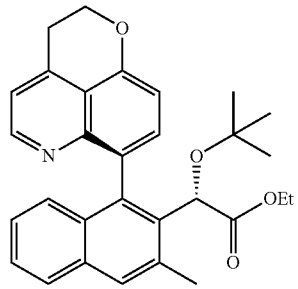

184
(S)-ethyl 2-tert-butoxy-2-((R-1-(2,3-dihydropyrano[4,3,2-de]quinolin-7-yl)-3-methylnaphthalen-2-yl)acetate

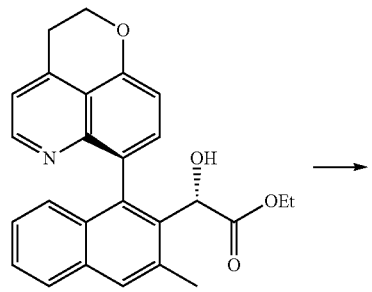

(S)-ethyl 2-((R-1-(2,3-dihydropyrano[4,3,2-de]quinolin-7-yl)-3-methylnaphthalen-2-yl)-2-hydroxyacetate

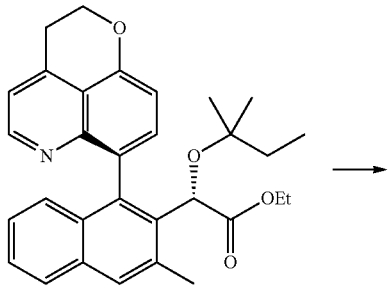

(S)-ethyl 2-((R-1-(2,3-dihydropyrano[4,3,2-de]quinolin-7-yl)-3-methylnaphthalen-2-yl)-2-(tert-pentyloxy)acetate

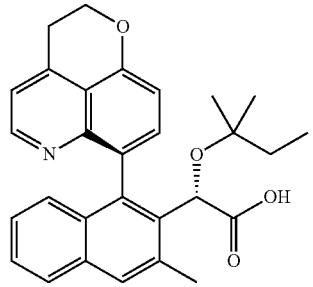

185
(S)-2-((R-1-(2,3-dihydropyrano[4,3,2-de]quinolin-7-yl)-3-methylnaphthalen-2-yl)-2-(tert-pentyloxy)acetic acid Preparation of (S)-ethyl 2-((R)-1-(2,3-dihydropyrano[4,3,2-de]quinolin-7-yl)-3-methylnaphthalen-2-yl)-2-hydroxyacetate: To a DCM solution (10 mL) of (S)-ethyl 2-tert-butoxy-2-((R)-1-(2,3-dihydropyrano[4,3,2-de]quinolin-7-yl)-3-methylnaphthalen-2-yl)acetate (184) (49.0 mg, 0.104 mmol) was added TFA (650 L, 0.0084 mmol) and stirred at rt overnight. The mixture was quenched by pouring into an ice-cold solution of saturated NaHCO$_3$ and extracted with EtOAc to give crude (S)-ethyl 2-((R)-1-(2,3-dihydropyrano[4,3,2-de]quinolin-7-yl)-3-methylnaphthalen-2-yl)-2-hydroxyacetate (30.3 mg, 70%). $^1$H-NMR: 400 MHz, (CDCl$_3$): δ 8.67 (d, J=4.0 Hz, 1H); 7.79-7.76 (m, 2H); 7.48 (d, J=7.6 Hz, 1H); 7.38 (t, J=7.8 Hz, 1H); 7.16-7.10 (m, 3H); 6.97 (d, J=8.4 Hz, 1H); 5.36 (s, 1H); 4.58-4.55 (m, 2H); 3.89-3.72 (m, 2H); 3.38-3.31 (m, 2H); 2.69 (s, 3H); 1.05 (t, J=7.0 Hz, 3H). LCMS-ESI$^+$ (m/z): [M+H]$^+$ calcd for C$_{26}$H$_{24}$NO$_4$; 414.17; Found: 414.1.

Preparation of (S)-ethyl 2-((R)-1-(2,3-dihydropyrano[4,3,2-de]quinolin-7-yl)-3-methylnaphthalen-2-yl)-2-(tert-pentyloxy)acetate: (S)-ethyl 2-((R)-1-(2,3-dihydropyrano[4,3,2-de]quinolin-7-yl)-3-methylnaphthalen-2-yl)-2-hydroxyacetate (57.6 mg, 0.139 mmol) was slurried in 2.0 mL of tert-pentyl acetate and 500 μL of DCM and treated with one drop of 70% perchloric acid. The mixture was allowed to stir 5 hours. The reaction was quenched by pouring into ice-cold saturated NaHCO$_3$. This mixture was extracted with EtOAc (3×20 mL), dried with sodium sulfate and concentrated in vacuo. Silica gel chromatography using EtOAc in hexanes produced the desired (S)-ethyl 2-((R)-1-(2,3-dihydropyrano[4,3,2-de]quinolin-7-yl)-3-methylnaphthalen-2-yl)-2-(tert-pentyloxy)acetate (58 mg). $^1$H-NMR: 400 MHz (CDCl$_3$): δ 8.66 (s, 1H); 7.77-7.75 (m, 2H); 7.49 (d, J=8.0 Hz, 1H); 7.35 (t, J=7.6 Hz, 1H), 7.13-7.07 (m, 3H); 7.02 (d, J=8.4 Hz, 1H); 5.08 (s, 1H); 4.45 (t, J=5.6 Hz, 2H); 4.02-3.76 (m, 2H); 3.39-3.29 (m, 2H); 2.79 (s, 3H); 1.28-1.24 (m, 2H); 0.97-0.84 (m, 9H); 0.70 (t, J=7.0 Hz, 3H). LCMS-ESI$^+$ (m/z): [M+H]$^+$ calcd for C$_{31}$H$_{34}$NO$_4$: 484.25; Found: 484.14.

Preparation of (S)-2-((R)-1-(2,3-dihydropyrano[4,3,2-de]quinolin-7-yl)-3-methylnaphthalen-2-yl)-2-(tert-pentyloxy)acetic acid (185): (S)-ethyl 2-((R)-1-(2,3-dihydropyrano[4,3,2-de]quinolin-7-yl)-3-methylnaphthalen-2-yl)-2-(tert-pentyloxy)acetate (58 mg, 0.12 mmol) was dissolved in THF (6.0 mL), MeOH (2 mL) and water (2 mL). LiOH was added (209 mg, 4.98 mmol) and the mixture was microwaved at 100° C. for 45 minutes. The mixture was then diluted 400% with EtOAc, washed with water, brine, dried and concentrated in vacuo. The crude product was dissolved in MeOH and purified via preparatory HPLC and lyophilized to produce (S)-2-((R)-1-(2,3-dihydropyrano[4,3,2-de]quinolin-7-yl)-3-methylnaphthalen-2-yl)-2-(tert-pentyloxy)acetic acid (185) as the TFA salt (11.6 mg). $^1$H-NMR: 400 MHz, (CD$_3$OD): δ 8.67 (d, J=5.6 Hz, 1H); 7.97 (s, 1H), 7.94 (d, J=8.0 Hz, 1H); 7.87 (d, J=8.4 Hz, 1H); 7.81 (d, J=5.6 Hz, 1H); 7.51-7.47 (m, 2H); 7.28-7.25 (m, 1H); 6.93 (d, J=8.8 Hz, 1H); 5.19 (s, 1H); 4.76-4.67 (m, 2H); 3.67 (t, J=6.0 Hz, 2H); 2.78 (s, 3H); 1.29-1.12 (m, 2H); 0.93 (d, J=8.4 Hz, 6H); 0.62 (t, J=7.0 Hz, 3H). LCMS-ESI$^+$ (m/z): [M+H]$^+$ calcd for C$_{29}$H$_{30}$NO$_4$: 456.55; Found: 456.11.

EXAMPLE 156

Preparation of (S)-2-tert-butoxy-2-((R)-1-(2,3-dihydropyrano[4,3,2-de]quinolin-7-yl)-6-((dimethylamino)methyl)-5-fluoro-3-methylnaphthalen-2-yl) acetic acid (186A) and (S)-2-tert-butoxy-2-((R)-1-(2,3-dihydropyrano[4,3,2-de]quinolin-7-yl)-5-fluoro-6-(hydroxymethyl)-3-methylnaphthalen-2-yl)acetic acid (186B)

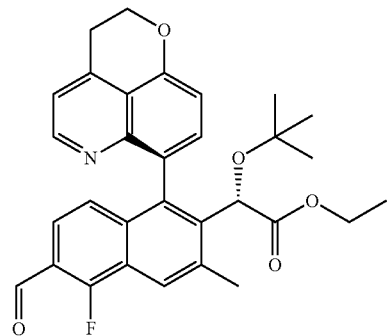

(S)-ethyl 2-tert-butoxy-2-((R)-1-(2,3-dihydropyrano[4,3,2-de]quinolin-7-yl)-5-fluoro-6-formyl-3-methylnaphthalen-2-yl)acetate

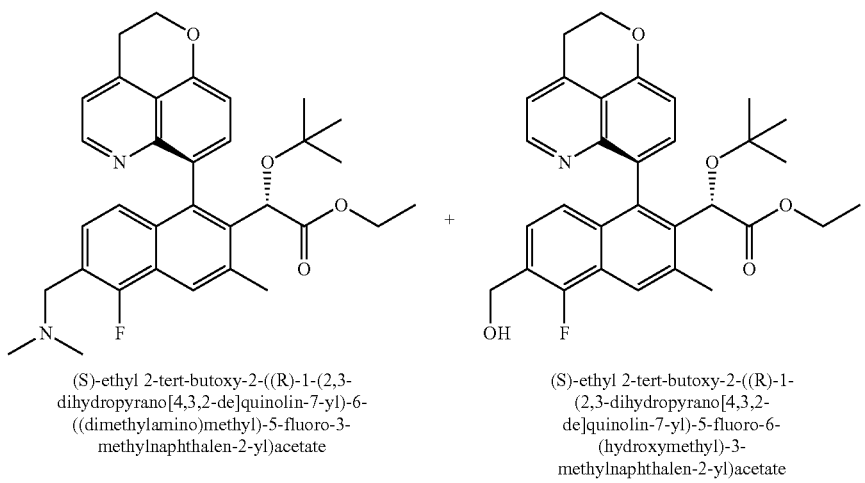

(S)-ethyl 2-tert-butoxy-2-((R)-1-(2,3-dihydropyrano[4,3,2-de]quinolin-7-yl)-6-((dimethylamino)methyl)-5-fluoro-3-methylnaphthalen-2-yl)acetate (S)-ethyl 2-tert-butoxy-2-((R)-1-(2,3-dihydropyrano[4,3,2-de]quinolin-7-yl)-5-fluoro-6-(hydroxymethyl)-3-methylnaphthalen-2-yl)acetate

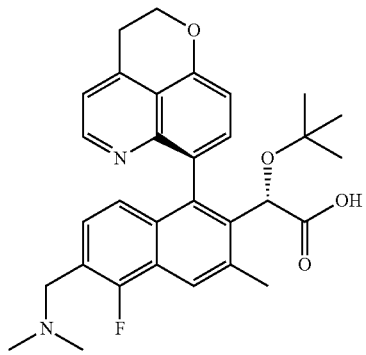

186A
(S)-2-tert-butoxy-2-((R)-1-(2,3-dihydropyrano[4,3,2-de]quinolin-7-yl)-6-((dimethylamino)methyl)-5-fluoro-3-methylnaphthalen-2-yl)acetic acid

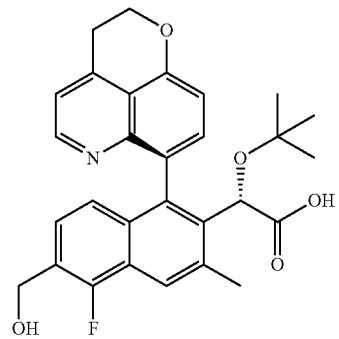

186B
(S)-2-tert-butoxy-2-((R)-1-(2,3-dihydropyrano[4,3,2-de]quinolin-7-yl)-5-fluoro-6-(hydroxymethyl)-3-methylnaphthalen-2-yl)acetic acid Preparation of (S)-ethyl 2-tert-butoxy-2-((R)-1-(2,3-dihydropyrano[4,3,2-de]quinolin-7-yl)-6-(dimethylaminomethyl)-5-fluoro-3-methylnaphthalen-2-yl)acetate and (S)-ethyl 2-tert-butoxy-2-((R)-1-(2,3-dihydropyrano[4,3,2-de]quinolin-7-yl)-5-fluoro-6-(hydroxymethyl)-3-methylnaphthalen-2-yl)acetate and (S)-ethyl 2-tert-butoxy-2-((R)-1-(2,3-dihydropyrano[4,3,2-de]quinolin-7-yl)-5-fluoro-6-(hydroxymethyl)-3-methylnaphthalen-2-yl)acetate: (S)-ethyl 2-tert-butoxy-2-((R)-1-(2,3-dihydropyrano[4,3,2-de]quinolin-7-yl)-5-fluoro-6-formyl-3-methylnaphthalen-2-yl)acetate (18 mg, 0.035 mmol, 1 eq.) and dimethylamine HCl salt (9 mg, 3 eq.) were mixed in 1 mL MeCN at room temperature for 1 hour. The reaction was cooled to 0° C. and NaHB(OAc)$_3$ (22 mg, 3 eq.) was added to the reaction. The reaction was stirred at 0° C. then warmed up to room temperature for 1 hour. The reaction mixture was diluted with ethyl acetate and washed with brine, dried (MgSO$_4$), filtered, concentrated and purified by reverse phase HPLC (Gemini, 5 to 100% ACN/H$_2$O+0.1% TFA). Products were lyophilized to give yellow powders of (S)-ethyl 2-tert-butoxy-2-((R)-1-(2,3-dihydropyrano[4,3,2-de]quinolin-7-yl)-6-((dimethylamino)methyl)-5-fluoro-3-methylnaphthalen-2-yl)acetate (5 mg); LCMS-ESI$^+$ (m/z): [M+H]$^+$ calcd for C$_{32}$H$_{37}$FN$_2$O$_4$: 545.66; Found: 545.21; and (S)-ethyl 2-tert-butoxy-2-((R)-1-(2,3-dihydropyrano[4,3,2-de]quinolin-7-yl)-5-fluoro-6-(hydroxymethyl)-3-methylnaphthalen-2-yl)acetate (4 mg), LCMS-ESI$^+$ (m/z): [M+H]$^+$ calcd for C$_{31}$H$_{32}$FNO$_5$: 518.59; Found: 518.12.

Preparation of (S)-2-tert-butoxy-2-((R)-1-(2,3-dihydropyrano[4,3,2-de]quinolin-7-yl)-6-((dimethylamino)methyl)-5-fluoro-3-methylnaphthalen-2-yl)acetic acid (186A): A solution of (S)-ethyl 2-tert-butoxy-2-((R)-1-(2,3-dihydropyrano[4,3,2-de]quinolin-7-yl)-6-((dimethylamino)methyl)-5-fluoro-3-methylnaphthalen-2-yl)acetate (5 mg) in tetrahydrofuran (0.5 mL) and ethanol (0.5 mL) and 2 M sodium hydroxide (0.5 mL) was heated at 50° C. for 2 hours. The reaction mixture was diluted with ethyl acetate and washed with brine. The aqueous layer was back-extracted with ethyl acetate and the combined organic layer was dried (MgSO$_4$), filtered, concentrated and purified by reverse phase HPLC (Gemini, 5 to 100% ACN/H$_2$O+0.1% TFA). Product lyophilized to give a yellow powder (3.4 mg). $^1$H-NMR: 400 MHz, (CD$_3$OD): δ 8.55 (d, J=5.08 Hz, 1H), 8.10 (s, 1H), 7.58 (d, J=8.21 Hz, 1H), 7.53 (d, J=4.69 Hz, 1H), 7.25 (d, J=8.22 Hz, 1H), 7.18 (dd, J=7.82 Hz, 1H), 6.78 (d, J=8.60 Hz, 1H), 5.15 (s, 1H), 4.55 (m, 2H), 4.44 (m, 2H), 3.48 (t, J=5.87 Hz, 2H), 2.81 (s, 6H), 2.72 (s, 3H), 0.82 (s, 9H). $^{19}$F-NMR: 377 MHz, (CD$_3$OD) δ: -77.7 (s, 3F), -126.37 (s, 1F). LCMS-ESI$^+$ (m/z): [M+H]$^+$ calcd for C$_{31}$H$_{34}$FN$_2$O$_4$: 517.60; Found: 517.17.

Preparation of (S)-2-tert-butoxy-2-((R)-1-(2,3-dihydropyrano[4,3,2-de]quinolin-7-yl)-5-fluoro-6-(hydroxymethyl)-3-methylnaphthalen-2-yl)acetic acid (186B): A solution of (S)-ethyl 2-tert-butoxy-2-((R)-1-(2,3-dihydropyrano[4,3,2-de]quinolin-7-yl)-5-fluoro-6-(hydroxymethyl)-3-methylnaphthalen-2-yl)acetate (4 mg) in tetrahydrofuran (0.5 mL) and ethanol (0.5 mL) and 2 M sodium hydroxide (0.5 mL) was heated at 50° C. for 2 hours. The reaction mixture was diluted with ethyl acetate and washed with brine. The aqueous layer was back-extracted with ethyl acetate and the combined organic layer was dried (MgSO$_4$), filtered, concentrated and purified by reverse phase HPLC (Gemini, 5 to 100% ACN/H$_2$O+0.1% TFA). Product lyophilized to give a yellow powder (2.1 mg). $^1$H-NMR: 400 MHz, (CD$_3$OD): δ 8.57 (d, J=5.08 Hz, 1H), 8.07 (s, 1H), 7.71-7.66 (m, 2H), 7.34 (d, J=8.22 Hz, 1H), 7.25 (dd, J=7.82 Hz, 1H), 6.66 (d, J=8.60 Hz, 1H), 5.14 (s, 1H), 4.62 (m, 2H), 3.54 (t, J=5.87 Hz, 2H), 2.70 (s, 3H), 0.83 (s, 9H). $^{19}$F-NMR: 377 MHz, (CD$_3$OD) δ: -77.7 (s, 3F), -132.63 (d, 1F). LCMS-ESI$^+$ (m/z): [M+H]$^+$ calcd for C$_{29}$H$_{29}$FNO$_5$: 490.53; Found: 490.1.

EXAMPLE 157

Preparation of (S)-2-tert-butoxy-2-(6-chloro-1-((R)-2,3-dihydropyrano[4,3,2-de]quinolin-7-yl)-5,7-difluoro-3-methylnaphthalen-2-yl)acetic acid (187)

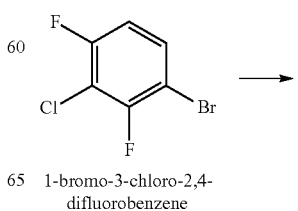

1-bromo-3-chloro-2,4-difluorobenzene

-continued

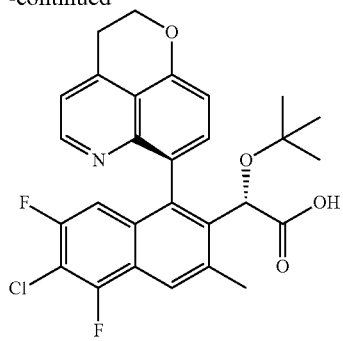

187
(S)-2-tert-butoxy-2-(6-chloro-1-((R)-2,3-dihydropyrano[4,3,2-de]quinolin-7-yl)-5,7-difluoro-3-methylnaphthalen-2-yl)acetic acid Preparation of (S)-2-tert-butoxy-2-(6-chloro-1-((R)-2,3-dihydropyrano[4,3,2-de]quinolin-7-yl)-5,7-difluoro-3-methylnaphthalen-2-yl)acetic acid: The title compound was prepared following a procedure similar to make (S)-2-tert-butoxy-2-((R)-5-chloro-1-(2,3-dihydropyrano[4,3,2-de]quinolin-7-yl)-3,6-dimethylnaphthalen-2-yl)acetic acid (116) of Example 114 except 1-bromo-3-chloro-2,4-difluoro-benzene was used instead of 1-bromo-2-chloro-3-methylbenzene. $^1$H-NMR: 400 MHz, (CD$_3$OD): δ 8.72 (d, J=5.48 Hz, 1H), 8.16 (s, 1H), 7.81 (m, 2H), 7.46 (d, J=8.21 Hz, 1H), 6.65 (d, J=10.56 Hz, 1H), 5.22 (s, 1H), 4.72 (m, 2H), 3.66 (dd, J=5.87 Hz, 2H), 2.81 (s, 3H), 0.93 (s, 9H). $^{19}$F-NMR: 377 MHz, (CD$_3$OD) δ: −77.8 (s, 3F), −118.07 (d, 1F), −123.12 (s, 1F). LCMS-ESI$^+$ (m/z): [M+H]$^+$ calcd for C$_{28}$H$_{25}$ClF$_2$NO$_4$: 512.94; Found: 512.1.

EXAMPLE 158

Preparation of (S)-2-tert-butoxy-2-(1-((R)-2,3-dihydropyrano[4,3,2-de]quinolin-7-yl)-5,7-difluoro-3,6-dimethylnaphthalen-2-yl)acetic acid (188)

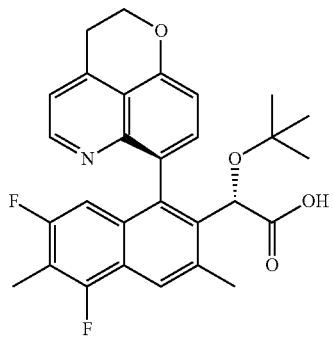

188
(S)-2-tert-butoxy-2-(1-((R)-2,3-dihydropyrano[4,3,2-de]quinolin-7-yl)-5,7-difluoro-3,6-methylnaphthalen-2-yl)acetic acid Preparation of (S)-2-tert-butoxy-2-(1-((R)-2,3-dihydropyrano[4,3,2-de]quinolin-7-yl)-5,7-difluoro-3,6-dimethylnaphthalen-2-yl)acetic acid (188): Following a procedure similar to the preparation of (S)-2-tert-butoxy-2-((R)-1-(2,3-dihydropyrano[4,3,2-de]quinolin-7-yl)-5-fluoro-3,6-dimethylnaphthalen-2-yl)acetic acid (119) of Example 117, (S)-ethyl 2-tert-butoxy-2-(6-chloro-1-((R)-2,3-dihydro-pyrano[4,3,2-de]quinolin-7-yl)-5,7-difluoro-3-methylnaphthalen-2-yl)acetate (from Example 157) was used instead of (S)-ethyl 2-tert-butoxy-2-((R)-6-chloro-1-(2,3-dihydropyrano[4,3,2-de]quinolin-7-yl)-5-fluoro-3-methylnaphthalen-2-yl)acetate. $^1$H-NMR: 400 MHz, (CD$_3$OD): δ 8.69 (d, J=5.47 Hz, 1H), 8.10 (s, 1H), 7.81 (m, 2H), 7.44 (d, J=8.21 Hz, 1H), 6.41 (d, J=10.95 Hz, 1H), 5.21 (s, 1H), 4.72 (m, 2H), 3.66 (dd, J=5.86 Hz, 2H), 2.78 (s, 3H), 2.32 (s, 3H), 0.93 (s, 9H). $^{19}$F-NMR: 377 MHz, (CD$_3$OD) δ: −77.8 (s, 3F), −117.62 (s, 1F), −126.33 (s, 1F). LCMS-ESI$^+$ (m/z): [M+H]$^+$ calc'd for C$_{29}$H$_{28}$F$_2$NO$_4$: 492.53; Found: 492.06.

EXAMPLE 159

Preparation of (S)-2-tert-butoxy-2-(1-((R)-2,3-dihydropyrano[4,3,2-de]quinolin-7-yl)-6-ethyl-5,7-difluoro-3-methylnaphthalen-2-yl)acetic acid (189)

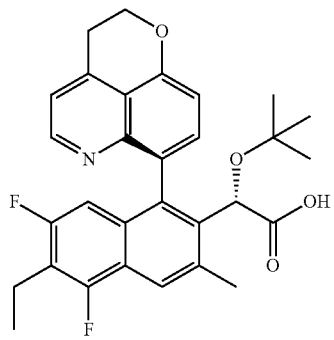

189
(S)-2-tert-butoxy-2-(1-((R)-2,3-dihydropyrano[4,3,2-de]quinolin-7-yl)-6-ethyl-5,7-difluoro-3-methylnaphthalen-2-yl)acetic acid Preparation of (S)-2-tert-butoxy-2-(1-((R)-2,3-dihydropyrano[4,3,2-de]quinolin-7-yl)-6-ethyl-5,7-difluoro-3-methylnaphthalen-2-yl)acetic acid (189): Following a procedure similar to the preparation of (S)-2-tert-butoxy-2-(1-((R)-2,3-dihydropyrano[4,3,2-de]quinolin-7-yl)-6-ethyl-5-fluoro-3-methylnaphthalen-2-yl)acetic acid (120) of Example 118, (S)-ethyl 2-tert-butoxy-2-(6-chloro-1-((R)-2,3-dihydropyrano[4,3,2-de]quinolin-7-yl)-5,7-difluoro-3-methylnaphthalen-2-yl)acetate (from Example 157) was used instead of (S)-ethyl 2-tert-butoxy-2-(6-chloro-1-((R)-2,3-dihydropyrano[4,3,2-de]quinolin-7-yl)-5-fluoro-3-methyl-naphthalen-2-yl)acetate. $^1$H-NMR: 400 MHz, (CD$_3$OD): δ 8.59 (d, J=5.47 Hz, 1H), 8.00 (s, 1H), 7.69 (m, 2H), 7.33 (d, J=8.21 Hz, 1H), 6.32 (d, J=11.34 Hz, 1H), 5.11 (s, 1H), 4.61 (m, 2H), 3.55 (dd, J=5.48 Hz, 2H), 2.73 (m, 2H), 2.68 (s, 3H), 1.18 (dd, J=7.42 Hz, 2H), 0.93 (s, 9H). $^{19}$F-NMR: 377 MHz, (CD$_3$OD)

δ: −77.6 (s, 3F), −119.81 (s, 1F), −128.26 (s, 1F). LCMS-ESI⁺ (m/z): [M+H]⁺ calc'd for $C_{30}H_{30}F_2NO_4$: 506.55; Found: 506.1.

EXAMPLE 160

Preparation of (S)-2-tert-butoxy-2-(1-((R)-2,3-dihydropyrano[4,3,2-de]quinolin-7-yl)-5,7-difluoro-3-methyl-6-(pyrimidin-5-yl)naphthalen-2-yl)acetic acid (190)

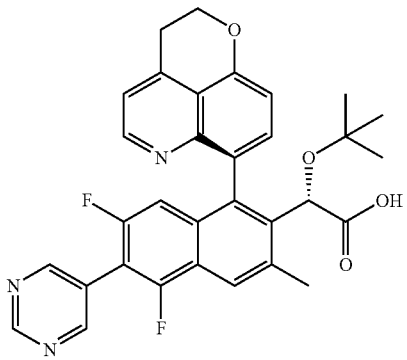

(S)-2-tert-butoxy-2-(1-((R)-2,3-dihydropyrano[4,3,2-de]quinolin-7-yl)-5,7-difluoro-3-methyl-6-(pyrimidin-5-yl)naphthalen-2-yl)acetic acid Preparation of (S)-2-tert-butoxy-2-(1-((R)-2,3-dihydropyrano[4,3,2-de]quinolin-7-yl)-5,7-difluoro-3-methyl-6-(pyrimidin-5-yl)naphthalen-2-yl)acetic acid (190): Following a procedure similar to the preparation of (S)-2-tert-butoxy-2-(1-((R)-2,3-dihydropyrano[4,3,2-de]quinolin-7-yl)-5,7-difluoro-3,6-dimethylnaphthalen-2-yl)acetic acid (188) of Example 158, pyrimidin-5-ylboronic acid was utilized instead of methylboronic acid to eventually afford the title compound. ¹H-NMR: 400 MHz, (CD₃OD): δ 9.22 (s, 1H), 8.99 (s, 1H), 8.74 (d, J=5.87 Hz, 1H), 8.24 (s, 1H), 7.84 (d, J=7.82 Hz 1H), 7.78 (d, J=5.48 Hz 1H), 7.46 (d, J=8.12 Hz, 1H), 6.69 (d, J=11.34 Hz, 1H), 5.26 (s, 1H), 4.78 (m, 2H), 3.66 (dd, J=5.86 Hz, 2H), 2.82 (m, 2H), 0.93 (s, 9H). ¹⁹F-NMR: 377 MHz, (CD₃OD) δ: −77.6 (s, 6F), −118.79 (s, 1F), −125.06 (s, 1F). LCMS-ESI⁺ (m/z): [M+H]⁺ calcd for $C_{32}H_{28}F_2N_3O_4$: 556.57; Found: 556.10.

EXAMPLE 161

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed:

1. A compound, or a pharmaceutically acceptable salt thereof, of formula Ib:

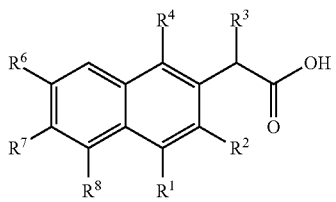

wherein:

$R^1$ is selected from the group consisting of:
a) H, halo and $(C_1-C_6)$alkyl;
b) $(C_2-C_6)$alkenyl, cyano, $(C_6-C_{20})$aryl, heterocycle and heteroaryl, wherein each $(C_6-C_{20})$aryl, heterocycle or heteroaryl is optionally independently substituted with 1 to 3 $Z^{10}$ groups;
c) —C(=O)—N($R^9$)$R^{10}$, —$(C_1-C_6)$alkyl-$R^{11}$ and —$(C_1-C_6)$alkyl-O—$R^{11}$, wherein each $R^{10}$ is independently selected from the group consisting of $R^{11}$, —$(C_1-C_6)$alkyl-$R^{11}$, —$SO_2$—$R^{11}$, —C(=O)—$R^{11}$, —C(=O)O$R^{11}$ and —C(=O)N($R^9$)$R^{11}$, each $R^9$ is independently selected from the group consisting of H, $(C_1-C_6)$alkyl and $(C_3-C_7)$cycloalkyl, and wherein each $R^{11}$ is independently selected from the group consisting of H, $(C_1-C_6)$alkyl, $(C_2-C_6)$alkenyl, $(C_2-C_6)$alkynyl, $(C_1-C_6)$haloalkyl, $(C_3-C_7)$cycloalkyl, $(C_6-C_{20})$aryl, heterocycle and heteroaryl, wherein each $(C_6-C_{20})$aryl, heterocycle or heteroaryl is optionally independently substituted with 1 to 3 $Z^{10}$ groups;
d) —$(C_1-C_6)$alkyl-N($R^9$)$R^{10}$, wherein each $R^{10}$ is independently selected from the group consisting of $R^{11}$, —$(C_1-C_6)$alkyl-$R^{11}$, —$SO_2$—$R^{11}$, —C(=O)—$R^{11}$, —C(=O)O$R^{11}$ and —C(=O)N($R^9$)$R^{11}$, each $R^9$ is independently selected from the group consisting of H, $(C_1-C_6)$alkyl and $(C_3-C_7)$cycloalkyl, and wherein each $R^{11}$ is independently selected from the group consisting of H, $(C_1-C_6)$alkyl, $(C_2-C_6)$alkenyl, $(C_2-C_6)$alkynyl, $(C_1-C_6)$haloalkyl, $(C_3-C_7)$cycloalkyl, $(C_6-C_{20})$aryl, heterocycle and heteroaryl, wherein each $(C_6-C_{20})$aryl, heterocycle or heteroaryl is optionally independently substituted with 1 to 3 $Z^{10}$ groups;
e) $(C_1-C_6)$alkyl, wherein $(C_1-C_6)$alkyl is independently substituted with 1 to 5 $Z^2$ groups and optionally independently substituted with 1 to 5 $Z^1$ groups;
f) $(C_6-C_{20})$aryl, heteroaryl and heterocycle, wherein each $(C_6-C_{20})$aryl heteroaryl and heterocycle is independently substituted with 1 to 5 $Z^5$ groups and optionally independently substituted with 1 to 5 $Z^1$ groups; and
g) $(C_2-C_6)$alkenyl, and $(C_2-C_6)$alkynyl, wherein each $(C_2-C_6)$alkenyl and $(C_2-C_6)$alkynyl is independently substituted with 1 to 5 $Z^6$ groups and optionally independently substituted with 1 to 5 $Z^1$ groups;

$R^2$ is selected from the group consisting of:
a) $(C_1-C_6)$alkyl and —O$(C_1-C_6)$alkyl;
b) $(C_2-C_6)$alkenyl, $(C_2-C_6)$alkynyl, $(C_1-C_6)$haloalkyl, $(C_3-C_7)$cycloalkyl, $(C_6-C_{20})$aryl, heterocycle, heteroaryl, halo, nitro and cyano;

c) C(=O)—$R^{11}$, —C(=O)—O—$R^{11}$, —S—$R^{11}$, —S(O)—$R^{11}$, —$SO_2$—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-$SO_2$—$R^{11}$, wherein each $R^{11}$ is independently selected from the group consisting of H, $(C_1-C_6)$alkyl, $(C_2-C_6)$alkenyl, $(C_2-C_6)$alkynyl, $(C_1-C_6)$haloalkyl, $(C_3-C_7)$cycloalkyl, $(C_6-C_{20})$aryl, heterocycle and heteroaryl, wherein each $(C_6-C_{20})$aryl, heterocycle or heteroaryl is optionally independently substituted with 1 to 3 $Z^{11}$ groups;

d) —N($R^9$)$R^{10}$, —C(=O)—N($R^9$)$R^{10}$, —O—C(=O)—N($R^9$)$R^{10}$, —$SO_2$—N($R^9$)$R^{10}$, —$(C_1-C_6)$alkyl-N($R^9$)$R^{10}$, —$(C_1C_6)$alkyl-C(=O)—N($R^9$)$R^{10}$, —$(C_1-C_6)$alkyl-O—C(=O)—N($R^9$)$R^{10}$, and —$(C_1-C_6)$alkyl-$SO_2$—N($R^9$)$R^{10}$, wherein each $R^{10}$ is independently selected from the group consisiting of $R^{11}$, —$(C_1-C_6)$alkyl-$R^{11}$, —$SO_2$—$R^{11}$, —C(=O)—$R^{11}$, —C(=O)O$R^{11}$ and —C(=O)N($R^9$)$R^{11}$, each $R^9$ is independently selected from the group consisting of H, $(C_1-C_6)$alkyl and $(C_3-C_7)$cycloalkyl, and wherein each $R^{11}$ is independently selected from the group consisting of H, $(C_1-C_6)$alkyl, $(C_2-C_6)$alkenyl, $(C_2-C_6)$alkynyl, $(C_1-C_6)$haloalkyl, $(C_3-C_7)$cycloalkyl, $(C_6-C_{20})$aryl, heterocycle and heteroaryl;

e) $(C_1-C_6)$alkyl, wherein $(C_1-C_6)$alkyl is independently substituted with 1 to 5 $Z^2$ groups and optionally independently substituted with 1 to 5 $Z^1$ groups; and f) $(C_1-C_6)$haloalkyl, $(C_3-C_7)$carbocycle, $(C_2-C_6)$alkenyl, and $(C_2-C_6)$alkynyl, wherein each $(C_1-C_6)$haloalkyl, $(C_3-C_7)$carbocycle, $(C_2-C_6)$alkenyl and $(C_2-C_6)$alkynyl is independently substituted with 1 to 5 $Z^6$ groups and optionally independently substituted with 1 to 5 $Z^1$ groups;

$R^3$ is —O$(C_1-C_6)$alkyl;

$R^4$ is selected from the group consisting of:

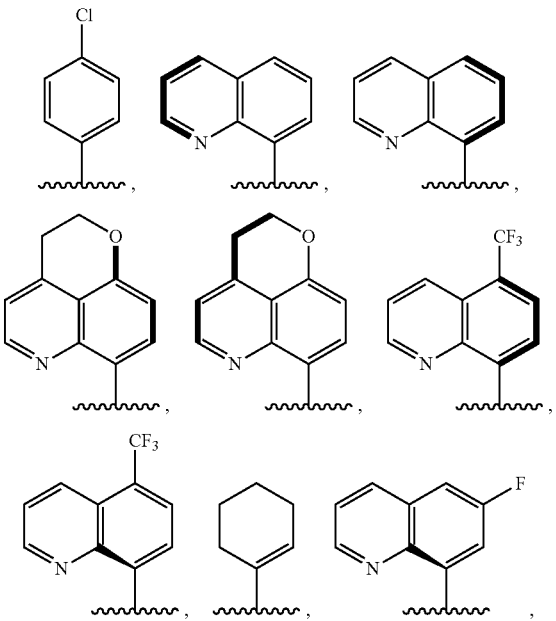

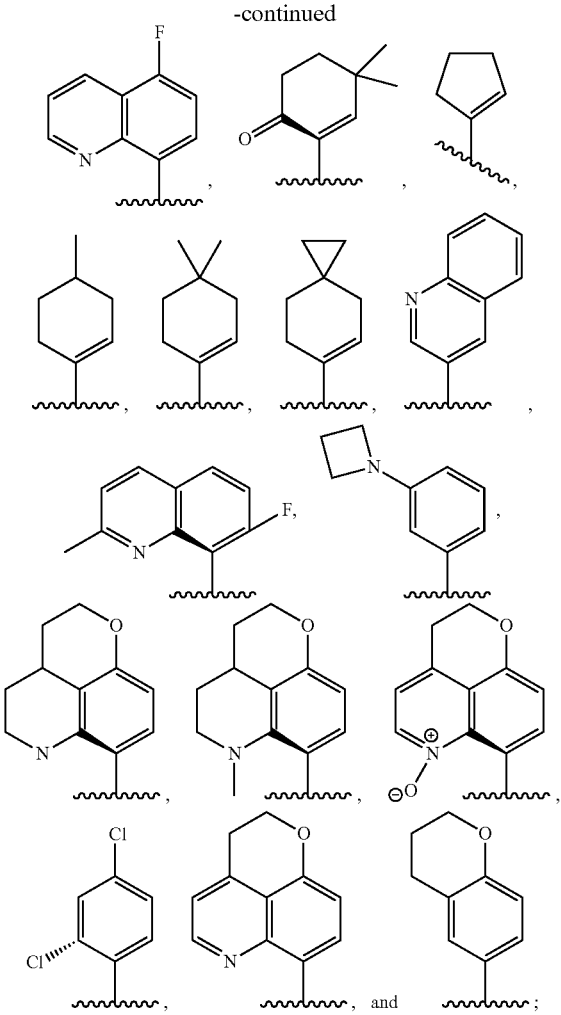

$R^6$ is selected from the group consisting of:
a) H, halo, $(C_1\text{-}C_6)$alkyl, and $(C_1\text{-}C_6)$haloalkyl;
b) $(C_2\text{-}C_6)$alkenyl, $(C_2\text{-}C_6)$alkynyl, $(C_3\text{-}C_7)$cycloalkyl, nitro, cyano, $(C_6\text{-}C_{20})$aryl, heterocycle and heteroaryl, wherein each $(C_6\text{-}C_{20})$aryl, heterocycle and heteroaryl is optionally independently substituted with 1 to 3 $Z^{10}$ groups;
c) —C(=O)—$R^{11}$, —C(=O)—O—$R^{11}$, —O—$R^{11}$, —S—$R^{11}$, —S(O)—$R^{11}$, —SO$_2$—$R^{11}$, —$(C_1\text{-}C_6)$alkyl-$R^{11}$, —$(C_1\text{-}C_6)$alkyl-C(=O)—$R^{11}$, —$(C_1\text{-}C_6)$alkyl-C(=O)—O—$R^{11}$, —$(C_1\text{-}C_6)$alkyl-O—$R^{11}$, —$(C_1\text{-}C_6)$alkyl-S—$R^{11}$, —$(C_1\text{-}C_6)$alkyl-S(O)—$R^{11}$ and —$(C_1\text{-}C_6)$alkyl-SO$_2$—$R^{11}$, wherein each $R^{11}$ is independently selected from the group consisting of H, $(C_1\text{-}C_6)$alkyl, $(C_2\text{-}C_6)$alkenyl, $(C_2\text{-}C_6)$alkynyl, $(C_1\text{-}C_6)$haloalkyl, $(C_3\text{-}C_7)$cycloalkyl, $(C_6\text{-}C_{20})$aryl, heterocycle and heteroaryl, wherein each $(C_6\text{-}C_{20})$ aryl, heterocycle and heteroaryl is optionally independently substituted with 1 to 3 $Z^{10}$ groups;
d) —$(C_1\text{-}C_6)$alkyl-O—$(C_1\text{-}C_6)$alkyl-$(C_3\text{-}C_7)$carbocycle, —$(C_1\text{-}C_6)$alkyl-S—$(C_1\text{-}C_6)$alkyl-$(C_3\text{-}C_7)$carbocycle, —$(C_1\text{-}C_6)$alkyl-S(O)—$(C_1\text{-}C_6)$alkyl-$(C_3\text{-}C_7)$carbocycle, —$(C_1\text{-}C_6)$alkyl-SO$_2$—$(C_1\text{-}C_6)$alkyl-$(C_3\text{-}C_7)$carbocycle, —$(C_2\text{-}C_6)$alkenyl-$(C_1\text{-}C_6)$haloalkyl, —$(C_2\text{-}C_6)$alkynyl—$(C_1\text{-}C_6)$haloalkyl, -halo$(C_3\text{-}C_7)$carbocycle, —NR$_a$SO$_2$NR$_c$R$_d$, —NR$_a$SO$_2$O$(C_3\text{-}C_7)$carbocycle, —NR$_a$SO$_2$O$(C_6\text{-}C_{20})$aryl, —$(C_2\text{-}C_6)$alkenyl-$(C_3\text{-}C_7)$carbocycle, —$(C_2\text{-}C_6)$alkenyl-$(C_6\text{-}C_{20})$aryl, —$(C_2\text{-}C_6)$alkenyl-heteroaryl, —$(C_2\text{-}C_6)$alkenyl-heterocycle, —$(C_2\text{-}C_6)$alkynyl-$(C_3\text{-}C_7)$carbocycle, —$(C_2\text{-}C_6)$alkynyl-$(C_6\text{-}C_{20})$aryl, —$(C_2\text{-}C_6)$alkynyl-heteroaryl, —$(C_2\text{-}C_6)$alkynyl-heterocycle, —$(C_2\text{-}C_8)$alkynyl-OR$_a$, —$(C_2\text{-}C_6)$alkyl-$(C_3\text{-}C_7)$carbocycle-OR$_a$, —$(C_3\text{-}C_7)$carbocycle-$Z^1$ and -halo$(C_1\text{-}C_6)$alkyl-$Z^3$, wherein each $(C_1\text{-}C_6)$alkyl, $(C_1\text{-}C_6)$haloalkyl, $(C_3\text{-}C_7)$carbocycle, $(C_2\text{-}C_6)$alkenyl, $(C_2\text{-}C_6)$alkynyl, $(C_6\text{-}C_{20})$aryl, heterocycle and heteroaryl, either alone or as part of a group, is optionally independently substituted with 1 to 5 $Z^1$ groups;
e) $(C_1\text{-}C_6)$alkyl, wherein $(C_1\text{-}C_6)$alkyl is independently substituted with 1 to 5 $Z^2$ groups and optionally independently substituted with 1 to 5 $Z^1$ groups;
f) $(C_6\text{-}C_{20})$aryl, heteroaryl, heterocycle, —X$(C_6\text{-}C_{20})$aryl, —Xheteroaryl and —Xheterocycle wherein each $(C_6\text{-}C_{20})$aryl, heteroaryl and heterocycle, either alone or as part of a group, is independently substituted with 1 to 5 $Z^5$ groups and optionally independently substituted with 1 to 5 $Z^1$ groups; and
g) $(C_1\text{-}C_6)$haloalkyl, $(C_3\text{-}C_7)$carbocycle, $(C_2\text{-}C_6)$alkenyl and $(C_2\text{-}C_6)$alkynyl, wherein each $(C_1\text{-}C_6)$haloalkyl, $(C_3\text{-}C_7)$carbocycle, $(C_2\text{-}C_6)$alkenyl and $(C_2\text{-}C_6)$alkynyl is independently substituted with 1 to 5 $Z^6$ groups and optionally substituted with 1 to 5 $Z^1$ groups;

$R^7$ is selected from the group consisting of:
a) H, halo, $(C_1\text{-}C_6)$alkyl and $(C_1\text{-}C_6)$haloalkyl;
b) $(C_2\text{-}C_6)$alkenyl, $(C_2\text{-}C_6)$alkynyl, $(C_3\text{-}C_7)$cycloalkyl, nitro, cyano, $(C_6\text{-}C_{20})$aryl, heterocycle and heteroaryl, wherein each $(C_6\text{-}C_{20})$aryl, heterocycle and heteroaryl is optionally independently substituted with 1 to 3 $Z^{10}$ groups;
c) —C(=O)—$R^{11}$, —C(=O)—O—$R^{11}$, —O—$R^{11}$, —S—$R^{11}$, —S(O)—$R^{11}$, —SO$_2$—$R^{11}$, —$(C_1\text{-}C_6)$alkyl-$R^{11}$, —$(C_1\text{-}C_6)$alkyl-C(=O)—$R^{11}$, —$(C_1\text{-}C_6)$alkyl-C(=O)—O—$R^{11}$, —$(C_1\text{-}C_6)$alkyl-O—$R^{11}$, —$(C_1\text{-}C_6)$alkyl-S—$R^{11}$, —$(C_1\text{-}C_6)$alkyl-S(O)—$R^{11}$ and —$(C_1\text{-}C_6)$alkyl-SO$_2$—$R^{11}$, wherein each $R^{11}$ is independently selected from the group consisting of H, $(C_1\text{-}C_6)$alkyl, $(C_2\text{-}C_6)$alkenyl, $(C_2\text{-}C_6)$alkynyl, $(C_1\text{-}C_6)$haloalkyl, $(C_3\text{-}C_7)$cycloalkyl, $(C_6\text{-}C_{20})$aryl, heterocycle and heteroaryl, wherein each $(C_6\text{-}C_{20})$aryl, heterocycle or heteroaryl is optionally independently substituted with 1 to 3 $Z^{10}$ groups;
d) —N(R$^9$)R$^{10}$, —C(=O)—N(R$^9$)R$^{10}$, —O—C(=O)—N(R$^9$)R$^{10}$, —SO$_2$—N(R$^9$)R$^{10}$, —$(C_1\text{-}C_6)$alkyl-N(R$^9$)R$^{10}$, —$(C_1\text{-}C_6)$alkyl-C(=O)—N(R$^9$)R$^{10}$, —$(C_1\text{-}C_6)$alkyl-O—C(=O)—N(R$^9$)R$^{10}$ and —$(C_1\text{-}C_6)$alkyl-SO$_2$—N(R$^9$)R$^{10}$, wherein each R$^{10}$ is independently selected from the group consisting of R$^{11}$, —$(C_1\text{-}C_6)$alkyl-R$^{11}$, —SO$_2$—R$^{11}$, —C(=O)R$^{11}$, —C(=O)OR$^{11}$ and —C(=O)N(R$^9$)R$^{11}$, each R$^9$ is independently selected from the group consisting of H, $(C_1\text{-}C_6)$alkyl and $(C_3\text{-}C_7)$cycloalkyl, and wherein each R$^{11}$ is independently selected from the group consisting of H, $(C_1\text{-}C_6)$alkyl, $(C_2\text{-}C_6)$alkenyl, $(C_2\text{-}C_6)$alkynyl, $(C_1\text{-}C_6)$haloalkyl, $(C_3\text{-}C_7)$cycloalkyl, $(C_6\text{-}C_{20})$aryl, heterocycle and heteroaryl, wherein each $(C_6\text{-}C_{20})$aryl, heterocycle or heteroaryl is optionally independently substituted with 1 to 3 $Z^{10}$ groups;
e) $(C_1\text{-}C_6)$alkyl, wherein $(C_1\text{-}C_6)$alkyl is independently substituted with 1 to 5 $Z^2$ groups and optionally independently substituted with 1 to 5 $Z^1$ groups;

f) $(C_6\text{-}C_{20})$aryl, heteroaryl, heterocycle, —X$(C_6\text{-}C_{20})$ aryl, —Xheteroaryl and —Xheterocycle, wherein each $(C_6\text{-}C_{20})$aryl, heteroaryl and heterocycle, either alone or as part of a group, is independently substituted with 1 to 5 $Z^5$ groups and optionally independently substituted with 1 to 5 $Z^1$ groups;

g) $(C_1\text{-}C_6)$haloalkyl, $(C_3\text{-}C_7)$carbocycle, $(C_2\text{-}C_6)$alkenyl, and $(C_2\text{-}C_6)$alkynyl, wherein each $(C_1\text{-}C_6)$haloalkyl, $(C_3\text{-}C_7)$carbocycle, $(C_2\text{-}C_6)$alkenyl and $(C_2\text{-}C_6)$alkynyl is independently substituted with 1 to 5 $Z^6$ groups and optionally independently substituted with 1 to 5 $Z^1$ groups; and h) —NR$_e$R$_f$, —C(O)NR$_e$R$_f$, —OC(O)NR$_e$R$_f$, —SO$_2$NR$_e$R$_f$, —$(C_1\text{-}C_6)$alkyl-NR$_e$R$_f$, —$(C_1\text{-}C_6)$alkylC(O)—NR$_e$R$_f$, —$(C_1\text{-}C_6)$ alkyl-O—C(O)—NR$_e$R$_f$ and —$(C_1\text{-}C_6)$alkyl-SO$_2$NR$_e$R$_f$, wherein each $(C_1\text{-}C_6)$alkyl, as part of a group, is independently substituted with 1 to 5 $Z^6$ groups and optionally independently substituted with 1 to 5 $Z^1$ groups;

$R^8$ is selected from the group consisting of:

a) halo, nitro and cyano;

b) $R^{11}$, —C(=O)—$R^{11}$, —C(=O)—O—$R^{11}$, —O—$R^{11}$, —S—$R^{11}$, —S(O)—$R^{11}$, —SO$_2$—$R^{11}$, —$(C_1\text{-}C_6)$alkyl-$R^{11}$, —$(C_1\text{-}C_6)$alkyl-C(=O)—$R^{11}$, —$(C_1\text{-}C_6)$alkyl-C(=O)—O—$R^{11}$, —$(C_1\text{-}C_6)$alkyl-O—$R^{11}$, —$(C_1\text{-}C_6)$alkyl-S—$R^{11}$, —$(C_1\text{-}C_6)$alkyl-S(O)—$R^{11}$ and —$(C_1\text{-}C_6)$alkyl-SO$_2$—$R^{11}$, wherein each $R^{11}$ is independently selected from the group consisting of H, $(C_1\text{-}C_6)$alkyl, $(C_2\text{-}C_6)$alkenyl, $(C_2\text{-}C_6)$alkynyl, $(C_1\text{-}C_6)$haloalkyl, $(C_3\text{-}C_7)$cycloalkyl, $(C_6\text{-}C_{20})$aryl, heterocycle and heteroaryl, wherein each $(C_6\text{-}C_{20})$aryl, heterocycle and heteroaryl is optionally independently substituted with 1 to 3 $Z^{11}$ groups;

c) —N(R$^9$)R$^{10}$, —C(=O)—N(R$^9$)R$^{10}$, —O—C(=O)—N(R$^9$)R$^{10}$, —SO$_2$—N(R$^9$)R$^{10}$, —$(C_1\text{-}C_6)$alkyl-N(R$^9$)R$^{10}$, —$(C_1\text{-}C_6)$alkyl-C(=O)—N(R$^9$)R$^{10}$, —$(C_1\text{-}C_6)$alkyl-O—C(=O)—N(R$^9$)R$^{10}$ and —$(C_1\text{-}C_6)$alkyl-SO$_2$—N(R$^9$)R$^{10}$, wherein each R$^{10}$ is independently selected from the group consisting of $R^{11}$, —$(C_1\text{-}C_6)$alkyl-$R^{11}$, —SO$_2$—$R^{11}$, —C(=O)—$R^{11}$, —C(=O)O$R^{11}$ and —C(=O)N(R$^9$)R$^{11}$, each $R^9$ is independently selected from the group consisting of H, $(C_1\text{-}C6)$alkyl and $(C_3\text{-}C_7)$cycloalkyl, and wherein each $R^{11}$ is independently selected from the group consisting of H, $(C_1\text{-}C_6)$alkyl, $(C_2\text{-}C_6)$alkenyl, $(C_2\text{-}C_6)$alkynyl, $(C_1\text{-}C_6)$haloalkyl, $(C_3\text{-}C_7)$cycloalkyl, $(C_6\text{-}C_{20})$aryl, heterocycle and heteroaryl;

d) $(C_1\text{-}C_6)$alkyl, wherein $(C_1\text{-}C_6)$alkyl is independently substituted with 1 to 5 $Z^2$ groups and optionally independently substituted with 1 to 5 $Z^1$ groups;

e) $(C_6\text{-}C_{20})$aryl, heteroaryl, heterocycle, —X$(C_6\text{-}C_{20})$ aryl, —Xheteroaryl and —Xheterocycle, wherein each $(C_6\text{-}C_{20})$aryl heteroaryl and heterocycle, either alone or as part of a group, is independently substituted with 1 to 5 $Z^5$ groups and optionally independently substituted with 1 to 5 $Z^1$ groups;

f) $(C_1\text{-}C_6)$haloalkyl, $(C_3\text{-}C_7)$carbocycle, $(C_2\text{-}C_6)$alkenyl and $(C_2\text{-}C_6)$alkynyl, wherein each $(C_1\text{-}C_6)$haloalkyl, $(C_3\text{-}C_7)$carbocycle, $(C_2\text{-}C_6)$alkenyl and $(C_2\text{-}C_6)$alkynyl is independently substituted with 1 to 5 $Z^6$ groups and optionally independently substituted with 1 to 5 $Z^1$ groups; and g) —NR$_e$R$_f$, —C(O)NR$_e$R$_f$, —OC(O)NR$_e$R$_f$, —SO$_2$NR$_e$R$_f$, —$(C_1\text{-}C_6)$alkyl-NR$_e$R$_f$, —$(C_1\text{-}C_6)$alkylC(O)—NR$_e$R$_f$, —$(C_1\text{-}C_6)$alkyl-O—C(O)—NR$_e$R$_f$ and —$(C_1\text{-}C_6)$alkyl-SO$_2$NR$_e$R$_f$, wherein each $(C_1\text{-}C_6)$alky, as part of a group, is independently substituted with 1 to 5 $Z^6$ groups and optionally independently substituted with 1 to 5 $Z^1$ groups;

X is independently selected from the group consisting of O, —C(O)—, —C(O)O—, —S—, —S(O)—, —SO$_2$—, —$(C_1\text{-}C_6)$alkylO—, —$(C_1\text{-}C_6)$alkylC(O)—, —$(C_1\text{-}C_6)$alkylC(O)O—, —$(C_1\text{-}C_6)$alkylS—, —$(C_1\text{-}C_6)$alkylS(O)— and —$(C_1\text{-}C_6)$alkylSO$_2$—;

each $Z^1$ is independently selected from the group consisting of halo, —NO$_2$, —OH, =NOR$_a$, —SH, —CN, $(C_1\text{-}C_6)$alkyl, $(C_2\text{-}C_6)$alkenyl, $(C_2\text{-}C_6)$alkynyl, $(C_1\text{-}C_6)$haloalkyl, $(C_3\text{-}C_7)$carbocycle, $(C_3\text{-}C_7)$halocarbocycle, $(C_6\text{-}C_{20})$aryl, heteroaryl, heterocycle, —O$(C_1\text{-}C_6)$alkyl, —O$(C_2\text{-}C_6)$alkenyl, —O$(C_2\text{-}C_6)$alkynyl, —O$(C_1\text{-}C_6)$haloalkyl, —O$(C_3\text{-}C_7)$carbocycle, —O$(C_3\text{-}C_7)$halocarbocycle, —O$(C_6\text{-}C_{20})$aryl, —Oheteroaryl, —Oheterocycle, —S$(C_1\text{-}C_6)$alkyl, —S$(C_2\text{-}C_6)$alkenyl, —S$(C_2\text{-}C_6)$alkynyl, —S$(C_1\text{-}C_6)$haloalkyl, —S$(C_3\text{-}C_7)$carbocycle, —S$(C_3\text{-}C_7)$halocarbocycle, —S$(C_6\text{-}C_{20})$aryl, —Sheteroaryl, —Sheterocycle, —S(O)$(C_1\text{-}C_6)$alkyl, —S(O)$(C_2\text{-}C_6)$alkenyl, —S(O)$(C_2\text{-}C_6)$alkynyl, —S(O)$(C_1\text{-}C_6)$haloalkyl, —S(O) $(C_3\text{-}C_7)$carbocycle, —S(O)$(C_3\text{-}C_7)$halocarbocycle, —SO$_2$$(C_1\text{-}C_6)$alkyl, —S(O)$(C_6\text{-}C_{20})$aryl, —S(O)carbocycle, —S(O)heteroaryl, —S(O)heterocycle, —SO$_2$$(C_2\text{-}C_6)$alkenyl, —SO$_2$$(C_2\text{-}C_6)$alkynyl, —SO$_2$$(C_1\text{-}C_6)$haloalkyl, —SO$_2$$(C_3\text{-}C_7)$carbocycle, —SO$_2$$(C_3\text{-}C_7)$halocarbocycle, —SO$_2$$(C_6\text{-}C_{20})$aryl, —SO$_2$heteroaryl, —SO$_2$heterocycle, —SO$_2$NR$_c$R$_d$, —NR$_c$R$_d$, —NR$_a$C(O)R$_a$, —NR$_a$C(O)OR$_a$, —NR$_a$C(O)NR$_c$R$_d$ —NR$_a$SO$_2$R$_b$, —NR$_a$SO$_2$NR$_c$R$_d$, —NR$_a$SO$_2$O$(C_3\text{-}C_7)$carbocycle, —NR$_a$SO$_2$O$(C_6\text{-}C_{20})$aryl, —OS(O)$_2$R$_a$, —C(O)R$_a$, —C(O)OR$_b$, —C(O)NR$_c$R$_d$, and —OC(O)NR$_c$R$_d$, wherein any $(C_1\text{-}C_6)$alkyl, —$(C_1\text{-}C_6)$haloalkyl, $(C_2\text{-}C_6)$alkenyl, $(C_2\text{-}C_6)$alkynyl, $(C_3\text{-}C_7)$halocarbocycle, $(C_3\text{-}C_7)$carbocycle, $(C_6\text{-}C_{20})$aryl, heteroaryl and heterocycle of $Z^1$, either alone or as part of a group, is optionally independently substituted with 1 to 5 halogen, —OH, —OR$_b$, —CN, —NR$_a$C(O)$_2$R$_b$, -heteroaryl, -heterocycle, —Oheteroaryl, —Oheterocycle, —NH-heteroaryl, —NHheterocycle, or —S(O)$_2$NR$_c$R$_d$;

each $Z^2$ is independently selected from the group consisting of —NO$_2$, —CN, spiro-heterocycle, bridge-heterocycle, spiro-bicyclic carbocycle, bridged-bicyclic carbocycle, NR$_a$SO$_2$$(C_3\text{-}C_7)$carbocycle, —NR$_a$SO$_2$$(C_6\text{-}C_{20})$aryl, —NR$_a$SO$_2$heteroaryl, —NR$_a$SO$_2$NR$_c$R$_d$, —NR$_a$SO$_2$O$(C_3\text{-}C_7)$carbocycle and —NR$_a$SO$_2$O$(C_6\text{-}C_{20})$aryl;

each $Z^3$ is independently selected from the group consisting of —NO$_2$, —CN, —OH, oxo, =NOR$_a$, thioxo, —$(C_6\text{-}C_{20})$aryl, -heterocycle, -heteroaryl, —$(C_3\text{-}C_7)$halocarbocycle, —O$(C_1\text{-}C_6)$alkyl, —O$(C_3\text{-}C_7)$carbocycle, —Ohalo$(C_3\text{-}C_7)$carbocycle, —O$(C_6\text{-}C_{20})$aryl, —Oheterocycle, —Oheteroaryl, —S$(C_1\text{-}C_6)$alkyl, —S$(C_3\text{-}C_7)$carbocycle, —S$(C_3\text{-}C_7)$halocarbocycle, —S$(C_6\text{-}C_{20})$aryl, —Sheterocycle, —Sheteroaryl, —S(O)$(C_1\text{-}C_6)$alkyl, —S(O)$(C_3\text{-}C_7)$carbocycle, —S(O)$(C_3\text{-}C_7)$halocarbocycle, —S(O)$(C_6\text{-}C_{20})$aryl, —S(O)heterocycle, —S(O)heteroaryl, —SO$_2$$(C_1\text{-}C_6)$alkyl, —SO$_2$$(C_3\text{-}C_7)$carbocycle, —SO$_2$$(C_3\text{-}C_7)$halocarbocycle, SO$_2$$(C_6\text{-}C_{20})$aryl, —SO$_2$heterocycle, —SO$_2$heteroaryl, —NR$_a$R$_b$, —NR$_a$C(O)R$_b$, —C(O)

NR$_c$R$_d$, —SO$_2$NR$_c$NR$_d$, —NR$_a$SO$_2$NR$_c$R$_d$, —NR$_a$SO$_2$O(C$_3$-C$_7$)carbocycle and —NR$_a$SO$_2$O(C$_6$-C$_{20}$)aryl;

each Z$^5$ is independently selected from the group consisting of —NO$_2$, —CN, —NR$_a$SO$_2$NR$_c$R$_d$, —NR$_a$SO$_2$O(C$_3$-C$_7$)carbocycle, —NR$_a$SO$_2$O(C$_6$-C$_{20}$)aryl, —NR$_a$SO$_2$(C$_1$-C$_6$)alkyl, 13 NR$_a$SO$_2$(C$_2$-C$_6$)alkenyl, —NR$_a$SO$_2$(C$_2$-C$_6$)alkynyl, —NR$_a$SO$_2$(C$_3$-C$_7$)carbocycle, —NR$_a$SO$_2$(C$_3$-C$_7$)halocarbocycle, —NR$_a$SO$_2$O(C$_6$-C$_{20}$)aryl, —NR$_a$SO$_2$heteroaryl, —NR$_a$SO$_2$heterocycle, —NR$_a$C(O)alkyl, —NR$_a$C(O)alkenyl, —NR$_a$C(O)alkynyl, —NR$_a$C(O)(C$_3$-C$_7$)carbocycle, —NR$_a$C(O)(C$_3$-C$_7$)halocarbocycle, —NR$_a$C(O)(C$_6$-C$_{20}$)aryl, —NR$_a$C(O)heteroaryl, —NR$_a$C(O)heterocycle, NR$_a$C(O)NR$_c$R$_d$ and NR$_a$C(O)OR$_b$;

each Z$^6$ is independently selected from the group consisting of —NO$_2$, —CN, —NR$_a$R$_a$, —NR$_a$C(O)R$_b$, —NR$_a$C(O)OR$_b$, —C(O)NR$_c$R$_d$, —(C$_3$-C$_7$)halocarbocycle, —(C$_6$-C$_{20}$)aryl, -heteroaryl, -heterocycle, —O(C$_6$-C$_{20}$)aryl, —Oheteroaryl, —Oheterocycle, —O(C$_3$-C$_7$)halocarbocycle, —O(C$_1$-C$_6$)alkyl, —O(C$_3$-C$_7$)carbocycle, —Ohalo(C$_1$-C$_6$)alkyl, —S(C$_6$-C$_{20}$)aryl, —Sheteroaryl, —Sheterocycle, —S(C$_3$-C$_7$)halocarbocycle, —S(C$_1$-C$_6$)alkyl, —S(C$_3$-C$_7$)carbocycle, —S(C$_1$-C$_6$)haloalkyl, —S(O)(C$_6$-C$_{20}$)aryl, —S(O)heteroaryl, —S(O)heterocycle, —S(O)(C$_3$-C$_7$)halocarbocycle, —S(O)(C$_1$-C$_6$)alkyl, —S(O)(C$_3$-C$_7$)carbocycle, —S(O)halo(C$_1$-C$_6$)alkyl, —SO$_2$(C$_6$-C$_{20}$)aryl, —SO$_2$heteroaryl, —SO$_2$heterocycle, —SO$_2$(C$_1$-C$_6$)alkyl, —SO$_2$halo(C$_1$-C$_6$)alkyl, —SO$_2$(C$_3$-C$_7$)carbocycle, —SO$_2$(C$_3$-C$_7$)halocarbocycle, —SO$_2$NR$_c$R$_d$, —NR$_a$SO$_2$(C$_3$-C$_7$)halocarbocycle, —NR$_a$SO$_2$(C$_6$-C$_{20}$)aryl, —NR$_a$SO$_2$heteroaryl, —NR$_a$SO$_2$NR$_c$R$_d$, —NR$_a$SO$_2$O(C$_3$-C$_7$)carbocycle and —NR$_a$SO$_2$O(C$_6$-C$_{20}$)aryl;

each Z$^{11}$ is independently selected from the group consisting of Z$^{10}$, —C(=O)—NH$_2$, —C(=O)—NH(C$_1$-C$_4$)alkyl, —C(=O)—N((C$_1$-C$_4$)alkyl)$_2$, —C(=O)—(C$_6$-C$_{20}$)aryl, —C(=O)-heterocycle and —C(=O)-heteroaryl;

each Z$^{10}$ is independently selected from the group consisting of:
i) halo, oxo, thioxo, (C$_2$-C$_6$)alkenyl, (C$_1$-C$_6$)haloalkyl, (C$_3$-C$_7$)cycloalkyl, (C$_3$-C$_7$)cycloalkyl-(C$_1$-C$_6$)alkyl-, —OH, —O(C$_1$-C$_6$)alkyl, —O(C$_1$-C$_6$)haloalkyl, —SH, —S(C$_1$-C$_6$)alkyl, —SO(C$_1$-C$_6$)alkyl, —SO$_2$(C$_1$-C$_6$)alkyl, —NH$_2$, —NH(C$_1$-C$_6$)alkyl and —N((C$_1$-C$_6$)alkyl)$_2$;
ii) (C$_1$-C$_6$)alkyl optionally independently substituted with —OH, —O—(C$_1$-C$_6$)haloalkyl or —O—(C$_1$-C$_6$)alkyl; and
iii) (C$_6$-C$_{20}$)aryl, heterocycle and heteroaryl, wherein each (C$_6$-C$_{20}$)aryl, heterocycle and heteroaryl is optionally independently substituted with halo, (C$_1$-C$_6$)alkyl or COOH;

each Z$^{12}$ is independently selected from the group consisting of —NO$_2$, =NOR$_a$, thioxo, (C$_6$-C$_{20}$)aryl, heterocycle, heteroaryl, (C$_3$-C$_7$)halocarbocycle, (C$_3$-C$_7$)carbocycle, —O(C$_3$-C$_7$)carbocycle, —Ohalo(C$_3$-C$_7$)carbocycle, —O(C$_6$-C$_{20}$)aryl, —Oheterocycle, —Oheteroaryl, —S(C$_1$-C$_6$)alkyl, —S(C$_3$-C$_7$)carbocycle, —Shalo(C$_3$-C$_7$)carbocycle, —S(C$_6$-C$_{20}$)aryl, —Sheterocycle, —Sheteroaryl, —S(O)(C$_1$-C$_6$)alkyl, —S(O)(C$_3$-C$_7$)carbocycle, —S(O)halo(C$_3$-C$_7$)carbocycle, —S(O)(C$_6$-C$_{20}$)aryl, —S(O)heterocycle, —S(O)heteroaryl, —SO$_2$(C$_1$-C$_6$)alkyl, —SO$_2$(C$_3$-C$_7$)carbocycle, —SO$_2$(C$_3$-C$_7$)halocarbocycle, SO$_2$(C$_6$-C$_{20}$)aryl, —SO$_2$heterocycle, —SO$_2$heteroaryl, —NR$_a$R$_a$, —NR$_a$C(O)R$_b$, —C(O)NR$_c$R$_d$, —SO$_2$NR$_c$R$_d$, —NR$_a$SO$_2$NR$_c$R$_d$, —NR$_a$SO$_2$O(C$_3$-C$_7$)carbocycle and —NR$_a$SO$_2$O(C$_6$-C$_{20}$)aryl;

each R$_a$ is independently H, (C$_1$-C$_6$)alkyl, (C$_2$-C$_6$)alkenyl, (C$_2$-C$_6$)alkynyl, (C$_3$-C$_7$)carbocycle, heterocycle, (C$_6$-C$_{20}$)aryl, (C$_6$-C$_{20}$)aryl(C$_1$-C$_6$)alkyl-, heteroaryl or heteroaryl(C$_1$-C$_6$)alkyl-, wherein any (C$_1$-C$_6$)alkyl, (C$_2$-C$_6$)alkenyl, (C$_2$-C$_6$)alkynyl, (C$_3$-C$_7$)carbocycle, heterocycle, (C$_6$-C$_{20}$)aryl or heteroaryl of R$_a$, either alone or as part of a group, is optionally independently substituted by halogen, OH or cyano;

each R$_b$ is independently (C$_1$-C$_6$)alkyl, (C$_2$-C$_6$)alkenyl, (C$_2$-C$_6$)alkynyl, (C$_3$-C$_7$)carbocycle, heterocycle, (C$_6$-C$_{20}$)aryl, (C$_6$-C$_{20}$)aryl(C$_1$-C$_6$)alkyl-, heteroaryl or heteroaryl(C$_1$-C$_6$)alkyl-, wherein any (C$_1$-C$_6$)alkyl, (C$_2$-C$_6$)alkenyl, (C$_2$-C$_6$)alkynyl, (C$_3$-C$_7$)carbocycle, heterocycle, (C$_6$-C$_{20}$)aryl or heteroaryl of R$_b$ is optionally independently substituted by halogen, OH or cyano;

R$_c$ and R$_d$ are each independently selected from the group consisting of H, (C$_1$-C$_6$)alkyl, (C$_2$-C$_6$)alkenyl, (C$_2$-C$_6$)alkynyl, (C$_3$-C$_7$)carbocycle, (C$_6$-C$_{20}$)aryl, (C$_6$-C$_{20}$)aryl(C$_1$-C$_6$)alkyl-, heterocycle, heteroaryl and heteroaryl(C$_1$-C$_6$)alkyl-, wherein any (C$_1$-C$_6$)alkyl, —(C$_2$-C$_6$)alkenyl, —(C$_2$-C$_6$)alkynyl, (C$_3$-C$_7$)carbocycle, heterocycle, (C$_6$-C$_{20}$)aryl and heteroaryl of R$_c$ or R$_d$, either alone or as part of a group, is optionally independently substituted by halogen, OH or cyano; or R$_c$ and R$_d$ together with the nitrogen to which they are attached form a heterocycle, wherein any heterocycle of R$_c$ and R$_d$ together with the nitrogen to which they are attached is optionally independently substituted by halogen, OH or cyano;

each R$_e$ is independently selected from the group consisting of —OR$_a$, (C$_1$-C$_6$)alkyl and (C$_3$-C$_7$)carbocycle, wherein each (C$_1$-C$_6$)alkyl and (C$_3$-C$_7$)carbocycle are independently substituted by 1 to 5 Z$^6$ and optionally independently substituted with 1 to 5 Z$^1$, (C$_2$-C$_6$)haloalkyl, (C$_2$-C$_6$)alkenyl and (C$_2$-C$_6$)alkynyl, wherein each (C$_2$-C$_6$)haloalkyl, (C$_2$-C$_6$)alkenyl and (C$_2$-C$_6$)alkynyl is optionally independently substituted with 1 to 5 Z$^1$, and (C$_6$-C$_{20}$)aryl, heterocycle and heteroaryl, wherein each (C$_6$-C$_{20}$)aryl, heterocycle and heteroaryl are independently substituted by 1 to 5 Z$^5$;

each R$_f$ is independently selected from the group consisting of —R$_g$, —OR$_a$, —(C$_1$-C$_6$)alkyl-Z$^6$, —SO$_2$R$_g$, —C(O)R$_g$, C(O)OR$_g$, and —C(O)NR$_e$R$_g$; and each R$_g$ is independently selected from the group consisting of H, —OR$_a$, (C$_1$-C$_6$)alkyl, (C$_3$-C$_7$)carbocycle, (C$_1$-C$_6$)haloalkyl, (C$_2$-C$_6$)alkenyl, (C$_2$-C$_6$)alkynyl, (C$_6$-C$_{20}$)aryl, heterocycle and heteroaryl, wherein any (C$_1$-C$_6$)alkyl, (C$_3$-C$_7$)carbocycle, (C$_1$-C$_6$)haloalkyl, (C$_2$-C$_6$)alkenyl, (C$_2$-C$_6$)alkynyl, (C$_6$-C$_{20}$)aryl, heterocycle or heteroaryl of R$_g$ is optionally independently substituted with 1 to 5 Z$^1$ groups;

wherein each heteroaryl has 1 to 6 carbon atoms and 1 to 4 heteroatoms selected from the group consisting of oxygen, nitrogen and sulfur, and each heterocycle has 1 to 6 carbon atoms and 1 to 3 heteroatoms selected from the group consisting of oxygen, nitrogen and sulfur.

2. The compound of claim 1, or a pharmaceutically acceptable salt thereof, which is a compound of formula Ie:

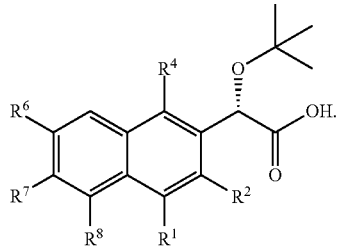

3. The compound of claim 1, or a pharmaceutically acceptable salt thereof, wherein:
$R^1$ is selected from the group consisting of:
  a) H, halo and $(C_1-C_6)$alkyl;
  b) $(C_2-C_6)$alkenyl, cyano, $(C_6-C_{20})$aryl, heterocycle and heteroaryl, wherein each $(C_6-C_{20})$aryl, heterocycle or heteroaryl is optionally independently substituted with 1 to 3 $Z^{10}$, groups;
  c) —C(=O)—N($R^9$)$R^{10}$, —$(C_1-C_6)$alkyl-$R^{11}$ and —$(C_1-C_6)$alkyl-O—$R^{11}$, wherein each $R^9$ is independently selected from the group consisting of H and $(C_1-C_6)$alkyl, each $R^{10}$ is independently selected from the group consisting of $R^{11}$ and —$(C_1-C_6)$alkyl-$R^{11}$, and wherein each $R^{11}$ is independently selected from the group consisting of H, $(C_1-C_6)$alkyl, $(C_1-C_6)$haloalkyl, $(C_3-C_7)$cycloalkyl, $(C_6-C_{20})$aryl, heterocycle and heteroaryl, wherein each $(C_6-C_{20})$aryl, heterocycle or heteroaryl is optionally independently substituted with 1 to 3 $Z^{10}$ groups;
  d) —$(C_1-C_6)$alkyl-N($R^9$)$R^{10}$, wherein each $R^9$ is independently selected from the group consisting of H and $(C_1-C_6)$alkyl, each $R^{10}$ is independently selected from the group consisting of $R^{11}$ and —$(C_1-C_6)$alkyl-$R^{11}$, and wherein each $R^{11}$ is independently selected from the group consisting of H, $(C_1-C_6)$alkyl, $(C_1-C_6)$haloalkyl, $(C_3-C_7)$cycloalkyl, $(C_6-C_{20})$aryl, heterocycle and heteroaryl, wherein each $(C_6-C_{20})$aryl, heterocycle or heteroaryl is optionally independently substituted with 1 to 3 $Z^{10}$ groups; and
  g) $(C_2-C_6)$alkenyl, and $(C_2-C_6)$alkynyl, wherein each $(C_2-C_6)$alkenyl and $(C_2-C_6)$alkynyl is independently substituted with 1 to 5 $Z^6$ groups and optionally independently substituted with 1 to 5 $Z^1$ groups;
$R^2$ is selected from the group consisting of:
  a) $(C_1-C_6)$alkyl and —O$(C_1-C_6)$alkyl;
  b) $(C_2-C_6)$alkenyl, $(C_2-C_6)$alkynyl, $(C_1-C_6)$haloalkyl, $(C_3-C_7)$cycloalkyl, $(C_6-C_{20})$aryl, heterocycle, heteroaryl, halo, nitro and cyano;
  c) C(=O)—$R^{11}$, —C(=O)—O—$R^{11}$, —S—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, and —$(C_1-C_6)$alkyl-S—$R^{11}$, wherein each $R^{11}$ is independently selected from the group consisting of H, $(C_1-C_6)$alkyl, $(C_1-C_6)$haloalkyl, $(C_3-C_7)$cycloalkyl, $(C_6-C_{20})$aryl, heterocycle and heteroaryl, wherein each $(C_6-C_{20})$aryl, heterocycle or heteroaryl is optionally independently substituted with 1 to 3 $Z^{11}$ groups; and
  d) —N($R^9$)$R^{10}$, —C(=O)—N($R^9$)$R^{10}$, —O—C(=O)—N($R^9$)$R^{10}$, —$(C_1-C_6)$alkyl-N($R^9$)$R^{10}$, —$(C_1-C_6)$alkyl-C(=O)—N($R^9$)$R^{10}$, and —$(C_1-C_6)$alkyl-O—C(=O)—N($R^9$)$R^{10}$, wherein each $R^9$ is independently selected from the group consisting of H and $(C_1-C_6)$alkyl, each $R^{10}$ is independently selected from the group consisting of $R^{11}$ and —$(C_1-C_6)$alkyl-$R^{11}$, and wherein each $R^{11}$ is independently selected from the group consisting of H, $(C_1-C_6)$alkyl, $(C_1-C_6)$haloalkyl, $(C_3-C_7)$cycloalkyl, $(C_6-C_{20})$aryl, heterocycle and heteroaryl;
$R^6$ is selected from the group consisting of:
  a) H, halo, $(C_1-C_6)$alkyl, and $(C_1-C_6)$haloalkyl;
  b) $(C_2-C_6)$alkenyl, $(C_2-C_6)$alkynyl, $(C_3-C_7)$cycloalkyl, nitro, cyano, $(C_6-C_{20})$aryl, heterocycle and heteroaryl, wherein each $(C_6-C_{20})$aryl, heterocycle and heteroaryl is optionally independently substituted with 1 to 3 $Z^{10}$ groups;
  c) —C(=O)—$R^{11}$, —C(=O)—O—$R^{11}$, —O—$R^{11}$, —S—$R^{11}$, —$(C_1-C_6)$alkyl-$R^{11}$, —$(C_1-C_6)$alkyl-(=O)—$R^{11}$, —$(C_1-C_6)$alkyl-C(=O)—O—$R^{11}$, —$(C_1-C_6)$alkyl-O—$R^{11}$, and —$(C_1-C_6)$alkyl-S—$R^{11}$, wherein each $R^{11}$ is independently selected from the group consisting of H, $(C_1-C_6)$alkyl, $(C_1-C_6)$haloalkyl, $(C_3-C_7)$cycloalkyl, $(C_6-C_{20})$aryl, heterocycle and heteroaryl, wherein each $(C_6-C_{20})$aryl, heterocycle and heteroaryl is optionally independently substituted with 1 to 3 $Z^{10}$ groups;
  d) —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_2-C_6)$alkenyl-$(C_1-C_6)$haloalkyl, —$(C_2-C_6)$alkynyl-$(C_1-C_6)$haloalkyl, -halo$(C_3-C_7)$carbocycle, —$(C_2-C_6)$alkenyl-$(C_3-C_7)$carbocycle, —$(C_2-C_6)$alkenyl-$(C_6-C_{20})$aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-$(C_6-C_{20})$aryl, —$(C_2-C_6)$alkynyl-heteroaryl, —$(C_2-C_6)$alkynyl-heterocycle, —$(C_2-C_8)$alkynyl-O$R_a$, —$(C_2-C_6)$alkyl-$(C_3-C_7)$carbocycle-O$R_a$, and —$(C_3-C_7)$carbocycle-$Z^1$, wherein each $(C_1-C_6)$alkyl, $(C_1-C_6)$haloalkyl, $(C_3-C_7)$carbocycle, $(C_2-C_6)$alkenyl, $(C_2-C_6)$alkynyl, $(C_6-C_{20})$aryl, heterocycle and heteroaryl, either alone or as part of a group, is optionally independently substituted with 1 to 5 $Z^1$ groups; and
  g) $(C_1-C_6)$haloalkyl, $(C_3-C_7)$carbocycle, $(C_2-C_6)$alkenyl and $(C_2-C_6)$alkynyl, wherein each $(C_1-C_6)$haloalkyl, $(C_3-C_7)$carbocycle, $(C_2-C_6)$alkenyl and $(C_2-C_6)$alkynyl is independently substituted with 1 to 5 $Z^6$ groups and optionally independently substituted with 1 to 5 $Z^1$ groups;
$R^7$ is selected from the group consisting of:
  a) H, halo, $(C_1-C_6)$alkyl and $(C_1-C_6)$haloalkyl;
  b) $(C_2-C_6)$alkenyl, $(C_2-C_6)$alkynyl, $(C_3-C_7)$cycloalkyl, nitro, cyano, $(C_6-C_{20})$aryl, heterocycle and heteroaryl, wherein each $(C_6-C_{20})$aryl, heterocycle and heteroaryl is optionally independently substituted with 1 to 3 $Z^{10}$ groups;
  c) —C(=O)—$R^{11}$, —C(=O)—O—$R^{11}$, —O—$R^{11}$, —S—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, and —$(C_1-C_6)$alkyl-S—$R^{11}$, wherein each $R^{11}$ is independently selected from the group consisting of H, $(C_1-C_6)$alkyl, $(C_1-C_6)$haloalkyl, $(C_3-C_7)$cycloalkyl, $(C_6-C_{20})$aryl, heterocycle and heteroaryl, wherein each $(C_6-C_{20})$aryl, heterocycle or heteroaryl is optionally independently substituted with 1 to 3 $Z^{10}$ groups; and
  d) —N($R^9$)$R^{10}$, —C(=O)—N($R^9$)$R^{10}$, —O—C(=O)—N($R^9$)$R^{10}$, —$(C_1-C_6)$alkyl-N($R^9$)$R^{10}$, —($C_1$-$C_6$)alkyl-C(=O)—N($R^9$)$R^{10}$, and —($C_1$-$C_6$)alkyl-O—C(=O)—N($R^9$)$R^{10}$, wherein each $R^9$ is independently selected from the group consisting of H and ($C_1$-$C_6$)alkyl, each $R^{10}$ is independently selected from the group consisting of $R^{11}$ and —($C_1$-$C_6$)alkyl-$R^{11}$, and wherein each $R^{11}$ is independently selected from the group consisting of H, ($C_1$-$C_6$)alkyl, ($C_1$-$C_6$)haloalkyl, ($C_3$-$C_7$)cycloalkyl, ($C_6$-$C_{20}$)aryl, heterocycle and heteroaryl, wherein each ($C_6$-$C_{20}$)aryl, heterocycle or heteroaryl is optionally independently substituted with 1 to 3 $Z^{10}$ groups;

$R^8$ is selected from the group consisting of:
a) halo, nitro and cyano;
b) $R^{11}$, —C(=O)—$R^{11}$, —C(=O)—O—$R^{11}$, —O—$R^{11}$, —S—$R^{11}$, —($C_1$-$C_6$)alkyl-$R^{11}$, —($C_1$-$C_6$)alkyl-C(=O)—$R^{11}$, —($C_1$-$C_6$)alkyl-C(=O)—O—$R^{11}$, —($C_1$-$C_6$)alkyl-O—$R^{11}$, and —($C_1$-$C_6$)alkyl-S—$R^{11}$, wherein each $R^{11}$ is independently selected from the group consisting of H, ($C_1$-$C_6$)alkyl, ($C_1$-$C_6$)haloalkyl, ($C_3$-$C_7$)cycloalkyl, ($C_6$-$C_{20}$)aryl, heterocycle and heteroaryl, wherein each ($C_6$-$C_{20}$)aryl, heterocycle and heteroaryl is optionally independently substituted with 1 to 3 $Z^{11}$ groups;
c) —N($R^9$)$R^{10}$, —C(=O)—N($R^9$)$R^{10}$, —O—C(=O)—N($R^9$)$R^{10}$, —($C_1$-$C_6$)alkyl-N($R^9$)$R^{10}$, —($C_1$-$C_6$)alkyl-C(=O)—N($R^9$)$R^{10}$, and —($C_1$-$C_6$)alkyl-O—C(=O)—N($R^9$)$R^{10}$, wherein each $R^9$ is independently selected from the group consisting of H and ($C_1$-$C_6$)alkyl, each $R^{10}$ is independently selected from the group consisting of $R^{11}$ and —($C_1$-$C_6$)alkyl-$R^{11}$, and wherein each $R^{11}$ is independently selected from the group consisting of H, ($C_1$-$C_6$)alkyl, ($C_1$-$C_6$)haloalkyl, ($C_3$-$C_7$)cycloalkyl, ($C_6$-$C_{20}$)aryl, heterocycle and heteroaryl; and
f) ($C_1$-$C_6$)haloalkyl, ($C_3$-$C_7$)carbocycle, ($C_2$-$C_6$)alkenyl and ($C_2$-$C_6$)alkynyl, wherein each ($C_1$-$C_6$)haloalkyl, ($C_3$-$C_7$)carbocycle, ($C_2$-$C_6$)alkenyl and ($C_2$-$C_6$)alkynyl is independently substituted with 1 to 5 $Z^6$ groups and optionally independently substituted with 1 to 5 $Z^1$ groups;

each $Z^1$ is independently selected from the group consisting of halo, —OH, —CN, ($C_1$-$C_6$)alkyl, and —$NR_cR_d$;
each $Z^6$ is independently selected from the group consisting of —$NR_aR_a$, —$NR_aC(O)R_b$, and —$NR_aC(O)OR_b$;
each $Z^{11}$ is independently $Z^{10}$;
each $Z^{10}$ is independently selected from the group consisting of:
i) halo, oxo, —OH, —O($C_1$-$C_6$)alkyl, —O($C_1$-$C_6$)haloalkyl, —$NH_2$, —NH($C_1$-$C_6$)alkyl and —N(($C_1$-$C_6$)alkyl)$_2$; and
ii) ($C_1$-$C_6$)alkyl optionally independently substituted with —OH, —O—($C_1$-$C_6$)haloalkyl or —O—($C_1$-$C_6$)alkyl;
each $R_a$ is independently H or ($C_1$-$C_6$)alkyl;
each $R_b$ is independently ($C_1$-$C_6$)alkyl; and
$R_c$, and $R_d$ are each independently selected from the group consisting of H and ($C_1$-$C_6$)alkyl.

4. The compound of claim 1, or a pharmaceutically acceptable salt thereof, wherein:
$R^1$ is selected from the group consisting of:
a) H, halo and ($C_1$-$C_6$)alkyl;
b) ($C_2$-$C_6$)alkenyl, cyano, ($C_6$-$C_{20}$)aryl, heterocycle and heteroaryl, wherein each ($C_6$-$C_{20}$)aryl, heterocycle or heteroaryl is optionally substituted with 1 to 3 $Z^{10}$ groups;
c) —C(=O)—N($R^9$)$R^{10}$, —($C_1$-$C_6$)alkyl-$R^{11}$ and —($C_1$-$C_6$)alkyl-O—$R^{11}$, wherein each $R^9$ is independently selected from the group consisting of H and ($C_1$-$C_6$)alkyl, each $R^{10}$ is independently $R^{11}$, and wherein each $R^{11}$ is independently selected from the group consisting of H and heterocycle;
d) —($C_1$-$C_6$)alkyl-N($R^9$)$R^{10}$, wherein each $R^9$ is independently selected from the group consisting of H and ($C_1$-$C_6$)alkyl, each $R^{10}$ is independently $R^{11}$, and wherein each $R^{11}$ is independently selected from the group consisting of H and ($C_1$-$C_6$)alkyl; and
g) ($C_2$-$C_6$)alkynyl, wherein ($C_2$-$C_6$)alkynyl is independently substituted with 1 $Z^6$ group;

$R^2$ is selected from the group consisting of:
a) ($C_1$-$C_6$)alkyl;
b) ($C_2$-$C_6$)alkenyl and ($C_1$-$C_6$)haloalkyl;
c) —($C_1$-$C_6$)alkyl-$R^{11}$ and —($C_1$-$C_6$)alkyl-O—$R^{11}$, wherein each $R^{11}$ is independently selected from the group consisting of H, ($C_1$-$C_6$)alkyl, heterocycle and heteroaryl; and
d) —($C_1$-$C_6$)alkyl-N($R^9$)$R^{10}$, wherein each $R^9$ is independently ($C_1$-$C_6$)alkyl, each $R^{10}$ is independently $R^{11}$, and wherein each $R^{11}$ is independently ($C_1$-$C_6$)alkyl;

$R^6$ is selected from the group consisting of:
a) H, halo, and ($C_1$-$C_6$)alkyl;
b) ($C_2$-$C_6$)alkenyl, ($C_2$-$C_6$)alkynyl and ($C_6$-$C_{20}$)aryl, wherein ($C_6$-$C_{20}$)aryl is optionally independently substituted with 1 to 3 $Z^1$ groups;
c) —($C_1$-$C_6$)alkyl-$R^{11}$ and —($C_1$-$C_6$)alkyl-O—$R^{11}$, wherein each $R^{11}$ is independently selected from the group consisting of H and ($C_3$-$C_7$)cycloalkyl;
d) —($C_2$-$C_6$)alkynyl-($C_3$-$C_7$)carbocycle, —($C_2$-$C_6$)alkynyl-($C_6$-$C_{20}$)aryl, —($C_2$-$C_6$)alkynyl-heteroaryl, —($C_2$-$C_6$)alkynyl-heterocycle, —($C_2$-$C_8$)alkynyl-$OR_a$ and —($C_2$-$C_6$)alkyl-($C_3$-$C_7$)carbocycle-$OR_a$, wherein each ($C_3$-$C_7$)carbocycle, ($C_2$-$C_6$)alkynyl, ($C_6$-$C_{20}$)aryl, heterocycle and heteroaryl, either alone or as part of a group, is optionally independently substituted with 1 or 2 $Z^1$ groups; and
g) ($C_2$-$C_6$)alkynyl substituted with 1 $Z^6$ group;

$R^7$ is selected from the group consisting of:
a) H, halo, ($C_1$-$C_6$)alkyl and ($C_1$-$C_6$)haloalkyl;
b) ($C_3$-$C_7$)cycloalkyl, cyano, ($C_6$-$C_{20}$)aryl and heteroaryl, wherein each ($C_6$-$C_{20}$)aryl and heteroaryl is optionally independently substituted with 1 to 3 $Z^{10}$ groups;
c) —O—$R^{11}$ and —($C_1$-$C_6$)alkyl-O—$R^{11}$, wherein each $R^{11}$ is independently selected from the group consisting of H and ($C_1$-$C_6$)alkyl; and
d) —C(=O)—N($R^9$)$R^{10}$ and —($C_1$-$C_6$)alkyl-N($R^9$)$R^{10}$, wherein each $R^9$ is independently selected from the group consisting of H and ($C_1$-$C_6$)alkyl, each $R^{10}$ is independently $R^{11}$, and wherein each $R^{11}$ is independently selected from the group consisting of H and ($C_1$-$C_6$)alkyl;

$R^8$ is selected from the group consisting of:
a) halo and cyano;
b) $R^{11}$, —O—$R^{11}$, —($C_1$-$C_6$)alkyl-$R^{11}$, wherein each $R^{11}$ is independently selected from the group consisting of H, ($C_1$-$C_6$)alkyl, ($C_6$-$C_{20}$)aryl and heteroaryl, wherein each ($C_6$-$C_{20}$)aryl and heteroaryl is optionally independently substituted with 1 to 3 $Z^{11}$ groups;
c) —C(=O)—N($R^9$)$R^{10}$, wherein $R^9$ is H, $R^{10}$ is $R^{11}$, and wherein $R^{11}$ is H; and
f) ($C_2$-$C_6$)alkynyl substituted with 1 $Z^6$ group;
each $Z^1$ is independently selected from the group consisting of halo, —OH, —CN, ($C_1$-$C_6$)alkyl, and —$NR_cR_d$;

each $Z^6$ is independently selected from the group consisting of —$NR_aR_a$, —$NR_aC(O)R_b$, and —$NR_aC(O)OR_b$;
each $Z^{11}$ is independently $Z^{10}$;
each $Z^{10}$ is independently selected from the group consisting of:
  i) halo, oxo, —OH, —O($C_1$-$C_6$)alkyl, —O($C_1$-$C_6$)haloalkyl, —$NH_2$, —NH($C_1$-$C_6$)alkyl and —N(($C_1$-$C_6$)alkyl)$_2$; and
  ii) ($C_1$-$C_6$)alkyl optionally independently substituted with —OH, —O—($C_1$-$C_6$)haloalkyl or —O—($C_1$-$C_6$)alkyl;
each $R_a$ is independently H or ($C_1$-$C_6$)alkyl;
each $R_b$ is independently ($C_1$-$C_6$)alkyl; and
$R_c$, and $R_d$ are each independently selected from the group consisting of H and ($C_1$-$C_6$)alkyl.

5. The compound of claim 1, or a pharmaceutically acceptable salt thereof, wherein:
$R^1$ is selected from the group consisting of:

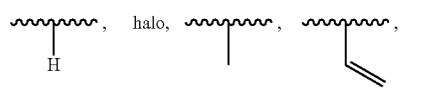

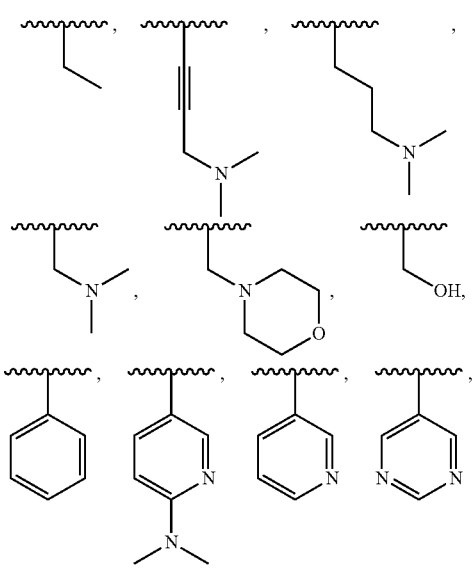

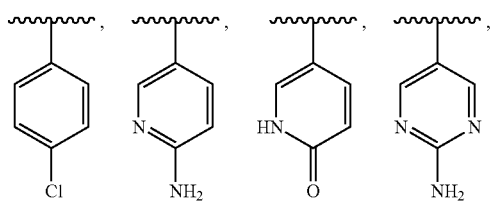

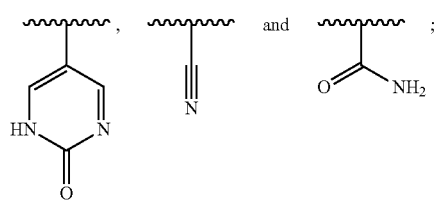

$R^2$ is selected from the group consisting of:

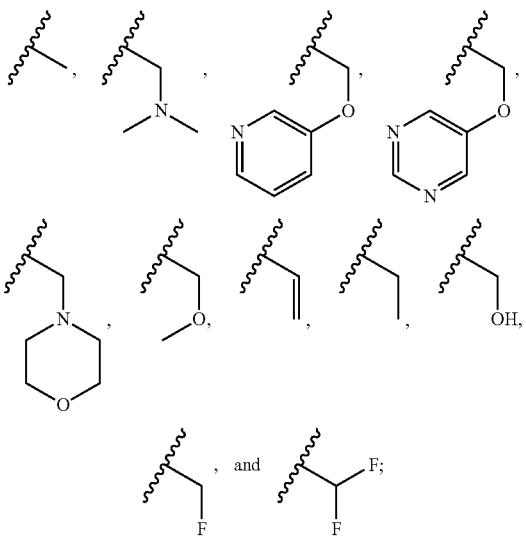

$R^6$ is selected from the group consisting of:

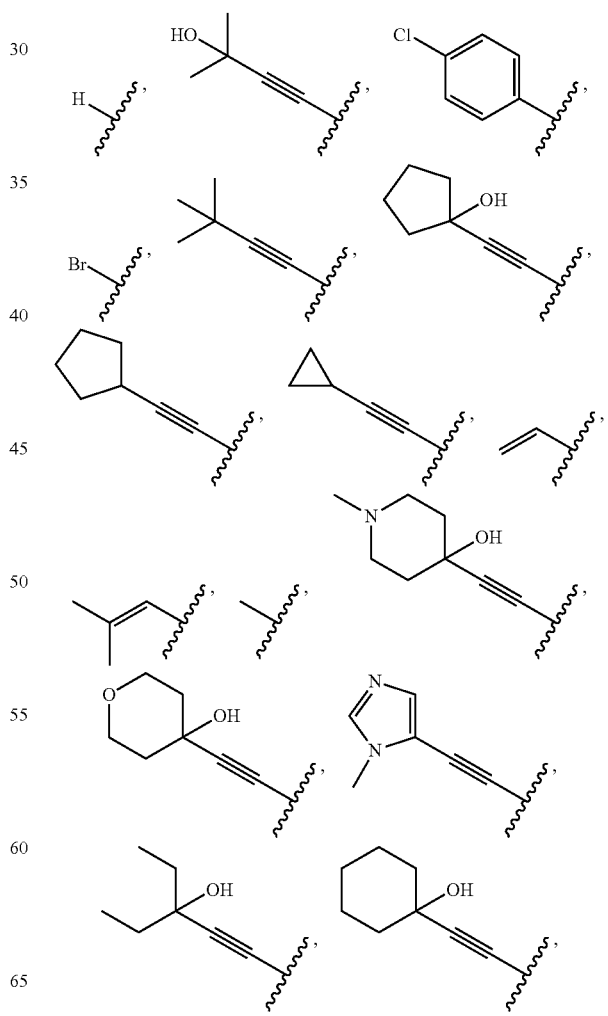

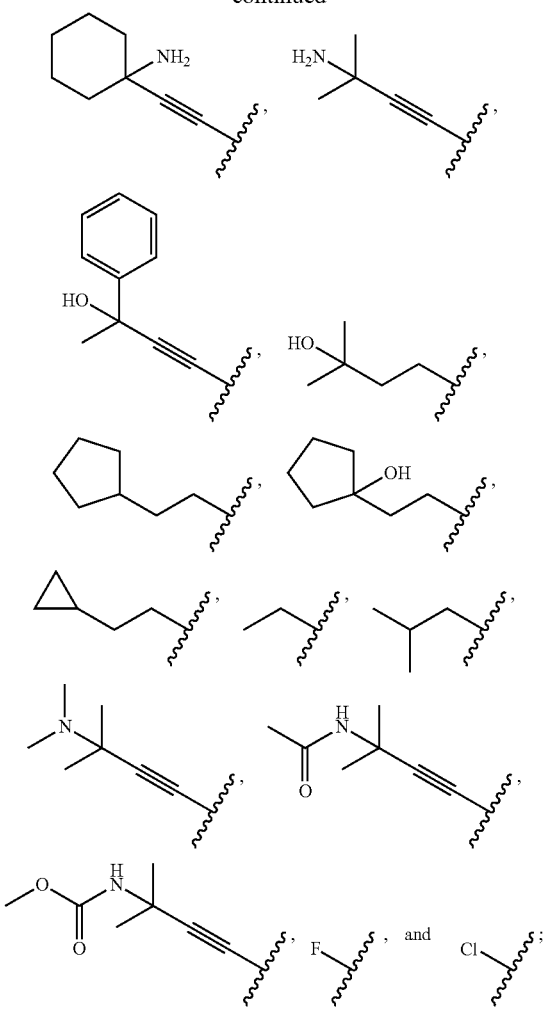
$R^7$ is selected from the group consisting of:
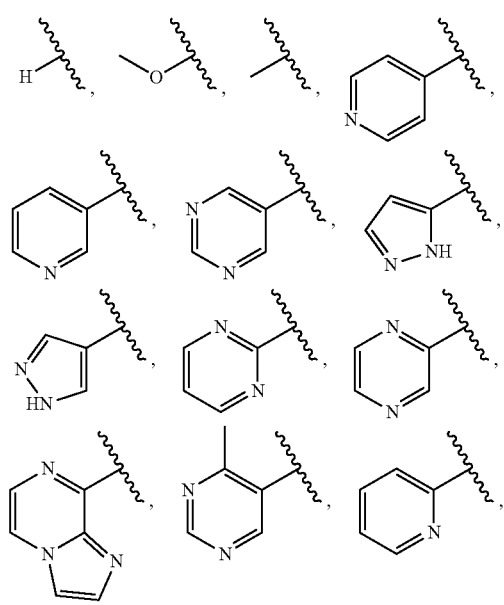
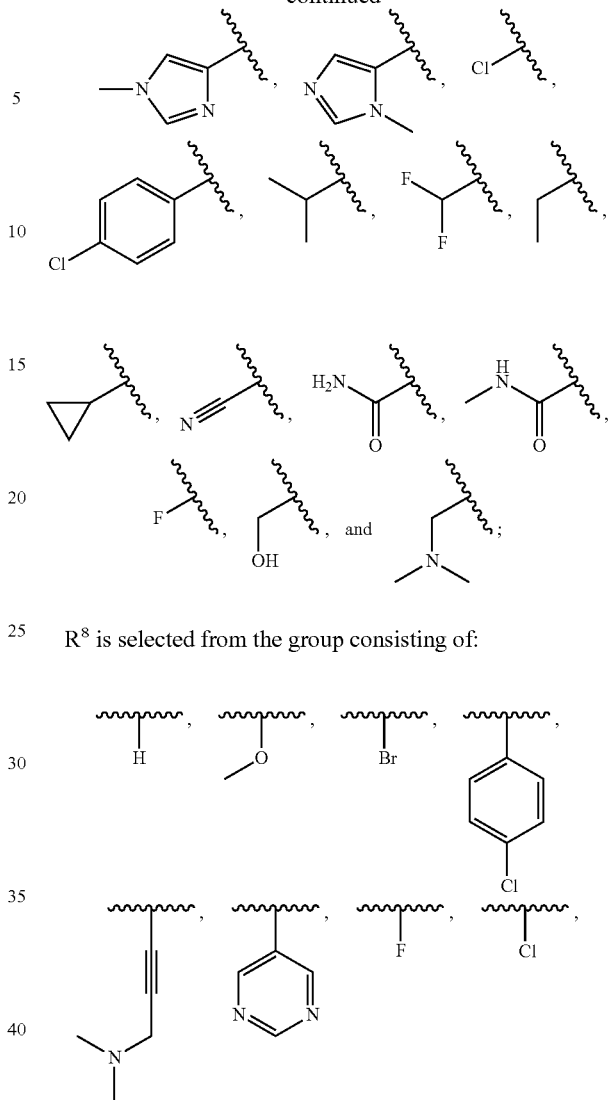
$R^8$ is selected from the group consisting of:
6. The compound of claim 1, or a pharmaceutically acceptable salt thereof, wherein $R^4$ is:
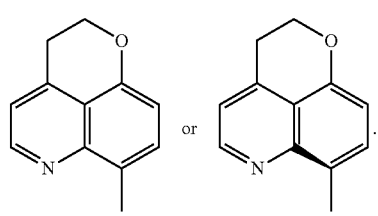

7. The compound of claim 1, or a pharmaceutically acceptable salt thereof, wherein $R^1$ is selected from a group consisting of:

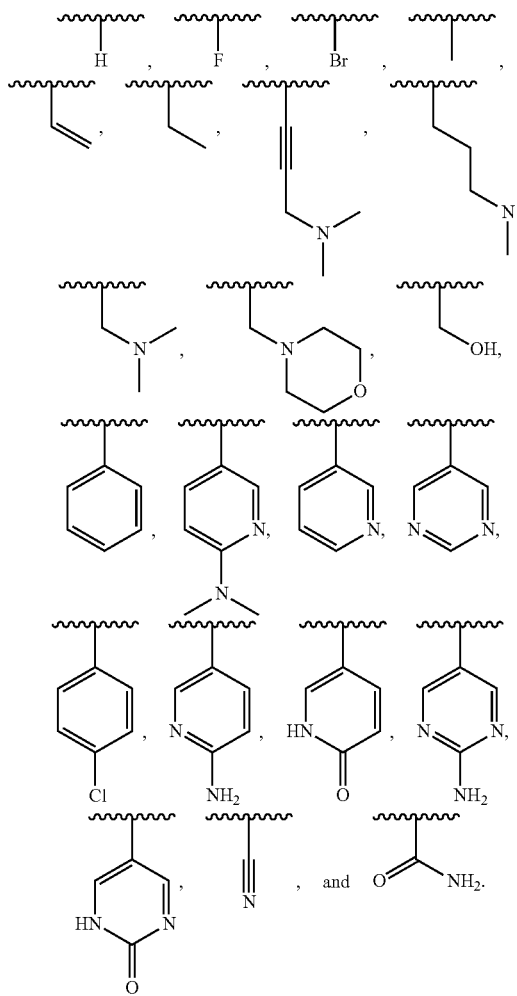

8. The compound of claim 1, or a pharmaceutically acceptable salt thereof, wherein $R^1$ is halo.

9. The compound of claim 1, or a pharmaceutically acceptable salt thereof, wherein $R^2$ is selected from the group consisting of:
a) $(C_1-C_6)$alkyl;
b) $(C_2-C_6)$alkenyl and $(C_1-C_6)$haloalkyl;
c) —$(C_1-C_6)$alkyl-$R^{11}$ and —$(C_1-C_6)$alkyl-O—$R^{11}$, wherein each $R^{11}$ is independently selected from the group consisting of H, $(C_1-C_6)$alkyl, $(C_2-C_6)$alkenyl, $(C_2-C_6)$alkynyl, $(C_1-C_6)$haloalkyl, $(C_3-C_7)$cycloalkyl, $(C_6-C_{20})$aryl, heterocycle and heteroaryl, wherein each $(C_6-C_{20})$aryl, heterocycle or heteroaryl is optionally independently substituted with 1 to 3 $Z^{11}$ groups;
d) —$(C_1-C_6)$alkyl-$N(R^9)R^{10}$, wherein each $R^{10}$ is independently selected from the group consisting of $R^{11}$, —$(C_1-C_6)$alkyl-$R^{11}$, —$SO_2$—$R^{11}$, —$C(=O)$—$R^{11}$, —$C(=O)OR^{11}$ and —$C(=O)N(R^9)R^{11}$, each $R^9$ is independently selected from the group consisting of H, $(C_1-C_6)$alkyl and $(C_3-C_7)$cycloalkyl, and wherein each $R^{11}$ is independently selected from the group consisting of H, $(C_1-C_6)$alkyl, $(C_2-C_6)$alkenyl, $(C_2-C_6)$alkynyl, $(C_1-C_6)$haloalkyl, $(C_3-C_7)$cycloalkyl, $(C_6-C_{20})$aryl, heterocycle and heteroaryl;
e) $(C_1-C_6)$alkyl, wherein $(C_1-C_6)$alkyl is independently substituted with 1 to 5 $Z^2$ groups and optionally independently substituted with 1 to 5 $Z^1$ groups; and
f) $(C_2-C_6)$alkenyl, wherein $(C_2-C_6)$alkenyl is independently substituted with 1 to 5 $Z^6$ groups and optionally independently substituted with 1 to 5 $Z^1$ groups.

10. The compound of claim 1, or a pharmaceutically acceptable salt thereof, wherein $R^2$ is:

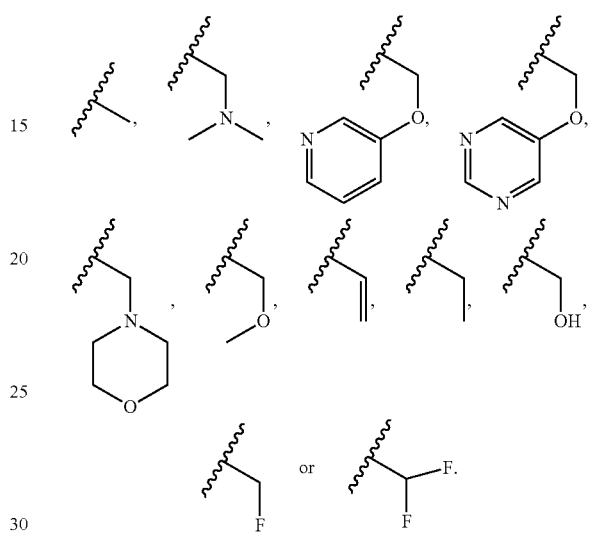

11. The compound of claim 1, or a pharmaceutically acceptable salt thereof, wherein $R^2$ is methyl.

12. The compound of claim 1, or a pharmaceutically acceptable salt thereof, wherein $R^6$ is selected from the group consisting of:
a) H, halo and $(C_1-C_6)$alkyl;
b) $(C_2-C_6)$alkenyl, $(C_2-C_6)$alkynyl and $(C_6-C_{20})$aryl, wherein each $(C_6-C_{20})$aryl is optionally independently substituted with 1 to 3 $Z^{10}$ groups;
c) —$(C_1-C_6)$alkyl-$R^{11}$ and —$(C_1-C_6)$alkyl-O—$R^{11}$, wherein each $R^{11}$ is independently selected from the group consisting of H, $(C_1-C_6)$alkyl, $(C_2-C_6)$alkenyl, $(C_2-C_6)$alkynyl, $(C_1-C_6)$haloalkyl, $(C_3-C_7)$cycloalkyl, $(C_6-C_{20})$aryl, heterocycle and heteroaryl, wherein each $(C_6-C_{20})$aryl, heterocycle or heteroaryl is optionally independently substituted with 1 to 3 $Z^{10}$ groups;
d) —$(C_2-C_6)$alkynyl-$(C_3-C_7)$carbocycle, —$(C_2-C_6)$alkynyl-$(C_6-C_{20})$aryl, —$(C_2-C_6)$alkynyl-heteroaryl —$(C_2-C_6)$alkynyl-heterocycle, —$(C_2-C_8)$alkynyl-$OR_a$ and —$(C_2-C_6)$alkyl-$(C_3-C_7)$carbocycle-$OR_a$, wherein each —$(C_2-C_6)$alkynyl-$(C_3-C_7)$carbocycle, —$(C_2-C_6)$alkynyl-$(C_6-C_{20})$aryl, —$(C_2-C_6)$alkynyl-heteroaryl and —$(C_2-C_6)$alkynyl-heterocycle, is optionally independently substituted with 1 to 5 $Z^1$ groups;
e) $(C_1-C_6)$alkyl, wherein $(C_1-C_6)$alkyl is independently substituted with 1 to 5 $Z^2$ groups and optionally independently substituted with 1 to 5 $Z^1$ groups;
f) $(C_6-C_{20})$aryl, wherein $(C_6-C_{20})$aryl is independently substituted with 1 to 5 $Z^5$ groups and optionally independently substituted with 1 to 5 $Z^1$ groups; and
g) $(C_2-C_6)$alkenyl and $(C_2-C_6)$alkynyl, wherein each $(C_2-C_6)$alkenyl and $(C_2-C_6)$alkynyl is independently substituted with 1 to 5 $Z^6$ groups and optionally independently substituted with 1 to 5 $Z^1$ groups.

13. The compound of claim 1, or a pharmaceutically acceptable salt thereof, wherein $R^6$ is selected from the group consisting of:

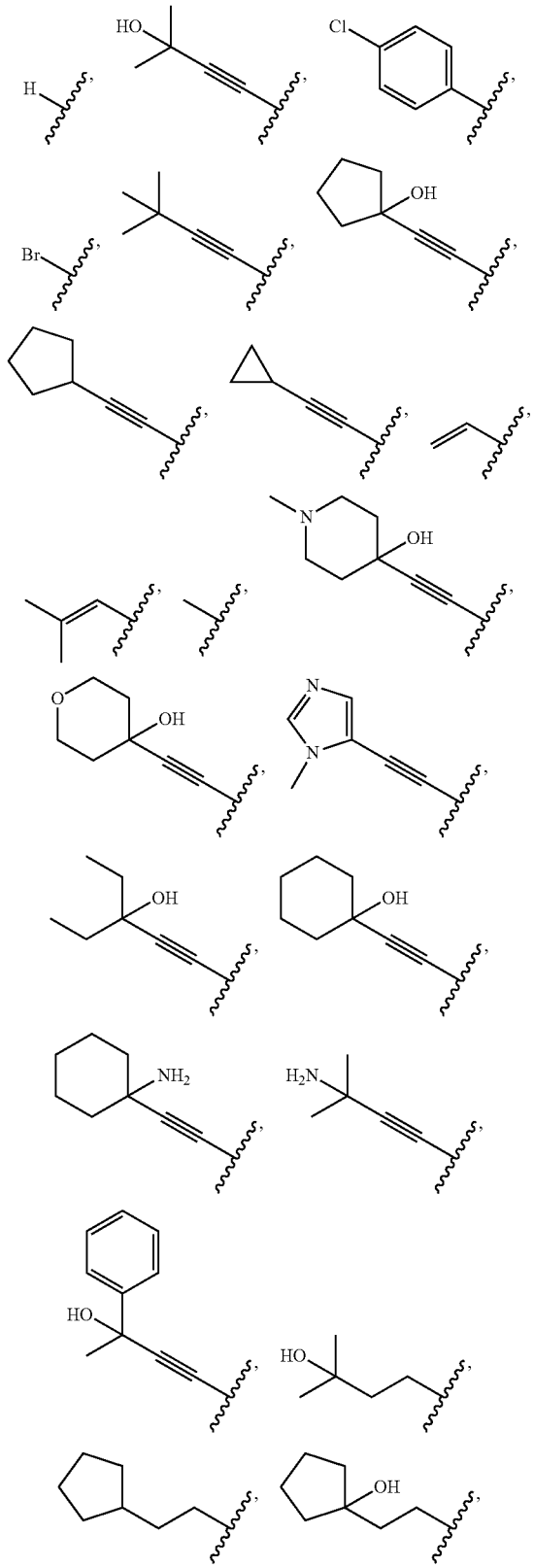

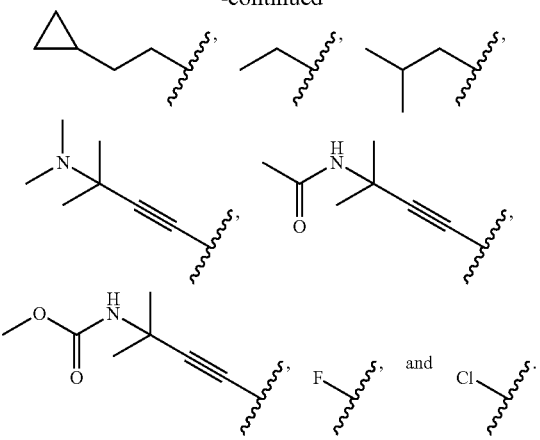

14. The compound of claim 1, or a pharmaceutically acceptable salt thereof, wherein $R^6$ is H.

15. The compound of claim 1, or a pharmaceutically acceptable salt thereof, wherein $R^7$ is selected from the group consisting of:

a) H, halo, $(C_1\text{-}C_6)$alkyl and $(C_1\text{-}C_6)$haloalkyl;

b) $(C_3\text{-}C_7)$cycloalkyl, cyano, $(C_6\text{-}C20)$aryl and heteroaryl, wherein each $(C_6\text{-}C_{20})$aryl and heteroaryl is optionally independently substituted with 1 to 3 $Z^{10}$ groups;

c) $—C(=O)—N(R^9)R^{10}$, wherein each $R^{10}$ is independently selected from the group consisting of $R^{11}$, $—(C_1\text{-}C_6)$alkyl-$R^{11}$, $—SO_2—R^{11}$, $—C(=O)—R^{11}$, $—C(=O)OR^{11}$ and $—C(=O)N(R^9)R^{11}$, each $R^9$ is independently selected from the group consisting of H, $(C_1\text{-}C_6)$alkyl and $(C_3\text{-}C_7)$cycloalkyl, and wherein each $R^{11}$ is independently selected from the group consisting of H, $(C_1\text{-}C_6)$alkyl, $(C_2\text{-}C_6)$alkenyl, $(C_2\text{-}C_6)$alkynyl, $(C_1\text{-}C_6)$haloalkyl, $(C_3\text{-}C_7)$cycloalkyl, $(C_6\text{-}C_{20})$aryl, heterocycle and heteroaryl, wherein each $(C_6\text{-}C_{20})$aryl, heterocycle or heteroaryl is optionally independently substituted with 1 to 3 $Z^{10}$ groups;

d) $(C_1\text{-}C_6)$alkyl, wherein $(C_1\text{-}C_6)$alkyl is independently substituted with 1 to 5 $Z^2$ groups and optionally independently substituted with 1 to 5 $Z^1$ groups;

e) $(C_6\text{-}C_{20})$aryl and heteroaryl, wherein each $(C_6\text{-}C_{20})$aryl and heteroaryl is independently substituted with 1 to 5 $Z^5$ groups and optionally independently substituted with 1 to 5 $Z^1$ groups;

f) $(C_1\text{-}C_6)$haloalkyl and $(C_3\text{-}C_7)$carbocycle, wherein each $(C_1\text{-}C_6)$haloalkyl and $(C_3\text{-}C_7)$carbocycle is independently substituted with 1 to 5 $Z^6$ groups and optionally independently substituted with 1 to 5 $Z^1$ groups; and g) $—C(O)NR_eR_f$.

16. The compound of claim 1, or a pharmaceutically acceptable salt thereof, wherein $R^7$ is selected from the group consisting of:

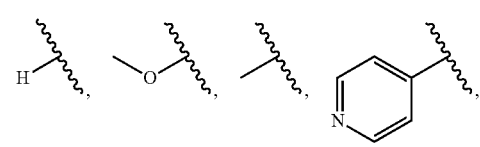

391

-continued

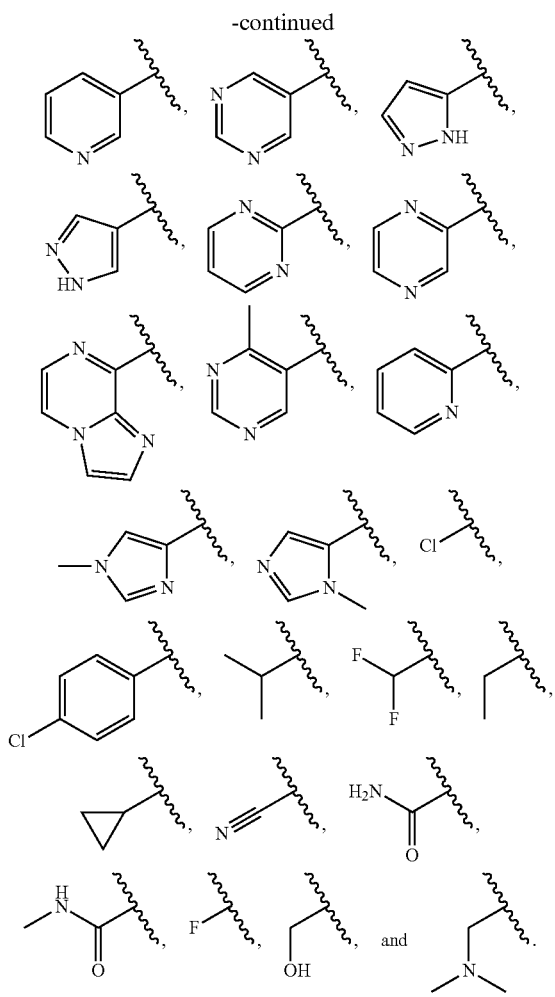

17. The compound of claim 1, or a pharmaceutically acceptable salt thereof, wherein $R^7$ is H.

18. The compound of claim 1, or a pharmaceutically acceptable salt thereof, wherein $R^8$ is selected from the group consisting of:

a) halo and cyano;

b) $R^{11}$, —O—$R^{11}$ and —($C_1$-$C_6$)alkyl-$R^{11}$, wherein each $R^{11}$ is independently selected from the group consisting of H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, ($C_6$-$C_{20}$)aryl, heterocycle and heteroaryl, wherein each ($C_6$-$C_{20}$)aryl, heterocycle and heteroaryl is optionally independently substituted with 1 to 3 $Z^{11}$ groups;

c) —C(=O)—N($R^9$)$R^{10}$, wherein each $R^{10}$ is independently selected from the group consisting of $R^{11}$, —($C_1$-$C_6$)alkyl-$R^{11}$, —$SO_2$—$R^{11}$, —C(=O)—$R^{11}$, —C(=O)O$R^{11}$ and —C(=O)N($R^9$)$R^{11}$, each $R^9$ is independently selected from the group consisting of H, ($C_1$-$C_6$)alkyl and ($C_3$-$C_7$)cycloalkyl, and wherein each $R^{11}$ is independently selected from the group consisting of H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, ($C_6$-$C_{20}$)aryl, heterocycle and heteroaryl;

d) ($C_1$-$C_6$)alkyl, wherein ($C_1$-$C_6$)alkyl is independently substituted with 1 to 5 $Z^2$ groups and optionally independently substituted with 1 to 5 $Z^1$ groups;

392 e) ($C_6$-$C_{20}$)aryl and heteroaryl, wherein each ($C_6$-$C_{20}$)aryl and heteroaryl is independently substituted with 1 to 5 $Z^5$ groups and optionally independently substituted with 1 to 5 $Z^1$ groups;

f) ($C_2$-$C_6$)alkynyl, wherein ($C_2$-$C_6$)alkynyl is independently substituted with 1 to 5 $Z^6$ groups and optionally independently substituted with 1 to 5 $Z^1$ groups; and g) —C(O)N$R_e R_f$.

19. The compound claim 1, or a pharmaceutically acceptable salt thereof, wherein $R^8$ is selected from the group consisting of:

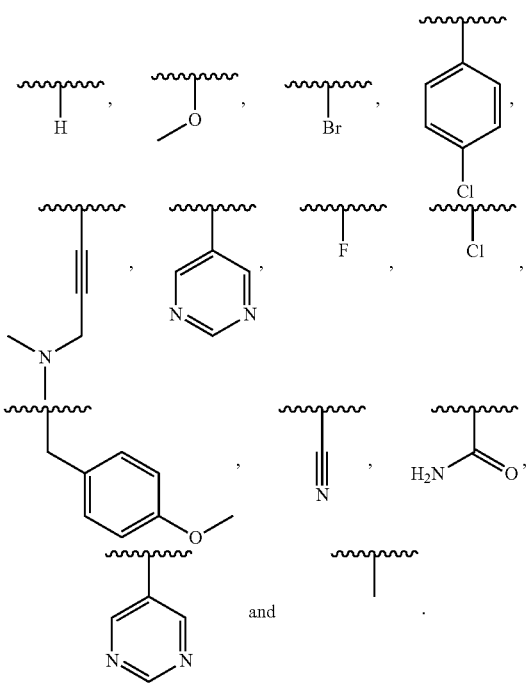

20. The compound of claim 1, or a pharmaceutically acceptable salt thereof, wherein $R^8$ is H.

21. The compound of claim 1, or a pharmaceutically acceptable salt thereof, selected from the group consisting of:

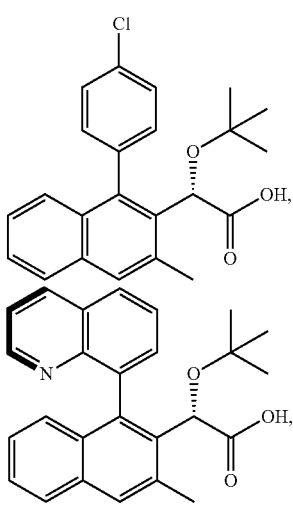

-continued
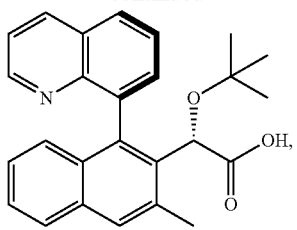
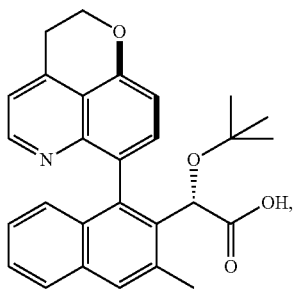
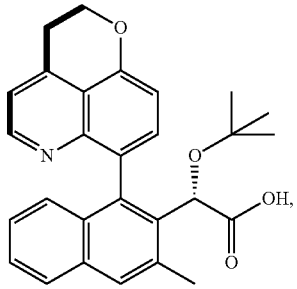
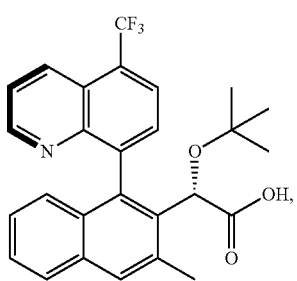
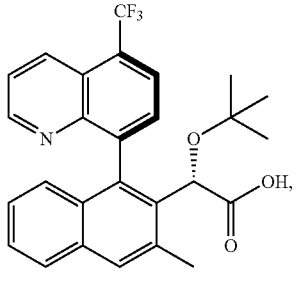
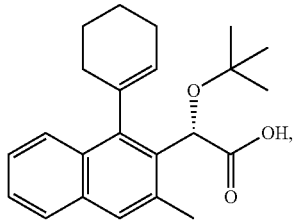
-continued
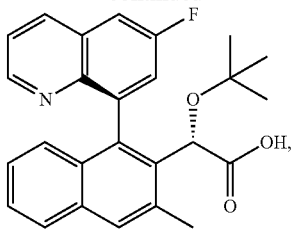
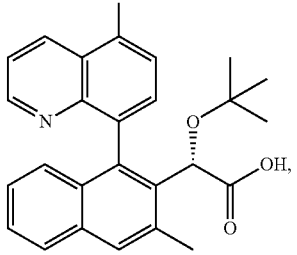
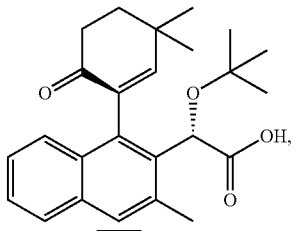
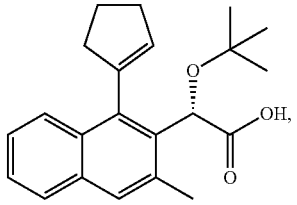
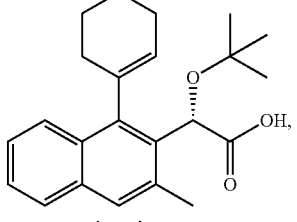
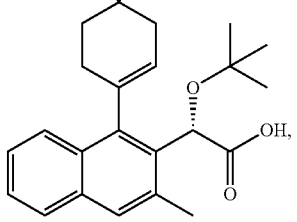
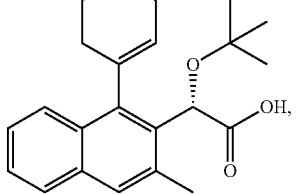

-continued
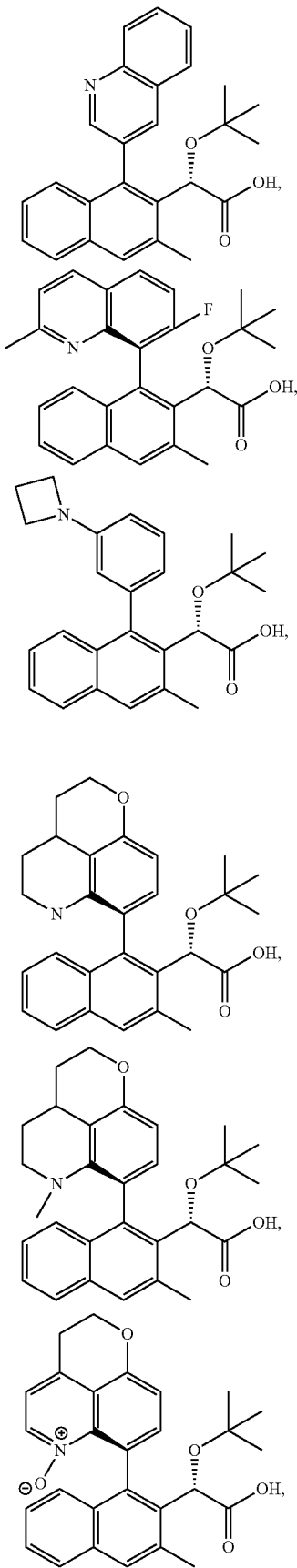
-continued
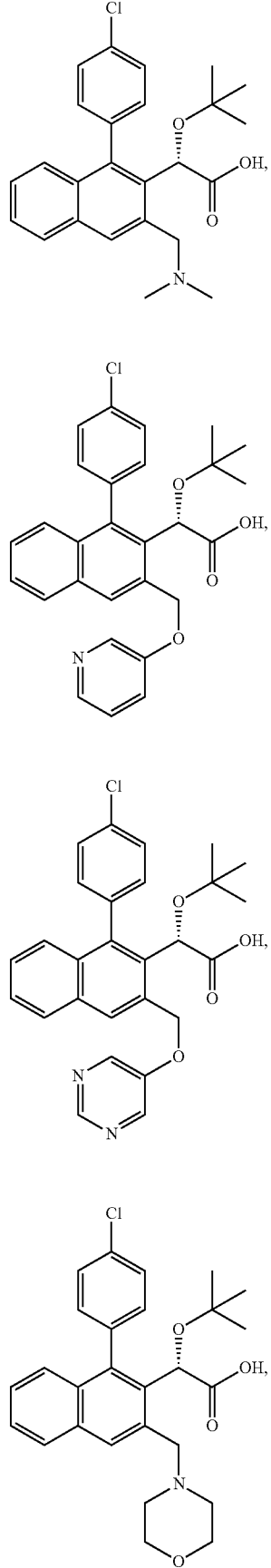

397
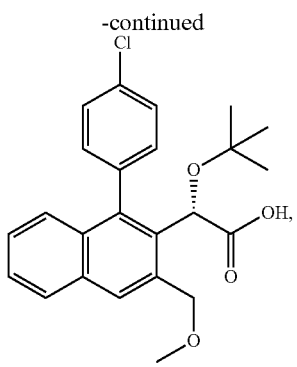
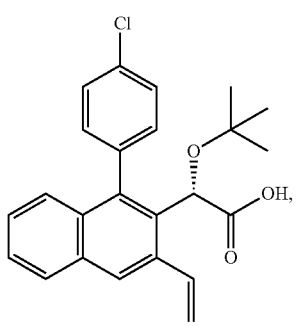
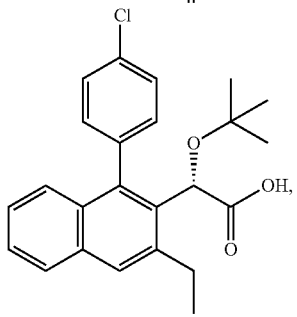
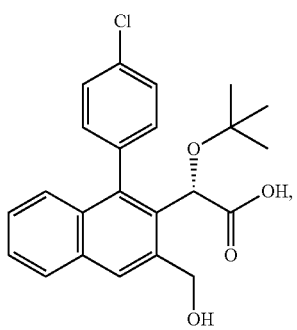
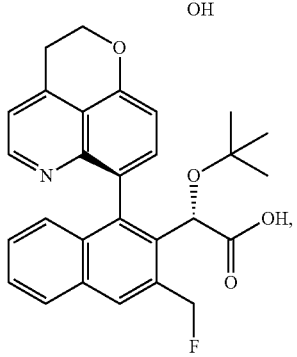
398
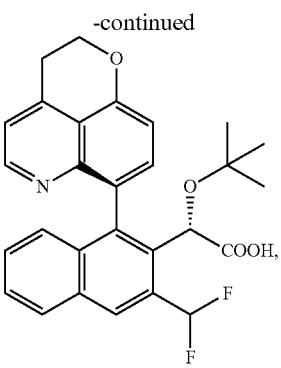
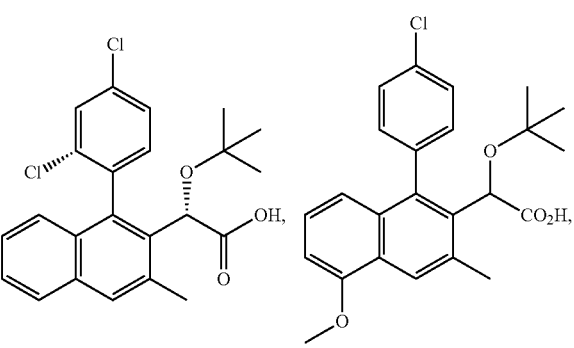
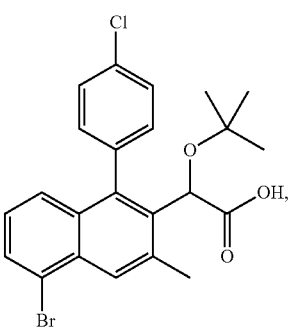
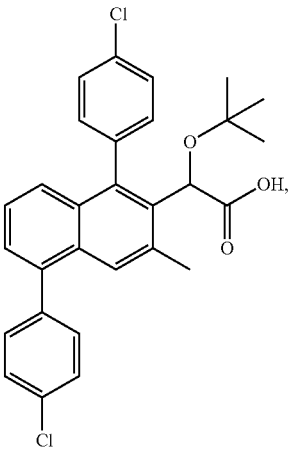

-continued
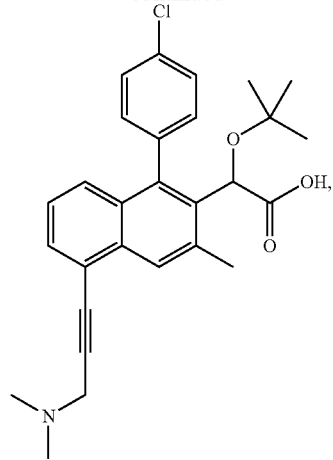
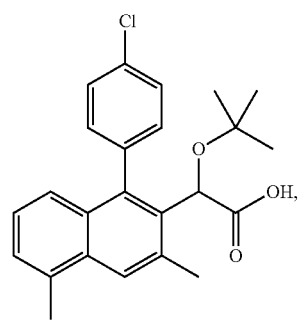
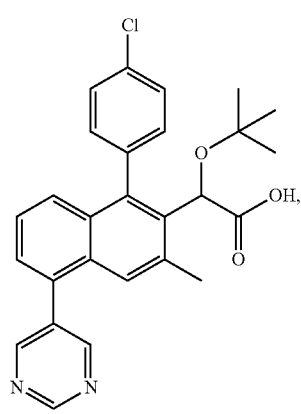
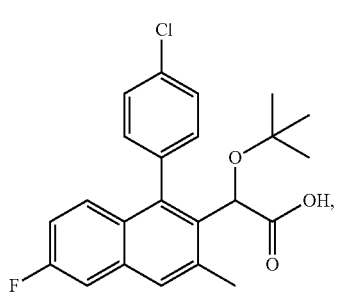
-continued
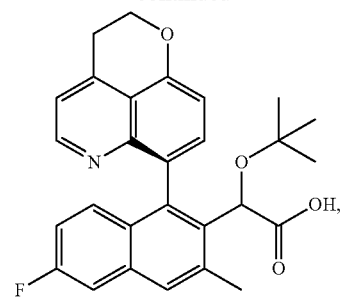
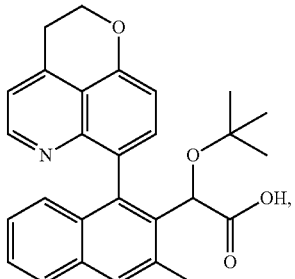
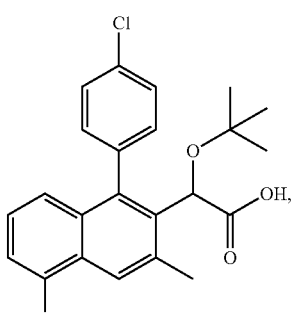
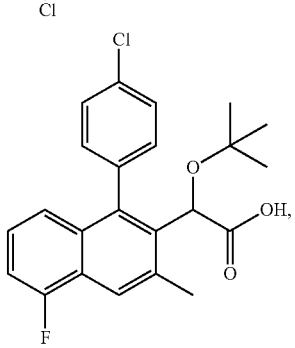
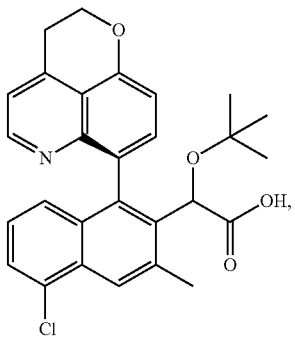

401
-continued
402
-continued
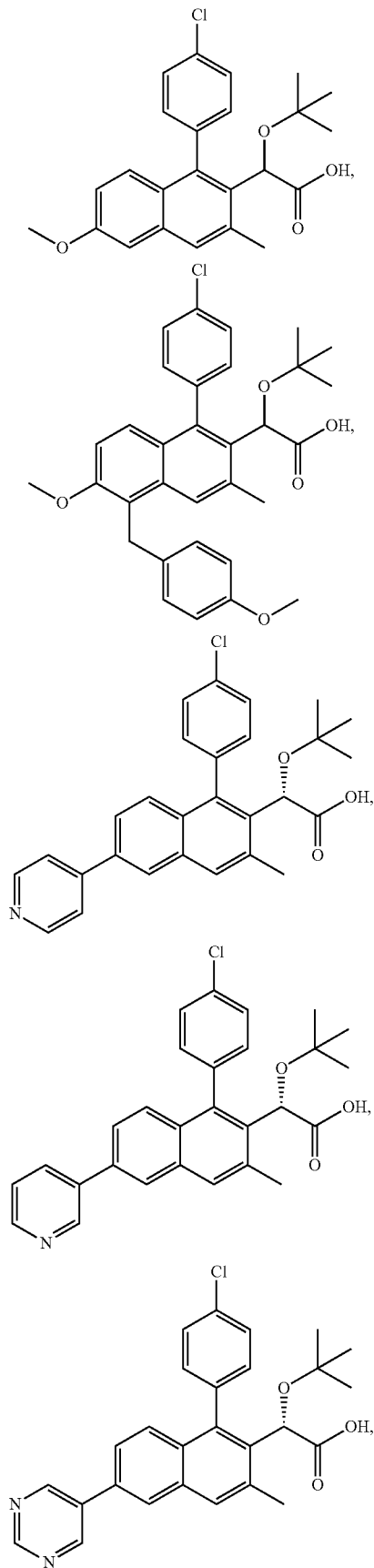
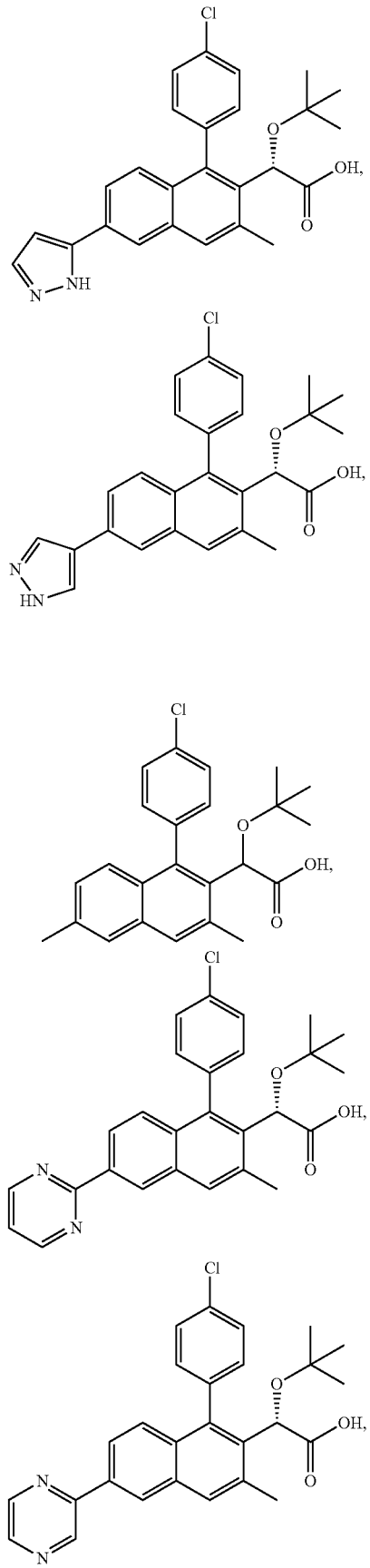

403
-continued
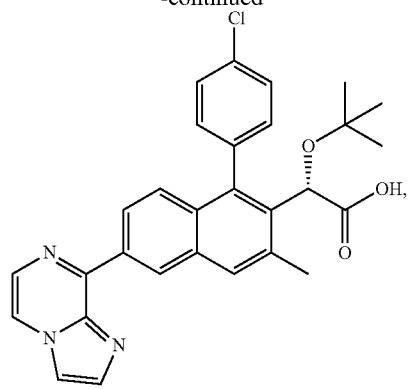
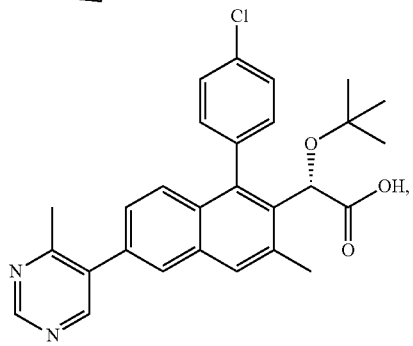
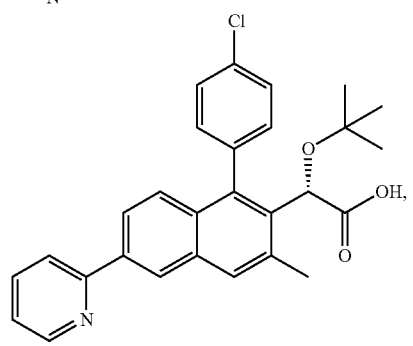
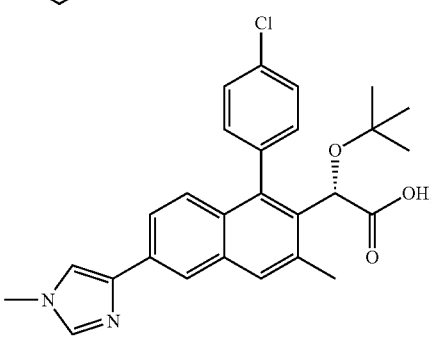
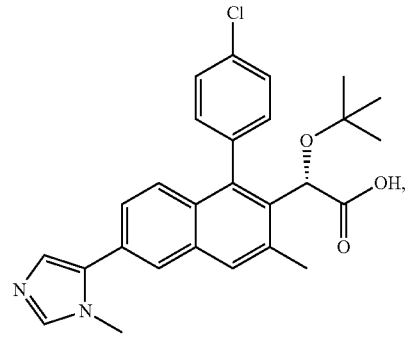
404
-continued
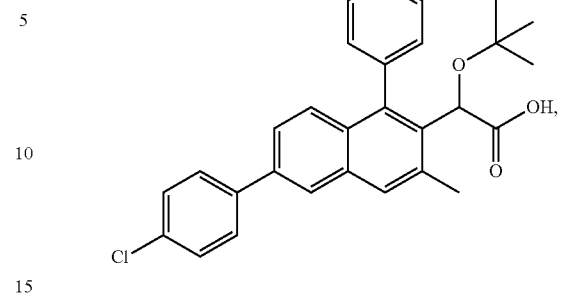
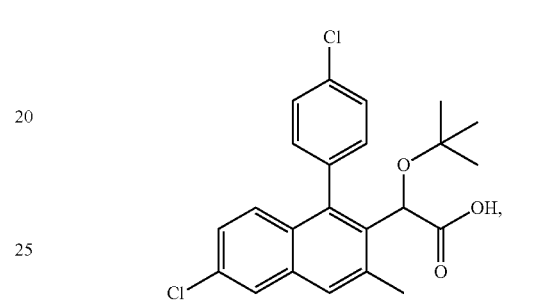
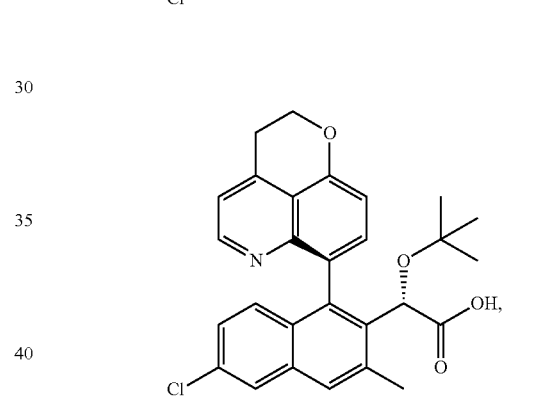
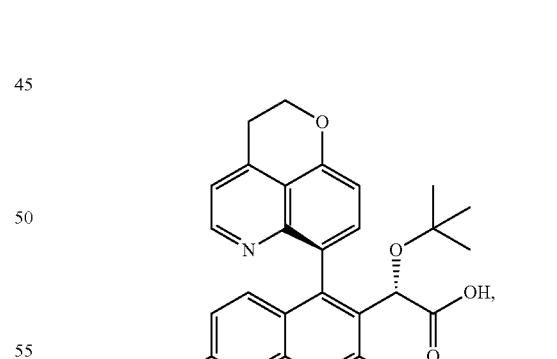
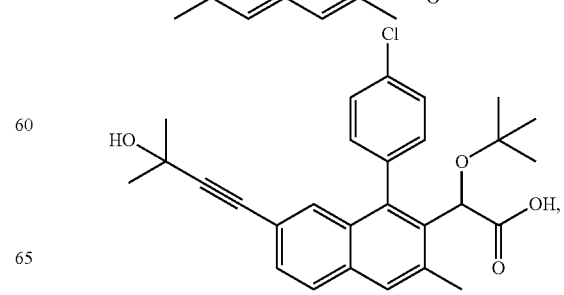

405
-continued
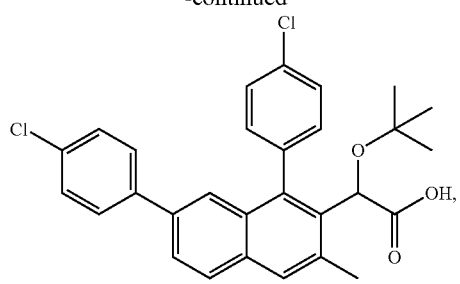
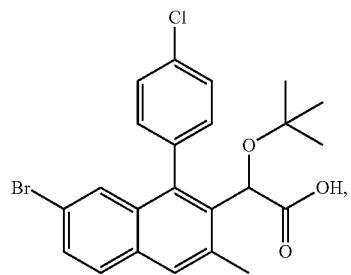
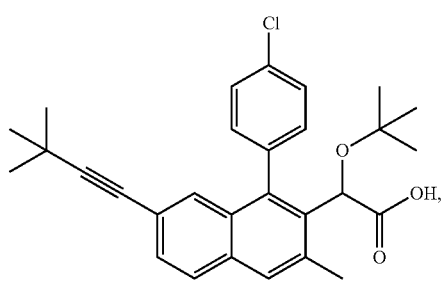
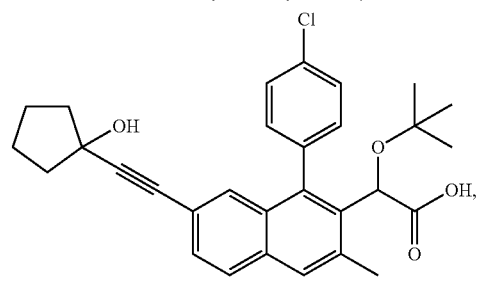
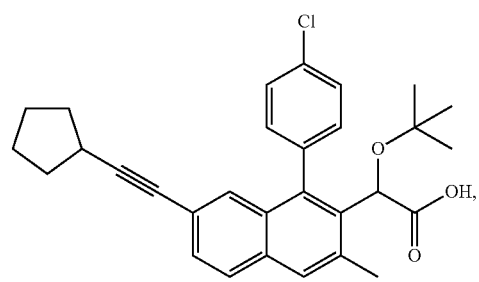
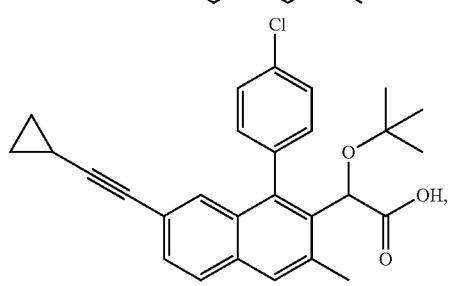
406
-continued
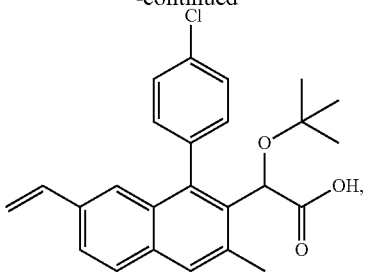
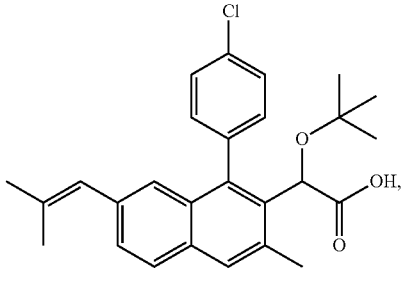
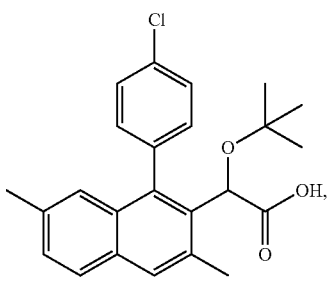
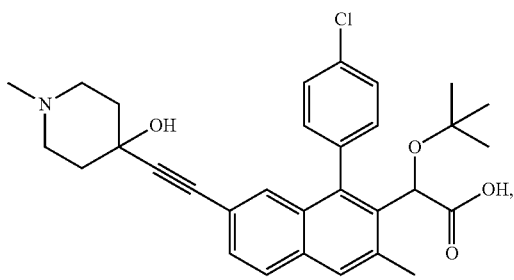
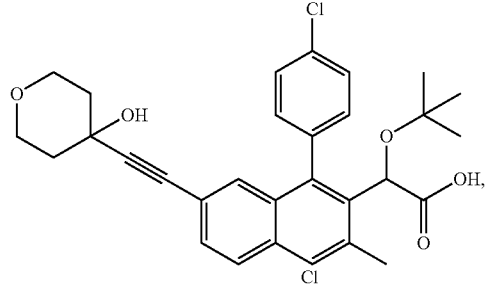
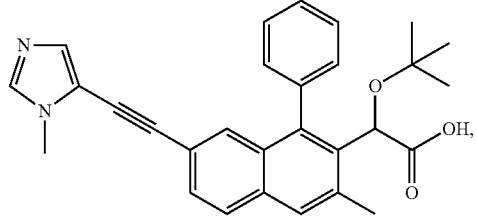

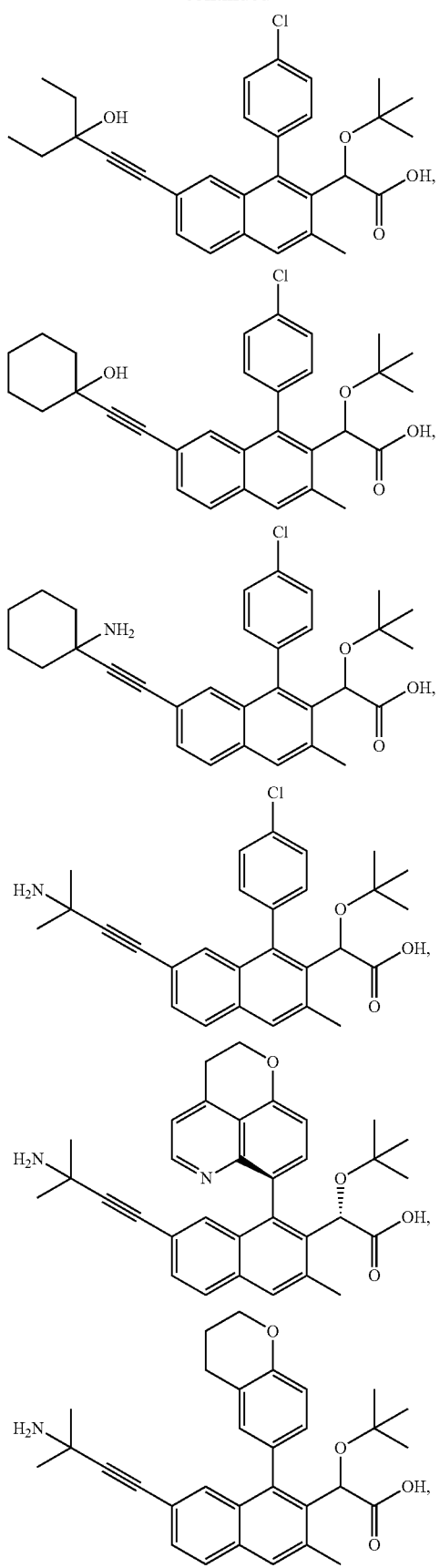
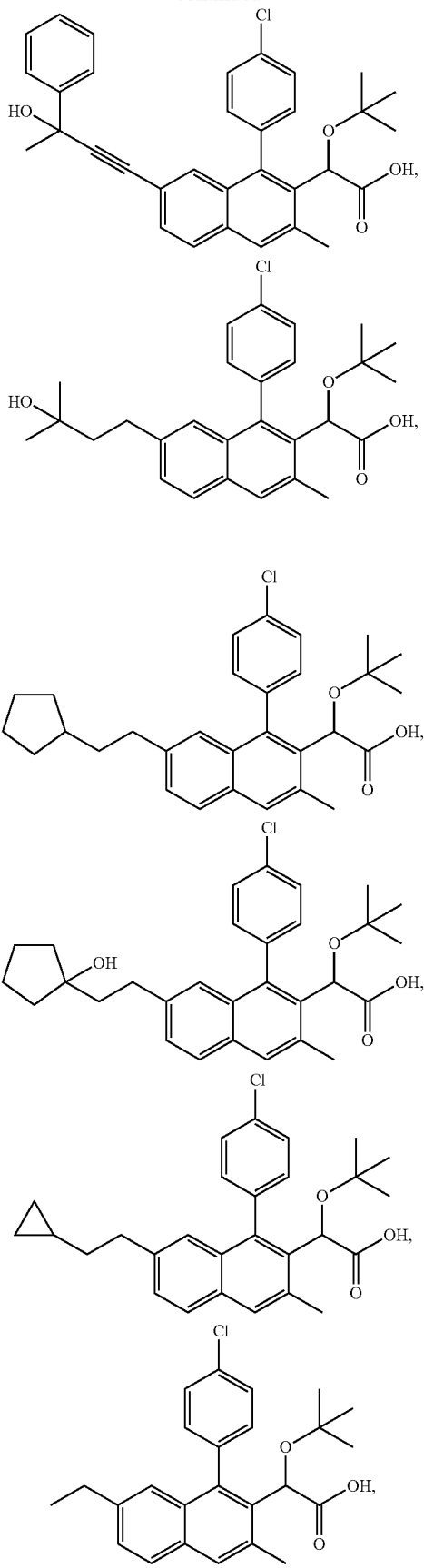

409
-continued
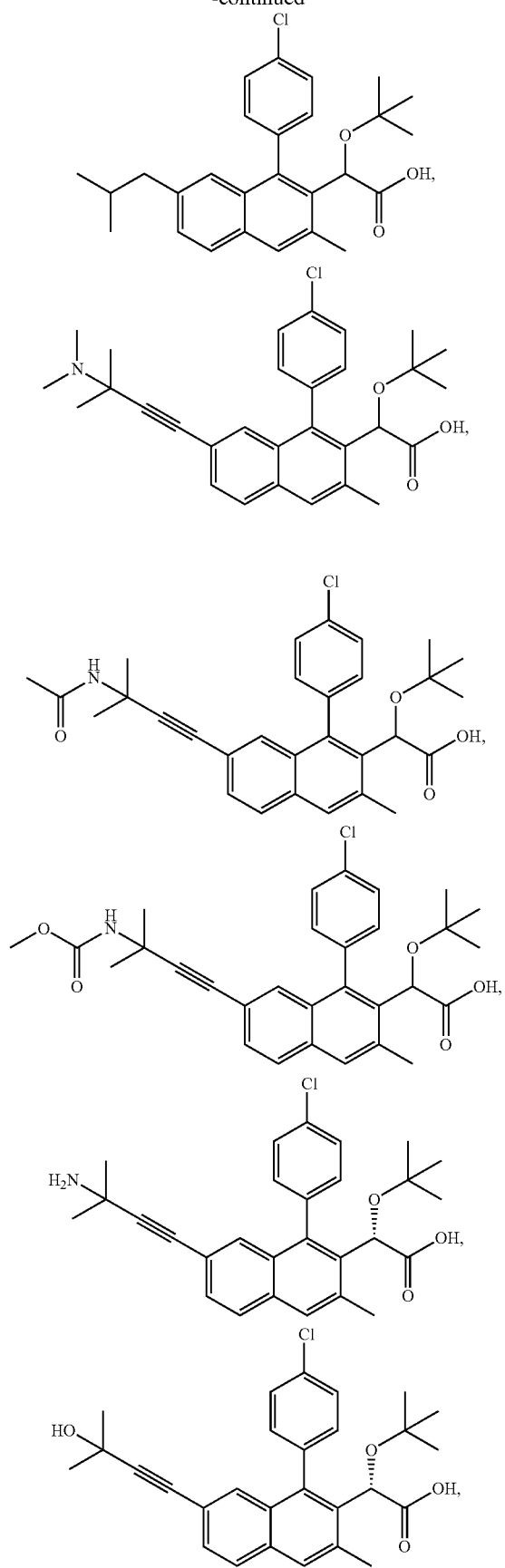
410
-continued
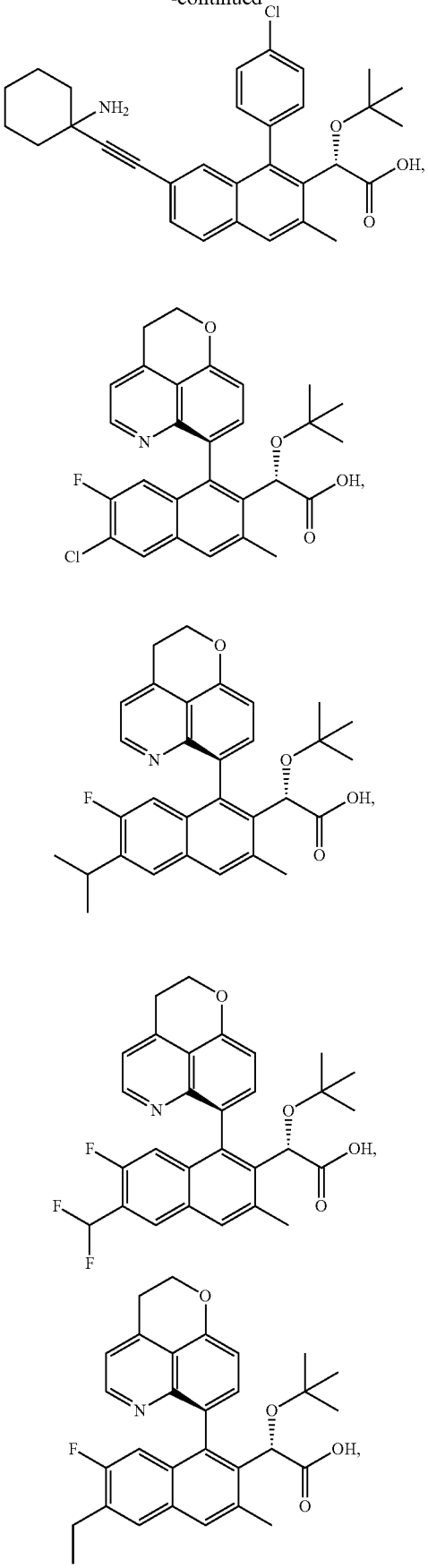

411
-continued
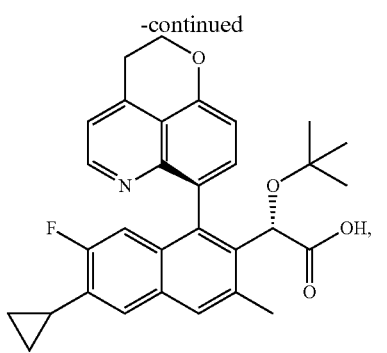
412
-continued
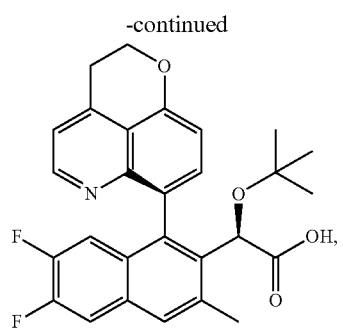
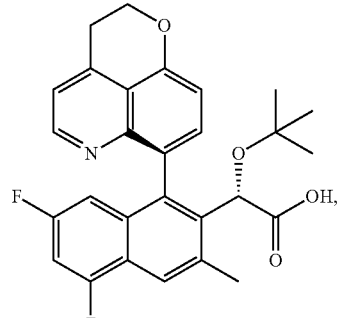
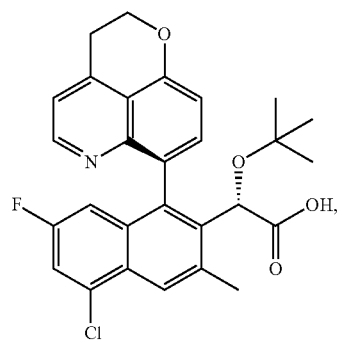
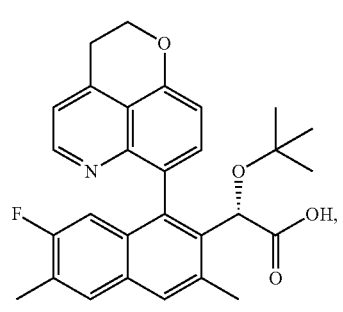
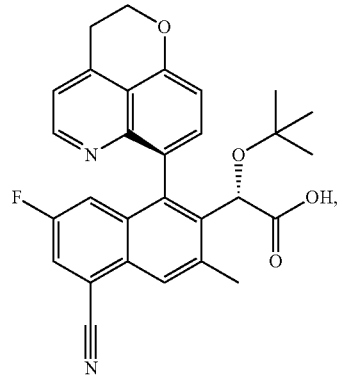

413
-continued
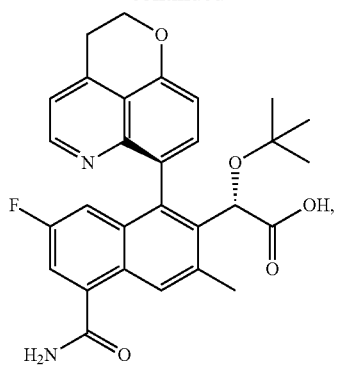
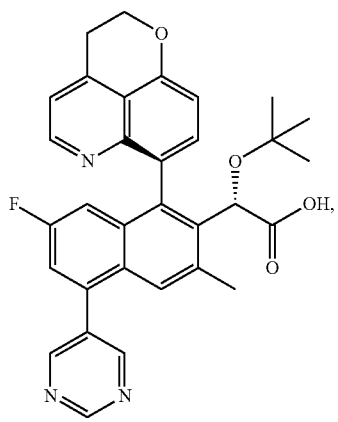
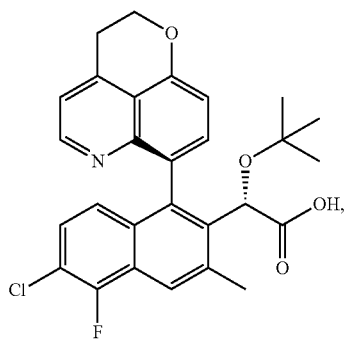
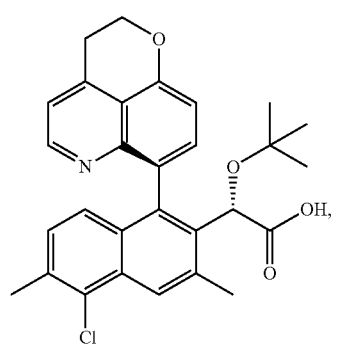
414
-continued
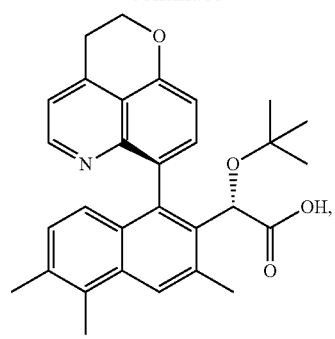
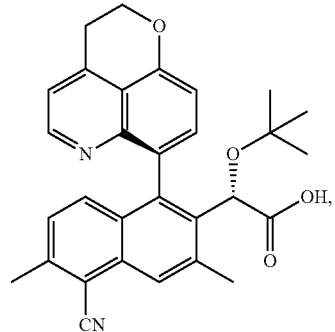
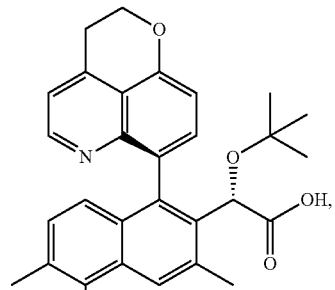
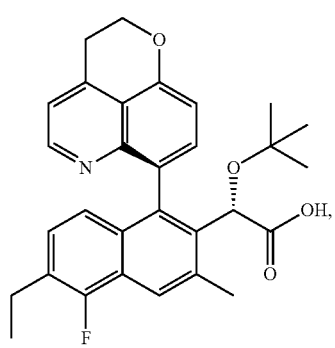
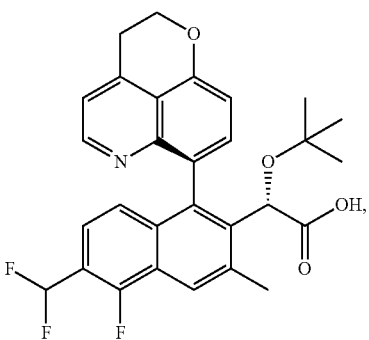

415
-continued
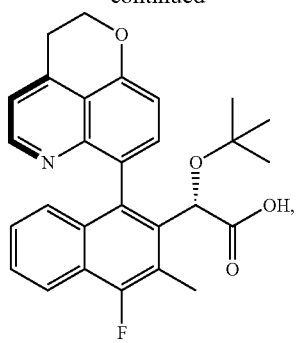
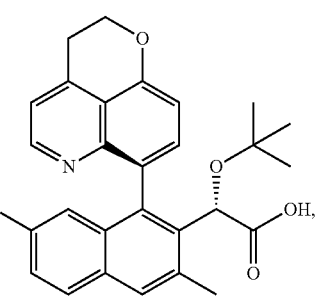
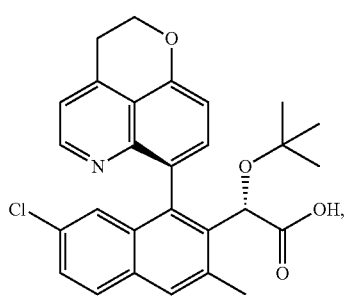
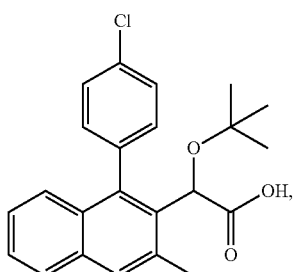
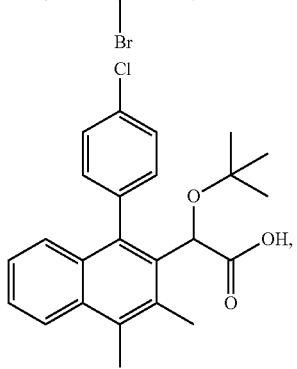
416
-continued
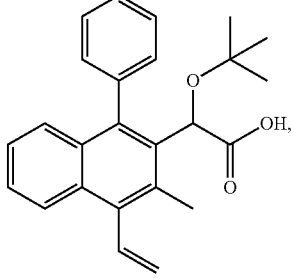
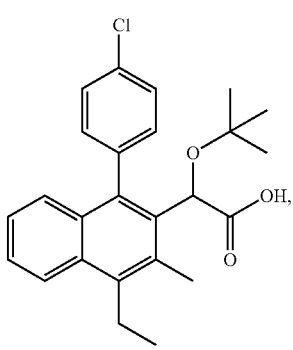
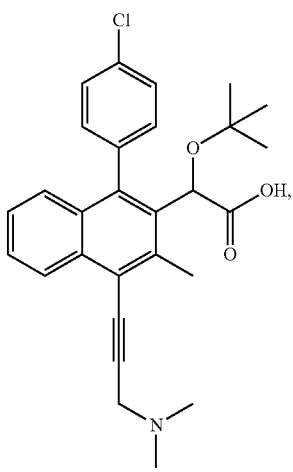
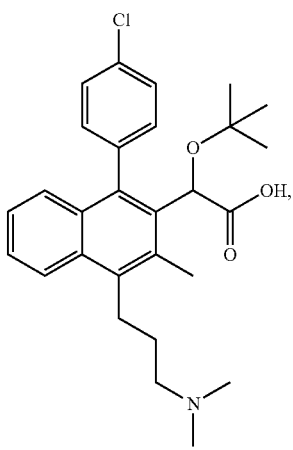

417
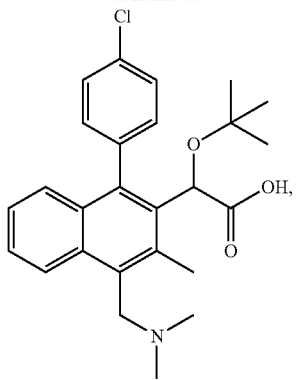
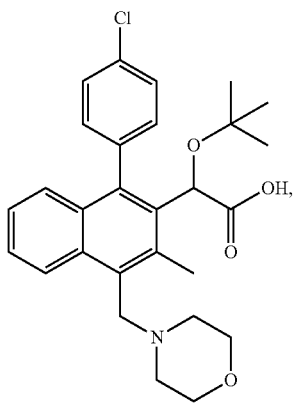
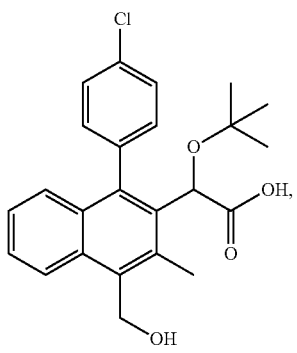
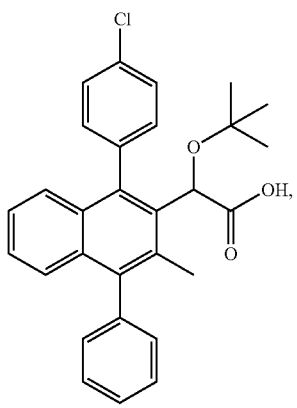
418
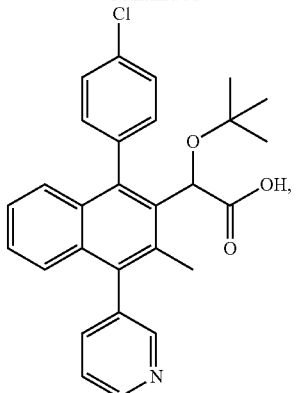
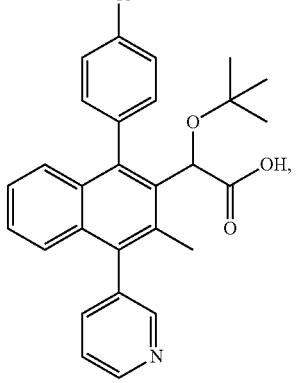
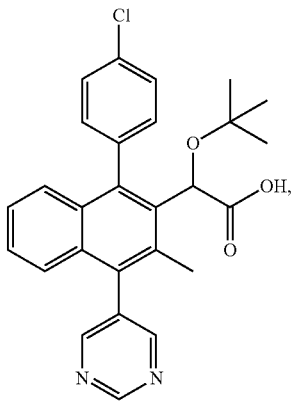
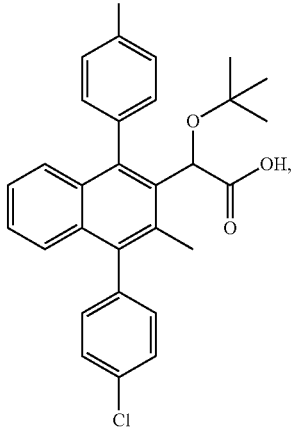

419
-continued
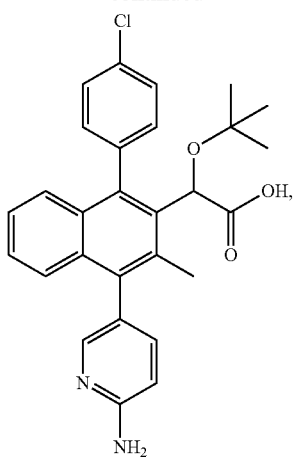
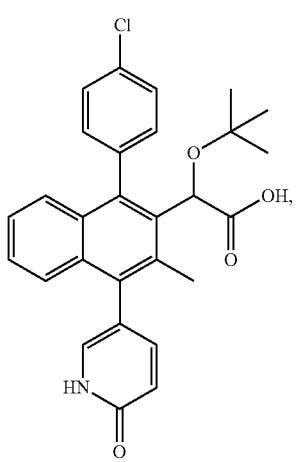
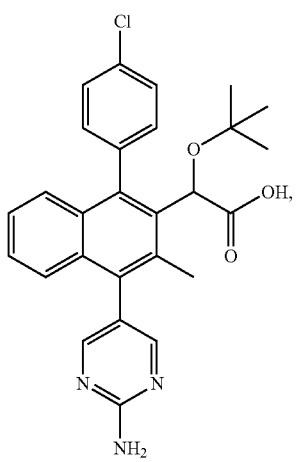
420
-continued
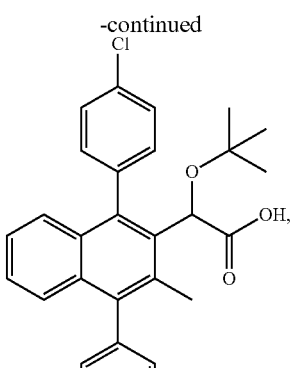
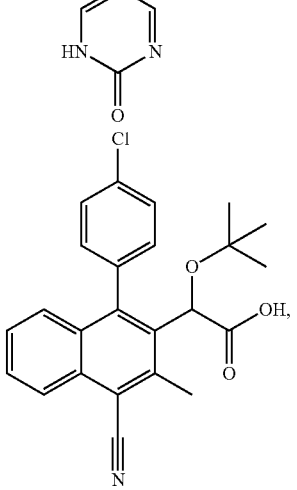
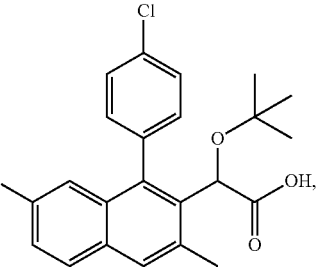
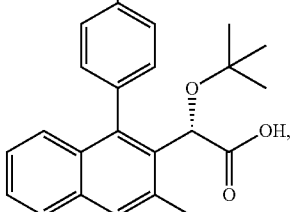
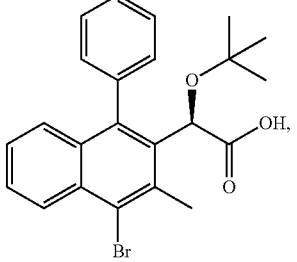

421

-continued

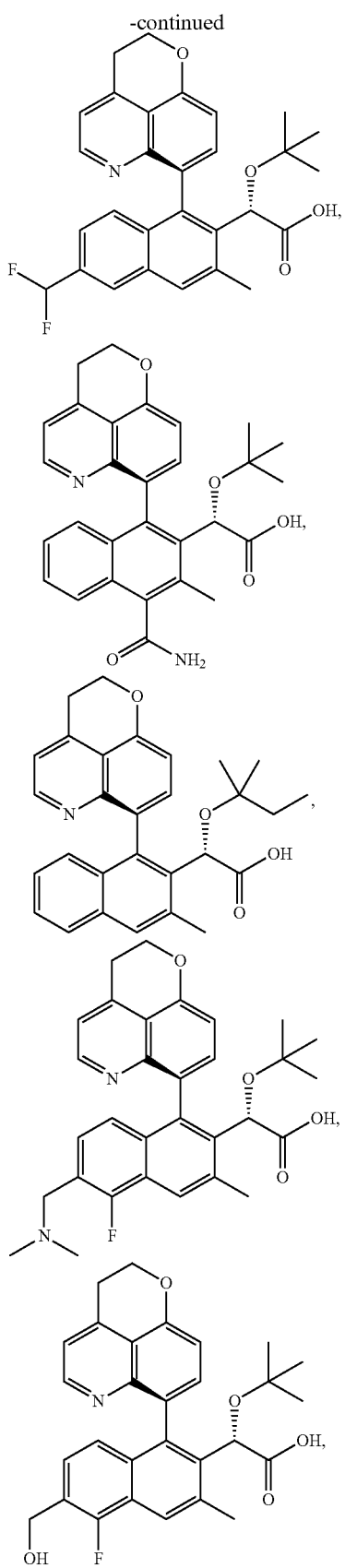

422

-continued

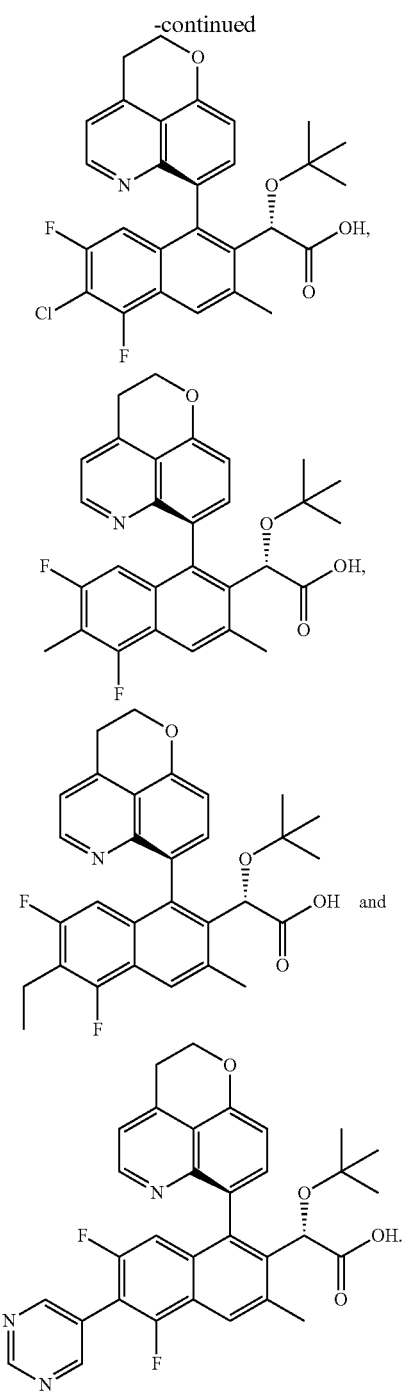

22. A pharmaceutical composition comprising a compound of formula Ib as described in claim 1 or a pharmaceutically acceptable salt thereof, in combination with a pharmaceutically acceptable carrier.

23. A method of treating the proliferation of the HIV virus, treating AIDS or delaying the onset of AIDS or ARC symptoms in a human comprising administering a compound of formula Ib as described in claim 1, or a pharmaceutically acceptable salt thereof, to the human.

* * * * *